US010689450B2

(12) United States Patent
Wiltzius et al.

(10) Patent No.: US 10,689,450 B2
(45) Date of Patent: Jun. 23, 2020

(54) BCMA BINDING MOLECULES AND METHODS OF USE THEREOF

(71) Applicant: KITE PHARMA, INC., Santa Monica, CA (US)

(72) Inventors: Jed Wiltzius, Woodland Hills, CA (US); Ruben Alvarez Rodriguez, Los Angeles, CA (US); Jonathan Belk, Lebanon, NJ (US)

(73) Assignee: KITE PHARMA, INC, Santa Monica, CA (US)

( * ) Notice: Subject to any disclaimer, the term of this patent is extended or adjusted under 35 U.S.C. 154(b) by 0 days.

(21) Appl. No.: 15/476,309

(22) Filed: Mar. 31, 2017

(65) Prior Publication Data

US 2017/0283504 A1 Oct. 5, 2017

Related U.S. Application Data

(60) Provisional application No. 62/317,334, filed on Apr. 1, 2016.

(51) Int. Cl.

| | |
|---|---|
| ***C07K 16/28*** | (2006.01) |
| ***C07K 14/705*** | (2006.01) |
| ***A61K 31/675*** | (2006.01) |
| ***A61K 31/7076*** | (2006.01) |
| ***A61K 31/7088*** | (2006.01) |
| ***A61P 35/02*** | (2006.01) |
| ***A61P 35/00*** | (2006.01) |
| ***A61K 45/06*** | (2006.01) |
| *A61K 35/00* | (2006.01) |

(52) U.S. Cl.

CPC ........ *C07K 16/2878* (2013.01); *A61K 31/675* (2013.01); *A61K 31/7076* (2013.01); *A61K 31/7088* (2013.01); *A61K 45/06* (2013.01); *A61P 35/00* (2018.01); *A61P 35/02* (2018.01); *C07K 14/70521* (2013.01); *A61K 35/00* (2013.01); *C07K 2317/53* (2013.01); *C07K 2317/565* (2013.01); *C07K 2317/622* (2013.01); *C07K 2317/92* (2013.01); *C07K 2319/03* (2013.01); *C07K 2319/30* (2013.01); *C07K 2319/33* (2013.01)

(58) Field of Classification Search

None

See application file for complete search history.

(56) References Cited

U.S. PATENT DOCUMENTS

| | | | | |
|---|---|---|---|---|
| 4,946,778 | A | 8/1990 | Ladner et al. | |
| 5,260,203 | A | 11/1993 | Ladner et al. | |
| 5,728,388 | A | 3/1998 | Terman | |
| 5,827,642 | A | 10/1998 | Riddell et al. | |
| 5,830,462 | A | 11/1998 | Crabtree et al. | |
| 5,834,266 | A | 11/1998 | Crabtree et al. | |
| 5,869,337 | A | 2/1999 | Crabtree et al. | |
| 6,040,177 | A | 3/2000 | Riddell et al. | |
| 6,165,787 | A | 12/2000 | Crabtree et al. | |
| 6,319,494 | B1 | 11/2001 | Capon et al. | |
| 6,797,514 | B2 | 9/2004 | Berenson et al. | |
| 6,867,041 | B2 | 3/2005 | Berenson et al. | |
| 6,905,874 | B2 | 6/2005 | Berenson et al. | |
| 7,709,226 | B2 | 5/2010 | Foote | |
| 7,741,465 | B1 | 6/2010 | Eshhar et al. | |
| 8,465,743 | B2 | 6/2013 | Rosenberg et al. | |
| 8,486,693 | B2 | 7/2013 | Park et al. | |
| 8,536,310 | B2 | 9/2013 | Abo et al. | |
| 9,034,324 | B2 | 5/2015 | Kalled et al. | |
| 9,163,090 | B2 | 10/2015 | Jiang et al. | |
| 9,845,362 | B2 | 12/2017 | Mukherjee | |
| 2002/0006409 | A1 | 1/2002 | Wood | |
| 2002/0164588 | A1 | 11/2002 | Eisenberg et al. | |
| 2004/0014194 | A1 | 1/2004 | Beyer et al. | |
| 2004/0197328 | A1* | 10/2004 | Young ................ | A61K 51/1045 424/141.1 |
| 2010/0285037 | A1 | 11/2010 | Abo | |
| 2011/0280889 | A1* | 11/2011 | Schendel ........... | C07K 14/7051 424/178.1 |
| 2011/0286980 | A1 | 11/2011 | Brenner | |
| 2012/0130076 | A1 | 5/2012 | Holt et al. | |
| 2012/0213783 | A1 | 8/2012 | Rosenberg et al. | |
| 2012/0227134 | A1 | 9/2012 | Schön et al. | |
| 2013/0079246 | A1 | 3/2013 | De Smedt et al. | |

(Continued)

FOREIGN PATENT DOCUMENTS

| | | | |
|---|---|---|---|
| JP | 6262724 | B2 | 1/2018 |
| WO | 88/01649 | A1 | 3/1988 |

(Continued)

OTHER PUBLICATIONS

Rudikoff et al. (PNAS USA, 1982, 79: 1979-1983) (Year: 1982).*
Coleman et al. (Research in Immunology, 1994; 145(1): 33-36) (Year: 1994).*
Ibragimova and Wade (Biophysical Journal, Oct 1999, vol. 77, pp. 2191-2198) (Year: 1999).*
Prazma and Tedder (Immunology Letters 2008, 115: 1-8) (Year: 2008).*
Jena et al. (Blood Aug. 19, 2010 116(7): 1035-1044) (Year: 2010).*
Bonini and Mondino (Eur. J. Immunol. 2015 45: 2457-2469) (Year: 2015).*

(Continued)

*Primary Examiner* — Peter J Reddig
(74) *Attorney, Agent, or Firm* — Arrigo, Lee, Guttman & Mouta-Bellum, LLP

(57) ABSTRACT

The invention provides antibodies, antigen binding fragments thereof, chimeric antigen receptors (CARs), and engineered T cell receptors, polynucleotides encoding the same, and in vitro cells comprising the same. The polynucleotides, polypeptides, and in vitro cells described herein can be used in an engineered CAR T cell therapy for the treatment of a patient suffering from a cancer. In one embodiment, the polynucleotides, polypeptides, and in vitro cells described herein can be used for the treatment of multiple myeloma.

71 Claims, 50 Drawing Sheets

Specification includes a Sequence Listing.

(56) References Cited

U.S. PATENT DOCUMENTS

| | | | | |
|---|---|---|---|---|
| 2013/0287748 | A1 | 10/2013 | June et al. | |
| 2013/0295118 | A1 | 11/2013 | Jiang | |
| 2014/0010861 | A1 | 1/2014 | Bancel et al. | |
| 2014/0050708 | A1 | 2/2014 | Powell et al. | |
| 2014/0099309 | A1 | 4/2014 | Powell, Jr. et al. | |
| 2014/0154228 | A1 | 6/2014 | Volk et al. | |
| 2014/0171649 | A1 | 6/2014 | Li et al. | |
| 2014/0227237 | A1 | 8/2014 | June et al. | |
| 2014/0286987 | A1 | 9/2014 | Spencer et al. | |
| 2014/0328812 | A1 | 11/2014 | Campana et al. | |
| 2015/0051266 | A1 | 2/2015 | Kochenderfer | |
| 2015/0225480 | A1 | 8/2015 | Powell, Jr. | |
| 2015/0266973 | A1 | 9/2015 | Jarjour et al. | |
| 2015/0368360 | A1* | 12/2015 | Liang | C07K 14/7051 435/325 |
| 2016/0046700 | A1 | 2/2016 | Foster et al. | |
| 2016/0046724 | A1 | 2/2016 | Brogdon et al. | |
| 2016/0051651 | A1 | 2/2016 | Brogdon et al. | |
| 2016/0297884 | A1 | 10/2016 | Kuo et al. | |
| 2016/0297885 | A1 | 10/2016 | Kuo et al. | |
| 2016/0311907 | A1 | 10/2016 | Brogdon et al. | |
| 2016/0340649 | A1* | 11/2016 | Brown | C07K 14/5437 |
| 2017/0183418 | A1 | 7/2017 | Galletto | |
| 2017/0281766 | A1* | 10/2017 | Wiltzius | A61K 39/39558 |
| 2017/0283500 | A1 | 10/2017 | Wiltzius et al. | |
| 2017/0283504 | A1 | 10/2017 | Wiltzius | |

FOREIGN PATENT DOCUMENTS

| | | | |
|---|---|---|---|
| WO | 2005000894 | A1 | 1/2005 |
| WO | 2012/031744 | A1 | 3/2012 |
| WO | 2012033885 | A1 | 3/2012 |
| WO | 2012/163805 | A1 | 5/2012 |
| WO | 2008081035 | A1 | 6/2012 |
| WO | 2012079000 | A1 | 6/2012 |
| WO | 2012129514 | A1 | 9/2012 |
| WO | 2013/154760 | A1 | 3/2013 |
| WO | 2013/072406 | A1 | 5/2013 |
| WO | 2013/142034 | A1 | 9/2013 |
| WO | 2013169625 | A1 | 11/2013 |
| WO | 2014/089335 | A2 | 6/2014 |
| WO | 2014/122143 | A1 | 8/2014 |
| WO | 2014127261 | A1 | 8/2014 |
| WO | 2014186469 | A1 | 11/2014 |
| WO | 2015077789 | A2 | 5/2015 |
| WO | 2015080981 | A1 | 6/2015 |
| WO | 2015090229 | A1 | 6/2015 |
| WO | 2015120096 | A2 | 8/2015 |
| WO | 2015142675 | A2 | 9/2015 |
| WO | 2015/158671 | A1 | 10/2015 |
| WO | 2016/014789 | A2 | 1/2016 |
| WO | 2016014535 | A1 | 1/2016 |
| WO | 2016014565 | A1 | 1/2016 |
| WO | 2016044745 | A1 | 3/2016 |
| WO | 2016/094304 | A2 | 6/2016 |
| WO | 2016090369 | A1 | 6/2016 |
| WO | 2017/173410 | A1 | 10/2017 |
| WO | 2017173256 | A1 | 10/2017 |
| WO | 2017173349 | A1 | 10/2017 |
| WO | 2017173384 | A1 | 10/2017 |
| WO | 2017173410 | A1 | 10/2017 |

OTHER PUBLICATIONS

Chames et al (British J. of Pharmacology, 2009, 157, 220-233) (Year: 2009).*

Gura (Science, 1997, 278:1041-1042) (Year: 1997).*

Kaiser (Science, 2006, 313: 1370) (Year: 2006).*

Hipp, S., et al. "A Novel BCMPJCD3 Bispecific T-cell Engager for the Treatment of Multiple Myeloma Induces Selective Lysis In Vitro and In Vivo", Leukemia (2017), pp. 1743-1751, 31, www.nature.com/leu, doi:10.1038/leu.2016.388.

Hymowitz, S.G. et al., "Structures of APRIL-Receptor Complexes", J. Biol. Chem. (2005), 280, pp. 7218-7227, doi: 10.1074/jbc.M411714200 originally published online Nov. 12, 2004.

Kochenderfer J N et al: "Construction and preclinical evaluation of an anti-CD19 chimeric antigen receptor", Journal of Immunotherapy, Lippincott Williams & Wilkins, Hagerstown, MD, US, vol. 32, No. 7, Sep. 1, 2009 (Sep. 1, 2009), pp. 689-702, ISSN: 1524-9557.

Kochenderfer J N et al: "A Phase I Clinical Trial of Treatment of B-Cell Malignancies with Autologous Anti-CD19-CAR-Transduced T Cells", Blood, vol. 116, No. 21, Nov. 2010 (Nov. 2010), pp. 1179-1180, & 52nd Annual Meeting of the American-Society-Ofhematology (ASH); Orlando, FL, USA; Dec. 4-7, 2010.

Yu, G., et al, "APRIL and TALL-1 and receptors BCMA and TACI: system for regulating humoral immunity", Nature Immunology, Sep. 2000, vol. 1, Issue 3, pp. 252-256, ISBN: 15292908.

Kowolik, Claudia M., "CD28 Costimulation Provided through a CD19-Specific ChimericAntigen Receptor EnhancesInvivoPersistence and AntitumorEfficacy of Adoptively Transferred T Cells", Cancer Res 2006; 66: (22). Nov. 15, 2006.

Sadelain, M., et al., "The Basic Principles of Chimeric Antigen Receptor Design", Cancer Discovery, Apr. 2, 2013, pp. 388-398.

Evans, E., et al., "Crystal Structure of a Soluble CD28-Fab Complex", Nature Immunology, vol. 6, No. 3 Mar. 2005, pp. 271-279.

Lovelock & Bishop, "Prevention of freezing damage to living cells by dimethyl sulphoxide.," Nature, 183:1394-1395 (1959).

Lu et al., "Targeting Human C-Type Lectin-like Molecule-1 (CLL 1) with a Bispecific Antibody for Immunotherapy of Acute Myeloid Leukemia," Angew Chem Int. Ed. Engl., 53(37):9841-9845 (2014).

Marshall et al., "Identification and characterization of a novel human myeloid inhibitory C-type lectin-like receptor MIGL) that is predominantly expressed on granulocytes and monocytes," J. Biol. Chem. 279:14792-14802 (2004).

Martin and Thornton, "Structural families in loops of homologous proteins: automatic classification, modelling and application to antibodies," J. Mol. Biol, 263:800-815 (1996).

Rinfret, Ann. NY., "Factors affecting the erythrocyte during rapid freezing and thawing," Acad. Sci., 85:576-594 (1960).

Sambrook et al., "Molecular Cloning A Laboratory Manual," 2001, Third Edition, Cold Spring Harbor Laboratory Press, Table of Contents Only.

Shen et al., "Chimeric antigen receptor containing ICOS signaling domain mediates specific and efficient antitumor effect of T cells against EGFRvIII expressing glioma,"Joumal of Hematology & Oncology, 6:33 (2013).

Sloviter & Ravdin, "Recovery and transfusion of human erythrocytes after freezing in polyglycol solutions," Nature, 196:899-900 (1962).

Song et al., "Pro-survival signaling via CD27 costimulation drives effective CAR T-cell therapy," Oncoimmunology,1;14): 547-549 (2012).

Tashiro et al., "Treatment of Acute Myeloid Leukemia with T Cells Expressing Chimeric Antigen Receptors Directed to C-type Lectin-like Molecule 1," Molecular Therapy, Jul. 1, 2017 {entire document).

UniProtKB—Q5QGZ9 (CL 12A_HUMAN), (2008), http://www.uniprot.org/Q5QGZ9, retrieved on Oct. 2, 2017.

Van Rhenen et al., "The novel AML stem cell associated antigen CLL-1 aids in discrimination between normal and eukemic stem cells" Blood, 110(7):2659-2666 (2007).

Veber & Freidinger, TINS, p. 392 (1985).

Wyckoff et al., eds., Methods in Enzymology vol. 114-Diffraction Methods for Biological Macromolecules, Academic Dress, Orlando, FL; title page, publication page, and table of contents only, 5 pages (1985).

Zhao et al., "Targeting C-type lectin-like molecule-1 for antibody-mediated immunotherapy in acute myeloid leukemia," Haematologica, 95(1):71-78 (2010).

International Search Report for PCT/US2017/025516 dated Jul. 21, 2017 (6 pages).

International Search Report for PCT/US2017/025573 dated Jul. 25, 2017 (6 pages).

Office Action for Cuban application No. 2018-0120 dated Jan. 8, 2019 (2 pages).

International Search Report for PCT/US2017/025613 dated Jun. 27, 2017 (13 pages).

(56) References Cited

OTHER PUBLICATIONS

Al-Lazikani Bet al., Standard conformations for the canonical structures of immunoglobulins, J Mol Biol, 273:927-948 1997).
Bricogne G., "Bayesian statistical viewpoint on structure determination: Basic concepts and examples," Meth Enzymol J76A:361-423 (1997).
Bricogne G., "Direct phase determination by entropy maximization and likelihood ranking: status report and perspectives," Acta Crystallogr D Biol Crystallogr, 49(Pt 1):37-60 (1993).
Champe M et al., "Monoclonal antibodies that block the activity of leukocyte function-associated antigen 1 recognize three discrete epitopes in the inserted domain of CD11a," J Biol Chem, 270:1388-1394 (1995).
Cheung, et al. "Epitope-specific antibody response to the surface antigen of duck hepatitis B virus in infected ducks," Virology, 176:546-552 (1990).
Chayen NE, "The role of oil in macromolecular crystallization," Structure, 5:1269-1274 (1997).
Chothia C & Lesk AM, "Canonical structures for the hypervariable regions of immunoglobulins," J Mol Biol 196:901-91, 1987).
Chothia C et al., "Structural repertoire of the human VH segments," J Mol Biol, 227:799-817 (1992).
Cunningham BC & Wells JA, "High-resolution epitope mapping of hGH-receptor interactions by alanine-scanning mutagenesis," Science, 244:1081-1085 (1989).
Dayhoff et al., 1978, Atlas of Protein Sequence and Structure 5:345-352.
Devereux et al., "A comprehensive set of sequence analysis programs for the VAX," Nucl. Acid Res., 12:387-395 1984).
Fegan et al., "Chemically controlled protein assembly: techniques and applications," Chem. Rev., 110:3315-3336 2010).
Finney et al., "Chimeric receptors providing both primary and coslimulatory signaling in T cells from a single gene product," Journal of Immunology,161:2791-2797 (1998).
Giege R. et al., "Crystallogenesis of biological macromolecules: facts and perspectives," Acta Crystallogr D Biol :; rystallogr, 50(PI 4):339-350 (1994).
Gross et al., "Therapeutic Potential of T Cell Chimeric Antigen Receptors (CARs) in Cancer Treatment: Counteracting : Off-Tumor Toxicities for Safe Cart Cell Therapy," Annu. Rev. Pharmacol. Toxicol., 56:59-83 (2016).
Henikoff et al., "Amino acid substitution matrices from protein blocks," Proc. Nall. Acad. Sci. U.S.A., 89:10915-10919 (1992).
Kabat EA & Wu TT, "Attempts to locate complementarity-determining residues in the variable positions of light and heavy chains," Ann NY Acad Sci, 190:382-391 (1971).
Kalos et al., "T cells with chimeric antigen receptors have potent antitumor effects and can establish memory in patients with advanced leukemia," Sci Transl. Med., 3:95 (2011).
Kirkland et al., "Analysis of the fine specificity and cross-reactivity of monoclonal anti-lipid A antibodies," J. Immunol. 137:3614-3619 (1986).
Krause et al., "Antigen-dependent CD28 signaling selectively enhances survival and proliferation in genetically modified activated human primary T lymphocytes," J. Exp. Med., 188(4):619-626 (1998).
McPherson A., "Crystallization of proteins from polyethylene glycol.," J Biol Chem, 251 :6300-6303 (1976).
McPherson A., "Current approaches to macromolecular crystallization," Eur J Biochem, 189:1-23 (1990).
Moldenhauer et al., "Identity of HML-1 antigen on intestinal intraepithelial T cells and of B-ly7 antigen on hairy cell eukaemia," Scand. J. Immunol., 32:77-82 (1990).
Morel et al., "Monoclonal antibodies to bovine serum albumin: affinity and specificity determinations," Molec. Immunol., 25:7-15 (1988).
Porter et al., "Chimeric antigen receptor-modified T cells in chronic lymphoid leukemia," N. Engl. J. Med., 365:725-33 (2011).
Roversi P et al., "Modelling prior distributions of atoms for macromolecular refinement and completion," Acta :; Crystallogr D Biol Crystallogr, 56{Pt 10):1316-1323 (2000).
Song et al., "CD27 costimulation augments the survival and anti-tumor activity of redirected human T cells in vivo," Blood, 119:696-706 (2012).
Stahli et al., "Distinction of epitopes by monoclonal antibodies," Methods in Enzymology, 9:242-253 (1983).
Tramontano A et al., "Framework residue 71 is a major determinant of the position and conformation of the second hypervariable region in the VH domains of immunoglobulins," J Mal Biol, 215(1):175-182 (1990).
Wu et al., "Remote control of therapeutic T Cells through a small molecule-gated chimeric receptor," Science, 350 6258):293 (2015).
International Search Report for PCT/US2017/025351 dated Aug. 22, 2017 (6 pages).
Ashwood-Smith, "Preservation of mouse bone marrow at -79 degrees C. with dimethyl sulphoxide," Nature, 190:1204-1205 (1961).
Bakker et al., "C-type lectin-like molecule-1: a novel myeloid cell surface marker associated with acute myeloid eukemia," Cancer Res., 64:8443-8450 (2004).
Chothia et al., "Conformations of immunoglobulin hypervariable regions," Nature, 342:877-883 (1989).
Chu et al., "SV40 DNA transfection of cells in suspension: analysis of efficiency of transcription and translation of T-antigen," Gene, 13:197-202 (1981).
C-type lectin domain family 12 member A isoform 1 [*Homo sapiens*], NCBI Reference Sequence: NP _612210.4, hllps://www.ncbi.nlm.nih.gov/protein/NP _61221A, retrieved on Oct. 2, 2017.
Davis et al., "Basic Methods in Molecular Biology," 1986, Elsevier, Table of Contents only.
Eshhar et al., "Tumor-specific T-bodies: towards clinical application," Cancer Immunol Immunotherapy, 45:131-136 (1997).
Evans et al., "Design of nonpeptidal ligands for a peptide receptor: cholecystokinin antagonists," J_ Med. Chem., 30:1229-1239 (1987).
Gautier et al., "Site-Specific Protein Labeling, Methods and Protocols," Springer 2015, pp. 1-267.
Golub et al., "Immunology—A Synthesis (2nd Edition)," Sinauer Association., Sunderland, Mass. (1991 ), table of contents only, 13 pages.
Graham et al., "A new technique for the assay of infectivity of human adenovirus 5 DNA," Virology, 52:456-467 (1973).
Guedan et al., "ICOS-based chimeric antigen receptors program bipolar TH17fTH1 cells," Blood, 124(7):1070-1080 (2014).
Harlow et al., "Antibodies: A Laboratory Manual," Cold Spring Harbor Laboratory, eds., 1988.
Hartl et al., "Genetics: Principles and Analysis," 1997, Jones and Bartlett Publishers.
Hombach et al., "OX40 costimulation by a chimeric antigen receptor abrogates CD28 and IL-2 induced IL-10 secretion by redirected CD4(+) T cells," Oncoimmunology, 1(4): 458-466 (2012).
Hombach et al., "Tumor-specific T cell activation by recombinnt immunorceptors: CD3 zeta signaling and CD28 costimulation are simultaneously required for efficient IL-2 secretion and can be integrated into one combined CD28/CD3 zeta signaling receptor molecule," Journal of Immun., 167:6123-6131 (2001).
Kabat et al., "Sequences of Proteins of Immunological Interest," 1991, 5th Ed., NIH Publication 91-3242, Bethesda, MD title page, publication page, and table of contents only, 10 pages.
Restriction Requirement for U.S. Appl. No. 15/476,699 dated Jan. 18, 2019 (11 pages).
Non-Final Office Action for U.S. Appl. No. 15/476,309 dated Mar. 1, 2019 (35 pages).
Restriction Requirement for U.S. Appl. No. 15/476,309 dated Sep. 4, 2018 (12 pages).
Written Opinion for PCT/US2017/025573 dated Aug. 11, 2017 (8 pages).
Written Opinion for PCT/US2017/025351 dated Aug. 22, 2017 (6 pages).
Written Opinion for PCT/US2017/025516 dated Aug. 25, 2017 (8 pages).
Dotti et al., "Design and Development of Therapies using Chimeric Antigen Receptor-Expressing T cells", Immunol Rev. Jan. 2014; vol. 257(1); pp. 1-28 (29 pages).

(56) References Cited

OTHER PUBLICATIONS

Geldres et al., "Chimeric antigen receptor-redirected T cells return to the bench", Seminars in Immunology, Jan. 12, 2016, vol. 28; pp. 3-9 (6 pages).
Fesnak et al., "Engineered T cells: the promise and challenges of cancer immunotherapy", Nature Reviews Cancer Sep. 2016; vol. 16: pp. 566-581 (15 pages).
De Oliveira et al., "Modification of Hematopoietic Stem/Progenitor Cells with CD19-Specific Chimeric Antigen Receptors as a Novel Approach for Cancer Immunotherapy", Human Gene Therapy; Oct. 2013; vol. 24: pp. 24-39 (8 pages).
Kariv et al., "Analysis of the Site of Interaction of CD28 with Its Counter-Receptors CD80 and CD86 and Correlation with Function", Journal of Immunology. Apr. 8, 1996; vol. 157: pp. 29-38 (9 pages).
Non-Final Office Action for U.S. Appl. No. 15/475,681, dated Dec. 5, 2018 (42 pages).
Notice of Allowance for U.S. Appl. No. 15/475,681, dated Jun. 24, 2019 (37 pages).
Notification Prior to Examination of Patent Application No. 261941 According to Section 18 of the Law and Regulation 36 of the Regulations, Nov. 17, 2019.
English Translation Law and Regulation notification Prior to Examination of Patent Application No. 261941 According to Section 18 of the 36 of the Regulations, Nov. 17, 2019.
Notification Prior to Examination of Patent Application No. 262041 According to Section 18 of the Law and Regulation 36 of the Regulations, Nov. 17, 2019.
English Translation Law and Regulation Notification Prior to Examination of Patent Application No. 262041 According to Section 18 of the 36 of the Regulations, Nov. 17, 2019.
Notification Prior to 36 of the Regulation Examination of Patent Application No. 261942 According to Section 18 of the Law and Regulation, Nov. 17, 2019.
English Translation Law and Regulation Notification Prior to Examination of Patent Application No. 261942 According to Section 18 of the 36 of the Regulations, Nov. 17, 2019.
Official Office Action in Colombia Patent Application No. NC2019/0008646, dated Dec. 6, 2019.
English Translation Official Office Action in Colombia Patent Application No. NC2019/0008646, dated Dec. 6, 2019.
Granting Resolution Colombian Patent Application National Phase No. NC2018/0010547, dated Nov. 25, 2019.
English Translation of Granting Resolution Colombian Patent Application National Phase No. NC2018/0010547, dated Nov. 25, 2019.
Grant of Request to add Co-Inventor (Jonathan Bellk added as an inventor to the application)(TH Patent Application No. 1801006120)—dated Oct. 29, 2019 (receipt serves as grantt).
English Translation of Grant of Request to add Co-Inventor (Jonathan Bellk added as an inventor to the application) (TH Patent Application No. 1801006120)—dated Oct. 29, 2019.
Original and English Translation of Office Action dated Jan. 6, 2020 in Korean Patent Application No. 10-2018-7031572.
Notice to Comply With Requirements for Sequence Disclosure (U.S. Appl. No. 15/476,699) dated Aug. 14, 2018.
First Notice of Allowance (U.S. Appl. No. 15/475,681) dated Jun. 24, 2019.
European search Report for Application No. 17776766.2, PCT/US2017025351 dated Nov. 5, 2019.
Leong S.R. et al.;"An anti-CD3/anti-CLL-1 bispecific antibody for the treatment of acute myeloid leukemia", Blood, Feb. 2, 2017, vol. 129, No. 5, pp. 609-618.
Wyckoff et al., eds., Methods in Enzymology vol. 115—Diffraction Methods for Biological Macromolecules, Academic Press, Orlando, FL; title page, publication page, and table of contents only, 4 pages (1985).
Guest Ryan D et al: The Role of Extracellular Spacer Regions in the Optimal Design of Dhimeric Immune Receptors—Evaluation of Four Different SCFVS and Antigens11 , Journal of Immunotherapy, Lippincott Williams & Wilkins, US, vol. 28, No. 3, pp. 203-211, Jan. 1, 2005 (Jan. 1, 2005).
Restriction Requirement for U.S. Appl. No. 15/476,699 dated Jan. 18, 2019 (11 pages), related to this subject application.
Australian examination report for application No. 2017240788 dated May 24, 2019 (3 pages), related to this subject application.
First Examination Report for Canadian Application No. 3019650, dated Sep. 19, 2019, which is related to this subject application.
Original version of Office Action for Japanese Patent Application No. 2018-551953, dated Oct. 29, 2019, which is related to this subject application.
English translation of Office Action for Japanese Patent Application No. 2018-551953, dated Oct. 29, 2019, which Is related to this application.
Original version of Official Action for Panamanian Patent Application No. PI/2018/92399-01, dated Mar. 14, 2019, which is related to this subject application.
English translation of Official Action for Panamanian Patent Application No. PI/2018/92399-01, dated Mar. 14, 2019, which is related to this subject application.
Moroccan examination report for application no. 43603 dated Mar. 14, 2018 (8 pages), related to this subject application.
First Examination Report of New Zealand Patent Application No. 747172 dated Aug. 29, 2019, related to this subject application.
Original version of Office Action for Taiwanese Patent Application No. 106111224, which was dated Sep. 10, 2019 and is relate to this subject application.
English translation of Office Action and Search Report for Taiwanese Patent Application No. 106111224, which was dated Sep. 20, 2019 and is related to this subject application.
Original version of Search Report for Taiwanese Patent Application No. 106111224, which was dated Sep. 10, 2019 and is related to this subject application.
Original First Office Action for Ukrainian Patent Application No. a 2018 09953, which was dated Oct. 31, 2019 and is related to this subject application.
English Translation of First Office Action for Ukrainian Patent Application No. a 2018 09953, which was mailed on Oct. 31, 2019 and is related to this subject application.
Original version of Official Action for Cuban application No. 2018-0121 dated Jan. 8, 2019 (2 Pages), related to this subject application.
English translation Office Action for Cuban application No. 2018-0121 dated Jan. 8, 2019 (2 pages), related to this subject application.
Office Action dated Oct. 2, 2019 for Taiwan Patent Application No. 106111226, which is related to this subject application.
Search Report dated Oct. 2, 2019 for Taiwan Patent Application No. 106111226, which is related to this subject application.
English Translation of Office Action dated Oct. 2, 2019 for Taiwan Patent Application No. 106111226, which is related to this subject application.
First Office Action in Primary Examination for Taiwanese Patent Application No. 106111228; 883738, dated Sep. 23, 2019, and is related to this subject application.
Search Report in Primary Examination for Taiwanese Patent Application No. 106111228; 883738, dated Sep. 23, 2019, and is related to this subject application.
English Translation of First Office Action and Search Report in Primary Examination for Taiwanese Patent Application No. 016111228; 883738, dated Sep. 23, 2019, and is related to this subject application.
Supplementary Partial European Search Report, dated Sep. 19, 2019 for European Patent Application No. 17776833, which is related to this subject application.
Supplementary European Search Report for EP Application No. EP 17776859, which was dated Oct. 7, 2019, and is related to this subject matter.
Fauchere et al (1996) "Elements for the rational design of peptide drugs" Adv Drug Res 15:29.
Notice of Allowance (U.S. Appl. No. 15/476,699) dated Jul. 22, 2019, related to this subject application.

(56) References Cited

OTHER PUBLICATIONS

Notice of Allowance (U.S. Appl. No. 15/476,699) dated Oct. 7, 2019, related to this subject application.
Final Office Action (U.S. Appl. No. 15/475,681) dated Apr. 23, 2019, related to this subject application.
First Official Action—dated Nov. 7, 2019 (EA Application No. 201891992), related to this subject application.
Communication 70a and 70a(2)(EP Application No. 17776859.5)(dated Oct. 24, 2019), related to this subject application.
MA Examination Report (english translation (MA Application No. MA 43603), dated Mar. 3, 2018, related to this subject application.
First Official Action—dated Nov. 7, 2019 (EA Application No. 201891992), English Translation, related to this subject application.
OA—English and Spanish (PE Patent Application No. 001934-2018/DIN)(dated Oct. 19, 2019), related to this subject application.
English translation of Office Action in PE Patent Application No. 001934-2018/DIN)(dated Oct. 19, 2019), related to this subject application.
Third Notice of Allowance (U.S. Appl. No. 15/476,699) dated Oct. 23, 2019, related to this subject application.
Communication Pursuant to Rule 164(1) EPC, Application No. EP17776833.0-1116 / 3436036 PCT/US2017025516related to this subject application, dated Oct. 2, 2019.
International Search Report for PCT/US2017/025613 dated Jul. 12, 2017.
Communication 70a and 70a(2)(EP Application No. 17776766.2)(dated Nov. 22, 2019), related to this subject application.
Examiner Initiated Interview Summary (U.S. Appl. No. 15/476,699) dated Jun. 14, 2019.
Request to add Co-Inventor (Jonathan Bellk added as an inventor to the application)(TH Patent Application No. 1801006120)—dated Oct. 29, 2019.
Addition of Inventor (Jonathan Bellk added as an inventor to the application)(SG Patent Application No. 11201808403S)—dated Nov. 6, 2019.
Amendment Notification—Request for Correction of Error Accepted Accepted (Jonathan Bellk added as an inventor to the application)(NZ Patent Application No. 746700)—dated Oct. 4, 2019.
Notice of Allowance (U.S. Appl. No. 15/475,681) dated Oct. 24, 2019.
Restriction Requirement (U.S. Appl. No. 15/475,681) dated Aug. 7, 2018.
Notice to File Missing Parts (U.S. Appl. No. 16/570,645) dated Sep. 24, 2019.
Notice to File Corrected Application Papers (U.S. Appl. No. 16/569,341) dated Sep. 25, 2019.
Notice to File Corrected Application Papers (U.S. Appl. No. 16/658,480) dated Oct. 29, 2019.
Decision of Rejection in Taiwan Patent Application No. 106111226, dated Feb. 20, 2020 (Original and English Translation).
Extended European Search Report received in European Patent Application Serial No. 17776833.0 dated Feb. 18, 2020, 22 pages.

* cited by examiner

FIG. 1A – Anti-BCMA Binding Molecules

```
                                 FR1                   CDR1         FR2             CDR2
FS-21495_VH  EVQLLESGGGLVQPGGSLRLSCAASG--FTFSSYAMSWVRQAPGKGLEWVSAISGSGGST
PC-21497_VH  QVQLVESGGGVVQPGRSLRLSCAASG--FTFSSYGMHWVRQAPGKGLEWVAVISYDGSNK
AJ-21508_VH  QVQLVQSGAEVKKPGASVKVSCKASG--YTFTSYYMHWVRQAPGQGLEWMGIINPSGGST
NM-21517_VH  QLQLQESGPGLVKPSETLSLTCTVSGGSISSSSYYWGWIRQPPGKGLEWIGSISYSG-ST
TS-21522_VH  EVQLVESGGGLVQPGGSLRLSCAASG--FTFSSYSMNWVRQAPGKGLEWVSFISSSSSTI
RY-21527_VH  QVQLVESGGGVVQPGRSLRLSCAASG--FTFSSYGMHWVRQAPGKGLEWVAVISYDGSNK
PP-21528_VH  QVQLVQSGAEVKKPGSSVKVSCKASG--GTFSSYAISWVRQAPGQGLEWMGGIIPIFGTA
RD-21530_VH  QVQLVESGGGVVQPGRSLRLSCAASG--FTFSSYGMHWVRQAPGKGLEWVAVISYDGSNK
             :;** :**  : :*. :: ::* .**   : :**    *:**.**:****:. *     .

              CDR2                FR3                      CDR3
FS-21495_VH  YYADSVKGRFTISRDNSKNTLYLQMNSLRAEDTAVYYCAR-AEM-------GAVFDIWGQ
PC-21497_VH  YYADSVKGRFTISRDNSKNTLYLQMNSLRAEDTAVYYCARDGTYLGGL---WY-FDLWGR
AJ-21508_VH  SYAQKFQGRVTMTRDTSTSTVYMELSSLRSEDTAVYYCAR----------ESWFMDVWGQ
NM-21517_VH  YYNPSLKSRVTISVDTSKNQFSLKLSSVTAADTAVYYCARGRGYATS-----LAFDIWGQ
TS-21522_VH  YYADSVKGRFTISRDNAKNSLYLQMNSLRAEDTAVYYCARGSQE-------HLTFDYWGQ
RY-21527_VH  YYADSVKGRFTISRDNSKNTLYLQMNSLRAEDTAVYYCARTDFWSGSP---PG-LDYWGQ
PP-21528_VH  NYAQKFQGRVTITADESTSTAYMELSSLRSEDTAVYYCARTPEYSSSIWHYYYGMDVWGQ
RD-21530_VH  YYADSVKGRFTISRDNSKNTLYLQMNSLRAEDTAVYYCVKGPLQEPPY---DYGMDVWGQ
              *   ..:.*.*:: * :..   :::.*: : *******.:            :*  **:

              FR4
FS-21495_VH  GTMVTVSS
PC-21497_VH  GTLVTVSS
AJ-21508_VH  GTTVTVSS
NM-21517_VH  GTMVTVSS
TS-21522_VH  GTLVTVSS
RY-21527_VH  GTLVTVSS
PP-21528_VH  GTTVTVSS
RD-21530_VH  GTTVTVSS
             ** *****
```

| FIG. 1B | SEQ ID NO: | | | | | | | |
|---|---|---|---|---|---|---|---|---|
| | VH | FR1 | CDR1 | FR2 | CDR2 | FR3 | CDR3 | FR4 |
| FS-21495 VH | 65 | 1 | 9 | 17 | 25 | 33 | 41 | 49 |
| PC-21497 VH | 66 | 2 | 10 | 18 | 26 | 34 | 42 | 50 |
| AJ-21508 VH | 67 | 3 | 11 | 19 | 27 | 35 | 43 | 51 |
| NM-21517 VH | 68 | 4 | 12 | 20 | 28 | 36 | 44 | 52 |
| TS-21522 VH | 69 | 5 | 13 | 21 | 29 | 37 | 45 | 53 |
| RY-21527 VH | 70 | 6 | 14 | 22 | 30 | 38 | 46 | 54 |
| PP-21528 VH | 71 | 7 | 15 | 23 | 31 | 39 | 47 | 55 |
| RD-21530 VH | 72 | 8 | 16 | 24 | 32 | 40 | 48 | 56 |

FIG. 1C – Anti-BCMA Binding Molecules

```
                                   FR1              CDR1         FR2         CDR2
FS-21495_VH  EVQLLESGGGLVQPGGSLRLSCAASG--FTFSSYAMSWVRQAPGKGLEWVSAISGSGGST
PC-21497_VH  QVQLVESGGGVVQPGRSLRLSCAASG--FTFSSYGMHWVRQAPGKGLEWVAVISYDGSNK
AJ-21508_VH  QVQLVQSGAEVKKPGASVKVSCKASG--YTFTSYYMHWVRQAPGQGLEWMGIINPSGGST
NM-21517_VH  QLQLQESGPGLVKPSETLSLTCTVSGGSISSSSYYWGWIRQPPGKGLEWIGSISYSG-ST
TS-21522_VH  EVQLVESGGGLVQPGGSLRLSCAASG--FTFSSYSMNWVRQAPGKGLEWVSEISSSSSTI
RY-21527_VH  QVQLVESGGGVVQPGRSLRLSCAASG--FTFSSYGMHWVRQAPGKGLEWVAVISYDGSNK
PP-21528_VH  QVQLVQSGAEVKKPGSSVKVSCKASG--GTFSSYAISWVRQAPGQGLEWMGGIIPIFGTA
RD-21530_VH  QVQLVESGGGVVQPGRSLRLSCAASG--FTFSSYGMHWVRQAPGKGLEWVAVISYDGSNK
             :;** :**  : :*. :: ::* .**   : :**  *:**.**:****:. *    .

               CDR2                 FR3                       CDR3
FS-21495_VH  YYADSVKGRFTISRDNSKNTLYLQMNSLRAEDTAVYYCAR-AEM-------SAVFDIWGQ
PC-21497_VH  YYADSVKGRFTISRDNSKNTLYLQMNSLRAEDTAVYYCARDGTYLGGL---WY-FDLWGR
AJ-21508_VH  SYAQKFQGRVTMTRDTSTSTVYMELSSLRSEDTAVYYCAR----------ESWPMDVWGQ
NM-21517_VH  YYNPSLKSRVTISVDTSKNQFSLKLSSVTAADTAVYYCARGRGYATS-----LAFDIWGQ
TS-21522_VH  YYADSVKGRFTISRDNAKNSLYLQMNSLRAEDTAVYYCARGSQE-------HLIFDYWGQ
RY-21527_VH  YYADSVKGRFTISRDNSKNTLYLQMNSLRAEDTAVYYCARTDFWSGSP---PG-LDYWGQ
PP-21528_VH  NYAQKFQGRVTITADESTSTAYMELSSLRSEDTAVYYCARTPEYSSSIWHYYYGMDVWGQ
RD-21530_VH  YYADSVKGRFTISRDNSKNTLYLQMNSLRAEDTAVYYCVKGPLQEPPY---DYGMDVWGQ
              *   ...:.*.*:: * :..   ::.*: : *******.:              :*  **:

               FR4
FS-21495_VH  GTMVTVSS
PC-21497_VH  GTLVTVSS
AJ-21508_VH  GTTVTVSS
NM-21517_VH  GTMVTVSS
TS-21522_VH  GTLVTVSS
RY-21527_VH  GTLVTVSS
PP-21528_VH  GTTVTVSS
RD-21530_VH  GTTVTVSS
             ** *****
```

| FIG. 1D | SEQ ID NO: | | | | | | | |
|---|---|---|---|---|---|---|---|---|
| | VH | FR1 | CDR1 | FR2 | CDR2 | FR3 | CDR3 | FR4 |
| FS-21495 VH | 65 | 207 | 215 | 223 | 231 | 239 | 247 | 255 |
| PC-21497 VH | 66 | 208 | 216 | 224 | 232 | 240 | 248 | 256 |
| AJ-21508 VH | 67 | 209 | 217 | 225 | 233 | 241 | 249 | 257 |
| NM-21517 VH | 68 | 210 | 218 | 226 | 234 | 242 | 250 | 258 |
| TS-21522 VH | 69 | 211 | 219 | 227 | 235 | 243 | 251 | 259 |
| RY-21527 VH | 70 | 212 | 220 | 228 | 236 | 244 | 252 | 260 |
| PP-21528 VH | 71 | 213 | 221 | 229 | 237 | 245 | 253 | 261 |
| RD-21530 VH | 72 | 214 | 222 | 230 | 238 | 246 | 254 | 262 |

FIG. 1E – Anti-BCMA Binding Molecules

```
                                   FR1                    CDR1            FR2        CDR2
FS-21495_VL  EIVLTQSPATLSLSPGERATLSCRASQSVSR------YLAWYQQKPGQAPRLLIYDASNR
PC-21497_VL  DIVMTQSPLSLPVTPGEPASISCRSSQSLLHSNG-YNYLDWYLQKPGQSPQLLIYLGSNR
AJ-21508_VL  EIVMTQSPATLSVSPGERATLSCRASQSVSS------NLAWYQQKPGQAPRLLIYGASTR
NM-21517_VL  EIVLTQSPATLSLSPGERATLSCRASQSVSS------YLAWYQQKPGQAPRLLIYDASNR
TS-21522_VL  EIVLTQSPATLSLSPGERATLSCRASQSVSR------YLAWYQQKPGQAPRLLIYDASNR
RY-21527_VL  DIQLTQSPSSVSASVGDRVTITCRASQGISS------WLAWYQQKPGKAPKLLIYGASSL
PP-21528_VL  DIVMTQSPDSLAVSLGERATINCKSSQSVLYSSNNKNYLAWYQQKPGQPPKLLIYWASTR
RD-21530_VL  EIVMTQSPATLSVSPGERATLSCRASQSVSS------NLAWYQQKPGQAPRLLIYSASTR
             :* :**** ::. : *: .::.*::**.:            * ** ****:.*:**** .*.

           CDR2                FR3                  CDR3      FR4
FS-21495_VL  ATGIPARFSGSGSGTDFTLTISSLEPEDFAVYYCQQRISWPFTFGGGTKVEIK
PC-21497_VL  ASGVPDRFSGSGSGTDFTLKISRVEAEDVGVYYCMQGLGLPLTFGGGTKVEIK
AJ-21508_VL  ATGIPARFSGSGSGTEFTLTISSLQSEDFAVYYCQQYAAYP-TFGGGTKVEIK
NM-21517_VL  ATGIPARFSGSGSGTDFTLTISSLEPEDFAVYYCQQPHVWPPTFGGGTKVEIK
TS-21522_VL  ATGIPARFSGSGSGTDFTLTISSLEPEDFAVYYCQQRFYYPWTFGGGTKVEIK
RY-21527_VL  QSGVPSRFSGSGSGTDFTLTISSLQPEDFATYYCQQIYTFPFTFGGGTKVEIK
PP-21528_VL  ESGVPDRFSGSGSGTDFTLTISSLQAEDVAVYYCQQFAHTPFTFGGGTKVEIK
RD-21530_VL  ATGIPARFSGSGSGTEFTLTISSLQSEDFAVYYCQQHHVWPLTFGGGTKVEIK
              :*:* **********:****.** ::.**...*** *     * ***********
```

| FIG. 1F | SEQ ID NO: | | | | | | | |
|---|---|---|---|---|---|---|---|---|
| | VL | FR1 | CDR1 | FR2 | CDR2 | FR3 | CDR3 | FR4 |
| FS-21495 VL | 137 | 73 | 81 | 89 | 97 | 105 | 113 | 121 |
| PC-21497 VL | 138 | 74 | 82 | 90 | 98 | 106 | 114 | 122 |
| AJ-21508 VL | 139 | 75 | 83 | 91 | 99 | 107 | 115 | 123 |
| NM-21517 VL | 140 | 76 | 84 | 92 | 100 | 108 | 116 | 124 |
| TS-21522 VL | 141 | 77 | 85 | 93 | 101 | 109 | 117 | 125 |
| RY-21527 VL | 142 | 78 | 86 | 94 | 102 | 110 | 118 | 126 |
| PP-21528 VL | 143 | 79 | 87 | 95 | 103 | 111 | 119 | 127 |
| RD-21530 VL | 144 | 80 | 88 | 96 | 104 | 112 | 120 | 128 |

FIG. 2A – Gene Expression in Multiple Myeloma Cells
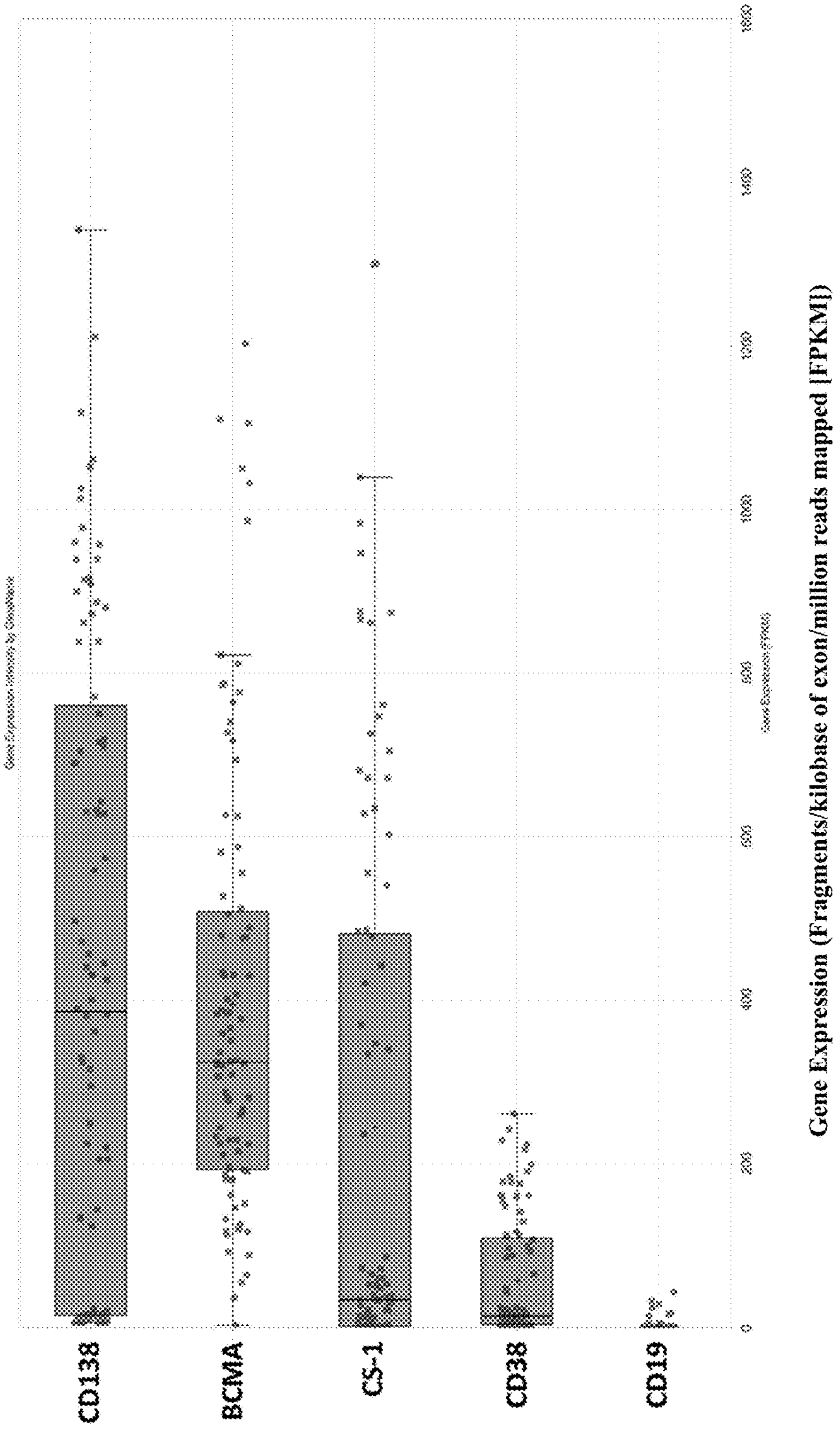

FIG. 2E – Gene Expression in Normal Immune Cells
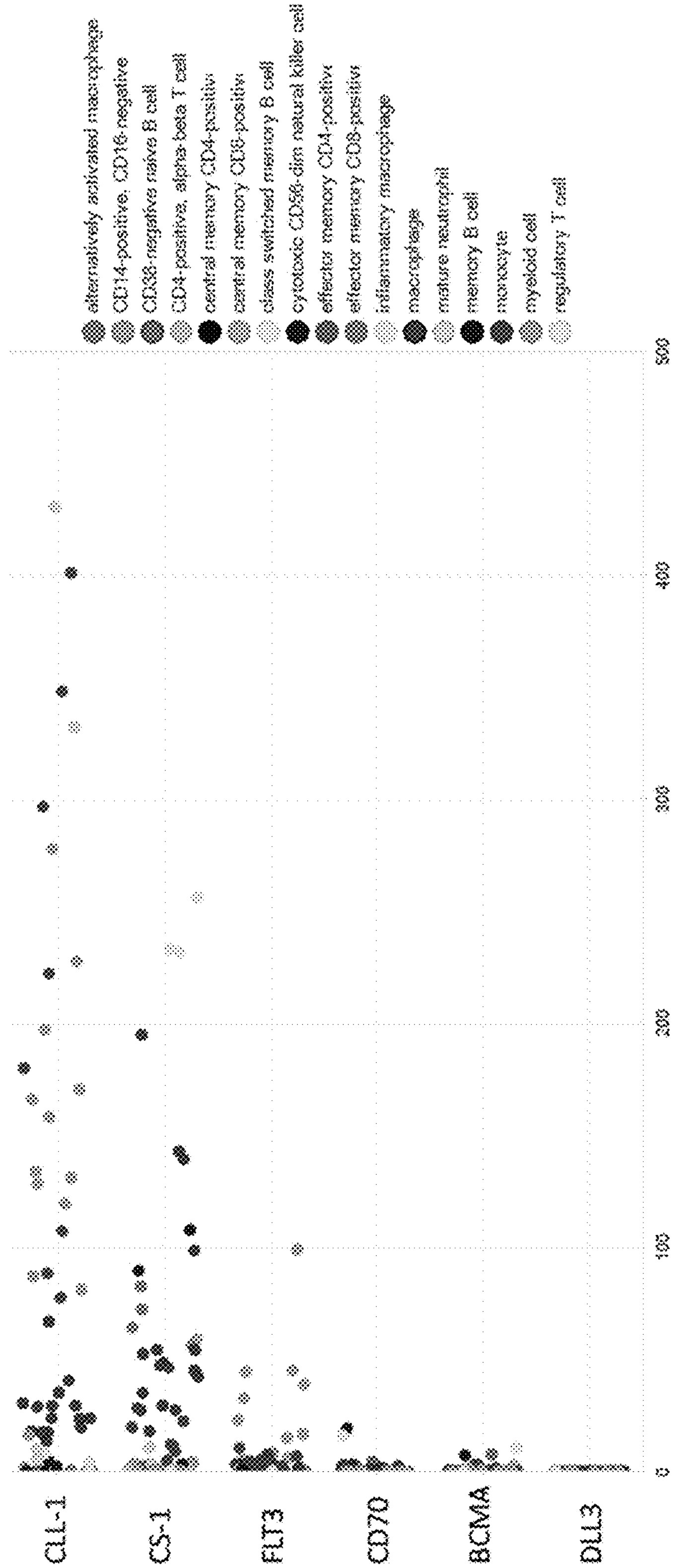
Gene Expression (Fragments/kilobase of exon/million reads mapped [FPKM])

FIG. 2F – Gene Expression in Normal Immune Cells
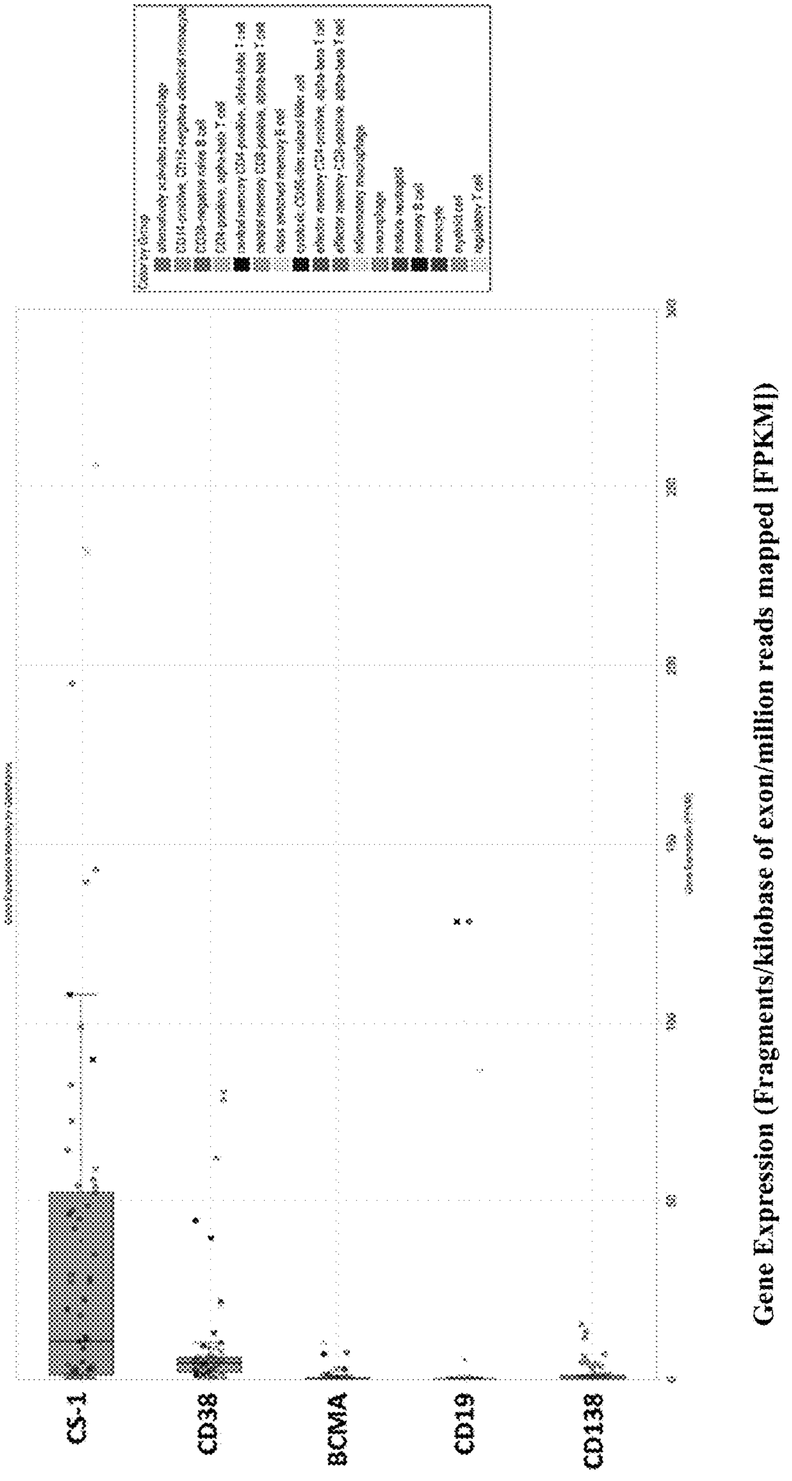

IR = Irrelevant CAR (Negative Control)
BM = Positive Control

Donor 1

Donor 2

FIG. 6A
FIG. 6B
Mock
IR
RD-21530
AJ-21508
PP-21528
TS-21522
FS-21495
PC-21497
NM-21517
RY-21527
BM1
BM2
CD3/CD28 beads
Eol-1
NCI-H929
MM1S
CFSE
Unstimulated T cells
T cells + indicated stimulus

FIG. 7A

Clone FS-26528 HC DNA (SEQ ID NO: 271)

GAGGTGCAGCTGTTGGAGTCTGGGGGAGGCTTGGTACAGCCTGGGGGGTCCCTGAGACTCTCC
TGTGCAGCCTCTGGATTCACCTTTGACGACTATGCCATGGCATGGGTCCGCCAGGCTCCAGGG
AAGGGGCTGGAGTGGGTCTCAGCTATTAGTGATGCAGGTGACAGAACATACTACGCAGACTCC
GTGAGGGGCCGGTTCACCATCTCCAGAGACAATTCCAAGAACACACTGTATCTGCAAATGAAC
AGCCTGAGAGCCGAGGACACGGCGGTGTACTACTGCGCAAGAGCCGAGATGGGAGCCGTATTC
GACATATGGGGTCAGGGTACAATGGTCACCGTCTCCTCA

FIG. 7B

Clone FS-26528 HC (SEQ ID NO: 272). CDRs 1, 2, and 3 are underlined.

EVQLLESGGG LVQPGGSLRL SCAASGFTFD DYAMAWVRQA PGKGLEWVSA
ISDAGDRTYY ADSVRGRFTI SRDNSKNTLY LQMNSLRAED TAVYYCARAE
MGAVFDIWGQ GTMVTVSS

FIG. 7C

SCAASGFTFDDYAMA (SEQ ID NO: 273) [HC CDR1]

AISDAGDRTYYADSVRG (SEQ ID NO: 274) [HC CDR2]

ARAEMGAVFDI (SEQ ID NO: 275) [HC CDR3]

FIG. 7D

Clone FS-26528 LC DNA (SEQ ID NO: 276)

GAAATTGTGTTGACACAGTCTCCAGCCACCCTGTCTTTGTCTCCAGGGGAAAGAGCCACCCTC
TCCTGCAGGGCCAGTCAGAGTGTTAGCAGGTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGAATCTCCTGGCCTTTCACTTTTGGCGGAGGGACCAAGGTTGAG
ATCAAACGG

FIG. 7E

Clone FS-26528 LC (SEQ ID NO: 277). CDRs 1, 2, and 3 are underlined.

EIVLTQSPAT LSLSPGERAT LSCRASQSVS RYLAWYQQKP GQAPRLLIYD
ASNRATGIPA RFSGSGSGTD FTLTISSLEP EDFAVYYCQQ RISWPFTFGG GTKVEIKR

FIG. 7F

RASQSVSRYLA (SEQ ID NO: 278) [LC CDR1]

DASNRAT (SEQ ID NO: 279) [LC CDR2]

QQRISWPFT (SEQ ID NO: 280) [LC CDR3]

FIG. 7G

Clone FS-26528 CAR DNA HxL (SEQ ID NO: 281)

ATGGCACTCCCCGTAACTGCTCTGCTGCTGCCGTTGGCATTGCTCCTGCACGCCGCACGCCCG
GAGGTGCAGCTGTTGGAGTCTGGGGGAGGCTTGGTACAGCCTGGGGGGTCCCTGAGACTCTCC
TGTGCAGCCTCTGGATTCACCTTTGACGACTATGCCATGGCATGGGTCCGCCAGGCTCCAGGG
AAGGGGCTGGAGTGGGTCTCAGCTATTAGTGATGCAGGTGACAGAACATACTACGCAGACTCC
GTGAGGGGCCGGTTCACCATCTCCAGAGACAATTCCAAGAACACACTGTATCTGCAAATGAAC
AGCCTGAGAGCCGAGGACACGGCGGTGTACTACTGCGCAAGAGCCGAGATGGGAGCCGTATTC
GACATATGGGGTCAGGGTACAATGGTCACCGTCTCCTCAGGGTCTACATCCGGCTCCGGGAAG
CCCGGAAGTGGCGAAGGTAGTACAAAGGGGGAAATTGTGTTGACACAGTCTCCAGCCACCCTG
TCTTTGTCTCCAGGGGAAAGAGCCACCCTCTCCTGCAGGGCCAGTCAGAGTGTTAGCAGGTAC
TTAGCCTGGTACCAACAGAAACCTGGCCAGGCTCCCAGGCTCCTCATCTATGATGCATCCAAC
AGGGCCACTGGCATCCCAGCCAGGTTCAGTGGCAGTGGGTCTGGGACAGACTTCACTCTCACC
ATCAGCAGCCTAGAGCCTGAAGATTTTGCAGTTTATTACTGTCAGCAGAGAATCTCCTGGCCT
TTCACTTTTGGCGGAGGGACCAAGGTTGAGATCAAACGGGCCGCTGCCCTTGATAATGAAAAG
TCAAACGGAACAATCATTCACGTGAAGGGCAAGCACCTCTGTCCGTCACCCTTGTTCCCTGGT
CCATCCAAGCCATTCTGGGTGTTGGTCGTAGTGGGTGGAGTCCTCGCTTGTTACTCTCTGCTC
GTCACCGTGGCTTTTATAATCTTCTGGGTTAGATCCAAAAGAAGCCGCCTGCTCCATAGCGAT
TACATGAATATGACTCCACGCCGCCCTGGCCCCACAAGGAAACACTACCAGCCTTACGCACCA
CCTAGAGATTTCGCTGCCTATCGGAGCAGGGTGAAGTTTTCCAGATCTGCAGATGCACCAGCG
TATCAGCAGGGCCAGAACCAACTGTATAACGAGCTCAACCTGGGACGCAGGGAAGAGTATGAC
GTTTTGGACAAGCGCAGAGGACGGGACCCTGAGATGGGTGGCAAACCAAGACGAAAAAACCCC
CAGGAGGGTCTCTATAATGAGCTGCAGAAGGATAAGATGGCTGAAGCCTATTCTGAAATAGGC
ATGAAAGGAGAGCGGAGAAGGGGAAAAGGGCACGACGGTTTGTACCAGGGACTCAGCACTGCT
ACGAAGGATACTTATGACGCTCTCCACATGCAAGCCCTGCCACCTAGG

FIG. 7H

Clone FS-26528 CAR HxL (SEQ ID NO: 282)

MALPVTALLL PLALLLHAAR PEVQLLESGG GLVQPGGSLR LSCAASGFTF
DDYAMAWVRQ APGKGLEWVS AISDAGDRTY YADSVRGRFT ISRDNSKNTL
YLQMNSLRAE DTAVYYCARA EMGAVFDIWG QGTMVTVSSG STSGSGKPGS
GEGSTKGEIV LTQSPATLSL SPGERATLSC RASQSVSRYL AWYQQKPGQA
PRLLIYDASN RATGIPARFS GSGSGTDFTL TISSLEPEDF AVYYCQQRIS
WPFTFGGGTK VEIKRAAALD NEKSNGTIIH VKGKHLCPSP LFPGPSKPFW
VLVVVGGVLA CYSLLVTVAF IIFWVRSKRS RLLHSDYMNM TPRRPGPTRK
HYQPYAPPRD FAAYRSRVKF SRSADAPAYQ QGQNQLYNEL NLGRREEYDV
LDKRRGRDPE MGGKPRRKNP QEGLYNELQK DKMAEAYSEI GMKGERRRGK
GHDGLYQGLS TATKDTYDAL HMQALPPR

FIG. 7I

Clone FS-26528 CAR DNA LxH (SEQ ID NO: 283)

ATGGCACTCCCCGTAACTGCTCTGCTGCTGCCGTTGGCATTGCTCCTGCACGCCGCACGCCCG
GAAATTGTGTTGACACAGTCTCCAGCCACCCTGTCTTTGTCTCCAGGGGAAAGAGCCACCCTC
TCCTGCAGGGCCAGTCAGAGTGTTAGCAGGTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGAATCTCCTGGCCTTTCACTTTTGGCGGAGGGACCAAGGTTGAG
ATCAAACGGGGGTCTACATCCGGCTCCGGGAAGCCCGGAAGTGGCGAAGGTAGTACAAAGGGG
GAGGTGCAGCTGTTGGAGTCTGGGGGAGGCTTGGTACAGCCTGGGGGGTCCCTGAGACTCTCC
TGTGCAGCCTCTGGATTCACCTTTGACGACTATGCCATGGCATGGGTCCGCCAGGCTCCAGGG
AAGGGGCTGGAGTGGGTCTCAGCTATTAGTGATGCAGGTGACAGAACATACTACGCAGACTCC
GTGAGGGGCCGGTTCACCATCTCCAGAGACAATTCCAAGAACACACTGTATCTGCAAATGAAC
AGCCTGAGAGCCGAGGACACGGCGGTGTACTACTGCGCAAGAGCCGAGATGGGAGCCGTATTC
GACATATGGGGTCAGGGTACAATGGTCACCGTCTCCTCAGCCGCTGCCCTTGATAATGAAAAG
TCAAACGGAACAATCATTCACGTGAAGGGCAAGCACCTCTGTCCGTCACCCTTGTTCCCTGGT
CCATCCAAGCCATTCTGGGTGTTGGTCGTAGTGGGTGGAGTCCTCGCTTGTTACTCTCTGCTC
GTCACCGTGGCTTTTATAATCTTCTGGGTTAGATCCAAAAGAAGCCGCCTGCTCCATAGCGAT
TACATGAATATGACTCCACGCCGCCCTGGCCCCACAAGGAAACACTACCAGCCTTACGCACCA
CCTAGAGATTTCGCTGCCTATCGGAGCAGGGTGAAGTTTTCCAGATCTGCAGATGCACCAGCG
TATCAGCAGGGCCAGAACCAACTGTATAACGAGCTCAACCTGGGACGCAGGGAAGAGTATGAC
GTTTTGGACAAGCGCAGAGGACGGGACCCTGAGATGGGTGGCAAACCAAGACGAAAAAACCCC
CAGGAGGGTCTCTATAATGAGCTGCAGAAGGATAAGATGGCTGAAGCCTATTCTGAAATAGGC
ATGAAAGGAGAGCGGAGAAGGGGAAAAGGGCACGACGGTTTGTACCAGGGACTCAGCACTGCT
ACGAAGGATACTTATGACGCTCTCCACATGCAAGCCCTGCCACCTAGG

FIG. 7J

Clone FS-26528 CAR LxH (SEQ ID NO: 284)

MALPVTALLL PLALLLHAAR PEIVLTQSPA TLSLSPGERA TLSCRASQSV
SRYLAWYQQK PGQAPRLLIY DASNRATGIP ARFSGSGSGT DFTLTISSLE
PEDFAVYYCQ QRISWPFTFG GGTKVEIKRG STSGSGKPGS GEGSTKGEVQ
LLESGGGLVQ PGGSLRLSCA ASGFTFDDYA MAWVRQAPGK GLEWVSAISD
AGDRTYYADS VRGRFTISRD NSKNTLYLQM NSLRAEDTAV YYCARAEMGA
VFDIWGQGTM VTVSSAAALD NEKSNGTIIH VKGKHLCPSP LFPGPSKPFW
VLVVVGGVLA CYSLLVTVAF IIFWVRSKRS RLLHSDYMNM TPRRPGPTRK
HYQPYAPPRD FAAYRSRVKF SRSADAPAYQ QGQNQLYNEL NLGRREEYDV
LDKRRGRDPE MGGKPRRKNP QEGLYNELQK DKMAEAYSEI GMKGERRRGK
GHDGLYQGLS TATKDTYDAL HMQALPPR

FIG. 8A

Clone PC-26534 HC DNA (SEQ ID NO: 285)

CAGGTGCAGCTGGTGGAGTCTGGGGGAGGCGTGGTCCAGCCTGGGAGGTCCCTGAGACTCTCC
TGTGCAGCGTCTGGATTCACCTTCAGTGAGCATGGCATGCACTGGGTCCGCCAGGCTCCAGGC
AAGGGGCTGGAGTGGGTGGCAGCTATATCTTATGATGGAAGGAATAAACACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGCCAGAGACGGTACTTATCTAGGTGGT
CTCTGGTACTTCGACTTATGGGGGAGAGGTACCTTGGTCACCGTCTCCTCA

FIG. 8B

Clone PC-26534 HC (SEQ ID NO: 286). CDRs 1, 2, and 3 are underlined.

QVQLVESGGG VVQPGRSLRL SCAASGFTFS EHGMHWVRQA PGKGLEWVAA
ISYDGRNKHY ADSVKGRFTI SRDNSKNTLY LQMNSLRAED TAVYYCARDG
TYLGGLWYFD LWGRGTLVTV SS

FIG 8C

FTFSEHGMH (SEQ ID NO: 287) [HC CDR1]

AISYDGRNKHYADSVKG (SEQ ID NO: 288) [HC CDR2]

ARDGTYLGGLWYFDL (SEQ ID NO: 289) [HC CDR3]

FIG. 8D

Clone PC-26534 LC DNA (SEQ ID NO: 290)

GATATTGTGATGACTCAGTCTCCACTCTCCCTGCCCGTCACCCCTGGAGAGCCGGCCTCCATC
TCCTGCAGGTCTAGTCAGAGCCTCCTGCATAGTAATGGATACAACTATTTGGATTGGTACCTG
CAGAAGCCAGGGCAGTCTCCACAGCTCCTGATCTATTTGGGTTCTAATCGGGCCTCCGGGGTC
CCTGACAGGTTCAGTGGCAGTGGATCAGGCACAGATTTTACACTGAAAATCAGCAGAGTGGAG
GCTGAGGATGTTGGGGTTTATTACTGCATGCAGGGACTCGGCCTCCCTCTCACTTTTGGCGGA
GGGACCAAGGTTGAGATCAAACGG

FIG. 8E

Clone PC-26534 LC (SEQ ID NO: 291). CDRs 1, 2, and 3 are underlined.

DIVMTQSPLS LPVTPGEPAS ISCRSSQSLL HSNGYNYLDW YLQKPGQSPQ
LLIYLGSNRA SGVPDRFSGS GSGTDFTLKI SRVEAEDVGV YYCMQGLGLP
LTFGGGTKVE IKR

FIG. 8F

RSSQSLLHSNGYNYLD (SEQ ID NO: 292) [LC CDR1]

FIG. 8F(continued)

LGSNRAS (SEQ ID NO: 293) [LC CDR2]

MQGLGLPLT (SEQ ID NO: 294) [LC CDR3]

FIG. 8G

Clone PC-26534 CAR DNA HxL (SEQ ID NO: 295)

ATGGCACTCCCCGTAACTGCTCTGCTGCTGCCGTTGGCATTGCTCCTGCACGCCGCACGCCCG
CAGGTGCAGCTGGTGGAGTCTGGGGGAGGCGTGGTCCAGCCTGGGAGGTCCCTGAGACTCTCC
TGTGCAGCGTCTGGATTCACCTTCAGTGAGCATGGCATGCACTGGGTCCGCCAGGCTCCAGGC
AAGGGGCTGGAGTGGGTGGCAGCTATATCTTATGATGGAAGGAATAAACACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGCCAGAGACGGTACTTATCTAGGTGGT
CTCTGGTACTTCGACTTATGGGGGAGAGGTACCTTGGTCACCGTCTCCTCAGGGTCTACATCC
GGCTCCGGGAAGCCCGGAAGTGGCGAAGGTAGTACAAAGGGGGATATTGTGATGACTCAGTCT
CCACTCTCCCTGCCCGTCACCCCTGGAGAGCCGGCCTCCATCTCCTGCAGGTCTAGTCAGAGC
CTCCTGCATAGTAATGGATACAACTATTTGGATTGGTACCTGCAGAAGCCAGGGCAGTCTCCA
CAGCTCCTGATCTATTTGGGTTCTAATCGGGCCTCCGGGGTCCCTGACAGGTTCAGTGGCAGT
GGATCAGGCACAGATTTTACACTGAAAATCAGCAGAGTGGAGGCTGAGGATGTTGGGGTTTAT
TACTGCATGCAGGGACTCGGCCTCCCTCTCACTTTTGGCGGAGGGACCAAGGTTGAGATCAAA
CGGGCCGCTGCCCTTGATAATGAAAAGTCAAACGGAACAATCATTCACGTGAAGGGCAAGCAC
CTCTGTCCGTCACCCTTGTTCCCTGGTCCATCCAAGCCATTCTGGGTGTTGGTCGTAGTGGGT
GGAGTCCTCGCTTGTTACTCTCTGCTCGTCACCGTGGCTTTTATAATCTTCTGGGTTAGATCC
AAAAGAAGCCGCCTGCTCCATAGCGATTACATGAATATGACTCCACGCCGCCCTGGCCCCACA
AGGAAACACTACCAGCCTTACGCACCACCTAGAGATTTCGCTGCCTATCGGAGCAGGGTGAAG
TTTTCCAGATCTGCAGATGCACCAGCGTATCAGCAGGGCCAGAACCAACTGTATAACGAGCTC
AACCTGGGACGCAGGGAAGAGTATGACGTTTTGGACAAGCGCAGAGGACGGGACCCTGAGATG
GGTGGCAAACCAAGACGAAAAAACCCCCAGGAGGGTCTCTATAATGAGCTGCAGAAGGATAAG
ATGGCTGAAGCCTATTCTGAAATAGGCATGAAAGGAGAGCGGAGAAGGGGAAAAGGGCACGAC
GGTTTGTACCAGGGACTCAGCACTGCTACGAAGGATACTTATGACGCTCTCCACATGCAAGCC
CTGCCACCTAGG

FIG. 8H

Clone PC-26534 CAR HxL (SEQ ID NO: 296)

MALPVTALLL PLALLLHAAR PQVQLVESGG GVVQPGRSLR LSCAASGFTF
SEHGMHWVRQ APGKGLEWVA AISYDGRNKH YADSVKGRFT ISRDNSKNTL
YLQMNSLRAE DTAVYYCARD GTYLGGLWYF DLWGRGTLVT VSSGSTSGSG
KPGSGEGSTK GDIVMTQSPL SLPVTPGEPA SISCRSSQSL LHSNGYNYLD
WYLQKPGQSP QLLIYLGSNR ASGVPDRFSG SGSGTDFTLK ISRVEAEDVG
VYYCMQGLGL PLTFGGGTKV EIKRAAALDN EKSNGTIIHV KGKHLCPSPL
FPGPSKPFWV LVVVGGVLAC YSLLVTVAFI IFWVRSKRSR LLHSDYMNMT
PRRPGPTRKH YQPYAPPRDF AAYRSRVKFS RSADAPAYQQ GQNQLYNELN
LGRREEYDVL DKRRGRDPEM GGKPRRKNPQ EGLYNELQKD KMAEAYSEIG
MKGERRRGKG HDGLYQGLST ATKDTYDALH MQALPPR

FIG. 8I

Clone PC-26534 CAR DNA LxH (SEQ ID NO: 297)

ATGGCACTCCCCGTAACTGCTCTGCTGCTGCCGTTGGCATTGCTCCTGCACGCCGCACGCCCG
GATATTGTGATGACTCAGTCTCCACTCTCCCTGCCCGTCACCCCTGGAGAGCCGGCCTCCATC
TCCTGCAGGTCTAGTCAGAGCCTCCTGCATAGTAATGGATACAACTATTTGGATTGGTACCTG
CAGAAGCCAGGGCAGTCTCCACAGCTCCTGATCTATTTGGGTTCTAATCGGGCCTCCGGGGTC
CCTGACAGGTTCAGTGGCAGTGGATCAGGCACAGATTTTACACTGAAAATCAGCAGAGTGGAG
GCTGAGGATGTTGGGGTTTATTACTGCATGCAGGGACTCGGCCTCCCTCTCACTTTTGGCGGA
GGGACCAAGGTTGAGATCAAACGGGGGTCTACATCCGGCTCCGGGAAGCCCGGAAGTGGCGAA
GGTAGTACAAAGGGGCAGGTGCAGCTGGTGGAGTCTGGGGGAGGCGTGGTCCAGCCTGGGAGG
TCCCTGAGACTCTCCTGTGCAGCGTCTGGATTCACCTTCAGTGAGCATGGCATGCACTGGGTC
CGCCAGGCTCCAGGCAAGGGGCTGGAGTGGGTGGCAGCTATATCTTATGATGGAAGGAATAAA
CACTATGCAGACTCCGTGAAGGGCCGATTCACCATCTCCAGAGACAATTCCAAGAACACGCTG
TATCTGCAAATGAACAGCCTGAGAGCCGAGGACACGGCGGTGTACTACTGCGCCAGAGACGGT
ACTTATCTAGGTGGTCTCTGGTACTTCGACTTATGGGGGAGAGGTACCTTGGTCACCGTCTCC
TCAGCCGCTGCCCTTGATAATGAAAAGTCAAACGGAACAATCATTCACGTGAAGGGCAAGCAC
CTCTGTCCGTCACCCTTGTTCCCTGGTCCATCCAAGCCATTCTGGGTGTTGGTCGTAGTGGGT
GGAGTCCTCGCTTGTTACTCTCTGCTCGTCACCGTGGCTTTTATAATCTTCTGGGTTAGATCC
AAAAGAAGCCGCCTGCTCCATAGCGATTACATGAATATGACTCCACGCCGCCCTGGCCCCACA
AGGAAACACTACCAGCCTTACGCACCACCTAGAGATTTCGCTGCCTATCGGAGCAGGGTGAAG
TTTTCCAGATCTGCAGATGCACCAGCGTATCAGCAGGGCCAGAACCAACTGTATAACGAGCTC
AACCTGGGACGCAGGGAAGAGTATGACGTTTTGGACAAGCGCAGAGGACGGGACCCTGAGATG
GGTGGCAAACCAAGACGAAAAAACCCCCAGGAGGGTCTCTATAATGAGCTGCAGAAGGATAAG
ATGGCTGAAGCCTATTCTGAAATAGGCATGAAAGGAGAGCGGAGAAGGGGAAAAGGGCACGAC
GGTTTGTACCAGGGACTCAGCACTGCTACGAAGGATACTTATGACGCTCTCCACATGCAAGCC
CTGCCACCTAGG

FIG. 8J

Clone PC-26534 CAR LxH (SEQ ID NO: 298)

MALPVTALLL PLALLLHAAR PDIVMTQSPL SLPVTPGEPA SISCRSSQSL
LHSNGYNYLD WYLQKPGQSP QLLIYLGSNR ASGVPDRFSG SGSGTDFTLK
ISRVEAEDVG VYYCMQGLGL PLTFGGGTKV EIKRGSTSGS GKPGSGEGST
KGQVQLVESG GGVVQPGRSL RLSCAASGFT FSEHGMHWVR QAPGKGLEWV
AAISYDGRNK HYADSVKGRF TISRDNSKNT LYLQMNSLRA EDTAVYYCAR
DGTYLGGLWY FDLWGRGTLV TVSSAAALDN EKSNGTIIHV KGKHLCPSPL
FPGPSKPFWV LVVVGGVLAC YSLLVTVAFI IFWVRSKRSR LLHSDYMNMT
PRRPGPTRKH YQPYAPPRDF AAYRSRVKFS RSADAPAYQQ GQNQLYNELN
LGRREEYDVL DKRRGRDPEM GGKPRRKNPQ EGLYNELQKD KMAEAYSEIG
MKGERRRGKG HDGLYQGLST ATKDTYDALH MQALPPR

FIG. 9A

Clone AJ-26545 HC DNA (SEQ ID NO: 299)

CAGGTGCAGCTGGTGCAGTCTGGGGCTGAGGTGAAGAAGCCTGGGGCCTCAGTGAAGGTTTCC
TGCAGGGCATCTGGATACACCTTCATGGAGCACTATATGCACTGGGTGCGACAGGCCCCTGGA
CAAGGGCTTGAGTGGATGGGAGTAATCGGGCCTAGTGGTGGTAAGACAAGCTACGCACAGAAG
TTCCAGGGCAGAGTCACCATGACCAGGGACACGTCCACGAGCACAGTCTACATGGAGCTGAGC
AGCCTGAGATCTGAGGACACGGCGGTGTACTACTGCGCCAGAGAGAATTGGCCAATGGACGTA
TGGGGCCAGGGAACAACTGTCACCGTCTCCTCA

FIG. 9B

Clone AJ-26545 HC (SEQ ID NO: 300). CDRs 1, 2, and 3 are underlined.

QVQLVQSGAE VKKPGASVKV SCRASGYTFM EHYMHWVRQA PGQGLEWMGV
IGPSGGKTSY AQKFQGRVTM TRDTSTSTVY MELSSLRSED TAVYYCARES
WPMDVWGQGT TVTVSS

FIG. 9C

YTFMEHYMH (SEQ ID NO: 301) (HC CDR1)

VIGPSGGKTSYAQKFQG (SEQ ID NO: 302) (HC CDR2)

ARESWPMDV (SEQ ID NO: 303) (HC CDR3)

FIG. 9D

Clone AJ-26545 LC DNA (SEQ ID NO: 304)

GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATGGTGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGTACGCCGCCTACCCTACTTTTGGCGGAGGGACCAAGGTTGAGATC
AAACGG

FIG. 9E

Clone AJ-26545 LC (SEQ ID NO: 305). CDRs 1, 2, and 3 are underlined.

EIVMTQSPAT LSVSPGERAT LSCRASQSVS SNLAWYQQKP GQAPRLLIYG
ASTRATGIPA RFSGSGSGTE FTLTISSLQS EDFAVYYCQQ YAAYPTFGGG TKVEIKR

FIG. 9F

RASQSVSSNLA (SEQ ID NO: 306) (LC CDR1)

GASTRAT (SEQ ID NO: 307) (LC CDR2)

QQYAAYPT (SEQ ID NO: 308) (LC CDR3)

FIG. 9G

Clone AJ-26545 CAR DNA HxL (SEQ ID NO: 309)

ATGGCACTCCCCGTAACTGCTCTGCTGCTGCCGTTGGCATTGCTCCTGCACGCCGCACGCCCG
CAGGTGCAGCTGGTGCAGTCTGGGGCTGAGGTGAAGAAGCCTGGGGCCTCAGTGAAGGTTTCC
TGCAGGGCATCTGGATACACCTTCATGGAGCACTATATGCACTGGGTGCGACAGGCCCCTGGA
CAAGGGCTTGAGTGGATGGGAGTAATCGGGCCTAGTGGTGGTAAGACAAGCTACGCACAGAAG
TTCCAGGGCAGAGTCACCATGACCAGGGACACGTCCACGAGCACAGTCTACATGGAGCTGAGC
AGCCTGAGATCTGAGGACACGGCGGTGTACTACTGCGCCAGAGAGAATTGGCCAATGGACGTA
TGGGGCCAGGGAACAACTGTCACCGTCTCCTCAGGGTCTACATCCGGCTCCGGGAAGCCCGGA
AGTGGCGAAGGTAGTACAAAGGGGGAAATAGTGATGACGCAGTCTCCAGCCACCCTGTCTGTG
TCTCCAGGGGAAAGAGCCACCCTCTCCTGCAGGGCCAGTCAGAGTGTTAGCAGCAACTTAGCC
TGGTACCAGCAGAAACCTGGCCAGGCTCCCAGGCTCCTCATCTATGGTGCATCCACCAGGGCC
ACTGGTATCCCAGCCAGGTTCAGTGGCAGTGGGTCTGGGACAGAGTTCACTCTCACCATCAGC
AGCCTGCAGTCTGAAGATTTTGCAGTTTATTACTGTCAGCAGTACGCCGCCTACCCTACTTTT
GGCGGAGGGACCAAGGTTGAGATCAAACGGGCCGCTGCCCTTGATAATGAAAAGTCAAACGGA
ACAATCATTCACGTGAAGGGCAAGCACCTCTGTCCGTCACCCTTGTTCCCTGGTCCATCCAAG
CCATTCTGGGTGTTGGTCGTAGTGGGTGGAGTCCTCGCTTGTTACTCTCTGCTCGTCACCGTG
GCTTTTATAATCTTCTGGGTTAGATCCAAAAGAAGCCGCCTGCTCCATAGCGATTACATGAAT
ATGACTCCACGCCGCCCTGGCCCCACAAGGAAACACTACCAGCCTTACGCACCACCTAGAGAT
TTCGCTGCCTATCGGAGCAGGGTGAAGTTTTCCAGATCTGCAGATGCACCAGCGTATCAGCAG
GGCCAGAACCAACTGTATAACGAGCTCAACCTGGGACGCAGGGAAGAGTATGACGTTTTGGAC
AAGCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAGGA
GAGCGGAGAAGGGGAAAAGGGCACGACGGTTTGTACCAGGGACTCAGCACTGCTACGAAGGAT
ACTTATGACGCTCTCCACATGCAAGCCCTGCCACCTAGG

FIG. 9H

Clone AJ-26545 CAR HxL (SEQ ID NO: 310)

MALPVTALLL PLALLLHAAR PQVQLVQSGA EVKKPGASVK VSCRASGYTF
MEHYMHWVRQ APGQGLEWMG VIGPSGGKTS YAQKFQGRVT MTRDTSTSTV
YMELSSLRSE DTAVYYCARE SWPMDVWGQG TTVTVSSGST SGSGKPGSGE
GSTKGEIVMT QSPATLSVSP GERATLSCRA SQSVSSNLAW YQQKPGQAPR
LLIYGASTRA TGIPARFSGS GSGTEFTLTI SSLQSEDFAV YYCQQYAAYP
TFGGGTKVEI KRAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

FIG. 9I

Clone AJ-26545 CAR DNA LxH (SEQ ID NO: 311)

ATGGCACTCCCCGTAACTGCTCTGCTGCTGCCGTTGGCATTGCTCCTGCACGCCGCACGCCCG
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATGGTGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGTACGCCGCCTACCCTACTTTTGGCGGAGGGACCAAGGTTGAGATC
AAACGGGGGTCTACATCCGGCTCCGGGAAGCCCGGAAGTGGCGAAGGTAGTACAAAGGGGCAG
GTGCAGCTGGTGCAGTCTGGGGCTGAGGTGAAGAAGCCTGGGGCCTCAGTGAAGGTTTCCTGC
AGGGCATCTGGATACACCTTCATGGAGCACTATATGCACTGGGTGCGACAGGCCCCTGGACAA
GGGCTTGAGTGGATGGGAGTAATCGGGCCTAGTGGTGGTAAGACAAGCTACGCACAGAAGTTC
CAGGGCAGAGTCACCATGACCAGGGACACGTCCACGAGCACAGTCTACATGGAGCTGAGCAGC
CTGAGATCTGAGGACACGGCGGTGTACTACTGCGCCAGAGAGAATTGGCCAATGGACGTATGG
GGCCAGGGAACAACTGTCACCGTCTCCTCAGCCGCTGCCCTTGATAATGAAAAGTCAAACGGA
ACAATCATTCACGTGAAGGGCAAGCACCTCTGTCCGTCACCCTTGTTCCCTGGTCCATCCAAG
CCATTCTGGGTGTTGGTCGTAGTGGGTGGAGTCCTCGCTTGTTACTCTCTGCTCGTCACCGTG
GCTTTTATAATCTTCTGGGTTAGATCCAAAAGAAGCCGCCTGCTCCATAGCGATTACATGAAT
ATGACTCCACGCCGCCCTGGCCCCACAAGGAAACACTACCAGCCTTACGCACCACCTAGAGAT
TTCGCTGCCTATCGGAGCAGGGTGAAGTTTTCCAGATCTGCAGATGCACCAGCGTATCAGCAG
GGCCAGAACCAACTGTATAACGAGCTCAACCTGGGACGCAGGGAAGAGTATGACGTTTTGGAC
AAGCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAGGA
GAGCGGAGAAGGGGAAAAGGGCACGACGGTTTGTACCAGGGACTCAGCACTGCTACGAAGGAT
ACTTATGACGCTCTCCACATGCAAGCCCTGCCACCTAGG

FIG. 9J

Clone AJ-26545 CAR LxH (SEQ ID NO: 312)

MALPVTALLL PLALLLHAAR PEIVMTQSPA TLSVSPGERA TLSCRASQSV
SSNLAWYQQK PGQAPRLLIY GASTRATGIP ARFSGSGSGT EFTLTISSLQ
SEDFAVYYCQ QYAAYPTFGG GTKVEIKRGS TSGSGKPGSG EGSTKGQVQL
VQSGAEVKKP GASVKVSCRA SGYTFMEHYM HWVRQAPGQG LEWMGVIGPS
GGKTSYAQKF QGRVTMTRDT STSTVYMELS SLRSEDTAVY YCARESWPMD
VWGQGTTVTV SSAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

FIG. 10A

Clone AJ-26554 HC DNA (SEQ ID NO: 313)
CAGGTGCAGCTGGTGCAGTCTGGGGCTGAGGTGAAGAAGCCTGGGGCCTCAGTGAAGGTTTCC
TGCAAGGCATCTGGATACACCTTCACGGAGCACTATATGCACTGGGTGCGACAGGCCCCTGGA
CAAAGGCTTGAGTGGATGGGAGTAATCGGGCCTAGTGGTGGTAAGACAAGCTACGCACAGAAG
TTCCAGGGCAGAGTCACCATGACCAGGGACACGTCCACGAGCACAGTCTACATGGAGCTGAGC
AGCCTGAGATCTGAGGACACGGCGGTGTACTACTGCGCCAGAGAGAGTTGGCCAATGGACGTA
TGGGGCCAGGGAACAACTGTCACCGTCTCCTCA

FIG. 10B

Clone AJ-26554 HC (SEQ ID NO: 314). CDRs 1, 2, and 3 are underlined.
QVQLVQSGAE VKKPGASVKV SCKASG<u>YTFT</u> <u>EHYMH</u>WVRQA PGQRLEWMG<u>V</u>
<u>IGPSGGKTSY</u> <u>AQKFQG</u>RVTM TRDTSTSTVY MELSSLRSED TAVYYC<u>ARES</u>
<u>WPMDV</u>WGQGT TVTVSS

FIG. 10C

YTFTEHYMH (SEQ ID NO: 315) (HC CDR1)

VIGPSGGKTSYAQKFQG (SEQ ID NO: 316) (HC CDR2)

ARESWPMDV (SEQ ID NO: 317) (HC CDR3)

FIG. 10D

Clone AJ-26554 LC DNA (SEQ ID NO: 318)
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATGGTGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGTACGCCGCCTACCCTACTTTTGGCGGAGGGACCAAGGTTGAGATC
AAACGG

FIG. 10E

Clone AJ-26554 LC (SEQ ID NO: 319). CDRs 1, 2, and 3 are underlined.
EIVMTQSPAT LSVSPGERAT LSC<u>RASQSVS</u> <u>SNLA</u>WYQQKP GQAPRLLIY<u>G</u>
<u>ASTRAT</u>GIPA RFSGSGSGTE FTLTISSLQS EDFAVYYC<u>QQ</u> <u>YAAYPT</u>FGGG TKVEIKR

FIG. 10F

RASQSVSSNLA (SEQ ID NO: 320) (LC CDR1)

FIG. 10F (continued)

GASTRAT (SEQ ID NO: 321) (LC CDR2)

QQYAAYPT (SEQ ID NO: 322) (LC CDR3)

FIG. 10G

Clone AJ-26554 CAR DNA HxL (SEQ ID NO: 323)

ATGGCACTCCCCGTAACTGCTCTGCTGCTGCCGTTGGCATTGCTCCTGCACGCCGCACGCCCG
CAGGTGCAGCTGGTGCAGTCTGGGGCTGAGGTGAAGAAGCCTGGGGCCTCAGTGAAGGTTTCC
TGCAAGGCATCTGGATACACCTTCACGGAGCACTATATGCACTGGGTGCGACAGGCCCCTGGA
CAAAGGCTTGAGTGGATGGGAGTAATCGGGCCTAGTGGTGGTAAGACAAGCTACGCACAGAAG
TTCCAGGGCAGAGTCACCATGACCAGGGACACGTCCACGAGCACAGTCTACATGGAGCTGAGC
AGCCTGAGATCTGAGGACACGGCGGTGTACTACTGCGCCAGAGAGAGTTGGCCAATGGACGTA
TGGGGCCAGGGAACAACTGTCACCGTCTCCTCAGGGTCTACATCCGGCTCCGGGAAGCCCGGA
AGTGGCGAAGGTAGTACAAAGGGGGAAATAGTGATGACGCAGTCTCCAGCCACCCTGTCTGTG
TCTCCAGGGGAAAGAGCCACCCTCTCCTGCAGGGCCAGTCAGAGTGTTAGCAGCAACTTAGCC
TGGTACCAGCAGAAACCTGGCCAGGCTCCCAGGCTCCTCATCTATGGTGCATCCACCAGGGCC
ACTGGTATCCCAGCCAGGTTCAGTGGCAGTGGGTCTGGGACAGAGTTCACTCTCACCATCAGC
AGCCTGCAGTCTGAAGATTTTGCAGTTTATTACTGTCAGCAGTACGCCGCCTACCCTACTTTT
GGCGGAGGGACCAAGGTTGAGATCAAACGGGCCGCTGCCCTTGATAATGAAAAGTCAAACGGA
ACAATCATTCACGTGAAGGGCAAGCACCTCTGTCCGTCACCCTTGTTCCCTGGTCCATCCAAG
CCATTCTGGGTGTTGGTCGTAGTGGGTGGAGTCCTCGCTTGTTACTCTCTGCTCGTCACCGTG
GCTTTTATAATCTTCTGGGTTAGATCCAAAAGAAGCCGCCTGCTCCATAGCGATTACATGAAT
ATGACTCCACGCCGCCCTGGCCCCACAAGGAAACACTACCAGCCTTACGCACCACCTAGAGAT
TTCGCTGCCTATCGGAGCAGGGTGAAGTTTTCCAGATCTGCAGATGCACCAGCGTATCAGCAG
GGCCAGAACCAACTGTATAACGAGCTCAACCTGGGACGCAGGGAAGAGTATGACGTTTTGGAC
AAGCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAGGA
GAGCGGAGAAGGGGAAAAGGGCACGACGGTTTGTACCAGGGACTCAGCACTGCTACGAAGGAT
ACTTATGACGCTCTCCACATGCAAGCCCTGCCACCTAGG

FIG. 10H

Clone AJ-26554 CAR HxL (SEQ ID NO: 324)

MALPVTALLL PLALLLHAAR PQVQLVQSGA EVKKPGASVK VSCKASGYTF
TEHYMHWVRQ APGQRLEWMG VIGPSGGKTS YAQKFQGRVT MTRDTSTSTV
YMELSSLRSE DTAVYYCARE SWPMDVWGQG TTVTVSSGST SGSGKPGSGE
GSTKGEIVMT QSPATLSVSP GERATLSCRA SQSVSSNLAW YQQKPGQAPR
LLIYGASTRA TGIPARFSGS GSGTEFTLTI SSLQSEDFAV YYCQQYAAYP
TFGGGTKVEI KRAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

FIG. 10I

Clone AJ-26554 CAR DNA LxH (SEQ ID NO: 325)

ATGGCACTCCCCGTAACTGCTCTGCTGCTGCCGTTGGCATTGCTCCTGCACGCCGCACGCCCG
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATGGTGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGTACGCCGCCTACCCTACTTTTGGCGGAGGGACCAAGGTTGAGATC
AAACGGGGGTCTACATCCGGCTCCGGGAAGCCCGGAAGTGGCGAAGGTAGTACAAAGGGGCAG
GTGCAGCTGGTGCAGTCTGGGGCTGAGGTGAAGAAGCCTGGGGCCTCAGTGAAGGTTTCCTGC
AAGGCATCTGGATACACCTTCACGGAGCACTATATGCACTGGGTGCGACAGGCCCCTGGACAA
AGGCTTGAGTGGATGGGAGTAATCGGGCCTAGTGGTGGTAAGACAAGCTACGCACAGAAGTTC
CAGGGCAGAGTCACCATGACCAGGGACACGTCCACGAGCACAGTCTACATGGAGCTGAGCAGC
CTGAGATCTGAGGACACGGCGGTGTACTACTGCGCCAGAGAGAGTTGGCCAATGGACGTATGG
GGCCAGGGAACAACTGTCACCGTCTCCTCAGCCGCTGCCCTTGATAATGAAAAGTCAAACGGA
ACAATCATTCACGTGAAGGGCAAGCACCTCTGTCCGTCACCCTTGTTCCCTGGTCCATCCAAG
CCATTCTGGGTGTTGGTCGTAGTGGGTGGAGTCCTCGCTTGTTACTCTCTGCTCGTCACCGTG
GCTTTTATAATCTTCTGGGTTAGATCCAAAAGAAGCCGCCTGCTCCATAGCGATTACATGAAT
ATGACTCCACGCCGCCCTGGCCCCACAAGGAAACACTACCAGCCTTACGCACCACCTAGAGAT
TTCGCTGCCTATCGGAGCAGGGTGAAGTTTTCCAGATCTGCAGATGCACCAGCGTATCAGCAG
GGCCAGAACCAACTGTATAACGAGCTCAACCTGGGACGCAGGGAAGAGTATGACGTTTTGGAC
AAGCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAGGA
GAGCGGAGAAGGGGAAAAGGGCACGACGGTTTGTACCAGGGACTCAGCACTGCTACGAAGGAT
ACTTATGACGCTCTCCACATGCAAGCCCTGCCACCTAGG

FIG. 10J

Clone AJ-26554 CAR LxH (SEQ ID NO: 326)

MALPVTALLL PLALLLHAAR PEIVMTQSPA TLSVSPGERA TLSCRASQSV
SSNLAWYQQK PGQAPRLLIY GASTRATGIP ARFSGSGSGT EFTLTISSLQ
SEDFAVYYCQ QYAAYPTFGG GTKVEIKRGS TSGSGKPGSG EGSTKGQVQL
VQSGAEVKKP GASVKVSCKA SGYTFTEHYM HWVRQAPGQR LEWMGVIGPS
GGKTSYAQKF QGRVTMTRDT STSTVYMELS SLRSEDTAVY YCARESWPMD
VWGQGTTVTV SSAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

FIG. 11A

Clone NM-26562 HC DNA (SEQ ID NO: 327)
CAGGTGCAGCTGCAGGAGTCGGGCCCAGGACTGGTGAAGCCTTCACAGACCCTGTCCCTCACC
TGTACTGTCTCTGGTGGCTCCATCGGGAGTGGTGGTAGTTACTGGAGCTGGATCCGCCAGCAC
CCAGGGAAGGGCCTGGAGTGGATTGGGTTGATCTATTACGATGGGAGCACCTACTACAACCCG
TCCCTCAAGAGTCGAGTTACCATATCAGTAGACACGTCTAAGAACCAGTTCTCCCTGAAGCTG
AGTTCTGTGACCGCCGCAGACACGGCGGTGTACTACTGCGCCAGAGGCAGGGGATATGAGACT
TCTTTAGCCTTCGATATCTGGGGTCAGGGTACAATGGTCACCGTCTCCTCA

FIG. 11B

Clone NM-26562 HC (SEQ ID NO: 328). CDRs 1, 2, and 3 are underlined.
QVQLQESGPG LVKPSQTLSL TCTVSGGSIG SGGSYWSWIR QHPGKGLEWI
GLIYYDGSTY YNPSLKSRVT ISVDTSKNQF SLKLSSVTAA DTAVYYCARG
RGYETSLAFD IWGQGTMVTV SS

FIG. 11C

GSIGSGGSYWS (SEQ ID NO: 329) (HC CDR1)

LIYYDGSTYYNPSLKS (SEQ ID NO: 330) (HC CDR2)

ARGRGYETSLAFDI (SEQ ID NO: 331) (HC CDR3)

FIG. 11D

Clone NM-26562 LC DNA (SEQ ID NO: 332)
GAAATTGTGTTGACACAGTCTCCAGCCACCCTGTCTTTGTCTCCAGGGGAAAGAGCCACCCTC
TCCTGCAGGGCCAGTCAGAGTGTTAGCAGCTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGACACGTCTGGCCTCCTACTTTTGGCGGAGGGACCAAGGTTGAG
ATCAAACGG

FIG. 11E

Clone NM-26562 LC (SEQ ID NO: 333). CDRs 1, 2, and 3 are underlined.
EIVLTQSPAT LSLSPGERAT LSCRASQSVS SYLAWYQQKP GQAPRLLIYD
ASNRATGIPA RFSGSGSGTD FTLTISSLEP EDFAVYYCQQ RHVWPPTFGG GTKVEIKR

FIG. 11F

RASQSVSSYLA (SEQ ID NO: 334) (LC CDR1)

DASNRAT (SEQ ID NO: 335) (LC CDR2)

FIG. 11F (continued)

QQRHVWPPT (SEQ ID NO: 336) (LC CDR3)

FIG. 11G

Clone NM-26562 CAR DNA HxL (SEQ ID NO: 337)

ATGGCACTCCCCGTAACTGCTCTGCTGCTGCCGTTGGCATTGCTCCTGCACGCCGCACGCCCG
CAGGTGCAGCTGCAGGAGTCGGGCCCAGGACTGGTGAAGCCTTCACAGACCCTGTCCCTCACC
TGTACTGTCTCTGGTGGCTCCATCGGGAGTGGTGGTAGTTACTGGAGCTGGATCCGCCAGCAC
CCAGGGAAGGGCCTGGAGTGGATTGGGTTGATCTATTACGATGGGAGCACCTACTACAACCCG
TCCCTCAAGAGTCGAGTTACCATATCAGTAGACACGTCTAAGAACCAGTTCTCCCTGAAGCTG
AGTTCTGTGACCGCCGCAGACACGGCGGTGTACTACTGCGCCAGAGGCAGGGGATATGAGACT
TCTTTAGCCTTCGATATCTGGGGTCAGGGTACAATGGTCACCGTCTCCTCAGGGTCTACATCC
GGCTCCGGGAAGCCCGGAAGTGGCGAAGGTAGTACAAAGGGGGAAATTGTGTTGACACAGTCT
CCAGCCACCCTGTCTTTGTCTCCAGGGGAAAGAGCCACCCTCTCCTGCAGGGCCAGTCAGAGT
GTTAGCAGCTACTTAGCCTGGTACCAACAGAAACCTGGCCAGGCTCCCAGGCTCCTCATCTAT
GATGCATCCAACAGGGCCACTGGCATCCCAGCCAGGTTCAGTGGCAGTGGGTCTGGGACAGAC
TTCACTCTCACCATCAGCAGCCTAGAGCCTGAAGATTTTGCAGTTTATTACTGTCAGCAGAGA
CACGTCTGGCCTCCTACTTTTGGCGGAGGGACCAAGGTTGAGATCAAACGGGCCGCTGCCCTT
GATAATGAAAAGTCAAACGGAACAATCATTCACGTGAAGGGCAAGCACCTCTGTCCGTCACCC
TTGTTCCCTGGTCCATCCAAGCCATTCTGGGTGTTGGTCGTAGTGGGTGGAGTCCTCGCTTGT
TACTCTCTGCTCGTCACCGTGGCTTTTATAATCTTCTGGGTTAGATCCAAAAGAAGCCGCCTG
CTCCATAGCGATTACATGAATATGACTCCACGCCGCCCTGGCCCCACAAGGAAACACTACCAG
CCTTACGCACCACCTAGAGATTTCGCTGCCTATCGGAGCAGGGTGAAGTTTTCCAGATCTGCA
GATGCACCAGCGTATCAGCAGGGCCAGAACCAACTGTATAACGAGCTCAACCTGGGACGCAGG
GAAGAGTATGACGTTTTGGACAAGCGCAGAGGACGGGACCCTGAGATGGGTGGCAAACCAAGA
CGAAAAAACCCCCAGGAGGGTCTCTATAATGAGCTGCAGAAGGATAAGATGGCTGAAGCCTAT
TCTGAAATAGGCATGAAAGGAGAGCGGAGAAGGGGAAAAGGGCACGACGGTTTGTACCAGGGA
CTCAGCACTGCTACGAAGGATACTTATGACGCTCTCCACATGCAAGCCCTGCCACCTAGG

FIG. 11H

Clone NM-26562 CAR HxL (SEQ ID NO: 338)

MALPVTALLL PLALLLHAAR PQVQLQESGP GLVKPSQTLS LTCTVSGGSI
GSGGSYWSWI RQHPGKGLEW IGLIYYDGST YYNPSLKSRV TISVDTSKNQ
FSLKLSSVTA ADTAVYYCAR GRGYETSLAF DIWGQGTMVT VSSGSTSGSG
KPGSGEGSTK GEIVLTQSPA TLSLSPGERA TLSCRASQSV SSYLAWYQQK
PGQAPRLLIY DASNRATGIP ARFSGSGSGT DFTLTISSLE PEDFAVYYCQ
QRHVWPPTFG GGTKVEIKRA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

FIG. 11I

Clone NM-26562 CAR DNA LxH (SEQ ID NO: 339)

ATGGCACTCCCCGTAACTGCTCTGCTGCTGCCGTTGGCATTGCTCCTGCACGCCGCACGCCCG
GAAATTGTGTTGACACAGTCTCCAGCCACCCTGTCTTTGTCTCCAGGGGAAAGAGCCACCCTC
TCCTGCAGGGCCAGTCAGAGTGTTAGCAGCTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGACACGTCTGGCCTCCTACTTTTGGCGGAGGGACCAAGGTTGAG
ATCAAACGGGGGTCTACATCCGGCTCCGGGAAGCCCGGAAGTGGCGAAGGTAGTACAAAGGGG
CAGGTGCAGCTGCAGGAGTCGGGCCCAGGACTGGTGAAGCCTTCACAGACCCTGTCCCTCACC
TGTACTGTCTCTGGTGGCTCCATCGGGAGTGGTGGTAGTTACTGGAGCTGGATCCGCCAGCAC
CCAGGGAAGGGCCTGGAGTGGATTGGGTTGATCTATTACGATGGGAGCACCTACTACAACCCG
TCCCTCAAGAGTCGAGTTACCATATCAGTAGACACGTCTAAGAACCAGTTCTCCCTGAAGCTG
AGTTCTGTGACCGCCGCAGACACGGCGGTGTACTACTGCGCCAGAGGCAGGGGATATGAGACT
TCTTTAGCCTTCGATATCTGGGGTCAGGGTACAATGGTCACCGTCTCCTCAGCCGCTGCCCTT
GATAATGAAAAGTCAAACGGAACAATCATTCACGTGAAGGGCAAGCACCTCTGTCCGTCACCC
TTGTTCCCTGGTCCATCCAAGCCATTCTGGGTGTTGGTCGTAGTGGGTGGAGTCCTCGCTTGT
TACTCTCTGCTCGTCACCGTGGCTTTTATAATCTTCTGGGTTAGATCCAAAAGAAGCCGCCTG
CTCCATAGCGATTACATGAATATGACTCCACGCCGCCCTGGCCCCACAAGGAAACACTACCAG
CCTTACGCACCACCTAGAGATTTCGCTGCCTATCGGAGCAGGGTGAAGTTTTCCAGATCTGCA
GATGCACCAGCGTATCAGCAGGGCCAGAACCAACTGTATAACGAGCTCAACCTGGGACGCAGG
GAAGAGTATGACGTTTTGGACAAGCGCAGAGGACGGGACCCTGAGATGGGTGGCAAACCAAGA
CGAAAAAACCCCCAGGAGGGTCTCTATAATGAGCTGCAGAAGGATAAGATGGCTGAAGCCTAT
TCTGAAATAGGCATGAAAGGAGAGCGGAGAAGGGGAAAAGGGCACGACGGTTTGTACCAGGGA
CTCAGCACTGCTACGAAGGATACTTATGACGCTCTCCACATGCAAGCCCTGCCACCTAGG

FIG. 11J

Clone NM-26562 CAR LxH (SEQ ID NO: 340)

MALPVTALLL PLALLLHAAR PEIVLTQSPA TLSLSPGERA TLSCRASQSV
SSYLAWYQQK PGQAPRLLIY DASNRATGIP ARFSGSGSGT DFTLTISSLE
PEDFAVYYCQ QRHVWPPTFG GGTKVEIKRG STSGSGKPGS GEGSTKGQVQ
LQESGPGLVK PSQTLSLTCT VSGGSIGSGG SYWSWIRQHP GKGLEWIGLI
YYDGSTYYNP SLKSRVTISV DTSKNQFSLK LSSVTAADTA VYYCARGRGY
ETSLAFDIWG QGTMVTVSSA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

FIG. 12A

Clone TS-26564 HC DNA (SEQ ID NO: 341)
GAGGTGCAGCTGGTGGAGTCTGGGGGAGGCTTGGTACAGCCTGGGGGGTCCCTGAGACTCTCC
TGTGCAGCCTCTGGATTCACCTTCAGTAGCTATAGCATGAACTGGGTCCGCCAGGCTCCAGGG
AAGGGGCTGGAGTGGGTTTCAACCATTAGTAGTAGTAGTAGTATCATATACTACGCAGACTCT
GTGAAGGGCCGATTCACCATCTCCAGAGACAATGCCAAGAACTCACTGTATCTGCAAATGAAC
AGCCTGAGAGCTGAGGACACGGCGGTGTACTACTGCGCCAGAGGTTCTCAGGAGCACCTGATT
TTCGATTATTGGGGACAGGGTACATTGGTCACCGTCTCCTCA

FIG. 12B

Clone TS-26564 HC (SEQ ID NO: 342). CDRs 1, 2, and 3 are underlined.
EVQLVESGGG LVQPGGSLRL SCAASGFTFS SYSMNWVRQA PGKGLEWVST
ISSSSSIIYY ADSVKGRFTI SRDNAKNSLY LQMNSLRAED TAVYYCARGS
QEHLIFDYWG QGTLVTVSS

FIG. 12C

FTFSSYSMN (SEQ ID NO: 343) (HC CDR1)

TISSSSSIIYYADSVKG (SEQ ID NO: 344) (HC CDR2)

ARGSQEHLIFDY (SEQ ID NO: 345) (HC CDR3)

FIG. 12D

Clone TS-26564 LC DNA (SEQ ID NO: 346)
GAAATTGTGTTGACACAGTCTCCAGCCACCCTGTCTTTGTCTCCAGGGGAAAGAGCCACCCTC
TCCTGCAGGGCCAGTCAGAGTGTTAGCAGGTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGATTCTACTACCCTTGGACTTTTGGCGGAGGGACCAAGGTTGAG
ATCAAACGG

FIG. 12E

Clone TS-26564 LC (SEQ ID NO: 347). CDRs 1, 2, and 3 are underlined.
EIVLTQSPAT LSLSPGERAT LSCRASQSVS RYLAWYQQKP GQAPRLLIYD
ASNRATGIPA RFSGSGSGTD FTLTISSLEP EDFAVYYCQQ RFYYPWTFGG GTKVEIKR

FIG. 12F

RASQSVSRYLA (SEQ ID NO: 347) (LC CDR1)

DASNRAT (SEQ ID NO: 349) (LC CDR2)

QQRFYYPWT (SEQ ID NO: 350) (LC CDR3)

IG. 12G

Clone TS-26564 CAR DNA HxL (SEQ ID NO: 351)

ATGGCACTCCCCGTAACTGCTCTGCTGCTGCCGTTGGCATTGCTCCTGCACGCCGCACGCCCG
GAGGTGCAGCTGGTGGAGTCTGGGGGAGGCTTGGTACAGCCTGGGGGGTCCCTGAGACTCTCC
TGTGCAGCCTCTGGATTCACCTTCAGTAGCTATAGCATGAACTGGGTCCGCCAGGCTCCAGGG
AAGGGGCTGGAGTGGGTTTCAACCATTAGTAGTAGTAGTAGTATCATATACTACGCAGACTCT
GTGAAGGGCCGATTCACCATCTCCAGAGACAATGCCAAGAACTCACTGTATCTGCAAATGAAC
AGCCTGAGAGCTGAGGACACGGCGGTGTACTACTGCGCCAGAGGTTCTCAGGAGCACCTGATT
TTCGATTATTGGGGACAGGGTACATTGGTCACCGTCTCCTCAGGGTCTACATCCGGCTCCGGG
AAGCCCGGAAGTGGCGAAGGTAGTACAAAGGGGGAAATTGTGTTGACACAGTCTCCAGCCACC
CTGTCTTTGTCTCCAGGGGAAAGAGCCACCCTCTCCTGCAGGGCCAGTCAGAGTGTTAGCAGG
TACTTAGCCTGGTACCAACAGAAACCTGGCCAGGCTCCCAGGCTCCTCATCTATGATGCATCC
AACAGGGCCACTGGCATCCCAGCCAGGTTCAGTGGCAGTGGGTCTGGGACAGACTTCACTCTC
ACCATCAGCAGCCTAGAGCCTGAAGATTTTGCAGTTTATTACTGTCAGCAGAGATTCTACTAC
CCTTGGACTTTTGGCGGAGGGACCAAGGTTGAGATCAAACGGGCCGCTGCCCTTGATAATGAA
AAGTCAAACGGAACAATCATTCACGTGAAGGGCAAGCACCTCTGTCCGTCACCCTTGTTCCCT
GGTCCATCCAAGCCATTCTGGGTGTTGGTCGTAGTGGGTGGAGTCCTCGCTTGTTACTCTCTG
CTCGTCACCGTGGCTTTTATAATCTTCTGGGTTAGATCCAAAAGAAGCCGCCTGCTCCATAGC
GATTACATGAATATGACTCCACGCCGCCCTGGCCCCACAAGGAAACACTACCAGCCTTACGCA
CCACCTAGAGATTTCGCTGCCTATCGGAGCAGGGTGAAGTTTTCCAGATCTGCAGATGCACCA
GCGTATCAGCAGGGCCAGAACCAACTGTATAACGAGCTCAACCTGGGACGCAGGGAAGAGTAT
GACGTTTTGGACAAGCGCAGAGGACGGGACCCTGAGATGGGTGGCAAACCAAGACGAAAAAAC
CCCCAGGAGGGTCTCTATAATGAGCTGCAGAAGGATAAGATGGCTGAAGCCTATTCTGAAATA
GGCATGAAAGGAGAGCGGAGAAGGGGAAAAGGGCACGACGGTTTGTACCAGGGACTCAGCACT
GCTACGAAGGATACTTATGACGCTCTCCACATGCAAGCCCTGCCACCTAGG

FIG. 12H

Clone TS-26564 CAR HxL (SEQ ID NO: 352)

MALPVTALLL PLALLLHAAR PEVQLVESGG GLVQPGGSLR LSCAASGFTF
SSYSMNWVRQ APGKGLEWVS TISSSSSIIY YADSVKGRFT ISRDNAKNSL
YLQMNSLRAE DTAVYYCARG SQEHLIFDYW GQGTLVTVSS GSTSGSGKPG
SGEGSTKGEI VLTQSPATLS LSPGERATLS CRASQSVSRY LAWYQQKPGQ
APRLLIYDAS NRATGIPARF SGSGSGTDFT LTISSLEPED FAVYYCQQRF
YYPWTFGGGT KVEIKRAAAL DNEKSNGTII HVKGKHLCPS PLFPGPSKPF
WVLVVVGGVL ACYSLLVTVA FIIFWVRSKR SRLLHSDYMN MTPRRPGPTR
KHYQPYAPPR DFAAYRSRVK FSRSADAPAY QQGQNQLYNE LNLGRREEYD
VLDKRRGRDP EMGGKPRRKN PQEGLYNELQ KDKMAEAYSE IGMKGERRRG
KGHDGLYQGL STATKDTYDA LHMQALPPR

FIG. 12I

Clone TS-26564 CAR DNA LxH (SEQ ID NO: 353)

ATGGCACTCCCCGTAACTGCTCTGCTGCTGCCGTTGGCATTGCTCCTGCACGCCGCACGCCCG
GAAATTGTGTTGACACAGTCTCCAGCCACCCTGTCTTTGTCTCCAGGGGAAAGAGCCACCCTC
TCCTGCAGGGCCAGTCAGAGTGTTAGCAGGTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGATTCTACTACCCTTGGACTTTTGGCGGAGGGACCAAGGTTGAG
ATCAAACGGGGGTCTACATCCGGCTCCGGGAAGCCCGGAAGTGGCGAAGGTAGTACAAAGGGG
GAGGTGCAGCTGGTGGAGTCTGGGGGAGGCTTGGTACAGCCTGGGGGGTCCCTGAGACTCTCC
TGTGCAGCCTCTGGATTCACCTTCAGTAGCTATAGCATGAACTGGGTCCGCCAGGCTCCAGGG
AAGGGGCTGGAGTGGGTTTCAACCATTAGTAGTAGTAGTAGTATCATATACTACGCAGACTCT
GTGAAGGGCCGATTCACCATCTCCAGAGACAATGCCAAGAACTCACTGTATCTGCAAATGAAC
AGCCTGAGAGCTGAGGACACGGCGGTGTACTACTGCGCCAGAGGTTCTCAGGAGCACCTGATT
TTCGATTATTGGGGACAGGGTACATTGGTCACCGTCTCCTCAGCCGCTGCCCTTGATAATGAA
AAGTCAAACGGAACAATCATTCACGTGAAGGGCAAGCACCTCTGTCCGTCACCCTTGTTCCCT
GGTCCATCCAAGCCATTCTGGGTGTTGGTCGTAGTGGGTGGAGTCCTCGCTTGTTACTCTCTG
CTCGTCACCGTGGCTTTTATAATCTTCTGGGTTAGATCCAAAAGAAGCCGCCTGCTCCATAGC
GATTACATGAATATGACTCCACGCCGCCCTGGCCCCACAAGGAAACACTACCAGCCTTACGCA
CCACCTAGAGATTTCGCTGCCTATCGGAGCAGGGTGAAGTTTTCCAGATCTGCAGATGCACCA
GCGTATCAGCAGGGCCAGAACCAACTGTATAACGAGCTCAACCTGGGACGCAGGGAAGAGTAT
GACGTTTTGGACAAGCGCAGAGGACGGGACCCTGAGATGGGTGGCAAACCAAGACGAAAAAAC
CCCCAGGAGGGTCTCTATAATGAGCTGCAGAAGGATAAGATGGCTGAAGCCTATTCTGAAATA
GGCATGAAAGGAGAGCGGAGAAGGGGAAAAGGGCACGACGGTTTGTACCAGGGACTCAGCACT
GCTACGAAGGATACTTATGACGCTCTCCACATGCAAGCCCTGCCACCTAGG

FIG. 12J

Clone TS-26564 CAR LxH (SEQ ID NO: 354)

MALPVTALLL PLALLLHAAR PEIVLTQSPA TLSLSPGERA TLSCRASQSV
SRYLAWYQQK PGQAPRLLIY DASNRATGIP ARFSGSGSGT DFTLTISSLE
PEDFAVYYCQ QRFYYPWTFG GGTKVEIKRG STSGSGKPGS GEGSTKGEVQ
LVESGGGLVQ PGGSLRLSCA ASGFTFSSYS MNWVRQAPGK GLEWVSTISS
SSSIIYYADS VKGRFTISRD NAKNSLYLQM NSLRAEDTAV YYCARGSQEH
LIFDYWGQGT LVTVSSAAAL DNEKSNGTII HVKGKHLCPS PLFPGPSKPF
WVLVVVGGVL ACYSLLVTVA FIIFWVRSKR SRLLHSDYMN MTPRRPGPTR
KHYQPYAPPR DFAAYRSRVK FSRSADAPAY QQGQNQLYNE LNLGRREEYD
VLDKRRGRDP EMGGKPRRKN PQEGLYNELQ KDKMAEAYSE IGMKGERRRG
KGHDGLYQGL STATKDTYDA LHMQALPPR

FIG. 13A

Clone RY-26568 HC DNA (SEQ ID NO: 355)

CAGGTGCAGCTGGTGGAGTCTGGGGGAGGCGTGGTCCAGCCTGGGAGGTCCCTGAGACTCTCC
TGTGCAGCGTCTGGATTCACCTTCGGGAGCTATGGCATGCACTGGGTCCGCCAGGCTCCAGGC
AAGGGGCTGGAGTGGGTGGCAGTTATACATTATGATGGAAGTGTTGAATACTATGCAGACTCC
GTGAAGGGCCGATTCACCATCTCCAGAGACAATTCCAAGGACACGCTGTATCTGCAAATGAAC
AGCCTGAGAGCCGAGGACACGGCGGTGTACTACTGCGCCAGAACTGACTTCTGGAGCGGATCC
CCTCCAAGCTTAGATTACTGGGGACAGGGTACATTGGTCACCGTCTCCTCA

FIG. 13B

Clone RY-26568 HC (SEQ ID NO: 356). CDRs 1, 2, and 3 are underlined.

QVQLVESGGG VVQPGRSLRL SCAASGFTFG SYGMHWVRQA PGKGLEWVAV
IHYDGSVEYY ADSVKGRFTI SRDNSKDTLY LQMNSLRAED TAVYYCARTD
FWSGSPPSLD YWGQGTLVTV SS

FIG. 13C

FTFGSYGMH (SEQ ID NO: 357) (HC CDR1)

VIHYDGSVEYYADSVKG (SEQ ID NO: 358) (HC CDR2)

ARTDFWSGSPPSLDY (SEQ ID NO: 359) (HC CDR3)

FIG. 13D

Clone RY-26568 LC DNA (SEQ ID NO: 360)

GACATCCAGTTGACCCAGTCTCCATCTTCCGTGTCTGCATCTGTAGGAGACAGAGTCACCATC
ACTTGTCGGGCGAGTCGGGGTATTAGCAGCTGGTTAGCCTGGTATCAGCAGAAACCAGGGAAA
GCCCCTAAGCTCCTGATCTATGGTGCATCCAGTTTGCAAAGTGGGGTCCCATCAAGGTTCAGC
GGCAGTGGATCTGGGACAGATTTCACTCTCACCATCAGCAGCCTGCAGCCTGAAGATTTTGCA
ACTTATTACTGTCAGCAGATATACACCTTCCCTTTCACTTTTGGCGGAGGGACCAAGGTTGAG
ATCAAACGG

FIG. 13E

Clone RY-26568 LC (SEQ ID NO: 361). CDRs 1, 2, and 3 are underlined.

DIQLTQSPSS VSASVGDRVT ITCRASRGIS SWLAWYQQKP GKAPKLLIYG
ASSLQSGVPS RFSGSGSGTD FTLTISSLQP EDFATYYCQQ IYTFPFTFGG GTKVEIKR

FIG. 13F

RASRGISSWLA (SEQ ID NO: 362) (LC CDR1)

GASSLQS (SEQ ID NO: 363) (LC CDR2)

QQIYTFPFT (SEQ ID NO: 364) (LC CDR3)

FIG. 13G

Clone RY-26568 CAR DNA HxL (SEQ ID NO: 365)

ATGGCACTCCCCGTAACTGCTCTGCTGCTGCCGTTGGCATTGCTCCTGCACGCCGCACGCCCG
CAGGTGCAGCTGGTGGAGTCTGGGGGAGGCGTGGTCCAGCCTGGGAGGTCCCTGAGACTCTCC
TGTGCAGCGTCTGGATTCACCTTCGGGAGCTATGGCATGCACTGGGTCCGCCAGGCTCCAGGC
AAGGGGCTGGAGTGGGTGGCAGTTATACATTATGATGGAAGTGTTGAATACTATGCAGACTCC
GTGAAGGGCCGATTCACCATCTCCAGAGACAATTCCAAGGACACGCTGTATCTGCAAATGAAC
AGCCTGAGAGCCGAGGACACGGCGGTGTACTACTGCGCCAGAACTGACTTCTGGAGCGGATCC
CCTCCAAGCTTAGATTACTGGGGACAGGGTACATTGGTCACCGTCTCCTCAGGGTCTACATCC
GGCTCCGGGAAGCCCGGAAGTGGCGAAGGTAGTACAAAGGGGGACATCCAGTTGACCCAGTCT
CCATCTTCCGTGTCTGCATCTGTAGGAGACAGAGTCACCATCACTTGTCGGGCGAGTCGGGGT
ATTAGCAGCTGGTTAGCCTGGTATCAGCAGAAACCAGGGAAAGCCCCTAAGCTCCTGATCTAT
GGTGCATCCAGTTTGCAAAGTGGGGTCCCATCAAGGTTCAGCGGCAGTGGATCTGGGACAGAT
TTCACTCTCACCATCAGCAGCCTGCAGCCTGAAGATTTTGCAACTTATTACTGTCAGCAGATA
TACACCTTCCCTTTCACTTTTGGCGGAGGGACCAAGGTTGAGATCAAACGGGCCGCTGCCCTT
GATAATGAAAAGTCAAACGGAACAATCATTCACGTGAAGGGCAAGCACCTCTGTCCGTCACCC
TTGTTCCCTGGTCCATCCAAGCCATTCTGGGTGTTGGTCGTAGTGGGTGGAGTCCTCGCTTGT
TACTCTCTGCTCGTCACCGTGGCTTTTATAATCTTCTGGGTTAGATCCAAAAGAAGCCGCCTG
CTCCATAGCGATTACATGAATATGACTCCACGCCGCCCTGGCCCCACAAGGAAACACTACCAG
CCTTACGCACCACCTAGAGATTTCGCTGCCTATCGGAGCAGGGTGAAGTTTTCCAGATCTGCA
GATGCACCAGCGTATCAGCAGGGCCAGAACCAACTGTATAACGAGCTCAACCTGGGACGCAGG
GAAGAGTATGACGTTTTGGACAAGCGCAGAGGACGGGACCCTGAGATGGGTGGCAAACCAAGA
CGAAAAAACCCCCAGGAGGGTCTCTATAATGAGCTGCAGAAGGATAAGATGGCTGAAGCCTAT
TCTGAAATAGGCATGAAAGGAGAGCGGAGAAGGGGAAAAGGGCACGACGGTTTGTACCAGGGA
CTCAGCACTGCTACGAAGGATACTTATGACGCTCTCCACATGCAAGCCCTGCCACCTAGG

FIG. 13H

Clone RY-26568 CAR HxL (SEQ ID NO: 366)

MALPVTALLL PLALLLHAAR PQVQLVESGG GVVQPGRSLR LSCAASGFTF
GSYGMHWVRQ APGKGLEWVA VIHYDGSVEY YADSVKGRFT ISRDNSKDTL
YLQMNSLRAE DTAVYYCART DFWSGSPPSL DYWGQGTLVT VSSGSTSGSG
KPGSGEGSTK GDIQLTQSPS SVSASVGDRV TITCRASRGI SSWLAWYQQK
PGKAPKLLIY GASSLQSGVP SRFSGSGSGT DFTLTISSLQ PEDFATYYCQ
QIYTFPFTFG GGTKVEIKRA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

FIG. 13I

Clone RY-26568 CAR DNA LxH (SEQ ID NO: 367)

ATGGCACTCCCCGTAACTGCTCTGCTGCTGCCGTTGGCATTGCTCCTGCACGCCGCACGCCCG
GACATCCAGTTGACCCAGTCTCCATCTTCCGTGTCTGCATCTGTAGGAGACAGAGTCACCATC
ACTTGTCGGGCGAGTCGGGGTATTAGCAGCTGGTTAGCCTGGTATCAGCAGAAACCAGGGAAA
GCCCCTAAGCTCCTGATCTATGGTGCATCCAGTTTGCAAAGTGGGGTCCCATCAAGGTTCAGC
GGCAGTGGATCTGGGACAGATTTCACTCTCACCATCAGCAGCCTGCAGCCTGAAGATTTTGCA
ACTTATTACTGTCAGCAGATATACACCTTCCCTTTCACTTTTGGCGGAGGGACCAAGGTTGAG
ATCAAACGGGGGTCTACATCCGGCTCCGGGAAGCCCGGAAGTGGCGAAGGTAGTACAAAGGGG
CAGGTGCAGCTGGTGGAGTCTGGGGGAGGCGTGGTCCAGCCTGGGAGGTCCCTGAGACTCTCC
TGTGCAGCGTCTGGATTCACCTTCGGGAGCTATGGCATGCACTGGGTCCGCCAGGCTCCAGGC
AAGGGGCTGGAGTGGGTGGCAGTTATACATTATGATGGAAGTGTTGAATACTATGCAGACTCC
GTGAAGGGCCGATTCACCATCTCCAGAGACAATTCCAAGGACACGCTGTATCTGCAAATGAAC
AGCCTGAGAGCCGAGGACACGGCGGTGTACTACTGCGCCAGAACTGACTTCTGGAGCGGATCC
CCTCCAAGCTTAGATTACTGGGGACAGGGTACATTGGTCACCGTCTCCTCAGCCGCTGCCCTT
GATAATGAAAAGTCAAACGGAACAATCATTCACGTGAAGGGCAAGCACCTCTGTCCGTCACCC
TTGTTCCCTGGTCCATCCAAGCCATTCTGGGTGTTGGTCGTAGTGGGTGGAGTCCTCGCTTGT
TACTCTCTGCTCGTCACCGTGGCTTTTATAATCTTCTGGGTTAGATCCAAAAGAAGCCGCCTG
CTCCATAGCGATTACATGAATATGACTCCACGCCGCCCTGGCCCCACAAGGAAACACTACCAG
CCTTACGCACCACCTAGAGATTTCGCTGCCTATCGGAGCAGGGTGAAGTTTTCCAGATCTGCA
GATGCACCAGCGTATCAGCAGGGCCAGAACCAACTGTATAACGAGCTCAACCTGGGACGCAGG
GAAGAGTATGACGTTTTGGACAAGCGCAGAGGACGGGACCCTGAGATGGGTGGCAAACCAAGA
CGAAAAAACCCCCAGGAGGGTCTCTATAATGAGCTGCAGAAGGATAAGATGGCTGAAGCCTAT
TCTGAAATAGGCATGAAAGGAGAGCGGAGAAGGGGAAAAGGGCACGACGGTTTGTACCAGGGA
CTCAGCACTGCTACGAAGGATACTTATGACGCTCTCCACATGCAAGCCCTGCCACCTAGG

FIG. 13J

Clone RY-26568 CAR LxH (SEQ ID NO: 368)

MALPVTALLL PLALLLHAAR PDIQLTQSPS SVSASVGDRV TITCRASRGI
SSWLAWYQQK PGKAPKLLIY GASSLQSGVP SRFSGSGSGT DFTLTISSLQ
PEDFATYYCQ QIYTFPFTFG GGTKVEIKRG STSGSGKPGS GEGSTKGQVQ
LVESGGGVVQ PGRSLRLSCA ASGFTFGSYG MHWVRQAPGK GLEWVAVIHY
DGSVEYYADS VKGRFTISRD NSKDTLYLQM NSLRAEDTAV YYCARTDFWS
GSPPSLDYWG QGTLVTVSSA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

FIG. 14A

Clone PP-26575 HC DNA (SEQ ID NO: 369)

CAGGTGCAGCTGGTGCAGTCTGGGGCTGAGGTGAAGAAGCCTGGGTCCTCGGTGAAGGTCTCC
TGCAAGGCTTCTGGAGGCACCCTCAGCAGCCTGGCTATCAGCTGGGTGCGACAGGCCCCTGGA
CAAGGGCTTGAGTGGATGGGAGGGGTCATCCCTATCTTGGGTCGGGCAAACTACGCACAGAAG
TTCCAGGGCAGAGTCACGATTACCGCGGACGAGTCCACGAGCACAGCCTACATGGAGCTGAGC
AGCCTGAGATCTGAGGACACGGCGGTGTACTACTGCGCCAGAACTCCTGAATACTCCTCCAGC
ATATGGCACTATTACTACGGCATGGACGTATGGGGCCAGGGAACAACTGTCACCGTCTCCTCA

FIG. 14B

Clone PP-26575 HC (SEQ ID NO: 370). CDRs 1, 2, and 3 are underlined.

QVQLVQSGAE VKKPGSSVKV SCKASGGTLS SLAISWVRQA PGQGLEWMGG
VIPILGRANY AQKFQGRVTI TADESTSTAY MELSSLRSED TAVYYCARTP
EYSSSIWHYY YGMDVWGQGT TVTVSS

FIG. 14C

GTLSSLAIS (SEQ ID NO: 371) (HC CDR1)

GVIPILGRANYAQKFQG (SEQ ID NO: 372) (HC CDR2)

ARTPEYSSSIWHYYYGMDV (SEQ ID NO: 373) (HC CDR3)

FIG. 14D

Clone PP-26575 LC DNA (SEQ ID NO: 374)

GACATCGTGATGACCCAGTCTCCAGACTCCCTGGCTGTGTCTCTGGGCGAGAGGGCCACCATC
AACTGCAAGTCCAGCCAGAGTGTTTTATACAGCTCCAACAATAAGAACTACTTAGCTTGGTAC
CAGCAGAAACCAGGACAGCCTCCTAAGCTGCTCATTTACTGGGCATCTACCCGGGAATCCGGG
GTCCCTGACCGATTCAGTGGCAGCGGGTCTGGGACAGATTTCACTCTCACCATCAGCAGCCTG
CAGGCTGAAGATGTGGCAGTTTATTACTGTCAGCAGTTCGCCCACACTCCTTTCACTTTTGGC
GGAGGGACCAAGGTTGAGATCAAACGG

FIG. 14E

Clone PP-26575 LC (SEQ ID NO: 375). CDRs 1, 2, and 3 are underlined.

DIVMTQSPDS LAVSLGERAT INCKSSQSVL YSSNNKNYLA WYQQKPGQPP
KLLIYWASTR ESGVPDRFSG SGSGTDFTLT ISSLQAEDVA VYYCQQFAHT
PFTFGGGTKV EIKR

FIG. 14F

KSSQSVLYSSNNKNYLA (SEQ ID NO: 376) (LC CDR1)

FIG. 14F (continued)

WASTRES (SEQ ID NO: 377) (LC CDR2)

QQFAHTPFT (SEQ ID NO: 378) (LC CDR3)

FIG. 14G

Clone PP-26575 CAR DNA HxL (SEQ ID NO: 379)

ATGGCACTCCCCGTAACTGCTCTGCTGCTGCCGTTGGCATTGCTCCTGCACGCCGCACGCCCG
CAGGTGCAGCTGGTGCAGTCTGGGGCTGAGGTGAAGAAGCCTGGGTCCTCGGTGAAGGTCTCC
TGCAAGGCTTCTGGAGGCACCCTCAGCAGCCTGGCTATCAGCTGGGTGCGACAGGCCCCTGGA
CAAGGGCTTGAGTGGATGGGAGGGGTCATCCCTATCTTGGGTCGGGCAAACTACGCACAGAAG
TTCCAGGGCAGAGTCACGATTACCGCGGACGAGTCCACGAGCACAGCCTACATGGAGCTGAGC
AGCCTGAGATCTGAGGACACGGCGGTGTACTACTGCGCCAGAACTCCTGAATACTCCTCCAGC
ATATGGCACTATTACTACGGCATGGACGTATGGGGCCAGGGAACAACTGTCACCGTCTCCTCA
GGGTCTACATCCGGCTCCGGGAAGCCCGGAAGTGGCGAAGGTAGTACAAAGGGGGACATCGTG
ATGACCCAGTCTCCAGACTCCCTGGCTGTGTCTCTGGGCGAGAGGGCCACCATCAACTGCAAG
TCCAGCCAGAGTGTTTTATACAGCTCCAACAATAAGAACTACTTAGCTTGGTACCAGCAGAAA
CCAGGACAGCCTCCTAAGCTGCTCATTTACTGGGCATCTACCCGGGAATCCGGGGTCCCTGAC
CGATTCAGTGGCAGCGGGTCTGGGACAGATTTCACTCTCACCATCAGCAGCCTGCAGGCTGAA
GATGTGGCAGTTTATTACTGTCAGCAGTTCGCCCACACTCCTTTCACTTTTGGCGGAGGGACC
AAGGTTGAGATCAAACGGGCCGCTGCCCTTGATAATGAAAAGTCAAACGGAACAATCATTCAC
GTGAAGGGCAAGCACCTCTGTCCGTCACCCTTGTTCCCTGGTCCATCCAAGCCATTCTGGGTG
TTGGTCGTAGTGGGTGGAGTCCTCGCTTGTTACTCTCTGCTCGTCACCGTGGCTTTTATAATC
TTCTGGGTTAGATCCAAAAGAAGCCGCCTGCTCCATAGCGATTACATGAATATGACTCCACGC
CGCCCTGGCCCCACAAGGAAACACTACCAGCCTTACGCACCACCTAGAGATTTCGCTGCCTAT
CGGAGCAGGGTGAAGTTTTCCAGATCTGCAGATGCACCAGCGTATCAGCAGGGCCAGAACCAA
CTGTATAACGAGCTCAACCTGGGACGCAGGGAAGAGTATGACGTTTTGGACAAGCGCAGAGGA
CGGGACCCTGAGATGGGTGGCAAACCAAGACGAAAAAACCCCCAGGAGGGTCTCTATAATGAG
CTGCAGAAGGATAAGATGGCTGAAGCCTATTCTGAAATAGGCATGAAAGGAGAGCGGAGAAGG
GGAAAAGGGCACGACGGTTTGTACCAGGGACTCAGCACTGCTACGAAGGATACTTATGACGCT
CTCCACATGCAAGCCCTGCCACCTAGG

FIG. 14H

Clone PP-26575 CAR HxL (SEQ ID NO: 380)

MALPVTALLL PLALLLHAAR PQVQLVQSGA EVKKPGSSVK VSCKASGGTL
SSLAISWVRQ APGQGLEWMG GVIPILGRAN YAQKFQGRVT ITADESTSTA
YMELSSLRSE DTAVYYCART PEYSSSIWHY YYGMDVWGQG TTVTVSSGST
SGSGKPGSGE GSTKGDIVMT QSPDSLAVSL GERATINCKS SQSVLYSSNN
KNYLAWYQQK PGQPPKLLIY WASTRESGVP DRFSGSGSGT DFTLTISSLQ
AEDVAVYYCQ QFAHTPFTFG GGTKVEIKRA AALDNEKSNG TIIHVKGKHL
CPSPLFPGPS KPFWVLVVVG GVLACYSLLV TVAFIIFWVR SKRSRLLHSD
YMNMTPRRPG PTRKHYQPYA PPRDFAAYRS RVKFSRSADA PAYQQGQNQL
YNELNLGRRE EYDVLDKRRG RDPEMGGKPR RKNPQEGLYN ELQKDKMAEA
YSEIGMKGER RRGKGHDGLY QGLSTATKDT YDALHMQALP PR

FIG. 14I

Clone PP-26575 CAR DNA LxH (SEQ ID NO: 381)

ATGGCACTCCCCGTAACTGCTCTGCTGCTGCCGTTGGCATTGCTCCTGCACGCCGCACGCCCG
GACATCGTGATGACCCAGTCTCCAGACTCCCTGGCTGTGTCTCTGGGCGAGAGGGCCACCATC
AACTGCAAGTCCAGCCAGAGTGTTTTATACAGCTCCAACAATAAGAACTACTTAGCTTGGTAC
CAGCAGAAACCAGGACAGCCTCCTAAGCTGCTCATTTACTGGGCATCTACCCGGGAATCCGGG
GTCCCTGACCGATTCAGTGGCAGCGGGTCTGGGACAGATTTCACTCTCACCATCAGCAGCCTG
CAGGCTGAAGATGTGGCAGTTTATTACTGTCAGCAGTTCGCCCACACTCCTTTCACTTTTGGC
GGAGGGACCAAGGTTGAGATCAAACGGGGGTCTACATCCGGCTCCGGGAAGCCCGGAAGTGGC
GAAGGTAGTACAAAGGGGCAGGTGCAGCTGGTGCAGTCTGGGGCTGAGGTGAAGAAGCCTGGG
TCCTCGGTGAAGGTCTCCTGCAAGGCTTCTGGAGGCACCCTCAGCAGCCTGGCTATCAGCTGG
GTGCGACAGGCCCCTGGACAAGGGCTTGAGTGGATGGGAGGGGTCATCCCTATCTTGGGTCGG
GCAAACTACGCACAGAAGTTCCAGGGCAGAGTCACGATTACCGCGGACGAGTCCACGAGCACA
GCCTACATGGAGCTGAGCAGCCTGAGATCTGAGGACACGGCGGTGTACTACTGCGCCAGAACT
CCTGAATACTCCTCCAGCATATGGCACTATTACTACGGCATGGACGTATGGGGCCAGGGAACA
ACTGTCACCGTCTCCTCAGCCGCTGCCCTTGATAATGAAAAGTCAAACGGAACAATCATTCAC
GTGAAGGGCAAGCACCTCTGTCCGTCACCCTTGTTCCCTGGTCCATCCAAGCCATTCTGGGTG
TTGGTCGTAGTGGGTGGAGTCCTCGCTTGTTACTCTCTGCTCGTCACCGTGGCTTTTATAATC
TTCTGGGTTAGATCCAAAAGAAGCCGCCTGCTCCATAGCGATTACATGAATATGACTCCACGC
CGCCCTGGCCCCACAAGGAAACACTACCAGCCTTACGCACCACCTAGAGATTTCGCTGCCTAT
CGGAGCAGGGTGAAGTTTTCCAGATCTGCAGATGCACCAGCGTATCAGCAGGGCCAGAACCAA
CTGTATAACGAGCTCAACCTGGGACGCAGGGAAGAGTATGACGTTTTGGACAAGCGCAGAGGA
CGGGACCCTGAGATGGGTGGCAAACCAAGACGAAAAAACCCCCAGGAGGGTCTCTATAATGAG
CTGCAGAAGGATAAGATGGCTGAAGCCTATTCTGAAATAGGCATGAAAGGAGAGCGGAGAAGG
GGAAAAGGGCACGACGGTTTGTACCAGGGACTCAGCACTGCTACGAAGGATACTTATGACGCT
CTCCACATGCAAGCCCTGCCACCTAGG

FIG. 14J

Clone PP-26575 CAR LxH (SEQ ID NO: 382)

MALPVTALLL PLALLLHAAR PDIVMTQSPD SLAVSLGERA TINCKSSQSV
LYSSNNKNYL AWYQQKPGQP PKLLIYWAST RESGVPDRFS GSGSGTDFTL
TISSLQAEDV AVYYCQQFAH TPFTFGGGTK VEIKRGSTSG SGKPGSGEGS
TKGQVQLVQS GAEVKKPGSS VKVSCKASGG TLSSLAISWV RQAPGQGLEW
MGGVIPILGR ANYAQKFQGR VTITADESTS TAYMELSSLR SEDTAVYYCA
RTPEYSSSIW HYYYGMDVWG QGTTVTVSSA AALDNEKSNG TIIHVKGKHL
CPSPLFPGPS KPFWVLVVVG GVLACYSLLV TVAFIIFWVR SKRSRLLHSD
YMNMTPRRPG PTRKHYQPYA PPRDFAAYRS RVKFSRSADA PAYQQGQNQL
YNELNLGRRE EYDVLDKRRG RDPEMGGKPR RKNPQEGLYN ELQKDKMAEA
YSEIGMKGER RRGKGHDGLY QGLSTATKDT YDALHMQALP PR

FIG. 15A

Clone RD-26576 HC DNA (SEQ ID NO: 383)

CAGGTGCGGCTGGTGGAGTCTGGGGGGGGCGTGGTCCAGCCTGGGAGGTCCCTGAGACTCTCC
TGTGCAGCGTCTGGATTCACCTTCAGTAGCTATGGCATACACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGCTTTTGGGATGGACGTATGGGGCCAGGGAACAACTGTCACCGTCTCCTCA

FIG. 15B

Clone RD-26576 HC (SEQ ID NO: 384). CDRs 1, 2, and 3 are underlined.

QVRLVESGGG VVQPGRSLRL SCAASGFTFS SYGIHWVRQA PGKGLEWVAV
IGYDGQEKYY ADSVKGRFTI SRDNSKNTLY LQMNSLRAED TAVYYCVKGP
LQEPPYAFGM DVWGQGTTVT VSS

FIG. 15C

FTFSSYGIH (SEQ ID NO: 385) (HC CDR1)

VIGYDGQEKYYADSVKG (SEQ ID NO: 386) (HC CDR2)

VKGPLQEPPYAFGMDV (SEQ ID NO: 387) (HC CDR3)

FIG. 15D

Clone RD-26576 LC DNA (SEQ ID NO: 388)

GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATAGCGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGCACCACGTCTGGCCTCTCACTTTTGGCGGAGGGACCAAGGTTGAG
ATCAAACGG

FIG. 15E

Clone RD-26576 LC (SEQ ID NO: 389). CDRs 1, 2, and 3 are underlined.

EIVMTQSPAT LSVSPGERAT LSCRASQSVS SNLAWYQQKP GQAPRLLIYS
ASTRATGIPA RFSGSGSGTE FTLTISSLQS EDFAVYYCQQ HHVWPLTFGG GTKVEIKR

FIG. 15F

RASQSVSSNLA (SEQ ID NO: 390) (LC CDR1)

SASTRAT (SEQ ID NO: 391) (LC CDR2)

FIG. 15F (continued)

QQHHVWPLT (SEQ ID NO: 392) (LC CDR3)

FIG. 15G

Clone RD-26576 CAR DNA HxL (SEQ ID NO: 393)

ATGGCACTCCCCGTAACTGCTCTGCTGCTGCCGTTGGCATTGCTCCTGCACGCCGCACGCCCG
CAGGTGCGGCTGGTGGAGTCTGGGGGGGGCGTGGTCCAGCCTGGGAGGTCCCTGAGACTCTCC
TGTGCAGCGTCTGGATTCACCTTCAGTAGCTATGGCATACACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGCTTTTGGGATGGACGTATGGGGCCAGGGAACAACTGTCACCGTCTCCTCAGGGTCTACA
TCCGGCTCCGGGAAGCCCGGAAGTGGCGAAGGTAGTACAAAGGGGGAAATAGTGATGACGCAG
TCTCCAGCCACCCTGTCTGTGTCTCCAGGGGAAAGAGCCACCCTCTCCTGCAGGGCCAGTCAG
AGTGTTAGCAGCAACTTAGCCTGGTACCAGCAGAAACCTGGCCAGGCTCCCAGGCTCCTCATC
TATAGCGCATCCACCAGGGCCACTGGTATCCCAGCCAGGTTCAGTGGCAGTGGGTCTGGGACA
GAGTTCACTCTCACCATCAGCAGCCTGCAGTCTGAAGATTTTGCAGTTTATTACTGTCAGCAG
CACCACGTCTGGCCTCTCACTTTTGGCGGAGGGACCAAGGTTGAGATCAAACGGGCCGCTGCC
CTTGATAATGAAAAGTCAAACGGAACAATCATTCACGTGAAGGGCAAGCACCTCTGTCCGTCA
CCCTTGTTCCCTGGTCCATCCAAGCCATTCTGGGTGTTGGTCGTAGTGGGTGGAGTCCTCGCT
TGTTACTCTCTGCTCGTCACCGTGGCTTTTATAATCTTCTGGGTTAGATCCAAAAGAAGCCGC
CTGCTCCATAGCGATTACATGAATATGACTCCACGCCGCCCTGGCCCCACAAGGAAACACTAC
CAGCCTTACGCACCACCTAGAGATTTCGCTGCCTATCGGAGCAGGGTGAAGTTTTCCAGATCT
GCAGATGCACCAGCGTATCAGCAGGGCCAGAACCAACTGTATAACGAGCTCAACCTGGGACGC
AGGGAAGAGTATGACGTTTTGGACAAGCGCAGAGGACGGGACCCTGAGATGGGTGGCAAACCA
AGACGAAAAAACCCCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGACGGTTTGTACCAG
GGACTCAGCACTGCTACGAAGGATACTTATGACGCTCTCCACATGCAAGCCCTGCCACCTAGG

FIG. 15H

Clone RD-26576 CAR HxL (SEQ ID NO: 394)

MALPVTALLL PLALLLHAAR PQVRLVESGG GVVQPGRSLR LSCAASGFTF
SSYGIHWVRQ APGKGLEWVA VIGYDGQEKY YADSVKGRFT ISRDNSKNTL
YLQMNSLRAE DTAVYYCVKG PLQEPPYAFG MDVWGQGTTV TVSSGSTSGS
GKPGSGEGST KGEIVMTQSP ATLSVSPGER ATLSCRASQS VSSNLAWYQQ
KPGQAPRLLI YSASTRATGI PARFSGSGSG TEFTLTISSL QSEDFAVYYC
QQHHVWPLTF GGGTKVEIKR AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

FIG. 15I

Clone RD-26576 CAR DNA LxH (SEQ ID NO: 395)

ATGGCACTCCCCGTAACTGCTCTGCTGCTGCCGTTGGCATTGCTCCTGCACGCCGCACGCCCG
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATAGCGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGCACCACGTCTGGCCTCTCACTTTTGGCGGAGGGACCAAGGTTGAG
ATCAAACGGGGGTCTACATCCGGCTCCGGGAAGCCCGGAAGTGGCGAAGGTAGTACAAAGGGG
CAGGTGCGGCTGGTGGAGTCTGGGGGGGGCGTGGTCCAGCCTGGGAGGTCCCTGAGACTCTCC
TGTGCAGCGTCTGGATTCACCTTCAGTAGCTATGGCATACACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGCTTTTGGGATGGACGTATGGGGCCAGGGAACAACTGTCACCGTCTCCTCAGCCGCTGCC
CTTGATAATGAAAAGTCAAACGGAACAATCATTCACGTGAAGGGCAAGCACCTCTGTCCGTCA
CCCTTGTTCCCTGGTCCATCCAAGCCATTCTGGGTGTTGGTCGTAGTGGGTGGAGTCCTCGCT
TGTTACTCTCTGCTCGTCACCGTGGCTTTTATAATCTTCTGGGTTAGATCCAAAAGAAGCCGC
CTGCTCCATAGCGATTACATGAATATGACTCCACGCCGCCCTGGCCCCACAAGGAAACACTAC
CAGCCTTACGCACCACCTAGAGATTTCGCTGCCTATCGGAGCAGGGTGAAGTTTTCCAGATCT
GCAGATGCACCAGCGTATCAGCAGGGCCAGAACCAACTGTATAACGAGCTCAACCTGGGACGC
AGGGAAGAGTATGACGTTTTGGACAAGCGCAGAGGACGGGACCCTGAGATGGGTGGCAAACCA
AGACGAAAAAACCCCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGACGGTTTGTACCAG
GGACTCAGCACTGCTACGAAGGATACTTATGACGCTCTCCACATGCAAGCCCTGCCACCTAGG

FIG. 15J

Clone RD-26576 CAR LxH (SEQ ID NO: 396)

MALPVTALLL PLALLLHAAR PEIVMTQSPA TLSVSPGERA TLSCRASQSV
SSNLAWYQQK PGQAPRLLIY SASTRATGIP ARFSGSGSGT EFTLTISSLQ
SEDFAVYYCQ QHHVWPLTFG GGTKVEIKRG STSGSGKPGS GEGSTKGQVR
LVESGGGVVQ PGRSLRLSCA ASGFTFSSYG IHWVRQAPGK GLEWVAVIGY
DGQEKYYADS VKGRFTISRD NSKNTLYLQM NSLRAEDTAV YYCVKGPLQE
PPYAFGMDVW GQGTTVTVSS AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

FIG. 16A

Clone RD-26578 HC DNA (SEQ ID NO: 397)

CAGGTGCAGCTGGTGGAGTCTGGGGGAGGCGTGGTCCAGCCTGGGAGGTCCCTGAGACTCTCC
TGTGCAGCGTCTGGATTCACCTTCAGTAGCCGTGGCATGCACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGATTATGGAATGGACGTATGGGGCCAGGGAACAACTGTCACCGTCTCCTCA

FIG. 16B

Clone RD-26578 HC (SEQ ID NO: 398) CDRs 1, 2, and 3 are underlined.

QVQLVESGGG VVQPGRSLRL SCAASG<u>FTFS</u> <u>SRGMH</u>WVRQA PGKGLEWVA<u>V</u>
<u>IGYDGQEKYY</u> <u>ADSVKG</u>RFTI SRDNSKNTLY LQMNSLRAED TAVYYC<u>VKGP</u>
<u>LQEPPYDYGM</u> <u>DV</u>WGQGTTVT VSS

FIG. 16C

FTFSSRGMH (SEQ ID NO: 399) (HC CDR1)

VIGYDGQEKYYADSVKG (SEQ ID NO: 400) (HC CDR2)

VKGPLQEPPYDYGMDV (SEQ ID NO: 401) (HC CDR3)

FIG. 16D

Clone RD-26578 LC DNA (SEQ ID NO: 402)

GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATAGCGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGCACCACGTCTGGCCTCTCACTTTTGGCGGAGGGACCAAGGTTGAG
ATCAAACGG

FIG. 16E

Clone RD-26578 LC (SEQ ID NO: 403). CDRs 1, 2, and 3 are underlined.

EIVMTQSPAT LSVSPGERAT LSC<u>RASQSVS</u> <u>SNLA</u>WYQQKP GQAPRLLIY<u>S</u>
<u>ASTRAT</u>GIPA RFSGSGSGTE FTLTISSLQS EDFAVYYC<u>QQ</u> <u>HHVWPLT</u>FGG GTKVEIKR

FIG. 16F

RASQSVSSNLA (SEQ ID NO: 404) (LC CDR1)

SASTRAT (SEQ ID NO: 405) (LC CDR2)

QQHHVWPLT (SEQ ID NO: 406) (LC CDR3)

FIG. 16G

Clone RD-26578 CAR DNA HxL (SEQ ID NO: 407)

ATGGCACTCCCCGTAACTGCTCTGCTGCTGCCGTTGGCATTGCTCCTGCACGCCGCACGCCCG
CAGGTGCAGCTGGTGGAGTCTGGGGGAGGCGTGGTCCAGCCTGGGAGGTCCCTGAGACTCTCC
TGTGCAGCGTCTGGATTCACCTTCAGTAGCCGTGGCATGCACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGATTATGGAATGGACGTATGGGGCCAGGGAACAACTGTCACCGTCTCCTCAGGGTCTACA
TCCGGCTCCGGGAAGCCCGGAAGTGGCGAAGGTAGTACAAAGGGGGAAATAGTGATGACGCAG
TCTCCAGCCACCCTGTCTGTGTCTCCAGGGGAAAGAGCCACCCTCTCCTGCAGGGCCAGTCAG
AGTGTTAGCAGCAACTTAGCCTGGTACCAGCAGAAACCTGGCCAGGCTCCCAGGCTCCTCATC
TATAGCGCATCCACCAGGGCCACTGGTATCCCAGCCAGGTTCAGTGGCAGTGGGTCTGGGACA
GAGTTCACTCTCACCATCAGCAGCCTGCAGTCTGAAGATTTTGCAGTTTATTACTGTCAGCAG
CACCACGTCTGGCCTCTCACTTTTGGCGGAGGGACCAAGGTTGAGATCAAACGGGCCGCTGCC
CTTGATAATGAAAAGTCAAACGGAACAATCATTCACGTGAAGGGCAAGCACCTCTGTCCGTCA
CCCTTGTTCCCTGGTCCATCCAAGCCATTCTGGGTGTTGGTCGTAGTGGGTGGAGTCCTCGCT
TGTTACTCTCTGCTCGTCACCGTGGCTTTTATAATCTTCTGGGTTAGATCCAAAAGAAGCCGC
CTGCTCCATAGCGATTACATGAATATGACTCCACGCCGCCCTGGCCCCACAAGGAAACACTAC
CAGCCTTACGCACCACCTAGAGATTTCGCTGCCTATCGGAGCAGGGTGAAGTTTTCCAGATCT
GCAGATGCACCAGCGTATCAGCAGGGCCAGAACCAACTGTATAACGAGCTCAACCTGGGACGC
AGGGAAGAGTATGACGTTTTGGACAAGCGCAGAGGACGGGACCCTGAGATGGGTGGCAAACCA
AGACGAAAAAACCCCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGACGGTTTGTACCAG
GGACTCAGCACTGCTACGAAGGATACTTATGACGCTCTCCACATGCAAGCCCTGCCACCTAGG

FIG. 16H

Clone RD-26578 CAR HxL (SEQ ID NO: 408)

MALPVTALLL PLALLLHAAR PQVQLVESGG GVVQPGRSLR LSCAASGFTF
SSRGMHWVRQ APGKGLEWVA VIGYDGQEKY YADSVKGRFT ISRDNSKNTL
YLQMNSLRAE DTAVYYCVKG PLQEPPYDYG MDVWGQGTTV TVSSGSTSGS
GKPGSGEGST KGEIVMTQSP ATLSVSPGER ATLSCRASQS VSSNLAWYQQ
KPGQAPRLLI YSASTRATGI PARFSGSGSG TEFTLTISSL QSEDFAVYYC
QQHHVWPLTF GGGTKVEIKR AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

FIG. 16I

Clone RD-26578 CAR DNA LxH (SEQ ID NO: 409)

ATGGCACTCCCCGTAACTGCTCTGCTGCTGCCGTTGGCATTGCTCCTGCACGCCGCACGCCCG
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATAGCGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGCACCACGTCTGGCCTCTCACTTTTGGCGGAGGGACCAAGGTTGAG
ATCAAACGGGGGTCTACATCCGGCTCCGGGAAGCCCGGAAGTGGCGAAGGTAGTACAAAGGGG
CAGGTGCAGCTGGTGGAGTCTGGGGGAGGCGTGGTCCAGCCTGGGAGGTCCCTGAGACTCTCC
TGTGCAGCGTCTGGATTCACCTTCAGTAGCCGTGGCATGCACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGATTATGGAATGGACGTATGGGGCCAGGGAACAACTGTCACCGTCTCCTCAGCCGCTGCC
CTTGATAATGAAAAGTCAAACGGAACAATCATTCACGTGAAGGGCAAGCACCTCTGTCCGTCA
CCCTTGTTCCCTGGTCCATCCAAGCCATTCTGGGTGTTGGTCGTAGTGGGTGGAGTCCTCGCT
TGTTACTCTCTGCTCGTCACCGTGGCTTTTATAATCTTCTGGGTTAGATCCAAAAGAAGCCGC
CTGCTCCATAGCGATTACATGAATATGACTCCACGCCGCCCTGGCCCCACAAGGAAACACTAC
CAGCCTTACGCACCACCTAGAGATTTCGCTGCCTATCGGAGCAGGGTGAAGTTTTCCAGATCT
GCAGATGCACCAGCGTATCAGCAGGGCCAGAACCAACTGTATAACGAGCTCAACCTGGGACGC
AGGGAAGAGTATGACGTTTTGGACAAGCGCAGAGGACGGGACCCTGAGATGGGTGGCAAACCA
AGACGAAAAAACCCCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGACGGTTTGTACCAG
GGACTCAGCACTGCTACGAAGGATACTTATGACGCTCTCCACATGCAAGCCCTGCCACCTAGG

FIG. 16J

Clone RD-26578 CAR LxH (SEQ ID NO: 410)

MALPVTALLL PLALLLHAAR PEIVMTQSPA TLSVSPGERA TLSCRASQSV
SSNLAWYQQK PGQAPRLLIY SASTRATGIP ARFSGSGSGT EFTLTISSLQ
SEDFAVYYCQ QHHVWPLTFG GGTKVEIKRG STSGSGKPGS GEGSTKGQVQ
LVESGGGVVQ PGRSLRLSCA ASGFTFSSRG MHWVRQAPGK GLEWVAVIGY
DGQEKYYADS VKGRFTISRD NSKNTLYLQM NSLRAEDTAV YYCVKGPLQE
PPYDYGMDVW GQGTTVTVSS AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

BCMA BINDING MOLECULES AND METHODS OF USE THEREOF

CROSS REFERENCE TO RELATED APPLICATIONS

This application claims the benefit of U.S. Provisional Patent Application No. 62/317,334, filed Apr. 1, 2016, which is hereby incorporated by reference in its entirety.

REFERENCE TO SEQUENCE LISTING

The instant application contains a Sequence Listing which has been submitted electronically in ASCII format and is hereby incorporated by reference in its entirety. Said ASCII copy, created on Jun. 11, 2019, is named K-1030 02US SL.txt and is 396,355 bytes in size.

FIELD OF THE INVENTION

This invention relates to chimeric antigen receptors (CARs) and engineered T cell receptors (TCRs) comprising an antigen binding molecule which binds to B-cell maturation antigen (BCMA), polynucleotides encoding the same, and methods of treating a cancer or other disease or disorder in a patient using the same.

BACKGROUND OF THE INVENTION

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Human T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen.

Current therapies for hematologic malignancies have shown varying levels of effectiveness with undesired side effects. Therefore, a need exists to identify novel and improved therapies for treating BCMA related diseases and disorders.

SUMMARY OF THE INVENTION

The present invention is directed to an isolated polynucleotide encoding a chimeric antigen receptor (CAR) or T cell receptor (TCR) comprising a binding molecule that specifically binds to B-cell maturation antigen (BCMA), wherein the binding molecule comprises: (a) a heavy chain variable region (VH) complementarity determining region (CDR) 1 comprising, consisting of, or consisting essentially of the amino acid sequence $GX_2X_3X_4X_5X_6X_7SY$ (SEQ ID NO: 145) wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$ is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y; and/or (d) a light chain variable region (VL) CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; (e) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (f) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In another embodiment, the invention is directed to an isolated polynucleotide encoding an antibody or an antigen binding molecule thereof that specifically binds to BCMA, wherein the antibody or the antigen binding molecule thereof comprises: (a) a heavy chain variable region (VH) complementarity determining region (CDR) 1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$ is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y;

$X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y; and/or (d) a light chain variable region (VL) CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; (e) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (f) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In some embodiments, the VH CDR1 comprises an amino acid sequence selected from the group consisting of SEQ ID NO: 9-16. In some embodiments, the VH CDR2 comprises an amino acid sequence selected from the group consisting of SEQ ID NO: 25-32. In some embodiments, the VL CDR1 comprises an amino acid sequence selected from the group consisting of SEQ ID NO: 81-88. In some embodiments, the VL CDR2 comprises an amino acid sequence selected from the group consisting of SEQ ID NO: 97-104. In some embodiments, the VL CDR3 comprises an amino acid sequence selected from the group consisting of SEQ ID NO: 113-120.

In some embodiments, the binding molecule comprises: (a) a VH CDR1 region comprising the amino acid sequence of SEQ ID NO: 9; a VH CDR2 region comprising the amino acid sequence of SEQ ID NO: 25; a VH CDR3 region comprising the amino acid sequence of SEQ ID NO: 41; a VL CDR1 region comprising the amino acid sequence of SEQ ID NO: 81; a VL CDR2 region comprising the amino acid sequence of SEQ ID NO: 97; and a VL CDR3 region comprising the amino acid sequence of SEQ ID NO: 113; (b) a VH CDR1 region comprising the amino acid sequence of SEQ ID NO: 10; a VH CDR2 region comprising the amino acid sequence of SEQ ID NO: 26; a VH CDR3 region comprising the amino acid sequence of SEQ ID NO: 42; a VL CDR1 region comprising the amino acid sequence of SEQ ID NO: 82; a VL CDR2 region comprising the amino acid sequence of SEQ ID NO: 98; and a VL CDR3 region comprising the amino acid sequence of SEQ ID NO: 114; (c) a VH CDR1 region comprising the amino acid sequence of SEQ ID NO: 11; a VH CDR2 region comprising the amino acid sequence of SEQ ID NO: 27; a VH CDR3 region comprising the amino acid sequence of SEQ ID NO: 43; a VL CDR1 region comprising the amino acid sequence of SEQ ID NO: 83; a VL CDR2 region comprising the amino acid sequence of SEQ ID NO: 99; and a VL CDR3 region comprising the amino acid sequence of SEQ ID NO: 115; (d) a VH CDR1 region comprising the amino acid sequence of SEQ ID NO: 12; a VH CDR2 region comprising the amino acid sequence of SEQ ID NO: 28; a VH CDR3 region comprising the amino acid sequence of SEQ ID NO: 44; a VL CDR1 region comprising the amino acid sequence of SEQ ID NO: 84; a VL CDR2 region comprising the amino acid sequence of SEQ ID NO: 100; and a VL CDR3 region comprising the amino acid sequence of SEQ ID NO: 116; (e) a VH CDR1 region comprising the amino acid sequence of SEQ ID NO: 13; a VH CDR2 region comprising the amino acid sequence of SEQ ID NO: 29; a VH CDR3 region comprising the amino acid sequence of SEQ ID NO: 45; a VL CDR1 region comprising the amino acid sequence of SEQ ID NO: 85; a VL CDR2 region comprising the amino acid sequence of SEQ ID NO: 101; and a VL CDR3 region comprising the amino acid sequence of SEQ ID NO: 117; (f) a VH CDR1 region comprising the amino acid sequence of SEQ ID NO: 14; a VH CDR2 region comprising the amino acid sequence of SEQ ID NO: 30; a VH CDR3 region comprising the amino acid sequence of SEQ ID NO: 46; a VL CDR1 region comprising the amino acid sequence of SEQ ID NO: 86; a VL CDR2 region comprising the amino acid sequence of SEQ ID NO: 102; and a VL CDR3 region comprising the amino acid sequence of SEQ ID NO: 118; (g) a VH CDR1 region comprising the amino acid sequence of SEQ ID NO: 15; a VH CDR2 region comprising the amino acid sequence of SEQ ID NO: 31; a VH CDR3 region comprising the amino acid sequence of SEQ ID NO: 47; a VL CDR1 region comprising the amino acid sequence of SEQ ID NO: 87; a VL CDR2 region comprising the amino acid sequence of SEQ ID NO: 103; and a VL CDR3 region comprising the amino acid sequence of SEQ ID NO: 119; or (h) a VH CDR1 region comprising the amino acid sequence of SEQ ID NO: 16; a VH CDR2 region comprising the amino acid sequence of SEQ ID NO: 32; a VH CDR3 region comprising the amino acid sequence of SEQ ID NO: 48; a VL CDR1 region comprising the amino acid sequence of SEQ ID NO: 88; a VL CDR2 region comprising the amino acid sequence of SEQ ID NO: 104; and a VL CDR3 region comprising the amino acid sequence of SEQ ID NO: 120.

In some embodiments, the binding molecule is single chained. In some embodiments, the binding molecule comprises an scFv.

In some embodiments, the CAR comprises a transmembrane domain. In some embodiments, the transmembrane domain is a transmembrane domain of CD28, 4-1BB/CD137, CD8 (e.g., CD8 alpha, CD4, CD19, CD3 epsilon, CD45, CD5, CD9, CD16, CD22, CD33, CD37, CD64, CD80, CD86, CD134, CD137, CD154, an alpha chain of a T cell receptor, a beta chain of a T cell receptor, a zeta chain of a T cell receptor, or any combination thereof. In some embodiments, the CAR comprises a hinge region between the transmembrane domain and the binding molecule. In some embodiments, the hinge region is of IgG1, IgG2, IgG3, IgG4, IgA, IgD, IgE, IgM, CD28, or CD8 alpha. In some embodiments, the CAR or TCR comprises a costimulatory region. In some embodiments, the costimulatory region is a signaling region of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1 (CD11a/CD18), CD3 gamma, CD3 delta, CD3 epsilon, CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/

RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof. In some embodiments, the CAR or TCR comprises an activation domain. In some embodiments, the activation domain is a CD3 zeta domain.

In other embodiments, the invention is directed to a vector comprising the polynucleotide or a polypeptide encoded by the polynucleotide.

In certain embodiments, the invention is directed to a cell comprising the polynucleotide, the vector, the polypeptide, or any combination thereof. In other embodiments, the invention is directed to a cell, e.g., an immune cell, e.g., a tumor-infiltrating lymphocyte (TIL), autologous T cell, engineered autologous T cell (eACT), an allogeneic T cell, or any combination thereof.

In other embodiments, the invention is directed to a method of inducing an immunity against a tumor comprising administering to a subject an effective amount of a cell comprising the polynucleotide, the vector, the polypeptide, or any combination thereof. Other aspects of the invention include a method of treating a cancer in a subject in need thereof comprising administering to the subject the polynucleotide, the vector, the polypeptide, the cell, or the composition. The cancer treatable by the method can be a hematologic cancer.

BRIEF DESCRIPTION OF THE FIGURES

FIG. 1A-1F show CLUTSTAL W (1.83) multiple sequence alignments of eight example anti-BCMA binding molecules disclosed herein. FIG. 1A shows a sequence alignment of example anti-BCMA binding molecules comprising a VH domain. Complementarity determining regions (CDRs) and framework regions (FRs) are shown, as determined by Chothia. FIG. 1B is a table providing the SEQ ID NO for each VH, CDR, and FR sequence illustrated in FIG. 1A. FIG. 1C shows a sequence alignment of example anti-BCMA binding molecules comprising a VH domain, with alternate CDRs and FRs shown. FIG. 1D is a table providing the SEQ ID NO for each VH, CDR, and FR sequence illustrated in FIG. 1C. FIG. 1E shows a sequence alignment of example anti-BCMA binding molecules comprising a VL domain. CDRs and FRs are shown, as determined by Chothia. FIG. 1F is a table providing the SEQ ID NO for each VH, CDR, and FR sequence illustrated in FIG. 1E.

FIGS. 2A-2F show BCMA expression in various cells. FIG. 2A shows multiple myeloma cell expression of BCMA, CD138, CS-1, CD38, and CD19. Box-plot analysis shows the distribution of gene expression levels in the various multiple myeloma cell lines tested (FIG. 2A). FIGS. 2B-2D show BCMA expression in EoL1 (FIG. 2B), MM1S (FIG. 2C), and NCI-H929 (FIG. 2D) cancer cell lines as measured by flow cytometric analysis of BCMA cell surface expression on the respective cell lines. FIG. 2E shows the expression of BCMA, CS-1, CLL-1, DLL3, CD70, and FLT3 in alternatively activated macrophages; CD14-positive, CD16-negative cells; CD38-negative naïve B cells; CD4-positive, alpha-beta T cells; central memory CD4-positive cells; central memory CD8-positive cells; class switched memory B cells; cytotoxic CD56-dim natural killer cell; effector memory CD4-positive cells; effector memory CD8-positive cells; inflammatory macrophages; macrophages; mature neutrophils; memory B cells; monocytes; myeloid cells; and regulatory T cells. FIG. 2F shows the expression of BCMA, CD138, CS-1, CD38, and CD19 in the same cell types as in FIG. 2E. Gene expression is shown as fragments per kilobase of exon per million reads mapped (FPKM) (FIG. 2A, FIG. 2E, and FIG. 2F).

FIGS. 4A and 4B show the IFNγ (pg/ml; y-axis) production in lentivirus transduced CAR T cells from a first donor (FIG. 4A) and a second donor (FIG. 4B). FIGS. 4C and 4D show the TNFα (pg/ml; y-axis) production in lentivirus transduced CAR T cells from a first donor (FIG. 4C) and a second donor (FIG. 4D). FIGS. 4E and 4F show the IL-2 production (pg/ml; y-axis) in lentivirus transduced CAR T cells from a first donor (FIG. 4E) and a second donor (FIG. 4F).

FIGS. 5A and 5B show the average cytolytic activity of transduced CAR T cells from a first donor (FIG. 5A) and a second donor (FIG. 5B) co-cultured with EoL1 target cells for 16 hours, 40 hours, 64 hours, 88 hours, or 112 hours. FIGS. 5C and 5D show the average cytolytic activity of transduced CAR T cells from a first donor (FIG. 5C) and a second donor (FIG. 5D) co-cultured with NCI-H929 target cells for 16 hours, 40 hours, 64 hours, 88 hours, or 112 hours. FIGS. 5E and 5F show the average cytolytic activity of transduced CAR T cells from a first donor (FIG. 5E) and a second donor (FIG. 5F) co-cultured with MM1S target cells for 16 hours, 40 hours, 64 hours, 88 hours, or 112 hours.

Figures 2B, 2C, 2D:
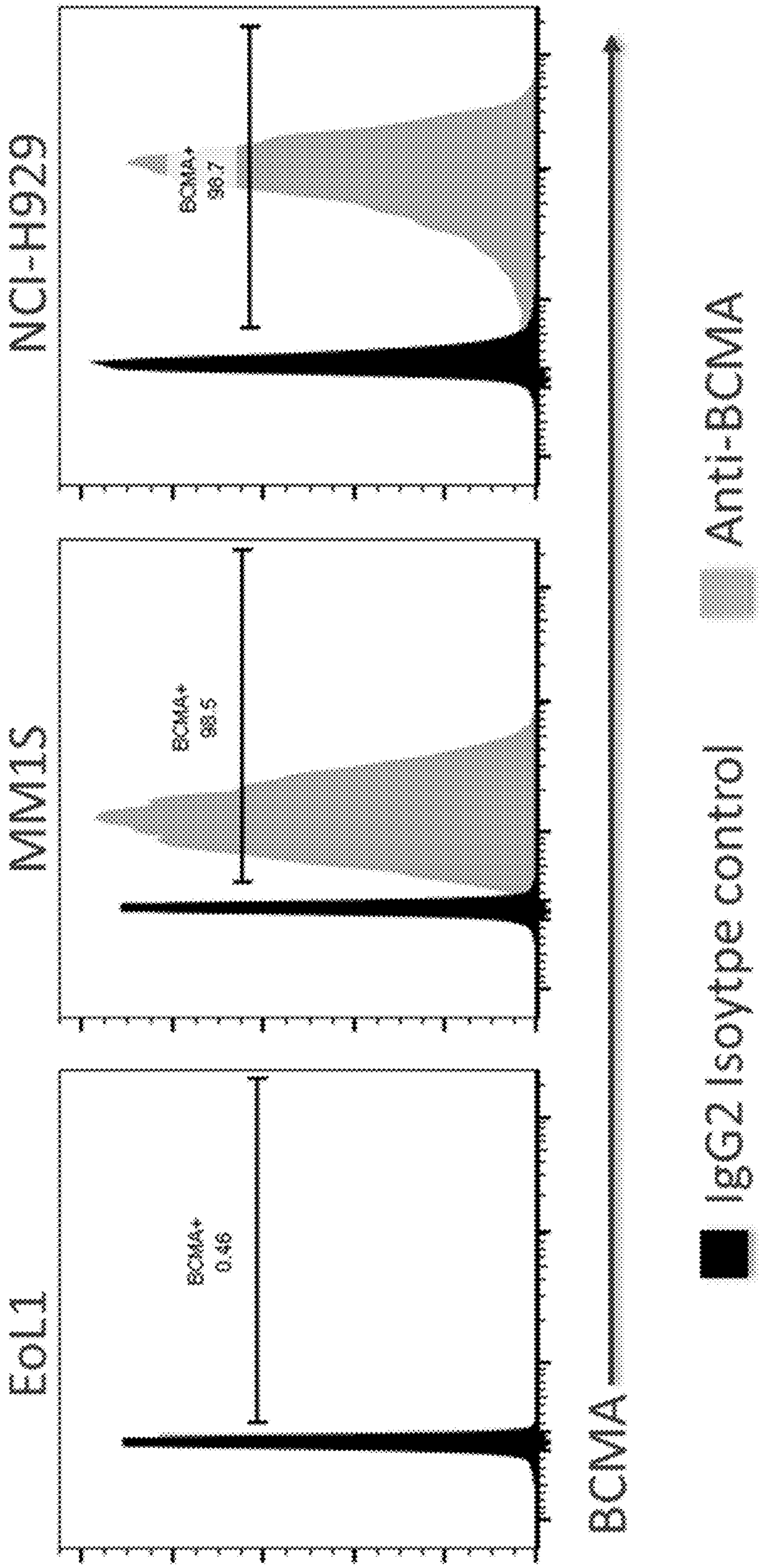

In the Figure descriptions below, underlined sequences denote CDR regions calculated using Chothia.

FIG. 7A shows Clone FS-26528 HC DNA sequence (SEQ ID NO: 271)

FIG. 7B shows Clone FS-26528 HC AA sequence (SEQ ID NO: 272)

FIG. 7C shows HC CDR sequences for clone FS-26528.

FIG. 7D shows Clone FS-26528 LC DNA sequence (SEQ ID NO: 276).

FIG. 7E shows Clone FS-26528 LC AA sequence (SEQ ID NO: 277).

FIG. 7F shows LC CDR sequences for clone FS-26528.

FIG. 7G shows Clone FS-26528 CAR DNA HxL sequences (SEQ ID NO: 281)

FIG. 7H shows Clone FS-26528 CAR HxL AA sequences (SEQ ID NO: 282)

FIG. 7I shows Clone FS-26528 CAR DNA LxH sequences (SEQ ID NO: 283).

FIG. 7J shows Clone FS-26528 CAR LxH sequences (SEQ ID NO: 284).

FIG. 8A shows Clone PC-26534 HC DNA sequence (SEQ ID NO: 285).

FIG. 8B shows Clone PC-26534 HC sequence (SEQ ID NO: 286).

FIG. 8C shows HC CDR sequences for clone FS-26528.

FIG. 8D shows Clone PC-26534 LC DNA sequences (SEQ ID NO: 290).

FIG. 8E shows the Clone PC-26534 LC sequence (SEQ ID NO: 291).

FIG. 8F shows LC CDR sequences for Clone PC-26534.

FIG. 8G shows the Clone PC-26534 CAR DNA HxL sequence (SEQ ID NO: 295).

FIG. 8H shows the Clone PC-26534 CAR HxL AA sequence (SEQ ID NO: 296)

FIG. 8I shows the Clone PC-26534 CAR DNA LxH sequence (SEQ ID NO: 297).

FIG. 8J shows Clone PC-26534 CAR LxH sequence (SEQ ID NO: 298).

FIG. 9A shows Clone AJ-26545 HC DNA sequence (SEQ ID NO: 299).

FIG. 9B shows Clone AJ-26545 variable HC sequence (SEQ ID NO: 300).

FIG. 9C shows HC CDR sequences for Clone AJ-26545.

FIG. 9D shows Clone AJ-26545 variable LC DNA sequence (SEQ ID NO: 304).

FIG. 9E shows Clone AJ-26545 variable LC AA sequence (SEQ ID NO: 305)

FIG. 9F shows Clone AJ-26545 LC CDR sequences.

FIG. 9G shows Clone AJ-26545 CAR DNA HxL sequence (SEQ ID NO: 309).

FIG. 9H shows Clone AJ-26545 CAR HxL AA sequence (SEQ ID NO: 310)

FIG. 9I shows Clone AJ-26545 CAR DNA LxH sequence (SEQ ID NO: 311)

FIG. 9J shows Clone AJ-26545 CAR LxH sequence (SEQ ID NO: 312).

FIG. 10A shows Clone AJ-26554 HC DNA sequence (SEQ ID NO: 313)

FIG. 10B shows Clone AJ-26554 HC AA sequence (SEQ ID NO: 314).

FIG. 10C shows Clone AJ-26554 HC CDR sequences

FIG. 10D shows Clone AJ-26554 LC DNA sequence (SEQ ID NO: 318).

FIG. 10E shows Clone AJ-26554 LC AA sequence (SEQ ID NO: 319).

FIG. 10F shows Clone AJ-26554 LC CDR sequences.

FIG. 10G shows Clone AJ-26554 CAR DNA HxL chain sequences (SEQ ID NO: 323).

FIG. 10H shows Clone AJ-26554 CAR HxL chain AA sequences (SEQ ID NO: 324).

FIG. 10I shows Clone AJ-26554 CAR DNA LxH chain sequences (SEQ ID NO: 325).

FIG. 10J shows Clone AJ-26554 CAR LxH AA sequences (SEQ ID NO: 326).

FIG. 11A shows Clone NM-26562 HC DNA sequence (SEQ ID NO: 327).

FIG. 11B shows Clone NM-26562 HC AA sequence (SEQ ID NO: 328).

FIG. 11C shows Clone NM-26562 HC CDR sequences.

FIG. 11D shows Clone NM-26562 LC DNA sequence (SEQ ID NO: 332).

FIG. 11E shows Clone NM-26562 LC AA sequence (SEQ ID NO: 333).

FIG. 11F shows the Clone NM-26562 LC CDR sequences.

FIG. 11G shows the Clone NM-26562 CAR DNA HxL sequences (SEQ ID NO: 337)

FIG. 11H shows Clone NM-26562 CAR HxL AA sequences (SEQ ID NO: 338).

FIG. 11I shows Clone NM-26562 CAR DNA LxH sequences (SEQ ID NO: 339).

FIG. 11J shows Clone NM-26562 CAR LxH AA sequences (SEQ ID NO: 340).

FIG. 12A shows Clone TS-26564 HC DNA sequence (SEQ ID NO: 341).

FIG. 12B shows Clone TS-26564 HC AA sequence (SEQ ID NO: 342).

FIG. 12C shows the Clone TS-26564 HC CDR sequences.

FIG. 12D shows the Clone TS-26564 LC DNA sequence (SEQ ID NO: 346).

FIG. 12E shows the Clone TS-26564 LC AA sequence (SEQ ID NO: 347).

FIG. 12F shows the Clone TS-26564 LC CDR sequences.

FIG. 12G shows the Clone TS-26564 CAR DNA HxL sequences (SEQ ID NO: 351).

FIG. 12H shows the Clone TS-26564 CAR HxL chain AA sequences (SEQ ID NO: 352).

FIG. 12I shows the Clone TS-26564 CAR DNA LxH sequences (SEQ ID NO: 353)

FIG. 12J shows the Clone TS-26564 CAR LxH AA sequences (SEQ ID NO: 354)

FIG. 13A shows the Clone RY-26568 HC DNA sequence (SEQ ID NO: 355)

FIG. 13B shows the Clone RY-26568 HC AA sequence (SEQ ID NO: 356).

FIG. 13C shows the Clone RY-26568 HC CDR sequences.

FIG. 13D shows the Clone RY-26568 LC DNA sequence (SEQ ID NO: 360).

FIG. 13E shows the Clone RY-26568 LC AA sequence (SEQ ID NO: 361).

FIG. 13F shows the Clone RY-26568 LC CDR AA sequences.

FIG. 13G shows the Clone RY-26568 CAR DNA HxL sequences (SEQ ID NO: 365)

FIG. 13H shows the Clone RY-26568 CAR HxL AA sequences (SEQ ID NO: 366).

FIG. 13I shows the Clone RY-26568 CAR DNA LxH sequences (SEQ ID NO: 367).

FIG. 13J shows the Clone RY-26568 CAR LxH AA sequences (SEQ ID NO: 368).

FIG. 14A shows the Clone PP-26575 HC DNA sequence (SEQ ID NO: 369).

FIG. 14B shows the Clone PP-26575 HC AA sequence (SEQ ID NO: 370).

FIG. 14C shows the Clone PP-26575 HC CDR AA sequences.

FIG. 14D shows the Clone PP-26575 LC DNA sequence (SEQ ID NO: 374).

FIG. 14E shows the Clone PP-26575 LC AA sequence (SEQ ID NO: 375).

FIG. 14F shows the Clone PP-26575 LC CDR AA sequences.

FIG. 14G shows the Clone PP-26575 CAR DNA HxL sequences (SEQ ID NO: 379).

FIG. 14H shows Clone PP-26575 CAR HxL AA sequences (SEQ ID NO: 380).

FIG. 14I shows Clone PP-26575 CAR DNA LxH sequence (SEQ ID NO: 381).

FIG. 14J shows the Clone PP-26575 CAR LxH AA sequence (SEQ ID NO: 382).

FIG. 15A shows the Clone RD-26576 HC DNA sequence (SEQ ID NO: 383)

FIG. 15B shows Clone RD-26576 HC AA sequence (SEQ ID NO: 384).

FIG. 15C shows the Clone RD-26576 HC CDR sequences.

FIG. 15D shows the Clone RD-26576 LC DNA sequence (SEQ ID NO: 388)

FIG. 15E shows the Clone RD-26576 LC AA sequence (SEQ ID NO: 389).

FIG. 15F shows the Clone RD-26576 LC CDR sequences.

FIG. 15G shoes the Clone RD-26576 CAR DNA HxL sequences (SEQ ID NO: 393).

FIG. 15H shows the Clone RD-26576 CAR HxL chain AA sequences (SEQ ID NO: 394).

FIG. 15I shows the Clone RD-26576 CAR DNA LxH sequences (SEQ ID NO: 395).

FIG. 15J shows the Clone RD-26576 CAR LxH AA sequences (SEQ ID NO: 396).

FIG. 16A shows the Clone RD-26578 HC DNA sequences (SEQ ID NO: 397).

FIG. 16B shows the Clone RD-26578 HC AA sequence (SEQ ID NO: 398).

FIG. 16C shows the Clone RD-26578 HC CDR AA sequences.

FIG. 16D shows the Clone RD-26578 LC DNA sequence (SEQ ID NO: 402).

FIG. 16E shows the Clone RD-26578 LC AA sequence (SEQ ID NO: 403)

FIG. 16F shows the Clone RD-26578 LC CDR sequences.

FIG. 16G shows the Clone RD-26578 CAR DNA HxL chain sequence (SEQ ID NO: 407).

FIG. 16H shows the Clone RD-26578 CAR HxL AA sequence (SEQ ID NO: 408).

FIG. 16I shows the Clone RD-26578 CAR DNA LxH sequences (SEQ ID NO: 409).

FIG. 16J shows the Clone RD-26578 CAR LxH AA sequence (SEQ ID NO: 410).

Figure 17:
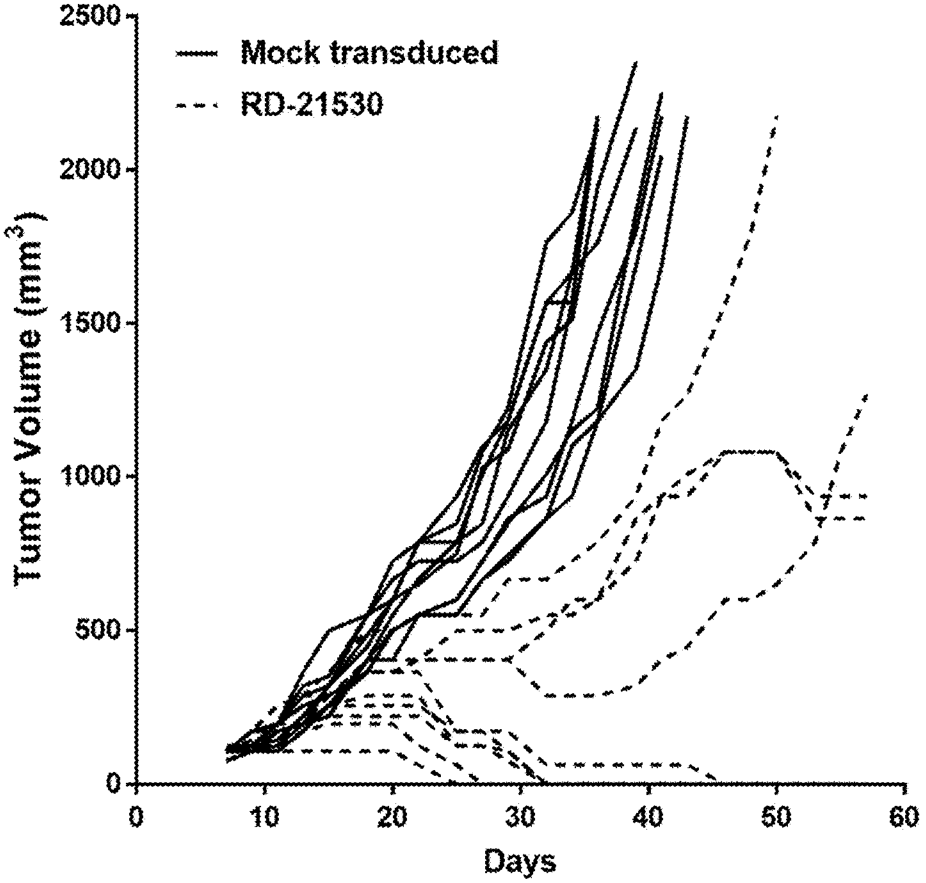

FIG. 17 shows the outcome of an in vivo study examining the efficacy of clone RD-21530 in a subcutaneous RPMI-8226 mouse model. Cohorts of 10 mice each were tested for the CAR (dashed lines) and mock transduced (bolded lines) T cells.

Figure 18A:
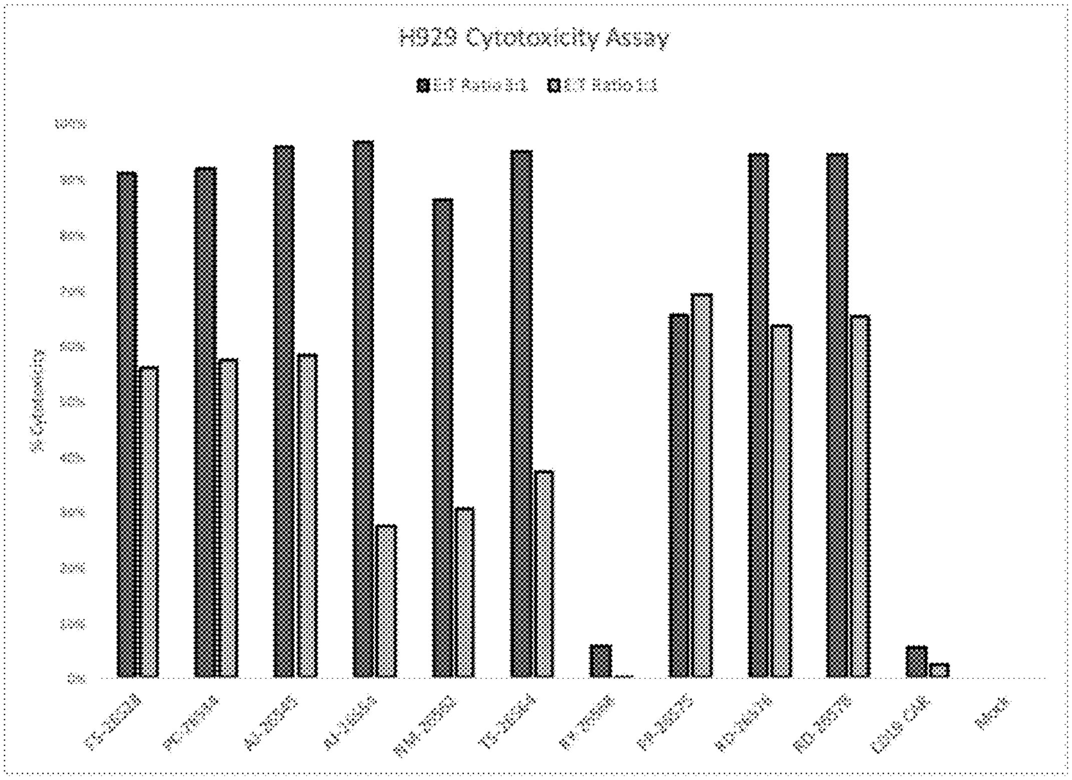
Figure 18B:
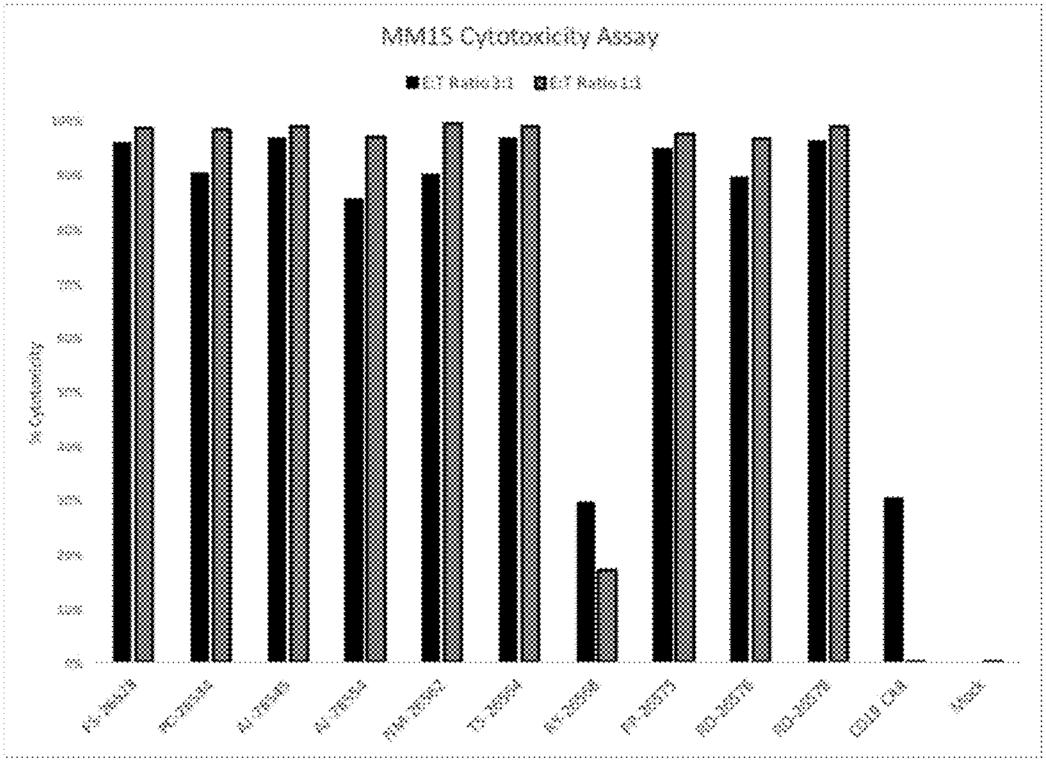

FIG. 18A and FIG. 18B show the outcome of an in vitro cytotoxicity assay using the optimized BCMA scFv variants cocultured with NCI-H929 and MM.1S cells, respectively. CAR T cells using these optimized scFvs were incubated overnight with luciferase labeled target cells in 3:1 and 1:1 effector to target cell ratios.

Figure 19:
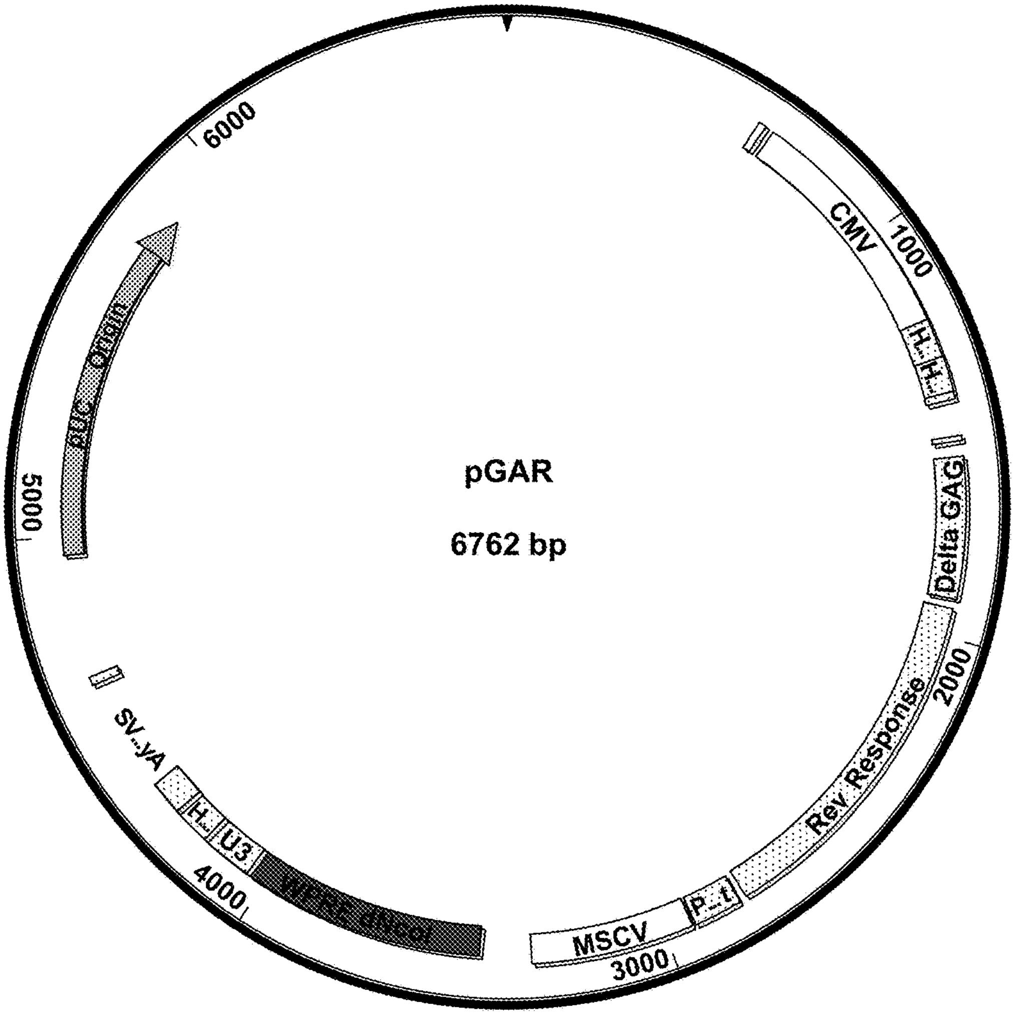

FIG. 19 shows the pGAR vector map.

DETAILED DESCRIPTION OF THE INVENTION

The present invention relates to antibodies, antigen binding molecules thereof, chimeric antigen receptors (CARs), and engineered T cell receptors, which bind BCMA, polynucleotides encoding the same, and in vitro cells comprising the same. The polynucleotides, polypeptides, and in vitro cells described herein can be used in an engineered CAR T cell therapy, e.g., an autologous cell therapy (eACT™), for the treatment of a patient suffering from a cancer. In particular, the polynucleotides, polypeptides, and in vitro cells described herein can be used for the treatment of multiple myeloma.

Definitions

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies can include, for example, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, $F(ab')_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In certain embodiments, antibodies described herein refer to polyclonal antibody populations.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen binding molecule of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments, the antigen binding molecule binds to BCMA. In further embodiments, the antigen binding molecule is an antibody of fragment thereof, including one or more of the complementarity determining regions (CDRs) thereof. In further embodiments, the antigen binding molecule is a single chain variable fragment (scFv). In some embodiments, the antigen binding molecule comprises or consists of avimers.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding fragment thereof.

The terms "VH" and "VH domain" are used interchangeably to refer to the heavy chain variable region of an antibody or an antigen-binding fragment thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

| CDR Numbering | | | | |
|---|---|---|---|---|
| Loop | Kabat | AbM | Chothia | Contact |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32 . . . 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen binding molecule thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding fragment thereof can be replaced with an amino acid residue with a similar side chain.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A:

361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

As used herein, an antigen binding molecule, an antibody, or an antigen binding molecule thereof "cross competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In certain embodiments, an antigen binding molecule that cross competes with a reference antigen binding molecule binds the same or an overlapping epitope as the reference antigen binding molecule. In other embodiments, the antigen binding molecule that cross competes with a reference antigen binding molecule binds a different epitope as the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

In another embodiment, specific embodiment, molecules that specifically bind to an antigen bind with a dissociation constant ($K_d$) of about $1\times10^{-7}$M. In some embodiments, the antigen binding molecule specifically binds an antigen with "high affinity" when the $K_d$ is about $1\times10^{-9}$ M to about $5\times10^{-9}$ M. In some embodiments, the antigen binding molecule specifically binds an antigen with "very high affinity" when the $K_d$ is $1\times10^{-10}$ M to about $5\times10^{-10}$ M. In one embodiment, the antigen binding molecule has a $K_d$ of $10^{-9}$ M. In one embodiment, the off-rate is less than about $1\times10^{-5}$. In other embodiments, the antigen binding molecule binds human BCMA with a $K_d$ of between about $1\times10^{-7}$ M and about $1\times10^{-13}$ M. In yet another embodiment, the antigen binding molecule binds human BCMA with a $K_d$ of about $1\times10^{-10}$ M to about $5\times10^{-10}$ M.

In another specific embodiment, molecules that specifically bind to an antigen do not cross react with other proteins under similar binding conditions. In another specific embodiment, molecules that specifically bind to an antigen do not cross react with other non-BCMA proteins. In a specific embodiment, provided herein is an antibody or fragment thereof that binds to BCMA with higher affinity than to another unrelated antigen. In certain embodiments, provided herein is an antibody or fragment thereof that binds to BCMA (e.g., human BCMA) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-BCMA antibody or antigen-binding fragment thereof described herein to an unrelated, non-BCMA protein is less than 10%, 15%, or 20% of the binding of the antibody to BCMA protein as measured by, e.g., a radioimmunoassay.

In a specific embodiment, provided herein is an antibody or fragment thereof that binds to human BCMA with higher affinity than to another species of BCMA. In certain embodiments, provided herein is an antibody or fragment thereof that binds to human BCMA with a 5%, 10%, 15%, 20%, 25%, 30%, 35%, 40%, 45%, 50%, 55%, 60%, 65%, 70% or higher affinity than to another species of BCMA as measured by, e.g., a radioimmunoassay, surface plasmon resonance, or kinetic exclusion assay. In a specific embodiment, an antibody or fragment thereof described herein, which binds to human BCMA, will bind to another species of BCMA protein with less than 10%, 15%, or 20% of the binding of the antibody or fragment thereof to the human BCMA protein as measured by, e.g., a radioimmunoassay, surface plasmon resonance, or kinetic exclusion assay.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is BCMA.

The term "neutralizing" refers to an antigen binding molecule, scFv, antibody, or a fragment thereof that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the term "BCMA" refers to B cell maturation antigen, which can include, but is not limited to, native BCMA, an isoform of BCMA, or an interspecies BCMA homolog of BCMA. BCMA (also known as TNFRSF17, CD269, and TNFRSF13A) is a member of the tumor necrosis factor (TNF)-receptor superfamily. BCMA is expressed on the surface of multiple myeloma cells, while highly restricted to plasma cells and a subset of mature B cells in healthy tissue (FIG. 2A and FIG. 2C). The amino acid sequence of human BCMA (hBCMA) is provided in NCBI Accession Q02223.2 (GI:313104029) (SEQ ID NO: 163). As used herein, BCMA includes human BCMA and non-human BCMA homologs, as well as variants, fragments, or post-transnationally modified forms thereof, including, but not limited to, N- and O-linked glycosylated forms of BCMA. BCMA proteins may further include fragments comprising all or a portion of the extracellular domain of BCMA (e.g., all or a portion of amino acids 1-54 of hBCMA).

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, myeloma, and other leukocyte malignancies. In some embodiments, the methods of the present invention can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1$\alpha$ (MIP-1$\alpha$, MIP-1a), MIP-1$\beta$ (MIP-1b), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CART cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2R13, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from, e.g., CD28, and the activating domain can be derived from, e.g., CD3-zeta. In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell can include a T cell.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

In some aspects, the polypeptides and/or proteins have deletions from, additions to, and/or substitutions of one or more amino acid of antigen-binding protein, and in some embodiments preferably no more than 8 amino acid substitutions therein. Useful polypeptide fragments may include immunologically functional fragments of antigen binding molecules, including not limited to one or more CDR regions, variable domains of a heavy and/or light chain, a portion of other portions of an antibody chain, and the like. Additionally, polypeptide fragments of activating and/or costimulatory molecules and the like are within the scope of the invention.

"Activation" or "Stimulation" as used herein, refers to a primary response induced by binding of an activating molecule with its cognate ligand, wherein the binding mediates a signal transduction event. An "activating molecule" or "stimulating molecule" refers to a molecule on a T cell, e.g., the TCR/CD3 complex that specifically binds with a cognate stimulatory ligand present on an antigen present cell. Suitable activating molecules are described herein.

A "stimulatory ligand" is a ligand that when present on an antigen presenting cell (e.g., an aAPC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class I molecule loaded with a peptide, an anti-CD3 antibody, a superagonist anti-CD28 antibody, and a superagonist anti-CD2 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand" as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (WIC) molecule loaded with peptide. A co-stimulatory ligand can include, but is not limited to, CD7, B7-1 (CD80), B7-2 (CD86), programmed death (PD) L1, PD-L2, 4-1BB ligand, OX40 ligand, inducible costimulatory ligand (ICOS-L), intercellular adhesion molecule (ICAM), CD30 ligand, CD40, CD70, CD83, human leukocyte antigen G (HLA-G), MHC class I chain-related protein A (MICA), WIC class I chain-related protein B (MICB), herpes virus entry mediator (HVEM), lymphotoxin beta receptor, 3/TR6, immunoglobulin-like transcript (ILT) 3, ILT4, an agonist or antibody that binds Toll ligand receptor and a ligand that specifically binds with B7-H3. A co-stimulatory ligand includes, without limitation, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, tumor necrosis factor superfamily member 14 (TNFSF14 or LIGHT), natural killer cell receptor C (NKG2C), B7-H3, and a ligand that specifically binds with CD83.

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, CD28, CD28T, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD11a/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

II. Binding Molecules and Polynucleotides Encoding the Same

The present invention is directed to a polynucleotide encoding an anti-BCMA antibody or antigen binding molecule thereof which cross competes with one or more antibodies described herein (i.e., one or more described in FIG. 1) or an antibody or antigen binding molecule thereof encoded by the polynucleotide. In one embodiment, the invention is directed to a polynucleotide encoding an anti-BCMA antibody or antigen binding molecule thereof which binds to the same epitope as one or more antibodies described in FIG. 1 or an antibody or antigen binding molecule thereof encoded by the polynucleotide. In some embodiments, the polynucleotide encodes an antibody or antigen binding molecule thereof that specifically binds to BCMA, wherein the antibody or binding molecule comprises a heavy chain VH comprising: (a) a VH CDR1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$ is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y.

In one particular embodiment, the polynucleotide encodes an antibody or antigen binding molecule that specifically binds to BCMA, wherein the antibody or antigen binding molecule comprises a VH comprising: (a) a VH CDR1 comprising, consisting of, or consisting essentially of the amino acid sequence $X_1X_2X_3X_4X_5X_6SYX_9X_{10}X_{11}$ (SEQ ID NO: 263), wherein: $X_1$ is not present or G; $X_2$ is not present or S; $X_3$ is F, G, I, or Y; $X_4$ is S or T; $X_5$ is F or S; $X_6$ is S or T; $X_9$ is A, G, S, or Y; $X_{10}$ is I, M, or W; and $X_{11}$ is G, H, N, or S; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is G or S; $X_8$ is not present or N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}X_{18}X_{19}DX_{21}$ (SEQ ID NO: 264), wherein: $X_1$ is A or V; $X_2$ is K or R; $X_3$ is not present or D, G, or T; $X_4$ is not present or D, G, or P; $X_5$ is not present or F, L, or T; $X_6$ is not present or P, Q, R, W, or Y; $X_7$ is not present or E, G, L, or S; $X_8$ is not present or A, G, P, S, or Y; $X_9$ is not present or A, E, G, P, Q, or S; $X_{10}$ is not present or E, L, M, PS, T, or Y; $X_{11}$ is not present or D, G, H, P, S or W; $X_{12}$ is not present or A, G, I, L, or Y; $X_{13}$ is not present or A, G, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y.

In another embodiment, the polynucleotide encodes an antibody or antigen binding molecule that specifically binds to BCMA, wherein the antibody or antigen binding molecule comprises a VL comprising: (a) a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (b) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (c) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In one particular embodiment, the polynucleotide encodes an antibody or antigen binding molecule that specifically binds to BCMA, wherein the antibody or antigen binding molecule comprises a VH comprising: (a) a VH CDR1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_{11}X_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$ is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y; and/or (d) a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (e) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (f) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In one particular embodiment, the polynucleotide encodes an antibody or antigen binding molecule that specifically binds to BCMA, wherein the antibody or antigen binding molecule comprises a VH comprising: (a) a VH CDR1 comprising, consisting of, or consisting essentially of the amino acid sequence $X_1X_2X_3X_4X_5X_6SYX_9X_{10}X_{11}$ (SEQ ID NO: 263), wherein: $X_1$ is not present or G; $X_2$ is not present or S; $X_3$ is F, G, I, or Y; $X_4$ is S or T; $X_5$ is F or S; $X_6$ is S or T; $X_9$ is A, G, S, or Y; $X_{10}$ is I, M, or W; and $X_{11}$ is G, H, N, or S; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is G or S; $X_8$ is not present or N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}X_{18}X_{19}DX_{21}$ (SEQ ID NO: 264), wherein: $X_1$ is A or V; $X_2$ is K or R; $X_3$ is not present or D, G, or T; $X_4$ is not present or D, G, or P; $X_5$ is not present or F, L, or T; $X_6$ is not present or P, Q, R, W, or Y; $X_7$ is not present or E, G, L, or S; $X_8$ is not present or A, G, P, S, or Y; $X_9$ is not present or A, E, G, P, Q, or S; $X_{10}$ is not present or E, L, M, PS, T, or Y; $X_{11}$ is not present or D, G, H, P, S or W; $X_{12}$ is not present or A, G, I, L, or Y; $X_{13}$ is not present or A, G, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y; and/or (d) a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (e) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (f) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In another embodiment, the polynucleotide encodes an antibody or antigen binding molecule that specifically binds to BCMA, wherein the antibody or antigen binding molecule comprises a VH and a VL, wherein: (i) the VH comprises: (a) a VH CDR1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$ is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y; and (ii) the VL comprises: (a)

a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (b) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (c) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In another embodiment, the polynucleotide encodes an antibody or antigen binding molecule that specifically binds to BCMA, wherein the antibody or antigen binding molecule comprises a VH and a VL, wherein: (i) the VH comprises: (a) a VH CDR1 comprising, consisting of, or consisting essentially of the amino acid sequence $X_1X_2X_3X_4X_5X_6SYX_9X_{10}X_{11}$ (SEQ ID NO: 263), wherein: $X_1$ is not present or G; $X_2$ is not present or S; $X_3$ is F, G, I, or Y; $X_4$ is S or T; $X_5$ is F or S; $X_6$ is S or T; $X_9$ is A, G, S, or Y; $X_{10}$ is I, M, or W; and $X_{11}$ is G, H, N, or S; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is G or S; $X_8$ is not present or N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}X_{18}X_{19}DX_{21}$ (SEQ ID NO: 264), wherein: $X_1$ is A or V; $X_2$ is K or R; $X_3$ is not present or D, G, or T; $X_4$ is not present or D, G, or P; $X_5$ is not present or F, L, or T; $X_6$ is not present or P, Q, R, W, or Y; $X_7$ is not present or E, G, L, or S; $X_8$ is not present or A, G, P, S, or Y; $X_9$ is not present or A, E, G, P, Q, or S; $X_{10}$ is not present or E, L, M, P, S, T, or Y; $X_{11}$ is not present or D, G, H, P, S or W; $X_{12}$ is not present or A, G, I, L, or Y; $X_{13}$ is not present or A, G, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y; and (ii) the VL comprises: (a) a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (b) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (c) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In one embodiment, the antibody or antigen binding molecule, which specifically binds to BCMA (e.g., hBCMA), comprises a VH CDR1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T.

In one embodiment, the antibody or antigen binding molecule, which specifically binds to BCMA (e.g., hBCMA), comprises a VH CDR1 comprising, consisting of, or consisting essentially of the amino acid sequence $GX_2TFSSY$ (SEQ ID NO: 151), wherein: $X_2$ is F or G.

In one embodiment, the antibody or antigen binding molecule, which specifically binds to BCMA (e.g., hBCMA), comprises a VH CDR1 comprising, consisting of, or consisting essentially of the amino acid sequence $GX_2X_3X_4X_5X_6SSY$ (SEQ ID NO: 152), wherein: $X_2$ is not present or G; $X_3$ is not present or S; $X_4$ is F, G, or I; $X_5$ is S or T; and $X_6$ is F or S.

In one embodiment, the antibody or antigen binding molecule, which specifically binds to BCMA (e.g., hBCMA), comprises a VH CDR1 comprising, consisting of, or consisting essentially of the amino acid sequence $X_1X_2X_3X_4X_5X_6SYX_9X_{10}X_{11}$ (SEQ ID NO: 263), wherein: $X_1$ is not present or G; $X_2$ is not present or S; $X_3$ is F, G, I, or Y; $X_4$ is S or T; $X_5$ is F or S; $X_6$ is S or T; $X_9$ is A, G, S, or Y; $X_{10}$ is I, M, or W; and $X_{11}$ is G, H, N, or S.

In one embodiment, the antibody or antigen binding molecule, which specifically binds to BCMA (e.g., hBCMA), comprises a VH CDR1 comprising, consisting of, or consisting essentially of the amino acid sequence $X_1TFX_4SYX_7X_8X_9$ (SEQ ID NO: 265), wherein: $X_1$ is F, G, or Y; $X_4$ is S or T; $X_7$ is A, G, S, or Y; $X_8$ is I or M; and $X_9$ is H, N, or S.

In one embodiment, the antibody or antigen binding molecule, which specifically binds to BCMA (e.g., hBCMA), comprises a VH CDR1 comprising, consisting of, or consisting essentially of the amino acid sequence $FTFSSYX_7MX_9$ (SEQ ID NO: 266), wherein: $X_7$ is A, G, or S; and $X_9$ is H, N, or S.

In one embodiment, the antibody or antigen binding molecule, which specifically binds to BCMA (e.g., hBCMA), comprises a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is G or S; $X_8$ is not present or N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S.

In one embodiment, the antibody or antigen binding molecule, which specifically binds to BCMA (e.g., hBCMA), comprises a VH CDR2 comprising, consisting of, or consisting essentially of the amino acid sequence $X_1IX_3X_4X_5X_6X_7X_8X_9X_{10}YAX_{13}X_{14}X_{15}X_{16}G$ (SEQ ID NO: 153), wherein: $X_1$ is A, G, I, T, or V; $X_3$ is I, N, or S; $X_4$ is G, P, S, or Y; $X_5$ is D, G, I, or S; $X_6$ is F, G, or S; $X_7$ is G or S; $X_8$ is N, S, or T; $X_9$ is A, I, K, or T; $X_{10}$ is N, S, or Y; $X_{13}$ is D or Q; $X_{14}$ is K or S; $X_{15}$ is F or V; and $X_{16}$ is K or Q.

In one embodiment, the antibody or antigen binding molecule, which specifically binds to BCMA (e.g., hBCMA), comprises a VH CDR2 comprising, consisting of, or consisting essentially of the amino acid sequence $X_1ISX_4X_5X_6X_7X_8X_9YYADSVKG$ (SEQ ID NO: 154), wherein: $X_1$ is A, T, or V; $X_4$ is G, S, or Y; $X_5$ is D or S; $X_6$ is G or S; $X_7$ is G or S; $X_8$ is N, S, or T; and $X_9$ is I, K, or T.

In one embodiment, the antibody or antigen binding molecule, which specifically binds to BCMA (e.g., hBCMA), comprises a VH CDR2 comprising, consisting of, or consisting essentially of the amino acid sequence $X_1IX_3PX_5X_6GX_8X_9X_{10}YAQKFQG$ (SEQ ID NO: 155), wherein: $X_1$ is G or I; $X_3$ is I or N; $X_5$ is G or I; $X_6$ is F or G; $X_8$ is S or T; $X_9$ is A or T; and $X_{10}$ is N or S.

In one embodiment, the antibody or antigen binding molecule, which specifically binds to BCMA (e.g., hBCMA), comprises three VH CDRs and three VL CDRs, wherein the VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147) and wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$ is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y.

In one embodiment, the antibody or antigen binding molecule, which specifically binds to BCMA (e.g., hBCMA), comprises three VH CDRs and three VL CDRs, wherein the VH CDR3 comprising, consisting of, or consisting essentially of the amino acid sequence $ARX_3X_4X_5X_6X_7X_8X_9X_{10}X_{11}X_{12}X_{13}X_{14}X_{15}X_{16}X_{17}DX_{19}$ (SEQ ID NO: 156) and wherein: $X_3$ is not present or D, G, or T; $X_4$ is not present or A, D, G, P, R, or S; $X_5$ is not present or E, F, G, Q, or T; $X_6$ is not present or E, M, W, or Y; $X_7$ is not present or A, L, or S; $X_8$ is not present or G, S, or T; $X_9$ is not present or G or S; $X_{10}$ is not present or I, L, or P; $X_{11}$ is not present or W; $X_{12}$ is not present or H; $X_{13}$ is not present or E or Y; $X_{14}$ is not present or G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y.

In one embodiment, the antibody or antigen binding molecule, which specifically binds to BCMA (e.g., hBCMA), comprises three VH CDRs and three VL CDRs, wherein the VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}X_{18}X_{19}DX_{21}$ (SEQ ID NO: 264) and wherein: $X_1$ is A or V; $X_2$ is K or R; $X_3$ is not present or D, G, or T; $X_4$ is not present or D, G, or P; $X_5$ is not present or F, L, or T; $X_6$ is not present or P, Q, R, W, or Y; $X_7$ is not present or E, G, L, or S; $X_8$ is not present or A, G, P, S, or Y; $X_9$ is A, E, G, P, Q, or S; $X_{10}$ is E, L, M, P, S, T, or Y; $X_{11}$ is not present or D, G, H, P, S or W; $X_{12}$ is not present or A, G, I, L, or Y; $X_{13}$ is not present or A, G, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y.

In one embodiment, the antibody or antigen binding molecule, which specifically binds to BCMA (e.g., hBCMA), comprises three VH CDRs and three VL CDRs, wherein the VH CDR3 comprising, consisting of, or consisting essentially of the amino acid sequence $ARX_3X_4X_5X_6X_7X_8X_9X_{10}X_{11}X_{12}X_{13}X_{14}X_{15}X_{16}X_{17}X_{18}X_{19}DX_{21}$ (SEQ ID NO: 267), wherein: $X_3$ is not present or D or T; $X_4$ is not present or D or G; $X_5$ is not present or F or T; $X_6$ is not present or P, R, W, or Y; $X_7$ is not present or E, G, L, or S; $X_8$ is not present or A, G, S, or Y; $X_9$ is A, E, G, Q, or S; $X_{10}$ is E, L, M, P, S, or T; $X_{11}$ is not present or G, H, P, S or W; $X_{12}$ is not present or A, G, I, L, or Y; $X_{13}$ is not present or A, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y.

In some embodiments, the polynucleotide encodes an antibody or antigen binding molecule that specifically binds to BCMA, wherein the antibody or antigen binding molecule comprises one, two, or all three of any of the VH CDRs listed above or described in FIG. 1A or FIG. 1B. In some embodiments, the antibody or antigen binding molecule comprises the VH framework regions (FRs) described herein. In specific embodiments, the antibody or antigen binding molecule comprises the VH FRs of an antibody set forth in FIG. 1A or FIG. 1B (e.g., one, two, three, or four of the FRs in one sequence of FIG. 1A).

In one embodiment, the antibody or antigen binding molecule, which specifically binds to BCMA (e.g., hBCMA), comprises a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein: $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D.

In one embodiment, the antibody or antigen binding molecule, which specifically binds to BCMA (e.g., hBCMA), comprises a VL CDR1 comprising, consisting of, or consisting essentially of the amino acid sequence $RASQX_5X_6SX_8X_9LA$ (SEQ ID NO: 157), wherein: $X_5$ is G or S; $X_6$ is I or V; $X_8$ is R or S; and $X_9$ is N, W, or Y.

In one embodiment, the antibody or antigen binding molecule, which specifically binds to BCMA (e.g., hBCMA), comprises a VL CDR1 comprising, consisting of, or consisting essentially of the amino acid sequence $X_1SSQSX_6LX_8SX_{10}X_{11}X_{12}X_{13}NYLX_{17}$ (SEQ ID NO: 158), wherein: $X_1$ is K or R; $X_6$ is L or V; $X_8$ is H or Y; $X_{10}$ is N or S; $X_{11}$ is G or N; $X_{12}$ is not present or N; $X_{13}$ is K or Y; and $X_{17}$ is A or D.

In one embodiment, the antibody or antigen binding molecule, which specifically binds to BCMA (e.g., hBCMA), comprises a VL CDR2 comprising, consisting of, or consisting essentially of the amino acid sequence $X_1X_2SX_4X_5X_6X_7$ (SEQ ID NO: 149), wherein: $X_1$ is D, G, L, S, or W; $X_2$ is A or G; $X_4$ is N, S, or T; $X_5$ is L or R; $X_6$ is A, E, or Q; and $X_7$ is S or T.

In one embodiment, the antibody or antigen binding molecule, which specifically binds to BCMA (e.g., hBCMA), comprises a VL CDR2 comprising, consisting of, or consisting essentially of the amino acid sequence $X_1ASX_4RAT$ (SEQ ID NO: 159), wherein: $X_1$ is D, G, or S; and $X_4$ is N or T.

In one embodiment, the antibody or antigen binding molecule, which specifically binds to BCMA (e.g., hBCMA), comprises a VL CDR2 comprising, consisting of, or consisting essentially of the amino acid sequence $X_1ASX_4X_5X_6X_7$ (SEQ ID NO: 160), wherein: $X_1$ is D, G, or S; $X_4$ is N, S, or T; $X_5$ is L or R; $X_6$ is A or Q; and $X_7$ is S or T.

In one embodiment, the antibody or antigen binding molecule, which specifically binds to BCMA (e.g., hBCMA), comprises a VL CDR2 comprising, consisting of, or consisting essentially of the amino acid sequence $X_1X_2SX_4RX_6S$ (SEQ ID NO: 161), wherein $X_1$ is L or W; $X_2$ is A or G; $X_4$ is N or T; and $X_6$ is A or E.

In one embodiment, the antibody or antigen binding molecule, which specifically binds to BCMA (e.g., hBCMA), comprises a VL CDR3 comprising, consisting of, or consisting essentially of the amino acid sequence $X_1QX_3X_4X_5X_6PX_8T$ (SEQ ID NO: 150), wherein: $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In one embodiment, the antibody or antigen binding molecule, which specifically binds to BCMA (e.g., hBCMA), comprises a VL CDR3 comprising, consisting of, or consisting essentially of the amino acid sequence $QQX_3X_4X_5X_6PX_8T$ (SEQ ID NO: 162), wherein: $X_3$ is H, I, R, or Y; $X_4$ is A, F, H, I, or Y; $X_5$ is A, S, T, V, or Y; $X_6$ is F, W, or Y; and $X_8$ is not present or F, L, P, or W.

In some embodiments, the polynucleotide encodes an antibody or antigen binding molecule that specifically binds to BCMA, wherein the antibody or antigen binding molecule comprises one, two, or all three of any of the VL CDRs listed above or described in FIG. 2. In some embodiments, the antibody or antigen binding molecule comprises the VL framework regions (FRs) described herein. In specific embodiments, the antibody or antigen binding molecule comprises the VL FRs of an antibody set forth in FIG. 4 (e.g., one, two, three, or four of the FRs in one row of FIG. 4).

In some embodiments, the polynucleotide encodes an antibody or antigen binding molecule that specifically binds to BCMA, wherein the antibody or antigen binding molecule comprises a VH CDR1, wherein the VH CDR1 comprises an amino acid sequence selected from the group consisting of SEQ ID NO: 9-16. In other embodiments, the antibody or antigen binding molecule comprises a VH CDR1, wherein the VH CDR1 comprises an amino acid sequence selected from the group consisting of SEQ ID NO: 215-222. In some embodiments, the antibody or antigen binding molecule comprises a VH CDR2, wherein the VH CDR2 comprises an amino acid sequence selected from the group consisting of SEQ ID NO: 25-32. In some embodiments, the antibody or antigen binding molecule comprises a VH CDR2, wherein the VH CDR2 comprises an amino acid sequence selected from the group consisting of SEQ ID NO: 231-238. In some embodiments, the antibody or antigen binding molecule comprises a VH CDR3, wherein the VH CDR3 comprises an amino acid sequence selected from the group consisting of SEQ ID NO: 41-48. In some embodiments, the antibody or antigen binding molecule comprises a VH CDR3, wherein the VH CDR3 comprises an amino acid sequence selected from the group consisting of SEQ ID NO: 247-254.

In some embodiments, the polynucleotide encodes an antibody or antigen binding molecule that specifically binds to BCMA, wherein the antibody or antigen binding molecule comprises a VH CDR1, a VH CDR2, and VH CDR3, wherein the VH CDR1, VH CDR2, and VH CDR3 comprise the amino acid sequence of the VH CDR1, VH CDR2, and VH CDR3 of an antibody in FIG. 1A or FIG. 1B, respectively.

In some embodiments, the polynucleotide encodes an antibody or antigen binding molecule that specifically binds to BCMA, wherein the antibody or antigen binding molecule comprises a VL CDR1, wherein the VL CDR1 comprises an amino acid sequence selected from the group consisting of SEQ ID NO: 81-88. In some embodiments, the antibody or antigen binding molecule comprises a VL CDR2, wherein the VL CDR2 comprises an amino acid sequence selected from the group consisting of SEQ ID NO: 97-104. In some embodiments, the antibody or antigen binding molecule comprises a VL CDR3, wherein the VL CDR3 comprises an amino acid sequence selected from the group consisting of SEQ ID NO: 113-120.

In some embodiments, the polynucleotide encodes an antibody or antigen binding molecule that specifically binds to BCMA, wherein the antibody or antigen binding molecule comprises a VL CDR1, a VL CDR2, and VL CDR3, wherein the VL CDR1, VL CDR2, and VL CDR3 comprise the amino acid sequence of the VL CDR1, VL CDR2, and VL CDR3 of an antibody in FIG. 1C, respectively.

In some embodiments, the polynucleotide encodes an antibody or antigen binding molecule that specifically binds to BCMA, wherein the antibody or antigen binding molecule comprises a VH framework region 1 (FR1), wherein the VH FR1 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 1-8 and 207-214. In some embodiments, the antibody or antigen binding molecule comprises a VH FR2, wherein the VH FR2 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 17-24 and 223-23. In some embodiments, the antibody or antigen binding molecule comprises a VH FR3, wherein the VH FR3 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 33-40 and 239-246. In some embodiments, the antibody or antigen binding molecule comprises a VH FR4, wherein the VH FR4 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 49-56 and 255-262.

In some embodiments, the antibody or antigen binding molecule or a fragment thereof comprises a VL FR1, wherein the VL FR1 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 73-80. In some embodiments, the antibody or antigen binding molecule or a fragment thereof comprises a VL FR2, wherein the VL FR2 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 89-96. In some embodiments, the antibody or antigen binding molecule or a fragment thereof comprises a VL FR3, wherein the VL FR3 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 105-112. In some embodiments, the antibody or antigen binding molecule or a fragment thereof comprises a VL FR4, wherein the VL FR4 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 121-128.

In some embodiments, the polynucleotide encodes an antibody or antigen binding molecule that specifically binds to BCMA, wherein the antibody or antigen binding molecule comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule comprises: (a) a VH CDR1 region comprising the amino acid sequence of SEQ ID NO: 9; (b) a VH CDR2 region comprising the amino acid sequence of SEQ ID NO: 25; (c) a VH CDR3 region comprising the amino acid sequence of SEQ ID NO: 41; (d) a VL CDR1 region comprising the amino acid sequence of SEQ ID NO: 81; (e) a VL CDR2 region comprising the amino acid sequence of SEQ ID NO: 97; and (f) a VL CDR3 region comprising the amino acid sequence of SEQ ID NO: 113.

In one embodiment, the antibody or antigen binding molecule comprises: (a) a VH CDR1 region comprising the amino acid sequence of SEQ ID NO: 10; (b) a VH CDR2 region comprising the amino acid sequence of SEQ ID NO: 26; (c) a VH CDR3 region comprising the amino acid sequence of SEQ ID NO: 42; (d) a VL CDR1 region comprising the amino acid sequence of SEQ ID NO: 82; (e) a VL CDR2 region comprising the amino acid sequence of SEQ ID NO: 98; and (f) a VL CDR3 region comprising the amino acid sequence of SEQ ID NO: 114.

In one embodiment, the antibody or antigen binding molecule comprises: (a) a VH CDR1 region comprising the amino acid sequence of SEQ ID NO: 11; (b) a VH CDR2 region comprising the amino acid sequence of SEQ ID NO: 27; (c) a VH CDR3 region comprising the amino acid sequence of SEQ ID NO: 43; (d) a VL CDR1 region comprising the amino acid sequence of SEQ ID NO: 83; (e) a VL CDR2 region comprising the amino acid sequence of SEQ ID NO: 99; and (f) a VL CDR3 region comprising the amino acid sequence of SEQ ID NO: 115.

In one embodiment, the antibody or antigen binding molecule comprises: (a) a VH CDR1 region comprising the amino acid sequence of SEQ ID NO: 12; (b) a VH CDR2 region comprising the amino acid sequence of SEQ ID NO: 28; (c) a VH CDR3 region comprising the amino acid sequence of SEQ ID NO: 44; (d) a VL CDR1 region comprising the amino acid sequence of SEQ ID NO: 84; (e) a VL CDR2 region comprising the amino acid sequence of SEQ ID NO: 100; and (f) a VL CDR3 region comprising the amino acid sequence of SEQ ID NO: 116.

In one embodiment, the antibody or antigen binding molecule comprises: (a) a VH CDR1 region comprising the amino acid sequence of SEQ ID NO: 13; (b) a VH CDR2 region comprising the amino acid sequence of SEQ ID NO: 29; (c) a VH CDR3 region comprising the amino acid sequence of SEQ ID NO: 45; (d) a VL CDR1 region comprising the amino acid sequence of SEQ ID NO: 85; (e) a VL CDR2 region comprising the amino acid sequence of SEQ ID NO: 101; and (f) a VL CDR3 region comprising the amino acid sequence of SEQ ID NO: 117.

In one embodiment, the antibody or antigen binding molecule comprises: (a) a VH CDR1 region comprising the amino acid sequence of SEQ ID NO: 14; (b) a VH CDR2 region comprising the amino acid sequence of SEQ ID NO: 30; (c) a VH CDR3 region comprising the amino acid sequence of SEQ ID NO: 46; (d) a VL CDR1 region comprising the amino acid sequence of SEQ ID NO: 86; (e) a VL CDR2 region comprising the amino acid sequence of SEQ ID NO: 102; and (f) a VL CDR3 region comprising the amino acid sequence of SEQ ID NO: 118.

In one embodiment, the antibody or antigen binding molecule comprises: (a) a VH CDR1 region comprising the amino acid sequence of SEQ ID NO: 15; (b) a VH CDR2 region comprising the amino acid sequence of SEQ ID NO: 31; (c) a VH CDR3 region comprising the amino acid sequence of SEQ ID NO: 47; (d) a VL CDR1 region comprising the amino acid sequence of SEQ ID NO: 87; (e) a VL CDR2 region comprising the amino acid sequence of SEQ ID NO: 103; and (f) a VL CDR3 region comprising the amino acid sequence of SEQ ID NO: 119.

In one embodiment, the antibody or antigen binding molecule comprises: (a) a VH CDR1 region comprising the amino acid sequence of SEQ ID NO: 16; (b) a VH CDR2 region comprising the amino acid sequence of SEQ ID NO: 32; (c) a VH CDR3 region comprising the amino acid sequence of SEQ ID NO: 48; (d) a VL CDR1 region comprising the amino acid sequence of SEQ ID NO: 88; (e) a VL CDR2 region comprising the amino acid sequence of SEQ ID NO: 104; and (f) a VL CDR3 region comprising the amino acid sequence of SEQ ID NO: 120.

In one embodiment, the antibody or antigen binding molecule comprises: (a) a VH CDR1 region comprising the amino acid sequence of SEQ ID NO: 215; (b) a VH CDR2 region comprising the amino acid sequence of SEQ ID NO: 231; (c) a VH CDR3 region comprising the amino acid sequence of SEQ ID NO: 247; (d) a VL CDR1 region comprising the amino acid sequence of SEQ ID NO: 81; (e) a VL CDR2 region comprising the amino acid sequence of SEQ ID NO: 97; and (f) a VL CDR3 region comprising the amino acid sequence of SEQ ID NO: 113.

In one embodiment, the antibody or antigen binding molecule comprises: (a) a VH CDR1 region comprising the amino acid sequence of SEQ ID NO: 216; (b) a VH CDR2 region comprising the amino acid sequence of SEQ ID NO: 232; (c) a VH CDR3 region comprising the amino acid sequence of SEQ ID NO: 248; (d) a VL CDR1 region comprising the amino acid sequence of SEQ ID NO: 82; (e) a VL CDR2 region comprising the amino acid sequence of SEQ ID NO: 98; and (f) a VL CDR3 region comprising the amino acid sequence of SEQ ID NO: 114.

In one embodiment, the antibody or antigen binding molecule comprises: (a) a VH CDR1 region comprising the amino acid sequence of SEQ ID NO: 217; (b) a VH CDR2 region comprising the amino acid sequence of SEQ ID NO: 233; (c) a VH CDR3 region comprising the amino acid sequence of SEQ ID NO: 249; (d) a VL CDR1 region comprising the amino acid sequence of SEQ ID NO: 83; (e) a VL CDR2 region comprising the amino acid sequence of SEQ ID NO: 99; and (f) a VL CDR3 region comprising the amino acid sequence of SEQ ID NO: 115.

In one embodiment, the antibody or antigen binding molecule comprises: (a) a VH CDR1 region comprising the amino acid sequence of SEQ ID NO:218; (b) a VH CDR2 region comprising the amino acid sequence of SEQ ID NO: 234; (c) a VH CDR3 region comprising the amino acid sequence of SEQ ID NO: 250; (d) a VL CDR1 region comprising the amino acid sequence of SEQ ID NO: 84; (e) a VL CDR2 region comprising the amino acid sequence of SEQ ID NO: 100; and (f) a VL CDR3 region comprising the amino acid sequence of SEQ ID NO: 116.

In one embodiment, the antibody or antigen binding molecule comprises: (a) a VH CDR1 region comprising the amino acid sequence of SEQ ID NO: 219; (b) a VH CDR2 region comprising the amino acid sequence of SEQ ID NO: 235; (c) a VH CDR3 region comprising the amino acid sequence of SEQ ID NO: 251; (d) a VL CDR1 region comprising the amino acid sequence of SEQ ID NO: 85; (e) a VL CDR2 region comprising the amino acid sequence of SEQ ID NO: 101; and (f) a VL CDR3 region comprising the amino acid sequence of SEQ ID NO: 117.

In one embodiment, the antibody or antigen binding molecule comprises: (a) a VH CDR1 region comprising the amino acid sequence of SEQ ID NO: 220; (b) a VH CDR2 region comprising the amino acid sequence of SEQ ID NO: 236; (c) a VH CDR3 region comprising the amino acid sequence of SEQ ID NO: 252; (d) a VL CDR1 region comprising the amino acid sequence of SEQ ID NO: 86; (e) a VL CDR2 region comprising the amino acid sequence of SEQ ID NO: 102; and (f) a VL CDR3 region comprising the amino acid sequence of SEQ ID NO: 118.

In one embodiment, the antibody or antigen binding molecule comprises: (a) a VH CDR1 region comprising the amino acid sequence of SEQ ID NO: 221; (b) a VH CDR2 region comprising the amino acid sequence of SEQ ID NO: 237; (c) a VH CDR3 region comprising the amino acid sequence of SEQ ID NO: 253; (d) a VL CDR1 region comprising the amino acid sequence of SEQ ID NO: 87; (e) a VL CDR2 region comprising the amino acid sequence of SEQ ID NO: 103; and (f) a VL CDR3 region comprising the amino acid sequence of SEQ ID NO: 119.

In one embodiment, the antibody or antigen binding molecule comprises: (a) a VH CDR1 region comprising the amino acid sequence of SEQ ID NO: 222; (b) a VH CDR2 region comprising the amino acid sequence of SEQ ID NO: 238; (c) a VH CDR3 region comprising the amino acid sequence of SEQ ID NO: 254; (d) a VL CDR1 region comprising the amino acid sequence of SEQ ID NO: 88; (e) a VL CDR2 region comprising the amino acid sequence of SEQ ID NO: 104; and (f) a VL CDR3 region comprising the amino acid sequence of SEQ ID NO: 120.

In some embodiments, the antibody or antigen binding molecule comprises a heavy chain variable region sequence comprising an amino acid sequence of FIG. 1A or FIG. 1B. In some embodiments, the antibody or antigen binding molecule comprises a heavy chain variable region sequence comprising an amino acid sequence selected from the group consisting of SEQ ID NOs: 65-72. In some embodiments, the antibody or antigen binding molecule comprises a light chain variable region sequence comprising an amino acid sequence selected from FIG. 1C. In some embodiments, the antibody or antigen binding molecule comprises a light chain variable region sequence comprising an amino acid sequence selected from the group consisting of SEQ ID NOs: 137-144.

In some embodiments, the antibody or antigen binding molecule comprises (a) a heavy chain variable region comprising the amino acid sequence of SEQ ID NO: 65; and (b) a light chain variable region comprising the amino acid sequence of SEQ ID NO 137.

In some embodiments, the antibody or antigen binding molecule comprises (a) a heavy chain variable region comprising the amino acid sequence of SEQ ID NO: 66; and (b) a light chain variable region comprising the amino acid sequence of SEQ ID NO: 138.

In some embodiments, the antibody or antigen binding molecule comprises (a) a heavy chain variable region comprising the amino acid sequence of SEQ ID NO: 67; and (b) a light chain variable region comprising the amino acid sequence of SEQ ID NO: 139.

In some embodiments, the antibody or antigen binding molecule comprises (a) a heavy chain variable region comprising the amino acid sequence of SEQ ID NO: 68; and (b) a light chain variable region comprising the amino acid sequence of SEQ ID NO: 140.

In some embodiments, the antibody or antigen binding molecule comprises (a) a heavy chain variable region comprising the amino acid sequence of SEQ ID NO: 69; and (b) a light chain variable region comprising the amino acid sequence of SEQ ID NO: 141.

In some embodiments, the antibody or antigen binding molecule comprises (a) a heavy chain variable region comprising the amino acid sequence of SEQ ID NO: 70; and (b) a light chain variable region comprising the amino acid sequence of SEQ ID NO: 142.

In some embodiments, the antibody or antigen binding molecule comprises (a) a heavy chain variable region comprising the amino acid sequence of SEQ ID NO: 71; and (b) a light chain variable region comprising the amino acid sequence of SEQ ID NO: 143.

In some embodiments, the antibody or antigen binding molecule comprises (a) a heavy chain variable region comprising the amino acid sequence of SEQ ID NO: 72; and (b) a light chain variable region comprising the amino acid sequence of SEQ ID NO: 144.

In one particular embodiment, the polynucleotide of the present invention comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 57-64. In another embodiment, the polynucleotide of the present invention comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 129-136.

The antibody or antigen binding molecule encoded by the polypeptide of the present invention can be single chained or double chained. In some embodiments, the antibody or antigen binding molecule comprises is single chained. In certain embodiments, the antigen binding molecule is selected from the group consisting of an scFv, an Fab, an Fab', an Fv, an F(ab')2, a dAb, and any combination thereof. In one particular embodiment, the antibody or antigen binding molecule comprises an scFv.

In certain embodiments, the antibody or antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises at least about 18 amino acids. In certain embodiments, the linker comprises an amino acid sequence that is at least about 75%, at least about 85%, at least about 85%, at least about 90%, at least about 95%, at least about 96%, at least about 97%, at least about 98%, at least about 99%, or 100% identical to the amino acid sequence GSTSGSGKPGSGEGSTKG (SEQ ID NO: 174) or a poly-Gly linker such as the amino acid sequence GGGGSGGGGSGGGGS (SEQ ID NO: 268). Or GGGGSGGGGSGGGGSGGGGS (SEQ ID NO: 411). In one embodiment, the linker is a Whitlow linker. In certain embodiments, the antibody or antigen binding molecule comprises a single chain, wherein the heavy chain variable region and the light chain variable region are connected by a linker, wherein the linker comprises the amino acid sequence of SEQ ID NO: 174.

In some embodiments, the antibody or antigen binding molecules of the present invention specifically bind BCMA (e.g., hBCMA). In certain embodiments, an anti-BCMA antibody or antigen binding molecule of the present invention binds human BCMA with a $K_D$ of less than $1\times10^{-6}$ M, less than $1\times10^{-7}$ M, less than $1\times10^{-8}$ M, or less than $1\times10^{-9}$ M. In one particular embodiment, the anti-BCMA antibody or antigen binding molecules binds human BCMA with a $K_D$ of less than $1\times10^{-7}$ M. In another embodiment, the anti-BCMA antibody or antigen binding molecules binds human BCMA with a $K_D$ of less than $1\times10^{-8}$ M. In some embodiments, the anti-BCMA antibody or antigen binding molecules binds human BCMA with a $K_D$ of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, or about $5\times10^{-10}$ M. In certain embodiments, the $K_D$ is calculated as the quotient of $k_{off}/k_{on}$, and the $k_{on}$ and $k_{off}$ are determined using a monovalent antibody, such as a Fab fragment, as measured by, e.g., BIAcore® surface plasmon resonance technology. In other embodiments, the $K_D$ is calculated as the quotient of $k_{off}/k_{on}$, and the $k_{on}$ and $k_{off}$ are determined using a bivalent antibody, such as a Fab fragment, as measured by, e.g., BIAcore® surface plasmon resonance technology.

In other embodiments, the anti-BCMA antibody or antigen binding molecule binds human BCMA-Fc with a $K_D$ of less than $1\times10^{-9}$ M, less than $3\times10^{-9}$ M, less than $5\times10^{-9}$ M, less than $1\times10^{-10}$ M, less than $3\times10^{-10}$ M, or less than $5\times10^{-10}$ M. In other embodiments, the anti-BCMA antibody or antigen binding molecules binds cyno BCMA-Fc with a $K_D$ of less than $1\times10^{-5}$ M, less than $1\times10^{-6}$ M, less than $1\times10^{-7}$ M, less than $1\times10^{-8}$ M, less than $1\times10^{-9}$ M, or less than $1\times10^{-10}$ M.

In some embodiments, the anti-BCMA antibody or antigen binding molecule binds human BCMA with an association rate ($k_{on}$) of less than $1\times10^{-4}$ $M^{-1}$ $s^{-1}$, less than $2\times10^{-4}$ $M^{-1}$ $s^{-1}$, less than $3\times10^{-4}$ $M^{-1}$ $s^{-1}$ less than $4\times10^{-4}$ $M^{-1}$ $s^{-1}$ less than $5\times10^{-4}$ $M^{-1}$ $s^{-1}$, less than $6\times10^{-4}$ $M^{-1}$ $s^{-1}$, less than $7\times10^{-4}$ $M^{-1}$ $s^{-1}$, less than $8\times10^{-4}$ $M^{-1}$ $s^{-1}$, less than $9\times10^{-4}$ $M^{-1}$ $s^{-1}$, less than $1\times10^{-5}$ $M^{-1}$ $s^{-1}$, less than $2\times10^{-5}$ $M^{-1}$ $s^{-1}$, less than $3\times10^{-5}$ $M^{-1}$ $s^{-1}$, less than $4\times10^{-5}$ $M^{-1}$ $s^{-1}$, less than $5\times10^{-5}$ $M^{-1}$ $s^{-1}$, less than $6\times10^{-5}$ $M^{-1}$ $s^{-1}$, less than $7\times10^{-5}$ $M^{-1}$ $s^{-1}$, less than $8\times10^{-5}$ $M^{-1}$ $s^{-1}$, less than $9\times10^{-5}$ $M^{-1}$ $s^{-1}$, less than $1\times10^{-6}$ $M^{-1}$ $s^{-1}$, less than $2\times10^{-6}$ $M^{-1}$ $s^{-1}$, less than $3\times10^{-6}$ $M^{-1}$ $s^{-1}$, less than $4\times10^{-6}$ $M^{-1}$ $s^{-1}$, less than $5\times10^{-6}$ $M^{-1}$ $s^{-1}$, less than $6\times10^{-6}$ $M^{-1}$ $s^{-1}$, less than $7\times10^{-6}$ $M^{-1}$ $s^{-1}$, less than $8\times10^{-6}$ $M^{-1}$ $s^{-1}$, less than $9\times10^{-6}$ $M^{-1}$ $s^{-1}$, or less than $1\times10^{-7}$ $M^{-1}$ $s^{-1}$. In certain embodiments, the $k_{on}$ is determined using a monovalent antibody, such as a Fab fragment, as measured by, e.g., BIAcore® surface plasmon resonance technology. In other embodiments, the $k_{on}$ is determined using a bivalent antibody as measured by, e.g., BIAcore® surface plasmon resonance technology.

In some embodiments, the anti-BCMA antibody or antigen binding molecule binds human BCMA with an dissociation rate ($k_{off}$) of less than $1\times10^{-2}$ $s^{-1}$, less than $2\times10^{-2}$ $s^{-1}$, less than $3\times10^{-2}$ $s^{-1}$, less than $4\times10^{-2}$ $s^{-1}$, less than $5\times10^{-2}$ $s^{-1}$, less than $6\times10^{-2}$ $s^{-1}$, less than $7\times10^{-2}$ $s^{-1}$, less than $8\times10^{-2}$ $s^{-1}$, less than $9\times10^{-2}$ $s^{-1}$, less than $1\times10^{-3}$ $s^{-1}$, less than $2\times10^{-3}$ $s^{-1}$, less than 3x10’s$^{-1}$, less than 4x10’s$^{-1}$, less than $5\times10^{-3}$ $s^{-1}$, less than $6\times10^{-3}$ $s^{-1}$, less than $7\times10^{-3}$ $s^{-1}$, less than $8\times10^{-3}$ $s^{-1}$, less than $9\times10^{-3}$ $s^{-1}$, less than $1\times10^{-4}$ $s^{-1}$, less than $2\times10^{-4}$ $s^{-1}$, less than $3\times10^{-4}$ $s^{-1}$, less than $4\times10^{-4}$ $s^{-1}$, less than $5\times10^{-4}$ $s^{-1}$, less than $6\times10^{-4}$ $s^{-1}$, less than $7\times10^{-4}$ $s^{-1}$, less than $8\times10^{-4}$ $s^{-1}$, less than 9x10’s$^{-1}$, less than $1\times10^{-4}$ $s^{-1}$, or less than $5\times10^{-4}$ $s^{-1}$. In certain embodiments, the $k_{off}$ is determined using a monovalent antibody, such as a Fab fragment, as measured by, e.g., BIAcore® surface plasmon resonance technology. In other embodiments, the $k_{off}$ is determined using a bivalent antibody as measured by, e.g., BIAcore® surface plasmon resonance technology.

In some embodiments, the polynucleotide of the present invention encodes an antibody or antigen binding molecule that specifically binds to BCMA, wherein the antibody or antigen binding molecule cross competes with a reference antibody disclosed herein. In certain embodiments, the antibody or antigen binding molecule cross competes with a reference antibody comprising an amino acid sequence selected from the group consisting of SEQ ID NOs: 1-56, 65-128, and 137-144. In some embodiments, the antibody or antigen binding molecule cross competes with a reference antibody comprising an amino acid sequence selected from the group consisting of SEQ ID NOs: 65-72 and 137-144. In certain embodiments, the antibody or antigen binding molecule cross competes with a reference antibody, wherein the reference antibody comprises a VH CDR1 comprising an amino acid sequence selected from the group consisting of SEQ ID NOs: 9-16. In certain embodiments, the antibody or antigen binding molecule cross competes with a reference antibody, wherein the reference antibody comprises a VH CDR2 comprising an amino acid sequence selected from the group consisting of SEQ ID NOs: 25-32. In certain embodiments, the antibody or antigen binding molecule cross competes with a reference antibody, wherein the reference antibody comprises a VH CDR3 comprising an amino acid sequence selected from the group consisting of SEQ ID NOs: 41-48. In some embodiments, the antibody or antigen binding molecule cross competes with a reference antibody, wherein the reference antibody comprises a VL CDR1 comprising an amino acid sequence selected from the group consisting of SEQ ID NOs: 89-96. In certain embodiments, the antibody or antigen binding molecule cross competes with a reference antibody, wherein the reference antibody comprises a VL CDR2 comprising an amino acid sequence selected from the group consisting of SEQ ID NOs: 105-112. In certain embodiments, the antibody or antigen binding molecule cross competes with a reference antibody, wherein the reference antibody comprises a VL CDR3 comprising an amino acid sequence selected from the group consisting of SEQ ID NOs: 121-128. In one embodiment, the antibody or antigen binding molecule cross competes with a reference antibody, wherein the reference antibody comprises a VH comprising an amino acid sequence selected from the group consisting of SEQ ID NOs: 65-72. In another embodiment, the antibody or antigen binding molecule cross competes with a reference antibody, wherein the reference antibody comprises a VL comprising an amino acid sequence selected from the group consisting of SEQ ID NOs: 137-144.

In some embodiments, the polynucleotide of the present invention encodes an antibody or antigen binding molecule that specifically binds to BCMA, wherein the antibody or antigen binding molecule binds the same or an overlapping epitope as a reference antibody disclosed herein (e.g., FIG. 1). In certain embodiments, the antibody or antigen binding molecule binds the same or an overlapping epitope as a reference antibody comprising an amino acid sequence selected from the group consisting of SEQ ID NOs: 1-56, 65-128, and 137-144. In some embodiments, the antibody or antigen binding molecule binds the same or an overlapping epitope as a reference antibody comprising an amino acid sequence selected from the group consisting of SEQ ID NOs: 65-72 and 137-144.

III Polynucleotides Encoding Chimeric Antigen Receptors and T Cell Receptors

The present invention is also directed to polynucleotides encoding chimeric antigen receptors (CARs) or T cell receptors (TCRs) comprising an antigen binding molecule that specifically binds to BCMA described in Section II, and engineered T cells comprising an antigen binding molecule that specifically binds to BCMA described in Section II. In some embodiments, an anti-BCMA CAR or TCR encoded by the polynucleotide of the present invention comprises an antigen binding molecule that specifically binds to BCMA. In some embodiments, the anti-BCMA CAR or TCR encoded by the polynucleotide further comprises a costimulatory domain. In some embodiments, the costimulatory domain in the anti-BCMA CAR or TCR encoded by the polynucleotide comprises an extracellular domain (i.e., a hinge region), a transmembrane domain, and/or an intracellular (signaling) domain. In some embodiments, the anti-BCMA CAR or TCR encoded by the polynucleotide further comprises a CD3 zeta activating domain. In one particular embodiment, the anti-BCMA CAR or TCR encoded by the polynucleotide comprises an antigen binding molecule that specifically binds BCMA (e.g., hBCMA), a costimulatory domain comprising an extracellular domain, a transmembrane domain, and an intracellular domain, and a CD3 zeta activating domain.

In some embodiments, the polynucleotide of the present invention encodes a TCR, wherein the TCR comprises an antigen binding molecule that specifically binds to BCMA, and wherein the TCR further comprises a fourth complementarity determining region (CDR4). In certain embodiments, the polynucleotide encodes a TCR, wherein the TCR comprises an antigen binding molecule that specifically binds to BCMA, and a constant region. In some embodiments, the constant region is selected from a constant region of IgG1, IgG2, IgG3, IgG4, IgA, IgD, IgE, and IgM.

III.A. Costimulatory Domain

In some embodiments, the polynucleotide of the present invention encodes a CAR, wherein the CAR comprises an antigen binding molecule that specifically binds to BCMA (one or more antigen binding molecules in Section II), and wherein the CAR further comprises a costimulatory domain. In some embodiments, the costimulatory domain is positioned between the antigen binding molecule and an activating domain. In certain embodiments, the costimulatory domain can comprise an extracellular domain, a transmembrane domain, and an intracellular signaling domain.

Extracellular Domain:

In one embodiment, the extracellular domain comprises a hinge region (e.g., a spacer region). In another embodiment, the extracellular domain is from or derived from (e.g., comprises) CD28, CD28T, OX40, 4-1BB/CD137, CD2, CD3 (alpha, beta, delta, epsilon, gamma, zeta), CD4, CD5, CD7, CD8, CD9, CD16, CD22, CD27, CD30, CD 33, CD37, CD40, CD 45, CD64, CD80, CD86, CD134, CD137, CD154, programmed death-1 (PD-1), ICOS, April, BAFF, lymphocyte function-associated antigen-1 (LFA-1 (CD11a/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. The extracellular domain can be derived either from a natural or from a synthetic source.

In some embodiments, the extracellular domain in the costimulatory domain is positioned between the antigen binding molecule and the transmembrane domain. In certain embodiments, the extracellular domain in the costimulatory domain is from or derived from an immunoglobulin. In some embodiments, the extracellular domain in the costimulatory domain is selected from the hinge regions of IgG1, IgG2, IgG3, IgG4, IgA, IgD, IgE, and IgM, or a fragment thereof. In other embodiments, the extracellular domain in the costimulatory domain is from or derived from the hinge region of CD8 alpha. In one particular embodiment, the extracellular domain in the costimulatory domain is from or derived from the hinge region of CD28. In certain embodiments, the extracellular domain in the costimulatory domain comprises a fragment of the hinge region of CD8 alpha or a fragment of the hinge region of CD28, wherein the fragment is anything less than the whole hinge region. In some embodiments, the fragment of the CD8 alpha hinge region or the fragment of the CD28 hinge region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge region of the CD28 hinge region.

In certain embodiments, the extracellular domain in the costimulatory domain comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence LDNEKSNGTIIHVKGKHLCPSPLFPGPSKP (SEQ ID NO: 167) or a fragment thereof. In some embodiments, the extracellular domain in the costimulatory domain comprises the amino acid sequence of SEQ ID NO: 167 or a fragment thereof.

In certain embodiments, the extracellular domain in the costimulatory domain is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence CTTGATAATGAAAAGTCAAACGGAACAATCATT CACGTGAAGGGCAAGCACCTCTGTCCGTCACCCTTGTTCCCTGGTCCATCCAAG CCA (SEQ ID NO: 166) or a fragment thereof. In some embodiments, the extracellular domain in the costimulatory domain is encoded by a nucleotide sequence that comprises the nucleotide sequence of SEQ ID NO: 166 or a fragment thereof.

In some embodiments, the CD28T domain is derived from a human CD28 hinge region. In other embodiments, the CD28T domain is derived from a rodent, murine, or primate (e.g., non-human primate) CD28 hinge region. In some embodiments, the CD28T domain is derived from a chimeric CD28 hinge region.

In some embodiments, the extracellular domain comprises some or all of a member of the immunoglobulin family such as IgG1, IgG2, IgG3, IgG4, IgA, IgD, IgE, IgM, or fragment thereof.

Transmembrane Domain:

The costimulatory domain for the CAR or TCR of the invention can further comprise a transmembrane domain. The transmembrane domain can be designed to be fused to the extracellular domain in the costimulatory domain. It can similarly be fused to the intracellular domain in the costimulatory domain. In one embodiment, the transmembrane domain that naturally is associated with one of the domains in a CAR is used. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain can be derived from any membrane-bound or transmembrane protein. In some embodiments, the transmembrane domain is derived from CD28, OX-40, 4-1BB/CD137, CD2, CD3 (alpha, beta, delta, epsilon, zeta), CD4, CD5, CD7, CD8, CD9, CD16, CD22, CD27, CD30, CD 33, CD37, CD40, CD 45, CD64, CD80, CD86, CD134, CD137, CD154, programmed death-1 (PD-1), ICOS, lymphocyte function-associated antigen-1 (LFA-1 (CD11a/CD18), CD3 gamma, CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or a fragment thereof.

Optionally, a short oligo or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain in the CAR of the invention comprises the CD8 transmembrane domain. In one embodiment, the CD8 transmembrane domain comprises the transmembrane portion of the nucleic acid sequence of GCTGCAGCATTGAGCAACTCAATAATGTATTTTAGTCACTTTGTACCAGTGTTCT TGCCGGCTAAGCCTACTACCACACCCGCTCCACGGCCACCTACCCCAGCTCCTA CCATCGCTTCACAGCCTCTGTCCCTGCGCCCAGAGGCTTGCCGACCGGCCGCAG GGGGCGCTGTTCATACCAGAGGACTGGATTTCGCCTGCGATATCTATATCTGGG CACCCCTGGCCGGAACCTGCGGCGTACTCCTGCTGTCCCTGGTCATCACGCTCT ATTGTAATCACAGGAAC (SEQ ID NO: 269). In one embodiment, the CD8 transmembrane domain comprises the nucleic acid sequence that encodes the transmembrane amino acid sequence contained within AAALSNSIMYFSHFVPVFLPAKPTTTPAPRPPTPAPTIASQP LSLRPEACRPAAGGAVHTRGLDFACDIYIWAPLAGTCGVLLLSLVITLYCNHRN (SEQ ID NO: 270).

In another embodiment, the transmembrane domain in the costimulating domain is a CD28 transmembrane domain. In some embodiments, the transmembrane domain comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence FWVLVVVGGVLACYSLLVTVAFIIFWV (SEQ ID NO: 169). In some embodiments, the transmembrane domain comprises the amino acid sequence of SEQ ID NO: 169.

In some embodiments, the transmembrane domain is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence TTCTGGGTGTTGGTCGTAGTGGGTGGAGTCCTCGCTTGTTACTCTCTGCTCGTCA CCGTGGCTTTTATAATCTTCTGGGTT (SEQ ID NO: 168). In some embodiments, the transmembrane domain is encoded by a nucleotide sequence that comprises the nucleotide sequence of SEQ ID NO: 168.

Intracellular (Signaling) Domain:

The intracellular (signaling) domain of the engineered T cells of the invention can provide signaling to an activating domain, which then activates at least one of the normal effector functions of the immune cell. Effector function of a T cell, for example, can be cytolytic activity or helper activity including the secretion of cytokines.

In certain embodiments, suitable intracellular signaling domain include (i.e., comprise), but are not limited to CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

An example of a nucleotide sequence encoding the intracellular signaling domain is set forth in SEQ ID NO. 170:

AGATCCAAAAGAAGCCGCCTGCTCCATAGCGATTACATGAATATGACTCC

ACGCCGCCCTGGCCCCACAAGGAAACACTACCAGCCTTACGCACCACCTA

GAGATTTCGCTGCCTATCGGAGC

In one embodiment, the polynucleotide encoding an intracellular signaling domain within a costimulatory domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 170.

An example of an intracellular signaling domain is set forth in SEQ ID NO. 171:

RSKRSRLLHSDYMNMTPRRPGPTRKHYQPYAPPRDFAAYRS.

In one particular embodiment, the intracellular signaling domain within a costimulatory domain comprises an amino acid sequence at least about 80%, at least about 85%, at least about 90%, at least about 95%, at least about 96%, at least about 97%, at least about 98%, at least about 99%, or about 100% identical to the amino acid sequence of SEQ ID NO: 171.

The intracellular signaling sequences within the CAR of the invention can be linked to each other or to an activating domain in a random or specified order. Optionally, a short oligo- or polypeptide linker, preferably between 2 and 10 amino acids in length may form the linkage. A glycine-serine doublet provides a particularly suitable linker.

It will further be appreciated that where desired, the costimulatory regions described herein can be expressed in a separate chain from the antigen binding molecule (e.g., scFv) and activating domains, in so-called "trans" configuration.

III.B Activating Domain

In some embodiments, intracellular domains for use in the engineered T cell of the invention include cytoplasmic sequences of the T cell receptor (TCR) and co-receptors that act in concert to initiate signal transduction following antigen/receptor engagement, as well as any derivative or variant of these sequences and any synthetic sequence that has the same functional capability. CD3 is an element of the T cell receptor on native T cells, and has been shown to be an important intracellular activating element in CARs. In one embodiment, the activating domain is CD3, e.g., CD3 zeta, the nucleotide sequence of which is set forth in SEQ ID NO. 172:

AGGGTGAAGTTTTCCAGATCTGCAGATGCACCAGCGTATCAGCAGGGCCA

GAACCAACTGTATAACGAGCTCAACCTGGGACGCAGGGAAGAGTATGACG

TTTTGGACAAGCGCAGAGGACGGGACCCTGAGATGGGTGGCAAACCAAGA

CGAAAAAACCCCCAGGAGGGTCTCTATAATGAGCTGCAGAAGGATAAGAT

GGCTGAAGCCTATTCTGAAATAGGCATGAAAGGAGAGCGGAGAAGGGGAA

AAGGGCACGACGGTTTGTACCAGGGACTCAGCACTGCTACGAAGGATACT

TATGACGCTCTCCACATGCAAGCCCTGCCACCTAGG.

In some embodiments, the polynucleotide encoding an activating domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 172.

The corresponding amino acid of intracellular CD3 zeta is set forth in SEQ ID NO. 173:

RVKFSRSADAPAYQQGQNQLYNELNLGRREEYDVLDKRRGRDPEMGGKPR

RKNPQEGLYNELQK

DKMAEAYSEIGMKGERRRGKGHDGLYQGLSTATKDTYDALHMQALPPR.

In some embodiments, the activating domain comprises an amino acid sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of SEQ ID NO: 173.

Additionally, in certain embodiments the activating domain comprises an amino acid sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of a CD3 zeta variant as set forth in SEQ ID NO: 412:

RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

III.C. Leader Peptide

In some embodiments, the polynucleotide of the present invention encodes a CAR or a TCR, wherein the CAR or the TCR comprises an antigen binding molecule that specifically binds to BCMA, and wherein the CAR or the TCR further comprises a leader peptide (also referred to herein as a "signal peptide"). In certain embodiments, the leader peptide comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence MALPVTALLL-PLALLLHAARP (SEQ ID NO: 165). In some embodiments, the signal peptide comprises the amino acid sequence of SEQ ID NO: 165. In some embodiments, the leader peptide is encoded by a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to SEQ ID NO: 164.

In some embodiments, the polynucleotide of the present invention encodes a CAR, wherein the CAR comprises a leader peptide (P), an antigen binding molecule (B), a hinge domain (H), a transmembrane domain (T), a costimulatory region (C), and an activation domain (A), wherein the CAR is configured according to the following: P-B-H-T-C-A. In some embodiments, the antigen binding molecule comprises a VH and a VL, wherein the CAR is configured according to the following: P-VH-VL-H-T-C-A or P-VL-VH-H-T-C-A. In some embodiments, the VH and the VL are connected by a linker (L), wherein the anti-BCMA CAR is configured according to the following, from N-terminus to C-terminus: P-VH-L-VL-H-T-C-A or P-VH-L-VL-H-T-C-A.

In some embodiments, the polynucleotide of the present invention encodes a CAR, wherein the CAR comprises an amino acid sequence at least about 75%, at least about 85%, at least about 85%, at least about 90%, at least about 95%, at least about 96%, at least about 97%, at least about 98%, at least about 99%, or 100% identical to an amino acid sequence selected from Table 2. In certain embodiments, the polynucleotide of the present invention encodes a CAR, wherein the CAR comprises an amino acid sequence selected from Table 2.

TABLE 2

Example CAR Sequences

| Anti-BCMA CAR | Nucleotide Sequence | SEQ ID NO: | Amino Acid Sequence | SEQ ID NO: |
|---|---|---|---|---|
| FS-21495CAR HxL | ATGGCACTCCCCGTAACTGCTCTGCTGCTGCCGTTGGCATTGCTCCTGCACGCCGCACGCCCGGAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGGCTCCAGGGAAGGGGCTGGAGTGGGTCTCAGCTATTAGTGGTAGTGGTGGTAGCACATACTACGCAGACTCCGTGAAGGGCCGGTTCACCATCTCCAGAGACAATTCCAAGAACACGCTGTATCTGCAAATGAACAGCCTGAGAGCCGAGGACACGGCGGTGTACTACTGCGCAAGAGCCGAGATGGGAGCCGTATTCGACATATGGGGTCAGGGTACAATGGTCACCGTCTCCTCAGGGTCTACATCCGGCTCCGGGAAGCCCGGAAGTGGCGAAGGTAGTACAAAGGGGGAAATTGTGTTGACACAGTCTCCAGCCACCCTGTCTTTGTCTCCAGGGGAAAGAGCCACCCTCTCCTGCAGGGCCAGTCAGAGTGTTAGCAGGTACTTAGCCTGGTACCAACAGAAACCTGGCCAGGCTCCCAGGCTCCTCATCTATGATGCATCCAACAGGGCCACTGGCATCCCAGCCAGGTTCAGTGGCAGTGGGTCTGGGACAGACTTCACTCTCACCATCAGCAGCCTAGAGCCTGAAGATTTTGCAGTTTATTACTGTCAGCAGAGAATCTCCTGGCCTTTCACTTTTGGCGGAGGGACCAAGGTTGAGATCAAACGGGCCGCTGCCCTTGATAATGAAAAGTCAAACGGAACAATCATTCACGTGAAGGGCAAGCACCTCTGTCCGTCACCCTTGTTCCCTGGTCCATCCAAGCCATTCTGGGTGTTGGTCGTAGTGGGTGGAGTCCTCGCTTGTTACTCTCTGCTCGTCACCGTGGCTTTTATAATCTTCTGGGTTAGATCCAAAAGAAGCCGCCTGCTCCATAGCGATTACATGAATATGACTCCACGCCGCCCTGGCCCCACAAGGAAACACTACCAGCCTTACGCACCACCTAGAGATTTCGCTGCCTATCGGAGCAGGGTGAAGTTTTCCAGATCTGCAGATGCACCAGCGTATCAGCAGGGCCAGAACCAACTGTATAACGAGCTCAACCTGGGACGCAGGGAAGAGTATGACGTTTTGGACAAGCGCAGAGGACGGGACCCTGAGATGGGTGGCAAACCAAGACGAAAAAACCCCCAGGAGGGTCTCTATAATGAGCTGCAGAAGGATAAGATGGCTGAAGCCTATTCTGAAATAGGCATGAAAGGAGAGCGGAGAAGGGGAAAAGGGCACGACGGTTTGTACCAGGGACTCAGCACTGCTACGAAGGATACTTATGACGCTCTCCACATGCAAGCCCTGCCACCTAGGTAA | 175 | MALPVTALLLPLALLLHAARPEVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARAEMGAVFDIWGQGTMVTVSSGSTSGSGKPGSGEGSTKGEIVLTQSPATLSLSPGERATLSCRASQSVSRYLAWYQQKPGQAPRLLIYDASNRATGIPARFSGSGSGTDFTLTISSLEPEDFAVYYCQQRISWPFTFGGGTKVEIKRAAALDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 176 |
| FS-21495CAR LxH | ATGGCACTCCCCGTAACTGCTCTGCTGCTGCCGTTGGCATTGCTCCTGCACGCCGCACGCCCGGAAATTGTGTTGACACAGTCTCCAGCCACCCTGTCTTTGTCTCCAGGGGAAAGAGCCACCCTCTCCTGCAGGGCCAGTCAGAGTGTTAGCAGGTACTTAGCCTGGTACCAACAGAAACCTGGCCAGGCTCCCAGGCTCCTCATCTATGATGCATCCAACAGGGCCACTGGCATCCCAGCCAGGTTCAGTGGCAGTGGGTCTGGGACAGACTTCACTCTCACCATCAGCAGCCTAGAGCCTGAAGATTTTGCAGTTTATTACTGTCAGCAGAGAATCTCCTGGCCTTTCACTTTTGGCGGAGGGACCAAGGTTGAGATCAAACGGGGGTCTACATCCGGCTCCGGGAAGCCCGGAAGTGGCGAAGGTAGTACAAAGGGGGAGGTGCAGCTGTTGGAGTCTGGGGGAGGCTTGGTACAGCCTGGGGGGTCCCTGAGACTCTCC | 177 | MALPVTALLLPLALLLHAARPEIVLTQSPATLSLSPGERATLSCRASQSVSRYLAWYQQKPGQAPRLLIYDASNRATGIPARFSGSGSGTDFTLTISSLEPEDFAVYYCQQRISWPFTFGGGTKVEIKRGSTSGSGKPGSGEGSTKGEVQLLESGGGLVQPGGSLRLSCAASGFTFSSYAMSWVRQAPGKGLEWVSAISGSGGSTYYADSVKGRFTISRDNSKNTLYL | 178 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| | TGTGCAGCCTCTGGATTCACCTTTAGCAGCTATGCCATGAGC<br>TGGGTCCGCCAGGCTCCAGGGAAGGGGCTGGAGTGGGTCTCA<br>GCTATTAGTGGTAGTGGTGGTAGCACATACTACGCAGACTCC<br>GTGAAGGGCCGGTTCACCATCTCCAGAGACAATTCCAAGAAC<br>ACGCTGTATCTGCAAATGAACAGCCTGAGAGCCGAGGACACG<br>GCGGTGTACTACTGCGCAAGAGCCGAGATGGGAGCCGTATTC<br>GACATATGGGGTCAGGGTACAATGGTCACCGTCTCCTCAGCC<br>GCTGCCCTTGATAATGAAAAGTCAAACGGAACAATCATTCAC<br>GTGAAGGGCAAGCACCTCTGTCCGTCACCCTTGTTCCCTGGT<br>CCATCCAAGCCATTCTGGGTGTTGGTCGTAGTGGGTGGAGTC<br>CTCGCTTGTTACTCTCTGCTCGTCACCGTGGCTTTTATAATC<br>TTCTGGGTTAGATCCAAAAGAAGCCGCCTGCTCCATAGCGAT<br>TACATGAATATGACTCCACGCCGCCCTGGCCCCACAAGGAAA<br>CACTACCAGCCTTACGCACCACCTAGAGATTTCGCTGCCTAT<br>CGGAGCAGGGTGAAGTTTTCCAGATCTGCAGATGCACCAGCG<br>TATCAGCAGGGCCAGAACCAACTGTATAACGAGCTCAACCTG<br>GGACGCAGGGAAGAGTATGACGTTTTGGACAAGCGCAGAGGA<br>CGGGACCCTGAGATGGGTGGCAAACCAAGACGAAAAAACCCC<br>CAGGAGGGTCTCTATAATGAGCTGCAGAAGGATAAGATGGCT<br>GAAGCCTATTCTGAAATAGGCATGAAAGGAGAGCGGAGAAGG<br>GGAAAAGGGCACGACGGTTTGTACCAGGGACTCAGCACTGCT<br>ACGAAGGATACTTATGACGCTCTCCACATGCAAGCCCTGCCA<br>CCTAGGTAA | | QMNSLRAEDTAVYYCARAE<br>MGAVFDIWGQGTMVTVSSA<br>AALDNEKSNGTIIHVKGKH<br>LCPSPLFPGPSKPFWVLVV<br>VGGVLACYSLLVTVAFIIF<br>WVRSKRSRLLHSDYMNMTP<br>RRPGPTRKHYQPYAPPRDF<br>AAYRSRVKFSRSADAPAYQ<br>QGQNQLYNELNLGRREEYD<br>VLDKRRGRDPEMGGKPRRK<br>NPQEGLYNELQKDKMAEAY<br>SEIGMKGERRRGKGHDGLY<br>QGLSTATKDTYDALHMQAL<br>PPR | |
| PC-21497CAR HxL | ATGGCACTCCCCGTAACTGCTCTGCTGCTGCCGTTGGCATTG<br>CTCCTGCACGCCGCACGCCCGCAGGTGCAGCTGGTGGAGTCT<br>GGGGGAGGCGTGGTCCAGCCTGGGAGGTCCCTGAGACTCTCC<br>TGTGCAGCGTCTGGATTCACCTTCAGTAGCTATGGCATGCAC<br>TGGGTCCGCCAGGCTCCAGGCAAGGGGCTGGAGTGGGTGGCA<br>GTTATATCGTATGATGGAAGTAATAAATACTATGCAGACTCC<br>GTGAAGGGCCGATTCACCATCTCCAGAGACAATTCCAAGAAC<br>ACGCTGTATCTGCAAATGAACAGCCTGAGAGCCGAGGACACG<br>GCGGTGTACTACTGCGCCAGAGACGGTACTTATCTAGGTGGT<br>CTCTGGTACTTCGACTTATGGGGGAGAGGTACCTTGGTCACC<br>GTCTCCTCAGGGTCTACATCCGGCTCCGGGAAGCCCGGAAGT<br>GGCGAAGGTAGTACAAAGGGGGATATTGTGATGACTCAGTCT<br>CCACTCTCCCTGCCCGTCACCCCTGGAGAGCCGGCCTCCATC<br>TCCTGCAGGTCTAGTCAGAGCCTCCTGCATAGTAATGGATAC<br>AACTATTTGGATTGGTACCTGCAGAAGCCAGGGCAGTCTCCA<br>CAGCTCCTGATCTATTTGGGTTCTAATCGGGCCTCCGGGGTC<br>CCTGACAGGTTCAGTGGCAGTGGATCAGGCACAGATTTTACA<br>CTGAAAATCAGCAGAGTGGAGGCTGAGGATGTTGGGGTTTAT<br>TACTGCATGCAGGGACTCGGCCTCCCTCTCACTTTTGGCGGA<br>GGGACCAAGGTTGAGATCAAACGGGCCGCTGCCCTTGATAAT<br>GAAAAGTCAAACGGAACAATCATTCACGTGAAGGGCAAGCAC<br>CTCTGTCCGTCACCCTTGTTCCCTGGTCCATCCAAGCCATTC<br>TGGGTGTTGGTCGTAGTGGGTGGAGTCCTCGCTTGTTACTCT<br>CTGCTCGTCACCGTGGCTTTTATAATCTTCTGGGTTAGATCC<br>AAAAGAAGCCGCCTGCTCCATAGCGATTACATGAATATGACT<br>CCACGCCGCCCTGGCCCCACAAGGAAACACTACCAGCCTTAC<br>GCACCACCTAGAGATTTCGCTGCCTATCGGAGCAGGGTGAAG<br>TTTTCCAGATCTGCAGATGCACCAGCGTATCAGCAGGGCCAG<br>AACCAACTGTATAACGAGCTCAACCTGGGACGCAGGGAAGAG<br>TATGACGTTTTGGACAAGCGCAGAGGACGGGACCCTGAGATG<br>GGTGGCAAACCAAGACGAAAAAACCCCCAGGAGGGTCTCTAT<br>AATGAGCTGCAGAAGGATAAGATGGCTGAAGCCTATTCTGAA<br>ATAGGCATGAAAGGAGAGCGGAGAAGGGGAAAAGGGCACGAC<br>GGTTTGTACCAGGGACTCAGCACTGCTACGAAGGATACTTAT<br>GACGCTCTCCACATGCAAGCCCTGCCACCTAGGTAA | 179 | MALPVTALLLPLALLLHAA<br>RPQVQLVESGGGVVQPGRS<br>LRLSCAASGFTFSSYGMHW<br>VRQAPGKGLEWVAVISYDG<br>SNKYYADSVKGRFTISRDN<br>SKNTLYLQMNSLRAEDTAV<br>YYCARDGTYLGGLWYFDLW<br>GRGTLVTVSSGSTSGSGKP<br>GSGEGSTKGDIVMTQSPLS<br>LPVTPGEPASISCRSSQSL<br>LHSNGYNYLDWYLQKPGQS<br>PQLLIYLGSNRASGVPDRF<br>SGSGSGTDFTLKISRVEAE<br>DVGVYYCMQGLGLPLTFGG<br>GTKVEIKRAAALDNEKSNG<br>TIIHVKGKHLCPSPLFPGP<br>SKPFWVLVVVGGVLACYSL<br>LVTVAFIIFWVRSKRSRLL<br>HSDYMNMTPRRPGPTRKHY<br>QPYAPPRDFAAYRSRVKFS<br>RSADAPAYQQGQNQLYNEL<br>NLGRREEYDVLDKRRGRDP<br>EMGGKPRRKNPQEGLYNEL<br>QKDKMAEAYSEIGMKGERR<br>RGKGHDGLYQGLSTATKDT<br>YDALHMQALPPR | 180 |
| PC-21497CAR HxL | ATGGCACTCCCCGTAACTGCTCTGCTGCTGCCGTTGGCATTG<br>CTCCTGCACGCCGCACGCCCGGATATTGTGATGACTCAGTCT<br>CCACTCTCCCTGCCCGTCACCCCTGGAGAGCCGGCCTCCATC<br>TCCTGCAGGTCTAGTCAGAGCCTCCTGCATAGTAATGGATAC<br>AACTATTTGGATTGGTACCTGCAGAAGCCAGGGCAGTCTCCA<br>CAGCTCCTGATCTATTTGGGTTCTAATCGGGCCTCCGGGGTC<br>CCTGACAGGTTCAGTGGCAGTGGATCAGGCACAGATTTTACA<br>CTGAAAATCAGCAGAGTGGAGGCTGAGGATGTTGGGGTTTAT<br>TACTGCATGCAGGGACTCGGCCTCCCTCTCACTTTTGGCGGA<br>GGGACCAAGGTTGAGATCAAACGGGGGTCTACATCCGGCTCC<br>GGGAAGCCCGGAAGTGGCGAAGGTAGTACAAAGGGGCAGGTG<br>CAGCTGGTGGAGTCTGGGGGAGGCGTGGTCCAGCCTGGGAGG<br>TCCCTGAGACTCTCCTGTGCAGCGTCTGGATTCACCTTCAGT<br>AGCTATGGCATGCACTGGGTCCGCCAGGCTCCAGGCAAGGGG | 181 | MALPVTALLLPLALLLHAA<br>RPDIVMTQSPLSLPVTPGE<br>PASISCRSSQSLLHSNGYN<br>YLDWYLQKPGQSPQLLIYL<br>GSNRASGVPDRFSGSGSGT<br>DFTLKISRVEAEDVGVYYC<br>MQGLGLPLTFGGGTKVEIK<br>RGSTSGSGKPGSGEGSTKG<br>QVQLVESGGGVVQPGRSLR<br>LSCAASGFTFSSYGMHWVR<br>QAPGKGLEWVAVISYDGSN<br>KYYADSVKGRFTISRDNSK<br>NTLYLQMNSLRAEDTAVYY<br>CARDGTYLGGLWYFDLWGR | 182 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| | CTGGAGTGGGTGGCAGTTATATCGTATGATGGAAGTAATAAA | | GTLVTVSSAAALDNEKSNG | |
| | TACTATGCAGACTCCGTGAAGGGCCGATTCACCATCTCCAGA | | TIIHVKGKHLCPSPLFPGP | |
| | GACAATTCCAAGAACACGCTGTATCTGCAAATGAACAGCCTG | | SKPFWVLVVVGGVLACYSL | |
| | AGAGCCGAGGACACGGCGGTGTACTACTGCGCCAGAGACGGT | | LVTVAFIIFWVRSKRSRLL | |
| | ACTTATCTAGGTGGTCTCTGGTACTTCGACTTATGGGGGAGA | | HSDYMNMTPRRPGPTRKHY | |
| | GGTACCTTGGTCACCGTCTCCTCAGCCGCTGCCCTTGATAAT | | QPYAPPRDFAAYRSRVKFS | |
| | GAAAAGTCAAACGGAACAATCATTCACGTGAAGGGCAAGCAC | | RSADAPAYQQGQNQLYNEL | |
| | CTCTGTCCGTCACCCTTGTTCCCTGGTCCATCCAAGCCATTC | | NLGRREEYDVLDKRRGRDP | |
| | TGGGTGTTGGTCGTAGTGGGTGGAGTCCTCGCTTGTTACTCT | | EMGGKPRRKNPQEGLYNEL | |
| | CTGCTCGTCACCGTGGCTTTTATAATCTTCTGGGTTAGATCC | | QKDKMAEAYSEIGMKGERR | |
| | AAAAGAAGCCGCCTGCTCCATAGCGATTACATGAATATGACT | | RGKGHDGLYQGLSTATKDT | |
| | CCACGCCGCCCTGGCCCCACAAGGAAACACTACCAGCCTTAC | | YDALHMQALPPR | |
| | GCACCACCTAGAGATTTCGCTGCCTATCGGAGCAGGGTGAAG | | | |
| | TTTTCCAGATCTGCAGATGCACCAGCGTATCAGCAGGGCCAG | | | |
| | AACCAACTGTATAACGAGCTCAACCTGGGACGCAGGGAAGAG | | | |
| | TATGACGTTTTGGACAAGCGCAGAGGACGGGACCCTGAGATG | | | |
| | GGTGGCAAACCAAGACGAAAAAACCCCCAGGAGGGTCTCTAT | | | |
| | AATGAGCTGCAGAAGGATAAGATGGCTGAAGCCTATTCTGAA | | | |
| | ATAGGCATGAAAGGAGAGCGGAGAAGGGGAAAAGGGCACGAC | | | |
| | GGTTTGTACCAGGGACTCAGCACTGCTACGAAGGATACTTAT | | | |
| | GACGCTCTCCACATGCAAGCCCTGCCACCTAGGTAA | | | |
| AJ- | ATGGCACTCCCCGTAACTGCTCTGCTGCTGCCGTTGGCATTG | 183 | MALPVTALLLPLALLLHAA | 184 |
| 21508CAR | CTCCTGCACGCCGCACGCCCGCAGGTGCAGCTGGTGCAGTCT | | RPQVQLVQSGAEVKKPGAS | |
| HxL | GGGGCTGAGGTGAAGAAGCCTGGGGCCTCAGTGAAGGTTTCC | | VKVSCKASGYTFTSYYMHW | |
| | TGCAAGGCATCTGGATACACCTTCACCAGCTACTATATGCAC | | VRQAPGQGLEWMGIINPGG | |
| | TGGGTGCGACAGGCCCCTGGACAAGGGCTTGAGTGGATGGGA | | GSTSYAQKFQGRVTMTRDT | |
| | ATAATCAACCCTGGTGGTGGTAGCACAAGCTACGCACAGAAG | | STSTVYMELSSLRSEDTAV | |
| | TTCCAGGGCAGAGTCACCATGACCAGGGACACGTCCACGAGC | | YYCARESWPMDVWGQGTTV | |
| | ACAGTCTACATGGAGCTGAGCAGCCTGAGATCTGAGGACACG | | TVSSGSTSGSGKPGSGEGS | |
| | GCGGTGTACTACTGCGCCAGAGAGAGTTGGCCAATGGACGTA | | TKGEIVMTQSPATLSVSPG | |
| | TGGGGCCAGGGAACAACTGTCACCGTCTCCTCAGGGTCTACA | | ERATLSCRASQSVSSNLAW | |
| | TCCGGCTCCGGGAAGCCCGGAAGTGGCGAAGGTAGTACAAAG | | YQQKPGQAPRLLIYGASTR | |
| | GGGGAAATAGTGATGACGCAGTCTCCAGCCACCCTGTCTGTG | | ATGIPARFSGSGSGTEFTL | |
| | TCTCCAGGGGAAAGAGCCACCCTCTCCTGCAGGGCCAGTCAG | | TISSLQSEDFAVYYCQQYA | |
| | AGTGTTAGCAGCAACTTAGCCTGGTACCAGCAGAAACCTGGC | | AYPTFGGGTKVEIKRAAAL | |
| | CAGGCTCCCAGGCTCCTCATCTATGGTGCATCCACCAGGGCC | | DNEKSNGTIIHVKGKHLCP | |
| | ACTGGTATCCCAGCCAGGTTCAGTGGCAGTGGGTCTGGGACA | | SPLFPGPSKPFWVLVVVGG | |
| | GAGTTCACTCTCACCATCAGCAGCCTGCAGTCTGAAGATTTT | | VLACYSLLVTVAFIIFWVR | |
| | GCAGTTTATTACTGTCAGCAGTACGCCGCCTACCCTACTTTT | | SKRSRLLHSDYMNMTPRRP | |
| | GGCGGAGGGACCAAGGTTGAGATCAAACGGGCCGCTGCCCTT | | GPTRKHYQPYAPPRDFAAY | |
| | GATAATGAAAAGTCAAACGGAACAATCATTCACGTGAAGGGC | | RSRVKFSRSADAPAYQQGQ | |
| | AAGCACCTCTGTCCGTCACCCTTGTTCCCTGGTCCATCCAAG | | NQLYNELNLGRREEYDVLD | |
| | CCATTCTGGGTGTTGGTCGTAGTGGGTGGAGTCCTCGCTTGT | | KRRGRDPEMGGKPRRKNPQ | |
| | TACTCTCTGCTCGTCACCGTGGCTTTTATAATCTTCTGGGTT | | EGLYNELQKDKMAEAYSEI | |
| | AGATCCAAAAGAAGCCGCCTGCTCCATAGCGATTACATGAAT | | GMKGERRRGKGHDGLYQGL | |
| | ATGACTCCACGCCGCCCTGGCCCCACAAGGAAACACTACCAG | | STATKDTYDALHMQALPPR | |
| | CCTTACGCACCACCTAGAGATTTCGCTGCCTATCGGAGCAGG | | | |
| | GTGAAGTTTTCCAGATCTGCAGATGCACCAGCGTATCAGCAG | | | |
| | GGCCAGAACCAACTGTATAACGAGCTCAACCTGGGACGCAGG | | | |
| | GAAGAGTATGACGTTTTGGACAAGCGCAGAGGACGGGACCCT | | | |
| | GAGATGGGTGGCAAACCAAGACGAAAAAACCCCCAGGAGGGT | | | |
| | CTCTATAATGAGCTGCAGAAGGATAAGATGGCTGAAGCCTAT | | | |
| | TCTGAAATAGGCATGAAAGGAGAGCGGAGAAGGGGAAAAGGG | | | |
| | CACGACGGTTTGTACCAGGGACTCAGCACTGCTACGAAGGAT | | | |
| | ACTTATGACGCTCTCCACATGCAAGCCCTGCCACCTAGGTAA | | | |
| AJ- | ATGGCACTCCCCGTAACTGCTCTGCTGCTGCCGTTGGCATTG | 185 | MALPVTALLLPLALLLHAA | 186 |
| 21508CAR | CTCCTGCACGCCGCACGCCCGGAAATAGTGATGACGCAGTCT | | RPEIVMTQSPATLSVSPGE | |
| LxH | CCAGCCACCCTGTCTGTGTCTCCAGGGGAAAGAGCCACCCTC | | RATLSCRASQSVSSNLAWY | |
| | TCCTGCAGGGCCAGTCAGAGTGTTAGCAGCAACTTAGCCTGG | | QQKPGQAPRLLIYGASTRA | |
| | TACCAGCAGAAACCTGGCCAGGCTCCCAGGCTCCTCATCTAT | | TGIPARFSGSGSGTEFTLT | |
| | GGTGCATCCACCAGGGCCACTGGTATCCCAGCCAGGTTCAGT | | ISSLQSEDFAVYYCQQYAA | |
| | GGCAGTGGGTCTGGGACAGAGTTCACTCTCACCATCAGCAGC | | YPTEGGGTKVEIKRGSTSG | |
| | CTGCAGTCTGAAGATTTTGCAGTTTATTACTGTCAGCAGTAC | | SGKPGSGEGSTKGQVQLVQ | |
| | GCCGCCTACCCTACTTTTGGCGGAGGGACCAAGGTTGAGATC | | SGAEVKKPGASVKVSCKAS | |
| | AAACGGGGGTCTACATCCGGCTCCGGGAAGCCCGGAAGTGGC | | GYTFTSYYMHWVRQAPGQG | |
| | GAAGGTAGTACAAAGGGGCAGGTGCAGCTGGTGCAGTCTGGG | | LEWMGIINPGGGSTSYAQK | |
| | GCTGAGGTGAAGAAGCCTGGGGCCTCAGTGAAGGTTTCCTGC | | FQGRVTMTRDTSTSTVYME | |
| | AAGGCATCTGGATACACCTTCACCAGCTACTATATGCACTGG | | LSSLRSEDTAVYYCARESW | |
| | GTGCGACAGGCCCCTGGACAAGGGCTTGAGTGGATGGGAATA | | PMDVWGQGTTVTVSSAAAL | |
| | ATCAACCCTGGTGGTGGTAGCACAAGCTACGCACAGAAGTTC | | DNEKSNGTIIHVKGKHLCP | |
| | CAGGGCAGAGTCACCATGACCAGGGACACGTCCACGAGCACA | | SPLFPGPSKPFWVLVVVGG | |
| | GTCTACATGGAGCTGAGCAGCCTGAGATCTGAGGACACGGCG | | VLACYSLLVTVAFIIFWVR | |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| | GTGTACTACTGCGCCAGAGAGAGTTGGCCAATGGACGTATGG<br>GGCCAGGGAACAACTGTCACCGTCTCCTCAGCCGCTGCCCTT<br>GATAATGAAAAGTCAAACGGAACAATCATTCACGTGAAGGGC<br>AAGCACCTCTGTCCGTCACCCTTGTTCCCTGGTCCATCCAAG<br>CCATTCTGGGTGTTGGTCGTAGTGGGTGGAGTCCTCGCTTGT<br>TACTCTCTGCTCGTCACCGTGGCTTTTATAATCTTCTGGGTT<br>AGATCCAAAAGAAGCCGCCTGCTCCATAGCGATTACATGAAT<br>ATGACTCCACGCCGCCCTGGCCCCACAAGGAAACACTACCAG<br>CCTTACGCACCACCTAGAGATTTCGCTGCCTATCGGAGCAGG<br>GTGAAGTTTTCCAGATCTGCAGATGCACCAGCGTATCAGCAG<br>GGCCAGAACCAACTGTATAACGAGCTCAACCTGGGACGCAGG<br>GAAGAGTATGACGTTTTGGACAAGCGCAGAGGACGGGACCCT<br>GAGATGGGTGGCAAACCAAGACGAAAAAACCCCCAGGAGGGT<br>CTCTATAATGAGCTGCAGAAGGATAAGATGGCTGAAGCCTAT<br>TCTGAAATAGGCATGAAAGGAGAGCGGAGAAGGGGAAAAGGG<br>CACGACGGTTTGTACCAGGGACTCAGCACTGCTACGAAGGAT<br>ACTTATGACGCTCTCCACATGCAAGCCCTGCCACCTAGGTAA | | SKRSRLLHSDYMNMTPRRP<br>GPTRKHYQPYAPPRDFAAY<br>RSRVKFSRSADAPAYQQGQ<br>NQLYNELNLGRREEYDVLD<br>KRRGRDPEMGGKPRRKNPQ<br>EGLYNELQKDKMAEAYSEI<br>GMKGERRRGKGHDGLYQGL<br>STATKDTYDALHMQALPPR | |
| NM-21517CAR HxL | ATGGCACTCCCCGTAACTGCTCTGCTGCTGCCGTTGGCATTG<br>CTCCTGCACGCCGCACGCCCGCAGCTGCAGCTGCAGGAGTCG<br>GGCCCAGGACTGGTGAAGCCTTCGGAGACCCTGTCCCTCACC<br>TGCACTGTCTCTGGTGGCTCCATCAGCAGTAGTAGTTACTAC<br>TGGGGCTGGATCCGCCAGCCCCCAGGGAAGGGGCTGGAGTGG<br>ATTGGGAGTATCTCCTATAGTGGGAGCACCTACTACAACCCG<br>TCCCTCAAGAGTCGAGTCACCATATCCGTAGACACGTCCAAG<br>AACCAGTTCTCCCTGAAGCTGAGTTCTGTGACCGCCGCAGAC<br>ACGGCGGTGTACTACTGCGCCAGAGGCAGGGGATATGCAACC<br>AGCTTAGCCTTCGATATCTGGGGTCAGGGTACAATGGTCACC<br>GTCTCCTCAGGGTCTACATCCGGCTCCGGGAAGCCCGGAAGT<br>GGCGAAGGTAGTACAAAGGGGGAAATTGTGTTGACACAGTCT<br>CCAGCCACCCTGTCTTTGTCTCCAGGGGAAAGAGCCACCCTC<br>TCCTGCAGGGCCAGTCAGAGTGTTAGCAGCTACTTAGCCTGG<br>TACCAACAGAAACCTGGCCAGGCTCCCAGGCTCCTCATCTAT<br>GATGCATCCAACAGGGCCACTGGCATCCCAGCCAGGTTCAGT<br>GGCAGTGGGTCTGGGACAGACTTCACTCTCACCATCAGCAGC<br>CTAGAGCCTGAAGATTTTGCAGTTTATTACTGTCAGCAGAGA<br>CACGTCTGGCCTCCTACTTTTGGCGGAGGGACCAAGGTTGAG<br>ATCAAACGGGCCGCTGCCCTTGATAATGAAAAGTCAAACGGA<br>ACAATCATTCACGTGAAGGGCAAGCACCTCTGTCCGTCACCC<br>TTGTTCCCTGGTCCATCCAAGCCATTCTGGGTGTTGGTCGTA<br>GTGGGTGGAGTCCTCGCTTGTTACTCTCTGCTCGTCACCGTG<br>GCTTTTATAATCTTCTGGGTTAGATCCAAAAGAAGCCGCCTG<br>CTCCATAGCGATTACATGAATATGACTCCACGCCGCCCTGGC<br>CCCACAAGGAAACACTACCAGCCTTACGCACCACCTAGAGAT<br>TTCGCTGCCTATCGGAGCAGGGTGAAGTTTTCCAGATCTGCA<br>GATGCACCAGCGTATCAGCAGGGCCAGAACCAACTGTATAAC<br>GAGCTCAACCTGGGACGCAGGGAAGAGTATGACGTTTTGGAC<br>AAGCGCAGAGGACGGGACCCTGAGATGGGTGGCAAACCAAGA<br>CGAAAAAACCCCCAGGAGGGTCTCTATAATGAGCTGCAGAAG<br>GATAAGATGGCTGAAGCCTATTCTGAAATAGGCATGAAAGGA<br>GAGCGGAGAAGGGGAAAAGGGCACGACGGTTTGTACCAGGGA<br>CTCAGCACTGCTACGAAGGATACTTATGACGCTCTCCACATG<br>CAAGCCCTGCCACCTAGGTAA | 187 | MALPVTALLLPLALLLHAA<br>RPQLQLQESGPGLVKPSET<br>LSLTCTVSGGSISSSSYYW<br>GWIRQPPGKGLEWIGSISY<br>SGSTYYNPSLKSRVTISVD<br>TSKNQFSLKLSSVTAADTA<br>VYYCARGRGYATSLAFDIW<br>GQGTMVTVSSGSTSGSGKP<br>GSGEGSTKGEIVLTQSPAT<br>LSLSPGERATLSCRASQSV<br>SSYLAWYQQKPGQAPRLLI<br>YDASNRATGIPARESGSGS<br>GTDFTLTISSLEPEDFAVY<br>YCQQRHVWPPTFGGGTKVE<br>IKRAAALDNEKSNGTIIHV<br>KGKHLCPSPLFPGPSKPFW<br>VLVVVGGVLACYSLLVTVA<br>FIIFWVRSKRSRLLHSDYM<br>NMTPRRPGPTRKHYQPYAP<br>PRDFAAYRSRVKFSRSADA<br>PAYQQGQNQLYNELNLGRR<br>EEYDVLDKRRGRDPEMGGK<br>PRRKNPQEGLYNELQKDKM<br>AEAYSEIGMKGERRRGKGH<br>DGLYQGLSTATKDTYDALH<br>MQALPPR | 188 |
| NM-21517CAR LxH | ATGGCACTCCCCGTAACTGCTCTGCTGCTGCCGTTGGCATTG<br>CTCCTGCACGCCGCACGCCCGGAAATTGTGTTGACACAGTCT<br>CCAGCCACCCTGTCTTTGTCTCCAGGGGAAAGAGCCACCCTC<br>TCCTGCAGGGCCAGTCAGAGTGTTAGCAGCTACTTAGCCTGG<br>TACCAACAGAAACCTGGCCAGGCTCCCAGGCTCCTCATCTAT<br>GATGCATCCAACAGGGCCACTGGCATCCCAGCCAGGTTCAGT<br>GGCAGTGGGTCTGGGACAGACTTCACTCTCACCATCAGCAGC<br>CTAGAGCCTGAAGATTTTGCAGTTTATTACTGTCAGCAGAGA<br>CACGTCTGGCCTCCTACTTTTGGCGGAGGGACCAAGGTTGAG<br>ATCAAACGGGGGTCTACATCCGGCTCCGGGAAGCCCGGAAGT<br>GGCGAAGGTAGTACAAAGGGGCAGCTGCAGCTGCAGGAGTCG<br>GGCCCAGGACTGGTGAAGCCTTCGGAGACCCTGTCCCTCACC<br>TGCACTGTCTCTGGTGGCTCCATCAGCAGTAGTAGTTACTAC<br>TGGGGCTGGATCCGCCAGCCCCCAGGGAAGGGGCTGGAGTGG<br>ATTGGGAGTATCTCCTATAGTGGGAGCACCTACTACAACCCG<br>TCCCTCAAGAGTCGAGTCACCATATCCGTAGACACGTCCAAG<br>AACCAGTTCTCCCTGAAGCTGAGTTCTGTGACCGCCGCAGAC<br>ACGGCGGTGTACTACTGCGCCAGAGGCAGGGGATATGCAACC<br>AGCTTAGCCTTCGATATCTGGGGTCAGGGTACAATGGTCACC<br>GTCTCCTCAGCCGCTGCCCTTGATAATGAAAAGTCAAACGGA | 189 | MALPVTALLLPLALLLHAA<br>RPEIVLTQSPATLSLSPGE<br>RATLSCRASQSVSSYLAWY<br>QQKPGQAPRLLIYDASNRA<br>TGIPARFSGSGSGTDFTLT<br>ISSLEPEDFAVYYCQQRHV<br>WPPTFGGGTKVEIKRGSTS<br>GSGKPGSGEGSTKGQLQLQ<br>ESGPGLVKPSETLSLTCTV<br>SGGSISSSSYYWGWIRQPP<br>GKGLEWIGSISYSGSTYYN<br>PSLKSRVTISVDTSKNQFS<br>LKLSSVTAADTAVYYCARG<br>RGYATSLAFDIWGQGTMVT<br>VSSAAALDNEKSNGTIIHV<br>KGKHLCPSPLFPGPSKPFW<br>VLVVVGGVLACYSLLVTVA<br>FIIFWVRSKRSRLLHSDYM<br>NMTPRRPGPTRKHYQPYAP<br>PRDFAAYRSRVKFSRSADA | 190 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| | ACAATCATTCACGTGAAGGGCAAGCACCTCTGTCCGTCACCC<br>TTGTTCCCTGGTCCATCCAAGCCATTCTGGGTGTTGGTCGTA<br>GTGGGTGGAGTCCTCGCTTGTTACTCTCTGCTCGTCACCGTG<br>GCTTTTATAATCTTCTGGGTTAGATCCAAAAGAAGCCGCCTG<br>CTCCATAGCGATTACATGAATATGACTCCACGCCGCCCTGGC<br>CCCACAAGGAAACACTACCAGCCTTACGCACCACCTAGAGAT<br>TTCGCTGCCTATCGGAGCAGGGTGAAGTTTTCCAGATCTGCA<br>GATGCACCAGCGTATCAGCAGGGCCAGAACCAACTGTATAAC<br>GAGCTCAACCTGGGACGCAGGGAAGAGTATGACGTTTTGGAC<br>AAGCGCAGAGGACGGGACCCTGAGATGGGTGGCAAACCAAGA<br>CGAAAAAACCCCCAGGAGGGTCTCTATAATGAGCTGCAGAAG<br>GATAAGATGGCTGAAGCCTATTCTGAAATAGGCATGAAAGGA<br>GAGCGGAGAAGGGGAAAAGGGCACGACGGTTTGTACCAGGGA<br>CTCAGCACTGCTACGAAGGATACTTATGACGCTCTCCACATG<br>CAAGCCCTGCCACCTAGGTAA | | PAYQQGQNQLYNELNLGRR<br>EEYDVLDKRRGRDPEMGGK<br>PRRKNPQEGLYNELQKDKM<br>AEAYSEIGMKGERRRGKGH<br>DGLYQGLSTATKDTYDALH<br>MQALPPR | |
| TS-21522CAR HxL | ATGGCACTCCCCGTAACTGCTCTGCTGCTGCCGTTGGCATTG<br>CTCCTGCACGCCGCACGCCCGGAGGTGCAGCTGGTGGAGTCT<br>GGGGGAGGCTTGGTACAGCCTGGGGGGTCCCTGAGACTCTCC<br>TGTGCAGCCTCTGGATTCACCTTCAGTAGCTATAGCATGAAC<br>TGGGTCCGCCAGGCTCCAGGGAAGGGGCTGGAGTGGGTTTCA<br>ACCATTAGTAGTAGTAGTAGTACCATATACTACGCAGACTCT<br>GTGAAGGGCCGATTCACCATCTCCAGAGACAATGCCAAGAAC<br>TCACTGTATCTGCAAATGAACAGCCTGAGAGCTGAGGACACG<br>GCGGTGTACTACTGCGCCAGAGGTTCTCAGGAGCACCTGATT<br>TTCGATTATTGGGGACAGGGTACATTGGTCACCGTCTCCTCA<br>GGGTCTACATCCGGCTCCGGGAAGCCCGGAAGTGGCGAAGGT<br>AGTACAAAGGGGGAAATTGTGTTGACACAGTCTCCAGCCACC<br>CTGTCTTTGTCTCCAGGGGAAAGAGCCACCCTCTCCTGCAGG<br>GCCAGTCAGAGTGTTAGCAGGTACTTAGCCTGGTACCAACAG<br>AAACCTGGCCAGGCTCCCAGGCTCCTCATCTATGATGCATCC<br>AACAGGGCCACTGGCATCCCAGCCAGGTTCAGTGGCAGTGGG<br>TCTGGGACAGACTTCACTCTCACCATCAGCAGCCTAGAGCCT<br>GAAGATTTTGCAGTTTATTACTGTCAGCAGAGATTCTACTAC<br>CCTTGGACTTTTGGCGGAGGGACCAAGGTTGAGATCAAACGG<br>GCCGCTGCCCTTGATAATGAAAAGTCAAACGGAACAATCATT<br>CACGTGAAGGGCAAGCACCTCTGTCCGTCACCCTTGTTCCCT<br>GGTCCATCCAAGCCATTCTGGGTGTTGGTCGTAGTGGGTGGA<br>GTCCTCGCTTGTTACTCTCTGCTCGTCACCGTGGCTTTTATA<br>ATCTTCTGGGTTAGATCCAAAAGAAGCCGCCTGCTCCATAGC<br>GATTACATGAATATGACTCCACGCCGCCCTGGCCCCACAAGG<br>AAACACTACCAGCCTTACGCACCACCTAGAGATTTCGCTGCC<br>TATCGGAGCAGGGTGAAGTTTTCCAGATCTGCAGATGCACCA<br>GCGTATCAGCAGGGCCAGAACCAACTGTATAACGAGCTCAAC<br>CTGGGACGCAGGGAAGAGTATGACGTTTTGGACAAGCGCAGA<br>GGACGGGACCCTGAGATGGGTGGCAAACCAAGACGAAAAAAC<br>CCCCAGGAGGGTCTCTATAATGAGCTGCAGAAGGATAAGATG<br>GCTGAAGCCTATTCTGAAATAGGCATGAAAGGAGAGCGGAGA<br>AGGGGAAAAGGGCACGACGGTTTGTACCAGGGACTCAGCACT<br>GCTACGAAGGATACTTATGACGCTCTCCACATGCAAGCCCTG<br>CCACCTAGGTAA | 191 | MALPVTALLLPLALLLHAA<br>RPEVQLVESGGGLVQPGGS<br>LRLSCAASGFTFSSYSMNW<br>VRQAPGKGLEWVSTISSSS<br>STIYYADSVKGRFTISRDN<br>AKNSLYLQMNSLRAEDTAV<br>YYCARGSQEHLIFDYWGQG<br>TLVTVSSGSTSGSGKPGSG<br>EGSTKGEIVLTQSPATLSL<br>SPGERATLSCRASQSVSRY<br>LAWYQQKPGQAPRLLIYDA<br>SNRATGIPARFSGSGSGTD<br>FTLTISSLEPEDFAVYYCQ<br>QRFYYPWTFGGGTKVEIKR<br>AAALDNEKSNGTIIHVKGK<br>HLCPSPLFPGPSKPFWVLV<br>VVGGVLACYSLLVTVAFII<br>FWVRSKRSRLLHSDYMNMT<br>PRRPGPTRKHYQPYAPPRD<br>FAAYRSRVKFSRSADAPAY<br>QQGQNQLYNELNLGRREEY<br>DVLDKRRGRDPEMGGKPRR<br>KNPQEGLYNELQKDKMAEA<br>YSEIGMKGERRRGKGHDGL<br>YQGLSTATKDTYDALHMQA<br>LPPR | 192 |
| TS-21522CAR LxH | ATGGCACTCCCCGTAACTGCTCTGCTGCTGCCGTTGGCATTG<br>CTCCTGCACGCCGCACGCCCGGAAATTGTGTTGACACAGTCT<br>CCAGCCACCCTGTCTTTGTCTCCAGGGGAAAGAGCCACCCTC<br>TCCTGCAGGGCCAGTCAGAGTGTTAGCAGGTACTTAGCCTGG<br>TACCAACAGAAACCTGGCCAGGCTCCCAGGCTCCTCATCTAT<br>GATGCATCCAACAGGGCCACTGGCATCCCAGCCAGGTTCAGT<br>GGCAGTGGGTCTGGGACAGACTTCACTCTCACCATCAGCAGC<br>CTAGAGCCTGAAGATTTTGCAGTTTATTACTGTCAGCAGAGA<br>TTCTACTACCCTTGGACTTTTGGCGGAGGGACCAAGGTTGAG<br>ATCAAACGGGGGTCTACATCCGGCTCCGGGAAGCCCGGAAGT<br>GGCGAAGGTAGTACAAAGGGGGAGGTGCAGCTGGTGGAGTCT<br>GGGGGAGGCTTGGTACAGCCTGGGGGGTCCCTGAGACTCTCC<br>TGTGCAGCCTCTGGATTCACCTTCAGTAGCTATAGCATGAAC<br>TGGGTCCGCCAGGCTCCAGGGAAGGGGCTGGAGTGGGTTTCA<br>ACCATTAGTAGTAGTAGTAGTACCATATACTACGCAGACTCT<br>GTGAAGGGCCGATTCACCATCTCCAGAGACAATGCCAAGAAC<br>TCACTGTATCTGCAAATGAACAGCCTGAGAGCTGAGGACACG<br>GCGGTGTACTACTGCGCCAGAGGTTCTCAGGAGCACCTGATT<br>TTCGATTATTGGGGACAGGGTACATTGGTCACCGTCTCCTCA<br>GCCGCTGCCCTTGATAATGAAAAGTCAAACGGAACAATCATT<br>CACGTGAAGGGCAAGCACCTCTGTCCGTCACCCTTGTTCCCT<br>GGTCCATCCAAGCCATTCTGGGTGTTGGTCGTAGTGGGTGGA | 193 | MALPVTALLLPLALLLHAA<br>RPEIVLTQSPATLSLSPGE<br>RATLSCRASQSVSRYLAWY<br>QQKPGQAPRLLIYDASNRA<br>TGIPARFSGSGSGTDFTLT<br>ISSLEPEDFAVYYCQQRFY<br>YPWTFGGGTKVEIKRGSTS<br>GSGKPGSGEGSTKGEVQLV<br>ESGGGLVQPGGSLRLSCAA<br>SGFTFSSYSMNWVRQAPGK<br>GLEWVSTISSSSSTIYYAD<br>SVKGRFTISRDNAKNSLYL<br>QMNSLRAEDTAVYYCARGS<br>QEHLIFDYWGQGTLVTVSS<br>AAALDNEKSNGTIIHVKGK<br>HLCPSPLFPGPSKPFWVLV<br>VVGGVLACYSLLVTVAFII<br>FWVRSKRSRLLHSDYMNMT<br>PRRPGPTRKHYQPYAPPRD<br>FAAYRSRVKFSRSADAPAY<br>QQGQNQLYNELNLGRREEY<br>DVLDKRRGRDPEMGGKPRR | 194 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| | GTCCTCGCTTGTTACTCTCTGCTCGTCACCGTGGCTTTTATA | | KNPQEGLYNELQKDKMAEA | |
| | ATCTTCTGGGTTAGATCCAAAAGAAGCCGCCTGCTCCATAGC | | YSEIGMKGERRRGKGHDGL | |
| | GATTACATGAATATGACTCCACGCCGCCCTGGCCCCACAAGG | | YQGLSTATKDTYDALHMQA | |
| | AAACACTACCAGCCTTACGCACCACCTAGAGATTTCGCTGCC | | LPPR | |
| | TATCGGAGCAGGGTGAAGTTTTCCAGATCTGCAGATGCACCA | | | |
| | GCGTATCAGCAGGGCCAGAACCAACTGTATAACGAGCTCAAC | | | |
| | CTGGGACGCAGGGAAGAGTATGACGTTTTGGACAAGCGCAGA | | | |
| | GGACGGGACCCTGAGATGGGTGGCAAACCAAGACGAAAAAAC | | | |
| | CCCCAGGAGGGTCTCTATAATGAGCTGCAGAAGGATAAGATG | | | |
| | GCTGAAGCCTATTCTGAAATAGGCATGAAAGGAGAGCGGAGA | | | |
| | AGGGGAAAAGGGCACGACGGTTTGTACCAGGGACTCAGCACT | | | |
| | GCTACGAAGGATACTTATGACGCTCTCCACATGCAAGCCCTG | | | |
| | CCACCTAGGTAA | | | |
| RY-21527CAR HxL | ATGGCACTCCCCGTAACTGCTCTGCTGCTGCCGTTGGCATTG | 195 | MALPVTALLLPLALLLHAA | 196 |
| | CTCCTGCACGCCGCACGCCCGCAGGTGCAGCTGGTGGAGTCT | | RPQVQLVESGGGVVQPGRS | |
| | GGGGGAGGCGTGGTCCAGCCTGGGAGGTCCCTGAGACTCTCC | | LRLSCAASGFTFSSYGMHW | |
| | TGTGCAGCGTCTGGATTCACCTTCAGTAGCTATGGCATGCAC | | VRQAPGKGLEWVAVISYDG | |
| | TGGGTCCGCCAGGCTCCAGGCAAGGGGCTGGAGTGGGTGGCA | | SNKYYADSVKGRFTISRDN | |
| | GTTATATCGTATGATGGAAGTAATAAATACTATGCAGACTCC | | SKNTLYLQMNSLRAEDTAV | |
| | GTGAAGGGCCGATTCACCATCTCCAGAGACAATTCCAAGAAC | | YYCARTDFWSGSPPGLDYW | |
| | ACGCTGTATCTGCAAATGAACAGCCTGAGAGCCGAGGACACG | | GQGTLVTVSSGSTSGSGKP | |
| | GCGGTGTACTACTGCGCCAGAACTGACTTCTGGAGCGGATCC | | GSGEGSTKGDIQLTQSPSS | |
| | CCTCCAGGCTTAGATTACTGGGGACAGGGTACATTGGTCACC | | VSASVGDRVTITCRASQGI | |
| | GTCTCCTCAGGGTCTACATCCGGCTCCGGGAAGCCCGGAAGT | | SSWLAWYQQKPGKAPKLLI | |
| | GGCGAAGGTAGTACAAAGGGGGACATCCAGTTGACCCAGTCT | | YGASSLQSGVPSRFSGSGS | |
| | CCATCTTCCGTGTCTGCATCTGTAGGAGACAGAGTCACCATC | | GTDFTLTISSLQPEDFATY | |
| | ACTTGTCGGGCGAGTCAGGGTATTAGCAGCTGGTTAGCCTGG | | YCQQIYTFPFTFGGGTKVE | |
| | TATCAGCAGAAACCAGGGAAAGCCCCTAAGCTCCTGATCTAT | | IKRAAALDNEKSNGTIIHV | |
| | GGTGCATCCAGTTTGCAAAGTGGGGTCCCATCAAGGTTCAGC | | KGKHLCPSPLFPGPSKPFW | |
| | GGCAGTGGATCTGGGACAGATTTCACTCTCACCATCAGCAGC | | VLVVVGGVLACYSLLVTVA | |
| | CTGCAGCCTGAAGATTTTGCAACTTATTACTGTCAGCAGATA | | FIIFWVRSKRSRLLHSDYM | |
| | TACACCTTCCCTTTCACTTTTGGCGGAGGGACCAAGGTTGAG | | NMTPRRPGPTRKHYQPYAP | |
| | ATCAAACGGGCCGCTGCCCTTGATAATGAAAAGTCAAACGGA | | PRDFAAYRSRVKFSRSADA | |
| | ACAATCATTCACGTGAAGGGCAAGCACCTCTGTCCGTCACCC | | PAYQQGQNQLYNELNLGRR | |
| | TTGTTCCCTGGTCCATCCAAGCCATTCTGGGTGTTGGTCGTA | | EEYDVLDKRRGRDPEMGGK | |
| | GTGGGTGGAGTCCTCGCTTGTTACTCTCTGCTCGTCACCGTG | | PRRKNPQEGLYNELQKDKM | |
| | GCTTTTATAATCTTCTGGGTTAGATCCAAAAGAAGCCGCCTG | | AEAYSEIGMKGERRRGKGH | |
| | CTCCATAGCGATTACATGAATATGACTCCACGCCGCCCTGGC | | DGLYQGLSTATKDTYDALH | |
| | CCCACAAGGAAACACTACCAGCCTTACGCACCACCTAGAGAT | | MQALPPR | |
| | TTCGCTGCCTATCGGAGCAGGGTGAAGTTTTCCAGATCTGCA | | | |
| | GATGCACCAGCGTATCAGCAGGGCCAGAACCAACTGTATAAC | | | |
| | GAGCTCAACCTGGGACGCAGGGAAGAGTATGACGTTTTGGAC | | | |
| | AAGCGCAGAGGACGGGACCCTGAGATGGGTGGCAAACCAAGA | | | |
| | CGAAAAAACCCCCAGGAGGGTCTCTATAATGAGCTGCAGAAG | | | |
| | GATAAGATGGCTGAAGCCTATTCTGAAATAGGCATGAAAGGA | | | |
| | GAGCGGAGAAGGGGAAAAGGGCACGACGGTTTGTACCAGGGA | | | |
| | CTCAGCACTGCTACGAAGGATACTTATGACGCTCTCCACATG | | | |
| | CAAGCCCTGCCACCTAGGTAA | | | |
| RY-21527CAR LxH | ATGGCACTCCCCGTAACTGCTCTGCTGCTGCCGTTGGCATTG | 197 | MALPVTALLLPLALLLHAA | 198 |
| | CTCCTGCACGCCGCACGCCCGGACATCCAGTTGACCCAGTCT | | RPDIQLTQSPSSVSASVGD | |
| | CCATCTTCCGTGTCTGCATCTGTAGGAGACAGAGTCACCATC | | RVTITCRASQGISSWLAWY | |
| | ACTTGTCGGGCGAGTCAGGGTATTAGCAGCTGGTTAGCCTGG | | QQKPGKAPKLLIYGASSLQ | |
| | TATCAGCAGAAACCAGGGAAAGCCCCTAAGCTCCTGATCTAT | | SGVPSRFSGSGSGTDFTLT | |
| | GGTGCATCCAGTTTGCAAAGTGGGGTCCCATCAAGGTTCAGC | | ISSLQPEDFATYYCQQIYT | |
| | GGCAGTGGATCTGGGACAGATTTCACTCTCACCATCAGCAGC | | FPFTFGGGTKVEIKRGSTS | |
| | CTGCAGCCTGAAGATTTTGCAACTTATTACTGTCAGCAGATA | | GSGKPGSGEGSTKGQVQLV | |
| | TACACCTTCCCTTTCACTTTTGGCGGAGGGACCAAGGTTGAG | | ESGGGWQPGRSLRLSCAA | |
| | ATCAAACGGGGGTCTACATCCGGCTCCGGGAAGCCCGGAAGT | | SGFTFSSYGMHWVRQAPGK | |
| | GGCGAAGGTAGTACAAAGGGGCAGGTGCAGCTGGTGGAGTCT | | GLEWVAVISYDGSNKYYAD | |
| | GGGGGAGGCGTGGTCCAGCCTGGGAGGTCCCTGAGACTCTCC | | SVKGRFTISRDNSKNTLYL | |
| | TGTGCAGCGTCTGGATTCACCTTCAGTAGCTATGGCATGCAC | | QMNSLRAEDTAVYYCARTD | |
| | TGGGTCCGCCAGGCTCCAGGCAAGGGGCTGGAGTGGGTGGCA | | FWSGSPPGLDYWGQGTLVT | |
| | GTTATATCGTATGATGGAAGTAATAAATACTATGCAGACTCC | | VSSAAALDNEKSNGTIIHV | |
| | GTGAAGGGCCGATTCACCATCTCCAGAGACAATTCCAAGAAC | | KGKHLCPSPLFPGPSKPFW | |
| | ACGCTGTATCTGCAAATGAACAGCCTGAGAGCCGAGGACACG | | VLVVVGGVLACYSLLVTVA | |
| | GCGGTGTACTACTGCGCCAGAACTGACTTCTGGAGCGGATCC | | FIIFWVRSKRSRLLHSDYM | |
| | CCTCCAGGCTTAGATTACTGGGGACAGGGTACATTGGTCACC | | NMTPRRPGPTRKHYQPYAP | |
| | GTCTCCTCAGCCGCTGCCCTTGATAATGAAAAGTCAAACGGA | | PRDFAAYRSRVKFSRSADA | |
| | ACAATCATTCACGTGAAGGGCAAGCACCTCTGTCCGTCACCC | | PAYQQGQNQLYNELNLGRR | |
| | TTGTTCCCTGGTCCATCCAAGCCATTCTGGGTGTTGGTCGTA | | EEYDVLDKRRGRDPEMGGK | |
| | GTGGGTGGAGTCCTCGCTTGTTACTCTCTGCTCGTCACCGTG | | PRRKNPQEGLYNELQKDKM | |
| | GCTTTTATAATCTTCTGGGTTAGATCCAAAAGAAGCCGCCTG | | AEAYSEIGMKGERRRGKGH | |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| | CTCCATAGCGATTACATGAATATGACTCCACGCCGCCCTGGC<br>CCCACAAGGAAACACTACCAGCCTTACGCACCACCTAGAGAT<br>TTCGCTGCCTATCGGAGCAGGGTGAAGTTTTCCAGATCTGCA<br>GATGCACCAGCGTATCAGCAGGGCCAGAACCAACTGTATAAC<br>GAGCTCAACCTGGGACGCAGGGAAGAGTATGACGTTTTGGAC<br>AAGCGCAGAGGACGGGACCCTGAGATGGGTGGCAAACCAAGA<br>CGAAAAAACCCCCAGGAGGGTCTCTATAATGAGCTGCAGAAG<br>GATAAGATGGCTGAAGCCTATTCTGAAATAGGCATGAAAGGA<br>GAGCGGAGAAGGGGAAAAGGGCACGACGGTTTGTACCAGGGA<br>CTCAGCACTGCTACGAAGGATACTTATGACGCTCTCCACATG<br>CAAGCCCTGCCACCTAGGTAA | | DGLYQGLSTATKDTYDALH<br>MQALPPR | |
| PP-21528CAR HxL | ATGGCACTCCCCGTAACTGCTCTGCTGCTGCCGTTGGCATTG<br>CTCCTGCACGCCGCACGCCCGCAGGTGCAGCTGGTGCAGTCT<br>GGGGCTGAGGTGAAGAAGCCTGGGTCCTCGGTGAAGGTCTCC<br>TGCAAGGCTTCTGGAGGCACCTTCAGCAGCTATGCTATCAGC<br>TGGGTGCGACAGGCCCCTGGACAAGGGCTTGAGTGGATGGGA<br>GGGATCATCCCTATCTTTGGTACAGCAAACTACGCACAGAAG<br>TTCCAGGGCAGAGTCACGATTACCGCGGACGAATCCACGAGC<br>ACAGCCTACATGGAGCTGAGCAGCCTGAGATCTGAGGACACG<br>GCGGTGTACTACTGCGCCAGAACTCCTGAATACTCCTCCAGC<br>ATATGGCACTATTACTACGGCATGGACGTATGGGGCCAGGGA<br>ACAACTGTCACCGTCTCCTCAGGGTCTACATCCGGCTCCGGG<br>AAGCCCGGAAGTGGCGAAGGTAGTACAAAGGGGGACATCGTG<br>ATGACCCAGTCTCCAGACTCCCTGGCTGTGTCTCTGGGCGAG<br>AGGGCCACCATCAACTGCAAGTCCAGCCAGAGTGTTTTATAC<br>AGCTCCAACAATAAGAACTACTTAGCTTGGTACCAGCAGAAA<br>CCAGGACAGCCTCCTAAGCTGCTCATTTACTGGGCATCTACC<br>CGGGAATCCGGGGTCCCTGACCGATTCAGTGGCAGCGGGTCT<br>GGGACAGATTTCACTCTCACCATCAGCAGCCTGCAGGCTGAA<br>GATGTGGCAGTTTATTACTGTCAGCAGTTCGCCCACACTCCT<br>TTCACTTTTGGCGGAGGGACCAAGGTTGAGATCAAACGGGCC<br>GCTGCCCTTGATAATGAAAAGTCAAACGGAACAATCATTCAC<br>GTGAAGGGCAAGCACCTCTGTCCGTCACCCTTGTTCCCTGGT<br>CCATCCAAGCCATTCTGGGTGTTGGTCGTAGTGGGTGGAGTC<br>CTCGCTTGTTACTCTCTGCTCGTCACCGTGGCTTTTATAATC<br>TTCTGGGTTAGATCCAAAAGAAGCCGCCTGCTCCATAGCGAT<br>TACATGAATATGACTCCACGCCGCCCTGGCCCCACAAGGAAA<br>CACTACCAGCCTTACGCACCACCTAGAGATTTCGCTGCCTAT<br>CGGAGCAGGGTGAAGTTTTCCAGATCTGCAGATGCACCAGCG<br>TATCAGCAGGGCCAGAACCAACTGTATAACGAGCTCAACCTG<br>GGACGCAGGGAAGAGTATGACGTTTTGGACAAGCGCAGAGGA<br>CGGGACCCTGAGATGGGTGGCAAACCAAGACGAAAAAACCCC<br>CAGGAGGGTCTCTATAATGAGCTGCAGAAGGATAAGATGGCT<br>GAAGCCTATTCTGAAATAGGCATGAAAGGAGAGCGGAGAAGG<br>GGAAAAGGGCACGACGGTTTGTACCAGGGACTCAGCACTGCT<br>ACGAAGGATACTTATGACGCTCTCCACATGCAAGCCCTGCCA<br>CCTAGGTAA | 199 | MALPVTALLLPLALLLHAA<br>RPQVQLVQSGAEVKKPGSS<br>VKVSCKASGGTFSSYAISW<br>VRQAPGQGLEWMGGIIPIF<br>GTANYAQKFQGRVTITADE<br>STSTAYMELSSLRSEDTAV<br>YYCARTPEYSSSIWHYYYG<br>MDVWGQGTTVTVSSGSTSG<br>SGKPGSGEGSTKGDIVMTQ<br>SPDSLAVSLGERATINCKS<br>SQSVLYSSNNKNYLAWYQQ<br>KPGQPPKLLIYWASTRESG<br>VPDRFSGSGSGTDFTLTIS<br>SLQAEDVAVYYCQQFAHTP<br>FTFGGGTKVEIKRAAALDN<br>EKSNGTIIHVKGKHLCPSP<br>LFPGPSKPFWVLVVVGGVL<br>ACYSLLVTVAFIIFWVRSK<br>RSRLLHSDYMNMTPRRPGP<br>TRKHYQPYAPPRDFAAYRS<br>RVKFSRSADAPAYQQGQNQ<br>LYNELNLGRREEYDVLDKR<br>RGRDPEMGGKPRRKNPQEG<br>LYNELQKDKMAEAYSEIGM<br>KGERRRGKGHDGLYQGLST<br>ATKDTYDALHMQALPPR | 200 |
| PP-21528CAR LxH | ATGGCACTCCCCGTAACTGCTCTGCTGCTGCCGTTGGCATTG<br>CTCCTGCACGCCGCACGCCCGGACATCGTGATGACCCAGTCT<br>CCAGACTCCCTGGCTGTGTCTCTGGGCGAGAGGGCCACCATC<br>AACTGCAAGTCCAGCCAGAGTGTTTTATACAGCTCCAACAAT<br>AAGAACTACTTAGCTTGGTACCAGCAGAAACCAGGACAGCCT<br>CCTAAGCTGCTCATTTACTGGGCATCTACCCGGGAATCCGGG<br>GTCCCTGACCGATTCAGTGGCAGCGGGTCTGGGACAGATTTC<br>ACTCTCACCATCAGCAGCCTGCAGGCTGAAGATGTGGCAGTT<br>TATTACTGTCAGCAGTTCGCCCACACTCCTTTCACTTTTGGC<br>GGAGGGACCAAGGTTGAGATCAAACGGGGGTCTACATCCGGC<br>TCCGGGAAGCCCGGAAGTGGCGAAGGTAGTACAAAGGGGCAG<br>GTGCAGCTGGTGCAGTCTGGGGCTGAGGTGAAGAAGCCTGGG<br>TCCTCGGTGAAGGTCTCCTGCAAGGCTTCTGGAGGCACCTTC<br>AGCAGCTATGCTATCAGCTGGGTGCGACAGGCCCCTGGACAA<br>GGGCTTGAGTGGATGGGAGGGATCATCCCTATCTTTGGTACA<br>GCAAACTACGCACAGAAGTTCCAGGGCAGAGTCACGATTACC<br>GCGGACGAATCCACGAGCACAGCCTACATGGAGCTGAGCAGC<br>CTGAGATCTGAGGACACGGCGGTGTACTACTGCGCCAGAACT<br>CCTGAATACTCCTCCAGCATATGGCACTATTACTACGGCATG<br>GACGTATGGGGCCAGGGAACAACTGTCACCGTCTCCTCAGCC<br>GCTGCCCTTGATAATGAAAAGTCAAACGGAACAATCATTCAC<br>GTGAAGGGCAAGCACCTCTGTCCGTCACCCTTGTTCCCTGGT<br>CCATCCAAGCCATTCTGGGTGTTGGTCGTAGTGGGTGGAGTC<br>CTCGCTTGTTACTCTCTGCTCGTCACCGTGGCTTTTATAATC<br>TTCTGGGTTAGATCCAAAAGAAGCCGCCTGCTCCATAGCGAT | 201 | MALPVTALLLPLALLLHAA<br>RPDIVMTQSPDSLAVSLGE<br>RATINCKSSQSVLYSSNNK<br>NYLAWYQQKPGQPPKLLIY<br>WASTRESGVPDRFSGSGSG<br>TDFTLTISSLQAEDVAVYY<br>CQQFAHTPFTFGGGTKVEI<br>KRGSTSGSGKPGSGEGSTK<br>GQVQLVQSGAEVKKPGSSV<br>KVSCKASGGTFSSYAISWV<br>RQAPGQGLEWMGGIIPIFG<br>TANYAQKFQGRVTITADES<br>TSTAYMELSSLRSEDTAVY<br>YCARTPEYSSSIWHYYYGM<br>DVWGQGTTVTVSSAAALDN<br>EKSNGTIIHVKGKHLCPSP<br>LFPGPSKPFWVLVVVGGVL<br>ACYSLLVTVAFIIFWVRSK<br>RSRLLHSDYMNMTPRRPGP<br>TRKHYQPYAPPRDFAAYRS<br>RVKFSRSADAPAYQQGQNQ<br>LYNELNLGRREEYDVLDKR<br>RGRDPEMGGKPRRKNPQEG<br>LYNELQKDKMAEAYSEIGM<br>KGERRRGKGHDGLYQGLST | 202 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| | TACATGAATATGACTCCACGCCGCCCTGGCCCCACAAGGAAA | | ATKDTYDALHMQALPPR | |
| | CACTACCAGCCTTACGCACCACCTAGAGATTTCGCTGCCTAT | | | |
| | CGGAGCAGGGTGAAGTTTTCCAGATCTGCAGATGCACCAGCG | | | |
| | TATCAGCAGGGCCAGAACCAACTGTATAACGAGCTCAACCTG | | | |
| | GGACGCAGGGAAGAGTATGACGTTTTGGACAAGCGCAGAGGA | | | |
| | CGGGACCCTGAGATGGGTGGCAAACCAAGACGAAAAAACCCC | | | |
| | CAGGAGGGTCTCTATAATGAGCTGCAGAAGGATAAGATGGCT | | | |
| | GAAGCCTATTCTGAAATAGGCATGAAAGGAGAGCGGAGAAGG | | | |
| | GGAAAAGGGCACGACGGTTTGTACCAGGGACTCAGCACTGCT | | | |
| | ACGAAGGATACTTATGACGCTCTCCACATGCAAGCCCTGCCA | | | |
| | CCTAGGTAA | | | |
| RD- | ATGGCACTCCCCGTAACTGCTCTGCTGCTGCCGTTGGCATTG | 203 | MALPVTALLLPLALLLHAA | 204 |
| 21530CAR | CTCCTGCACGCCGCACGCCCGCAGGTGCAGCTGGTGGAGTCT | | RPQVQLVESGGGVVQPGRS | |
| HxL | GGGGGAGGCGTGGTCCAGCCTGGGAGGTCCCTGAGACTCTCC | | LRLSCAASGFTFSSYGMHW | |
| | TGTGCAGCGTCTGGATTCACCTTCAGTAGCTATGGCATGCAC | | VRQAPGKGLEWVAVISYDG | |
| | TGGGTCCGCCAGGCTCCAGGCAAGGGGCTGGAGTGGGTGGCA | | SNKYYADSVKGRFTISRDN | |
| | GTTATATCGTATGATGGAAGTAATAAATACTATGCAGACTCC | | SKNTLYLQMNSLRAEDTAV | |
| | GTGAAGGGCCGATTCACCATCTCCAGAGACAATTCCAAGAAC | | YYCVKGPLQEPPYDYGMDV | |
| | ACGCTGTATCTGCAAATGAACAGCCTGAGAGCCGAGGACACG | | WGQGTTVTVSSGSTSGSGK | |
| | GCGGTGTACTACTGCGTCAAGGGGCCGTTGCAGGAGCCGCCA | | PGSGEGSTKGEIVMTQSPA | |
| | TACGATTATGGAATGGACGTATGGGGCCAGGGAACAACTGTC | | TLSVSPGERATLSCRASQS | |
| | ACCGTCTCCTCAGGGTCTACATCCGGCTCCGGGAAGCCCGGA | | VSSNLAWYQQKPGQAPRLL | |
| | AGTGGCGAAGGTAGTACAAAGGGGGAAATAGTGATGACGCAG | | IYSASTRATGIPARFSGSG | |
| | TCTCCAGCCACCCTGTCTGTGTCTCCAGGGGAAAGAGCCACC | | SGTEFTLTISSLQSEDFAV | |
| | CTCTCCTGCAGGGCCAGTCAGAGTGTTAGCAGCAACTTAGCC | | YYCQQHHVWPLTFGGGTKV | |
| | TGGTACCAGCAGAAACCTGGCCAGGCTCCCAGGCTCCTCATC | | EIKRAAALDNEKSNGTIIH | |
| | TATAGCGCATCCACCAGGGCCACTGGTATCCCAGCCAGGTTC | | VKGKHLCPSPLFPGPSKPF | |
| | AGTGGCAGTGGGTCTGGGACAGAGTTCACTCTCACCATCAGC | | WVLVVVGGVLACYSLLVTV | |
| | AGCCTGCAGTCTGAAGATTTTGCAGTTTATTACTGTCAGCAG | | AFIIFWVRSKRSRLLHSDY | |
| | CACCACGTCTGGCCTCTCACTTTTGGCGGAGGGACCAAGGTT | | MNMTPRRPGPTRKHYQPYA | |
| | GAGATCAAACGGGCCGCTGCCCTTGATAATGAAAAGTCAAAC | | PPRDFAAYRSRVKFSRSAD | |
| | GGAACAATCATTCACGTGAAGGGCAAGCACCTCTGTCCGTCA | | APAYQQGQNQLYNELNLGR | |
| | CCCTTGTTCCCTGGTCCATCCAAGCCATTCTGGGTGTTGGTC | | REEYDVLDKRRGRDPEMGG | |
| | GTAGTGGGTGGAGTCCTCGCTTGTTACTCTCTGCTCGTCACC | | KPRRKNPQEGLYNELQKDK | |
| | GTGGCTTTTATAATCTTCTGGGTTAGATCCAAAAGAAGCCGC | | MAEAYSEIGMKGERRRGKG | |
| | CTGCTCCATAGCGATTACATGAATATGACTCCACGCCGCCCT | | HDGLYQGLSTATKDTYDAL | |
| | GGCCCCACAAGGAAACACTACCAGCCTTACGCACCACCTAGA | | HMQALPPR | |
| | GATTTCGCTGCCTATCGGAGCAGGGTGAAGTTTTCCAGATCT | | | |
| | GCAGATGCACCAGCGTATCAGCAGGGCCAGAACCAACTGTAT | | | |
| | AACGAGCTCAACCTGGGACGCAGGGAAGAGTATGACGTTTTG | | | |
| | GACAAGCGCAGAGGACGGGACCCTGAGATGGGTGGCAAACCA | | | |
| | AGACGAAAAAACCCCCAGGAGGGTCTCTATAATGAGCTGCAG | | | |
| | AAGGATAAGATGGCTGAAGCCTATTCTGAAATAGGCATGAAA | | | |
| | GGAGAGCGGAGAAGGGGAAAAGGGCACGACGGTTTGTACCAG | | | |
| | GGACTCAGCACTGCTACGAAGGATACTTATGACGCTCTCCAC | | | |
| | ATGCAAGCCCTGCCACCTAGGTAA | | | |
| RD- | ATGGCACTCCCCGTAACTGCTCTGCTGCTGCCGTTGGCATTG | 205 | MALPVTALLLPLALLLHAA | 206 |
| 21530CAR | CTCCTGCACGCCGCACGCCCGGAAATAGTGATGACGCAGTCT | | RPEIVMTQSPATLSVSPGE | |
| LxH | CCAGCCACCCTGTCTGTGTCTCCAGGGGAAAGAGCCACCCTC | | RATLSCRASQSVSSNLAWY | |
| | TCCTGCAGGGCCAGTCAGAGTGTTAGCAGCAACTTAGCCTGG | | QQKPGQAPRLLIYSASTRA | |
| | TACCAGCAGAAACCTGGCCAGGCTCCCAGGCTCCTCATCTAT | | TGIPARFSGSGSGTEFTLT | |
| | AGCGCATCCACCAGGGCCACTGGTATCCCAGCCAGGTTCAGT | | ISSLQSEDFAVYYCQQHHV | |
| | GGCAGTGGGTCTGGGACAGAGTTCACTCTCACCATCAGCAGC | | WPLTFGGGTKVEIKRGSTS | |
| | CTGCAGTCTGAAGATTTTGCAGTTTATTACTGTCAGCAGCAC | | GSGKPGSGEGSTKGQVQLV | |
| | CACGTCTGGCCTCTCACTTTTGGCGGAGGGACCAAGGTTGAG | | ESGGGVVQPGRSLRLSCAA | |
| | ATCAAACGGGGGTCTACATCCGGCTCCGGGAAGCCCGGAAGT | | SGFTFSSYGMHWVRQAPGK | |
| | GGCGAAGGTAGTACAAAGGGGCAGGTGCAGCTGGTGGAGTCT | | GLEWVAVISYDGSNKYYAD | |
| | GGGGGAGGCGTGGTCCAGCCTGGGAGGTCCCTGAGACTCTCC | | SVKGRFTISRDNSKNTLYL | |
| | TGTGCAGCGTCTGGATTCACCTTCAGTAGCTATGGCATGCAC | | QMNSLRAEDTAVYYCVKGP | |
| | TGGGTCCGCCAGGCTCCAGGCAAGGGGCTGGAGTGGGTGGCA | | LQEPPYDYGMDVWGQGTTV | |
| | GTTATATCGTATGATGGAAGTAATAAATACTATGCAGACTCC | | TVSSAAALDNEKSNGTIIH | |
| | GTGAAGGGCCGATTCACCATCTCCAGAGACAATTCCAAGAAC | | VKGKHLCPSPLFPGPSKPF | |
| | ACGCTGTATCTGCAAATGAACAGCCTGAGAGCCGAGGACACG | | WVLVVVGGVLACYSLLVTV | |
| | GCGGTGTACTACTGCGTCAAGGGGCCGTTGCAGGAGCCGCCA | | AFIIFWVRSKRSRLLHSDY | |
| | TACGATTATGGAATGGACGTATGGGGCCAGGGAACAACTGTC | | MNMTPRRPGPTRKHYQPYA | |
| | ACCGTCTCCTCAGCCGCTGCCCTTGATAATGAAAAGTCAAAC | | PPRDFAAYRSRVKFSRSAD | |
| | GGAACAATCATTCACGTGAAGGGCAAGCACCTCTGTCCGTCA | | APAYQQGQNQLYNELNLGR | |
| | CCCTTGTTCCCTGGTCCATCCAAGCCATTCTGGGTGTTGGTC | | REEYDVLDKRRGRDPEMGG | |
| | GTAGTGGGTGGAGTCCTCGCTTGTTACTCTCTGCTCGTCACC | | KPRRKNPQEGLYNELQKDK | |
| | GTGGCTTTTATAATCTTCTGGGTTAGATCCAAAAGAAGCCGC | | MAEAYSEIGMKGERRRGKG | |
| | CTGCTCCATAGCGATTACATGAATATGACTCCACGCCGCCCT | | HDGLYQGLSTATKDTYDAL | |
| | GGCCCCACAAGGAAACACTACCAGCCTTACGCACCACCTAGA | | HMQALPPR | |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| | GATTTCGCTGCCTATCGGAGCAGGGTGAAGTTTTCCAGATCT GCAGATGCACCAGCGTATCAGCAGGGCCAGAACCAACTGTAT AACGAGCTCAACCTGGGACGCAGGGAAGAGTATGACGTTTTG GACAAGCGCAGAGGACGGGACCCTGAGATGGGTGGCAAACCA AGACGAAAAAACCCCCAGGAGGGTCTCTATAATGAGCTGCAG AAGGATAAGATGGCTGAAGCCTATTCTGAAATAGGCATGAAA GGAGAGCGGAGAAGGGGAAAAGGGCACGACGGTTTGTACCAG GGACTCAGCACTGCTACGAAGGATACTTATGACGCTCTCCAC ATGCAAGCCCTGCCACCTAGGTAA | | | |

In some embodiments, the polynucleotide of the present invention encodes a CAR, wherein the CAR comprises an amino acid sequence at least about 75%, at least about 85%, at least about 85%, at least about 90%, at least about 95%, at least about 96%, at least about 97%, at least about 98%, at least about 99%, or 100% identical to an amino acid sequence selected from the group consisting of SEQ ID NOs: 176, 178, 180, 182, 184, 186, 188, 190, 192, 194, 196, 198, 200, 202, 204, and 206. In certain embodiments, the CAR comprises an amino acid sequence selected from the group consisting of SEQ ID NOs: 176, 178, 180, 182, 184, 186, 188, 190, 192, 194, 196, 198, 200, 202, 204, and 206. In one embodiment, the CAR comprises the amino acid sequence of SEQ ID NO: 176. In another embodiment, the CAR comprises the amino acid sequence of SEQ ID NO: 178. In another embodiment, the CAR comprises the amino acid sequence of SEQ ID NO: 180. In another embodiment, the CAR comprises the amino acid sequence of SEQ ID NO: 182. In another embodiment, the CAR comprises the amino acid sequence of SEQ ID NO: 184. In another embodiment, the CAR comprises the amino acid sequence of SEQ ID NO: 186. In another embodiment, the CAR comprises the amino acid sequence of SEQ ID NO: 188. In another embodiment, the CAR comprises the amino acid sequence of SEQ ID NO: 190. In another embodiment, the CAR comprises the amino acid sequence of SEQ ID NO: 192. In another embodiment, the CAR comprises the amino acid sequence of SEQ ID NO: 194. In another embodiment, the CAR comprises the amino acid sequence of SEQ ID NO: 196. In another embodiment, the CAR comprises the amino acid sequence of SEQ ID NO: 198. In another embodiment, the CAR comprises the amino acid sequence of SEQ ID NO: 200. In another embodiment, the CAR comprises the amino acid sequence of SEQ ID NO: 202. In another embodiment, the CAR comprises the amino acid sequence of SEQ ID NO: 204. In another embodiment, the CAR comprises the amino acid sequence of SEQ ID NO: 206.

In some embodiments, the polynucleotide of the present invention comprises an nucleotide sequence at least about 50%, at least about 60%, at least about 65%, at least about 70%, at least about 75%, at least about 85%, at least about 85%, at least about 90%, at least about 95%, at least about 96%, at least about 97%, at least about 98%, at least about 99%, or 100% identical to an amino acid sequence selected from the group consisting of SEQ ID NOs: 175, 177, 179, 181, 183, 185, 187, 189, 191, 193, 195, 197, 199, 201, 203, and 205. In certain embodiments, the polynucleotide comprises a nucleotide sequence selected from the group consisting of SEQ ID NOs: 175, 177, 179, 181, 183, 185, 187, 189, 191, 193, 195, 197, 199, 201, 203, and 205. In one embodiment, the polynucleotide comprises the nucleotide sequence of SEQ ID NO: 175. In another embodiment, the polynucleotide comprises the nucleotide sequence of SEQ ID NO: 177. In another embodiment, the polynucleotide comprises the nucleotide sequence of SEQ ID NO: 179. In another embodiment, the polynucleotide comprises the nucleotide sequence of SEQ ID NO: 181. In another embodiment, the polynucleotide comprises the nucleotide sequence of SEQ ID NO: 183. In another embodiment, the polynucleotide comprises the nucleotide sequence of SEQ ID NO: 185. In another embodiment, the polynucleotide comprises the nucleotide sequence of SEQ ID NO: 187. In another embodiment, the polynucleotide comprises the nucleotide sequence of SEQ ID NO: 189. In another embodiment, the polynucleotide comprises the nucleotide sequence of SEQ ID NO: 191. In another embodiment, the polynucleotide comprises the nucleotide sequence of SEQ ID NO: 193. In another embodiment, the polynucleotide comprises the nucleotide sequence of SEQ ID NO: 195. In another embodiment, the polynucleotide comprises the nucleotide sequence of SEQ ID NO: 197. In another embodiment, the polynucleotide comprises the nucleotide sequence of SEQ ID NO: 199. In another embodiment, the polynucleotide comprises the nucleotide sequence of SEQ ID NO: 201. In another embodiment, the polynucleotide comprises the nucleotide sequence of SEQ ID NO: 203. In another embodiment, the polynucleotide comprises the nucleotide sequence of SEQ ID NO: 205.

In further embodiments, the invention relates to Clone FS-26528 HC DNA (SEQ ID NO: 271) as follows:

GAGGTGCAGCTGTTGGAGTCTGGGGGAGGCTTGGTACAGCCTGGGGGGTC

CCTGAGACTCTCCTGTGCAGCCTCTGGATTCACCTTTGACGACTATGCCA

TGGCATGGGTCCGCCAGGCTCCAGGGAAGGGGCTGGAGTGGGTCTCAGCT

ATTAGTGATGCAGGTGACAGAACATACTACGCAGACTCCGTGAGGGGCCG

GTTCACCATCTCCAGAGACAATTCCAAGAACACACTGTATCTGCAAATGA

ACAGCCTGAGAGCCGAGGACACGGCGGTGTACTACTGCGCAAGAGCCGAG

ATGGGAGCCGTATTCGACATATGGGGTCAGGGTACAATGGTCACCGTCTC

CTCA

In further embodiments, the invention relates to the Clone FS-26528 HC amino acid sequence (SEQ ID NO: 272):

EVQLLESGGG LVQPGGSLRL SCAASGFTFD DYAMAWVRQA

PGKGLEWVSA ISDAGDRTYY ADSVRGRFTI SRDNSKNTLY

LQMNSLRAED TAVYYCARAE MGAVFDIWGQ GTMVTVSS

In further embodiments, the invention relates to HC CDR1 thereof: SCAASGFTFDDYAMA (SEQ ID NO: 273). In further embodiments, the invention relates to HC CDR2 thereof: AISDAGDRTYYADSVRG (SEQ ID NO: 274). In further embodiments, the invention relates to HC CDR3 thereof: ARAEMGAVFDI (SEQ ID NO: 275) [HC CDR3]

In further embodiments, the invention relates to Clone FS-26528 LC DNA (SEQ ID NO: 276):

GAAATTGTGTTGACACAGTCTCCAGCCACCCTGTCTTTGTCTCCAGGGGA

AAGAGCCACCCTCTCCTGCAGGGCCAGTCAGAGTGTTAGCAGGTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCCTAGAGCCTGAAGATTTTG

CAGTTTATTACTGTCAGCAGAGAATCTCCTGGCCTTTCACTTTTGGCGGA

GGGACCAAGGTTGAGATCAAACGG

In further embodiments, the invention relates to Clone FS-26528 LC AA sequence (SEQ ID NO: 277):

EIVLTQSPAT LSLSPGERAT LSCRASQSVS RYLAWYQQKP

GQAPRLLIYD ASNRATGIPA RFSGSGSGTD FTLTISSLEP

EDFAVYYCQQ RISWPFTFGG GTKVEIKR.

In further embodiments, the invention relates to LC CDR1 thereof: RASQSVSRYLA (SEQ ID NO: 278). In further embodiments, the invention relates to LC CDR2 thereof: DASNRAT (SEQ ID NO: 279). In further embodiments, the invention relates to the LC CDR3 thereof: QQRISWPFT (SEQ ID NO: 280).

In further embodiments, the invention relates to Clone FS-26528 CAR DNA HxL (SEQ ID NO: 281):

ATGGCACTCCCCGTAACTGCTCTGCTGCTGCCGTTGGCATTGCTCCTGCA

CGCCGCACGCCCGGAGGTGCAGCTGTTGGAGTCTGGGGGAGGCTTGGTAC

AGCCTGGGGGGTCCCTGAGACTCTCCTGTGCAGCCTCTGGATTCACCTTT

GACGACTATGCCATGGCATGGGTCCGCCAGGCTCCAGGGAAGGGGCTGGA

GTGGGTCTCAGCTATTAGTGATGCAGGTGACAGAACATACTACGCAGACT

CCGTGAGGGGCCGGTTCACCATCTCCAGAGACAATTCCAAGAACACACTG

TATCTGCAAATGAACAGCCTGAGAGCCGAGGACACGGCGGTGTACTACTG

CGCAAGAGCCGAGATGGGAGCCGTATTCGACATATGGGGTCAGGGTACAA

TGGTCACCGTCTCCTCAGGGTCTACATCCGGCTCCGGGAAGCCCGGAAGT

GGCGAAGGTAGTACAAAGGGGGAAATTGTGTTGACACAGTCTCCAGCCAC

CCTGTCTTTGTCTCCAGGGGAAAGAGCCACCCTCTCCTGCAGGGCCAGTC

-continued

AGAGTGTTAGCAGGTACTTAGCCTGGTACCAACAGAAACCTGGCCAGGCT

CCCAGGCTCCTCATCTATGATGCATCCAACAGGGCCACTGGCATCCCAGC

CAGGTTCAGTGGCAGTGGGTCTGGGACAGACTTCACTCTCACCATCAGCA

GCCTAGAGCCTGAAGATTTTGCAGTTTATTACTGTCAGCAGAGAATCTCC

TGGCCTTTCACTTTTGGCGGAGGGACCAAGGTTGAGATCAAACGGGCCGC

TGCCCTTGATAATGAAAAGTCAAACGGAACAATCATTCACGTGAAGGGCA

AGCACCTCTGTCCGTCACCCTTGTTCCCTGGTCCATCCAAGCCATTCTGG

GTGTTGGTCGTAGTGGGTGGAGTCCTCGCTTGTTACTCTCTGCTCGTCAC

CGTGGCTTTTATAATCTTCTGGGTTAGATCCAAAAGAAGCCGCCTGCTCC

ATAGCGATTACATGAATATGACTCCACGCCGCCCTGGCCCCACAAGGAAA

CACTACCAGCCTTACGCACCACCTAGAGATTTCGCTGCCTATCGGAGCAG

GGTGAAGTTTTCCAGATCTGCAGATGCACCAGCGTATCAGCAGGGCCAGA

ACCAACTGTATAACGAGCTCAACCTGGGACGCAGGGAAGAGTATGACGTT

TTGGACAAGCGCAGAGGACGGGACCCTGAGATGGGTGGCAAACCAAGACG

AAAAAACCCCCAGGAGGGTCTCTATAATGAGCTGCAGAAGGATAAGATGG

CTGAAGCCTATTCTGAAATAGGCATGAAAGGAGAGCGGAGAAGGGGAAAA

GGGCACGACGGTTTGTACCAGGGACTCAGCACTGCTACGAAGGATACTTA

TGACGCTCTCCACATGCAAGCCCTGCCACCTAGG

In further embodiments, the invention relates to Clone FS-26528 CAR HxL AA sequence (SEQ ID NO: 282):

MALPVTALLL PLALLLHAAR PEVQLLESGG GLVQPGGSLR

LSCAASGFTF DDYAMAWVRQ APGKGLEWVS AISDAGDRTY

YADSVRGRFT ISRDNSKNTL YLQMNSLRAE DTAVYYCARA

EMGAVFDIWG QGTMVTVSSG STSGSGKPGS GEGSTKGEIV

LTQSPATLSL SPGERATLSC RASQSVSRYL AWYQQKPGQA

PRLLIYDASN RATGIPARFS GSGSGTDFTL TISSLEPEDF

AVYYCQQRIS WPFTFGGGTK VEIKRAAALD NEKSNGTIIH

VKGKHLCPSP LFPGPSKPFW VLVVVGGVLA CYSLLVTVAF

IIFWVRSKRS RLLHSDYMNM TPRRPGPTRK HYQPYAPPRD

FAAYRSRVKF SRSADAPAYQ QGQNQLYNEL NLGRREEYDV

LDKRRGRDPE MGGKPRRKNP QEGLYNELQK DKMAEAYSEI

GMKGERRRGK GHDGLYQGLS TATKDTYDAL HMQALPPR

In further embodiments, the invention relates to Clone FS-26528 CAR DNA LxH (SEQ ID NO: 283):

ATGGCACTCCCCGTAACTGCTCTGCTGCTGCCGTTGGCATTGCTCCTGCA

CGCCGCACGCCCGGAAATTGTGTTGACACAGTCTCCAGCCACCCTGTCTT

TGTCTCCAGGGGAAAGAGCCACCCTCTCCTGCAGGGCCAGTCAGAGTGTT

AGCAGGTACTTAGCCTGGTACCAACAGAAACCTGGCCAGGCTCCCAGGCT

CCTCATCTATGATGCATCCAACAGGGCCACTGGCATCCCAGCCAGGTTCA

GTGGCAGTGGGTCTGGGACAGACTTCACTCTCACCATCAGCAGCCTAGAG

-continued

```
CCTGAAGATTTTGCAGTTTATTACTGTCAGCAGAGAATCTCCTGGCCTTT
CACTTTTGGCGGAGGGACCAAGGTTGAGATCAAACGGGGGTCTACATCCG
GCTCCGGGAAGCCCGGAAGTGGCGAAGGTAGTACAAAGGGGGAGGTGCAG
CTGTTGGAGTCTGGGGGAGGCTTGGTACAGCCTGGGGGGTCCCTGAGACT
CTCCTGTGCAGCCTCTGGATTCACCTTTGACGACTATGCCATGGCATGGG
TCCGCCAGGCTCCAGGGAAGGGGCTGGAGTGGGTCTCAGCTATTAGTGAT
GCAGGTGACAGAACATACTACGCAGACTCCGTGAGGGGCCGGTTCACCAT
CTCCAGAGACAATTCCAAGAACACACTGTATCTGCAAATGAACAGCCTGA
GAGCCGAGGACACGGCGGTGTACTACTGCGCAAGAGCCGAGATGGGAGCC
GTATTCGACATATGGGGTCAGGGTACAATGGTCACCGTCTCCTCAGCCGC
TGCCCTTGATAATGAAAAGTCAAACGGAACAATCATTCACGTGAAGGGCA
AGCACCTCTGTCCGTCACCCTTGTTCCCTGGTCCATCCAAGCCATTCTGG
GTGTTGGTCGTAGTGGGTGGAGTCCTCGCTTGTTACTCTCTGCTCGTCAC
CGTGGCTTTTATAATCTTCTGGGTTAGATCCAAAAGAAGCCGCCTGCTCC
ATAGCGATTACATGAATATGACTCCACGCCGCCCTGGCCCCACAAGGAAA
CACTACCAGCCTTACGCACCACCTAGAGATTTCGCTGCCTATCGGAGCAG
GGTGAAGTTTTCCAGATCTGCAGATGCACCAGCGTATCAGCAGGGCCAGA
ACCAACTGTATAACGAGCTCAACCTGGGACGCAGGGAAGAGTATGACGTT
TTGGACAAGCGCAGAGGACGGGACCCTGAGATGGGTGGCAAACCAAGACG
AAAAAACCCCCAGGAGGGTCTCTATAATGAGCTGCAGAAGGATAAGATGG
CTGAAGCCTATTCTGAAATAGGCATGAAAGGAGAGCGGAGAAGGGGAAAA
GGGCACGACGGTTTGTACCAGGGACTCAGCACTGCTACGAAGGATACTTA
TGACGCTCTCCACATGCAAGCCCTGCCACCTAGG
```

In further embodiments, the invention relates to the Clone FS-26528 CAR LxH AA sequence (SEQ ID NO: 284):

```
MALPVTALLL PLALLLHAAR PEIVLTQSPA TLSLSPGERA
TLSCRASQSV SRYLAWYQQK PGQAPRLLIY DASNRATGIP
ARFSGSGSGT DFTLTISSLE PEDFAVYYCQ QRISWPFTFG
GGTKVEIKRG STSGSGKPGS GEGSTKGEVQ LLESGGGLVQ
PGGSLRLSCA ASGFTFDDYA MAWVRQAPGK GLEWVSAISD
AGDRTYYADS VRGRFTISRD NSKNTLYLQM NSLRAEDTAV
YYCARAEMGA VFDIWGQGTM VTVSSAAALD NEKSNGTIIH
VKGKHLCPSP LFPGPSKPFW VLVVVGGVLA CYSLLVTVAF
IIFWVRSKRS RLLHSDYMNM TPRRPGPTRK HYQPYAPPRD
FAAYRSRVKF SRSADAPAYQ QGQNQLYNEL NLGRREEYDV
LDKRRGRDPE MGGKPRRKNP QEGLYNELQK DKMAEAYSEI
GMKGERRRGK GHDGLYQGLS TATKDTYDAL HMQALPPR
```

In further embodiments, the invention relates to Clone PC-26534 HC DNA (SEQ ID NO: 285) as follows:

```
CAGGTGCAGCTGGTGGAGTCTGGGGGAGGCGTGGTCCAGCCTGGGAGGTC
CCTGAGACTCTCCTGTGCAGCGTCTGGATTCACCTTCAGTGAGCATGGCA
TGCACTGGGTCCGCCAGGCTCCAGGCAAGGGGCTGGAGTGGGTGGCAGCT
ATATCTTATGATGGAAGGAATAAACACTATGCAGACTCCGTGAAGGGCCG
ATTCACCATCTCCAGAGACAATTCCAAGAACACGCTGTATCTGCAAATGA
ACAGCCTGAGAGCCGAGGACACGGCGGTGTACTACTGCGCCAGAGACGGT
ACTTATCTAGGTGGTCTCTGGTACTTCGACTTATGGGGGAGAGGTACCTT
GGTCACCGTCTCCTCA
```

In further embodiments, the invention relates to Clone PC-26534 HC (SEQ ID NO: 286):

```
QVQLVESGGG VVQPGRSLRL SCAASGFTFS EHGMHWVRQA
PGKGLEWVAA ISYDGRNKHY ADSVKGRFTI SRDNSKNTLY
LQMNSLRAED TAVYYCARDG TYLGGLWYFD LWGRGTLVTV
SS.
```

In further embodiments, the invention relates to HC CDR1 thereof: FTFSEHGMH (SEQ ID NO: 287). In further embodiments, the invention relates to HC CDR2 thereof: AISYDGRNKHYADSVKG (SEQ ID NO: 288). In further embodiments, the invention relates to HC CDR3 thereof: ARDGTYLGGLWYFDL (SEQ ID NO: 289).

In further embodiments, the invention relates to Clone PC-26534 LC DNA (SEQ ID NO: 290) as follows:

```
GATATTGTGATGACTCAGTCTCCACTCTCCCTGCCCGTCACCCCTGGAGA
GCCGGCCTCCATCTCCTGCAGGTCTAGTCAGAGCCTCCTGCATAGTAATG
GATACAACTATTTGGATTGGTACCTGCAGAAGCCAGGGCAGTCTCCACAG
CTCCTGATCTATTTGGGTTCTAATCGGGCCTCCGGGGTCCCTGACAGGTT
CAGTGGCAGTGGATCAGGCACAGATTTTACACTGAAAATCAGCAGAGTGG
AGGCTGAGGATGTTGGGGTTTATTACTGCATGCAGGGACTCGGCCTCCCT
CTCACTTTTGGCGGAGGGACCAAGGTTGAGATCAAACGG
```

In further embodiments, the invention relates to Clone PC-26534 LC AA sequence (SEQ ID NO: 291):

```
DIVMTQSPLS LPVTPGEPAS ISCRSSQSLL HSNGYNYLDW
YLQKPGQSPQ LLIYLGSNRA SGVPDRFSGS GSGTDFTLKI
SRVEAEDVGV YYCMQGLGLP LTFGGGTKVE IKR.
```

In further embodiments, the invention relates to LC CDR1 AA sequence thereof: RSSQSLLHSNGYNYLD (SEQ ID NO: 292). In further embodiments, the invention relates to LC CDR2 thereof: LGSNRAS (SEQ ID NO: 293). In further embodiments, the invention relates to LC CDR3 thereof: MQGLGLPLT (SEQ ID NO: 294).

In further embodiments, the invention relates to Clone PC-26534 CAR DNA HxL (SEQ ID NO: 295) as follows:

```
ATGGCACTCCCCGTAACTGCTCTGCTGCTGCCGTTGGCATTGCTCCTGCA
CGCCGCACGCCCGCAGGTGCAGCTGGTGGAGTCTGGGGGAGGCGTGGTCC
```

-continued

AGCCTGGGAGGTCCCTGAGACTCTCCTGTGCAGCGTCTGGATTCACCTTC

AGTGAGCATGGCATGCACTGGGTCCGCCAGGCTCCAGGCAAGGGGCTGGA

GTGGGTGGCAGCTATATCTTATGATGGAAGGAATAAACACTATGCAGACT

CCGTGAAGGGCCGATTCACCATCTCCAGAGACAATTCCAAGAACACGCTG

TATCTGCAAATGAACAGCCTGAGAGCCGAGGACACGGCGGTGTACTACTG

CGCCAGAGACGGTACTTATCTAGGTGGTCTCTGGTACTTCGACTTATGGG

GGAGAGGTACCTTGGTCACCGTCTCCTCAGGGTCTACATCCGGCTCCGGG

AAGCCCGGAAGTGGCGAAGGTAGTACAAAGGGGGATATTGTGATGACTCA

GTCTCCACTCTCCCTGCCCGTCACCCCTGGAGAGCCGGCCTCCATCTCCT

GCAGGTCTAGTCAGAGCCTCCTGCATAGTAATGGATACAACTATTTGGAT

TGGTACCTGCAGAAGCCAGGGCAGTCTCCACAGCTCCTGATCTATTTGGG

TTCTAATCGGGCCTCCGGGGTCCCTGACAGGTTCAGTGGCAGTGGATCAG

GCACAGATTTTACACTGAAAATCAGCAGAGTGGAGGCTGAGGATGTTGGG

GTTTATTACTGCATGCAGGGACTCGGCCTCCCTCTCACTTTTGGCGGAGG

GACCAAGGTTGAGATCAAACGGGCCGCTGCCCTTGATAATGAAAAGTCAA

ACGGAACAATCATTCACGTGAAGGGCAAGCACCTCTGTCCGTCACCCTTG

TTCCCTGGTCCATCCAAGCCATTCTGGGTGTTGGTCGTAGTGGGTGGAGT

CCTCGCTTGTTACTCTCTGCTCGTCACCGTGGCTTTTATAATCTTCTGGG

TTAGATCCAAAAGAAGCCGCCTGCTCCATAGCGATTACATGAATATGACT

CCACGCCGCCCTGGCCCCACAAGGAAACACTACCAGCCTTACGCACCACC

TAGAGATTTCGCTGCCTATCGGAGCAGGGTGAAGTTTTCCAGATCTGCAG

ATGCACCAGCGTATCAGCAGGGCCAGAACCAACTGTATAACGAGCTCAAC

CTGGGACGCAGGGAAGAGTATGACGTTTTGGACAAGCGCAGAGGACGGGA

CCCTGAGATGGGTGGCAAACCAAGACGAAAAAACCCCCAGGAGGGTCTCT

ATAATGAGCTGCAGAAGGATAAGATGGCTGAAGCCTATTCTGAAATAGGC

ATGAAAGGAGAGCGGAGAAGGGGAAAAGGGCACGACGGTTTGTACCAGGG

ACTCAGCACTGCTACGAAGGATACTTATGACGCTCTCCACATGCAAGCCC

TGCCACCTAGG

In further embodiments, the invention relates to Clone PC-26534 CAR HxL AA sequence (SEQ ID NO: 296):

MALPVTALLL PLALLLHAAR PQVQLVESGG GVVQPGRSLR

LSCAASGFTF SEHGMHWVRQ APGKGLEWVA AISYDGRNKH

YADSVKGRFT ISRDNSKNTL YLQMNSLRAE DTAVYYCARD

GTYLGGLWYF DLWGRGTLVT VSSGSTSGSG KPGSGEGSTK

GDIVMTQSPL SLPVTPGEPA SISCRSSQSL LHSNGYNYLD

WYLQKPGQSP QLLIYLGSNR ASGVPDRFSG SGSGTDFTLK

ISRVEAEDVG VYYCMQGLGL PLTFGGGTKV EIKRAAALDN

EKSNGTIIHV KGKHLCPSPL FPGPSKPFWV LVVVGGVLAC

YSLLVTVAFI IFWVRSKRSR LLHSDYMNMT PRRPGPTRKH

YQPYAPPRDF AAYRSRVKFS RSADAPAYQQ GQNQLYNELN

LGRREEYDVL DKRRGRDPEM GGKPRRKNPQ EGLYNELQKD

KMAEAYSEIG MKGERRRGKG HDGLYQGLST ATKDTYDALH

MQALPPR

In further embodiments, the invention relates to Clone PC-26534 CAR DNA LxH (SEQ ID NO: 297):

ATGGCACTCCCCGTAACTGCTCTGCTGCTGCCGTTGGCATTGCTCCTGCA

CGCCGCACGCCCGGATATTGTGATGACTCAGTCTCCACTCTCCCTGCCCG

TCACCCCTGGAGAGCCGGCCTCCATCTCCTGCAGGTCTAGTCAGAGCCTC

CTGCATAGTAATGGATACAACTATTTGGATTGGTACCTGCAGAAGCCAGG

GCAGTCTCCACAGCTCCTGATCTATTTGGGTTCTAATCGGGCCTCCGGGG

TCCCTGACAGGTTCAGTGGCAGTGGATCAGGCACAGATTTTACACTGAAA

ATCAGCAGAGTGGAGGCTGAGGATGTTGGGGTTTATTACTGCATGCAGGG

ACTCGGCCTCCCTCTCACTTTTGGCGGAGGGACCAAGGTTGAGATCAAAC

GGGGGTCTACATCCGGCTCCGGGAAGCCCGGAAGTGGCGAAGGTAGTACA

AAGGGGCAGGTGCAGCTGGTGGAGTCTGGGGGAGGCGTGGTCCAGCCTGG

GAGGTCCCTGAGACTCTCCTGTGCAGCGTCTGGATTCACCTTCAGTGAGC

ATGGCATGCACTGGGTCCGCCAGGCTCCAGGCAAGGGGCTGGAGTGGGTG

GCAGCTATATCTTATGATGGAAGGAATAAACACTATGCAGACTCCGTGAA

GGGCCGATTCACCATCTCCAGAGACAATTCCAAGAACACGCTGTATCTGC

AAATGAACAGCCTGAGAGCCGAGGACACGGCGGTGTACTACTGCGCCAGA

GACGGTACTTATCTAGGTGGTCTCTGGTACTTCGACTTATGGGGGAGAGG

TACCTTGGTCACCGTCTCCTCAGCCGCTGCCCTTGATAATGAAAAGTCAA

ACGGAACAATCATTCACGTGAAGGGCAAGCACCTCTGTCCGTCACCCTTG

TTCCCTGGTCCATCCAAGCCATTCTGGGTGTTGGTCGTAGTGGGTGGAGT

CCTCGCTTGTTACTCTCTGCTCGTCACCGTGGCTTTTATAATCTTCTGGG

TTAGATCCAAAAGAAGCCGCCTGCTCCATAGCGATTACATGAATATGACT

CCACGCCGCCCTGGCCCCACAAGGAAACACTACCAGCCTTACGCACCACC

TAGAGATTTCGCTGCCTATCGGAGCAGGGTGAAGTTTTCCAGATCTGCAG

ATGCACCAGCGTATCAGCAGGGCCAGAACCAACTGTATAACGAGCTCAAC

CTGGGACGCAGGGAAGAGTATGACGTTTTGGACAAGCGCAGAGGACGGGA

CCCTGAGATGGGTGGCAAACCAAGACGAAAAAACCCCCAGGAGGGTCTCT

ATAATGAGCTGCAGAAGGATAAGATGGCTGAAGCCTATTCTGAAATAGGC

ATGAAAGGAGAGCGGAGAAGGGGAAAAGGGCACGACGGTTTGTACCAGGG

ACTCAGCACTGCTACGAAGGATACTTATGACGCTCTCCACATGCAAGCCC

TGCCACCTAGG

In further embodiments, the invention relates to Clone PC-26534 CAR LxH chain sequences (SEQ ID NO: 298):

MALPVTALLL PLALLLHAAR PDIVMTQSPL SLPVTPGEPA

SISCRSSQSL LHSNGYNYLD WYLQKPGQSP QLLIYLGSNR

-continued

```
ASGVPDRFSG SGSGTDFTLK ISRVEAEDVG VYYCMQGLGL
PLTFGGGTKV EIKRGSTSGS GKPGSGEGST KGQVQLVESG
GGVVQPGRSL RLSCAASGFT FSEHGMHWVR QAPGKGLEWV
AAISYDGRNK HYADSVKGRF TISRDNSKNT LYLQMNSLRA
EDTAVYYCAR DGTYLGGLWY FDLWGRGTLV TVSSAAALDN
EKSNGTIIHV KGKHLCPSPL FPGPSKPFWV LVVVGGVLAC
YSLLVTVAFI IFWVRSKRSR LLHSDYMNMT PRRPGPTRKH
YQPYAPPRDF AAYRSRVKFS RSADAPAYQQ GQNQLYNELN
LGRREEYDVL DKRRGRDPEM GGKPRRKNPQ EGLYNELQKD
KMAEAYSEIG MKGERRRGKG HDGLYQGLST ATKDTYDALH
MQALPPR
```

In further embodiments, the invention relates to Clone AJ-26545 HC DNA (SEQ ID NO: 299):

```
CAGGTGCAGCTGGTGCAGTCTGGGGCTGAGGTGAAGAAGCCTGGGGCCTC
AGTGAAGGTTTCCTGCAGGGCATCTGGATACACCTTCATGGAGCACTATA
TGCACTGGGTGCGACAGGCCCCTGGACAAGGGCTTGAGTGGATGGGAGTA
ATCGGGCCTAGTGGTGGTAAGACAAGCTACGCACAGAAGTTCCAGGGCAG
AGTCACCATGACCAGGGACACGTCCACGAGCACAGTCTACATGGAGCTGA
GCAGCCTGAGATCTGAGGACACGGCGGTGTACTACTGCGCCAGAGAGAAT
TGGCCAATGGACGTATGGGGCCAGGGAACAACTGTCACCGTCTCCTCA
```

In further embodiments, the invention relates to Clone AJ-26545 HC AA sequence (SEQ ID NO: 300):

```
QVQLVQSGAE VKKPGASVKV SCRASGYTFM EHYMHWVRQA
PGQGLEWMGV IGPSGGKTSY AQKFQGRVTM TRDTSTSTVY
MELSSLRSED TAVYYCARES WPMDVWGQGT TVTVSS.
```

In further embodiments, the invention relates to HC CDR1 thereof: YTFMEHYMH (SEQ ID NO: 301). In further embodiments, the invention relates to HC CDR2 thereof: VIGPSGGKTSYAQKFQG (SEQ ID NO: 302). In further embodiments, the invention relates to HC CDR3 thereof: ARESWPMDV (SEQ ID NO: 303).

In further embodiments, the invention relates to Clone AJ-26545 LC DNA (SEQ ID NO: 304):

```
GAAATAGTGATGACGCAGTCTCCAGCCACCCTGTCTGTGTCTCCAGGGGA
AAGAGCCACCCTCTCCTGCAGGGCCAGTCAGAGTGTTAGCAGCAACTTAG
CCTGGTACCAGCAGAAACCTGGCCAGGCTCCCAGGCTCCTCATCTATGGT
GCATCCACCAGGGCCACTGGTATCCCAGCCAGGTTCAGTGGCAGTGGGTC
TGGGACAGAGTTCACTCTCACCATCAGCAGCCTGCAGTCTGAAGATTTTG
CAGTTTATTACTGTCAGCAGTACGCCGCCTACCCTACTTTTGGCGGAGGG
ACCAAGGTTGAGATCAAACGG
```

In further embodiments, the invention relates to Clone AJ-26545 LC AA sequence (SEQ ID NO: 305):

```
EIVMTQSPAT LSVSPGERAT LSCRASQSVS SNLAWYQQKP
GQAPRLLIYG ASTRATGIPA RFSGSGSGTE FTLTISSLQS
EDFAVYYCQQ YAAYPTFGGG TKVEIKR.
```

In further embodiments, the invention relates to LC CDR1 thereof: RASQSVSSNLA (SEQ ID NO: 306). In further embodiments, the invention relates to LC CDR2 thereof: GASTRAT (SEQ ID NO: 307). In further embodiments, the invention relates to the LC CDR3 thereof: QQYAAYPT (SEQ ID NO: 308).

In further embodiments, the invention relates to Clone AJ-26545 CAR DNA HxL (SEQ ID NO: 309):

```
ATGGCACTCCCCGTAACTGCTCTGCTGCTGCCGTTGGCATTGCTCCTGCA
CGCCGCACGCCCGCAGGTGCAGCTGGTGCAGTCTGGGGCTGAGGTGAAGA
AGCCTGGGGCCTCAGTGAAGGTTTCCTGCAGGGCATCTGGATACACCTTC
ATGGAGCACTATATGCACTGGGTGCGACAGGCCCCTGGACAAGGGCTTGA
GTGGATGGGAGTAATCGGGCCTAGTGGTGGTAAGACAAGCTACGCACAGA
AGTTCCAGGGCAGAGTCACCATGACCAGGGACACGTCCACGAGCACAGTC
TACATGGAGCTGAGCAGCCTGAGATCTGAGGACACGGCGGTGTACTACTG
CGCCAGAGAGAATTGGCCAATGGACGTATGGGGCCAGGGAACAACTGTCA
CCGTCTCCTCAGGGTCTACATCCGGCTCCGGGAAGCCCGGAAGTGGCGAA
GGTAGTACAAAGGGGGAAATAGTGATGACGCAGTCTCCAGCCACCCTGTC
TGTGTCTCCAGGGGAAAGAGCCACCCTCTCCTGCAGGGCCAGTCAGAGTG
TTAGCAGCAACTTAGCCTGGTACCAGCAGAAACCTGGCCAGGCTCCCAGG
CTCCTCATCTATGGTGCATCCACCAGGGCCACTGGTATCCCAGCCAGGTT
CAGTGGCAGTGGGTCTGGGACAGAGTTCACTCTCACCATCAGCAGCCTGC
AGTCTGAAGATTTTGCAGTTTATTACTGTCAGCAGTACGCCGCCTACCCT
ACTTTTGGCGGAGGGACCAAGGTTGAGATCAAACGGGCCGCTGCCCTTGA
TAATGAAAAGTCAAACGGAACAATCATTCACGTGAAGGGCAAGCACCTCT
GTCCGTCACCCTTGTTCCCTGGTCCATCCAAGCCATTCTGGGTGTTGGTC
GTAGTGGGTGGAGTCCTCGCTTGTTACTCTCTGCTCGTCACCGTGGCTTT
TATAATCTTCTGGGTTAGATCCAAAAGAAGCCGCCTGCTCCATAGCGATT
ACATGAATATGACTCCACGCCGCCCTGGCCCCACAAGGAAACACTACCAG
CCTTACGCACCACCTAGAGATTTCGCTGCCTATCGGAGCAGGGTGAAGTT
TTCCAGATCTGCAGATGCACCAGCGTATCAGCAGGGCCAGAACCAACTGT
ATAACGAGCTCAACCTGGGACGCAGGGAAGAGTATGACGTTTTGGACAAG
CGCAGAGGACGGGACCCTGAGATGGGTGGCAAACCAAGACGAAAAAACCC
CCAGGAGGGTCTCTATAATGAGCTGCAGAAGGATAAGATGGCTGAAGCCT
ATTCTGAAATAGGCATGAAAGGAGAGCGGAGAAGGGGAAAAGGGCACGAC
GGTTTGTACCAGGGACTCAGCACTGCTACGAAGGATACTTATGACGCTCT
CCACATGCAAGCCCTGCCACCTAGG
```

In further embodiments, the invention relates to Clone AJ-26545 CAR HxL AA sequence (SEQ ID NO: 310):

MALPVTALLL PLALLLHAAR PQVQLVQSGA EVKKPGASVK
VSCRASGYTF MEHYMHWVRQ APGQGLEWMG VIGPSGGKTS
YAQKFQGRVT MTRDTSTSTV YMELSSLRSE DTAVYYCARE
SWPMDVWGQG TTVTVSSGST SGSGKPGSGE GSTKGEIVMT
QSPATLSVSP GERATLSCRA SQSVSSNLAW YQQKPGQAPR
LLIYGASTRA TGIPARFSGS GSGTEFTLTI SSLQSEDFAV
YYCQQYAAYP TFGGGTKVEI KRAAALDNEK SNGTIIHVKG
KHLCPSPLFP GPSKPFWVLV VVGGVLACYS LLVTVAFIIF
WVRSKRSRLL HSDYMNMTPR RPGPTRKHYQ PYAPPRDFAA
YRSRVKFSRS ADAPAYQQGQ NQLYNELNLG RREEYDVLDK
RRGRDPEMGG KPRRKNPQEG LYNELQKDKM AEAYSEIGMK
GERRRGKGHD GLYQGLSTAT KDTYDALHMQ ALPPR

In further embodiments, the invention relates to Clone AJ-26545 CAR DNA LxH (SEQ ID NO: 311):

ATGGCACTCCCCGTAACTGCTCTGCTGCTGCCGTTGGCATTGCTCCTGCA
CGCCGCACGCCCGGAAATAGTGATGACGCAGTCTCCAGCCACCCTGTCT
GTGTCTCCAGGGGAAAGAGCCACCCTCTCCTGCAGGGCCAGTCAGAGTG
TTAGCAGCAACTTAGCCTGGTACCAGCAGAAACCTGGCCAGGCTCCCAG
GCTCCTCATCTATGGTGCATCCACCAGGGCCACTGGTATCCCAGCCAGGT
TCAGTGGCAGTGGGTCTGGGACAGAGTTCACTCTCACCATCAGCAGCCT
GCAGTCTGAAGATTTTGCAGTTTATTACTGTCAGCAGTACGCCGCCTACC
CTACTTTTGGCGGAGGGACCAAGGTTGAGATCAAACGGGGGTCTACATC
CGGCTCCGGGAAGCCCGGAAGTGGCGAAGGTAGTACAAAGGGGCAGGT
GCAGCTGGTGCAGTCTGGGGCTGAGGTGAAGAAGCCTGGGGCCTCAGTG
AAGGTTTCCTGCAGGGCATCTGGATACACCTTCATGGAGCACTATATGCA
CTGGGTGCGACAGGCCCCTGGACAAGGGCTTGAGTGGATGGGAGTAATC
GGGCCTAGTGGTGGTAAGACAAGCTACGCACAGAAGTTCCAGGGCAGA
GTCACCATGACCAGGGACACGTCCACGAGCACAGTCTACATGGAGCTGA
GCAGCCTGAGATCTGAGGACACGGCGGTGTACTACTGCGCCAGAGAGAA
TTGGCCAATGGACGTATGGGGCCAGGGAACAACTGTCACCGTCTCCTCA
GCCGCTGCCCTTGATAATGAAAAGTCAAACGGAACAATCATTCACGTGA
AGGGCAAGCACCTCTGTCCGTCACCCTTGTTCCCTGGTCCATCCAAGCCA
TTCTGGGTGTTGGTCGTAGTGGGTGGAGTCCTCGCTTGTTACTCTCTGCT
CGTCACCGTGGCTTTTATAATCTTCTGGGTTAGATCCAAAAGAAGCCGCC
TGCTCCATAGCGATTACATGAATATGACTCCACGCCGCCCTGGCCCCACA
AGGAAACACTACCAGCCTTACGCACCACCTAGAGATTTCGCTGCCTATC
GGAGCAGGGTGAAGTTTTCCAGATCTGCAGATGCACCAGCGTATCAGCA
GGGCCAGAACCAACTGTATAACGAGCTCAACCTGGGACGCAGGGAAGA
GTATGACGTTTTGGACAAGCGCAGAGGACGGGACCCTGAGATGGGTGGC
AAACCAAGACGAAAAAACCCCCAGGAGGGTCTCTATAATGAGCTGCAG

-continued

AAGGATAAGATGGCTGAAGCCTATTCTGAAATAGGCATGAAAGGAGAG
CGGAGAAGGGGAAAAGGGCACGACGGTTTGTACCAGGGACTCAGCACT
GCTACGAAGGATACTTATGACGCTCTCCACATGCAAGCCCTGCCACCTA
GG

In further embodiments, the invention relates to Clone AJ-26545 CAR LxH AA sequence (SEQ ID NO: 312):

MALPVTALLL PLALLLHAAR PEIVMTQSPA TLSVSPGERA
TLSCRASQSV SSNLAWYQQK PGQAPRLLIY GASTRATGIP
ARFSGSGSGT EFTLTISSLQ SEDFAVYYCQ QYAAYPTFGG
GTKVEIKRGS TSGSGKPGSG EGSTKGQVQL VQSGAEVKKP
GASVKVSCRA SGYTFMEHYM HWVRQAPGQG LEWMGVIGPS
GGKTSYAQKF QGRVTMTRDT STSTVYMELS SLRSEDTAVY
YCARESWPMD VWGQGTTVTV SSAAALDNEK SNGTIIHVKG
KHLCPSPLFP GPSKPFWVLV VVGGVLACYS LLVTVAFIIF
WVRSKRSRLL HSDYMNMTPR RPGPTRKHYQ PYAPPRDFAA
YRSRVKFSRS ADAPAYQQGQ NQLYNELNLG RREEYDVLDK
RRGRDPEMGG KPRRKNPQEG LYNELQKDKM AEAYSEIGMK
GERRRGKGHD GLYQGLSTAT KDTYDALHMQ ALPPR

In further embodiments, the invention relates to Clone AJ-26554 HC DNA (SEQ ID NO: 313):

CAGGTGCAGCTGGTGCAGTCTGGGGCTGAGGTGAAGAAGCCTGGGGCCT
CAGTGAAGGTTTCCTGCAAGGCATCTGGATACACCTTCACGGAGCACTA
TATGCACTGGGTGCGACAGGCCCCTGGACAAAGGCTTGAGTGGATGGGA
GTAATCGGGCCTAGTGGTGGTAAGACAAGCTACGCACAGAAGTTCCAGG
GCAGAGTCACCATGACCAGGGACACGTCCACGAGCACAGTCTACATGGA
GCTGAGCAGCCTGAGATCTGAGGACACGGCGGTGTACTACTGCGCCAGA
GAGAGTTGGCCAATGGACGTATGGGGCCAGGGAACAACTGTCACCGTCT
CCTCA

In further embodiments, the invention relates to Clone AJ-26554 HC (SEQ ID NO: 314):

QVQLVQSGAE VKKPGASVKV SCKASGYTFT EHYMHWVRQA
PGQRLEWMGV IGPSGGKTSY AQKFQGRVTM TRDTSTSTVY
MELSSLRSED TAVYYCARES WPMDVWGQGT TVTVSS

In further embodiments, the invention relates to HC CDR1 thereof: YTFTEHYMH (SEQ ID NO: 315). In further embodiments, the invention relates to HC CDR2 thereof: VIGPSGGKTSYAQKFQG (SEQ ID NO: 316). In further embodiments, the invention relates to HC CDR3 thereof: ARESWPMDV (SEQ ID NO: 317).

In further embodiments, the invention relates to Clone AJ-26554 LC DNA (SEQ ID NO: 318):

GAAATAGTGATGACGCAGTCTCCAGCCACCCTGTCTGTGTCTCCAGGGG

AAAGAGCCACCCTCTCCTGCAGGGCCAGTCAGAGTGTTAGCAGCAACTT

AGCCTGGTACCAGCAGAAACCTGGCCAGGCTCCCAGGCTCCTCATCTAT

GGTGCATCCACCAGGGCCACTGGTATCCCAGCCAGGTTCAGTGGCAGTG

GGTCTGGGACAGAGTTCACTCTCACCATCAGCAGCCTGCAGTCTGAAGA

TTTTGCAGTTTATTACTGTCAGCAGTACGCCGCCTACCCTACTTTTGGCG

GAGGGACCAAGGTTGAGATCAAACGG

In further embodiments, the invention relates to Clone AJ-26554 LC AA sequence (SEQ ID NO: 319):

EIVMTQSPAT LSVSPGERAT LSCRASQSVS

SNLAWYQQKP GQAPRLLIYG ASTRATGIPA RFSGSGSGTE

FTLTISSLQS EDFAVYYCQQ YAAYPTFGGG TKVEIKR.

In further embodiments, the invention relates to the LC CDR1 thereof: RASQSVSSNLA (SEQ ID NO: 320). In further embodiments, the invention relates to the LC CDR2 thereof: GASTRAT (SEQ ID NO: 321). In further embodiments, the invention relates to LC CDR3 thereof: QQYAAYPT (SEQ ID NO: 322).

In further embodiments, the invention relates to Clone AJ-26554 CAR DNA HxL (SEQ ID NO: 323):

ATGGCACTCCCCGTAACTGCTCTGCTGCTGCCGTTGGCATTGCTCCTGCA

CGCCGCACGCCCGCAGGTGCAGCTGGTGCAGTCTGGGGCTGAGGTGAAG

AAGCCTGGGGCCTCAGTGAAGGTTTCCTGCAAGGCATCTGGATACACCT

TCACGGAGCACTATATGCACTGGGTGCGACAGGCCCCTGGACAAAGGCT

TGAGTGGATGGGAGTAATCGGGCCTAGTGGTGGTAAGACAAGCTACGCA

CAGAAGTTCCAGGGCAGAGTCACCATGACCAGGGACACGTCCACGAGCA

CAGTCTACATGGAGCTGAGCAGCCTGAGATCTGAGGACACGGCGGTGTA

CTACTGCGCCAGAGAGAGTTGGCCAATGGACGTATGGGGCCAGGGAACA

ACTGTCACCGTCTCCTCAGGGTCTACATCCGGCTCCGGGAAGCCCGGAA

GTGGCGAAGGTAGTACAAAGGGGGAAATAGTGATGACGCAGTCTCCAG

CCACCCTGTCTGTGTCTCCAGGGGAAAGAGCCACCCTCTCCTGCAGGGCC

AGTCAGAGTGTTAGCAGCAACTTAGCCTGGTACCAGCAGAAACCTGGCC

AGGCTCCCAGGCTCCTCATCTATGGTGCATCCACCAGGGCCACTGGTATC

CCAGCCAGGTTCAGTGGCAGTGGGTCTGGGACAGAGTTCACTCTCACCA

TCAGCAGCCTGCAGTCTGAAGATTTTGCAGTTTATTACTGTCAGCAGTAC

GCCGCCTACCCTACTTTTGGCGGAGGGACCAAGGTTGAGATCAAACGGG

CCGCTGCCCTTGATAATGAAAAGTCAAACGGAACAATCATTCACGTGAA

GGGCAAGCACCTCTGTCCGTCACCCTTGTTCCCTGGTCCATCCAAGCCAT

TCTGGGTGTTGGTCGTAGTGGGTGGAGTCCTCGCTTGTTACTCTCTGCTC

GTCACCGTGGCTTTTATAATCTTCTGGGTTAGATCCAAAAGAAGCCGCCT

-continued

GCTCCATAGCGATTACATGAATATGACTCCACGCCGCCCTGGCCCCACA

AGGAAACACTACCAGCCTTACGCACCACCTAGAGATTTCGCTGCCTATC

GGAGCAGGGTGAAGTTTTCCAGATCTGCAGATGCACCAGCGTATCAGCA

GGGCCAGAACCAACTGTATAACGAGCTCAACCTGGGACGCAGGGAAGA

GTATGACGTTTTGGACAAGCGCAGAGGACGGGACCCTGAGATGGGTGGC

AAACCAAGACGAAAAAACCCCCAGGAGGGTCTCTATAATGAGCTGCAG

AAGGATAAGATGGCTGAAGCCTATTCTGAAATAGGCATGAAAGGAGAG

CGGAGAAGGGGAAAAGGGCACGACGGTTTGTACCAGGGACTCAGCACT

GCTACGAAGGATACTTATGACGCTCTCCACATGCAAGCCCTGCCACCTA

GG

In further embodiments, the invention relates to Clone AJ-26554 CAR HxL AA sequence (SEQ ID NO: 324):

MALPVTALLL PLALLLHAAR PQVQLVQSGA EVKKPGASVK

VSCKASGYTF TEHYMHWVRQ APGQRLEWMG VIGPSGGKTS

YAQKFQGRVT MTRDTSTSTV YMELSSLRSE DTAVYYCARE

SWPMDVWGQG TTVTVSSGST SGSGKPGSGE GSTKGEIVMT

QSPATLSVSP GERATLSCRA SQSVSSNLAW YQQKPGQAPR

LLIYGASTRA TGIPARFSGS GSGTEFTLTI SSLQSEDFAV

YYCQQYAAYP TFGGGTKVEI KRAAALDNEK SNGTIIHVKG

KHLCPSPLFP GPSKPFWVLV VVGGVLACYS LLVTVAFIIF

WVRSKRSRLL HSDYMNMTPR RPGPTRKHYQ PYAPPRDFAA

YRSRVKFSRS ADAPAYQQGQ NQLYNELNLG RREEYDVLDK

RRGRDPEMGG KPRRKNPQEG LYNELQKDKM AEAYSEIGMK

GERRRGKGHD GLYQGLSTAT KDTYDALHMQ ALPPR.

In further embodiments, the invention relates to Clone AJ-26554 CAR DNA LxH (SEQ ID NO: 325):

ATGGCACTCCCCGTAACTGCTCTGCTGCTGCCGTTGGCATTGCTCCTGCA

CGCCGCACGCCCGGAAATAGTGATGACGCAGTCTCCAGCCACCCTGTCT

GTGTCTCCAGGGGAAAGAGCCACCCTCTCCTGCAGGGCCAGTCAGAGTG

TTAGCAGCAACTTAGCCTGGTACCAGCAGAAACCTGGCCAGGCTCCCAG

GCTCCTCATCTATGGTGCATCCACCAGGGCCACTGGTATCCCAGCCAGGT

TCAGTGGCAGTGGGTCTGGGACAGAGTTCACTCTCACCATCAGCAGCCT

GCAGTCTGAAGATTTTGCAGTTTATTACTGTCAGCAGTACGCCGCCTACC

CTACTTTTGGCGGAGGGACCAAGGTTGAGATCAAACGGGGGTCTACATC

CGGCTCCGGGAAGCCCGGAAGTGGCGAAGGTAGTACAAAGGGGCAGGT

GCAGCTGGTGCAGTCTGGGGCTGAGGTGAAGAAGCCTGGGGCCTCAGTG

AAGGTTTCCTGCAAGGCATCTGGATACACCTTCACGGAGCACTATATGC

ACTGGGTGCGACAGGCCCCTGGACAAAGGCTTGAGTGGATGGGAGTAAT

CGGGCCTAGTGGTGGTAAGACAAGCTACGCACAGAAGTTCCAGGGCAGA

GTCACCATGACCAGGGACACGTCCACGAGCACAGTCTACATGGAGCTGA

-continued

GCAGCCTGAGATCTGAGGACACGGCGGTGTACTACTGCGCCAGAGAGAG

TTGGCCAATGGACGTATGGGGCCAGGGAACAACTGTCACCGTCTCCTCA

GCCGCTGCCCTTGATAATGAAAAGTCAAACGGAACAATCATTCACGTGA

AGGGCAAGCACCTCTGTCCGTCACCCTTGTTCCCTGGTCCATCCAAGCCA

TTCTGGGTGTTGGTCGTAGTGGGTGGAGTCCTCGCTTGTTACTCTCTGCT

CGTCACCGTGGCTTTTATAATCTTCTGGGTTAGATCCAAAAGAAGCCGCC

TGCTCCATAGCGATTACATGAATATGACTCCACGCCGCCCTGGCCCCACA

AGGAAACACTACCAGCCTTACGCACCACCTAGAGATTTCGCTGCCTATC

GGAGCAGGGTGAAGTTTTCCAGATCTGCAGATGCACCAGCGTATCAGCA

GGGCCAGAACCAACTGTATAACGAGCTCAACCTGGGACGCAGGGAAGA

GTATGACGTTTTGGACAAGCGCAGAGGACGGGACCCTGAGATGGGTGGC

AAACCAAGACGAAAAAACCCCCAGGAGGGTCTCTATAATGAGCTGCAG

AAGGATAAGATGGCTGAAGCCTATTCTGAAATAGGCATGAAAGGAGAG

CGGAGAAGGGGAAAAGGGCACGACGGTTTGTACCAGGGACTCAGCACT

GCTACGAAGGATACTTATGACGCTCTCCACATGCAAGCCCTGCCACCTA

GG

In further embodiments, the invention relates to Clone AJ-26554 CAR LxH AA sequence (SEQ ID NO: 326):

MALPVTALLL PLALLLHAAR PEIVMTQSPA TLSVSPGERA

TLSCRASQSV SSNLAWYQQK PGQAPRLLIY GASTRATGIP

ARFSGSGSGT EFTLTISSLQ SEDFAVYYCQ QYAAYPTFGG

GTKVEIKRGS TSGSGKPGSG EGSTKGQVQL VQSGAEVKKP

GASVKVSCKA SGYTFTEHYM HWVRQAPGQR LEWMGVIGPS

GGKTSYAQKF QGRVTMTRDT STSTVYMELS SLRSEDTAVY

YCARESWPMD VWGQGTTVTV SSAAALDNEK SNGTIIHVKG

KHLCPSPLFP GPSKPFWVLV VVGGVLACYS LLVTVAFIIF

WVRSKRSRLL HSDYMNMTPR RPGPTRKHYQ PYAPPRDFAA

YRSRVKFSRS ADAPAYQQGQ NQLYNELNLG RREEYDVLDK

RRGRDPEMGG KPRRKNPQEG LYNELQKDKM AEAYSEIGMK

GERRRGKGHD GLYQGLSTAT KDTYDALHMQ ALPPR

In further embodiments, the invention relates to Clone NM-26562 HC DNA (SEQ ID NO: 327):

CAGGTGCAGCTGCAGGAGTCGGGCCCAGGACTGGTGAAGCCTTCACAGA

CCCTGTCCCTCACCTGTACTGTCTCTGGTGGCTCCATCGGGAGTGGTGGT

AGTTACTGGAGCTGGATCCGCCAGCACCCAGGGAAGGGCCTGGAGTGGA

TTGGGTTGATCTATTACGATGGGAGCACCTACTACAACCCGTCCCTCAAG

AGTCGAGTTACCATATCAGTAGACACGTCTAAGAACCAGTTCTCCCTGA

AGCTGAGTTCTGTGACCGCCGCAGACACGGCGGTGTACTACTGCGCCAG

-continued

AGGCAGGGGATATGAGACTTCTTTAGCCTTCGATATCTGGGGTCAGGGT

ACAATGGTCACCGTCTCCTCA

In further embodiments, the invention relates to Clone NM-26562 HC AA sequence (SEQ ID NO: 328):

QVQLQESGPG LVKPSQTLSL TCTVSGGSIG

SGGSYWSWIR QHPGKGLEWI GLIYYDGSTY YNPSLKSRVT

ISVDTSKNQF SLKLSSVTAA DTAVYYCARG RGYETSLAFD

IWGQGTMVTV SS.

In further embodiments, the invention relates to HC CDR1 thereof: GSIGSGGSYWS (SEQ ID NO: 329). In further embodiments, the invention relates to HC CDR2 thereof: LIYYDGSTYYNPSLKS (SEQ ID NO: 330). In further embodiments, the invention relates to HC CDR3 thereof: ARGRGYETSLAFDI (SEQ ID NO: 331).

In further embodiments, the invention relates to Clone NM-26562 LC DNA (SEQ ID NO: 332):

GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTA

GCCTGGTACCAACAGAAACCTGGCCAGGCTCCCAGGCTCCTCATCTATG

ATGCATCCAACAGGGCCACTGGCATCCCAGCCAGGTTCAGTGGCAGTGG

GTCTGGGACAGACTTCACTCTCACCATCAGCAGCCTAGAGCCTGAAGAT

TTTGCAGTTTATTACTGTCAGCAGAGACACGTCTGGCCTCCTACTTTTGG

CGGAGGGACCAAGGTTGAGATCAAACGG

In further embodiments, the invention relates to Clone NM-26562 LC AA sequence (SEQ ID NO: 333):

EIVLTQSPAT LSLSPGERAT LSCRASQSVS SYLAWYQQKP

GQAPRLLIYD ASNRATGIPA RFSGSGSGTD FTLTISSLEP

EDFAVYYCQQ RHVWPPTFGG GTKVEIKR

In further embodiments, the invention relates to LC CDR1 AA sequence thereof: RASQSVSSYLA (SEQ ID NO: 334) In further embodiments, the invention relates to LC CDR2 AA sequence thereof: DASNRAT (SEQ ID NO: 335). In further embodiments, the invention relates to LC CDR3 AA sequence thereof: QQRHVWPPT (SEQ ID NO: 336) (LC CDR3).

In further embodiments, the invention relates to Clone NM-26562 CAR DNA HxL (SEQ ID NO: 337):

ATGGCACTCCCCGTAACTGCTCTGCTGCTGCCGTTGGCATTGCTCCTGCA

CGCCGCACGCCCGCAGGTGCAGCTGCAGGAGTCGGGCCCAGGACTGGTG

AAGCCTTCACAGACCCTGTCCCTCACCTGTACTGTCTCTGGTGGCTCCAT

CGGGAGTGGTGGTAGTTACTGGAGCTGGATCCGCCAGCACCCAGGGAAG

GGCCTGGAGTGGATTGGGTTGATCTATTACGATGGGAGCACCTACTACA

ACCCGTCCCTCAAGAGTCGAGTTACCATATCAGTAGACACGTCTAAGAA

CCAGTTCTCCCTGAAGCTGAGTTCTGTGACCGCCGCAGACACGGCGGTGT

-continued

ACTACTGCGCCAGAGGCAGGGGATATGAGACTTCTTTAGCCTTCGATATC
TGGGGTCAGGGTACAATGGTCACCGTCTCCTCAGGGTCTACATCCGGCTC
CGGGAAGCCCGGAAGTGGCGAAGGTAGTACAAAGGGGGAAATTGTGTT
GACACAGTCTCCAGCCACCCTGTCTTTGTCTCCAGGGGAAAGAGCCACC
CTCTCCTGCAGGGCCAGTCAGAGTGTTAGCAGCTACTTAGCCTGGTACCA
ACAGAAACCTGGCCAGGCTCCCAGGCTCCTCATCTATGATGCATCCAAC
AGGGCCACTGGCATCCCAGCCAGGTTCAGTGGCAGTGGGTCTGGGACAG
ACTTCACTCTCACCATCAGCAGCCTAGAGCCTGAAGATTTTGCAGTTTAT
TACTGTCAGCAGAGACACGTCTGGCCTCCTACTTTTGGCGGAGGGACCA
AGGTTGAGATCAAACGGGCCGCTGCCCTTGATAATGAAAAGTCAAACGG
AACAATCATTCACGTGAAGGGCAAGCACCTCTGTCCGTCACCCTTGTTCC
CTGGTCCATCCAAGCCATTCTGGGTGTTGGTCGTAGTGGGTGGAGTCCTC
GCTTGTTACTCTCTGCTCGTCACCGTGGCTTTTATAATCTTCTGGGTTAG
ATCCAAAAGAAGCCGCCTGCTCCATAGCGATTACATGAATATGACTCCAC
GCCGCCCTGGCCCCACAAGGAAACACTACCAGCCTTACGCACCACCTAG
AGATTTCGCTGCCTATCGGAGCAGGGTGAAGTTTTCCAGATCTGCAGATG
CACCAGCGTATCAGCAGGGCCAGAACCAACTGTATAACGAGCTCAACCT
GGGACGCAGGGAAGAGTATGACGTTTTGGACAAGCGCAGAGGACGGGA
CCCTGAGATGGGTGGCAAACCAAGACGAAAAAACCCCCAGGAGGGTCT
CTATAATGAGCTGCAGAAGGATAAGATGGCTGAAGCCTATTCTGAAATA
GGCATGAAAGGAGAGCGGAGAAGGGGAAAAGGGCACGACGGTTTGTAC
CAGGGACTCAGCACTGCTACGAAGGATACTTATGACGCTCTCCACATGC
AAGCCCTGCCACCTAGG.

In further embodiments, the invention relates to Clone NM-26562 CAR HxL (SEQ ID NO: 338):

MALPVTALLL PLALLLHAAR PQVQLQESGP GLVKPSQTLS
LTCTVSGGSI GSGGSYWSWI RQHPGKGLEW IGLIYYDGST
YYNPSLKSRV TISVDTSKNQ FSLKLSSVTA ADTAVYYCAR
GRGYETSLAF DIWGQGTMVT VSSGSTSGSG KPGSGEGSTK
GEIVLTQSPA TLSLSPGERA TLSCRASQSV SSYLAWYQQK
PGQAPRLLIY DASNRATGIP ARFSGSGSGT DFTLTISSLE
PEDFAVYYCQ QRHVWPPTFG GGTKVEIKRA AALDNEKSNG
TIIHVKGKHL CPSPLFPGPS KPFWVLVVVG GVLACYSLLV
TVAFIIFWVR SKRSRLLHSD YMNMTPRRPG PTRKHYQPYA
PPRDFAAYRS RVKFSRSADA PAYQQGQNQL YNELNLGRRE
EYDVLDKRRG RDPEMGGKPR RKNPQEGLYN ELQKDKMAEA
YSEIGMKGER RRGKGHDGLY QGLSTATKDT YDALHMQALP PR.

In further embodiments, the invention relates to Clone NM-26562 CAR DNA LxH (SEQ ID NO: 339):

ATGGCACTCCCCGTAACTGCTCTGCTGCTGCCGTTGGCATTGCTCCTGCA
CGCCGCACGCCCGGAAATTGTGTTGACACAGTCTCCAGCCACCCTGTCTT
TGTCTCCAGGGGAAAGAGCCACCCTCTCCTGCAGGGCCAGTCAGAGTGT
TAGCAGCTACTTAGCCTGGTACCAACAGAAACCTGGCCAGGCTCCCAGG
CTCCTCATCTATGATGCATCCAACAGGGCCACTGGCATCCCAGCCAGGTT
CAGTGGCAGTGGGTCTGGGACAGACTTCACTCTCACCATCAGCAGCCTA
GAGCCTGAAGATTTTGCAGTTTATTACTGTCAGCAGAGACACGTCTGGCC
TCCTACTTTTGGCGGAGGGACCAAGGTTGAGATCAAACGGGGGTCTACA
TCCGGCTCCGGGAAGCCCGGAAGTGGCGAAGGTAGTACAAAGGGGCAG
GTGCAGCTGCAGGAGTCGGGCCCAGGACTGGTGAAGCCTTCACAGACCC
TGTCCCTCACCTGTACTGTCTCTGGTGGCTCCATCGGGAGTGGTGGTAGT
TACTGGAGCTGGATCCGCCAGCACCCAGGGAAGGGCCTGGAGTGGATTG
GGTTGATCTATTACGATGGGAGCACCTACTACAACCCGTCCCTCAAGAGT
CGAGTTACCATATCAGTAGACACGTCTAAGAACCAGTTCTCCCTGAAGCT
GAGTTCTGTGACCGCCGCAGACACGGCGGTGTACTACTGCGCCAGAGGC
AGGGGATATGAGACTTCTTTAGCCTTCGATATCTGGGGTCAGGGTACAAT
GGTCACCGTCTCCTCAGCCGCTGCCCTTGATAATGAAAAGTCAAACGGA
ACAATCATTCACGTGAAGGGCAAGCACCTCTGTCCGTCACCCTTGTTCCC
TGGTCCATCCAAGCCATTCTGGGTGTTGGTCGTAGTGGGTGGAGTCCTCG
CTTGTTACTCTCTGCTCGTCACCGTGGCTTTTATAATCTTCTGGGTTAGA
TCCAAAAGAAGCCGCCTGCTCCATAGCGATTACATGAATATGACTCCACG
CCGCCCTGGCCCCACAAGGAAACACTACCAGCCTTACGCACCACCTAGA
GATTTCGCTGCCTATCGGAGCAGGGTGAAGTTTTCCAGATCTGCAGATGC
ACCAGCGTATCAGCAGGGCCAGAACCAACTGTATAACGAGCTCAACCTG
GGACGCAGGGAAGAGTATGACGTTTTGGACAAGCGCAGAGGACGGGAC
CCTGAGATGGGTGGCAAACCAAGACGAAAAAACCCCCAGGAGGGTCTCT
ATAATGAGCTGCAGAAGGATAAGATGGCTGAAGCCTATTCTGAAATAGG
CATGAAAGGAGAGCGGAGAAGGGGAAAAGGGCACGACGGTTTGTACCA
GGGACTCAGCACTGCTACGAAGGATACTTATGACGCTCTCCACATGCAA
GCCCTGCCACCTAGG

In further embodiments, the invention relates to Clone NM-26562 CAR LxH (SEQ ID NO: 340):

MALPVTALLL PLALLLHAAR PEIVLTQSPA TLSLSPGERA
TLSCRASQSV SSYLAWYQQK PGQAPRLLIY DASNRATGIP
ARFSGSGSGT DFTLTISSLE PEDFAVYYCQ QRHVWPPTFG
GGTKVEIKRG STSGSGKPGS GEGSTKGQVQ LQESGPGLVK
PSQTLSLTCT VSGGSIGSGG SYWSWIRQHP GKGLEWIGLI
YYDGSTYYNP SLKSRVTISV DTSKNQFSLK LSSVTAADTA
VYYCARGRGY ETSLAFDIWG QGTMVTVSSA AALDNEKSNG
TIIHVKGKHL CPSPLFPGPS KPFWVLVVVG GVLACYSLLV

-continued

```
TVAFIIFWVR SKRSRLLHSD YMNMTPRRPG PTRKHYQPYA
PPRDFAAYRS RVKFSRSADA PAYQQGQNQL YNELNLGRRE
EYDVLDKRRG RDPEMGGKPR RKNPQEGLYN ELQKDKMAEA
YSEIGMKGER RRGKGHDGLY QGLSTATKDT YDALHMQALP PR
```

In further embodiments, the invention relates to Clone TS-26564 HC DNA sequence (SEQ ID NO: 341):

```
GAGGTGCAGCTGGTGGAGTCTGGGGGAGGCTTGGTACAGCCTGGGGGGT
CCCTGAGACTCTCCTGTGCAGCCTCTGGATTCACCTTCAGTAGCTATAGC
ATGAACTGGGTCCGCCAGGCTCCAGGGAAGGGGCTGGAGTGGGTTTCAA
CCATTAGTAGTAGTAGTAGTATCATATACTACGCAGACTCTGTGAAGGG
CCGATTCACCATCTCCAGAGACAATGCCAAGAACTCACTGTATCTGCAA
ATGAACAGCCTGAGAGCTGAGGACACGGCGGTGTACTACTGCGCCAGAG
GTTCTCAGGAGCACCTGATTTTCGATTATTGGGGACAGGGTACATTGGTC
ACCGTCTCCTCA
```

In further embodiments, the invention relates to Clone TS-26564 HC AA sequence (SEQ ID NO: 342): EVQLVES-GGG LVQPGGSLRL SCAASGFTFS

```
SYSMNWVRQA PGKGLEWVST ISSSSSIIYY ADSVKGRFTI
SRDNAKNSLY LQMNSLRAED TAVYYCARGS QEHLIFDYWG
QGTLVTVSS
```

In further embodiments, the invention relates to HC CDR1 AA sequence thereof: FTFSSYSMN (SEQ ID NO: 343). In further embodiments, the invention relates to HC CDR2 AA sequence thereof: TISSSSSIIYYADSVKG (SEQ ID NO: 344). In further embodiments, the invention relates to HC CDR3 AA sequence thereof: ARGSQEHLIFDY (SEQ ID NO: 345).

In further embodiments, the invention relates to Clone TS-26564 LC DNA (SEQ ID NO: 346):

```
GAAATTGTGTTGACACAGTCTCCAGCCACCCTGTCTTTGTCTCCAGGGGA
AAGAGCCACCCTCTCCTGCAGGGCCAGTCAGAGTGTTAGCAGGTACTTA
GCCTGGTACCAACAGAAACCTGGCCAGGCTCCCAGGCTCCTCATCTATG
ATGCATCCAACAGGGCCACTGGCATCCCAGCCAGGTTCAGTGGCAGTGG
GTCTGGGACAGACTTCACTCTCACCATCAGCAGCCTAGAGCCTGAAGAT
TTTGCAGTTTATTACTGTCAGCAGAGATTCTACTACCCTTGGACTTTTGG
CGGAGGGACCAAGGTTGAGATCAAACGG
```

In further embodiments, the invention relates to Clone TS-26564 LC AA sequence (SEQ ID NO: 347):

```
EIVLTQSPAT LSLSPGERAT LSCRASQSVS RYLAWYQQKP
GQAPRLLIYD ASNRATGIPA RFSGSGSGTD FTLTISSLEP
EDFAVYYCQQ RFYYPWTFGG GTKVEIKR.
```

In further embodiments, the invention relates to LC CDR1 AA sequence thereof: RASQSVSRYLA (SEQ ID NO: 348). In further embodiments, the invention relates to LC CDR2 AA sequence thereof: DASNRAT (SEQ ID NO: 349). In further embodiments, the invention relates to LC CDR3 AA sequence thereof: QQRFYYPWT (SEQ ID NO: 350).

In further embodiments, the invention relates to Clone TS-26564 CAR DNA HxL (SEQ ID NO: 351):

```
ATGGCACTCCCCGTAACTGCTCTGCTGCTGCCGTTGGCATTGCTCCTGCA
CGCCGCACGCCCGGAGGTGCAGCTGGTGGAGTCTGGGGGAGGCTTGGTA
CAGCCTGGGGGGTCCCTGAGACTCTCCTGTGCAGCCTCTGGATTCACCTT
CAGTAGCTATAGCATGAACTGGGTCCGCCAGGCTCCAGGGAAGGGGCTG
GAGTGGGTTTCAACCATTAGTAGTAGTAGTAGTATCATATACTACGCAG
ACTCTGTGAAGGGCCGATTCACCATCTCCAGAGACAATGCCAAGAACTC
ACTGTATCTGCAAATGAACAGCCTGAGAGCTGAGGACACGGCGGTGTAC
TACTGCGCCAGAGGTTCTCAGGAGCACCTGATTTTCGATTATTGGGGACA
GGGTACATTGGTCACCGTCTCCTCAGGGTCTACATCCGGCTCCGGGAAGC
CCGGAAGTGGCGAAGGTAGTACAAAGGGGGAAATTGTGTTGACACAGTC
TCCAGCCACCCTGTCTTTGTCTCCAGGGGAAAGAGCCACCCTCTCCTGCA
GGGCCAGTCAGAGTGTTAGCAGGTACTTAGCCTGGTACCAACAGAAACC
TGGCCAGGCTCCCAGGCTCCTCATCTATGATGCATCCAACAGGGCCACTG
GCATCCCAGCCAGGTTCAGTGGCAGTGGGTCTGGGACAGACTTCACTCT
CACCATCAGCAGCCTAGAGCCTGAAGATTTTGCAGTTTATTACTGTCAGC
AGAGATTCTACTACCCTTGGACTTTTGGCGGAGGGACCAAGGTTGAGAT
CAAACGGGCCGCTGCCCTTGATAATGAAAAGTCAAACGGAACAATCATT
CACGTGAAGGGCAAGCACCTCTGTCCGTCACCCTTGTTCCCTGGTCCATC
CAAGCCATTCTGGGTGTTGGTCGTAGTGGGTGGAGTCCTCGCTTGTTACT
CTCTGCTCGTCACCGTGGCTTTTATAATCTTCTGGGTTAGATCCAAAAGA
AGCCGCCTGCTCCATAGCGATTACATGAATATGACTCCACGCCGCCCTGG
CCCCACAAGGAAACACTACCAGCCTTACGCACCACCTAGAGATTTCGCT
GCCTATCGGAGCAGGGTGAAGTTTTCCAGATCTGCAGATGCACCAGCGT
ATCAGCAGGGCCAGAACCAACTGTATAACGAGCTCAACCTGGGACGCAG
GGAAGAGTATGACGTTTTGGACAAGCGCAGAGGACGGGACCCTGAGAT
GGGTGGCAAACCAAGACGAAAAAACCCCCAGGAGGGTCTCTATAATGA
GCTGCAGAAGGATAAGATGGCTGAAGCCTATTCTGAAATAGGCATGAAA
GGAGAGCGGAGAAGGGGAAAAGGGCACGACGGTTTGTACCAGGGACTC
AGCACTGCTACGAAGGATACTTATGACGCTCTCCACATGCAAGCCCTGC
CACCTAGG
```

In further embodiments, the invention relates to Clone TS-26564 CAR HxL AA sequence (SEQ ID NO: 352):

```
MALPVTALLL PLALLLHAAR PEVQLVESGG GLVQPGGSLR
LSCAASGFTF SSYSMNWVRQ APGKGLEWVS TISSSSSIIY
YADSVKGRFT ISRDNAKNSL YLQMNSLRAE DTAVYYCARG
```

-continued

SQEHLIFDYW GQGTLVTVSS GSTSGSGKPG SGEGSTKGEI

VLTQSPATLS LSPGERATLS CRASQSVSRY LAWYQQKPGQ

APRLLIYDAS NRATGIPARF SGSGSGTDFT LTISSLEPED

FAVYYCQQRF YYPWTFGGGT KVEIKRAAAL DNEKSNGTII

HVKGKHLCPS PLFPGPSKPF WVLVVVGGVL ACYSLLVTVA

FIIFWVRSKR SRLLHSDYMN MTPRRPGPTR KHYQPYAPPR

DFAAYRSRVK FSRSADAPAY QQGQNQLYNE LNLGRREEYD

VLDKRRGRDP EMGGKPRRKN PQEGLYNELQ KDKMAEAYSE

IGMKGERRRG KGHDGLYQGL STATKDTYDA LHMQALPPR

In further embodiments, the invention relates to Clone TS-26564 CAR DNA LxH (SEQ ID NO: 353):

ATGGCACTCCCCGTAACTGCTCTGCTGCTGCCGTTGGCATTGCTCCTGCA

CGCCGCACGCCCGGAAATTGTGTTGACACAGTCTCCAGCCACCCTGTCTT

TGTCTCCAGGGGAAAGAGCCACCCTCTCCTGCAGGGCCAGTCAGAGTGT

TAGCAGGTACTTAGCCTGGTACCAACAGAAACCTGGCCAGGCTCCCAGG

CTCCTCATCTATGATGCATCCAACAGGGCCACTGGCATCCCAGCCAGGTT

CAGTGGCAGTGGGTCTGGGACAGACTTCACTCTCACCATCAGCAGCCTA

GAGCCTGAAGATTTTGCAGTTTATTACTGTCAGCAGAGATTCTACTACCC

TTGGACTTTTGGCGGAGGGACCAAGGTTGAGATCAAACGGGGGTCTACA

TCCGGCTCCGGGAAGCCCGGAAGTGGCGAAGGTAGTACAAAGGGGGAG

GTGCAGCTGGTGGAGTCTGGGGGAGGCTTGGTACAGCCTGGGGGGTCCC

TGAGACTCTCCTGTGCAGCCTCTGGATTCACCTTCAGTAGCTATAGCATG

AACTGGGTCCGCCAGGCTCCAGGGAAGGGGCTGGAGTGGGTTTCAACCA

TTAGTAGTAGTAGTAGTATCATATACTACGCAGACTCTGTGAAGGGCCG

ATTCACCATCTCCAGAGACAATGCCAAGAACTCACTGTATCTGCAAATG

AACAGCCTGAGAGCTGAGGACACGGCGGTGTACTACTGCGCCAGAGGTT

CTCAGGAGCACCTGATTTTCGATTATTGGGGACAGGGTACATTGGTCACC

GTCTCCTCAGCCGCTGCCCTTGATAATGAAAAGTCAAACGGAACAATCA

TTCACGTGAAGGGCAAGCACCTCTGTCCGTCACCCTTGTTCCCTGGTCCA

TCCAAGCCATTCTGGGTGTTGGTCGTAGTGGGTGGAGTCCTCGCTTGTTA

CTCTCTGCTCGTCACCGTGGCTTTTATAATCTTCTGGGTTAGATCCAAAA

GAAGCCGCCTGCTCCATAGCGATTACATGAATATGACTCCACGCCGCCCT

GGCCCCACAAGGAAACACTACCAGCCTTACGCACCACCTAGAGATTTCG

CTGCCTATCGGAGCAGGGTGAAGTTTTCCAGATCTGCAGATGCACCAGC

GTATCAGCAGGGCCAGAACCAACTGTATAACGAGCTCAACCTGGGACGC

AGGGAAGAGTATGACGTTTTGGACAAGCGCAGAGGACGGGACCCTGAG

ATGGGTGGCAAACCAAGACGAAAAAACCCCCAGGAGGGTCTCTATAATG

AGCTGCAGAAGGATAAGATGGCTGAAGCCTATTCTGAAATAGGCATGAA

AGGAGAGCGGAGAAGGGGAAAAGGGCACGACGGTTTGTACCAGGGACT

-continued

CAGCACTGCTACGAAGGATACTTATGACGCTCTCCACATGCAAGCCCTG

CCACCTAGG

In further embodiments, the invention relates to Clone TS-26564 CAR LxH AA sequence (SEQ ID NO: 354):

MALPVTALLL PLALLLHAAR PEIVLTQSPA TLSLSPGERA

TLSCRASQSV SRYLAWYQQK PGQAPRLLIY DASNRATGIP

ARFSGSGSGT DFTLTISSLE PEDFAVYYCQ QRFYYPWTFG

GGTKVEIKRG STSGSGKPGS GEGSTKGEVQ LVESGGGLVQ

PGGSLRLSCA ASGFTFSSYS MNWVRQAPGK GLEWVSTISS

SSSIIYYADS VKGRFTISRD NAKNSLYLQM NSLRAEDTAV

YYCARGSQEH LIFDYWGQGT LVTVSSAAAL DNEKSNGTII

HVKGKHLCPS PLFPGPSKPF WVLVVVGGVL ACYSLLVTVA

FIIFWVRSKR SRLLHSDYMN MTPRRPGPTR KHYQPYAPPR

DFAAYRSRVK FSRSADAPAY QQGQNQLYNE LNLGRREEYD

VLDKRRGRDP EMGGKPRRKN PQEGLYNELQ KDKMAEAYSE

IGMKGERRRG KGHDGLYQGL STATKDTYDA LHMQALPPR

In further embodiments, the invention relates to Clone RY-26568 HC DNA (SEQ ID NO: 355):

CAGGTGCAGCTGGTGGAGTCTGGGGGAGGCGTGGTCCAGCCTGGGAGGT

CCCTGAGACTCTCCTGTGCAGCGTCTGGATTCACCTTCGGGAGCTATGGC

ATGCACTGGGTCCGCCAGGCTCCAGGCAAGGGGCTGGAGTGGGTGGCAG

TTATACATTATGATGGAAGTGTTGAATACTATGCAGACTCCGTGAAGGG

CCGATTCACCATCTCCAGAGACAATTCCAAGGACACGCTGTATCTGCAA

ATGAACAGCCTGAGAGCCGAGGACACGGCGGTGTACTACTGCGCCAGAA

CTGACTTCTGGAGCGGATCCCCTCCAAGCTTAGATTACTGGGGACAGGG

TACATTGGTCACCGTCTCCTCA

In further embodiments, the invention relates to Clone RY-26568 HC AA sequence (SEQ ID NO: 356):

QVQLVESGGG VVQPGRSLRL SCAASGFTFG SYGMHWVRQA

PGKGLEWVAV IHYDGSVEYY ADSVKGRFTI SRDNSKDTLY

LQMNSLRAED TAVYYCARTD FWSGSPPSLD YWGQGTLVTV SS

In further embodiments, the invention relates to HC CDR1 thereof: FTFGSYGMH (SEQ ID NO: 357). In further embodiments, the invention relates to HC CDR2 thereof: VIHYDGSVEYYADSVKG (SEQ ID NO: 358). In further embodiments, the invention relates to HC CDR3 thereof: ARTDFWSGSPPSLDY (SEQ ID NO: 359).

In further embodiments, the invention relates to Clone RY-26568 LC DNA (SEQ ID NO: 360):

GACATCCAGTTGACCCAGTCTCCATCTTCCGTGTCTGCATCTGTAGGAGA

CAGAGTCACCATCACTTGTCGGGCGAGTCGGGGTATTAGCAGCTGGTTA

GCCTGGTATCAGCAGAAACCAGGGAAAGCCCCTAAGCTCCTGATCTATG

-continued

GTGCATCCAGTTTGCAAAGTGGGGTCCCATCAAGGTTCAGCGGCAGTGG

ATCTGGGACAGATTTCACTCTCACCATCAGCAGCCTGCAGCCTGAAGATT

TTGCAACTTATTACTGTCAGCAGATATACACCTTCCCTTTCACTTTTGGC

GGAGGGACCAAGGTTGAGATCAAACGG

In further embodiments, the invention relates to Clone RY-26568 LC AA sequence (SEQ ID NO: 361):

DIQLTQSPSS VSASVGDRVT ITCRASRGIS SWLAWYQQKP

GKAPKLLIYG ASSLQSGVPS RFSGSGSGTD FTLTISSLQP

EDFATYYCQQ IYTFPFTFGG GTKVEIKR.

In further embodiments, the invention relates to LC CDR1 AA sequence thereof: RASRGISSWLA (SEQ ID NO: 362). In further embodiments, the invention relates to LC CDR2 AA sequence thereof: GAS SLQS (SEQ ID NO: 363). In further embodiments, the invention relates to LC CDR3 AA sequence thereof: QQIYTFPFT (SEQ ID NO: 364) (LC CDR3).

In further embodiments, the invention relates to Clone RY-26568 CAR DNA HxL (SEQ ID NO: 365):

ATGGCACTCCCCGTAACTGCTCTGCTGCTGCCGTTGGCATTGCTCCTGCA

CGCCGCACGCCCGCAGGTGCAGCTGGTGGAGTCTGGGGGAGGCGTGGTCC

AGCCTGGGAGGTCCCTGAGACTCTCCTGTGCAGCGTCTGGATTCACCTTC

GGGAGCTATGGCATGCACTGGGTCCGCCAGGCTCCAGGCAAGGGGCTGGA

GTGGGTGGCAGTTATACATTATGATGGAAGTGTTGAATACTATGCAGACT

CCGTGAAGGGCCGATTCACCATCTCCAGAGACAATTCCAAGGACACGCTG

TATCTGCAAATGAACAGCCTGAGAGCCGAGGACACGGCGGTGTACTACTG

CGCCAGAACTGACTTCTGGAGCGGATCCCCTCCAAGCTTAGATTACTGGG

GACAGGGTACATTGGTCACCGTCTCCTCAGGGTCTACATCCGGCTCCGGG

AAGCCCGGAAGTGGCGAAGGTAGTACAAAGGGGGACATCCAGTTGACCCA

GTCTCCATCTTCCGTGTCTGCATCTGTAGGAGACAGAGTCACCATCACTT

GTCGGGCGAGTCGGGGTATTAGCAGCTGGTTAGCCTGGTATCAGCAGAAA

CCAGGGAAAGCCCCTAAGCTCCTGATCTATGGTGCATCCAGTTTGCAAAG

TGGGGTCCCATCAAGGTTCAGCGGCAGTGGATCTGGGACAGATTTCACTC

TCACCATCAGCAGCCTGCAGCCTGAAGATTTTGCAACTTATTACTGTCAG

CAGATATACACCTTCCCTTTCACTTTTGGCGGAGGGACCAAGGTTGAGAT

CAAACGGGCCGCTGCCCTTGATAATGAAAAGTCAAACGGAACAATCATTC

ACGTGAAGGGCAAGCACCTCTGTCCGTCACCCTTGTTCCCTGGTCCATCC

AAGCCATTCTGGGTGTTGGTCGTAGTGGGTGGAGTCCTCGCTTGTTACTC

TCTGCTCGTCACCGTGGCTTTTATAATCTTCTGGGTTAGATCCAAAAGAA

GCCGCCTGCTCCATAGCGATTACATGAATATGACTCCACGCCGCCCTGGC

CCCACAAGGAAACACTACCAGCCTTACGCACCACCTAGAGATTTCGCTGC

CTATCGGAGCAGGGTGAAGTTTTCCAGATCTGCAGATGCACCAGCGTATC

AGCAGGGCCAGAACCAACTGTATAACGAGCTCAACCTGGGACGCAGGGAA

GAGTATGACGTTTTGGACAAGCGCAGAGGACGGGACCCTGAGATGGGTGG

-continued

CAAACCAAGACGAAAAAACCCCCAGGAGGGTCTCTATAATGAGCTGCAGA

AGGATAAGATGGCTGAAGCCTATTCTGAAATAGGCATGAAAGGAGAGCGG

AGAAGGGGAAAAGGGCACGACGGTTTGTACCAGGGACTCAGCACTGCTAC

GAAGGATACTTATGACGCTCTCCACATGCAAGCCCTGCCACCTAGG

In further embodiments, the invention relates to Clone RY-26568 CAR HxL AA sequence (SEQ ID NO: 366):

MALPVTALLL PLALLLHAAR PQVQLVESGG GVVQPGRSLR

LSCAASGFTF GSYGMHWVRQ APGKGLEWVA VIHYDGSVEY

YADSVKGRFT ISRDNSKDTL YLQMNSLRAE DTAVYYCART

DFWSGSPPSL DYWGQGTLVT VSSGSTSGSG KPGSGEGSTK

GDIQLTQSPS SVSASVGDRV TITCRASRGI SSWLAWYQQK

PGKAPKLLIY GASSLQSGVP SRFSGSGSGT DFTLTISSLQ

PEDFATYYCQ QIYTFPFTFG GGTKVEIKRA AALDNEKSNG

TIIHVKGKHL CPSPLFPGPS KPFWVLVVVG GVLACYSLLV

TVAFIIFWVR SKRSRLLHSD YMNMTPRRPG PTRKHYQPYA

PPRDFAAYRS RVKFSRSADA PAYQQGQNQL YNELNLGRRE

EYDVLDKRRG RDPEMGGKPR RKNPQEGLYN ELQKDKMAEA

YSEIGMKGER RRGKGHDGLY QGLSTATKDT YDALHMQALP

PR

In further embodiments, the invention relates to Clone RY-26568 CAR DNA LxH (SEQ ID NO: 367):

ATGGCACTCCCCGTAACTGCTCTGCTGCTGCCGTTGGCATTGCTCCTGCA

CGCCGCACGCCCGGACATCCAGTTGACCCAGTCTCCATCTTCCGTGTCTG

CATCTGTAGGAGACAGAGTCACCATCACTTGTCGGGCGAGTCGGGGTATT

AGCAGCTGGTTAGCCTGGTATCAGCAGAAACCAGGGAAAGCCCCTAAGCT

CCTGATCTATGGTGCATCCAGTTTGCAAAGTGGGGTCCCATCAAGGTTCA

GCGGCAGTGGATCTGGGACAGATTTCACTCTCACCATCAGCAGCCTGCAG

CCTGAAGATTTTGCAACTTATTACTGTCAGCAGATATACACCTTCCCTTT

CACTTTTGGCGGAGGGACCAAGGTTGAGATCAAACGGGGGTCTACATCCG

GCTCCGGGAAGCCCGGAAGTGGCGAAGGTAGTACAAAGGGGCAGGTGCAG

CTGGTGGAGTCTGGGGGAGGCGTGGTCCAGCCTGGGAGGTCCCTGAGACT

CTCCTGTGCAGCGTCTGGATTCACCTTCGGGAGCTATGGCATGCACTGGG

TCCGCCAGGCTCCAGGCAAGGGGCTGGAGTGGGTGGCAGTTATACATTAT

GATGGAAGTGTTGAATACTATGCAGACTCCGTGAAGGGCCGATTCACCAT

CTCCAGAGACAATTCCAAGGACACGCTGTATCTGCAAATGAACAGCCTGA

GAGCCGAGGACACGGCGGTGTACTACTGCGCCAGAACTGACTTCTGGAGC

GGATCCCCTCCAAGCTTAGATTACTGGGGACAGGGTACATTGGTCACCGT

CTCCTCAGCCGCTGCCCTTGATAATGAAAAGTCAAACGGAACAATCATTC

ACGTGAAGGGCAAGCACCTCTGTCCGTCACCCTTGTTCCCTGGTCCATCC

-continued

```
AAGCCATTCTGGGTGTTGGTCGTAGTGGGTGGAGTCCTCGCTTGTTACTC
TCTGCTCGTCACCGTGGCTTTTATAATCTTCTGGGTTAGATCCAAAAGAA
GCCGCCTGCTCCATAGCGATTACATGAATATGACTCCACGCCGCCCTGGC
CCCACAAGGAAACACTACCAGCCTTACGCACCACCTAGAGATTTCGCTGC
CTATCGGAGCAGGGTGAAGTTTTCCAGATCTGCAGATGCACCAGCGTATC
AGCAGGGCCAGAACCAACTGTATAACGAGCTCAACCTGGGACGCAGGGAA
GAGTATGACGTTTTGGACAAGCGCAGAGGACGGGACCCTGAGATGGGTGG
CAAACCAAGACGAAAAAACCCCCAGGAGGGTCTCTATAATGAGCTGCAGA
AGGATAAGATGGCTGAAGCCTATTCTGAAATAGGCATGAAAGGAGAGCGG
AGAAGGGGAAAAGGGCACGACGGTTTGTACCAGGGACTCAGCACTGCTAC
GAAGGATACTTATGACGCTCTCCACATGCAAGCCCTGCCACCTAGG
```

In further embodiments, the invention relates to Clone RY-26568 CAR LxH AA sequence (SEQ ID NO: 368):

```
MALPVTALLL PLALLLHAAR PDIQLTQSPS SVSASVGDRV
TITCRASRGI SSWLAWYQQK PGKAPKLLIY GASSLQSGVP
SRFSGSGSGT DFTLTISSLQ PEDFATYYCQ QIYTFPFTFG
GGTKVEIKRG STSGSGKPGS GEGSTKGQVQ LVESGGGVVQ
PGRSLRLSCA ASGFTFGSYG MHWVRQAPGK GLEWVAVIHY
DGSVEYYADS VKGRFTISRD NSKDTLYLQM NSLRAEDTAV
YYCARTDFWS GSPPSLDYWG QGTLVTVSSA AALDNEKSNG
TIIHVKGKHL CPSPLFPGPS KPFWVLVVVG GVLACYSLLV
TVAFIIFWVR SKRSRLLHSD YMNMTPRRPG PTRKHYQPYA
PPRDFAAYRS RVKFSRSADA PAYQQGQNQL YNELNLGRRE
EYDVLDKRRG RDPEMGGKPR RKNPQEGLYN ELQKDKMAEA
YSEIGMKGER RRGKGHDGLY QGLSTATKDT YDALHMQALP
PR
```

In further embodiments, the invention relates to Clone PP-26575 HC DNA (SEQ ID NO: 369):

```
CAGGTGCAGCTGGTGCAGTCTGGGGCTGAGGTGAAGAAGCCTGGGTCCTC
GGTGAAGGTCTCCTGCAAGGCTTCTGGAGGCACCCTCAGCAGCCTGGCTA
TCAGCTGGGTGCGACAGGCCCCTGGACAAGGGCTTGAGTGGATGGGAGGG
GTCATCCCTATCTTGGGTCGGGCAAACTACGCACAGAAGTTCCAGGGCAG
AGTCACGATTACCGCGGACGAGTCCACGAGCACAGCCTACATGGAGCTGA
GCAGCCTGAGATCTGAGGACACGGCGGTGTACTACTGCGCCAGAACTCCT
GAATACTCCTCCAGCATATGGCACTATTACTACGGCATGGACGTATGGGG
CCAGGGAACAACTGTCACCGTCTCCTCA
```

In further embodiments, the invention relates to Clone PP-26575 HC AA sequence (SEQ ID NO: 370):

```
QVQLVQSGAE VKKPGSSVKV SCKASGGTLS SLAISWVRQA
PGQGLEWMGG VIPILGRANY AQKFQGRVTI TADESTSTAY
```

-continued

```
MELSSLRSED TAVYYCARTP EYSSSIWHYY YGMDVWGQGT
TVTVSS.
```

In further embodiments, the invention relates to HC CDR1 AA sequence thereof: GTLSSLAIS (SEQ ID NO: 371). In further embodiments, the invention relates to HC CDR2 AA sequence thereof: GVIPILGRANYAQKFQG (SEQ ID NO: 372). In further embodiments, the invention relates to HC CDR3 thereof: ARTPEYSSSIWHYYYG-MDV (SEQ ID NO: 373).

In further embodiments, the invention relates to Clone PP-26575 LC DNA (SEQ ID NO: 374):

```
GACATCGTGATGACCCAGTCTCCAGACTCCCTGGCTGTGTCTCTGGGCGA
GAGGGCCACCATCAACTGCAAGTCCAGCCAGAGTGTTTTATACAGCTCCA
ACAATAAGAACTACTTAGCTTGGTACCAGCAGAAACCAGGACAGCCTCCT
AAGCTGCTCATTTACTGGGCATCTACCCGGGAATCCGGGGTCCCTGACCG
ATTCAGTGGCAGCGGGTCTGGGACAGATTTCACTCTCACCATCAGCAGCC
TGCAGGCTGAAGATGTGGCAGTTTATTACTGTCAGCAGTTCGCCCACACT
CCTTTCACTTTTGGCGGAGGGACCAAGGTTGAGATCAAACGG
```

In further embodiments, the invention relates to Clone PP-26575 LC AA sequence (SEQ ID NO: 375):

```
DIVMTQSPDS LAVSLGERAT INCKSSQSVL YSSNNKNYLA
WYQQKPGQPP KLLIYWASTR ESGVPDRFSG SGSGTDFTLT
ISSLQAEDVA VYYCQQFAHT PFTFGGGTKV EIKR.
```

In further embodiments, the invention relates to LC CDR 1 AA sequence thereof: KSSQSVLYSSNNKNYLA (SEQ ID NO: 376). In further embodiments, the invention relates to LC CDR2 AA sequence thereof: WASTRES (SEQ ID NO: 377). In further embodiments, the invention relates to LC CDR3 AA sequence thereof: QQFAHTPFT (SEQ ID NO: 378).

In further embodiments, the invention relates to Clone PP-26575 CAR DNA HxL (SEQ ID NO: 379):

```
ATGGCACTCCCCGTAACTGCTCTGCTGCTGCCGTTGGCATTGCTCCTGCA
CGCCGCACGCCCGCAGGTGCAGCTGGTGCAGTCTGGGGCTGAGGTGAAGA
AGCCTGGGTCCTCGGTGAAGGTCTCCTGCAAGGCTTCTGGAGGCACCCTC
AGCAGCCTGGCTATCAGCTGGGTGCGACAGGCCCCTGGACAAGGGCTTGA
GTGGATGGGAGGGGTCATCCCTATCTTGGGTCGGGCAAACTACGCACAGA
AGTTCCAGGGCAGAGTCACGATTACCGCGGACGAGTCCACGAGCACAGCC
TACATGGAGCTGAGCAGCCTGAGATCTGAGGACACGGCGGTGTACTACTG
CGCCAGAACTCCTGAATACTCCTCCAGCATATGGCACTATTACTACGGCA
TGGACGTATGGGGCCAGGGAACAACTGTCACCGTCTCCTCAGGGTCTACA
TCCGGCTCCGGGAAGCCCGGAAGTGGCGAAGGTAGTACAAAGGGGGACAT
CGTGATGACCCAGTCTCCAGACTCCCTGGCTGTGTCTCTGGGCGAGAGGG
CCACCATCAACTGCAAGTCCAGCCAGAGTGTTTTATACAGCTCCAACAAT
```

-continued

```
AAGAACTACTTAGCTTGGTACCAGCAGAAACCAGGACAGCCTCCTAAGCT
GCTCATTTACTGGGCATCTACCCGGGAATCCGGGGTCCCTGACCGATTCA
GTGGCAGCGGGTCTGGGACAGATTTCACTCTCACCATCAGCAGCCTGCAG
GCTGAAGATGTGGCAGTTTATTACTGTCAGCAGTTCGCCCACACTCCTTT
CACTTTTGGCGGAGGGACCAAGGTTGAGATCAAACGGGCCGCTGCCCTTG
ATAATGAAAAGTCAAACGGAACAATCATTCACGTGAAGGGCAAGCACCTC
TGTCCGTCACCCTTGTTCCCTGGTCCATCCAAGCCATTCTGGGTGTTGGT
CGTAGTGGGTGGAGTCCTCGCTTGTTACTCTCTGCTCGTCACCGTGGCTT
TTATAATCTTCTGGGTTAGATCCAAAAGAAGCCGCCTGCTCCATAGCGAT
TACATGAATATGACTCCACGCCGCCCTGGCCCCACAAGGAAACACTACCA
GCCTTACGCACCACCTAGAGATTTCGCTGCCTATCGGAGCAGGGTGAAGT
TTTCCAGATCTGCAGATGCACCAGCGTATCAGCAGGGCCAGAACCAACTG
TATAACGAGCTCAACCTGGGACGCAGGGAAGAGTATGACGTTTTGGACAA
GCGCAGAGGACGGGACCCTGAGATGGGTGGCAAACCAAGACGAAAAAACC
CCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGA
CGGTTTGTACCAGGGACTCAGCACTGCTACGAAGGATACTTATGACGCTC
TCCACATGCAAGCCCTGCCACCTAGG
```

In further embodiments, the invention relates to Clone PP-26575 CAR HxL AA sequence (SEQ ID NO: 380):

```
MALPVTALLL PLALLLHAAR PQVQLVQSGA EVKKPGSSVK
VSCKASGGTL SSLAISWVRQ APGQGLEWMG GVIPILGRAN
YAQKFQGRVT ITADESTSTA YMELSSLRSE DTAVYYCART
PEYSSSIWHY YYGMDVWGQG TTVTVSSGST SGSGKPGSGE
GSTKGDIVMT QSPDSLAVSL GERATINCKS SQSVLYSSNN
KNYLAWYQQK PGQPPKLLIY WASTRESGVP DRFSGSGSGT
DFTLTISSLQ AEDVAVYYCQ QFAHTPFTFG GGTKVEIKRA
AALDNEKSNG TIIHVKGKHL CPSPLFPGPS KPFWVLVVVG
GVLACYSLLV TVAFIIFWVR SKRSRLLHSD YMNMTPRRPG
PTRKHYQPYA PPRDFAAYRS RVKFSRSADA PAYQQGQNQL
YNELNLGRRE EYDVLDKRRG RDPEMGGKPR RKNPQEGLYN
ELQKDKMAEA YSEIGMKGER RRGKGHDGLY QGLSTATKDT
YDALHMQALP PR
```

In further embodiments, the invention relates to Clone PP-26575 CAR DNA LxH (SEQ ID NO: 381):

```
ATGGCACTCCCCGTAACTGCTCTGCTGCTGCCGTTGGCATTGCTCCTGCA
CGCCGCACGCCCGGACATCGTGATGACCCAGTCTCCAGACTCCCTGGCTG
TGTCTCTGGGCGAGAGGGCCACCATCAACTGCAAGTCCAGCCAGAGTGTT
TTATACAGCTCCAACAATAAGAACTACTTAGCTTGGTACCAGCAGAAACC
AGGACAGCCTCCTAAGCTGCTCATTTACTGGGCATCTACCCGGGAATCCG
```

-continued

```
GGGTCCCTGACCGATTCAGTGGCAGCGGGTCTGGGACAGATTTCACTCTC
ACCATCAGCAGCCTGCAGGCTGAAGATGTGGCAGTTTATTACTGTCAGCA
GTTCGCCCACACTCCTTTCACTTTTGGCGGAGGGACCAAGGTTGAGATCA
AACGGGGGTCTACATCCGGCTCCGGGAAGCCCGGAAGTGGCGAAGGTAGT
ACAAAGGGGCAGGTGCAGCTGGTGCAGTCTGGGGCTGAGGTGAAGAAGCC
TGGGTCCTCGGTGAAGGTCTCCTGCAAGGCTTCTGGAGGCACCCTCAGCA
GCCTGGCTATCAGCTGGGTGCGACAGGCCCCTGGACAAGGGCTTGAGTGG
ATGGGAGGGGTCATCCCTATCTTGGGTCGGGCAAACTACGCACAGAAGTT
CCAGGGCAGAGTCACGATTACCGCGGACGAGTCCACGAGCACAGCCTACA
TGGAGCTGAGCAGCCTGAGATCTGAGGACACGGCGGTGTACTACTGCGCC
AGAACTCCTGAATACTCCTCCAGCATATGGCACTATTACTACGGCATGGA
CGTATGGGGCCAGGGAACAACTGTCACCGTCTCCTCAGCCGCTGCCCTTG
ATAATGAAAAGTCAAACGGAACAATCATTCACGTGAAGGGCAAGCACCTC
TGTCCGTCACCCTTGTTCCCTGGTCCATCCAAGCCATTCTGGGTGTTGGT
CGTAGTGGGTGGAGTCCTCGCTTGTTACTCTCTGCTCGTCACCGTGGCTT
TTATAATCTTCTGGGTTAGATCCAAAAGAAGCCGCCTGCTCCATAGCGAT
TACATGAATATGACTCCACGCCGCCCTGGCCCCACAAGGAAACACTACCA
GCCTTACGCACCACCTAGAGATTTCGCTGCCTATCGGAGCAGGGTGAAGT
TTTCCAGATCTGCAGATGCACCAGCGTATCAGCAGGGCCAGAACCAACTG
TATAACGAGCTCAACCTGGGACGCAGGGAAGAGTATGACGTTTTGGACAA
GCGCAGAGGACGGGACCCTGAGATGGGTGGCAAACCAAGACGAAAAAACC
CCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGA
CGGTTTGTACCAGGGACTCAGCACTGCTACGAAGGATACTTATGACGCTC
TCCACATGCAAGCCCTGCCACCTAGG
```

In further embodiments, the invention relates to Clone PP-26575 CAR LxH AA sequence (SEQ ID NO: 382):

```
MALPVTALLL PLALLLHAAR PDIVMTQSPD SLAVSLGERA
TINCKSSQSV LYSSNNKNYL AWYQQKPGQP PKLLIYWAST
RESGVPDRFS GSGSGTDFTL TISSLQAEDV AVYYCQQFAH
TPFTFGGGTK VEIKRGSTSG SGKPGSGEGS TKGQVQLVQS
GAEVKKPGSS VKVSCKASGG TLSSLAISWV RQAPGQGLEW
MGGVIPILGR ANYAQKFQGR VTITADESTS TAYMELSSLR
SEDTAVYYCA RTPEYSSSIW HYYYGMDVWG QGTTVTVSSA
AALDNEKSNG TIIHVKGKHL CPSPLFPGPS KPFWVLVVVG
GVLACYSLLV TVAFIIFWVR SKRSRLLHSD YMNMTPRRPG
PTRKHYQPYA PPRDFAAYRS RVKFSRSADA PAYQQGQNQL
YNELNLGRRE EYDVLDKRRG RDPEMGGKPR RKNPQEGLYN
ELQKDKMAEA YSEIGMKGER RRGKGHDGLY QGLSTATKDT
YDALHMQALP PR
```

In further embodiments, the invention relates to Clone RD-26576 HC DNA (SEQ ID NO: 383):

CAGGTGCGGCTGGTGGAGTCTGGGGGGGGCGTGGTCCAGCCTGGGAGGTC
CCTGAGACTCTCCTGTGCAGCGTCTGGATTCACCTTCAGTAGCTATGGCA
TACACTGGGTCCGCCAGGCTCCAGGCAAGGGGCTGGAGTGGGTGGCAGTT
ATAGGGTATGATGGACAGGAGAAATACTATGCAGACTCCGTGAAGGGCCG
ATTCACCATCTCCAGAGACAATTCCAAGAACACGCTGTATCTGCAAATGA
ACAGCCTGAGAGCCGAGGACACGGCGGTGTACTACTGCGTCAAGGGGCCG
TTGCAGGAGCCGCCATACGCTTTTGGGATGGACGTATGGGGCCAGGGAAC
AACTGTCACCGTCTCCTCA

In further embodiments, the invention relates to Clone RD-26576 HC AA sequence (SEQ ID NO: 384):

QVRLVESGGG VVQPGRSLRL SCAASGFTFS SYGIHWVRQA
PGKGLEWVAV IGYDGQEKYY ADSVKGRFTI SRDNSKNTLY
LQMNSLRAED TAVYYCVKGP LQEPPYAFGM DVWGQGTTVT
VSS.

In further embodiments, the invention relates to HC CDR1 AA sequence thereof: FTFSSYGIH (SEQ ID NO: 385). In further embodiments, the invention relates to HC CDR2 AA sequence thereof: VIGYDGQEKYYADSVKG (SEQ ID NO: 386). In further embodiments, the invention relates to the HC CDR3 AA sequence thereof: VKGPLQEPPYAFGMDV (SEQ ID NO: 387).

In further embodiments, the invention relates to Clone RD-26576 LC DNA (SEQ ID NO: 388):

GAAATAGTGATGACGCAGTCTCCAGCCACCCTGTCTGTGTCTCCAGGGGA
AAGAGCCACCCTCTCCTGCAGGGCCAGTCAGAGTGTTAGCAGCAACTTAG
CCTGGTACCAGCAGAAACCTGGCCAGGCTCCCAGGCTCCTCATCTATAGC
GCATCCACCAGGGCCACTGGTATCCCAGCCAGGTTCAGTGGCAGTGGGTC
TGGGACAGAGTTCACTCTCACCATCAGCAGCCTGCAGTCTGAAGATTTTG
CAGTTTATTACTGTCAGCAGCACCACGTCTGGCCTCTCACTTTTGGCGGA
GGGACCAAGGTTGAGATCAAACGG

In further embodiments, the invention relates to Clone RD-26576 LC AA sequence (SEQ ID NO: 389):

EIVMTQSPAT LSVSPGERAT LSCRASQSVS SNLAWYQQKP
GQAPRLLIYS ASTRATGIPA RFSGSGSGTE FTLTISSLQS
EDFAVYYCQQ HHVWPLTFGG GTKVEIKR.

In further embodiments, the invention relates to LC CDR1 AA sequence thereof: RASQSVSSNLA (SEQ ID NO: 390). In further embodiments, the invention relates to LC CDR2 AA sequence thereof: SASTRAT (SEQ ID NO: 391). In further embodiments, the invention relates to LC CDR3 AA sequence thereof: QQHHVWPLT (SEQ ID NO: 392).

In further embodiments, the invention relates to Clone RD-26576 CAR DNA HxL (SEQ ID NO: 393):

ATGGCACTCCCCGTAACTGCTCTGCTGCTGCCGTTGGCATTGCTCCTGCA
CGCCGCACGCCCGCAGGTGCGGCTGGTGGAGTCTGGGGGGGGCGTGGTC
CAGCCTGGGAGGTCCCTGAGACTCTCCTGTGCAGCGTCTGGATTCACCTT
CAGTAGCTATGGCATACACTGGGTCCGCCAGGCTCCAGGCAAGGGGCTG
GAGTGGGTGGCAGTTATAGGGTATGATGGACAGGAGAAATACTATGCAG
ACTCCGTGAAGGGCCGATTCACCATCTCCAGAGACAATTCCAAGAACAC
GCTGTATCTGCAAATGAACAGCCTGAGAGCCGAGGACACGGCGGTGTAC
TACTGCGTCAAGGGGCCGTTGCAGGAGCCGCCATACGCTTTTGGGATGG
ACGTATGGGGCCAGGGAACAACTGTCACCGTCTCCTCAGGGTCTACATC
CGGCTCCGGGAAGCCCGGAAGTGGCGAAGGTAGTACAAAGGGGGAAAT
AGTGATGACGCAGTCTCCAGCCACCCTGTCTGTGTCTCCAGGGGAAAGA
GCCACCCTCTCCTGCAGGGCCAGTCAGAGTGTTAGCAGCAACTTAGCCT
GGTACCAGCAGAAACCTGGCCAGGCTCCCAGGCTCCTCATCTATAGCGC
ATCCACCAGGGCCACTGGTATCCCAGCCAGGTTCAGTGGCAGTGGGTCT
GGGACAGAGTTCACTCTCACCATCAGCAGCCTGCAGTCTGAAGATTTTGC
AGTTTATTACTGTCAGCAGCACCACGTCTGGCCTCTCACTTTTGGCGGAG
GGACCAAGGTTGAGATCAAACGGGCCGCTGCCCTTGATAATGAAAAGTC
AAACGGAACAATCATTCACGTGAAGGGCAAGCACCTCTGTCCGTCACCC
TTGTTCCCTGGTCCATCCAAGCCATTCTGGGTGTTGGTCGTAGTGGGTGG
AGTCCTCGCTTGTTACTCTCTGCTCGTCACCGTGGCTTTTATAATCTTCT
GGGTTAGATCCAAAAGAAGCCGCCTGCTCCATAGCGATTACATGAATATG
ACTCCACGCCGCCCTGGCCCCACAAGGAAACACTACCAGCCTTACGCAC
CACCTAGAGATTTCGCTGCCTATCGGAGCAGGGTGAAGTTTTCCAGATCT
GCAGATGCACCAGCGTATCAGCAGGGCCAGAACCAACTGTATAACGAGC
TCAACCTGGGACGCAGGGAAGAGTATGACGTTTTGGACAAGCGCAGAGG
ACGGGACCCTGAGATGGGTGGCAAACCAAGACGAAAAAACCCCCAGGA
GGGTCTCTATAATGAGCTGCAGAAGGATAAGATGGCTGAAGCCTATTCT
GAAATAGGCATGAAAGGAGAGCGGAGAAGGGGAAAAGGGCACGACGG
TTTGTACCAGGGACTCAGCACTGCTACGAAGGATACTTATGACGCTCTCC
ACATGCAAGCCCTGCCACCTAGG

In further embodiments, the invention relates to Clone RD-26576 CAR HxL AA sequence (SEQ ID NO: 394);

MALPVTALLL PLALLLHAAR PQVRLVESGG GVVQPGRSLR
LSCAASGFTF SSYGIHWVRQ APGKGLEWVA VIGYDGQEKY
YADSVKGRFT ISRDNSKNTL YLQMNSLRAE DTAVYYCVKG
PLQEPPYAFG MDVWGQGTTV TVSSGSTSGS GKPGSGEGST
KGEIVMTQSP ATLSVSPGER ATLSCRASQS VSSNLAWYQQ
KPGQAPRLLI YSASTRATGI PARFSGSGSG TEFTLTISSL
QSEDFAVYYC QQHHVWPLTF GGGTKVEIKR AAALDNEKSN
GTIIHVKGKH LCPSPLFPGP SKPFWVLVVV GGVLACYSLL

-continued

VTVAFIIFWV RSKRSRLLHS DYMNMTPRRP GPTRKHYQPY

APPRDFAAYR SRVKFSRSAD APAYQQGQNQ LYNELNLGRR

EEYDVLDKRR GRDPEMGGKP RRKNPQEGLY NELQKDKMAE

AYSEIGMKGE RRRGKGHDGL YQGLSTATKD TYDALHMQAL PPR.

In further embodiments, the invention relates to Clone RD-26576 CAR DNA LxH (SEQ ID NO: 395):

ATGGCACTCCCCGTAACTGCTCTGCTGCTGCCGTTGGCATTGCTCCTGCA

CGCCGCACGCCCGGAAATAGTGATGACGCAGTCTCCAGCCACCCTGTCT

GTGTCTCCAGGGGAAAGAGCCACCCTCTCCTGCAGGGCCAGTCAGAGTG

TTAGCAGCAACTTAGCCTGGTACCAGCAGAAACCTGGCCAGGCTCCCAG

GCTCCTCATCTATAGCGCATCCACCAGGGCCACTGGTATCCCAGCCAGGT

TCAGTGGCAGTGGGTCTGGGACAGAGTTCACTCTCACCATCAGCAGCCT

GCAGTCTGAAGATTTTGCAGTTTATTACTGTCAGCAGCACCACGTCTGGC

CTCTCACTTTTGGCGGAGGGACCAAGGTTGAGATCAAACGGGGGTCTAC

ATCCGGCTCCGGGAAGCCCGGAAGTGGCGAAGGTAGTACAAAGGGGCA

GGTGCGGCTGGTGGAGTCTGGGGGGGGCGTGGTCCAGCCTGGGAGGTCC

CTGAGACTCTCCTGTGCAGCGTCTGGATTCACCTTCAGTAGCTATGGCAT

ACACTGGGTCCGCCAGGCTCCAGGCAAGGGGCTGGAGTGGGTGGCAGTT

ATAGGGTATGATGGACAGGAGAAATACTATGCAGACTCCGTGAAGGGCC

GATTCACCATCTCCAGAGACAATTCCAAGAACACGCTGTATCTGCAAAT

GAACAGCCTGAGAGCCGAGGACACGGCGGTGTACTACTGCGTCAAGGG

GCCGTTGCAGGAGCCGCCATACGCTTTTGGGATGGACGTATGGGGCCAG

GGAACAACTGTCACCGTCTCCTCAGCCGCTGCCCTTGATAATGAAAAGTC

AAACGGAACAATCATTCACGTGAAGGGCAAGCACCTCTGTCCGTCACCC

TTGTTCCCTGGTCCATCCAAGCCATTCTGGGTGTTGGTCGTAGTGGGTGG

AGTCCTCGCTTGTTACTCTCTGCTCGTCACCGTGGCTTTTATAATCTTCT

GGGTTAGATCCAAAAGAAGCCGCCTGCTCCATAGCGATTACATGAATATG

ACTCCACGCCGCCCTGGCCCCACAAGGAAACACTACCAGCCTTACGCAC

CACCTAGAGATTTCGCTGCCTATCGGAGCAGGGTGAAGTTTTCCAGATCT

GCAGATGCACCAGCGTATCAGCAGGGCCAGAACCAACTGTATAACGAGC

TCAACCTGGGACGCAGGGAAGAGTATGACGTTTTGGACAAGCGCAGAGG

ACGGGACCCTGAGATGGGTGGCAAACCAAGACGAAAAAACCCCCAGGA

GGGTCTCTATAATGAGCTGCAGAAGGATAAGATGGCTGAAGCCTATTCT

GAAATAGGCATGAAAGGAGAGCGGAGAAGGGGAAAAGGGCACGACGG

TTTGTACCAGGGACTCAGCACTGCTACGAAGGATACTTATGACGCTCTCC

ACATGCAAGCCCTGCCACCTAGG

In further embodiments, the invention relates to Clone RD-26576 CAR LxH AA sequence (SEQ ID NO: 396):

MALPVTALLL PLALLLHAAR PEIVMTQSPA TLSVSPGERA

TLSCRASQSV SSNLAWYQQK PGQAPRLLIY SASTRATGIP

-continued

ARFSGSGSGT EFTLTISSLQ SEDFAVYYCQ QHHVWPLTFG

GGTKVEIKRG STSGSGKPGS GEGSTKGQVR LVESGGGVVQ

PGRSLRLSCA ASGFTFSSYG IHWVRQAPGK GLEWVAVIGY

DGQEKYYADS VKGRFTISRD NSKNTLYLQM NSLRAEDTAV

YYCVKGPLQE PPYAFGMDVW GQGTTVTVSS AAALDNEKSN

GTIIHVKGKH LCPSPLFPGP SKPFWVLVVV GGVLACYSLL

VTVAFIIFWV RSKRSRLLHS DYMNMTPRRP GPTRKHYQPY

APPRDFAAYR SRVKFSRSAD APAYQQGQNQ LYNELNLGRR

EEYDVLDKRR GRDPEMGGKP RRKNPQEGLY NELQKDKMAE

AYSEIGMKGE RRRGKGHDGL YQGLSTATKD TYDALHMQAL PPR.

In further embodiments, the invention relates to Clone RD-26578 HC DNA (SEQ ID NO: 397):

CAGGTGCAGCTGGTGGAGTCTGGGGGAGGCGTGGTCCAGCCTGGGAGGT

CCCTGAGACTCTCCTGTGCAGCGTCTGGATTCACCTTCAGTAGCCGTGGC

ATGCACTGGGTCCGCCAGGCTCCAGGCAAGGGGCTGGAGTGGGTGGCAG

TTATAGGGTATGATGGACAGGAGAAATACTATGCAGACTCCGTGAAGGG

CCGATTCACCATCTCCAGAGACAATTCCAAGAACACGCTGTATCTGCAA

ATGAACAGCCTGAGAGCCGAGGACACGGCGGTGTACTACTGCGTCAAGG

GGCCGTTGCAGGAGCCGCCATACGATTATGGAATGGACGTATGGGGCCA

GGGAACAACTGTCACCGTCTCCTCA

In further embodiments, the invention relates to Clone RD-26578 HC AA sequence (SEQ ID NO: 398):

QVQLVESGGG VVQPGRSLRL SCAASGFTFS SRGMHWVRQA

PGKGLEWVAV IGYDGQEKYY ADSVKGRFTI SRDNSKNTLY

LQMNSLRAED TAVYYCVKGP LQEPPYDYGM DVWGQGTTVT VSS.

In further embodiments, the invention relates to HC CDR1 AA sequence thereof: FTFSSRGMH (SEQ ID NO: 399). In further embodiments, the invention relates to HC CDR2 AA sequence thereof: VIGYDGQEKYYADSVKG (SEQ ID NO: 400). In further embodiments, the invention relates to HC CDR3 thereof: VKGPLQEPPYDYGMDV (SEQ ID NO: 401).

In further embodiments, the invention relates to Clone RD-26578 LC DNA (SEQ ID NO: 402):

GAAATAGTGATGACGCAGTCTCCAGCCACCCTGTCTGTGTCTCCAGGGG

AAAGAGCCACCCTCTCCTGCAGGGCCAGTCAGAGTGTTAGCAGCAACTT

AGCCTGGTACCAGCAGAAACCTGGCCAGGCTCCCAGGCTCCTCATCTAT

AGCGCATCCACCAGGGCCACTGGTATCCCAGCCAGGTTCAGTGGCAGTG

GGTCTGGGACAGAGTTCACTCTCACCATCAGCAGCCTGCAGTCTGAAGA

TTTTGCAGTTTATTACTGTCAGCAGCACCACGTCTGGCCTCTCACTTTT

GGCGGAGGGACCAAGGTTGAGATCAAACGG

In further embodiments, the invention relates to Clone RD-26578 LC AA sequence (SEQ ID NO: 403):

EIVMTQSPAT LSVSPGERAT LSCRASQSVS SNLAWYQQKP
GQAPRLLIYS ASTRATGIPA RFSGSGSGTE FTLTISSLQS
EDFAVYYCQQ HHVWPLTFGG GTKVEIKR.

In further embodiments, the invention relates to LC CDR1 AA sequence: RASQSVSSNLA (SEQ ID NO: 404). In further embodiments, the invention relates to LC CDR2 AA sequence thereof: SASTRAT (SEQ ID NO: 405). In further embodiments, the invention relates to LC CDR3 AA sequence thereof: QQHHVWPLT (SEQ ID NO: 406).

In further embodiments, the invention relates to Clone RD-26578 CAR DNA HxL (SEQ ID NO: 407):

ATGGCACTCCCCGTAACTGCTCTGCTGCTGCCGTTGGCATTGCTCCTGCA
CGCCGCACGCCCGCAGGTGCAGCTGGTGGAGTCTGGGGGAGGCGTGGTC
CAGCCTGGGAGGTCCCTGAGACTCTCCTGTGCAGCGTCTGGATTCACCTT
CAGTAGCCGTGGCATGCACTGGGTCCGCCAGGCTCCAGGCAAGGGGCTG
GAGTGGGTGGCAGTTATAGGGTATGATGGACAGGAGAAATACTATGCAG
ACTCCGTGAAGGGCCGATTCACCATCTCCAGAGACAATTCCAAGAACAC
GCTGTATCTGCAAATGAACAGCCTGAGAGCCGAGGACACGGCGGTGTAC
TACTGCGTCAAGGGGCCGTTGCAGGAGCCGCCATACGATTATGGAATGG
ACGTATGGGGCCAGGGAACAACTGTCACCGTCTCCTCAGGGTCTACATC
CGGCTCCGGGAAGCCCGGAAGTGGCGAAGGTAGTACAAAGGGGGAAAT
AGTGATGACGCAGTCTCCAGCCACCCTGTCTGTGTCTCCAGGGGAAAGA
GCCACCCTCTCCTGCAGGGCCAGTCAGAGTGTTAGCAGCAACTTAGCCT
GGTACCAGCAGAAACCTGGCCAGGCTCCCAGGCTCCTCATCTATAGCGC
ATCCACCAGGGCCACTGGTATCCCAGCCAGGTTCAGTGGCAGTGGGTCT
GGGACAGAGTTCACTCTCACCATCAGCAGCCTGCAGTCTGAAGATTTTGC
AGTTTATTACTGTCAGCAGCACCACGTCTGGCCTCTCACTTTTGGCGGAG
GGACCAAGGTTGAGATCAAACGGGCCGCTGCCCTTGATAATGAAAAGTC
AAACGGAACAATCATTCACGTGAAGGGCAAGCACCTCTGTCCGTCACCC
TTGTTCCCTGGTCCATCCAAGCCATTCTGGGTGTTGGTCGTAGTGGGTGG
AGTCCTCGCTTGTTACTCTCTGCTCGTCACCGTGGCTTTTATAATCTTCT
GGGTTAGATCCAAAAGAAGCCGCCTGCTCCATAGCGATTACATGAATATG
ACTCCACGCCGCCCTGGCCCCACAAGGAAACACTACCAGCCTTACGCAC
CACCTAGAGATTTCGCTGCCTATCGGAGCAGGGTGAAGTTTTCCAGATCT
GCAGATGCACCAGCGTATCAGCAGGGCCAGAACCAACTGTATAACGAGC
TCAACCTGGGACGCAGGGAAGAGTATGACGTTTTGGACAAGCGCAGAGG
ACGGGACCCTGAGATGGGTGGCAAACCAAGACGAAAAAACCCCCAGGA
GGGTCTCTATAATGAGCTGCAGAAGGATAAGATGGCTGAAGCCTATTCT
GAAATAGGCATGAAAGGAGAGCGGAGAAGGGGAAAAGGGCACGACGG
TTTGTACCAGGGACTCAGCACTGCTACGAAGGATACTTATGACGCTCTCC
ACATGCAAGCCCTGCCACCTAGG

In further embodiments, the invention relates to Clone RD-26578 CAR HxL AA sequence (SEQ ID NO: 408):

MALPVTALLL PLALLLHAAR PQVQLVESGG GVVQPGRSLR
LSCAASGFTF SSRGMHWVRQ APGKGLEWVA VIGYDGQEKY
YADSVKGRFT ISRDNSKNTL YLQMNSLRAE DTAVYYCVKG
PLQEPPYDYG MDVWGQGTTV TVSSGSTSGS GKPGSGEGST
KGEIVMTQSP ATLSVSPGER ATLSCRASQS VSSNLAWYQQ
KPGQAPRLLI YSASTRATGI PARFSGSGSG TEFTLTISSL
QSEDFAVYYC QQHHVWPLTF GGGTKVEIKR AAALDNEKSN
GTIIHVKGKH LCPSPLFPGP SKPFWVLVVV GGVLACYSLL
VTVAFIIFWV RSKRSRLLHS DYMNMTPRRP GPTRKHYQPY
APPRDFAAYR SRVKFSRSAD APAYQQGQNQ LYNELNLGRR
EEYDVLDKRR GRDPEMGGKP RRKNPQEGLY NELQKDKMAE
AYSEIGMKGE RRRGKGHDGL YQGLSTATKD TYDALHMQAL
PPR

In further embodiments, the invention relates to Clone RD-26578 CAR DNA LxH (SEQ ID NO: 409):

ATGGCACTCCCCGTAACTGCTCTGCTGCTGCCGTTGGCATTGCTCCTGCA
CGCCGCACGCCCGGAAATAGTGATGACGCAGTCTCCAGCCACCCTGTCTG
TGTCTCCAGGGGAAAGAGCCACCCTCTCCTGCAGGGCCAGTCAGAGTGTT
AGCAGCAACTTAGCCTGGTACCAGCAGAAACCTGGCCAGGCTCCCAGGCT
CCTCATCTATAGCGCATCCACCAGGGCCACTGGTATCCCAGCCAGGTTCA
GTGGCAGTGGGTCTGGGACAGAGTTCACTCTCACCATCAGCAGCCTGCAG
TCTGAAGATTTTGCAGTTTATTACTGTCAGCAGCACCACGTCTGGCCTCT
CACTTTTGGCGGAGGGACCAAGGTTGAGATCAAACGGGGGTCTACATCCG
GCTCCGGGAAGCCCGGAAGTGGCGAAGGTAGTACAAAGGGGCAGGTGCAG
CTGGTGGAGTCTGGGGGAGGCGTGGTCCAGCCTGGGAGGTCCCTGAGACT
CTCCTGTGCAGCGTCTGGATTCACCTTCAGTAGCCGTGGCATGCACTGG
TCCGCCAGGCTCCAGGCAAGGGGCTGGAGTGGGTGGCAGTTATAGGGTAT
GATGGACAGGAGAAATACTATGCAGACTCCGTGAAGGGCCGATTCACCAT
CTCCAGAGACAATTCCAAGAACACGCTGTATCTGCAAATGAACAGCCTGA
GAGCCGAGGACACGGCGGTGTACTACTGCGTCAAGGGGCCGTTGCAGGAG
CCGCCATACGATTATGGAATGGACGTATGGGGCCAGGGAACAACTGTCAC
CGTCTCCTCAGCCGCTGCCCTTGATAATGAAAAGTCAAACGGAACAATCA
TTCACGTGAAGGGCAAGCACCTCTGTCCGTCACCCTTGTTCCCTGGTCCA
TCCAAGCCATTCTGGGTGTTGGTCGTAGTGGGTGGAGTCCTCGCTTGTTA
CTCTCTGCTCGTCACCGTGGCTTTTATAATCTTCTGGGTTAGATCCAAAA
GAAGCCGCCTGCTCCATAGCGATTACATGAATATGACTCCACGCCGCCCT
GGCCCCACAAGGAAACACTACCAGCCTTACGCACCACCTAGAGATTTCGC
TGCCTATCGGAGCAGGGTGAAGTTTTCCAGATCTGCAGATGCACCAGCGT
ATCAGCAGGGCCAGAACCAACTGTATAACGAGCTCAACCTGGGACGCAGG
GAAGAGTATGACGTTTTGGACAAGCGCAGAGGACGGGACCCTGAGATGGG

-continued

```
TGGCAAACCAAGACGAAAAAACCCCCAGGAGGGTCTCTATAATGAGCTGC
AGAAGGATAAGATGGCTGAAGCCTATTCTGAAATAGGCATGAAAGGAGAG
CGGAGAAGGGGAAAAGGGCACGACGGTTTGTACCAGGGACTCAGCACTGC
TACGAAGGATACTTATGACGCTCTCCACATGCAAGCCCTGCCACCTAGG
```

In further embodiments, the invention relates to Clone RD-26578 CAR LxH AA sequence (SEQ ID NO: 410):

```
MALPVTALLL PLALLLHAAR PEIVMTQSPA TLSVSPGERA
TLSCRASQSV SSNLAWYQQK PGQAPRLLIY SASTRATGIP
ARFSGSGSGT EFTLTISSLQ SEDFAVYYCQ QHHVWPLTFG
GGTKVEIKRG STSGSGKPGS GEGSTKGQVQ LVESGGGVVQ
PGRSLRLSCA ASGFTFSSRG MHWVRQAPGK GLEWVAVIGY
DGQEKYYADS VKGRFTISRD NSKNTLYLQM NSLRAEDTAV
YYCVKGPLQE PPYDYGMDVW GQGTTVTVSS AAALDNEKSN
GTIIHVKGKH LCPSPLFPGP SKPFWVLVVV GGVLACYSLL
VTVAFIIFWV RSKRSRLLHS DYMNMTPRRP GPTRKHYQPY
APPRDFAAYR SRVKFSRSAD APAYQQGQNQ LYNELNLGRR
EEYDVLDKRR GRDPEMGGKP RRKNPQEGLY NELQKDKMAE
AYSEIGMKGE RRRGKGHDGL YQGLSTATKD TYDALHMQAL
PPR.
```

It will be appreciated that the sequences recited herein can be useful by themselves, in combination with one or more sequences recited herein, and/or incorporated into cells (such as CAR or TCR-based T cells) for use in immune- or other therapies. It will be further appreciated that these sequences can be used in accordance with the invention incorporated in vectors for transduction, transfection, and the like, into cells.

It will be appreciated that adverse events may be minimized by transducing the immune cells (containing one or more CARs or TCRs) with a suicide gene. It may also be desired to incorporate an inducible "on" or "accelerator" switch into the immune cells. Suitable techniques include use of inducible caspase-9 (U.S. Appl. 2011/0286980) or a thymidine kinase, before, after or at the same time, as the cells are transduced with the CAR construct of the present invention. Additional methods for introducing suicide genes and/or "on" switches include TALENS, zinc fingers, RNAi, siRNA, shRNA, antisense technology, and other techniques known in the art.

In accordance with the invention, additional on-off or other types of control switch techniques may be incorporated herein. These techniques may employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO2014/127261, WO2015/090229, US2014/0286987, US2015/0266973, US2016/0046700, U.S. Pat. No. 8,486,693, US2014/0171649, and US2012/0130076, the contents of which are further incorporated by reference herein in their entirety.

IV. Vectors, Cells, and Pharmaceutical Compositions

In certain aspects, provided herein are vectors comprising a polynucleotide of the present invention. In some embodiments, the present invention is directed to a vector or a set of vectors comprising a polynucleotide encoding a CAR or a TCR, as described herein. In other embodiments, the present invention is directed to a vector or a set of vectors comprising a polynucleotide encoding an antibody or an antigen binding molecule thereof that specifically binds to BCMA, as disclosed herein.

Any vector known in the art can be suitable for the present invention. In some embodiments, the vector is a viral vector. In some embodiments, the vector is a retroviral vector (such as pMSVG1), a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector (such as pGAR), or any combination thereof.

The pGAR sequence is as follows:

```
CTGACGCGCCCTGTAGCGGCGCATTAAGCGCGGCGGGTGTGGTGGTTACG
CGCAGCGTGACCGCTACACTTGCCAGCGCCCTAGCGCCCGCTCCTTTCGC
TTTCTTCCCTTCCTTTCTCGCCACGTTCGCCGGCTTTCCCCGTCAAGCTC
TAAATCGGGGGCTCCCTTTAGGGTTCCGATTTAGTGCTTTACGGCACCTC
GACCCCAAAAAACTTGATTAGGGTGATGGTTCACGTAGTGGGCCATCGCC
CTGATAGACGGTTTTTCGCCCTTTGACGTTGGAGTCCACGTTCTTTAATA
GTGGACTCTTGTTCCAAACTGGAACAACACTCAACCCTATCTCGGTCTAT
TCTTTTGATTTATAAGGGATTTTGCCGATTTCGGCCTATTGGTTAAAAAA
TGAGCTGATTTAACAAAAATTTAACGCGAATTTTAACAAAATATTAACGC
TTACAATTTGCCATTCGCCATTCAGGCTGCGCAACTGTTGGGAAGGGCGA
TCGGTGCGGGCCTCTTCGCTATTACGCCAGCTGGCGAAAGGGGGATGTGC
TGCAAGGCGATTAAGTTGGGTAACGCCAGGGTTTTCCCAGTCACGACGTT
GTAAAACGACGGCCAGTGAATTGTAATACGACTCACTATAGGGCGACCCG
GGGATGGCGCGCCAGTAATCAATTACGGGGTCATTAGTTCATAGCCCATA
TATGGAGTTCCGCGTTACATAACTTACGGTAAATGGCCCGCCTGGCTGAC
CGCCCAACGACCCCCGCCCATTGACGTCAATAATGACGTATGTTCCCATA
GTAACGCCAATAGGGACTTTCCATTGACGTCAATGGGTGGAGTATTTACG
GTAAACTGCCCACTTGGCAGTACATCAAGTGTATCATATGCCAAGTACGC
CCCCTATTGACGTCAATGACGGTAAATGGCCCGCCTGGCATTATGCCCAG
TACATGACCTTATGGGACTTTCCTACTTGGCAGTACATCTACGTATTAGT
CATCGCTATTACCATGCTGATGCGGTTTTGGCAGTACATCAATGGGCGTG
GATAGCGGTTTGACTCACGGGGATTTCCAAGTCTCCACCCCATTGACGTC
```

-continued

AATGGGAGTTTGTTTTGGCACCAAAATCAACGGGACTTTCCAAAATGTCG
TAACAACTCCGCCCCATTGACGCAAATGGGCGGTAGGCGTGTACGGTGGG
AGGTCTATATAAGCAGAGCTGGTTTAGTGAACCGGGGTCTCTCTGGTTAG
ACCAGATCTGAGCCTGGGAGCTCTCTGGCTAACTAGGGAACCCACTGCTT
AAGCCTCAATAAAGCTTGCCTTGAGTGCTTCAAGTAGTGTGTGCCCGTCT
GTTGTGTGACTCTGGTAACTAGAGATCCCTCAGACCCTTTTAGTCAGTGT
GGAAAATCTCTAGCAGTGGCGCCCGAACAGGGACTTGAAAGCGAAAGGGA
AACCAGAGGAGCTCTCTCGACGCAGGACTCGGCTTGCTGAAGCGCGCACG
GCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGG
GGAGAATTAGATCGCGATGGGAAAAAATTCGGTTAAGGCCAGGGGGAAAG
AAAAAATATAAATTAAAACATATAGTATGGGCAAGCAGGGAGCTAGAACG
ATTCGCAGTTAATCCTGGCCTGTTAGAAACATCAGAAGGCTGTAGACAAA
TACTGGGACAGCTACAACCATCCCTTCAGACAGGATCAGAAGAACTTAGA
TCATTATATAATACAGTAGCAACCCTCTATTGTGTGCATCAAAGGATAGA
GATAAAAGACACCAAGGAAGCTTTAGACAAGATAGAGGAAGAGCAAAACA
AAAGTAAGACCACCGCACAGCAAGCCGCCGCTGATCTTCAGACCTGGAGG
AGGAGATATGAGGGACAATTGGAGAAGTGAATTATATAAATATAAAGTAG
TAAAAATTGAACCATTAGGAGTAGCACCCACCAAGGCAAAGAGAAGAGTG
GTGCAGAGAGAAAAAAGAGCAGTGGGAATAGGAGCTTTGTTCCTTGGGTT
CTTGGGAGCAGCAGGAAGCACTATGGGCGCAGCGTCAATGACGCTGACGG
TACAGGCCAGACAATTATTGTCTGGTATAGTGCAGCAGCAGAACAATTTG
CTGAGGGCTATTGAGGCGCAACAGCATCTGTTGCAACTCACAGTCTGGGG
CATCAAGCAGCTCCAGGCAAGAATCCTGGCTGTGGAAAGATACCTAAAGG
ATCAACAGCTCCTGGGGATTTGGGGTTGCTCTGGAAAACTCATTTGCACC
ACTGCTGTGCCTTGGAATGCTAGTTGGAGTAATAAATCTCTGGAACAGAT
TTGGAATCACACGACCTGGATGGAGTGGGACAGAGAAATTAACAATTACA
CAAGCTTAATACACTCCTTAATTGAAGAATCGCAAAACCAGCAAGAAAAG
AATGAACAAGAATTATTGGAATTAGATAAATGGGCAAGTTTGTGGAATTG
GTTTAACATAACAAATTGGCTGTGGTATATAAAATTATTCATAATGATAG
TAGGAGGCTTGGTAGGTTTAAGAATAGTTTTTGCTGTACTTTCTATAGTG
AATAGAGTTAGGCAGGGATATTCACCATTATCGTTTCAGACCCACCTCCC
AACCCCGAGGGGACCCGACAGGCCCGAAGGAATAGAAGAAGAAGGTGGAG
AGAGAGACAGAGACAGATCCATTCGATTAGTGAACGGATCTCGACGGTAT
CGGTTAACTTTTAAAAGAAAAGGGGGGATTGGGGGGTACAGTGCAGGGGA
AAGAATAGTAGACATAATAGCAACAGACATACAAACTAAAGAATTACAAA
AACAAATTACAAAATTCAAAATTTTATCGCGATCGCGGAATGAAAGACCC
CACCTGTAGGTTTGGCAAGCTAGCTTAAGTAACGCCATTTTGCAAGGCAT
GGAAAATACATAACTGAGAATAGAGAAGTTCAGATCAAGGTTAGGAACAG
AGAGACAGCAGAATATGGGCCAAACAGGATATCTGTGGTAAGCAGTTCCT

-continued

GCCCCGGCTCAGGGCCAAGAACAGATGGTCCCCAGATGCGGTCCCGCCCT
CAGCAGTTTCTAGAGAACCATCAGATGTTTCCAGGGTGCCCCAAGGACCT
GAAAATGACCCTGTGCCTTATTTGAACTAACCAATCAGTTCGCTTCTCGC
TTCTGTTCGCGCGCTTCTGCTCCCCGAGCTCAATAAAAGAGCCCACAACC
CCTCACTCGGCGCGCCAGTCCTTCGAAGTAGATCTTTGTCGATCCTACCA
TCCACTCGACACACCCGCCAGCGGCCGCTGCCAAGCTTCCGAGCTCTCGA
ATTAATTCACGGTACCCACCATGGCCTAGGGAGACTAGTCGAATCGATAT
CAACCTCTGGATTACAAAATTTGTGAAAGATTGACTGGTATTCTTAACTA
TGTTGCTCCTTTTACGCTATGTGGATACGCTGCTTTAATGCCTTTGTATC
ATGCTATTGCTTCCCGTATGGCTTTCATTTTCTCCTCCTTGTATAAATCC
TGGTTGCTGTCTCTTTATGAGGAGTTGTGGCCCGTTGTCAGGCAACGTGG
CGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATT
GCCACGGCGGAACTCATCGCCGCCTGCCTTGCCCGCTGCTGGACAGGGGC
TCGGCTGTTGGGCACTGACAATTCCGTGGTGTTGTCGGGGAAGCTGACGT
CCTTTTCATGGCTGCTCGCCTGTGTTGCCACCTGGATTCTGCGCGGGACG
TCCTTCTGCTACGTCCCTTCGGCCCTCAATCCAGCGGACCTTCCTTCCCG
CGGCCTGCTGCCGGCTCTGCGGCCTCTTCCGCGTCTTCGCCTTCGCCCTC
AGACGAGTCGGATCTCCCTTTGGGCCGCCTCCCCGCCTGGTTAATTAAAG
TACCTTTAAGACCAATGACTTACAAGGCAGCTGTAGATCTTAGCCACTTT
TTAAAAGAAAAGGGGGGACTGGAAGGGCGAATTCACTCCCAACGAAGACA
AGATCTGCTTTTTGCTTGTACTGGGTCTCTCTGGTTAGACCAGATCTGAG
CCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTC
TGGTAACTAGAGATCCCTCAGACCCTTTTAGTCAGTGTGGAAAATCTCTA
GCAGGCATGCCAGACATGATAAGATACATTGATGAGTTTGGACAAACCAC
AACTAGAATGCAGTGAAAAAAATGCTTTATTTGTGAAATTTGTGATGCTA
TTGCTTTATTTGTAACCATTATAAGCTGCAATAAACAAGTTAACAACAAC
AATTGCATTCATTTTATGTTTCAGGTTCAGGGGGAGGTGTGGGAGGTTTT
TTGGCGCGCCATCGTCGAGGTTCCCTTTAGTGAGGGTTAATTGCGAGCTT
GGCGTAATCATGGTCATAGCTGTTTCCTGTGTGAAATTGTTATCCGCTCA
CAATTCCACACAACATACGAGCCGGAAGCATAAAGTGTAAAGCCTGGGGT
GCCTAATGAGTGAGCTAACTCACATTAATTGCGTTGCGCTCACTGCCCGC
TTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTC
ACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAA
AGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAA
AAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACC

-continued

```
CTGCCGCTTACCGGATACCTGTCCGCCTTTCTCCCTTCGGGAAGCGTGGC

GCTTTCTCATAGCTCACGCTGTAGGTATCTCAGTTCGGTGTAGGTCGTTC

GCTCCAAGCTGGGCTGTGTGCACGAACCCCCCGTTCAGCCCGACCGCTGC

GCCTTATCCGGTAACTATCGTCTTGAGTCCAACCCGGTAAGACACGACTT

ATCGCCACTGGCAGCAGCCACTGGTAACAGGATTAGCAGAGCGAGGTATG

TAGGCGGTGCTACAGAGTTCTTGAAGTGGTGGCCTAACTACGGCTACACT

AGAAGAACAGTATTTGGTATCTGCGCTCTGCTGAAGCCAGTTACCTTCGG

AAAAAGAGTTGGTAGCTCTTGATCCGGCAAACAAACCACCGCTGGTAGCG

GTGGTTTTTTTGTTTGCAAGCAGCAGATTACGCGCAGAAAAAAAGGATCT

CAAGAAGATCCTTTGATCTTTTCTACGGGGTCTGACGCTCAGTGGAACGA

AAACTCACGTTAAGGGATTTTGGTCATGAGATTATCAAAAAGGATCTTCA

CCTAGATCCTTTTAAATTAAAAATGAAGTTTTAAATCAATCTAAAGTATA

TATGAGTAAACTTGGTCTGACAGTTACCAATGCTTAATCAGTGAGGCACC

TATCTCAGCGATCTGTCTATTTCGTTCATCCATAGTTGCCTGACTCCCCG

TCGTGTAGATAACTACGATACGGGAGGGCTTACCATCTGGCCCCAGTGCT

GCAATGATACCGCGAGACCCACGCTCACCGGCTCCAGATTTATCAGCAAT

AAACCAGCCAGCCGGAAGGGCCGAGCGCAGAAGTGGTCCTGCAACTTTAT

CCGCCTCCATCCAGTCTATTAATTGTTGCCGGGAAGCTAGAGTAAGTAGT

TCGCCAGTTAATAGTTTGCGCAACGTTGTTGCCATTGCTACAGGCATCGT

GGTGTCACGCTCGTCGTTTGGTATGGCTTCATTCAGCTCCGGTTCCCAAC

GATCAAGGCGAGTTACATGATCCCCCATGTTGTGCAAAAAAGCGGTTAGC

TCCTTCGGTCCTCCGATCGTTGTCAGAAGTAAGTTGGCCGCAGTGTTATC

ACTCATGGTTATGGCAGCACTGCATAATTCTCTTACTGTCATGCCATCCG

TAAGATGCTTTTCTGTGACTGGTGAGTACTCAACCAAGTCATTCTGAGAA

TAGTGTATGCGGCGACCGAGTTGCTCTTGCCCGGCGTCAATACGGGATAA

TACCGCGCCACATAGCAGAACTTTAAAAGTGCTCATCATTGGAAAACGTT

CTTCGGGGCGAAAACTCTCAAGGATCTTACCGCTGTTGAGATCCAGTTCG

ATGTAACCCACTCGTGCACCCAACTGATCTTCAGCATCTTTTACTTTCAC

CAGCGTTTCTGGGTGAGCAAAAACAGGAAGGCAAAATGCCGCAAAAAAGG

GAATAAGGGCGACACGGAAATGTTGAATACTCATACTCTTCCTTTTTCAA

TATTATTGAAGCATTTATCAGGGTTATTGTCTCATGAGCGGATACATATT

TGAATGTATTTAGAAAAATAAACAAATAGGGGTTCCGCGCACATTTCCCC

GAAAAGTGCCAC
```

The pGAR vector map is set forth in FIG. 19.

Suitable additional exemplary vectors include e.g., pBABE-puro, pBABE-neo largeTcDNA, pBABE-hygro-hTERT, pMKO.1 GFP, MSCV-IRES-GFP, pMSCV PIG (Puro IRES GFP empty plasmid), pMSCV-loxp-dsRed-loxp-eGFP-Puro-WPRE, MSCV IRES Luciferase, pMIG, MDH1-PGK-GFP_2.0, TtRMPVIR, pMSCV-IRES-mCherry FP, pRetroX GFP T2A Cre, pRXTN, pLncEXP, and pLXIN-Luc.

In other aspects, provided herein are cells comprising a polynucleotide or a vector of the present invention. In some embodiments, the present invention is directed to cells, in vitro cells, comprising a polynucleotide encoding a CAR or a TCR, as described herein. In some embodiments, the present invention is directed to cells, e.g., in vitro cells, comprising a polynucleotide encoding an antibody or an antigen binding molecule thereof that specifically binds to BCMA, as disclosed herein. In other embodiments, the present invention is directed to in vitro cells comprising a polypeptide encoded by a polynucleotide encoding a CAR or a TCR, as disclosed herein. In other embodiments, the present invention is directed to cells, in vitro cells, comprising a polypeptide encoded by a polynucleotide encoding an antibody or an antigen binding molecule thereof that specifically binds to BCMA, as disclosed herein.

Any cell may be used as a host cell for the polynucleotides, the vectors, or the polypeptides of the present invention. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof.

The cell of the present invention can be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In certain embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semiautomated flowthrough centrifuge, e.g., the COBE™ 2991 cell processor, the Baxter CYTOMATE™, or the like. In some embodiments, the washed cells are resuspended in one or more biocompatible buffers, or other saline solution with or without buffer. In certain embodiments, the undesired components of the apheresis sample are removed. Additional methods of isolating T cells for a T cell therapy are disclosed in U.S. Patent Publication No. 2013/0287748, which is herein incorporated by references in its entirety.

In certain embodiments, T cells are isolated from PBMCs by lysing the red blood cells and depleting the monocytes, e.g., by using centrifugation through a PERCOLL' gradient.

In some embodiments, a specific subpopulation of T cells, such as $CD28^+$, $CD4^+$, $CD8^+$, $CD45RA^+$, and $CD45RO^+$ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for $CD4^+$ cells by negative selection, a monoclonal antibody cocktail typically includes antibodies to CD14, CD20, CD11b, CD16, HLA-DR, and CD8. In certain embodiments, flow cytometry and cell sorting are used to isolate cell populations of interest for use in the present invention.

In some embodiments, PBMCs are used directly for genetic modification with the immune cells (such as CARs or TCRs) using methods as described herein. In certain embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, $CD8^+$ cells are further sorted into naive, central memory, and effector cells by identifying cell surface antigens that are associated with each of these types of $CD8^+$ cells. In some embodiments, the expression of phenotypic markers of central memory T cells includes CD45RO, CD62L, CCR7, CD28, CD3, and CD127 and are negative for granzyme B. In some embodiments, central memory T cells are $CD45RO^+$, $CD62L^+$, $CD8^+$ T cells. In some embodiments, effector T cells are negative for CD62L, CCR7, CD28, and CD127 and positive for granzyme B and perforin. In certain embodiments, $CD4^+$ T cells are further sorted into subpopulations. For example, $CD4^+$ T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In certain embodiments, the T cells are obtained from a donor subject. In some embodiments, the donor subject is human patient afflicted with a cancer or a tumor. In other embodiments, the donor subject is a human patient not afflicted with a cancer or a tumor.

Other aspects of the present invention are directed to compositions comprising a polynucleotide described herein, a vector described herein, a polypeptide described herein, or an in vitro cell described herein. In some embodiments, the composition comprises a pharmaceutically acceptable carrier, diluent, solubilizer, emulsifier, preservative and/or adjuvant. In some embodiments, the composition comprises an excipient. In one embodiment, the composition comprises a polynucleotide encoding a CAR or a TCR, wherein the CAR or the TCR comprises an antigen binding molecule that specifically binds to BCMA. In another embodiment, the composition comprises a CAR or a TCR encoded by a polynucleotide of the present invention, wherein the CAR or the TCR comprises an antigen binding molecule that specifically binds to BCMA. In another embodiment, the composition comprises a T cell comprising a polynucleotide encoding a CAR or a TCR, wherein the CAR or the TCR comprises an antigen binding molecule that specifically binds to BCMA. In another embodiment, the composition comprises an antibody or an antigen binding molecule thereof encoded by a polynucleotide of the present invention. In another embodiment, the composition comprises an in vitro cell comprising a polynucleotide encoding an antibody or an antigen binding molecule thereof encoded by a polynucleotide of the present invention.

In some embodiments, the composition includes more than one different antigen binding molecule to BMCA. In some embodiments, the composition included more than one antigen binding molecule to BCMA, wherein the antigen binding molecules to BCMA bind more than one epitope. In some embodiments, the antigen binding molecules will not compete with one another for binding to BCMA. In some embodiments, any of the antigen binding molecules provided herein are combined together in a pharmaceutical composition.

In other embodiments, the composition is selected for parenteral delivery, for inhalation, or for delivery through the digestive tract, such as orally. The preparation of such pharmaceutically acceptable compositions is within the ability of one skilled in the art. In certain embodiments, buffers are used to maintain the composition at physiological pH or at a slightly lower pH, typically within a pH range of from about 5 to about 8. In certain embodiments, when parenteral administration is contemplated, the composition is in the form of a pyrogen-free, parenterally acceptable aqueous solution comprising a desired antigen binding molecule to BCMA, with or without additional therapeutic agents, in a pharmaceutically acceptable vehicle. In certain embodiments, the vehicle for parenteral injection is sterile distilled water in which an antigen binding molecule to BCMA, with or without at least one additional therapeutic agent, is formulated as a sterile, isotonic solution, properly preserved. In certain embodiments, the preparation involves the formulation of the desired molecule with polymeric compounds (such as polylactic acid or polyglycolic acid), beads or liposomes, that provide for the controlled or sustained release of the product, which are then be delivered via a depot injection. In certain embodiments, implantable drug delivery devices are used to introduce the desired molecule.

V. Methods of the Invention

Another aspect of the invention is directed to a method of making a cell expressing a CAR or a TCR comprising transducing a cell with a polynucleotide disclosed herein under suitable conditions. In some embodiments, the method comprises transducing a cell with a polynucleotide encoding a CAR or a TCR, wherein the CAR or the TCR comprises an antigen binding molecule that specifically binds to BCMA, as disclosed herein. In some embodiments, the method comprises transducing a cell with a vector comprising the polynucleotide encoding a CAR or a TCR, wherein the CAR or the TCR comprises an antigen binding molecule that specifically binds to BCMA. In other embodiments, the method comprises transducing a cell with a polynucleotide encoding an antibody or an antigen binding molecule thereof that specifically binds to BCMA, as disclosed herein. In some embodiments, the method comprises transducing a cell with a vector comprising the polynucleotide encoding an antibody or an antigen binding molecule thereof that specifically binds to BCMA, as described herein. In some embodiments, the method further comprises isolating the cell.

Another aspect of the present invention is directed to a method of inducing an immunity against a tumor comprising administering to a subject an effective amount of a cell comprising a polynucleotide described herein, a vector described herein, or a CAR or a TCR described herein. In one embodiment, the method comprises administering to a subject an effective amount of a cell comprising a polynucleotide encoding a CAR or a TCR, wherein the CAR or the TCR comprises an antigen binding molecule that specifically binds to BCMA, as disclosed herein. In another embodiment, the method comprises administering to a subject an effective amount of a cell comprising a vector comprising a polynucleotide encoding a CAR or a TCR, wherein the CAR or the TCR comprises an antigen binding molecule that specifically binds to BCMA, as disclosed herein. In another embodiment, the method comprises administering to a subject an effective amount of a cell comprising a CAR or a TCR encoded by a polynucleotide disclosed herein, wherein the CAR or the TCR comprises an antigen binding molecule that specifically binds to BCMA. In other embodiments, the method comprises administering to a subject an effective amount of a cell comprising a polynucleotide encoding an antibody or an antigen binding molecule thereof that specifically binds to BCMA, as disclosed herein. In another embodiment, the method comprises administering to a subject an effective amount of a cell comprising a vector comprising a polynucleotide encoding an antibody or an antigen binding molecule thereof that specifically binds to BCMA, as disclosed herein. In another embodiment, the method comprises administering to a subject an effective amount of a cell comprising an antibody or antigen binding molecule thereof encoded by a polynucleotide disclosed herein, wherein the antibody or antigen binding molecule thereof specifically binds to BCMA.

Another aspect of the present invention is directed to a method of inducing an immune response in a subject comprising administering an effective amount of the engineered immune cells of the present application. In some embodiments, the immune response is a T cell-mediated immune response. In some embodiments, the T cell-mediated immune response is directed against one or more target cells. In some embodiments, the engineered immune cell comprises a CAR or a TCR. In some embodiments, the target cell is a tumor cell.

Another aspect of the present invention is directed to a method for treating or preventing a malignancy, said method comprising administering to a subject in need thereof an effective amount of at least one isolated antigen binding molecule described herein or at least one immune cell, wherein the immune cell comprises at least one CAR, TCR, and/or an isolated antigen binding molecule as described herein.

Another aspect of the present invention is directed to a method of treating a hyperproliferative disorder or an inflammatory disease in a subject in need thereof comprising administering to the subject a polynucleotide disclosed herein, a vector disclosed herein, a CAR or a TCR disclosed herein, a cell disclosed herein, or a composition disclosed herein. In some embodiments, the inflammatory disease is selected from the group consisting of rheumatoid arthritis, psoriasis, allergies, asthma, autoimmune diseases such as Crohn's, IBD, fibromyalga, mastocytosis, Celiac disease, and any combination thereof. Additionally, the present invention may be useful to treat diabetes, particularly Type 1 diabetes.

Another aspect of the present invention is directed to a method of treating a cancer in a subject in need thereof comprising administering to the subject a polynucleotide disclosed herein, a vector disclosed herein, a CAR or a TCR disclosed herein, a cell disclosed herein, or a composition disclosed herein. In one embodiment, the method comprises administering a polynucleotide encoding a CAR or a TCR, wherein the CAR or the TCR comprises an antigen binding molecule that specifically binds to BCMA, as disclosed herein. In another embodiment, the method comprises administering a vector comprising a polynucleotide encoding a CAR or a TCR, wherein the CAR or the TCR comprises an antigen binding molecule that specifically binds to BCMA, as disclosed herein. In another embodiment, the method comprises administering a CAR or a TCR encoded by a polynucleotide disclosed herein, wherein the CAR or the TCR comprises an antigen binding molecule that specifically binds to BCMA. In another embodiment, the method comprises administering a cell comprising the polynucleotide, or a vector comprising the polynucleotide, encoding a CAR or a TCR, wherein the CAR or the TCR comprises an antigen binding molecule that specifically binds to BCMA, as disclosed herein. In other embodiments, the method comprises administering a polynucleotide encoding an antibody or an antigen binding molecule thereof that specifically binds to BCMA, as disclosed herein. In another embodiment, the method comprises administering a vector comprising a polynucleotide encoding an antibody or an antigen binding molecule thereof that specifically binds to BCMA, as disclosed herein. In another embodiment, the method comprises administering an antibody or an antigen binding molecule thereof encoded by a polynucleotide disclosed herein, wherein the antibody or the antigen binding molecule thereof specifically binds to BCMA. In another embodiment, the method comprises administering a cell comprising the polynucleotide, or a vector comprising the polynucleotide, encoding an antibody or an antigen binding molecule thereof that specifically binds to BCMA, as disclosed herein.

In some embodiments, an antigen binding molecule to BCMA is administered alone. In certain embodiments, an antigen binding molecule to BCMA is administered as part of a CAR, TCR, or other immune cell. In such immune cells, the antigen binding molecule to BCMA can be under the control of the same promoter region, or a separate promoter.

In certain embodiments, the genes encoding protein agents and/or an antigen binding molecule to BCMA can be in separate vectors.

In some embodiments, the methods of treating a cancer in a subject in need thereof comprise a T cell therapy. In one embodiment, the T cell therapy of the present invention is engineered Autologous Cell Therapy (eACT™). According to this embodiment, the method can include collecting blood cells from the patient. The isolated blood cells (e.g., T cells) can then be engineered to express an anti-BCMA CAR of the present invention ("anti-BCMA CAR T cells"). In a particular embodiment, the anti-BCMA CAR T cells are administered to the patient. In some embodiments, the anti-BCMA CAR T cells treat a tumor or a cancer in the patient. In one embodiment the anti-BCMA CAR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient.

The T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$ cells, at least about $10^{10}$ cells, or at least about $10^{11}$ cells. In another embodiment, the therapeutically effective amount of the T cells is about $10^4$ cells, about $10^5$ cells, about $10^6$ cells, about $10^7$ cells, or about $10^8$ cells. In one particular embodiment, the therapeutically effective amount of the anti-BCMA CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

Another aspect of the present invention is directed to methods of diagnosis, detection, or validation. In some embodiments, the antigen binding molecule is used as a diagnostic or validation tool. In certain embodiments, the antigen binding molecules disclosed herein are used to assay the amount of BCMA present in a sample and/or subject. In some embodiments, the diagnostic antigen binding molecule is not neutralizing. In some embodiments, the antigen binding molecules disclosed herein are used or provided in an assay kit and/or method for the detection of BCMA in mammalian tissues or cells in order to screen/diagnose for a disease or disorder associated with changes in levels of BCMA. In some embodiments, the kit comprises an antigen binding molecule that binds BCMA, along with means for indicating the binding of the antigen binding molecule with BCMA, if present, and optionally BCMA protein levels. Various means for indicating the presence of an antigen binding molecule can be used. For example, fluorophores, other molecular probes, or enzymes can be linked to the antigen binding molecule and the presence of the antigen binding molecule can be observed in a variety of ways. As will be appreciated by one of skill in the art, the degree of antigen binding molecule binding can be used to determine how much BCMA is in a sample.

V.A. Cancer Treatment

The methods of the invention can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In certain embodiments, the cancer is multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, myeloid diseases including but not limited to acute myeloid leukemia (AML), chronic myeloid leukemia (CML), acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome (MDS), hemophagocytic syndrome (Macrophage Activating Syndrome (MAS), and hemophagocytic lymphohistocytosis (HLH)), chronic or acute granulomatous disease, large cell granuloma, leukocyte adhesion deficiency, plasmablastic lymphoma, plasmacytoid dendritic cell neoplasm, Waldenstrom macroglobulinemia, plasma cell proliferative disorders (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (Crow-Fukase syndrome, Takatsuki disease, PEP syndrome), or combinations thereof. In one embodiment, the cancer is a myeloma. In one particular embodiment, the cancer is multiple myeloma.

In some embodiments, the methods further comprise administering a chemotherapeutic. In certain embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 $mg/m^2$/day and 2000 $mg/m^2$/day) and specified doses of fludarabine (between 20 $mg/m^2$/day and 900 $mg/m^2$/day). A preferred dose regimen involves treating a patient comprising administering daily to the patient about 500 $mg/m^2$/day of cyclophosphamide and about 60 $mg/m^2$/day of fludarabine for three days prior to administration of a therapeutically effective amount of engineered T cells to the patient.

In other embodiments, the antigen binding molecule, transduced (or otherwise engineered) cells (such as CARs or TCRs), and the chemotherapeutic agent are administered each in an amount effective to treat the disease or condition in the subject.

In certain embodiments, compositions comprising CAR- and/or TCR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL', Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretie™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (Opdivo®), pembrolizumab (Keytruda®), pembrolizumab, pidilizumab (CureTech), and atezolizumab (Roche).

Additional therapeutic agents suitable for use in combination with the invention include, but are not limited to, ibrutinib (Imbruvica®), ofatumumab (Arzerra®), rituximab (Rituxan®), bevacizumab (Avastin®), trastuzumab (Herceptin®), trastuzumab emtansine (KADCYLA®), imatinib (Gleevec®), cetuximab (Erbitux®), panitumumab (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR- and/or TCR-containing immune are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In certain embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The present invention is further illustrated by the following examples which should not be construed as further limiting. The contents of all references cited throughout this application are expressly incorporated herein by reference.

EXAMPLES

Example 1

BCMA expression was measured in various cell lines. BCMA was found to be expressed, with a fragments/kilobase of exon/million reads mapped (FPKM) greater than 35, in 99% of multiple myeloma tumor cell lines tested (FIG. 2A). BCMA expression was greater than that of CD70, CS-1, CLL-1, DLL-1 and FLT3 (FIG. 2A). To further characterize the expression of BCMA, EoL-1 (Sigma), NCI-H929 (Molecular Imaging), and MM1S (Molecular Imaging) cells were stained with an anti-BCMA antibody conjugated to PE (Biolegend, San Diego, Calif.) in stain buffer (BD Pharmingen, San Jose, Calif.) for 30 minutes at 4° C. Cells were then washed and resuspended in stain buffer with propidium iodide (BD Pharmingen) prior to data acquisition. Samples were then acquired by flow cytometry and data analyzed (FIGS. 2B-2C). BCMA expression was observed in the myeloma cell lines MM1S (FIG. 2C) and NCI-H929 (FIG. 2D), but not in the human eosinophil cell line EoL-1 (FIG. 2B). In addition, little to no BCMA expression was observed in normal immune cells (FIG. 2E).

Example 2

A third generation lentiviral transfer vector containing the BCMA CAR constructs was used along with the ViraPower™ Lentiviral Packaging Mix (Life Technologies, FIX™) to generate the lentiviral supernatants. Briefly, a transfection mix was generated by mixing 15 μg of DNA and 22.5 μl of polyethileneimine (Polysciences, 1 mg/ml) in 600 μl of OptiMEM media. The transfection mix was incubated for 5 minutes at room temperature. Simultaneously, 293T cells (ATCC) were trypsinized and counted. A total of $10\times10^6$ total 293T cells were then plated in a T75 flask with the transfection mix. Following culture for three days, supernatants were collected and filtered through a 0.45 μm filter and stored at −80° C.

Peripheral blood mononuclear cells (PBMCs) were isolated from two different healthy donor leukopaks (Hemacare) using ficoll-paque density centrifugation according to the manufacturer's instructions. PBMCs were stimulated using OKT3 (Muromonab-CD3, 50 ng/ml, Miltenyi Biotec) in R10 media supplemented with IL-2 (300 IU/ml, Proleukin®, Prometheus® Therapeutics and Diagnostics). Forty-eight hours post-stimulation, cells were transduced using lentivirus containing the different BCMA CAR constructs at a multiplicity of infection (MOI) of 10. Cells were maintained at $0.5\times10^6$-$2.0\times10^6$ cells/ml prior to use in activity assays.

Figure 3A:
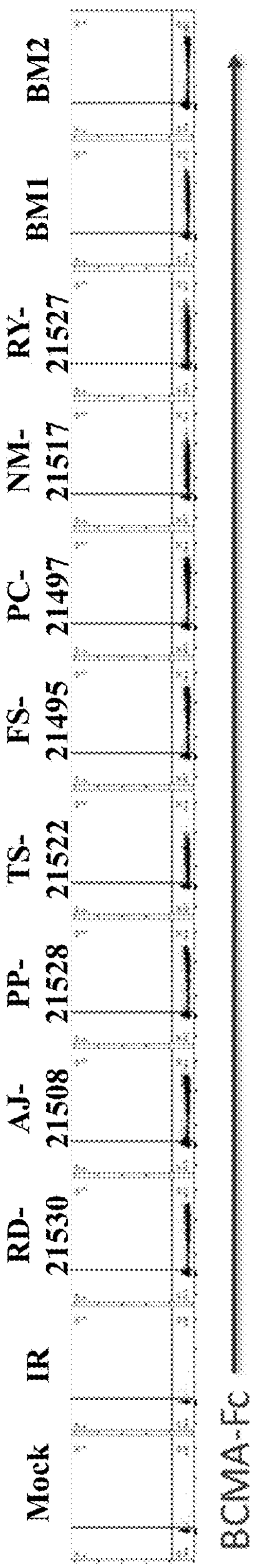
FIG. 3A and FIG. 3B show CAR expression in lentivirus transduced primary human T cells from a first healthy donor (FIG. 3A) and a second healthy donor (FIG. 3B).
Figure 3B:
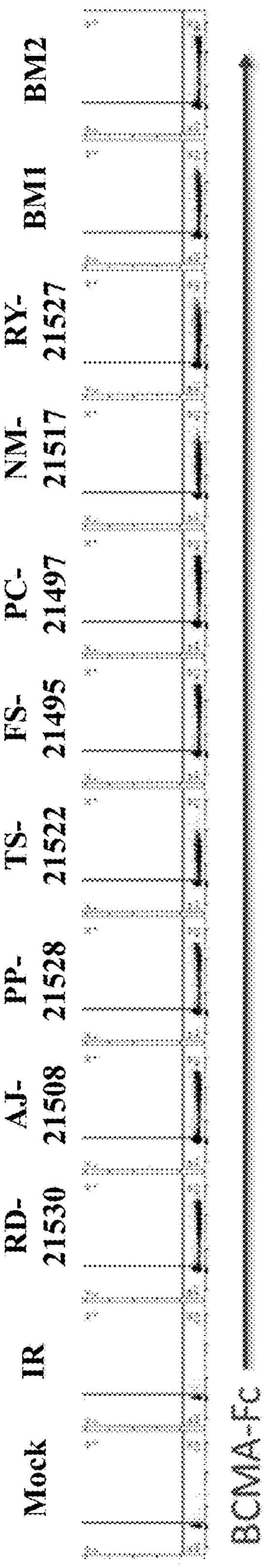

At day 12 post-stimulation, transduced T cells were stained with recombinant BCMA-Fc (R&D Systems) in stain buffer (BD Pharmingen) for 30 minutes at 4° C. Cells were then washed and stained with goat anti-human IgG Fc PE (Jackson ImmunoResearch, West Grove, Pa.) in stain buffer for 30 minutes at 4° C. Cells were then washed and resuspended in stain buffer with propidium iodide (BD Pharmingen) prior to data acquisition. All experiments were performed in two different donors. BCMA CAR expression was observed for each of the constructs in both Donor 1 (FIG. 3A) and Donor 2 (FIG. 3B) transduced cells.

Figure 4A:
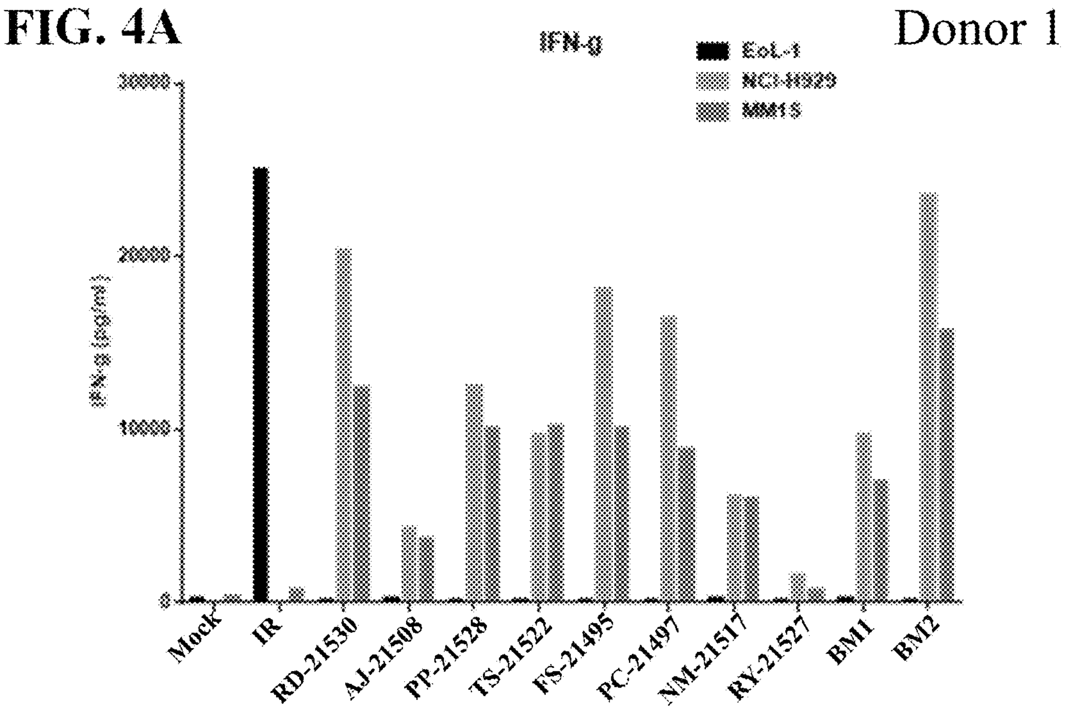
FIGS. 4A-4F shows IFNγ, TNFα, and IL-2 production by lentivirus transduced CAR T cells from two healthy donors following 16 hours of co-cultured with EoL-1 (Black), NCI-H929 (light grey), or MM1S (grey) target cell lines.
Figure 4B:
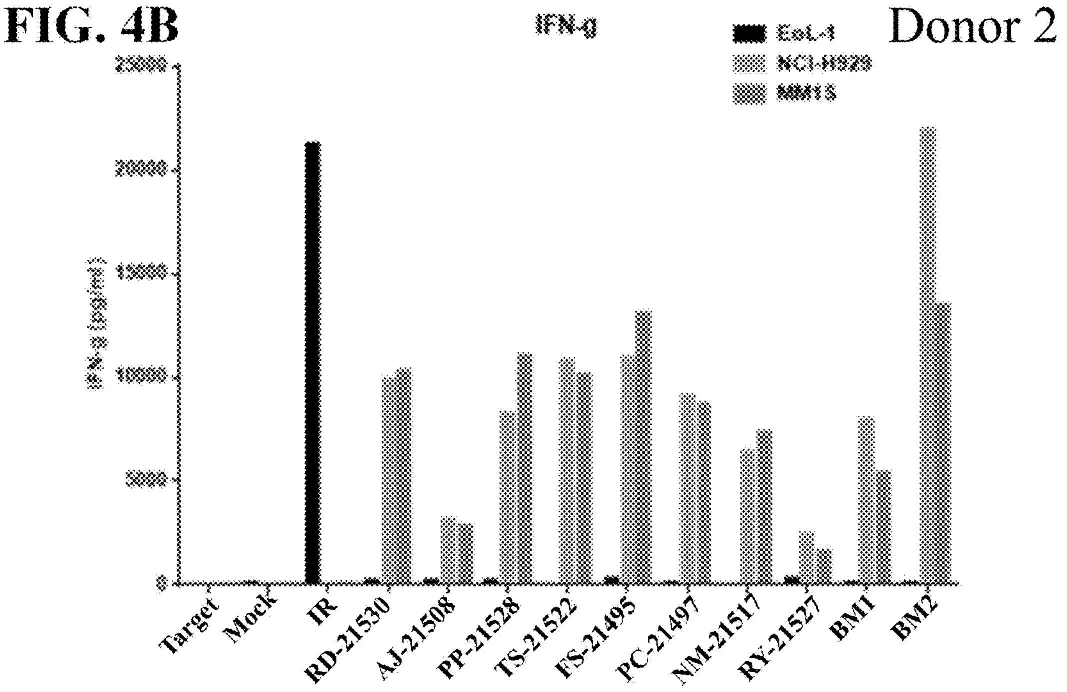
Figure 4C:
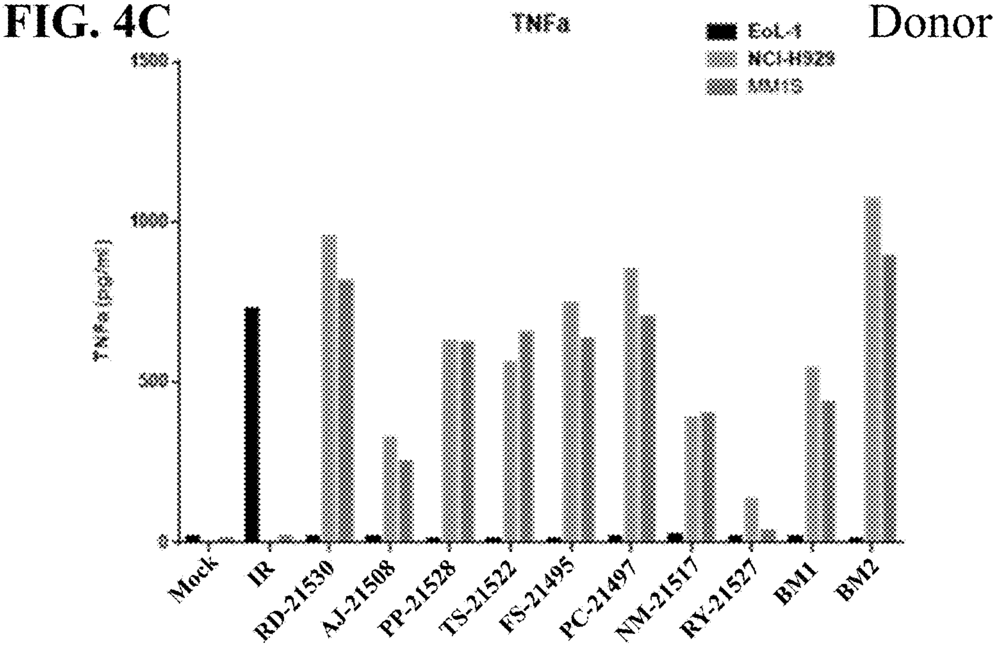
Figure 4D:
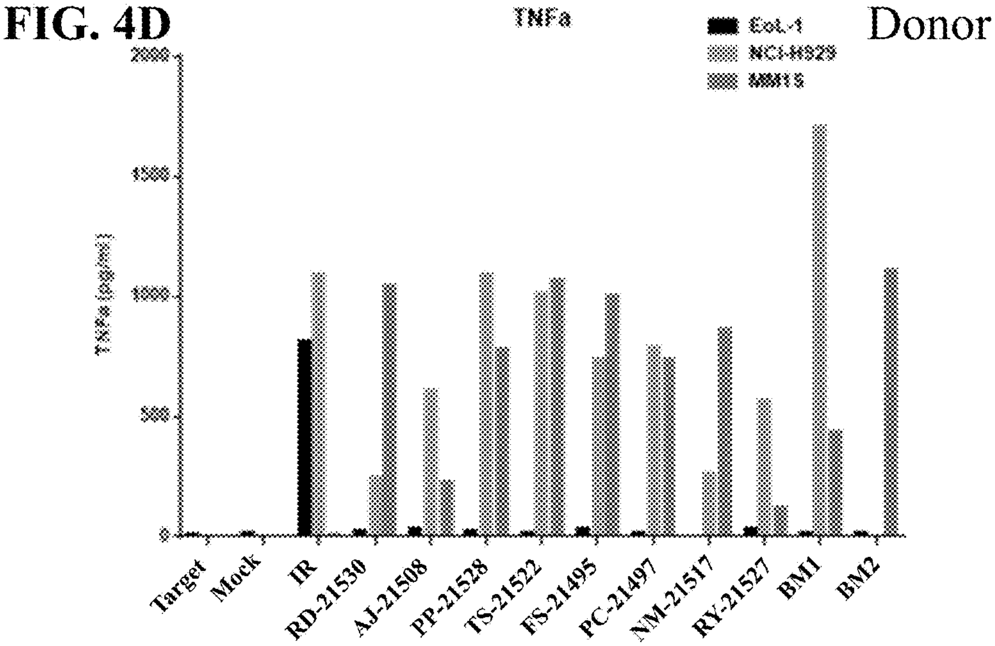
Figure 4E:
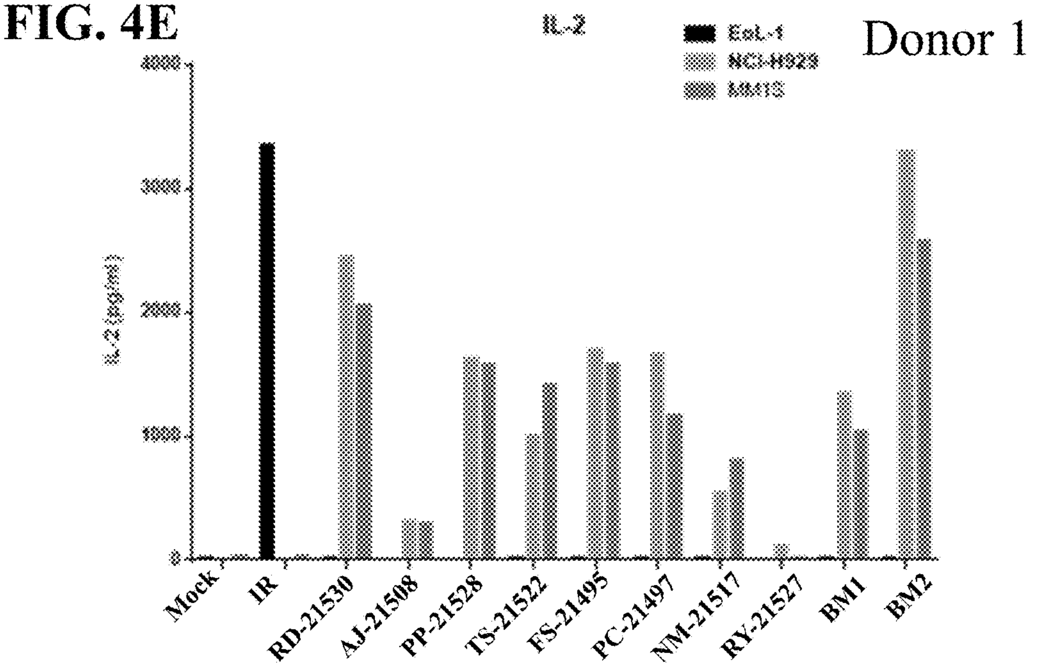
Figure 4F:
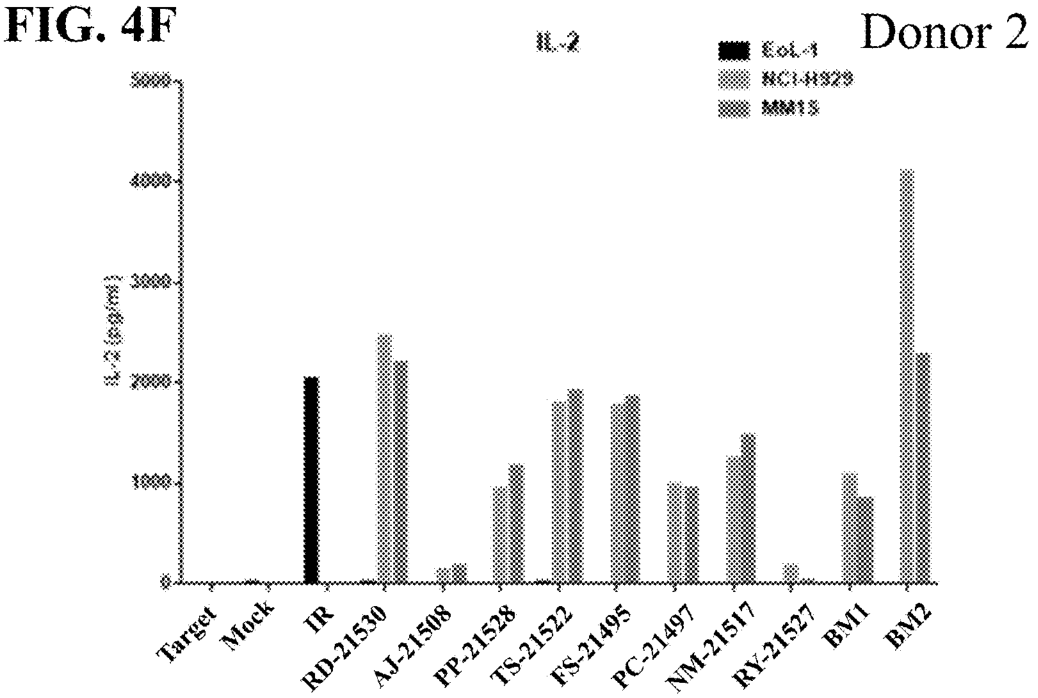

Effector cells, e.g., anti-BCMA CAR T cells, were cultured with target cells at a 1:1 effector cell to target cell (E:T) ratio in R10 media 12 days after T cell stimulation. Cell lines tested included EoL-1, NCI-H929 and MM1S. Sixteen hours post-co-culture, supernatants were analyzed by Luminex (EMD Millipore), according to the manufacturer's instructions, for production of the cytokines IFNγ (FIGS. 4A-4B), TNFα (FIG. 4C-4D), and IL-2 (FIG. 4E-4F). IFNγ (FIGS. 4A-4B), TNFα (FIG. 4C-4D), and IL-2 (FIG. 4E-4F) were observed in the supernatant of NCI-H929 and MM1S target cell co-cultures for each anti-BCMA CAR T cell tested in both donors (FIGS. 4A-4B); however, IFNγ (FIGS. 4A-4B), TNFα (FIG. 4C-4D), and IL-2 (FIG. 4E-4F) were only observed in the supernatant of EoL-1 target cell co-cultures above background for the IR negative control T cells (FIG. 4A).

Figure 5A:
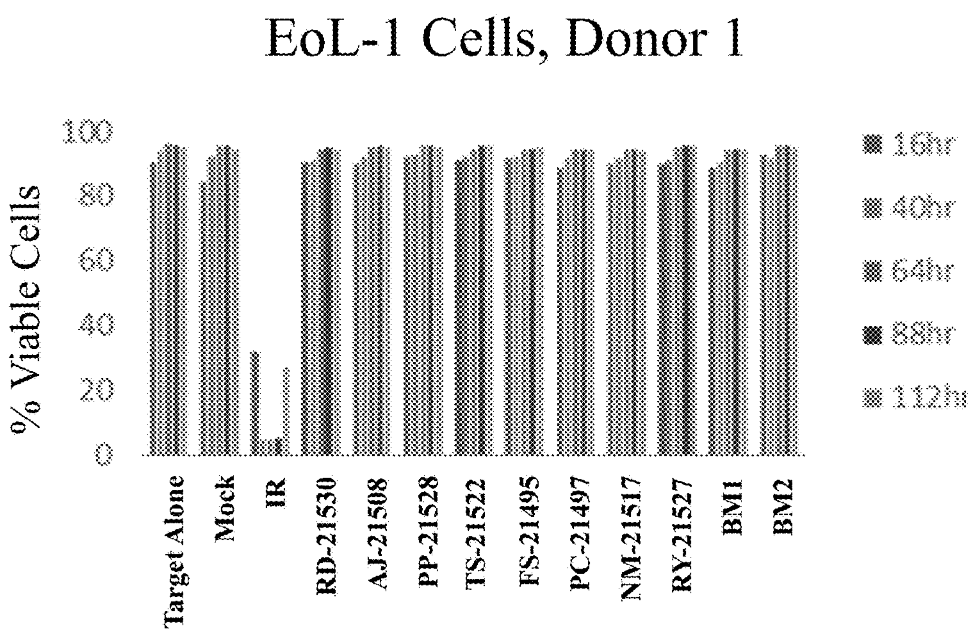
FIGS. 5A-5F show the average cytolytic activity (as a percentage of viable target cells remaining; y-axis) over time from two healthy donors expressing the indicated CARs co-cultured with EoL1 (FIGS. 5A and 5B), NCI-H929 (FIGS. 5C and 5D), or MM1S (FIGS. 5E and 5F) target cells for 16 hours, 40 hours, 64 hours, 88 hours, or 112 hours.
Figure 5B:
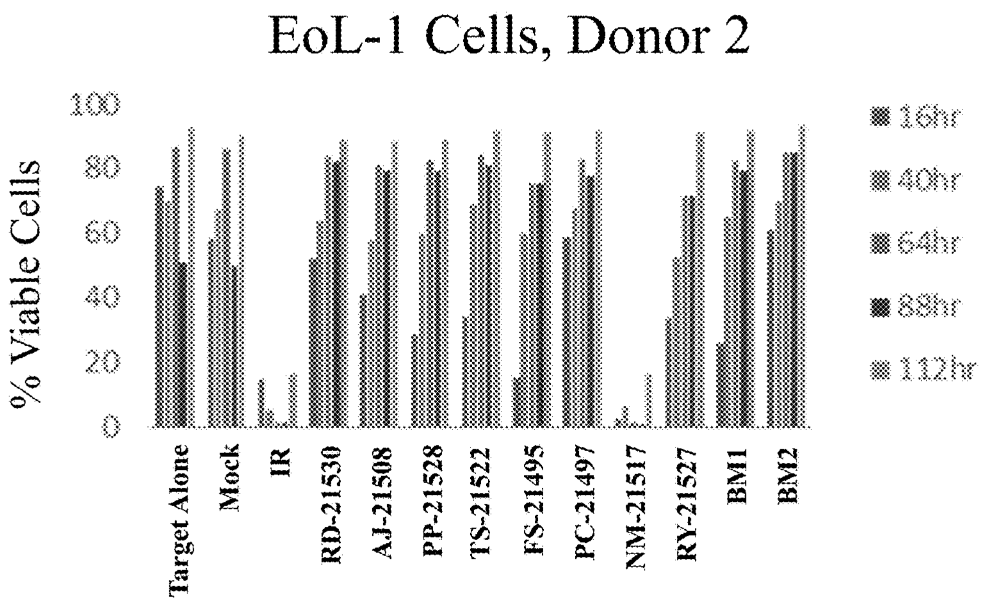
Figure 5C:
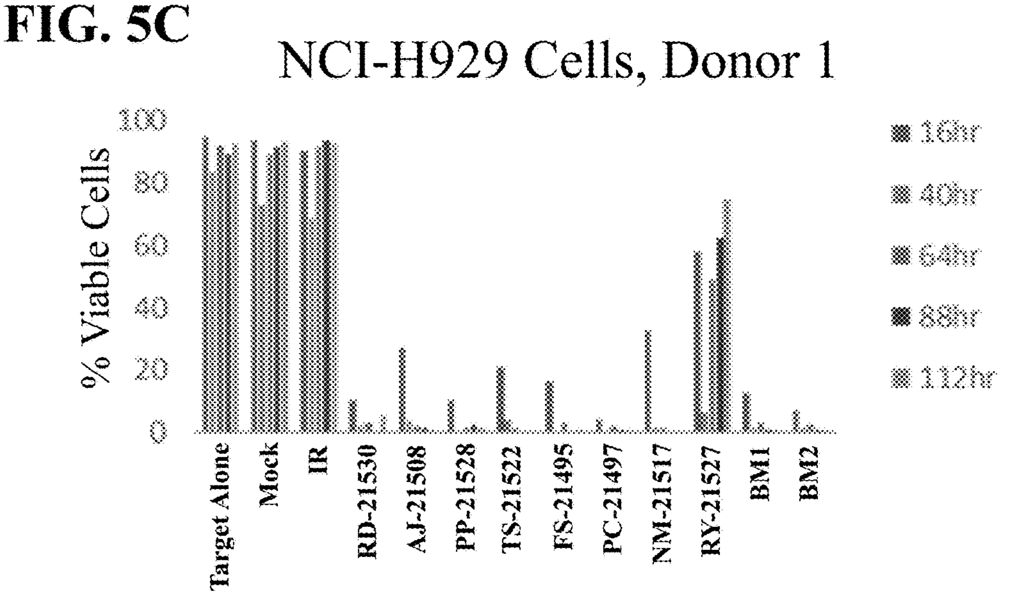
Figure 5D:
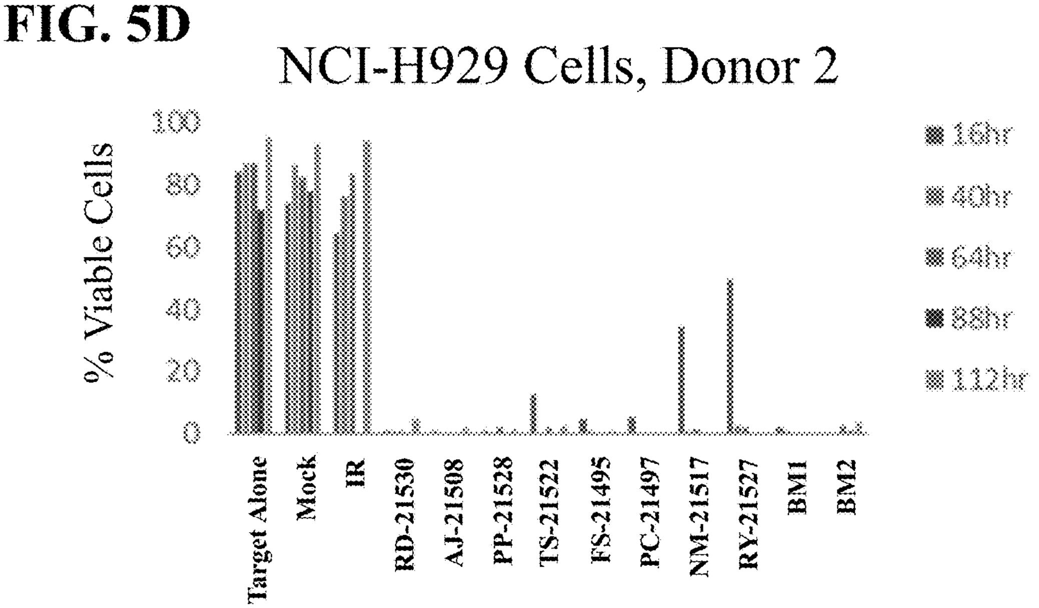
Figure 5E:
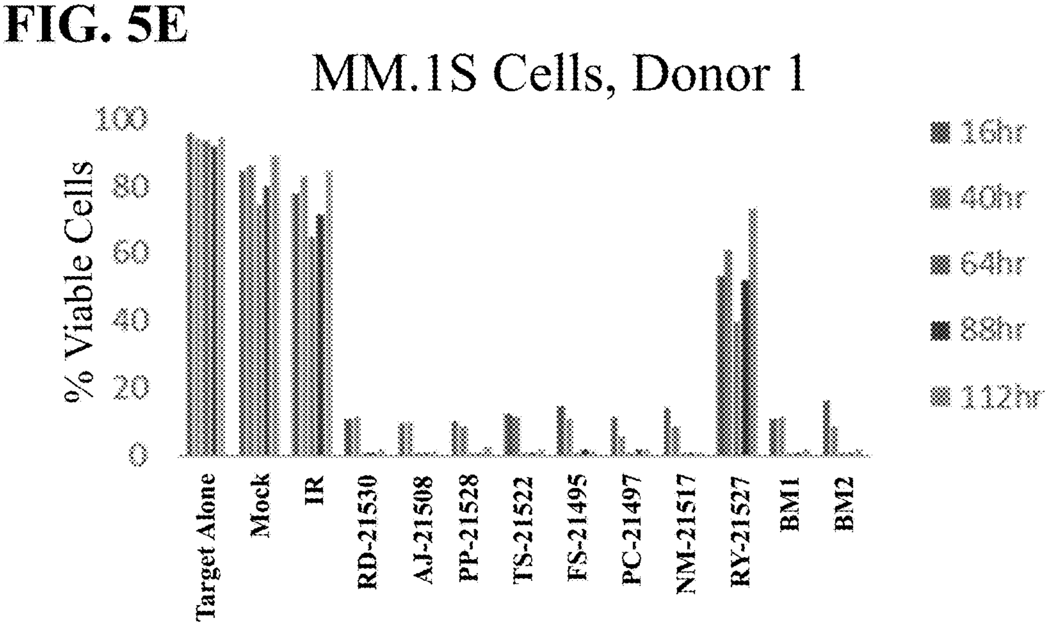
Figure 5F:
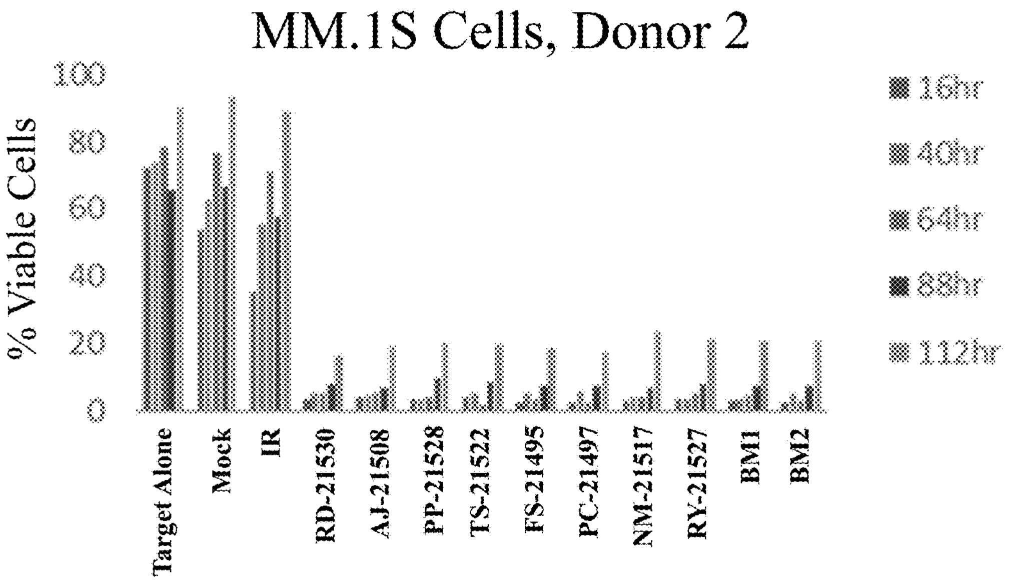

Target cell viability was assessed by flow cytometric analysis of propidium iodide (PI) uptake of CD3 negative cells. The anti-BCMA CAR T cells were co-cultured with EoL1 (FIGS. 5A-5B), NCI-H929 (FIGS. 5C-5D), or MM1S (FIGS. 5E-5F) target cells for 16 hours, 40 hours, 64 hours, 88 hours, or 112 hours. Little cytolytic activity was observed in the EoL-1 co-cultures at any time period for the anti-BCMA CAR T cells (FIG. 5A-5B). However, co-culture of the anti-BCMA CAR T cells and the NCI-H929 or MM1S target cells resulted in a decrease in the percentage of viable target cells at each time point measured for each of the anti-BCMA CAR T cells.

Figures 6A, 6B:
FIGS. 6A and 6B show proliferation of CFSE-labeled lentivirus transduced CAR T cells from a first healthy donor (FIG. 6A) and a second healthy donor (FIG. 6B) following 5 days of co-culture with CD3-CD28 beads (top row), EoL-1 (second row), NCI-H929 (third row), or MM1S (bottom row) target cell lines.

To examine proliferation, anti-BCMA CAR T cells were labeled with carboxyfluorescein succinimidyl ester (CFSE) prior to co-culture with EoL-1, NCI-H929, or MM1S target cells at a 1:1 E:T ratio in R10 media. Five days later, T cell proliferation was assessed by flow cytometric analysis of CFSE dilution. Data was analyzed and plotted as histogram using FlowJo™ (FIGS. 6A-6B). All experiments were performed in two different donors.

Example 3

Antigens were biotinylated using the EZ-Link Sulfo-NHS-Biotinylation Kit from Pierce/ThermoFisher (Waltham, Mass.). Goat anti-human F(ab')2 kappa-FITC (LC-FITC), Extravidin-PE (EA-PE) and streptavidin-633 (SA-633) were obtained from Southern Biotech (Birmingham, Ala.), Sigma (St. Louis, Mo.) and Molecular Probes/Invitrogen (Waltham, Mass.), respectively. Streptavidin MicroBeads and MACS LC separation columns were purchased from Miltenyi Biotec (Gladbachn, Germany).

Naïve Discovery

Eight naïve human synthetic yeast libraries each of ~109 diversity were propagated as described herein (see WO2009036379, WO2010105256, and WO2012009568 to Xu et al.). For the first two rounds of selection, a magnetic bead sorting technique utilizing the Miltenyi MACs system was performed, as described (Siegel et al., 2004). Briefly, yeast cells (~1010 cells/library) were incubated with 3 ml of 100 nM biotinylated monomeric antigen or 10 nM biotinylated Fc fusion antigen for 15 minutes at room temperature in FACS wash buffer (phosphate-buffered saline (PBS)/0.1% bovine serum albumin (BSA)). After washing once with 50 ml ice-cold wash buffer, the cell pellet was resuspended in 40 mL wash buffer, and Streptavidin MicroBeads (500 μl) were added to the yeast and incubated for 15 minutes at 4° C. Next, the yeast were pelleted, resuspended in 5 mL wash buffer, and loaded onto a Miltenyi LS column. After the 5 mL was loaded, the column was washed 3 times with 3 ml FACS wash buffer. The column was then removed from the magnetic field, and the yeast were eluted with 5 mL of growth media and then grown overnight. The following rounds of sorting were performed using flow cytometry. Approximately 1×108 yeast were pelleted, washed three times with wash buffer, and incubated with decreasing concentrations of biotinylated monomeric or Fc fusion antigen (100 to 1 nM) under equilibrium conditions at room temperature. Yeast were then washed twice and stained with LC-FITC (diluted 1:100) and either SA-633 (diluted 1:500) or EA-PE (diluted 1:50) secondary reagents for 15 minutes at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences, San Jose, Calif.) and sort gates were assigned to select for specific binders relative to a background control. Subsequent rounds of selection were focused on reduction of non-specific reagent binders (utilizing soluble membrane proteins from CHO cell), as well as pressuring for affinity to BCMA. After the final round of sorting, yeast were plated and individual colonies were picked for characterization.

Affinity Maturation

Binding optimization of naïve clones was carried out using three maturation strategies: light chain diversification, diversification of VH CDRH1/CDRH2, and performing VHmut/VKmut selections.

Light Chain Diversification:

Heavy chain plasmids were extracted and transformed into a light chain library with a diversity of $1\times10^6$. Selections were performed as described above with one round of MACS sorting and two rounds of FACS sorting using 10 nM or 1 nM biotinylated antigen for respective rounds.

CDRH1 and CDRH2 Selection:

A selected donor CDRH3 was recombined into a premade library with CDRH1 and CDRH2 variants of a diversity of $1\times10^8$ and selections were performed as described above. Affinity pressures were applied by incubating the biotinylated antigen-antibody yeast complex with unbiotinylated antigen for varying amounts of time to select for the highest affinity antibodies.

VHmut/VKmut Selection:

This round of affinity maturation included error prone PCR-based mutagenesis of the heavy chain and/or light chain. Selections were performed similar to previous cycles, but employing FACS sorting for all selection rounds. Antigen concentration was reduced and cold antigen competition times were increased to pressure further for optimal affinity.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect™ (GE Healthcare LifeSciences, Pittsburgh, Pa.).

ForteBio KD Measurements

ForteBio affinity measurements were performed generally as previously described (Estep et al., 2013). Briefly, ForteBio affinity measurements were performed by loading IgGs on-line onto AHQ sensors. Sensors were equilibrated off-line in assay buffer for 30 minutes and then monitored on-line for 60 seconds for baseline establishment. Sensors with loaded IgGs were exposed to 100 nM antigen for 5 minutes, afterwards they were transferred to assay buffer for 5 minutes for off-rate measurement. Kinetics were analyzed using the 1:1 binding model.

MSD-SET KD Measurements

Equilibrium affinity measurements performed generally as previously described (Estep et al., 2013). Briefly, solution equilibrium titrations (SET) were performed in PBS+0.1% IgG-Free BSA (PBSF) with antigen (BCMA monomer) held constant at 10-100 pM and incubated with 3- to 5-fold serial dilutions of Fab or mAbs starting at 10 pM-10 nM (experimental condition is sample dependent). Antibodies (20 nM in PBS) were coated onto standard bind MSD-ECL plates overnight at 4° C. or at room temperature for 30 minutes. Plates were then blocked by BSA for 30 minutes with shaking at 700 rpm, followed by three washes with wash buffer (PBSF+0.05% Tween 20). SET samples were applied and incubated on the plates for 150 seconds with shaking at 700 rpm followed by one wash. Antigen captured on a plate was detected with 250 ng/mL Sulfotag™-labeled streptavidin in PBSF by incubation on the plate for 3 minutes. The plates were washed three times with wash buffer and then read on the MSD Sector Imager 2400™ instrument using 1× Read Buffer T with surfactant. The percent free antigen was plotted as a function of titrated antibody in Prism™ and fit to a quadratic equation to extract the KD. To improve throughput, liquid handling robots were used throughout MSD-SET experiments, including SET sample preparation.

Octet Red384 Epitope Binning/Ligand Blocking

Epitope binning/ligand blocking was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Data was processed using ForteBio's Data Analysis Software 7.0. Additional binding by the second antibody or ligand after antigen association indicates an unoccupied epitope (non-competitor), while no binding indicates epitope blocking (competitor or ligand blocking).

Size Exclusion Chromatography

A TSKgel SuperSW mAb HTP column (22855) was used for fast SEC analysis of yeast produced mAbs at 0.4 mL/minute with a cycle time of 6 minutes/run. 200 mM Sodium Phosphate and 250 mM Sodium Chloride was used as the mobile phase.

Dynamic Scanning Fluorimetry 10 uL of 20× Sypro Orange™ is added to 20 uL of 0.2-1 mg/mL mAb or Fab solution. A RT-PCR instrument (BioRad CFX96 RT PCR) is used to ramp the sample plate temperature from 40° to 95° C. at 0.5 C increment, with 2 minutes to equilibrate at each temperature. The negative of first derivative for the raw data is used to extract Tm.

Clone FS-26528 HC DNA (SEQ ID NO: 271)

```
GAGGTGCAGCTGTTGGAGTCTGGGGGAGGCTTGGTACAGCCTGGGGGGTCCCTGAGACTCT
CCTGTGCAGCCTCTGGATTCACCTTTGACGACTATGCCATGGCATGGGTCCGCCAGGCTCC
AGGGAAGGGGCTGGAGTGGGTCTCAGCTATTAGTGATGCAGGTGACAGAACATACTACGCA
GACTCCGTGAGGGGCCGGTTCACCATCTCCAGAGACAATTCCAAGAACACACTGTATCTGC
AAATGAACAGCCTGAGAGCCGAGGACACGGCGGTGTACTACTGCGCAAGAGCCGAGATGGG
AGCCGTATTCGACATATGGGGTCAGGGTACAATGGTCACCGTCTCCTCA
```

Clone FS-26528 HC. CDRs 1, 2, and 3 are underlined.

(SEQ ID NO: 272)

EVQLLESGGGLVQPGGSLRLSCAASGFTFDDYAMAWVRQAPGKGLEWVSAISDAGDRTYY
ADSVRGRFTISRDNSKNTLYLQMNSLRAEDTAVYYCARAEMGAVFDIWGQGTMVTVSS (SEQ ID NO: 273)

SCAASGFTFDDYAMA [HC CDR1]

(SEQ ID NO: 274)

AISDAGDRTYYADSVRG [HC CDR2]

(SEQ ID NO: 275)

ARAEMGAVFDI [HC CDR3]

Clone FS-26528 LC DNA (SEQ ID NO: 276)

```
GAAATTGTGTTGACACAGTCTCCAGCCACCCTGTCTTTGTCTCCAGGGGAAAGAGCCACCC
TCTCCTGCAGGGCCAGTCAGAGTGTTAGCAGGTACTTAGCCTGGTACCAACAGAAACCTGG
CCAGGCTCCCAGGCTCCTCATCTATGATGCATCCAACAGGGCCACTGGCATCCCAGCCAGG
TTCAGTGGCAGTGGGTCTGGGACAGACTTCACTCTCACCATCAGCAGCCTAGAGCCTGAAG
ATTTTGCAGTTTATTACTGTCAGCAGAGAATCTCCTGGCCTTTCACTTTTGGCGGAGGGAC
CAAGGTTGAGATCAAACGG
```

Clone FS-26528 LC. CDRs 1, 2, and 3 are underlined.

(SEQ ID NO: 277)

EIVLTQSPATLSLSPGERATLSCRASQSVSRYLAWYQQKPGQAPRLLIYDASNRATGIPAR
FSGSGSGTDFTLTISSLEPEDFAVYYCQQ RISWPFTFGGGTKVEIKR (SEQ ID NO: 278)

RASQSVSRYLA [LC CDR1]

(SEQ ID NO: 279)

DASNRAT [LC CDR2]

(SEQ ID NO: 280)

QQRISWPFT [LC CDR3]

Clone FS-26528 CAR DNA HxL (SEQ ID NO: 281)

```
ATGGCACTCCCCGTAACTGCTCTGCTGCTGCCGTTGGCATTGCTCCTGCACGCCGCACGCC
CGGAGGTGCAGCTGTTGGAGTCTGGGGGAGGCTTGGTACAGCCTGGGGGGTCCCTGAGACT
CTCCTGTGCAGCCTCTGGATTCACCTTTGACGACTATGCCATGGCATGGGTCCGCCAGGCT
CCAGGGAAGGGGCTGGAGTGGGTCTCAGCTATTAGTGATGCAGGTGACAGAACATACTACG
CAGACTCCGTGAGGGGCCGGTTCACCATCTCCAGAGACAATTCCAAGAACACACTGTATCT
GCAAATGAACAGCCTGAGAGCCGAGGACACGGCGGTGTACTACTGCGCAAGAGCCGAGATG
GGAGCCGTATTCGACATATGGGGTCAGGGTACAATGGTCACCGTCTCCTCAGGGTCTACAT
CCGGCTCCGGGAAGCCCGGAAGTGGCGAAGGTAGTACAAAGGGGGAAATTGTGTTGACACA
GTCTCCAGCCACCCTGTCTTTGTCTCCAGGGGAAAGAGCCACCCTCTCCTGCAGGGCCAGT
CAGAGTGTTAGCAGGTACTTAGCCTGGTACCAACAGAAACCTGGCCAGGCTCCCAGGCTCC
TCATCTATGATGCATCCAACAGGGCCACTGGCATCCCAGCCAGGTTCAGTGGCAGTGGGTC
TGGGACAGACTTCACTCTCACCATCAGCAGCCTAGAGCCTGAAGATTTTGCAGTTTATTAC
TGTCAGCAGAGAATCTCCTGGCCTTTCACTTTTGGCGGAGGGACCAAGGTTGAGATCAAAC
GGGCCGCTGCCCTTGATAATGAAAAGTCAAACGGAACAATCATTCACGTGAAGGGCAAGCA
CCTCTGTCCGTCACCCTTGTTCCCTGGTCCATCCAAGCCATTCTGGGTGTTGGTCGTAGTG
GGTGGAGTCCTCGCTTGTTACTCTCTGCTCGTCACCGTGGCTTTTATAATCTTCTGGGTTA
```

-continued

GATCCAAAAGAAGCCGCCTGCTCCATAGCGATTACATGAATATGACTCCACGCCGCCCTGG
CCCCACAAGGAAACACTACCAGCCTTACGCACCACCTAGAGATTTCGCTGCCTATCGGAGC
AGGGTGAAGTTTTCCAGATCTGCAGATGCACCAGCGTATCAGCAGGGCCAGAACCAACTGT
ATAACGAGCTCAACCTGGGACGCAGGGAAGAGTATGACGTTTTGGACAAGCGCAGAGGACG
GGACCCTGAGATGGGTGGCAAACCAAGACGAAAAAACCCCCAGGAGGGTCTCTATAATGAG
CTGCAGAAGGATAAGATGGCTGAAGCCTATTCTGAAATAGGCATGAAAGGAGAGCGGAGAA
GGGGAAAAGGGCACGACGGTTTGTACCAGGGACTCAGCACTGCTACGAAGGATACTTATGA
CGCTCTCCACATGCAAGCCCTGCCACCTAGG

Clone FS-26528 CAR HxL (SEQ ID NO: 282)

MALPVTALLLPLALLLHAARPEVQLLESGGGLVQPGGSLRLSCAASGFTFDDYAMAWVRQA
PGKGLEWVSAISDAGDRTYYADSVRGRFTISRDNSKNTLYLQMNSLRAEDTAVYYCARAEM
GAVFDIWGQGTMVTVSSGSTSGSGKPGSGEGSTKGEIVLTQSPATLSLSPGERATLSCRAS
QSVSRYLAWYQQKPGQAPRLLIYDASNRATGIPARFSGSGSGTDFTLTISSLEPEDFAVYY
CQQRISWPFTFGGGTKVEIKRAAALDNEKSNGTIIHVKGKHLCPSPLFPGPSKPFWVLVVV
GGVLACYSLLVTVAFIIFWVRSKRSRLLHSDYMNMTPRRPGPTRKHYQPYAPPRDFAAYRS
RVKFSRSADAPAYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR

Clone FS-26528 CAR DNA LxH (SEQ ID NO: 283)

ATGGCACTCCCCGTAACTGCTCTGCTGCTGCCGTTGGCATTGCTCCTGCACGCCGCACGCC
CGGAAATTGTGTTGACACAGTCTCCAGCCACCCTGTCTTTGTCTCCAGGGGAAAGAGCCAC
CCTCTCCTGCAGGGCCAGTCAGAGTGTTAGCAGGTACTTAGCCTGGTACCAACAGAAACCT
GGCCAGGCTCCCAGGCTCCTCATCTATGATGCATCCAACAGGGCCACTGGCATCCCAGCCA
GGTTCAGTGGCAGTGGGTCTGGGACAGACTTCACTCTCACCATCAGCAGCCTAGAGCCTGA
AGATTTTGCAGTTTATTACTGTCAGCAGAGAATCTCCTGGCCTTTCACTTTTGGCGGAGGG
ACCAAGGTTGAGATCAAACGGGGGTCTACATCCGGCTCCGGGAAGCCCGGAAGTGGCGAAG
GTAGTACAAAGGGGGAGGTGCAGCTGTTGGAGTCTGGGGGAGGCTTGGTACAGCCTGGGGG
GTCCCTGAGACTCTCCTGTGCAGCCTCTGGATTCACCTTTGACGACTATGCCATGGCATGG
GTCCGCCAGGCTCCAGGGAAGGGGCTGGAGTGGGTCTCAGCTATTAGTGATGCAGGTGACA
GAACATACTACGCAGACTCCGTGAGGGGCCGGTTCACCATCTCCAGAGACAATTCCAAGAA
CACACTGTATCTGCAAATGAACAGCCTGAGAGCCGAGGACACGGCGGTGTACTACTGCGCA
AGAGCCGAGATGGGAGCCGTATTCGACATATGGGGTCAGGGTACAATGGTCACCGTCTCCT
CAGCCGCTGCCCTTGATAATGAAAAGTCAAACGGAACAATCATTCACGTGAAGGGCAAGCA
CCTCTGTCCGTCACCCTTGTTCCCTGGTCCATCCAAGCCATTCTGGGTGTTGGTCGTAGTG
GGTGGAGTCCTCGCTTGTTACTCTCTGCTCGTCACCGTGGCTTTTATAATCTTCTGGGTTA
GATCCAAAAGAAGCCGCCTGCTCCATAGCGATTACATGAATATGACTCCACGCCGCCCTGG
CCCCACAAGGAAACACTACCAGCCTTACGCACCACCTAGAGATTTCGCTGCCTATCGGAGC
AGGGTGAAGTTTTCCAGATCTGCAGATGCACCAGCGTATCAGCAGGGCCAGAACCAACTGT
ATAACGAGCTCAACCTGGGACGCAGGGAAGAGTATGACGTTTTGGACAAGCGCAGAGGACG
GGACCCTGAGATGGGTGGCAAACCAAGACGAAAAAACCCCCAGGAGGGTCTCTATAATGAG
CTGCAGAAGGATAAGATGGCTGAAGCCTATTCTGAAATAGGCATGAAAGGAGAGCGGAGAA
GGGGAAAAGGGCACGACGGTTTGTACCAGGGACTCAGCACTGCTACGAAGGATACTTATGA
CGCTCTCCACATGCAAGCCCTGCCACCTAGG

Clone FS-26528 CAR LxH (SEQ ID NO: 284)

MALPVTALLLPLALLLHAARPEIVLTQSPATLSLSPGERATLSCRASQSVSRYLAWYQQKP
GQAPRLLIYDASNRATGIPARFSGSGSGTDFTLTISSLEPEDFAVYYCQQRISWPFTFGGG
TKVEIKRGSTSGSGKPGSGEGSTKGEVQLLESGGGLVQPGGSLRLSCAASGFTFDDYAMAW
VRQAPGKGLEWVSAISDAGDRTYYADSVRGRFTISRDNSKNTLYLQMNSLRAEDTAVYYCA
RAEMGAVFDIWGQGTMVTVSSAAALDNEKSNGTIIHVKGKHLCPSPLFPGPSKPFWVLVVV
GGVLACYSLLVTVAFIIFWVRSKRSRLLHSDYMNMTPRRPGPTRKHYQPYAPPRDFAAYRS
RVKFSRSADAPAYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR

Clone PC-26534 HC DNA (SEQ ID NO: 285)

CAGGTGCAGCTGGTGGAGTCTGGGGGAGGCGTGGTCCAGCCTGGGAGGTCCCTGAGACTCT
CCTGTGCAGCGTCTGGATTCACCTTCAGTGAGCATGGCATGCACTGGGTCCGCCAGGCTCC
AGGCAAGGGGCTGGAGTGGGTGGCAGCTATATCTTATGATGGAAGGAATAAACACTATGCA
GACTCCGTGAAGGGCCGATTCACCATCTCCAGAGACAATTCCAAGAACACGCTGTATCTGC
AAATGAACAGCCTGAGAGCCGAGGACACGGCGGTGTACTACTGCGCCAGAGACGGTACTTA
TCTAGGTGGTCTCTGGTACTTCGACTTATGGGGGAGAGGTACCTTGGTCACCGTCTCCTCA

Clone PC-26534 HC. CDRs 1, 2, and 3 are underlined.

(SEQ ID NO: 286)

QVQLVESGGGVVQPGRSLRLSCAASGFTFSEHGMHWVRQAPGKGLEWVAAISYDGRNKHY
ADSVKGRFTISRDNSKNTLYLQMNSLRAEDTAVYYCARDGTYLGGLWYFDLWGRGTLVTVSS (SEQ ID NO: 287)

FTFSEHGMH [HC CDR1]

(SEQ ID NO: 288)

AISYDGRNKHYADSVKG [HC CDR2]

(SEQ ID NO: 289)

ARDGTYLGGLWYFDL [HC CDR3]

-continued

Clone PC-26534 LC DNA (SEQ ID NO: 290)

GATATTGTGATGACTCAGTCTCCACTCTCCCTGCCCGTCACCCCTGGAGAGCCGGCCTCCA
TCTCCTGCAGGTCTAGTCAGAGCCTCCTGCATAGTAATGGATACAACTATTTGGATTGGTA
CCTGCAGAAGCCAGGGCAGTCTCCACAGCTCCTGATCTATTTGGGTTCTAATCGGGCCTCC
GGGGTCCCTGACAGGTTCAGTGGCAGTGGATCAGGCACAGATTTTACACTGAAAATCAGCA
GAGTGGAGGCTGAGGATGTTGGGGTTTATTACTGCATGCAGGGACTCGGCCTCCCTCTCAC
TTTTGGCGGAGGGACCAAGGTTGAGATCAAACGG

Clone PC-26534 LC. CDRs 1, 2, and 3 are underlined.

(SEQ ID NO: 291)

DIVMTQSPLSLPVTPGEPASISCRSSQSLLHSNGYNYLDWYLQKPGQSPQLLIYLGSNRA
SGVPDRFSGSGSGTDFTLKISRVEAEDVGVYYCMQGLGLPLTFGGGTKVEIKR (SEQ ID NO: 292)

RSSQSLLHSNGYNYLD [LC CDR1]

(SEQ ID NO: 293)

LGSNRAS [LC CDR2]

(SEQ ID NO: 294)

MQGLGLPLT [LC CDR3]

Clone PC-26534 CAR DNA HxL (SEQ ID NO: 295)

ATGGCACTCCCCGTAACTGCTCTGCTGCTGCCGTTGGCATTGCTCCTGCACGCCGCACGCC
CGCAGGTGCAGCTGGTGGAGTCTGGGGGAGGCGTGGTCCAGCCTGGGAGGTCCCTGAGACT
CTCCTGTGCAGCGTCTGGATTCACCTTCAGTGAGCATGGCATGCACTGGGTCCGCCAGGCT
CCAGGCAAGGGGCTGGAGTGGGTGGCAGCTATATCTTATGATGGAAGGAATAAACACTATG
CAGACTCCGTGAAGGGCCGATTCACCATCTCCAGAGACAATTCCAAGAACACGCTGTATCT
GCAAATGAACAGCCTGAGAGCCGAGGACACGGCGGTGTACTACTGCGCCAGAGACGGTACT
TATCTAGGTGGTCTCTGGTACTTCGACTTATGGGGGAGAGGTACCTTGGTCACCGTCTCCT
CAGGGTCTACATCCGGCTCCGGGAAGCCCGGAAGTGGCGAAGGTAGTACAAAGGGGGATAT
TGTGATGACTCAGTCTCCACTCTCCCTGCCCGTCACCCCTGGAGAGCCGGCCTCCATCTCC
TGCAGGTCTAGTCAGAGCCTCCTGCATAGTAATGGATACAACTATTTGGATTGGTACCTGC
AGAAGCCAGGGCAGTCTCCACAGCTCCTGATCTATTTGGGTTCTAATCGGGCCTCCGGGGT
CCCTGACAGGTTCAGTGGCAGTGGATCAGGCACAGATTTTACACTGAAAATCAGCAGAGTG
GAGGCTGAGGATGTTGGGGTTTATTACTGCATGCAGGGACTCGGCCTCCCTCTCACTTTTG
GCGGAGGGACCAAGGTTGAGATCAAACGGGCCGCTGCCCTTGATAATGAAAAGTCAAACGG
AACAATCATTCACGTGAAGGGCAAGCACCTCTGTCCGTCACCCTTGTTCCCTGGTCCATCC
AAGCCATTCTGGGTGTTGGTCGTAGTGGGTGGAGTCCTCGCTTGTTACTCTCTGCTCGTCA
CCGTGGCTTTTATAATCTTCTGGGTTAGATCCAAAAGAAGCCGCCTGCTCCATAGCGATTA
CATGAATATGACTCCACGCCGCCCTGGCCCCACAAGGAAACACTACCAGCCTTACGCACCA
CCTAGAGATTTCGCTGCCTATCGGAGCAGGGTGAAGTTTTCCAGATCTGCAGATGCACCAG
CGTATCAGCAGGGCCAGAACCAACTGTATAACGAGCTCAACCTGGGACGCAGGGAAGAGTA
TGACGTTTTGGACAAGCGCAGAGGACGGGACCCTGAGATGGGTGGCAAACCAAGACGAAAA
AACCCCCAGGAGGGTCTCTATAATGAGCTGCAGAAGGATAAGATGGCTGAAGCCTATTCTG
AAATAGGCATGAAAGGAGAGCGGAGAAGGGGAAAAGGGCACGACGGTTTGTACCAGGGACT
CAGCACTGCTACGAAGGATACTTATGACGCTCTCCACATGCAAGCCCTGCCACCTAGG

Clone PC-26534 CAR HxL (SEQ ID NO: 296)

MALPVTALLLPLALLLHAARPQVQLVESGGGVVQPGRSLRLSCAASGFTFSEHGMHWVRQA
PGKGLEWVAAISYDGRNKHYADSVKGRFTISRDNSKNTLYLQMNSLRAEDTAVYYCARDGT
YLGGLWYFDLWGRGTLVTVSSGSTSGSGKPGSGEGSTKGDIVMTQSPLSLPVTPGEPASIS
CRSSQSLLHSNGYNYLDWYLQKPGQSPQLLIYLGSNRASGVPDRFSGSGSGTDFTLKISRV
EAEDVGVYYCMQGLGLPLTFGGGTKVEIKRAAALDNEKSNGTIIHVKGKHLCPSPLFPGPS
KPFWVLVVVGGVLACYSLLVTVAFIIFWVRSKRSRLLHSDYMNMTPRRPGPTRKHYQPYAP
PRDFAAYRSRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHMQALPPR

Clone PC-26534 CAR DNA LxH (SEQ ID NO: 297)

ATGGCACTCCCCGTAACTGCTCTGCTGCTGCCGTTGGCATTGCTCCTGCACGCCGCACGCC
CGGATATTGTGATGACTCAGTCTCCACTCTCCCTGCCCGTCACCCCTGGAGAGCCGGCCTC
CATCTCCTGCAGGTCTAGTCAGAGCCTCCTGCATAGTAATGGATACAACTATTTGGATTGG
TACCTGCAGAAGCCAGGGCAGTCTCCACAGCTCCTGATCTATTTGGGTTCTAATCGGGCCT
CCGGGGTCCCTGACAGGTTCAGTGGCAGTGGATCAGGCACAGATTTTACACTGAAAATCAG
CAGAGTGGAGGCTGAGGATGTTGGGGTTTATTACTGCATGCAGGGACTCGGCCTCCCTCTC
ACTTTTGGCGGAGGGACCAAGGTTGAGATCAAACGGGGGGTCTACATCCGGCTCCGGGAAGC
CCGGAAGTGGCGAAGGTAGTACAAAGGGGCAGGTGCAGCTGGTGGAGTCTGGGGGAGGCGT
GGTCCAGCCTGGGAGGTCCCTGAGACTCTCCTGTGCAGCGTCTGGATTCACCTTCAGTGAG
CATGGCATGCACTGGGTCCGCCAGGCTCCAGGCAAGGGGCTGGAGTGGGTGGCAGCTATAT
CTTATGATGGAAGGAATAAACACTATGCAGACTCCGTGAAGGGCCGATTCACCATCTCCAG
AGACAATTCCAAGAACACGCTGTATCTGCAAATGAACAGCCTGAGAGCCGAGGACACGGCG
GTGTACTACTGCGCCAGAGACGGTACTTATCTAGGTGGTCTCTGGTACTTCGACTTATGGG
GGAGAGGTACCTTGGTCACCGTCTCCTCAGCCGCTGCCCTTGATAATGAAAAGTCAAACGG
AACAATCATTCACGTGAAGGGCAAGCACCTCTGTCCGTCACCCTTGTTCCCTGGTCCATCC
AAGCCATTCTGGGTGTTGGTCGTAGTGGGTGGAGTCCTCGCTTGTTACTCTCTGCTCGTCA
CCGTGGCTTTTATAATCTTCTGGGTTAGATCCAAAAGAAGCCGCCTGCTCCATAGCGATTA
CATGAATATGACTCCACGCCGCCCTGGCCCCACAAGGAAACACTACCAGCCTTACGCACCA
CCTAGAGATTTCGCTGCCTATCGGAGCAGGGTGAAGTTTTCCAGATCTGCAGATGCACCAG
CGTATCAGCAGGGCCAGAACCAACTGTATAACGAGCTCAACCTGGGACGCAGGGAAGAGTA
TGACGTTTTGGACAAGCGCAGAGGACGGGACCCTGAGATGGGTGGCAAACCAAGACGAAAA

-continued

AACCCCCAGGAGGGTCTCTATAATGAGCTGCAGAAGGATAAGATGGCTGAAGCCTATTCTG
AAATAGGCATGAAAGGAGAGCGGAGAAGGGGAAAAGGGCACGACGGTTTGTACCAGGGACT
CAGCACTGCTACGAAGGATACTTATGACGCTCTCCACATGCAAGCCCTGCCACCTAGG

Clone PC-26534 CAR LxH (SEQ ID NO: 298)

MALPVTALLL PLALLLHAAR PDIVMTQSPL SLPVTPGEPA SISCRSSQSL
LHSNGYNYLD WYLQKPGQSP QLLIYLGSNR ASGVPDRFSG SGSGTDFTLK
ISRVEAEDVG VYYCMQGLGL PLTFGGGTKV EIKRGSTSGS GKPGSGEGST
KGQVQLVESG GGVVQPGRSL RLSCAASGFT FSEHGMHWVR QAPGKGLEWV
AAISYDGRNK HYADSVKGRF TISRDNSKNT LYLQMNSLRA EDTAVYYCAR
DGTYLGGLWY FDLWGRGTLV TVSSAAALDN EKSNGTIIHV KGKHLCPSPL
FPGPSKPFWV LVVVGGVLAC YSLLVTVAFI IFWVRSKRSR LLHSDYMNMT
PRRPGPTRKH YQPYAPPRDF AAYRSRVKFS RSADAPAYQQ GQNQLYNELN
LGRREEYDVL DKRRGRDPEM GGKPRRKNPQ EGLYNELQKD KMAEAYSEIG
MKGERRRGKG HDGLYQGLST ATKDTYDALH MQALPPR

Clone AJ-26545 HC DNA (SEQ ID NO: 299)

CAGGTGCAGCTGGTGCAGTCTGGGGCTGAGGTGAAGAAGCCTGGGGCCTCAGTGAAGGTTT
CCTGCAGGGCATCTGGATACACCTTCATGGAGCACTATATGCACTGGGTGCGACAGGCCCC
TGGACAAGGGCTTGAGTGGATGGGAGTAATCGGGCCTAGTGGTGGTAAGACAAGCTACGCA
CAGAAGTTCCAGGGCAGAGTCACCATGACCAGGGACACGTCCACGAGCACAGTCTACATGG
AGCTGAGCAGCCTGAGATCTGAGGACACGGCGGTGTACTACTGCGCCAGAGAGAATTGGCC
AATGGACGTATGGGGCCAGGGAACAACTGTCACCGTCTCCTCA

Clone AJ-26545 HC. CDRs 1, 2, and 3 are underlined.

(SEQ ID NO: 300)

QVQLVQSGAEVKKPGASVKVSCRASGYTFMEHYMHWVRQAPGQGLEWMGVIGPSGGKTSY
AQKFQGRVTMTRDTSTSTVYMELSSLRSEDTAVYYCARESWPMDVWGQGTTVTVSS (SEQ ID NO: 301)

YTFMEHYMH (HC CDR1)

(SEQ ID NO: 302)

VIGPSGGKTSYAQKFQG (HC CDR2)

(SEQ ID NO: 303)

ARESWPMDV (HC CDR3)

Clone AJ-26545 LC DNA (SEQ ID NO: 304)

GAAATAGTGATGACGCAGTCTCCAGCCACCCTGTCTGTGTCTCCAGGGGAAAGAGCCACCC
TCTCCTGCAGGGCCAGTCAGAGTGTTAGCAGCAACTTAGCCTGGTACCAGCAGAAACCTGG
CCAGGCTCCCAGGCTCCTCATCTATGGTGCATCCACCAGGGCCACTGGTATCCCAGCCAGG
TTCAGTGGCAGTGGGTCTGGGACAGAGTTCACTCTCACCATCAGCAGCCTGCAGTCTGAAG
ATTTTGCAGTTTATTACTGTCAGCAGTACGCCGCCTACCCTACTTTTGGCGGAGGGACCAA
GGTTGAGATCAAACGG

Clone AJ-26545 LC. CDRs 1, 2, and 3 are underlined.

(SEQ ID NO: 305)

EIVMTQSPATLSVSPGERATLSCRASQSVSSNLAWYQQKPGQAPRLLIYGASTRATGIPAR
FSGSGSGTEFTLTISSLQSEDFAVYYCQQYAAYPTFGGGTKVEIKR (SEQ ID NO: 306)

RASQSVSSNLA (LC CDR1)

(SEQ ID NO: 307)

GASTRAT (LC CDR2)

(SEQ ID NO: 308)

QQYAAYPT (LC CDR3)

Clone AJ-26545 CAR DNA HxL (SEQ ID NO: 309)

ATGGCACTCCCCGTAACTGCTCTGCTGCTGCCGTTGGCATTGCTCCTGCACGCCGCACGCC
CGCAGGTGCAGCTGGTGCAGTCTGGGGCTGAGGTGAAGAAGCCTGGGGCCTCAGTGAAGGT
TTCCTGCAGGGCATCTGGATACACCTTCATGGAGCACTATATGCACTGGGTGCGACAGGCC
CCTGGACAAGGGCTTGAGTGGATGGGAGTAATCGGGCCTAGTGGTGGTAAGACAAGCTACG
CACAGAAGTTCCAGGGCAGAGTCACCATGACCAGGGACACGTCCACGAGCACAGTCTACAT
GGAGCTGAGCAGCCTGAGATCTGAGGACACGGCGGTGTACTACTGCGCCAGAGAGAATTGG
CCAATGGACGTATGGGGCCAGGGAACAACTGTCACCGTCTCCTCAGGGTCTACATCCGGCT
CCGGGAAGCCCGGAAGTGGCGAAGGTAGTACAAAGGGGGAAATAGTGATGACGCAGTCTCC
AGCCACCCTGTCTGTGTCTCCAGGGGAAAGAGCCACCCTCTCCTGCAGGGCCAGTCAGAGT
GTTAGCAGCAACTTAGCCTGGTACCAGCAGAAACCTGGCCAGGCTCCCAGGCTCCTCATCT
ATGGTGCATCCACCAGGGCCACTGGTATCCCAGCCAGGTTCAGTGGCAGTGGGTCTGGGAC
AGAGTTCACTCTCACCATCAGCAGCCTGCAGTCTGAAGATTTTGCAGTTTATTACTGTCAG
CAGTACGCCGCCTACCCTACTTTTGGCGGAGGGACCAAGGTTGAGATCAAACGGGCCGCTG
CCCTTGATAATGAAAAGTCAAACGGAACAATCATTCACGTGAAGGGCAAGCACCTCTGTCC
GTCACCCTTGTTCCCTGGTCCATCCAAGCCATTCTGGGTGTTGGTCGTAGTGGGTGGAGTC
CTCGCTTGTTACTCTCTGCTCGTCACCGTGGCTTTTATAATCTTCTGGGTTAGATCCAAAA
GAAGCCGCCTGCTCCATAGCGATTACATGAATATGACTCCACGCCGCCCTGGCCCCACAAG
GAAACACTACCAGCCTTACGCACCACCTAGAGATTTCGCTGCCTATCGGAGCAGGGTGAAG
TTTTCCAGATCTGCAGATGCACCAGCGTATCAGCAGGGCCAGAACCAACTGTATAACGAGC
TCAACCTGGGACGCAGGGAAGAGTATGACGTTTTGGACAAGCGCAGAGGACGGGACCCTGA
GATGGGTGGCAAACCAAGACGAAAAAACCCCCAGGAGGGTCTCTATAATGAGCTGCAGAAG
GATAAGATGGCTGAAGCCTATTCTGAAATAGGCATGAAAGGAGAGCGGAGAAGGGGAAAAG

-continued

GGCACGACGGTTTGTACCAGGGACTCAGCACTGCTACGAAGGATACTTATGACGCTCTCCA
CATGCAAGCCCTGCCACCTAGG

Clone AJ-26545 CAR HxL (SEQ ID NO: 310)

MALPVTALLL PLALLLHAAR PQVQLVQSGA EVKKPGASVK VSCRASGYTF
MEHYMHWVRQ APGQGLEWMG VIGPSGGKTS YAQKFQGRVT MTRDTSTSTV
YMELSSLRSE DTAVYYCARE SWPMDVWGQG TTVTVSSGST SGSGKPGSGE
GSTKGEIVMT QSPATLSVSP GERATLSCRA SQSVSSNLAW YQQKPGQAPR
LLIYGASTRA TGIPARFSGS GSGTEFTLTI SSLQSEDFAV YYCQQYAAYP
TFGGGTKVEI KRAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

Clone AJ-26545 CAR DNA LxH (SEQ ID NO: 311)

ATGGCACTCCCCGTAACTGCTCTGCTGCTGCCGTTGGCATTGCTCCTGCACGCCGCACGCC
CGGAAATAGTGATGACGCAGTCTCCAGCCACCCTGTCTGTGTCTCCAGGGGAAAGAGCCAC
CCTCTCCTGCAGGGCCAGTCAGAGTGTTAGCAGCAACTTAGCCTGGTACCAGCAGAAACCT
GGCCAGGCTCCCAGGCTCCTCATCTATGGTGCATCCACCAGGGCCACTGGTATCCCAGCCA
GGTTCAGTGGCAGTGGGTCTGGGACAGAGTTCACTCTCACCATCAGCAGCCTGCAGTCTGA
AGATTTTGCAGTTTATTACTGTCAGCAGTACGCCGCCTACCCTACTTTTGGCGGAGGGACC
AAGGTTGAGATCAAACGGGGGTCTACATCCGGCTCCGGGAAGCCCGGAAGTGGCGAAGGTA
GTACAAAGGGGCAGGTGCAGCTGGTGCAGTCTGGGGCTGAGGTGAAGAAGCCTGGGGCCTC
AGTGAAGGTTTCCTGCAGGGCATCTGGATACACCTTCATGGAGCACTATATGCACTGGGTG
CGACAGGCCCCTGGACAAGGGCTTGAGTGGATGGGAGTAATCGGGCCTAGTGGTGGTAAGA
CAAGCTACGCACAGAAGTTCCAGGGCAGAGTCACCATGACCAGGGACACGTCCACGAGCAC
AGTCTACATGGAGCTGAGCAGCCTGAGATCTGAGGACACGGCGGTGTACTACTGCGCCAGA
GAGAATTGGCCAATGGACGTATGGGGCCAGGGAACAACTGTCACCGTCTCCTCAGCCGCTG
CCCTTGATAATGAAAAGTCAAACGGAACAATCATTCACGTGAAGGGCAAGCACCTCTGTCC
GTCACCCTTGTTCCCTGGTCCATCCAAGCCATTCTGGGTGTTGGTCGTAGTGGGTGGAGTC
CTCGCTTGTTACTCTCTGCTCGTCACCGTGGCTTTTATAATCTTCTGGGTTAGATCCAAAA
GAAGCCGCCTGCTCCATAGCGATTACATGAATATGACTCCACGCCGCCCTGGCCCCACAAG
GAAACACTACCAGCCTTACGCACCACCTAGAGATTTCGCTGCCTATCGGAGCAGGGTGAAG
TTTTCCAGATCTGCAGATGCACCAGCGTATCAGCAGGGCCAGAACCAACTGTATAACGAGC
TCAACCTGGGACGCAGGGAAGAGTATGACGTTTTGGACAAGCGCAGAGGACGGGACCCTGA
GATGGGTGGCAAACCAAGACGAAAAAACCCCCAGGAGGGTCTCTATAATGAGCTGCAGAAG
GATAAGATGGCTGAAGCCTATTCTGAAATAGGCATGAAAGGAGAGCGGAGAAGGGGAAAAG
GGCACGACGGTTTGTACCAGGGACTCAGCACTGCTACGAAGGATACTTATGACGCTCTCCA
CATGCAAGCCCTGCCACCTAGG

Clone AJ-26545 CAR LxH (SEQ ID NO: 312)

MALPVTALLL PLALLLHAAR PEIVMTQSPA TLSVSPGERA TLSCRASQSV
SSNLAWYQQK PGQAPRLLIY GASTRATGIP ARFSGSGSGT EFTLTISSLQ
SEDFAVYYCQ QYAAYPTFGG GTKVEIKRGS TSGSGKPGSG EGSTKGQVQL
VQSGAEVKKP GASVKVSCRA SGYTFMEHYM HWVRQAPGQG LEWMGVIGPS
GGKTSYAQKF QGRVTMTRDT STSTVYMELS SLRSEDTAVY YCARESWPMD
VWGQGTTVTV SSAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

Clone AJ-26554 HC DNA (SEQ ID NO: 313)

CAGGTGCAGCTGGTGCAGTCTGGGGCTGAGGTGAAGAAGCCTGGGGCCTCAGTGAAGGTTT
CCTGCAAGGCATCTGGATACACCTTCACGGAGCACTATATGCACTGGGTGCGACAGGCCCC
TGGACAAAGGCTTGAGTGGATGGGAGTAATCGGGCCTAGTGGTGGTAAGACAAGCTACGCA
CAGAAGTTCCAGGGCAGAGTCACCATGACCAGGGACACGTCCACGAGCACAGTCTACATGG
AGCTGAGCAGCCTGAGATCTGAGGACACGGCGGTGTACTACTGCGCCAGAGAGAGTTGGCC
AATGGACGTATGGGGCCAGGGAACAACTGTCACCGTCTCCTCA

Clone AJ-26554 HC. CDRs 1, 2, and 3 are underlined.

(SEQ ID NO: 314)

QVQLVQSGAE VKKPGASVKV SCKASGYTFT EHYMHWVRQA PGQRLEWMGV
IGPSGGKTSY AQKFQGRVTM TRDTSTSTVY MELSSLRSED TAVYYCARES
WPMDVWGQGT TVTVSS (SEQ ID NO: 315)

YTFTEHYMH (HC CDR1)

(SEQ ID NO: 316)

VIGPSGGKTSYAQKFQG (HC CDR2)

(SEQ ID NO: 317)

ARESWPMDV (HC CDR3)

Clone AJ-26554 LC DNA (SEQ ID NO: 318)

GAAATAGTGATGACGCAGTCTCCAGCCACCCTGTCTGTGTCTCCAGGGGAAAGAGCCACCC
TCTCCTGCAGGGCCAGTCAGAGTGTTAGCAGCAACTTAGCCTGGTACCAGCAGAAACCTGG

-continued

CCAGGCTCCCAGGCTCCTCATCTATGGTGCATCCACCAGGGCCACTGGTATCCCAGCCAGG
TTCAGTGGCAGTGGGTCTGGGACAGAGTTCACTCTCACCATCAGCAGCCTGCAGTCTGAAG
ATTTTGCAGTTTATTACTGTCAGCAGTACGCCGCCTACCCTACTTTTGGCGGAGGGACCAA
GGTTGAGATCAAACGG

Clone AJ-26554 LC. CDRs 1, 2, and 3 are underlined.

(SEQ ID NO: 319)
EIVMTQSPATLSVSPGERATLSCRASQSVSSNLAWYQQKPGQAPRLLIYGASTRATGIPA
RFSGSGSGTEFTLTISSLQSEDFAVYYCQQYAAYPTFGGGTKVEIKR (SEQ ID NO: 320)
RASQSVSSNLA (LC CDR1)

(SEQ ID NO: 321)
GASTRAT (LC CDR2)

(SEQ ID NO: 322)
QQYAAYPT (LC CDR3)

Clone AJ-26554 CAR DNA HxL (SEQ ID NO: 323)
ATGGCACTCCCCGTAACTGCTCTGCTGCTGCCGTTGGCATTGCTCCTGCACGCCGCACGCC
CGCAGGTGCAGCTGGTGCAGTCTGGGGCTGAGGTGAAGAAGCCTGGGGCCTCAGTGAAGGT
TTCCTGCAAGGCATCTGGATACACCTTCACGGAGCACTATATGCACTGGGTGCGACAGGCC
CCTGGACAAAGGCTTGAGTGGATGGGAGTAATCGGGCCTAGTGGTGGTAAGACAAGCTACG
CACAGAAGTTCCAGGGCAGAGTCACCATGACCAGGGACACGTCCACGAGCACAGTCTACAT
GGAGCTGAGCAGCCTGAGATCTGAGGACACGGCGGTGTACTACTGCGCCAGAGAGAGTTGG
CCAATGGACGTATGGGGCCAGGGAACAACTGTCACCGTCTCCTCAGGGTCTACATCCGGCT
CCGGGAAGCCCGGAAGTGGCGAAGGTAGTACAAAGGGGGAAATAGTGATGACGCAGTCTCC
AGCCACCCTGTCTGTGTCTCCAGGGGAAAGAGCCACCCTCTCCTGCAGGGCCAGTCAGAGT
GTTAGCAGCAACTTAGCCTGGTACCAGCAGAAACCTGGCCAGGCTCCCAGGCTCCTCATCT
ATGGTGCATCCACCAGGGCCACTGGTATCCCAGCCAGGTTCAGTGGCAGTGGGTCTGGGAC
AGAGTTCACTCTCACCATCAGCAGCCTGCAGTCTGAAGATTTTGCAGTTTATTACTGTCAG
CAGTACGCCGCCTACCCTACTTTTGGCGGAGGGACCAAGGTTGAGATCAAACGGGCCGCTG
CCCTTGATAATGAAAAGTCAAACGGAACAATCATTCACGTGAAGGGCAAGCACCTCTGTCC
GTCACCCTTGTTCCCTGGTCCATCCAAGCCATTCTGGGTGTTGGTCGTAGTGGGTGGAGTC
CTCGCTTGTTACTCTCTGCTCGTCACCGTGGCTTTTATAATCTTCTGGGTTAGATCCAAAA
GAAGCCGCCTGCTCCATAGCGATTACATGAATATGACTCCACGCCGCCCTGGCCCCACAAG
GAAACACTACCAGCCTTACGCACCACCTAGAGATTTCGCTGCCTATCGGAGCAGGGTGAAG
TTTTCCAGATCTGCAGATGCACCAGCGTATCAGCAGGGCCAGAACCAACTGTATAACGAGC
TCAACCTGGGACGCAGGGAAGAGTATGACGTTTTGGACAAGCGCAGAGGACGGGACCCTGA
GATGGGTGGCAAACCAAGACGAAAAAACCCCCAGGAGGGTCTCTATAATGAGCTGCAGAAG
GATAAGATGGCTGAAGCCTATTCTGAAATAGGCATGAAAGGAGAGCGGAGAAGGGGAAAAG
GGCACGACGGTTTGTACCAGGGACTCAGCACTGCTACGAAGGATACTTATGACGCTCTCCA
CATGCAAGCCCTGCCACCTAGG Clone AJ-26554 CAR HxL (SEQ ID NO: 324)
MALPVTALLL PLALLLHAAR PQVQLVQSGA EVKKPGASVK VSCKASGYTF
TEHYMHWVRQ APGQRLEWMG VIGPSGGKTS YAQKFQGRVT MTRDTSTSTV
YMELSSLRSE DTAVYYCARE SWPMDVWGQG TTVTVSSGST SGSGKPGSGE
GSTKGEIVMT QSPATLSVSP GERATLSCRA SQSVSSNLAW YQQKPGQAPR
LLIYGASTRA TGIPARFSGS GSGTEFTLTI SSLQSEDFAV YYCQQYAAYP
TFGGGTKVEI KRAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR Clone AJ-26554 CAR DNA LxH (SEQ ID NO: 325)
ATGGCACTCCCCGTAACTGCTCTGCTGCTGCCGTTGGCATTGCTCCTGCACGCCGCACGCC
CGGAAATAGTGATGACGCAGTCTCCAGCCACCCTGTCTGTGTCTCCAGGGGAAAGAGCCAC
CCTCTCCTGCAGGGCCAGTCAGAGTGTTAGCAGCAACTTAGCCTGGTACCAGCAGAAACCT
GGCCAGGCTCCCAGGCTCCTCATCTATGGTGCATCCACCAGGGCCACTGGTATCCCAGCCA
GGTTCAGTGGCAGTGGGTCTGGGACAGAGTTCACTCTCACCATCAGCAGCCTGCAGTCTGA
AGATTTTGCAGTTTATTACTGTCAGCAGTACGCCGCCTACCCTACTTTTGGCGGAGGGACC
AAGGTTGAGATCAAACGGGGGGTCTACATCCGGCTCCGGGAAGCCCGGAAGTGGCGAAGGTA
GTACAAAGGGGCAGGTGCAGCTGGTGCAGTCTGGGGCTGAGGTGAAGAAGCCTGGGGCCTC
AGTGAAGGTTTCCTGCAAGGCATCTGGATACACCTTCACGGAGCACTATATGCACTGGGTG
CGACAGGCCCCTGGACAAAGGCTTGAGTGGATGGGAGTAATCGGGCCTAGTGGTGGTAAGA
CAAGCTACGCACAGAAGTTCCAGGGCAGAGTCACCATGACCAGGGACACGTCCACGAGCAC
AGTCTACATGGAGCTGAGCAGCCTGAGATCTGAGGACACGGCGGTGTACTACTGCGCCAGA
GAGAGTTGGCCAATGGACGTATGGGGCCAGGGAACAACTGTCACCGTCTCCTCAGCCGCTG
CCCTTGATAATGAAAAGTCAAACGGAACAATCATTCACGTGAAGGGCAAGCACCTCTGTCC
GTCACCCTTGTTCCCTGGTCCATCCAAGCCATTCTGGGTGTTGGTCGTAGTGGGTGGAGTC
CTCGCTTGTTACTCTCTGCTCGTCACCGTGGCTTTTATAATCTTCTGGGTTAGATCCAAAA
GAAGCCGCCTGCTCCATAGCGATTACATGAATATGACTCCACGCCGCCCTGGCCCCACAAG
GAAACACTACCAGCCTTACGCACCACCTAGAGATTTCGCTGCCTATCGGAGCAGGGTGAAG
TTTTCCAGATCTGCAGATGCACCAGCGTATCAGCAGGGCCAGAACCAACTGTATAACGAGC
TCAACCTGGGACGCAGGGAAGAGTATGACGTTTTGGACAAGCGCAGAGGACGGGACCCTGA
GATGGGTGGCAAACCAAGACGAAAAAACCCCCAGGAGGGTCTCTATAATGAGCTGCAGAAG -continued GATAAGATGGCTGAAGCCTATTCTGAAATAGGCATGAAAGGAGAGCGGAGAAGGGGAAAAG
GGCACGACGGTTTGTACCAGGGACTCAGCACTGCTACGAAGGATACTTATGACGCTCTCCA
CATGCAAGCCCTGCCACCTAGG Clone AJ-26554 CAR LxH (SEQ ID NO: 326)

MALPVTALLL PLALLLHAAR PEIVMTQSPA TLSVSPGERA TLSCRASQSV
SSNLAWYQQK PGQAPRLLIY GASTRATGIP ARFSGSGSGT EFTLTISSLQ
SEDFAVYYCQ QYAAYPTFGG GTKVEIKRGS TSGSGKPGSG EGSTKGQVQL
VQSGAEVKKP GASVKVSCKA SGYTFTEHYM HWVRQAPGQR LEWMGVIGPS
GGKTSYAQKF QGRVTMTRDT STSTVYMELS SLRSEDTAVY YCARESWPMD
VWGQGTTVTV SSAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

Clone NM-26562 HC DNA (SEQ ID NO: 327)

CAGGTGCAGCTGCAGGAGTCGGGCCCAGGACTGGTGAAGCCTTCACAGACCCTGTCCCTCA
CCTGTACTGTCTCTGGTGGCTCCATCGGGAGTGGTGGTAGTTACTGGAGCTGGATCCGCCA
GCACCCAGGGAAGGGCCTGGAGTGGATTGGGTTGATCTATTACGATGGGAGCACCTACTAC
AACCCGTCCCTCAAGAGTCGAGTTACCATATCAGTAGACACGTCTAAGAACCAGTTCTCCC
TGAAGCTGAGTTCTGTGACCGCCGCAGACACGGCGGTGTACTACTGCGCCAGAGGCAGGGG
ATATGAGACTTCTTTAGCCTTCGATATCTGGGGTCAGGGTACAATGGTCACCGTCTCCTCA

Clone NM-26562 HC. CDRs 1, 2, and 3 are underlined.

(SEQ ID NO: 328)

QVQLQESGPGLVKPSQTLSLTCTVSG<u>GSIGSGGSYWS</u>WIRQHPGKGLEWIG<u>LIYYDGSTY
YNPSLKS</u>RVTISVDTSKNQFSLKLSSVTAADTAVYYC<u>ARGRGYETSLAFDI</u>WGQGTMVTVS
S (SEQ ID NO: 329)

GSIGSGGSYWS (HC CDR1)

(SEQ ID NO: 330)

LIYYDGSTYYNPSLKS (HC CDR2)

(SEQ ID NO: 331)

ARGRGYETSLAFDI (HC CDR3)

Clone NM-26562 LC DNA (SEQ ID NO: 332)

GAAATTGTGTTGACACAGTCTCCAGCCACCCTGTCTTTGTCTCCAGGGGAAAGAGCCACCC
TCTCCTGCAGGGCCAGTCAGAGTGTTAGCAGCTACTTAGCCTGGTACCAACAGAAACCTGG
CCAGGCTCCCAGGCTCCTCATCTATGATGCATCCAACAGGGCCACTGGCATCCCAGCCAGG
TTCAGTGGCAGTGGGTCTGGGACAGACTTCACTCTCACCATCAGCAGCCTAGAGCCTGAAG
ATTTTGCAGTTTATTACTGTCAGCAGAGACACGTCTGGCCTCCTACTTTTGGCGGAGGGAC
CAAGGTTGAGATCAAACGG

Clone NM-26562 LC. CDRs 1, 2, and 3 are underlined.

(SEQ ID NO: 333)

EIVLTQSPATLSLSPGERATLSC<u>RASQSVSSYLA</u>WYQQKPGQAPRLLIY<u>DASNRAT</u>GIPA
RFSGSGSGTDFTLTISSLEPEDFAVYYC<u>QQRHVWPPT</u>FGGGTKVEIKR (SEQ ID NO: 334)

RASQSVSSYLA (LC CDR1)

(SEQ ID NO: 335)

DASNRAT (LC CDR2)

(SEQ ID NO: 336)

QQRHVWPPT (LC CDR3)

Clone NM-26562 CAR DNA HxL (SEQ ID NO: 337)

ATGGCACTCCCCGTAACTGCTCTGCTGCTGCCGTTGGCATTGCTCCTGCACGCCGCACGCC
CGCAGGTGCAGCTGCAGGAGTCGGGCCCAGGACTGGTGAAGCCTTCACAGACCCTGTCCCT
CACCTGTACTGTCTCTGGTGGCTCCATCGGGAGTGGTGGTAGTTACTGGAGCTGGATCCGC
CAGCACCCAGGGAAGGGCCTGGAGTGGATTGGGTTGATCTATTACGATGGGAGCACCTACT
ACAACCCGTCCCTCAAGAGTCGAGTTACCATATCAGTAGACACGTCTAAGAACCAGTTCTC
CCTGAAGCTGAGTTCTGTGACCGCCGCAGACACGGCGGTGTACTACTGCGCCAGAGGCAGG
GGATATGAGACTTCTTTAGCCTTCGATATCTGGGGTCAGGGTACAATGGTCACCGTCTCCT
CAGGGTCTACATCCGGCTCCGGGAAGCCCGGAAGTGGCGAAGGTAGTACAAAGGGGGAAAT
TGTGTTGACACAGTCTCCAGCCACCCTGTCTTTGTCTCCAGGGGAAAGAGCCACCCTCTCC
TGCAGGGCCAGTCAGAGTGTTAGCAGCTACTTAGCCTGGTACCAACAGAAACCTGGCCAGG
CTCCCAGGCTCCTCATCTATGATGCATCCAACAGGGCCACTGGCATCCCAGCCAGGTTCAG
TGGCAGTGGGTCTGGGACAGACTTCACTCTCACCATCAGCAGCCTAGAGCCTGAAGATTTT
GCAGTTTATTACTGTCAGCAGAGACACGTCTGGCCTCCTACTTTTGGCGGAGGGACCAAGG
TTGAGATCAAACGGGCCGCTGCCCTTGATAATGAAAAGTCAAACGGAACAATCATTCACGT
GAAGGGCAAGCACCTCTGTCCGTCACCCTTGTTCCCTGGTCCATCCAAGCCATTCTGGGTG
TTGGTCGTAGTGGGTGGAGTCCTCGCTTGTTACTCTCTGCTCGTCACCGTGGCTTTTATAA
TCTTCTGGGTTAGATCCAAAAGAAGCCGCCTGCTCCATAGCGATTACATGAATATGACTCC
ACGCCGCCCTGGCCCCACAAGGAAACACTACCAGCCTTACGCACCACCTAGAGATTTCGCT
GCCTATCGGAGCAGGGTGAAGTTTTCCAGATCTGCAGATGCACCAGCGTATCAGCAGGGCC
AGAACCAACTGTATAACGAGCTCAACCTGGGACGCAGGGAAGAGTATGACGTTTTGGACAA
GCGCAGAGGACGGGACCCTGAGATGGGTGGCAAACCAAGACGAAAAAACCCCCAGGAGGGT

-continued

CTCTATAATGAGCTGCAGAAGGATAAGATGGCTGAAGCCTATTCTGAAATAGGCATGAAAG
GAGAGCGGAGAAGGGGAAAAGGGCACGACGGTTTGTACCAGGGACTCAGCACTGCTACGAA
GGATACTTATGACGCTCTCCACATGCAAGCCCTGCCACCTAGG

Clone NM-26562 CAR HxL (SEQ ID NO: 338)

MALPVTALLL PLALLLHAAR PQVQLQESGP GLVKPSQTLS LTCTVSGGSI
GSGGSYWSWI RQHPGKGLEW IGLIYYDGST YYNPSLKSRV TISVDTSKNQ
FSLKLSSVTA ADTAVYYCAR GRGYETSLAF DIWGQGTMVT VSSGSTSGSG
KPGSGEGSTK GEIVLTQSPA TLSLSPGERA TLSCRASQSV SSYLAWYQQK
PGQAPRLLIY DASNRATGIP ARFSGSGSGT DFTLTISSLE PEDFAVYYCQ
QRHVWPPTFG GGTKVEIKRA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

Clone NM-26562 CAR DNA LxH (SEQ ID NO: 339)

ATGGCACTCCCCGTAACTGCTCTGCTGCTGCCGTTGGCATTGCTCCTGCACGCCGCACGCC
CGGAAATTGTGTTGACACAGTCTCCAGCCACCCTGTCTTTGTCTCCAGGGGAAAGAGCCAC
CCTCTCCTGCAGGGCCAGTCAGAGTGTTAGCAGCTACTTAGCCTGGTACCAACAGAAACCT
GGCCAGGCTCCCAGGCTCCTCATCTATGATGCATCCAACAGGGCCACTGGCATCCCAGCCA
GGTTCAGTGGCAGTGGGTCTGGGACAGACTTCACTCTCACCATCAGCAGCCTAGAGCCTGA
AGATTTTGCAGTTTATTACTGTCAGCAGAGACACGTCTGGCCTCCTACTTTTGGCGGAGGG
ACCAAGGTTGAGATCAAACGGGGGTCTACATCCGGCTCCGGGAAGCCCGGAAGTGGCGAAG
GTAGTACAAAGGGGCAGGTGCAGCTGCAGGAGTCGGGCCCAGGACTGGTGAAGCCTTCACA
GACCCTGTCCCTCACCTGTACTGTCTCTGGTGGCTCCATCGGGAGTGGTGGTAGTTACTGG
AGCTGGATCCGCCAGCACCCAGGGAAGGGCCTGGAGTGGATTGGGTTGATCTATTACGATG
GGAGCACCTACTACAACCCGTCCCTCAAGAGTCGAGTTACCATATCAGTAGACACGTCTAA
GAACCAGTTCTCCCTGAAGCTGAGTTCTGTGACCGCCGCAGACACGGCGGTGTACTACTGC
GCCAGAGGCAGGGGATATGAGACTTCTTTAGCCTTCGATATCTGGGGTCAGGGTACAATGG
TCACCGTCTCCTCAGCCGCTGCCCTTGATAATGAAAAGTCAAACGGAACAATCATTCACGT
GAAGGGCAAGCACCTCTGTCCGTCACCCTTGTTCCCTGGTCCATCCAAGCCATTCTGGGTG
TTGGTCGTAGTGGGTGGAGTCCTCGCTTGTTACTCTCTGCTCGTCACCGTGGCTTTTATAA
TCTTCTGGGTTAGATCCAAAAGAAGCCGCCTGCTCCATAGCGATTACATGAATATGACTCC
ACGCCGCCCTGGCCCCACAAGGAAACACTACCAGCCTTACGCACCACCTAGAGATTTCGCT
GCCTATCGGAGCAGGGTGAAGTTTTCCAGATCTGCAGATGCACCAGCGTATCAGCAGGGCC
AGAACCAACTGTATAACGAGCTCAACCTGGGACGCAGGGAAGAGTATGACGTTTTGGACAA
GCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAG
GAGAGCGGAGAAGGGGAAAAGGGCACGACGGTTTGTACCAGGGACTCAGCACTGCTACGAA
GGATACTTATGACGCTCTCCACATGCAAGCCCTGCCACCTAGG

Clone NM-26562 CAR LxH (SEQ ID NO: 340)

MALPVTALLL PLALLLHAAR PEIVLTQSPA TLSLSPGERA TLSCRASQSV
SSYLAWYQQK PGQAPRLLIY DASNRATGIP ARFSGSGSGT DFTLTISSLE
PEDFAVYYCQ QRHVWPPTFG GGTKVEIKRG STSGSGKPGS GEGSTKGQVQ
LQESGPGLVK PSQTLSLTCT VSGGSIGSGG SYWSWIRQHP GKGLEWIGLI
YYDGSTYYNP SLKSRVTISV DTSKNQFSLK LSSVTAADTA VYYCARGRGY
ETSLAFDIWG QGTMVTVSSA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

Clone TS-26564 HC DNA (SEQ ID NO: 341)

GAGGTGCAGCTGGTGGAGTCTGGGGGAGGCTTGGTACAGCCTGGGGGGTCCCTGAGACTCT
CCTGTGCAGCCTCTGGATTCACCTTCAGTAGCTATAGCATGAACTGGGTCCGCCAGGCTCC
AGGGAAGGGGCTGGAGTGGGTTTCAACCATTAGTAGTAGTAGTAGTATCATATACTACGCA
GACTCTGTGAAGGGCCGATTCACCATCTCCAGAGACAATGCCAAGAACTCACTGTATCTGC
AAATGAACAGCCTGAGAGCTGAGGACACGGCGGTGTACTACTGCGCCAGAGGTTCTCAGGA
GCACCTGATTTTCGATTATTGGGGACAGGGTACATTGGTCACCGTCTCCTCA

Clone TS-26564 HC. CDRs 1, 2, and 3 are underlined.

(SEQ ID NO: 342)

EVQLVESGGGLVQPGGSLRLSCAASGFTFSSYSMNWVRQAPGKGLEWVSTISSSSSIIYY
ADSVKGRFTISRDNAKNSLYLQMNSLRAEDTAVYYCARGSQEHLIFDYWGQGTLVTVSS (SEQ ID NO: 343)

FTFSSYSMN (HC CDR1)

(SEQ ID NO: 344)

TISSSSSIIYYADSVKG (HC CDR2)

(SEQ ID NO: 345)

ARGSQEHLIFDY (HC CDR3)

Clone TS-26564 LC DNA (SEQ ID NO: 346)

GAAATTGTGTTGACACAGTCTCCAGCCACCCTGTCTTTGTCTCCAGGGGAAAGAGCCACCC
TCTCCTGCAGGGCCAGTCAGAGTGTTAGCAGGTACTTAGCCTGGTACCAACAGAAACCTGG

-continued

CCAGGCTCCCAGGCTCCTCATCTATGATGCATCCAACAGGGCCACTGGCATCCCAGCCAGG
TTCAGTGGCAGTGGGTCTGGGACAGACTTCACTCTCACCATCAGCAGCCTAGAGCCTGAAG
ATTTTGCAGTTTATTACTGTCAGCAGAGATTCTACTACCCTTGGACTTTTGGCGGAGGGAC
CAAGGTTGAGATCAAACGG

Clone TS-26564 LC. CDRs 1, 2, and 3 are underlined.

(SEQ ID NO: 347)
EIVLTQSPATLSLSPGERATLSCRASQSVSRYLAWYQQKPGQAPRLLIYDASNRATGIPA
RFSGSGSGTDFTLTISSLEPEDFAVYYCQQRFYYPWTFGGGTKVEIKR (SEQ ID NO: 348)
RASQSVSRYLA (LC CDR1)

(SEQ ID NO: 349)
DASNRAT (LC CDR2)

(SEQ ID NO: 350)
QQRFYYPWT (LC CDR3)

Clone TS-26564 CAR DNA HxL (SEQ ID NO: 351)
ATGGCACTCCCCGTAACTGCTCTGCTGCTGCCGTTGGCATTGCTCCTGCACGCCGCACGCC
CGGAGGTGCAGCTGGTGGAGTCTGGGGGAGGCTTGGTACAGCCTGGGGGGTCCCTGAGACT
CTCCTGTGCAGCCTCTGGATTCACCTTCAGTAGCTATAGCATGAACTGGGTCCGCCAGGCT
CCAGGGAAGGGGCTGGAGTGGGTTTCAACCATTAGTAGTAGTAGTAGTATCATATACTACG
CAGACTCTGTGAAGGGCCGATTCACCATCTCCAGAGACAATGCCAAGAACTCACTGTATCT
GCAAATGAACAGCCTGAGAGCTGAGGACACGGCGGTGTACTACTGCGCCAGAGGTTCTCAG
GAGCACCTGATTTTCGATTATTGGGGACAGGGTACATTGGTCACCGTCTCCTCAGGGTCTA
CATCCGGCTCCGGGAAGCCCGGAAGTGGCGAAGGTAGTACAAAGGGGGAAATTGTGTTGAC
ACAGTCTCCAGCCACCCTGTCTTTGTCTCCAGGGGAAAGAGCCACCCTCTCCTGCAGGGCC
AGTCAGAGTGTTAGCAGGTACTTAGCCTGGTACCAACAGAAACCTGGCCAGGCTCCCAGGC
TCCTCATCTATGATGCATCCAACAGGGCCACTGGCATCCCAGCCAGGTTCAGTGGCAGTGG
GTCTGGGACAGACTTCACTCTCACCATCAGCAGCCTAGAGCCTGAAGATTTTGCAGTTTAT
TACTGTCAGCAGAGATTCTACTACCCTTGGACTTTTGGCGGAGGGACCAAGGTTGAGATCA
AACGGGCCGCTGCCCTTGATAATGAAAAGTCAAACGGAACAATCATTCACGTGAAGGGCAA
GCACCTCTGTCCGTCACCCTTGTTCCCTGGTCCATCCAAGCCATTCTGGGTGTTGGTCGTA
GTGGGTGGAGTCCTCGCTTGTTACTCTCTGCTCGTCACCGTGGCTTTTATAATCTTCTGGG
TTAGATCCAAAAGAAGCCGCCTGCTCCATAGCGATTACATGAATATGACTCCACGCCGCCC
TGGCCCCACAAGGAAACACTACCAGCCTTACGCACCACCTAGAGATTTCGCTGCCTATCGG
AGCAGGGTGAAGTTTTCCAGATCTGCAGATGCACCAGCGTATCAGCAGGGCCAGAACCAAC
TGTATAACGAGCTCAACCTGGGACGCAGGGAAGAGTATGACGTTTTGGACAAGCGCAGAGG
ACGGGACCCTGAGATGGGTGGCAAACCAAGACGAAAAAACCCCCAGGAGGGTCTCTATAAT
GAGCTGCAGAAGGATAAGATGGCTGAAGCCTATTCTGAAATAGGCATGAAAGGAGAGCGGA
GAAGGGGAAAAGGGCACGACGGTTTGTACCAGGGACTCAGCACTGCTACGAAGGATACTTA
TGACGCTCTCCACATGCAAGCCCTGCCACCTAGG Clone TS-26564 CAR HxL (SEQ ID NO: 352)
MALPVTALLL PLALLLHAAR PEVQLVESGG GLVQPGGSLR LSCAASGFTF
SSYSMNWVRQ APGKGLEWVS TISSSSSIIY YADSVKGRFT ISRDNAKNSL
YLQMNSLRAE DTAVYYCARG SQEHLIFDYW GQGTLVTVSS GSTSGSGKPG
SGEGSTKGEI VLTQSPATLS LSPGERATLS CRASQSVSRY LAWYQQKPGQ
APRLLIYDAS NRATGIPARF SGSGSGTDFT LTISSLEPED FAVYYCQQRF
YYPWTFGGGT KVEIKRAAAL DNEKSNGTII HVKGKHLCPS PLFPGPSKPF
WVLVVVGGVL ACYSLLVTVA FIIFWVRSKR SRLLHSDYMN MTPRRPGPTR
KHYQPYAPPR DFAAYRSRVK FSRSADAPAY QQGQNQLYNE LNLGRREEYD
VLDKRRGRDP EMGGKPRRKN PQEGLYNELQ KDKMAEAYSE IGMKGERRRG
KGHDGLYQGL STATKDTYDA LHMQALPPR Clone TS-26564 CAR DNA LxH (SEQ ID NO: 353)
ATGGCACTCCCCGTAACTGCTCTGCTGCTGCCGTTGGCATTGCTCCTGCACGCCGCACGCC
CGGAAATTGTGTTGACACAGTCTCCAGCCACCCTGTCTTTGTCTCCAGGGGAAAGAGCCAC
CCTCTCCTGCAGGGCCAGTCAGAGTGTTAGCAGGTACTTAGCCTGGTACCAACAGAAACCT
GGCCAGGCTCCCAGGCTCCTCATCTATGATGCATCCAACAGGGCCACTGGCATCCCAGCCA
GGTTCAGTGGCAGTGGGTCTGGGACAGACTTCACTCTCACCATCAGCAGCCTAGAGCCTGA
AGATTTTGCAGTTTATTACTGTCAGCAGAGATTCTACTACCCTTGGACTTTTGGCGGAGGG
ACCAAGGTTGAGATCAAACGGGGGTCTACATCCGGCTCCGGGAAGCCCGGAAGTGGCGAAG
GTAGTACAAAGGGGGAGGTGCAGCTGGTGGAGTCTGGGGGAGGCTTGGTACAGCCTGGGGG
GTCCCTGAGACTCTCCTGTGCAGCCTCTGGATTCACCTTCAGTAGCTATAGCATGAACTGG
GTCCGCCAGGCTCCAGGGAAGGGGCTGGAGTGGGTTTCAACCATTAGTAGTAGTAGTAGTA
TCATATACTACGCAGACTCTGTGAAGGGCCGATTCACCATCTCCAGAGACAATGCCAAGAA
CTCACTGTATCTGCAAATGAACAGCCTGAGAGCTGAGGACACGGCGGTGTACTACTGCGCC
AGAGGTTCTCAGGAGCACCTGATTTTCGATTATTGGGGACAGGGTACATTGGTCACCGTCT
CCTCAGCCGCTGCCCTTGATAATGAAAAGTCAAACGGAACAATCATTCACGTGAAGGGCAA
GCACCTCTGTCCGTCACCCTTGTTCCCTGGTCCATCCAAGCCATTCTGGGTGTTGGTCGTA
GTGGGTGGAGTCCTCGCTTGTTACTCTCTGCTCGTCACCGTGGCTTTTATAATCTTCTGGG
TTAGATCCAAAAGAAGCCGCCTGCTCCATAGCGATTACATGAATATGACTCCACGCCGCCC
TGGCCCCACAAGGAAACACTACCAGCCTTACGCACCACCTAGAGATTTCGCTGCCTATCGG
AGCAGGGTGAAGTTTTCCAGATCTGCAGATGCACCAGCGTATCAGCAGGGCCAGAACCAAC
TGTATAACGAGCTCAACCTGGGACGCAGGGAAGAGTATGACGTTTTGGACAAGCGCAGAGG
ACGGGACCCTGAGATGGGTGGCAAACCAAGACGAAAAAACCCCCAGGAGGGTCTCTATAAT
GAGCTGCAGAAGGATAAGATGGCTGAAGCCTATTCTGAAATAGGCATGAAAGGAGAGCGGA
GAAGGGGAAAAGGGCACGACGGTTTGTACCAGGGACTCAGCACTGCTACGAAGGATACTTA -continued

TGACGCTCTCCACATGCAAGCCCTGCCACCTAGG

Clone TS-26564 CAR LxH (SEQ ID NO: 354)

MALPVTALLL PLALLLHAAR PEIVLTQSPA TLSLSPGERA TLSCRASQSV
SRYLAWYQQK PGQAPRLLIY DASNRATGIP ARFSGSGSGT DFTLTISSLE
PEDFAVYYCQ QRFYYPWTFG GGTKVEIKRG STSGSGKPGS GEGSTKGEVQ
LVESGGGLVQ PGGSLRLSCA ASGFTFSSYS MNWVRQAPGK GLEWVSTISS
SSSIIYYADS VKGRFTISRD NAKNSLYLQM NSLRAEDTAV YYCARGSQEH
LIFDYWGQGT LVTVSSAAAL DNEKSNGTII HVKGKHLCPS PLFPGPSKPF
WVLVVVGGVL ACYSLLVTVA FIIFWVRSKR SRLLHSDYMN MTPRRPGPTR
KHYQPYAPPR DFAAYRSRVK FSRSADAPAY QQGQNQLYNE LNLGRREEYD
VLDKRRGRDP EMGGKPRRKN PQEGLYNELQ KDKMAEAYSE IGMKGERRRG
KGHDGLYQGL STATKDTYDA LHMQALPPR

Clone RY-26568 HC DNA (SEQ ID NO: 355)

CAGGTGCAGCTGGTGGAGTCTGGGGGAGGCGTGGTCCAGCCTGGGAGGTCCCTGAGACTCT
CCTGTGCAGCGTCTGGATTCACCTTCGGGAGCTATGGCATGCACTGGGTCCGCCAGGCTCC
AGGCAAGGGGCTGGAGTGGGTGGCAGTTATACATTATGATGGAAGTGTTGAATACTATGCA
GACTCCGTGAAGGGCCGATTCACCATCTCCAGAGACAATTCCAAGGACACGCTGTATCTGC
AAATGAACAGCCTGAGAGCCGAGGACACGGCGGTGTACTACTGCGCCAGAACTGACTTCTG
GAGCGGATCCCCTCCAAGCTTAGATTACTGGGGACAGGGTACATTGGTCACCGTCTCCTCA

Clone RY-26568 HC. CDRs 1, 2, and 3 are underlined.

(SEQ ID NO: 356)

QVQLVESGGG VVQPGRSLRL SCAASGFTFG SYGMHWVRQA PGKGLEWVAV
IHYDGSVEYY ADSVKGRFTI SRDNSKDTLY LQMNSLRAED TAVYYCARTD
FWSGSPPSLD YWGQGTLVTV SS (SEQ ID NO: 357)

FTFGSYGMH (HC CDR1)

(SEQ ID NO: 358)

VIHYDGSVEYYADSVKG (HC CDR2)

(SEQ ID NO: 359)

ARTDFWSGSPPSLDY (HC CDR3)

Clone RY-26568 LC DNA (SEQ ID NO: 360)

GACATCCAGTTGACCCAGTCTCCATCTTCCGTGTCTGCATCTGTAGGAGACAGAGTCACCA
TCACTTGTCGGGCGAGTCGGGGTATTAGCAGCTGGTTAGCCTGGTATCAGCAGAAACCAGG
GAAAGCCCCTAAGCTCCTGATCTATGGTGCATCCAGTTTGCAAAGTGGGGTCCCATCAAGG
TTCAGCGGCAGTGGATCTGGGACAGATTTCACTCTCACCATCAGCAGCCTGCAGCCTGAAG
ATTTTGCAACTTATTACTGTCAGCAGATATACACCTTCCCTTTCACTTTTGGCGGAGGGAC
CAAGGTTGAGATCAAACGG

Clone RY-26568 LC. CDRs 1, 2, and 3 are underlined.

(SEQ ID NO: 361)

DIQLTQSPSSVSASVGDRVTITCRASRGISSWLAWYQQKPGKAPKLLIYGASSLQSGVPSR
FSGSGSGTDFTLTISSLQPEDFATYYCQQIYTFPFTFGGGTKVEIKR (SEQ ID NO: 362)

RASRGISSWLA (LC CDR1)

(SEQ ID NO: 363)

GASSLQS (LC CDR2)

(SEQ ID NO: 364)

QQIYTFPFT (LC CDR3)

Clone RY-26568 CAR DNA HxL (SEQ ID NO: 365)

ATGGCACTCCCCGTAACTGCTCTGCTGCTGCCGTTGGCATTGCTCCTGCACGCCGCACGCC
CGCAGGTGCAGCTGGTGGAGTCTGGGGGAGGCGTGGTCCAGCCTGGGAGGTCCCTGAGACT
CTCCTGTGCAGCGTCTGGATTCACCTTCGGGAGCTATGGCATGCACTGGGTCCGCCAGGCT
CCAGGCAAGGGGCTGGAGTGGGTGGCAGTTATACATTATGATGGAAGTGTTGAATACTATG
CAGACTCCGTGAAGGGCCGATTCACCATCTCCAGAGACAATTCCAAGGACACGCTGTATCT
GCAAATGAACAGCCTGAGAGCCGAGGACACGGCGGTGTACTACTGCGCCAGAACTGACTTC
TGGAGCGGATCCCCTCCAAGCTTAGATTACTGGGGACAGGGTACATTGGTCACCGTCTCCT
CAGGGTCTACATCCGGCTCCGGGAAGCCCGGAAGTGGCGAAGGTAGTACAAAGGGGGACAT
CCAGTTGACCCAGTCTCCATCTTCCGTGTCTGCATCTGTAGGAGACAGAGTCACCATCACT
TGTCGGGCGAGTCGGGGTATTAGCAGCTGGTTAGCCTGGTATCAGCAGAAACCAGGGAAAG
CCCCTAAGCTCCTGATCTATGGTGCATCCAGTTTGCAAAGTGGGGTCCCATCAAGGTTCAG
CGGCAGTGGATCTGGGACAGATTTCACTCTCACCATCAGCAGCCTGCAGCCTGAAGATTTT
GCAACTTATTACTGTCAGCAGATATACACCTTCCCTTTCACTTTTGGCGGAGGGACCAAGG
TTGAGATCAAACGGGCCGCTGCCCTTGATAATGAAAAGTCAAACGGAACAATCATTCACGT
GAAGGGCAAGCACCTCTGTCCGTCACCCTTGTTCCCTGGTCCATCCAAGCCATTCTGGGTG
TTGGTCGTAGTGGGTGGAGTCCTCGCTTGTTACTCTCTGCTCGTCACCGTGGCTTTTATAA
TCTTCTGGGTTAGATCCAAAAGAAGCCGCCTGCTCCATAGCGATTACATGAATATGACTCC
ACGCCGCCCTGGCCCCACAAGGAAACACTACCAGCCTTACGCACCACCTAGAGATTTCGCT
GCCTATCGGAGCAGGGTGAAGTTTTCCAGATCTGCAGATGCACCAGCGTATCAGCAGGGCC
AGAACCAACTGTATAACGAGCTCAACCTGGGACGCAGGGAAGAGTATGACGTTTTGGACAA

-continued

GCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAG
GAGAGCGGAGAAGGGGAAAAGGGCACGACGGTTTGTACCAGGGACTCAGCACTGCTACGAA
GGATACTTATGACGCTCTCCACATGCAAGCCCTGCCACCTAGG

Clone RY-26568 CAR HxL (SEQ ID NO: 366)

MALPVTALLL PLALLLHAAR PQVQLVESGG GVVQPGRSLR LSCAASGFTF
GSYGMHWVRQ APGKGLEWVA VIHYDGSVEY YADSVKGRFT ISRDNSKDTL
YLQMNSLRAE DTAVYYCART DFWSGSPPSL DYWGQGTLVT VSSGSTSGSG
KPGSGEGSTK GDIQLTQSPS SVSASVGDRV TITCRASRGI SSWLAWYQQK
PGKAPKLLIY GASSLQSGVP SRFSGSGSGT DFTLTISSLQ PEDFATYYCQ
QIYTFPFTFG GGTKVEIKRA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

Clone RY-26568 CAR DNA LxH (SEQ ID NO: 367)

ATGGCACTCCCCGTAACTGCTCTGCTGCTGCCGTTGGCATTGCTCCTGCACGCCGCACGCC
CGGACATCCAGTTGACCCAGTCTCCATCTTCCGTGTCTGCATCTGTAGGAGACAGAGTCAC
CATCACTTGTCGGGCGAGTCGGGGTATTAGCAGCTGGTTAGCCTGGTATCAGCAGAAACCA
GGGAAAGCCCCTAAGCTCCTGATCTATGGTGCATCCAGTTTGCAAAGTGGGGTCCCATCAA
GGTTCAGCGGCAGTGGATCTGGGACAGATTTCACTCTCACCATCAGCAGCCTGCAGCCTGA
AGATTTTGCAACTTATTACTGTCAGCAGATATACACCTTCCCTTTCACTTTTGGCGGAGGG
ACCAAGGTTGAGATCAAACGGGGGTCTACATCCGGCTCCGGGAAGCCCGGAAGTGGCGAAG
GTAGTACAAAGGGGCAGGTGCAGCTGGTGGAGTCTGGGGGAGGCGTGGTCCAGCCTGGGAG
GTCCCTGAGACTCTCCTGTGCAGCGTCTGGATTCACCTTCGGGAGCTATGGCATGCACTGG
GTCCGCCAGGCTCCAGGCAAGGGGCTGGAGTGGGTGGCAGTTATACATTATGATGGAAGTG
TTGAATACTATGCAGACTCCGTGAAGGGCCGATTCACCATCTCCAGAGACAATTCCAAGGA
CACGCTGTATCTGCAAATGAACAGCCTGAGAGCCGAGGACACGGCGGTGTACTACTGCGCC
AGAACTGACTTCTGGAGCGGATCCCCTCCAAGCTTAGATTACTGGGGACAGGGTACATTGG
TCACCGTCTCCTCAGCCGCTGCCCTTGATAATGAAAAGTCAAACGGAACAATCATTCACGT
GAAGGGCAAGCACCTCTGTCCGTCACCCTTGTTCCCTGGTCCATCCAAGCCATTCTGGGTG
TTGGTCGTAGTGGGTGGAGTCCTCGCTTGTTACTCTCTGCTCGTCACCGTGGCTTTTATAA
TCTTCTGGGTTAGATCCAAAAGAAGCCGCCTGCTCCATAGCGATTACATGAATATGACTCC
ACGCCGCCCTGGCCCCACAAGGAAACACTACCAGCCTTACGCACCACCTAGAGATTTCGCT
GCCTATCGGAGCAGGGTGAAGTTTTCCAGATCTGCAGATGCACCAGCGTATCAGCAGGGCC
AGAACCAACTGTATAACGAGCTCAACCTGGGACGCAGGGAAGAGTATGACGTTTTGGACAA
GCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAG
GAGAGCGGAGAAGGGGAAAAGGGCACGACGGTTTGTACCAGGGACTCAGCACTGCTACGAA
GGATACTTATGACGCTCTCCACATGCAAGCCCTGCCACCTAGG

Clone RY-26568 CAR LxH (SEQ ID NO: 368)

MALPVTALLL PLALLLHAAR PDIQLTQSPS SVSASVGDRV TITCRASRGI
SSWLAWYQQK PGKAPKLLIY GASSLQSGVP SRFSGSGSGT DFTLTISSLQ
PEDFATYYCQ QIYTFPFTFG GGTKVEIKRG STSGSGKPGS GEGSTKGQVQ
LVESGGGVVQ PGRSLRLSCA ASGFTFGSYG MHWVRQAPGK GLEWVAVIHY
DGSVEYYADS VKGRFTISRD NSKDTLYLQM NSLRAEDTAV YYCARTDFWS
GSPPSLDYWG QGTLVTVSSA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

Clone PP-26575 HC DNA (SEQ ID NO: 369)

CAGGTGCAGCTGGTGCAGTCTGGGGCTGAGGTGAAGAAGCCTGGGTCCTCGGTGAAGGTCT
CCTGCAAGGCTTCTGGAGGCACCCTCAGCAGCCTGGCTATCAGCTGGGTGCGACAGGCCCC
TGGACAAGGGCTTGAGTGGATGGGAGGGGTCATCCCTATCTTGGGTCGGGCAAACTACGCA
CAGAAGTTCCAGGGCAGAGTCACGATTACCGCGGACGAGTCCACGAGCACAGCCTACATGG
AGCTGAGCAGCCTGAGATCTGAGGACACGGCGGTGTACTACTGCGCCAGAACTCCTGAATA
CTCCTCCAGCATATGGCACTATTACTACGGCATGGACGTATGGGGCCAGGGAACAACTGTC
ACCGTCTCCTCA

Clone PP-26575 HC. CDRs 1, 2, and 3 are underlined.

(SEQ ID NO: 370)

QVQLVQSGAEVKKPGSSVKVSCKASGGTLSSLAISWVRQAPGQGLEWMGGVIPILGRANYA
QKFQGRVTITADESTSTAYMELSSLRSEDTAVYYCARTPEYSSSIWHYYYGMDVWGQGTTV
TVSS (SEQ ID NO: 371)

GTLSSLAIS (HC CDR1)

(SEQ ID NO: 372)

GVIPILGRANYAQKFQG (HC CDR2)

(SEQ ID NO: 373)

ARTPEYSSSIWHYYYGMDV (HC CDR3)

-continued

Clone PP-26575 LC DNA (SEQ ID NO: 374)

GACATCGTGATGACCCAGTCTCCAGACTCCCTGGCTGTGTCTCTGGGCGAGAGGGCCACCA
TCAACTGCAAGTCCAGCCAGAGTGTTTTATACAGCTCCAACAATAAGAACTACTTAGCTTG
GTACCAGCAGAAACCAGGACAGCCTCCTAAGCTGCTCATTTACTGGGCATCTACCCGGGAA
TCCGGGGTCCCTGACCGATTCAGTGGCAGCGGGTCTGGGACAGATTTCACTCTCACCATCA
GCAGCCTGCAGGCTGAAGATGTGGCAGTTTATTACTGTCAGCAGTTCGCCCACACTCCTTT
CACTTTTGGCGGAGGGACCAAGGTTGAGATCAAACGG

Clone PP-26575 LC. CDRs 1, 2, and 3 are underlined.

(SEQ ID NO: 375)

DIVMTQSPDSLAVSLGERATINCKSSQSVLYSSNNKNYLAWYQQKPGQPPKLLIYWASTR
ESGVPDRFSGSGSGTDFTLTISSLQAEDVAVYYCQQFAHTPFTFGGGTKVEIKR (SEQ ID NO: 376)

KSSQSVLYSSNNKNYLA (LC CDR1)

(SEQ ID NO: 377)

WASTRES (LC CDR2)

(SEQ ID NO: 378)

QQFAHTPFT (LC CDR3)

Clone PP-26575 CAR DNA HxL (SEQ ID NO: 379)

ATGGCACTCCCCGTAACTGCTCTGCTGCTGCCGTTGGCATTGCTCCTGCACGCCGCACGCC
CGCAGGTGCAGCTGGTGCAGTCTGGGGCTGAGGTGAAGAAGCCTGGGTCCTCGGTGAAGGT
CTCCTGCAAGGCTTCTGGAGGCACCCTCAGCAGCCTGGCTATCAGCTGGGTGCGACAGGCC
CCTGGACAAGGGCTTGAGTGGATGGGAGGGGTCATCCCTATCTTGGGTCGGGCAAACTACG
CACAGAAGTTCCAGGGCAGAGTCACGATTACCGCGGACGAGTCCACGAGCACAGCCTACAT
GGAGCTGAGCAGCCTGAGATCTGAGGACACGGCGGTGTACTACTGCGCCAGAACTCCTGAA
TACTCCTCCAGCATATGGCACTATTACTACGGCATGGACGTATGGGGCCAGGGAACAACTG
TCACCGTCTCCTCAGGGTCTACATCCGGCTCCGGGAAGCCCGGAAGTGGCGAAGGTAGTAC
AAAGGGGGACATCGTGATGACCCAGTCTCCAGACTCCCTGGCTGTGTCTCTGGGCGAGAGG
GCCACCATCAACTGCAAGTCCAGCCAGAGTGTTTTATACAGCTCCAACAATAAGAACTACT
TAGCTTGGTACCAGCAGAAACCAGGACAGCCTCCTAAGCTGCTCATTTACTGGGCATCTAC
CCGGGAATCCGGGGTCCCTGACCGATTCAGTGGCAGCGGGTCTGGGACAGATTTCACTCTC
ACCATCAGCAGCCTGCAGGCTGAAGATGTGGCAGTTTATTACTGTCAGCAGTTCGCCCACA
CTCCTTTCACTTTTGGCGGAGGGACCAAGGTTGAGATCAAACGGGCCGCTGCCCTTGATAA
TGAAAAGTCAAACGGAACAATCATTCACGTGAAGGGCAAGCACCTCTGTCCGTCACCCTTG
TTCCCTGGTCCATCCAAGCCATTCTGGGTGTTGGTCGTAGTGGGTGGAGTCCTCGCTTGTT
ACTCTCTGCTCGTCACCGTGGCTTTTATAATCTTCTGGGTTAGATCCAAAAGAAGCCGCCT
GCTCCATAGCGATTACATGAATATGACTCCACGCCGCCCTGGCCCCACAAGGAAACACTAC
CAGCCTTACGCACCACCTAGAGATTTCGCTGCCTATCGGAGCAGGGTGAAGTTTTCCAGAT
CTGCAGATGCACCAGCGTATCAGCAGGGCCAGAACCAACTGTATAACGAGCTCAACCTGGG
ACGCAGGGAAGAGTATGACGTTTTGGACAAGCGCAGAGGACGGGACCCTGAGATGGGTGGC
AAACCAAGACGAAAAAACCCCCAGGAGGGTCTCTATAATGAGCTGCAGAAGGATAAGATGG
CTGAAGCCTATTCTGAAATAGGCATGAAAGGAGAGCGGAGAAGGGGAAAAGGGCACGACGG
TTTGTACCAGGGACTCAGCACTGCTACGAAGGATACTTATGACGCTCTCCACATGCAAGCC
CTGCCACCTAGG

Clone PP-26575 CAR HxL (SEQ ID NO: 380)

MALPVTALLL PLALLLHAAR PQVQLVQSGA EVKKPGSSVK VSCKASGGTL
SSLAISWVRQ APGQGLEWMG GVIPILGRAN YAQKFQGRVT ITADESTSTA
YMELSSLRSE DTAVYYCART PEYSSSIWHY YYGMDVWGQG TTVTVSSGST
SGSGKPGSGE GSTKGDIVMT QSPDSLAVSL GERATINCKS SQSVLYSSNN
KNYLAWYQQK PGQPPKLLIY WASTRESGVP DRFSGSGSGT DFTLTISSLQ
AEDVAVYYCQ QFAHTPFTFG GGTKVEIKRA AALDNEKSNG TIIHVKGKHL
CPSPLFPGPS KPFWVLVVVG GVLACYSLLV TVAFIIFWVR SKRSRLLHSD
YMNMTPRRPG PTRKHYQPYA PPRDFAAYRS RVKFSRSADA PAYQQGQNQL
YNELNLGRRE EYDVLDKRRG RDPEMGGKPR RKNPQEGLYN ELQKDKMAEA
YSEIGMKGER RRGKGHDGLY QGLSTATKDT YDALHMQALP PR

Clone PP-26575 CAR DNA LxH (SEQ ID NO: 381)

ATGGCACTCCCCGTAACTGCTCTGCTGCTGCCGTTGGCATTGCTCCTGCACGCCGCACGCC
CGGACATCGTGATGACCCAGTCTCCAGACTCCCTGGCTGTGTCTCTGGGCGAGAGGGCCAC
CATCAACTGCAAGTCCAGCCAGAGTGTTTTATACAGCTCCAACAATAAGAACTACTTAGCT
TGGTACCAGCAGAAACCAGGACAGCCTCCTAAGCTGCTCATTTACTGGGCATCTACCCGGG
AATCCGGGGTCCCTGACCGATTCAGTGGCAGCGGGTCTGGGACAGATTTCACTCTCACCAT
CAGCAGCCTGCAGGCTGAAGATGTGGCAGTTTATTACTGTCAGCAGTTCGCCCACACTCCT
TTCACTTTTGGCGGAGGGACCAAGGTTGAGATCAAACGGGGGTCTACATCCGGCTCCGGGA
AGCCCGGAAGTGGCGAAGGTAGTACAAAGGGGCAGGTGCAGCTGGTGCAGTCTGGGGCTGA
GGTGAAGAAGCCTGGGTCCTCGGTGAAGGTCTCCTGCAAGGCTTCTGGAGGCACCCTCAGC
AGCCTGGCTATCAGCTGGGTGCGACAGGCCCCTGGACAAGGGCTTGAGTGGATGGGAGGGG
TCATCCCTATCTTGGGTCGGGCAAACTACGCACAGAAGTTCCAGGGCAGAGTCACGATTAC
CGCGGACGAGTCCACGAGCACAGCCTACATGGAGCTGAGCAGCCTGAGATCTGAGGACACG
GCGGTGTACTACTGCGCCAGAACTCCTGAATACTCCTCCAGCATATGGCACTATTACTACG
GCATGGACGTATGGGGCCAGGGAACAACTGTCACCGTCTCCTCAGCCGCTGCCCTTGATAA
TGAAAAGTCAAACGGAACAATCATTCACGTGAAGGGCAAGCACCTCTGTCCGTCACCCTTG
TTCCCTGGTCCATCCAAGCCATTCTGGGTGTTGGTCGTAGTGGGTGGAGTCCTCGCTTGTT
ACTCTCTGCTCGTCACCGTGGCTTTTATAATCTTCTGGGTTAGATCCAAAAGAAGCCGCCT
GCTCCATAGCGATTACATGAATATGACTCCACGCCGCCCTGGCCCCACAAGGAAACACTAC

-continued

CAGCCTTACGCACCACCTAGAGATTTCGCTGCCTATCGGAGCAGGGTGAAGTTTTCCAGAT
CTGCAGATGCACCAGCGTATCAGCAGGGCCAGAACCAACTGTATAACGAGCTCAACCTGGG
ACGCAGGGAAGAGTATGACGTTTTGGACAAGCGCAGAGGACGGGACCCTGAGATGGGTGGC
AAACCAAGACGAAAAAACCCCCAGGAGGGTCTCTATAATGAGCTGCAGAAGGATAAGATGG
CTGAAGCCTATTCTGAAATAGGCATGAAAGGAGAGCGGAGAAGGGGAAAAGGGCACGACGG
TTTGTACCAGGGACTCAGCACTGCTACGAAGGATACTTATGACGCTCTCCACATGCAAGCC
CTGCCACCTAGG

Clone PP-26575 CAR LxH (SEQ ID NO: 382)

MALPVTALLL PLALLLHAAR PDIVMTQSPD SLAVSLGERA TINCKSSQSV
LYSSNNKNYL AWYQQKPGQP PKLLIYWAST RESGVPDRFS GSGSGTDFTL
TISSLQAEDV AVYYCQQFAH TPFTFGGGTK VEIKRGSTSG SGKPGSGEGS
TKGQVQLVQS GAEVKKPGSS VKVSCKASGG TLSSLAISWV RQAPGQGLEW
MGGVIPILGR ANYAQKFQGR VTITADESTS TAYMELSSLR SEDTAVYYCA
RTPEYSSSIW HYYYGMDVWG QGTTVTVSSA AALDNEKSNG TIIHVKGKHL
CPSPLFPGPS KPFWVLVVVG GVLACYSLLV TVAFIIFWVR SKRSRLLHSD
YMNMTPRRPG PTRKHYQPYA PPRDFAAYRS RVKFSRSADA PAYQQGQNQL
YNELNLGRRE EYDVLDKRRG RDPEMGGKPR RKNPQEGLYN ELQKDKMAEA
YSEIGMKGER RRGKGHDGLY QGLSTATKDT YDALHMQALP PR

Clone RD-26576 HC DNA (SEQ ID NO: 383)

CAGGTGCGGCTGGTGGAGTCTGGGGGGGGCGTGGTCCAGCCTGGGAGGTCCCTGAGACTCT
CCTGTGCAGCGTCTGGATTCACCTTCAGTAGCTATGGCATACACTGGGTCCGCCAGGCTCC
AGGCAAGGGGCTGGAGTGGGTGGCAGTTATAGGGTATGATGGACAGGAGAAATACTATGCA
GACTCCGTGAAGGGCCGATTCACCATCTCCAGAGACAATTCCAAGAACACGCTGTATCTGC
AAATGAACAGCCTGAGAGCCGAGGACACGGCGGTGTACTACTGCGTCAAGGGGCCGTTGCA
GGAGCCGCCATACGCTTTTGGGATGGACGTATGGGGCCAGGGAACAACTGTCACCGTCTCC
TCA

Clone RD-26576 HC. CDRs 1, 2, and 3 are underlined.

(SEQ ID NO: 384)

QVRLVESGGGVVQPGRSLRLSCAASGFTFSSYGIHWVRQAPGKGLEWVAVIGYDGQEKYYA
DSVKGRFTISRDNSKNTLYLQMNSLRAEDTAVYYCVKGPLQEPPYAFGMDVWGQGTTVTVS
S (SEQ ID NO: 385)

FTFSSYGIH (HC CDR1)

(SEQ ID NO: 386)

VIGYDGQEKYYADSVKG (HC CDR2)

(SEQ ID NO: 387)

VKGPLQEPPYAFGMDV (HC CDR3)

Clone RD-26576 LC DNA (SEQ ID NO: 388)

GAAATAGTGATGACGCAGTCTCCAGCCACCCTGTCTGTGTCTCCAGGGGAAAGAGCCACCC
TCTCCTGCAGGGCCAGTCAGAGTGTTAGCAGCAACTTAGCCTGGTACCAGCAGAAACCTGG
CCAGGCTCCCAGGCTCCTCATCTATAGCGCATCCACCAGGGCCACTGGTATCCCAGCCAGG
TTCAGTGGCAGTGGGTCTGGGACAGAGTTCACTCTCACCATCAGCAGCCTGCAGTCTGAAG
ATTTTGCAGTTTATTACTGTCAGCAGCACCACGTCTGGCCTCTCACTTTTGGCGGAGGGAC
CAAGGTTGAGATCAAACGG

Clone RD-26576 LC. CDRs 1, 2, and 3 are underlined.

(SEQ ID NO: 389)

EIVMTQSPATLSVSPGERATLSCRASQSVSSNLAWYQQKPGQAPRLLIYSASTRATGIPA
RFSGSGSGTEFTLTISSLQSEDFAVYYCQQHHVWPLTFGGGTKVEIKR (SEQ ID NO: 390)

RASQSVSSNLA (LC CDR1)

(SEQ ID NO: 391)

SASTRAT (LC CDR2)

(SEQ ID NO: 392)

QQHHVWPLT (LC CDR3)

Clone RD-26576 CAR DNA HxL (SEQ ID NO: 393)

ATGGCACTCCCCGTAACTGCTCTGCTGCTGCCGTTGGCATTGCTCCTGCACGCCGCACGCC
CGCAGGTGCGGCTGGTGGAGTCTGGGGGGGGCGTGGTCCAGCCTGGGAGGTCCCTGAGACT
CTCCTGTGCAGCGTCTGGATTCACCTTCAGTAGCTATGGCATACACTGGGTCCGCCAGGCT
CCAGGCAAGGGGCTGGAGTGGGTGGCAGTTATAGGGTATGATGGACAGGAGAAATACTATG
CAGACTCCGTGAAGGGCCGATTCACCATCTCCAGAGACAATTCCAAGAACACGCTGTATCT
GCAAATGAACAGCCTGAGAGCCGAGGACACGGCGGTGTACTACTGCGTCAAGGGGCCGTTG
CAGGAGCCGCCATACGCTTTTGGGATGGACGTATGGGGCCAGGGAACAACTGTCACCGTCT
CCTCAGGGTCTACATCCGGCTCCGGGAAGCCCGGAAGTGGCGAAGGTAGTACAAAGGGGGA
AATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCC
AGGCTCCCAGGCTCCTCATCTATAGCGCATCCACCAGGGCCACTGGTATCCCAGCCAGGTT
CAGTGGCAGTGGGTCTGGGACAGAGTTCACTCTCACCATCAGCAGCCTGCAGTCTGAAGAT
TTTGCAGTTTATTACTGTCAGCAGCACCACGTCTGGCCTCTCACTTTTGGCGGAGGGACCA
AGGTTGAGATCAAACGGGCCGCTGCCCTTGATAATGAAAAGTCAAACGGAACAATCATTCA
CGTGAAGGGCAAGCACCTCTGTCCGTCACCCTTGTTCCCTGGTCCATCCAAGCCATTCTGG
GTGTTGGTCGTAGTGGGTGGAGTCCTCGCTTGTTACTCTCTGCTCGTCACCGTGGCTTTTA

-continued

TAATCTTCTGGGTTAGATCCAAAAGAAGCCGCCTGCTCCATAGCGATTACATGAATATGAC
TCCACGCCGCCCTGGCCCCACAAGGAAACACTACCAGCCTTACGCACCACCTAGAGATTTC
GCTGCCTATCGGAGCAGGGTGAAGTTTTCCAGATCTGCAGATGCACCAGCGTATCAGCAGG
GCCAGAACCAACTGTATAACGAGCTCAACCTGGGACGCAGGGAAGAGTATGACGTTTTGGA
CAAGCGCAGAGGACGGGACCCTGAGATGGGTGGCAAACCAAGACGAAAAAACCCCCAGGAG
GGTCTCTATAATGAGCTGCAGAAGGATAAGATGGCTGAAGCCTATTCTGAAATAGGCATGA
AAGGAGAGCGGAGAAGGGGAAAAGGGCACGACGGTTTGTACCAGGGACTCAGCACTGCTAC
GAAGGATACTTATGACGCTCTCCACATGCAAGCCCTGCCACCTAGG

Clone RD-26576 CAR HxL (SEQ ID NO: 394)

MALPVTALLL PLALLLHAAR PQVRLVESGG GVVQPGRSLR LSCAASGFTF
SSYGIHWVRQ APGKGLEWVA VIGYDGQEKY YADSVKGRFT ISRDNSKNTL
YLQMNSLRAE DTAVYYCVKG PLQEPPYAFG MDVWGQGTTV TVSSGSTSGS
GKPGSGEGST KGEIVMTQSP ATLSVSPGER ATLSCRASQS VSSNLAWYQQ
KPGQAPRLLI YSASTRATGI PARFSGSGSG TEFTLTISSL QSEDFAVYYC
QQHHVWPLTF GGGTKVEIKR AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

Clone RD-26576 CAR DNA LxH (SEQ ID NO: 395)

ATGGCACTCCCCGTAACTGCTCTGCTGCTGCCGTTGGCATTGCTCCTGCACGCCGCACGCC
CGGAAATAGTGATGACGCAGTCTCCAGCCACCCTGTCTGTGTCTCCAGGGGAAAGAGCCAC
CCTCTCCTGCAGGGCCAGTCAGAGTGTTAGCAGCAACTTAGCCTGGTACCAGCAGAAACCT
GGCCAGGCTCCCAGGCTCCTCATCTATAGCGCATCCACCAGGGCCACTGGTATCCCAGCCA
GGTTCAGTGGCAGTGGGTCTGGGACAGAGTTCACTCTCACCATCAGCAGCCTGCAGTCTGA
AGATTTTGCAGTTTATTACTGTCAGCAGCACCACGTCTGGCCTCTCACTTTTGGCGGAGGG
ACCAAGGTTGAGATCAAACGGGGGTCTACATCCGGCTCCGGGAAGCCCGGAAGTGGCGAAG
GTAGTACAAAGGGGCAGGTGCGGCTGGTGGAGTCTGGGGGGGGCGTGGTCCAGCCTGGGAG
GTCCCTGAGACTCTCCTGTGCAGCGTCTGGATTCACCTTCAGTAGCTATGGCATACACTGG
GTCCGCCAGGCTCCAGGCAAGGGGCTGGAGTGGGTGGCAGTTATAGGGTATGATGGACAGG
AGAAATACTATGCAGACTCCGTGAAGGGCCGATTCACCATCTCCAGAGACAATTCCAAGAA
CACGCTGTATCTGCAAATGAACAGCCTGAGAGCCGAGGACACGGCGGTGTACTACTGCGTC
AAGGGGCCGTTGCAGGAGCCGCCATACGCTTTTGGGATGGACGTATGGGGCCAGGGAACAA
CTGTCACCGTCTCCTCAGCCGCTGCCCTTGATAATGAAAAGTCAAACGGAACAATCATTCA
CGTGAAGGGCAAGCACCTCTGTCCGTCACCCTTGTTCCCTGGTCCATCCAAGCCATTCTGG
GTGTTGGTCGTAGTGGGTGGAGTCCTCGCTTGTTACTCTCTGCTCGTCACCGTGGCTTTTA
TAATCTTCTGGGTTAGATCCAAAAGAAGCCGCCTGCTCCATAGCGATTACATGAATATGAC
TCCACGCCGCCCTGGCCCCACAAGGAAACACTACCAGCCTTACGCACCACCTAGAGATTTC
GCTGCCTATCGGAGCAGGGTGAAGTTTTCCAGATCTGCAGATGCACCAGCGTATCAGCAGG
GCCAGAACCAACTGTATAACGAGCTCAACCTGGGACGCAGGGAAGAGTATGACGTTTTGGA
CAAGCGCAGAGGACGGGACCCTGAGATGGGTGGCAAACCAAGACGAAAAAACCCCCAGGAG
GGTCTCTATAATGAGCTGCAGAAGGATAAGATGGCTGAAGCCTATTCTGAAATAGGCATGA
AAGGAGAGCGGAGAAGGGGAAAAGGGCACGACGGTTTGTACCAGGGACTCAGCACTGCTAC
GAAGGATACTTATGACGCTCTCCACATGCAAGCCCTGCCACCTAGG

Clone RD-26576 CAR LxH (SEQ ID NO: 396)

MALPVTALLL PLALLLHAAR PEIVMTQSPA TLSVSPGERA TLSCRASQSV
SSNLAWYQQK PGQAPRLLIY SASTRATGIP ARFSGSGSGT EFTLTISSLQ
SEDFAVYYCQ QHHVWPLTFG GGTKVEIKRG STSGSGKPGS GEGSTKGQVR
LVESGGGVVQ PGRSLRLSCA ASGFTFSSYG IHWVRQAPGK GLEWVAVIGY
DGQEKYYADS VKGRFTISRD NSKNTLYLQM NSLRAEDTAV YYCVKGPLQE
PPYAFGMDVW GQGTTVTVSS AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

Clone RD-26578 HC DNA (SEQ ID NO: 397)

CAGGTGCAGCTGGTGGAGTCTGGGGGAGGCGTGGTCCAGCCTGGGAGGTCCCTGAGACTCT
CCTGTGCAGCGTCTGGATTCACCTTCAGTAGCCGTGGCATGCACTGGGTCCGCCAGGCTCC
AGGCAAGGGGCTGGAGTGGGTGGCAGTTATAGGGTATGATGGACAGGAGAAATACTATGCA
GACTCCGTGAAGGGCCGATTCACCATCTCCAGAGACAATTCCAAGAACACGCTGTATCTGC
AAATGAACAGCCTGAGAGCCGAGGACACGGCGGTGTACTACTGCGTCAAGGGGCCGTTGCA
GGAGCCGCCATACGATTATGGAATGGACGTATGGGGCCAGGGAACAACTGTCACCGTCTCC
TCA

Clone RD-26578 HC CDRs 1, 2, and 3 are underlined.

(SEQ ID NO: 398)

QVQLVESGGGVVQPGRSLRLSCAASGFTFSSRGMHWVRQAPGKGLEWVAVIGYDGQEKYYA
DSVKGRFTISRDNSKNTLYLQMNSLRAEDTAVYYCVKGPLQEPPYDYGMDVWGQGTTVTVS
S (SEQ ID NO: 399)

FTFSSRGMH (HC CDR1)

(SEQ ID NO: 400)

VIGYDGQEKYYADSVKG (HC CDR2)

-continued (SEQ ID NO: 401)
VKGPLQEPPYDYGMDV (HC CDR3)

Clone RD-26578 LC DNA (SEQ ID NO: 402)
GAAATAGTGATGACGCAGTCTCCAGCCACCCTGTCTGTGTCTCCAGGGGAAAGAGCCACCC
TCTCCTGCAGGGCCAGTCAGAGTGTTAGCAGCAACTTAGCCTGGTACCAGCAGAAACCTGG
CCAGGCTCCCAGGCTCCTCATCTATAGCGCATCCACCAGGGCCACTGGTATCCCAGCCAGG
TTCAGTGGCAGTGGGTCTGGGACAGAGTTCACTCTCACCATCAGCAGCCTGCAGTCTGAAG
ATTTTGCAGTTTATTACTGTCAGCAGCACCACGTCTGGCCTCTCACTTTTGGCGGAGGGAC
CAAGGTTGAGATCAAACGG Clone RD-26578 LC. CDRs 1, 2, and 3 are underlined.

(SEQ ID NO: 403)
EIVMTQSPATLSVSPGERATLSCRASQSVSSNLAWYQQKPGQAPRLLIYS
ASTRATGIPARFSGSGSGTEFTLTISSLQSEDFAVYYCQQHHVWPLTFGGGTKVEIKR (SEQ ID NO: 404)
RASQSVSSNLA (LC CDR1)

(SEQ ID NO: 405)
SASTRAT (LC CDR2)

(SEQ ID NO: 406)
QQHHVWPLT (LC CDR3)

Clone RD-26578 CAR DNA HxL (SEQ ID NO: 407)
ATGGCACTCCCCGTAACTGCTCTGCTGCTGCCGTTGGCATTGCTCCTGCACGCCGCACGCC
CGCAGGTGCAGCTGGTGGAGTCTGGGGGAGGCGTGGTCCAGCCTGGGAGGTCCCTGAGACT
CTCCTGTGCAGCGTCTGGATTCACCTTCAGTAGCCGTGGCATGCACTGGGTCCGCCAGGCT
CCAGGCAAGGGGCTGGAGTGGGTGGCAGTTATAGGGTATGATGGACAGGAGAAATACTATG
CAGACTCCGTGAAGGGCCGATTCACCATCTCCAGAGACAATTCCAAGAACACGCTGTATCT
GCAAATGAACAGCCTGAGAGCCGAGGACACGGCGGTGTACTACTGCGTCAAGGGGCCGTTG
CAGGAGCCGCCATACGATTATGGAATGGACGTATGGGGCCAGGGAACAACTGTCACCGTCT
CCTCAGGGTCTACATCCGGCTCCGGGAAGCCCGGAAGTGGCGAAGGTAGTACAAAGGGGGA
AATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCC
AGGCTCCCAGGCTCCTCATCTATAGCGCATCCACCAGGGCCACTGGTATCCCAGCCAGGTT
CAGTGGCAGTGGGTCTGGGACAGAGTTCACTCTCACCATCAGCAGCCTGCAGTCTGAAGAT
TTTGCAGTTTATTACTGTCAGCAGCACCACGTCTGGCCTCTCACTTTTGGCGGAGGGACCA
AGGTTGAGATCAAACGGGCCGCTGCCCTTGATAATGAAAAGTCAAACGGAACAATCATTCA
CGTGAAGGGCAAGCACCTCTGTCCGTCACCCTTGTTCCCTGGTCCATCCAAGCCATTCTGG
GTGTTGGTCGTAGTGGGTGGAGTCCTCGCTTGTTACTCTCTGCTCGTCACCGTGGCTTTTA
TAATCTTCTGGGTTAGATCCAAAAGAAGCCGCCTGCTCCATAGCGATTACATGAATATGAC
TCCACGCCGCCCTGGCCCCACAAGGAAACACTACCAGCCTTACGCACCACCTAGAGATTTC
GCTGCCTATCGGAGCAGGGTGAAGTTTTCCAGATCTGCAGATGCACCAGCGTATCAGCAGG
GCCAGAACCAACTGTATAACGAGCTCAACCTGGGACGCAGGGAAGAGTATGACGTTTTGGA
CAAGCGCAGAGGACGGGACCCTGAGATGGGTGGCAAACCAAGACGAAAAAACCCCCAGGAG
GGTCTCTATAATGAGCTGCAGAAGGATAAGATGGCTGAAGCCTATTCTGAAATAGGCATGA
AAGGAGAGCGGAGAAGGGGAAAAGGGCACGACGGTTTGTACCAGGGACTCAGCACTGCTAC
GAAGGATACTTATGACGCTCTCCACATGCAAGCCCTGCCACCTAGG Clone RD-26578 CAR HxL (SEQ ID NO: 408)
MALPVTALLL PLALLLHAAR PQVQLVESGG GVVQPGRSLR LSCAASGFTF
SSRGMHWVRQ APGKGLEWVA VIGYDGQEKY YADSVKGRFT ISRDNSKNTL
YLQMNSLRAE DTAVYYCVKG PLQEPPYDYG MDVWGQGTTV TVSSGSTSGS
GKPGSGEGST KGEIVMTQSP ATLSVSPGER ATLSCRASQS VSSNLAWYQQ
KPGQAPRLLI YSASTRATGI PARFSGSGSG TEFTLTISSL QSEDFAVYYC
QQHHVWPLTF GGGTKVEIKR AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR Clone RD-26578 CAR DNA LxH (SEQ ID NO: 409)
ATGGCACTCCCCGTAACTGCTCTGCTGCTGCCGTTGGCATTGCTCCTGCACGCCGCACGCC
CGGAAATAGTGATGACGCAGTCTCCAGCCACCCTGTCTGTGTCTCCAGGGGAAAGAGCCAC
CCTCTCCTGCAGGGCCAGTCAGAGTGTTAGCAGCAACTTAGCCTGGTACCAGCAGAAACCT
GGCCAGGCTCCCAGGCTCCTCATCTATAGCGCATCCACCAGGGCCACTGGTATCCCAGCCA
GGTTCAGTGGCAGTGGGTCTGGGACAGAGTTCACTCTCACCATCAGCAGCCTGCAGTCTGA
AGATTTTGCAGTTTATTACTGTCAGCAGCACCACGTCTGGCCTCTCACTTTTGGCGGAGGG
ACCAAGGTTGAGATCAAACGGGGGTCTACATCCGGCTCCGGGAAGCCCGGAAGTGGCGAAG
GTAGTACAAAGGGGCAGGTGCAGCTGGTGGAGTCTGGGGGAGGCGTGGTCCAGCCTGGGAG
GTCCCTGAGACTCTCCTGTGCAGCGTCTGGATTCACCTTCAGTAGCCGTGGCATGCACTGG
GTCCGCCAGGCTCCAGGCAAGGGGCTGGAGTGGGTGGCAGTTATAGGGTATGATGGACAGG
AGAAATACTATGCAGACTCCGTGAAGGGCCGATTCACCATCTCCAGAGACAATTCCAAGAA
CACGCTGTATCTGCAAATGAACAGCCTGAGAGCCGAGGACACGGCGGTGTACTACTGCGTC
AAGGGGCCGTTGCAGGAGCCGCCATACGATTATGGAATGGACGTATGGGGCCAGGGAACAA
CTGTCACCGTCTCCTCAGCCGCTGCCCTTGATAATGAAAAGTCAAACGGAACAATCATTCA
CGTGAAGGGCAAGCACCTCTGTCCGTCACCCTTGTTCCCTGGTCCATCCAAGCCATTCTGG
GTGTTGGTCGTAGTGGGTGGAGTCCTCGCTTGTTACTCTCTGCTCGTCACCGTGGCTTTTA -continued TAATCTTCTGGGTTAGATCCAAAAGAAGCCGCCTGCTCCATAGCGATTACATGAATATGAC
TCCACGCCGCCCTGGCCCCACAAGGAAACACTACCAGCCTTACGCACCACCTAGAGATTTC
GCTGCCTATCGGAGCAGGGTGAAGTTTTCCAGATCTGCAGATGCACCAGCGTATCAGCAGG
GCCAGAACCAACTGTATAACGAGCTCAACCTGGGACGCAGGGAAGAGTATGACGTTTTGGA
CAAGCGCAGAGGACGGGACCCTGAGATGGGTGGCAAACCAAGACGAAAAAACCCCCAGGAG
GGTCTCTATAATGAGCTGCAGAAGGATAAGATGGCTGAAGCCTATTCTGAAATAGGCATGA
AAGGAGAGCGGAGAAGGGGAAAAGGGCACGACGGTTTGTACCAGGGACTCAGCACTGCTAC
GAAGGATACTTATGACGCTCTCCACATGCAAGCCCTGCCACCTAGG Clone RD-26578 CAR LxH (SEQ ID NO: 410)

MALPVTALLL PLALLLHAAR PEIVMTQSPA TLSVSPGERA TLSCRASQSV
SSNLAWYQQK PGQAPRLLIY SASTRATGIP ARFSGSGSGT EFTLTISSLQ
SEDFAVYYCQ QHHVWPLTFG GGTKVEIKRG STSGSGKPGS GEGSTKGQVQ
LVESGGGVVQ PGRSLRLSCA ASGFTFSSRG MHWVRQAPGK GLEWVAVIGY
DGQEKYYADS VKGRFTISRD NSKNTLYLQM NSLRAEDTAV YYCVKGPLQE
PPYDYGMDVW GQGTTVTVSS AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

---

What is claimed is:

1. An isolated polynucleotide encoding a chimeric antigen receptor (CAR) or T cell receptor (TCR) comprising an antigen binding molecule that specifically binds to B-cell maturation antigen (BCMA), wherein the antigen binding molecule comprises:

(a) a VH CDR1 region comprising the amino acid sequence of SEQ ID NO: 9; a VH CDR2 region comprising the amino acid sequence of SEQ ID NO: 25; a VH CDR3 region comprising the amino acid sequence of SEQ ID NO: 41; a VL CDR1 region comprising the amino acid sequence of SEQ ID NO: 81; a VL CDR2 region comprising the amino acid sequence of SEQ ID NO: 97; and a VL CDR3 region comprising the amino acid sequence of SEQ ID NO: 113;

(b) a VH CDR1 region comprising the amino acid sequence of SEQ ID NO: 10; a VH CDR2 region comprising the amino acid sequence of SEQ ID NO: 26; a VH CDR3 region comprising the amino acid sequence of SEQ ID NO: 42; a VL CDR1 region comprising the amino acid sequence of SEQ ID NO: 82; a VL CDR2 region comprising the amino acid sequence of SEQ ID NO: 98; and a VL CDR3 region comprising the amino acid sequence of SEQ ID NO: 114;

(c) a VH CDR1 region comprising the amino acid sequence of SEQ ID NO: 11; a VH CDR2 region comprising the amino acid sequence of SEQ ID NO: 27; a VH CDR3 region comprising the amino acid sequence of SEQ ID NO: 43; a VL CDR1 region comprising the amino acid sequence of SEQ ID NO: 83; a VL CDR2 region comprising the amino acid sequence of SEQ ID NO: 99; and a VL CDR3 region comprising the amino acid sequence of SEQ ID NO: 115;

(d) a VH CDR1 region comprising the amino acid sequence of SEQ ID NO: 12; a VH CDR2 region comprising the amino acid sequence of SEQ ID NO: 28; a VH CDR3 region comprising the amino acid sequence of SEQ ID NO: 44; a VL CDR1 region comprising the amino acid sequence of SEQ ID NO: 84; a VL CDR2 region comprising the amino acid sequence of SEQ ID NO: 100; and a VL CDR3 region comprising the amino acid sequence of SEQ ID NO: 116;

(e) a VH CDR1 region comprising the amino acid sequence of SEQ ID NO: 13; a VH CDR2 region comprising the amino acid sequence of SEQ ID NO: 29; a VH CDR3 region comprising the amino acid sequence of SEQ ID NO: 45; a VL CDR1 region comprising the amino acid sequence of SEQ ID NO: 85; a VL CDR2 region comprising the amino acid sequence of SEQ ID NO: 101; and a VL CDR3 region comprising the amino acid sequence of SEQ ID NO: 117;

(f) a VH CDR1 region comprising the amino acid sequence of SEQ ID NO: 14; a VH CDR2 region comprising the amino acid sequence of SEQ ID NO: 30; a VH CDR3 region comprising the amino acid sequence of SEQ ID NO: 46; a VL CDR1 region comprising the amino acid sequence of SEQ ID NO: 86; a VL CDR2 region comprising the amino acid sequence of SEQ ID NO: 102; and a VL CDR3 region comprising the amino acid sequence of SEQ ID NO: 118;

(g) a VH CDR1 region comprising the amino acid sequence of SEQ ID NO: 15; a VH CDR2 region comprising the amino acid sequence of SEQ ID NO: 31; a VH CDR3 region comprising the amino acid sequence of SEQ ID NO: 47; a VL CDR1 region comprising the amino acid sequence of SEQ ID NO: 87; a VL CDR2 region comprising the amino acid sequence of SEQ ID NO: 103; and a VL CDR3 region comprising the amino acid sequence of SEQ ID NO: 119; or (h) a VH CDR1 region comprising the amino acid sequence of SEQ ID NO: 16; a VH CDR2 region comprising the amino acid sequence of SEQ ID NO: 32; a VH CDR3 region comprising the amino acid sequence of SEQ ID NO: 48; a VL CDR1 region comprising the amino acid sequence of SEQ ID NO: 88; a VL CDR2 region comprising the amino acid sequence of SEQ ID NO: 104; and a VL CDR3 region comprising the amino acid sequence of SEQ ID NO: 120.

2. The polynucleotide of claim 1, wherein the antigen binding molecule comprises:

(a) a VH comprising the amino acid sequence of SEQ ID NO: 65; and a VL comprising the amino acid sequence of SEQ ID NO: 137;

(b) a VH comprising the amino acid sequence of SEQ ID NO: 66; and a VL comprising the amino acid sequence of SEQ ID NO: 138;

(c) a VH comprising the amino acid sequence of SEQ ID NO: 67; and a VL comprising the amino acid sequence of SEQ ID NO: 139;

(d) a VH comprising the amino acid sequence of SEQ ID NO: 68; and a VL comprising the amino acid sequence of SEQ ID NO: 140;

(e) a VH comprising the amino acid sequence of SEQ ID NO: 69; and a VL comprising the amino acid sequence of SEQ ID NO: 141;

(f) a VH comprising the amino acid sequence of SEQ ID NO: 70; and a VL comprising the amino acid sequence of SEQ ID NO: 142;

(g) a VH comprising the amino acid sequence of SEQ ID NO: 71; and a VL comprising the amino acid sequence of SEQ ID NO: 143; or (h) a VH comprising the amino acid sequence of SEQ ID NO: 72; and a VL comprising the amino acid sequence of SEQ ID NO: 144.

3. The polynucleotide of claim 2, which comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 57-64, wherein the nucleotide sequence encodes the VH of the antigen binding molecule.

4. The polynucleotide of claim 2, which comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 129-136, wherein the nucleotide sequence encodes the VL of the antigen binding molecule.

5. The polynucleotide of claim 1, wherein the antigen binding molecule is single chained.

6. The polynucleotide of claim 1, wherein the antigen binding molecule is selected from the group consisting of scFv, Fab, Fab', Fv, F(ab')2, and any combination thereof.

7. The polynucleotide of claim 1, wherein the antigen binding molecule comprises an scFv.

8. The polynucleotide of claim 1, wherein the VH and the VL are connected by a linker.

9. The polynucleotide of claim 8, wherein the VH is located at the N terminus of the linker and the VL is located at the C terminus of the linker.

10. The polynucleotide of claim 8, wherein the VL is located at the N terminus of the linker and the VH is located at the N terminus of the linker.

11. The polynucleotide of claim 8, wherein the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids.

12. The polynucleotide of claim 8, wherein the linker comprises an amino acid sequence at least 75%, at least 85%, at least 85%, at least 90%, at least 95%, at least 96%, at least 97%, at least 98%, at least 99%, or 100% identical to the amino acid sequence of SEQ ID NO: 174.

13. The polynucleotide of claim 1, wherein the antigen binding molecule binds to BCMA with a $K_D$ of less than about $1\times10^{-6}$ M, less than about $1\times10^{-7}$M, less than about $1\times10^{-8}$M, or less than about $1\times10^{-9}$ M.

14. The polynucleotide of claim 1, wherein the TCR further comprises a CDR4.

15. The polynucleotide of claim 1, wherein the TCR further comprises a constant region.

16. The polynucleotide of claim 1, wherein the CAR comprises a transmembrane domain, wherein the transmembrane domain is a transmembrane domain of CD28, 4-1BB/CD137, CD8 alpha, CD4, CD19, CD3 epsilon, CD45, CD5, CD9, CD16, CD22, CD33, CD37, CD64, CD80, CD86, CD134, CD137, CD154, an alpha chain of a T cell receptor, a beta chain of a T cell receptor, a zeta chain of a T cell receptor, or any combination thereof.

17. The polynucleotide of claim 16, wherein the transmembrane domain is a CD28 transmembrane domain.

18. The polynucleotide of claim 17, wherein the CD28 transmembrane domain comprises an amino acid sequence at least about 80%, at least about 85%, at least about 90%, at least about 95%, at least about 96%, at least about 97%, at least about 98%, at least about 99%, or about 100% identical to SEQ ID NO: 169.

19. The polynucleotide of claim 18, wherein the CD28 transmembrane domain is encoded by a nucleotide sequence at least about 80%, at least about 85%, at least about 90%, at least about 95%, at least about 96%, at least about 97%, at least about 98%, at least about 99%, or about 100% identical to SEQ ID NO: 168.

20. The polynucleotide of claim 16, wherein the CAR comprises a hinge region between the transmembrane domain and the antigen binding molecule.

21. The polynucleotide of claim 20, wherein the hinge region is of IgG1, IgG2, IgG3, IgG4, IgA, IgD, IgE, IgM, CD28, or CD8 alpha.

22. The polynucleotide of claim 20, wherein the hinge region is of CD28.

23. The polynucleotide of claim 22, wherein the hinge region comprises an amino acid sequence at least about 80%, at least about 85%, at least about 90%, at least about 95%, at least about 96%, at least about 97%, at least about 98%, at least about 99%, or about 100% identical to SEQ ID NO: 167.

24. The polynucleotide of claim 22, wherein the hinge region is encoded by a nucleotide sequence at least about 80%, at least about 85%, at least about 90%, at least about 95%, at least about 96%, at least about 97%, at least about 98%, at least about 99%, or about 100% identical to SEQ ID NO: 166.

25. The polynucleotide of claim 1, wherein the CAR or TCR comprises a costimulatory region.

26. The polynucleotide of claim 25, wherein the costimulatory region is a signaling region of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1)(CD11a/CD18), CD3 gamma, CD3 delta, CD3 epsilon, CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD (CD11d), ITGAE (CD103), ITGAL (CD11a), LFA-1, ITGAM (CD11b), ITGAX (CD11C), ITGB1, CD29, ITGB2, CD18, ITGB7, NKG2D, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, or any combination thereof.

27. The polynucleotide of claim 25, wherein the costimulatory region is a CD28 costimulatory region.

28. The polynucleotide of claim 25, wherein the costimulatory region is a 4-1BB/CD137 costimulatory region.

29. The polynucleotide of claim 25, wherein the costimulatory region comprises an amino acid sequence at least about 80%, at least about 85%, at least about 90%, at least about 95%, at least about 96%, at least about 97%, at least about 98%, at least about 99%, or about 100% identical to SEQ ID NO: 171.

30. The polynucleotide of claim 29, wherein the costimulatory region is encoded by a nucleotide sequence at least about 80%, at least about 85%, at least about 90%, at least about 95%, at least about 96%, at least about 97%, at least about 98%, at least about 99%, or about 100% identical to SEQ ID NO: 170.

31. The polynucleotide of claim 1, wherein the CAR or TCR comprises an activation domain.

32. The polynucleotide of claim 31, wherein the activation domain is a CD3 zeta domain.

33. The polynucleotide of claim 31, wherein the activation domain comprises an amino acid sequence at least about 80%, at least about 85%, at least about 90%, at least about 95%, at least about 96%, at least about 97%, at least about 98%, at least about 99%, or about 100% identical to SEQ ID NO: 173.

34. The polynucleotide of claim 32, wherein the activation domain is encoded by a nucleotide sequence at least about 80%, at least about 85%, at least about 90%, at least about 95%, at least about 96%, at least about 97%, at least about 98%, at least about 99%, or about 100% identical to SEQ ID NO: 172.

35. The polynucleotide of any one of claim 1, wherein the CAR or TCR further comprises a leader peptide.

36. The polynucleotide of claim 35, wherein the leader peptide comprises an amino acid sequence at least about 80%, at least about 85%, at least about 90%, at least about 95%, at least about 96%, at least about 97%, at least about 98%, at least about 99%, or about 100% identical to SEQ ID NO: 165.

37. The polynucleotide of claim 35, wherein the leader peptide is encoded by a nucleotide sequence at least about 80%, at least about 85%, at least about 90%, at least about 95%, at least about 96%, at least about 97%, at least about 98%, at least about 99%, or about 100% identical to SEQ ID NO: 164.

38. A vector comprising the polynucleotide of claim 1.

39. The vector of claim 38, which is a retroviral vector, a DNA vector, a plasmid, a RNA vector, an adenoviral vector, an adenovirus associated vector, a lentiviral vector, or any combination thereof.

40. A CAR or TCR encoded by the polynucleotide of claim 1.

41. A cell comprising the polynucleotide of claim 1, the vector of claim 38, the CAR or TCR of claim 40, or any combination thereof.

42. The cell of claim 41, wherein the T cell is a tumor-infiltrating lymphocyte (TIL), autologous T cell, engineered autologous T cell (eACT), an allogeneic T cell, or any combination thereof.

43. A composition comprising the polynucleotide of claim 1, the vector of claim 38, the CAR or TCR of claim 40, or the cell of claim 41.

44. A method of making a cell expressing a CAR or TCR comprising transducing a cell with the polynucleotide of claim 1 under suitable conditions.

45. The method of claim 44, further comprising isolating the cell.

46. A method of inducing an immunity against a tumor in a subject in need thereof, comprising administering to the subject an effective amount of a T-cell or NK-cell comprising the polynucleotide of claim 1, wherein the antigen binding molecule of the CAR or TCR encoded by the polynucleotide of claim 1 is linked to an intracellular signaling domain comprising at least one costimulatory domain and at least one activating domain.

47. A method treating a cancer in a subject in need thereof, comprising administering to the subject a T-cell or NK-cell comprising the polynucleotide of claim 1, wherein the antigen binding molecule of the CAR or TCR encoded by the polynucleotide of claim 1 is linked to an intracellular signaling domain comprising at least one costimulatory domain and at least one activating domain.

48. The method of claim 47, wherein the cancer is multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder, monoclonal gammapathy of undetermined significance (MGUS), a plasmacytomas, systemic amyloid light chain amyloidosis, POEMS syndrome (also known as Crow-Fukase syndrome, Takatsuki disease, and PEP syndrome), or a combination thereof.

49. An isolated polynucleotide encoding an antibody or an antigen binding molecule thereof that specifically binds to BCMA, wherein the antibody or antigen binding molecule thereof comprises:

(a) a VH CDR1 region comprising the amino acid sequence of SEQ ID NO: 9; a VH CDR2 region comprising the amino acid sequence of SEQ ID NO: 25; a VH CDR3 region comprising the amino acid sequence of SEQ ID NO: 41; a VL CDR1 region comprising the amino acid sequence of SEQ ID NO: 81; a VL CDR2 region comprising the amino acid sequence of SEQ ID NO: 97; and a VL CDR3 region comprising the amino acid sequence of SEQ ID NO: 113;

(b) a VH CDR1 region comprising the amino acid sequence of SEQ ID NO: 10; a VH CDR2 region comprising the amino acid sequence of SEQ ID NO: 26; a VH CDR3 region comprising the amino acid sequence of SEQ ID NO: 42; a VL CDR1 region comprising the amino acid sequence of SEQ ID NO: 82; a VL CDR2 region comprising the amino acid sequence of SEQ ID NO: 98; and a VL CDR3 region comprising the amino acid sequence of SEQ ID NO: 114;

(c) a VH CDR1 region comprising the amino acid sequence of SEQ ID NO: 11; a VH CDR2 region comprising the amino acid sequence of SEQ ID NO: 27; a VH CDR3 region comprising the amino acid sequence of SEQ ID NO: 43; a VL CDR1 region comprising the amino acid sequence of SEQ ID NO: 83; a VL CDR2 region comprising the amino acid sequence of SEQ ID NO: 99; and a VL CDR3 region comprising the amino acid sequence of SEQ ID NO: 115;

(d) a VH CDR1 region comprising the amino acid sequence of SEQ ID NO: 12; a VH CDR2 region comprising the amino acid sequence of SEQ ID NO:

28; a VH CDR3 region comprising the amino acid sequence of SEQ ID NO: 44; a VL CDR1 region comprising the amino acid sequence of SEQ ID NO: 84; a VL CDR2 region comprising the amino acid sequence of SEQ ID NO: 100; and a VL CDR3 region comprising the amino acid sequence of SEQ ID NO: 116;

(e) a VH CDR1 region comprising the amino acid sequence of SEQ ID NO: 13; a VH CDR2 region comprising the amino acid sequence of SEQ ID NO: 29; a VH CDR3 region comprising the amino acid sequence of SEQ ID NO: 45; a VL CDR1 region comprising the amino acid sequence of SEQ ID NO: 85; a VL CDR2 region comprising the amino acid sequence of SEQ ID NO: 101; and a VL CDR3 region comprising the amino acid sequence of SEQ ID NO: 117;

(f) a VH CDR1 region comprising the amino acid sequence of SEQ ID NO: 14; a VH CDR2 region comprising the amino acid sequence of SEQ ID NO: 30; a VH CDR3 region comprising the amino acid sequence of SEQ ID NO: 46; a VL CDR1 region comprising the amino acid sequence of SEQ ID NO: 86; a VL CDR2 region comprising the amino acid sequence of SEQ ID NO: 102; and a VL CDR3 region comprising the amino acid sequence of SEQ ID NO: 118;

(g) a VH CDR1 region comprising the amino acid sequence of SEQ ID NO: 15; a VH CDR2 region comprising the amino acid sequence of SEQ ID NO: 31; a VH CDR3 region comprising the amino acid sequence of SEQ ID NO: 47; a VL CDR1 region comprising the amino acid sequence of SEQ ID NO: 87; a VL CDR2 region comprising the amino acid sequence of SEQ ID NO: 103; and a VL CDR3 region comprising the amino acid sequence of SEQ ID NO: 119; or (h) a VH CDR1 region comprising the amino acid sequence of SEQ ID NO: 16; a VH CDR2 region comprising the amino acid sequence of SEQ ID NO: 32; a VH CDR3 region comprising the amino acid sequence of SEQ ID NO: 48; a VL CDR1 region comprising the amino acid sequence of SEQ ID NO: 88; a VL CDR2 region comprising the amino acid sequence of SEQ ID NO: 104; and a VL CDR3 region comprising the amino acid sequence of SEQ ID NO: 120.

50. The polynucleotide of claim 49, wherein the antibody or antigen binding molecule thereof comprises:

(a) a VH comprising the amino acid sequence of SEQ ID NO: 65; and a VL comprising the amino acid sequence of SEQ ID NO: 137;

(b) a VH comprising the amino acid sequence of SEQ ID NO: 66; and a VL comprising the amino acid sequence of SEQ ID NO: 138;

(c) a VH comprising the amino acid sequence of SEQ ID NO: 67; and a VL comprising the amino acid sequence of SEQ ID NO: 139;

(d) a VH comprising the amino acid sequence of SEQ ID NO: 68; and a VL comprising the amino acid sequence of SEQ ID NO: 140;

(e) a VH comprising the amino acid sequence of SEQ ID NO: 69; and a VL comprising the amino acid sequence of SEQ ID NO: 141;

(f) a VH comprising the amino acid sequence of SEQ ID NO: 70; and a VL comprising the amino acid sequence of SEQ ID NO: 142;

(g) a VH comprising the amino acid sequence of SEQ ID NO: 71; and a VL comprising the amino acid sequence of SEQ ID NO: 143; or (h) a VH comprising the amino acid sequence of SEQ ID NO: 72; and a VL comprising the amino acid sequence of SEQ ID NO: 144.

51. The polynucleotide of claim 50, which comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 57-64, wherein the nucleotide sequence encodes the VH of the antibody or antigen binding molecule thereof.

52. The polynucleotide of claim 50, which comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 129-136, wherein the nucleotide sequence encodes the VL of the antibody or antigen binding molecule thereof.

53. The polynucleotide of claim 49, wherein the antibody or antigen binding molecule thereof is single chained.

54. The polynucleotide of claim 49, wherein the antibody or antigen binding molecule thereof is selected from the group consisting of scFv, Fab, Fab', Fv, F(ab')2, and any combination thereof.

55. The polynucleotide of claim 49, wherein the antibody or antigen binding molecule thereof comprises a scFv.

56. The polynucleotide of claim 49, wherein the VH and the VL are connected by a linker.

57. The polynucleotide of claim 56, wherein the VH is located at the N terminus of the linker and the VL is located at the C terminus of the linker.

58. The polynucleotide of claim 56, wherein the VL is located at the N terminus of the linker and the VH is located at the N terminus of the linker.

59. The polynucleotide of claim 56, wherein the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids.

60. The polynucleotide of claim 56, wherein the linker comprises an amino acid sequence at least 75%, at least 85%, at least 85%, at least 90%, at least 95%, at least 96%, at least 97%, at least 98%, at least 99%, or 100% identical to the amino acid sequence of SEQ ID NO: 174.

61. The polynucleotide of claim 49, wherein the antibody or antigen binding molecule thereof binds to BCMA with a $K_D$ of less than about $1\times10^{-6}$ M, less than about $1\times10^{-7}$ M, less than about $1\times10^{-8}$M, or less than about $1\times10^{-9}$ M.

62. A vector comprising the polynucleotide of claim 49.

63. The vector of claim 62, which is a retroviral vector, a DNA vector, a plasmid, a RNA vector, an adenoviral vector, an adenovirus associated vector, a lentiviral vector, or any combination thereof.

64. An antibody or an antigen binding molecule thereof encoded by the polynucleotide of claim 49.

65. A polypeptide encoding a chimeric antigen receptor (CAR) or T cell receptor (TCR), wherein the CAR or the TCR comprises the antibody of the antigen binding molecule thereof of claim 64.

66. A cell comprising the polynucleotide of claim 49, the vector of claim 62, the antibody or the antigen binding molecule thereof of claim 64, or any combination thereof.

67. A composition comprising the polynucleotide of claim 49, the vector of claim 62, or the antibody or the antigen binding molecule thereof of claim 64.

68. A method of making an antibody or an antigen binding molecule thereof comprising transducing a cell with the polynucleotide of claim 49 under suitable conditions.

69. A method of inducing an immunity against a tumor in a subject in need thereof, comprising administering to a subject an effective amount of a T-cell or NK-cell comprising a CAR or TCR, wherein the antigen binding molecule of the CAR or TCR is encoded by the polynucleotide of claim 49 and is linked to an intracellular signaling domain comprising at least one costimulatory domain and at least one activating domain.

70. A method of treating a cancer in a subject in need thereof, comprising administering to the subject a T-cell or NK-cell comprising a CAR or TCR, wherein the antigen binding molecule of the CAR or TCR is encoded by the polynucleotide of claim 49 and is linked to an intracellular signaling domain comprising at least one costimulatory domain and at least one activating domain.

71. The method of claim 70, wherein the cancer is multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder, monoclonal gammapathy of undetermined significance (MGUS), a plasmacytoma, systemic amyloid light chain amyloidosis, POEMS syndrome (also known as Crow-Fukase syndrome, Takatsuki disease, and PEP syndrome), or a combination thereof.

* * * * *

SEQUENCE LISTING

<160> NUMBER OF SEQ ID NOS: 413

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 1

Glu Val Gln Leu Leu Glu Ser Gly Gly Gly Leu Val Gln Pro Gly Gly
1 5 10 15

Ser Leu Arg Leu Ser Cys Ala Ala Ser
20 25

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 2

Gln Val Gln Leu Val Glu Ser Gly Gly Gly Val Val Gln Pro Gly Arg
1 5 10 15

Ser Leu Arg Leu Ser Cys Ala Ala Ser
20 25

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 3

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 4

Gln Leu Gln Leu Gln Glu Ser Gly Pro Gly Leu Val Lys Pro Ser Glu
1 5 10 15

Thr Leu Ser Leu Thr Cys Thr Val Ser
20 25

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 5

Glu Val Gln Leu Val Glu Ser Gly Gly Gly Leu Val Gln Pro Gly Gly
1 5 10 15

Ser Leu Arg Leu Ser Cys Ala Ala Ser
20 25

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 6

Gln Val Gln Leu Val Glu Ser Gly Gly Gly Val Val Gln Pro Gly Arg
1 5 10 15

Ser Leu Arg Leu Ser Cys Ala Ala Ser
20 25

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 7

Gln Val Gln Leu Val Gln Ser Gly Ala Glu Val Lys Lys Pro Gly Ser
1 5 10 15

Ser Val Lys Val Ser Cys Lys Ala Ser
20 25

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 8

Gln Val Gln Leu Val Glu Ser Gly Gly Gly Val Val Gln Pro Gly Arg

```
1               5                   10                  15

Ser Leu Arg Leu Ser Cys Ala Ala Ser
            20                  25


<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 9

Gly Phe Thr Phe Ser Ser Tyr
1               5


<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 10

Gly Phe Thr Phe Ser Ser Tyr
1               5


<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 11

Gly Tyr Thr Phe Thr Ser Tyr
1               5


<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 12

Gly Gly Ser Ile Ser Ser Ser Ser Tyr
1               5


<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 13

Gly Phe Thr Phe Ser Ser Tyr
1               5


<210> SEQ ID NO 14
<211> LENGTH: 7
<212> TYPE: PRT
```

<213> ORGANISM: Artificial Sequence
<220> FEATURE:
<223> OTHER INFORMATION: Description of Artificial Sequence: Synthetic
VH CDR1 peptide

<400> SEQUENCE: 14

Gly Phe Thr Phe Ser Ser Tyr
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 15

Gly Gly Thr Phe Ser Ser Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 16

Gly Phe Thr Phe Ser Ser Tyr
1               5

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 17

Ala Met Ser Trp Val Arg Gln Ala Pro Gly Lys Gly Leu Glu Trp Val
1               5                   10                  15

Ser

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 18

Gly Met His Trp Val Arg Gln Ala Pro Gly Lys Gly Leu Glu Trp Val
1               5                   10                  15

Ala

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 19

Tyr Met His Trp Val Arg Gln Ala Pro Gly Gln Gly Leu Glu Trp Met
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 20

Tyr Trp Gly Trp Ile Arg Gln Pro Pro Gly Lys Gly Leu Glu Trp Ile
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 21

Ser Met Asn Trp Val Arg Gln Ala Pro Gly Lys Gly Leu Glu Trp Val
1               5                   10                  15

Ser

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 22

Gly Met His Trp Val Arg Gln Ala Pro Gly Lys Gly Leu Glu Trp Val
1               5                   10                  15

Ala

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 23

Ala Ile Ser Trp Val Arg Gln Ala Pro Gly Gln Gly Leu Glu Trp Met
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 24

Gly Met His Trp Val Arg Gln Ala Pro Gly Lys Gly Leu Glu Trp Val
1 5 10 15

Ala

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
VH CDR2 peptide

<400> SEQUENCE: 25

Ala Ile Ser Gly Ser Gly Gly Ser Thr Tyr Tyr Ala Asp Ser Val Lys
1 5 10 15

Gly

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
VH CDR2 peptide

<400> SEQUENCE: 26

Val Ile Ser Tyr Asp Gly Ser Asn Lys Tyr Tyr Ala Asp Ser Val Lys
1 5 10 15

Gly

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
VH CDR2 peptide

<400> SEQUENCE: 27

Ile Ile Asn Pro Gly Gly Gly Ser Thr Ser Tyr Ala Gln Lys Phe Gln
1 5 10 15

Gly

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
VH CDR2 peptide

<400> SEQUENCE: 28

Ser Ile Ser Tyr Ser Gly Ser Thr Tyr Tyr Asn Pro Ser Leu Lys Ser
1 5 10 15

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
VH CDR2 peptide

<400> SEQUENCE: 29

Thr Ile Ser Ser Ser Ser Ser Thr Ile Tyr Tyr Ala Asp Ser Val Lys
1 5 10 15

Gly

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic VH CDR2 peptide

<400> SEQUENCE: 30

Val Ile Ser Tyr Asp Gly Ser Asn Lys Tyr Tyr Ala Asp Ser Val Lys
1 5 10 15

Gly

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic VH CDR2 peptide

<400> SEQUENCE: 31

Gly Ile Ile Pro Ile Phe Gly Thr Ala Asn Tyr Ala Gln Lys Phe Gln
1 5 10 15

Gly

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic VH CDR2 peptide

<400> SEQUENCE: 32

Val Ile Ser Tyr Asp Gly Ser Asn Lys Tyr Tyr Ala Asp Ser Val Lys
1 5 10 15

Gly

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic VH FR3 polypeptide

<400> SEQUENCE: 33

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys
20 25 30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic VH FR3 polypeptide

<400> SEQUENCE: 34

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys
20 25 30

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic
VH FR3 polypeptide

<400> SEQUENCE: 35

Arg Val Thr Met Thr Arg Asp Thr Ser Thr Ser Thr Val Tyr Met Glu
1 5 10 15

Leu Ser Ser Leu Arg Ser Glu Asp Thr Ala Val Tyr Tyr Cys
20 25 30

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
VH FR3 polypeptide

<400> SEQUENCE: 36

Arg Val Thr Ile Ser Val Asp Thr Ser Lys Asn Gln Phe Ser Leu Lys
1 5 10 15

Leu Ser Ser Val Thr Ala Ala Asp Thr Ala Val Tyr Tyr Cys
20 25 30

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
VH FR3 polypeptide

<400> SEQUENCE: 37

Arg Phe Thr Ile Ser Arg Asp Asn Ala Lys Asn Ser Leu Tyr Leu Gln
1 5 10 15

Met Asn Ser Leu Arg Ala Glu Asp Thr Ala Val Tyr Tyr Cys
20 25 30

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
VH FR3 polypeptide

<400> SEQUENCE: 38

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys
20 25 30

-continued

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
VH FR3 polypeptide

<400> SEQUENCE: 39

Arg Val Thr Ile Thr Ala Asp Glu Ser Thr Ser Thr Ala Tyr Met Glu
1 5 10 15

Leu Ser Ser Leu Arg Ser Glu Asp Thr Ala Val Tyr Tyr Cys
20 25 30

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
VH FR3 polypeptide

<400> SEQUENCE: 40

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys
20 25 30

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
VH CDR3 peptide

<400> SEQUENCE: 41

Ala Arg Ala Glu Met Gly Ala Val Phe Asp Ile
1 5 10

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
VH CDR3 peptide

<400> SEQUENCE: 42

Ala Arg Asp Gly Thr Tyr Leu Gly Gly Leu Trp Tyr Phe Asp Leu
1 5 10 15

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR3 peptide

<400> SEQUENCE: 43

Ala Arg Glu Ser Trp Pro Met Asp Val
1 5

<210> SEQ ID NO 44
<211> LENGTH: 14
<212> TYPE: PRT

<213> ORGANISM: Artificial Sequence
<220> FEATURE:
<223> OTHER INFORMATION: Description of Artificial Sequence: Synthetic
VH CDR3 peptide

<400> SEQUENCE: 44

Ala Arg Gly Arg Gly Tyr Ala Thr Ser Leu Ala Phe Asp Ile
1 5 10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
VH CDR3 peptide

<400> SEQUENCE: 45

Ala Arg Gly Ser Gln Glu His Leu Ile Phe Asp Tyr
1 5 10

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
VH CDR3 peptide

<400> SEQUENCE: 46

Ala Arg Thr Asp Phe Trp Ser Gly Ser Pro Pro Gly Leu Asp Tyr
1 5 10 15

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
VH CDR3 peptide

<400> SEQUENCE: 47

Ala Arg Thr Pro Glu Tyr Ser Ser Ser Ile Trp His Tyr Tyr Tyr Gly
1 5 10 15

Met Asp Val

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
VH CDR3 peptide

<400> SEQUENCE: 48

Val Lys Gly Pro Leu Gln Glu Pro Pro Tyr Asp Tyr Gly Met Asp Val
1 5 10 15

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
VH FR4 peptide

<400> SEQUENCE: 49

Trp Gly Gln Gly Thr Met Val Thr Val Ser Ser
1 5 10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic VH FR4 peptide

<400> SEQUENCE: 50

Trp Gly Arg Gly Thr Leu Val Thr Val Ser Ser
1 5 10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic VH FR4 peptide

<400> SEQUENCE: 51

Trp Gly Gln Gly Thr Thr Val Thr Val Ser Ser
1 5 10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic VH FR4 peptide

<400> SEQUENCE: 52

Trp Gly Gln Gly Thr Met Val Thr Val Ser Ser
1 5 10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic VH FR4 peptide

<400> SEQUENCE: 53

Trp Gly Gln Gly Thr Leu Val Thr Val Ser Ser
1 5 10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic VH FR4 peptide

<400> SEQUENCE: 54

Trp Gly Gln Gly Thr Leu Val Thr Val Ser Ser
1 5 10

<210> SEQ ID NO 55
<211> LENGTH: 11
<212> TYPE: PRT
<213> ORGANISM: Artificial Sequence
<220> FEATURE:

<223> OTHER INFORMATION: Description of Artificial Sequence: Synthetic
VH FR4 peptide

<400> SEQUENCE: 55

Trp Gly Gln Gly Thr Thr Val Thr Val Ser Ser
1 5 10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
VH FR4 peptide

<400> SEQUENCE: 56

Trp Gly Gln Gly Thr Thr Val Thr Val Ser Ser
1 5 10

<210> SEQ ID NO 57
<211> LENGTH: 354
<212> TYPE: DNA
<213> ORGANISM: Artificial Sequence
<220> FEATURE:
<223> OTHER INFORMATION: Description of Artificial Sequence: Synthetic
VH polynucleotide

<400> SEQUENCE: 57
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggcggtgt actactgcgc aagagccgag 300
atgggagccg tattcgacat atggggtcag ggtacaatgg tcaccgtctc ctca 354

<210> SEQ ID NO 58
<211> LENGTH: 366
<212> TYPE: DNA
<213> ORGANISM: Artificial Sequence
<220> FEATURE:
<223> OTHER INFORMATION: Description of Artificial Sequence: Synthetic
VH polynucleotide

<400> SEQUENCE: 58
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatcgtatg atggaagtaa taaatactat 180
gcagactccg tgaagggccg attcaccatc tccagagaca attccaagaa cacgctgtat 240
ctgcaaatga acagcctgag agccgaggac acggcggtgt actactgcgc cagagacggt 300
acttatctag gtggtctctg gtacttcgac ttatggggga gaggtacctt ggtcaccgtc 360
tcctca 366

<210> SEQ ID NO 59
<211> LENGTH: 348
<212> TYPE: DNA
<213> ORGANISM: Artificial Sequence
<220> FEATURE:
<223> OTHER INFORMATION: Description of Artificial Sequence: Synthetic
VH polynucleotide

<400> SEQUENCE: 59
caggtgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaaccctg gtggtggtag cacaagctac 180
gcacagaagt tccagggcag agtcaccatg accagggaca cgtccacgag cacagtctac 240
atggagctga gcagcctgag atctgaggac acggcggtgt actactgcgc cagagagagt 300
tggccaatgg acgtatgggg ccagggaaca actgtcaccg tctcctca 348

<210> SEQ ID NO 60
<211> LENGTH: 366
<212> TYPE: DNA
<213> ORGANISM: Artificial Sequence
<220> FEATURE:
<223> OTHER INFORMATION: Description of Artificial Sequence: Synthetic
VH polynucleotide

<400> SEQUENCE: 60
cagctgcagc tgcaggagtc gggcccagga ctggtgaagc cttcggagac cctgtccctc 60
acctgcactg tctctggtgg ctccatcagc agtagtagtt actactgggg ctggatccgc 120
cagcccccag ggaaggggct ggagtggatt gggagtatct cctatagtgg gagcacctac 180
tacaacccgt ccctcaagag tcgagtcacc atatccgtag acacgtccaa gaaccagttc 240
tccctgaagc tgagttctgt gaccgccgca gacacggcgg tgtactactg cgccagaggc 300
aggggatatg caaccagctt agccttcgat atctggggtc agggtacaat ggtcaccgtc 360
tcctca 366

<210> SEQ ID NO 61
<211> LENGTH: 357
<212> TYPE: DNA
<213> ORGANISM: Artificial Sequence
<220> FEATURE:
<223> OTHER INFORMATION: Description of Artificial Sequence: Synthetic
VH polynucleotide

<400> SEQUENCE: 61
gaggtgcagc tggtggagtc tgggggaggc ttggtacagc ctggggggtc cctgagactc 60
tcctgtgcag cctctggatt caccttcagt agctatagca tgaactgggt ccgccaggct 120
ccagggaagg ggctggagtg ggtttcaacc attagtagta gtagtagtac catatactac 180
gcagactctg tgaagggccg attcaccatc tccagagaca atgccaagaa ctcactgtat 240
ctgcaaatga acagcctgag agctgaggac acggcggtgt actactgcgc cagaggttct 300
caggagcacc tgattttcga ttattgggga cagggtacat tggtcaccgt ctcctca 357

<210> SEQ ID NO 62
<211> LENGTH: 366
<212> TYPE: DNA
<213> ORGANISM: Artificial Sequence
<220> FEATURE:
<223> OTHER INFORMATION: Description of Artificial Sequence: Synthetic
VH polynucleotide

<400> SEQUENCE: 62
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatcgtatg atggaagtaa taaatactat 180
gcagactccg tgaagggccg attcaccatc tccagagaca attccaagaa cacgctgtat 240
ctgcaaatga acagcctgag agccgaggac acggcggtgt actactgcgc cagaactgac 300
ttctggagcg gatcccctcc aggcttagat tactggggac agggtacatt ggtcaccgtc 360
tcctca 366

<210> SEQ ID NO 63
<211> LENGTH: 378
<212> TYPE: DNA
<213> ORGANISM: Artificial Sequence
<220> FEATURE:
<223> OTHER INFORMATION: Description of Artificial Sequence: Synthetic
VH polynucleotide

<400> SEQUENCE: 63
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggcggtgt actactgcgc cagaactcct 300
gaatactcct ccagcatatg gcactattac tacggcatgg acgtatgggg ccagggaaca 360
actgtcaccg tctcctca 378

<210> SEQ ID NO 64
<211> LENGTH: 369
<212> TYPE: DNA
<213> ORGANISM: Artificial Sequence
<220> FEATURE:
<223> OTHER INFORMATION: Description of Artificial Sequence: Synthetic
VH polynucleotide

<400> SEQUENCE: 64
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatcgtatg atggaagtaa taaatactat 180
gcagactccg tgaagggccg attcaccatc tccagagaca attccaagaa cacgctgtat 240
ctgcaaatga acagcctgag agccgaggac acggcggtgt actactgcgt caaggggccg 300
ttgcaggagc cgccatacga ttatggaatg gacgtatggg gccagggaac aactgtcacc 360
gtctcctca 369

<210> SEQ ID NO 65
<211> LENGTH: 118
<212> TYPE: PRT
<213> ORGANISM: Artificial Sequence
<220> FEATURE:
<223> OTHER INFORMATION: Description of Artificial Sequence: Synthetic
VH polypeptide

<400> SEQUENCE: 65

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Glu Met Gly Ala Val Phe Asp Ile Trp Gly Gln Gly Thr
            100                 105                 110

Met Val Thr Val Ser Ser
        115
```

<210> SEQ ID NO 66
<211> LENGTH: 122
<212> TYPE: PRT
<213> ORGANISM: Artificial Sequence
<220> FEATURE:
<223> OTHER INFORMATION: Description of Artificial Sequence: Synthetic VH polypeptide

<400> SEQUENCE: 66

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Tyr Leu Gly Gly Leu Trp Tyr Phe Asp Leu Trp
            100                 105                 110

Gly Arg Gly Thr Leu Val Thr Val Ser Ser
        115                 120
```

<210> SEQ ID NO 67
<211> LENGTH: 116
<212> TYPE: PRT
<213> ORGANISM: Artificial Sequence
<220> FEATURE:
<223> OTHER INFORMATION: Description of Artificial Sequence: Synthetic VH polypeptide

<400> SEQUENCE: 67

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Gly Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
```

100 105 110

Thr Val Ser Ser
115

<210> SEQ ID NO 68
<211> LENGTH: 122
<212> TYPE: PRT
<213> ORGANISM: Artificial Sequence
<220> FEATURE:
<223> OTHER INFORMATION: Description of Artificial Sequence: Synthetic
VH polypeptide

<400> SEQUENCE: 68

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

Trp Ile Gly Ser Ile Ser Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Gly Arg Gly Tyr Ala Thr Ser Leu Ala Phe Asp Ile Trp
100 105 110

Gly Gln Gly Thr Met Val Thr Val Ser Ser
115 120

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic
VH polypeptide

<400> SEQUENCE: 69

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Thr Ile Ser Ser Ser Ser Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Ser Gln Glu His Leu Ile Phe Asp Tyr Trp Gly Gln Gly
100 105 110

Thr Leu Val Thr Val Ser Ser
115

<210> SEQ ID NO 70
<211> LENGTH: 122
<212> TYPE: PRT

<213> ORGANISM: Artificial Sequence
<220> FEATURE:
<223> OTHER INFORMATION: Description of Artificial Sequence: Synthetic
VH polypeptide

<400> SEQUENCE: 70

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Phe Trp Ser Gly Ser Pro Pro Gly Leu Asp Tyr Trp
            100                 105                 110

Gly Gln Gly Thr Leu Val Thr Val Ser Ser
        115                 120

<210> SEQ ID NO 71
<211> LENGTH: 126
<212> TYPE: PRT
<213> ORGANISM: Artificial Sequence
<220> FEATURE:
<223> OTHER INFORMATION: Description of Artificial Sequence: Synthetic
VH polypeptide

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Glu Tyr Ser Ser Ser Ile Trp His Tyr Tyr Tyr Gly
            100                 105                 110

Met Asp Val Trp Gly Gln Gly Thr Thr Val Thr Val Ser Ser
        115                 120                 125

<210> SEQ ID NO 72
<211> LENGTH: 123
<212> TYPE: PRT
<213> ORGANISM: Artificial Sequence
<220> FEATURE:
<223> OTHER INFORMATION: Description of Artificial Sequence: Synthetic
VH polypeptide

<400> SEQUENCE: 72

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Asp Tyr Gly Met Asp Val
            100                 105                 110

Trp Gly Gln Gly Thr Thr Val Thr Val Ser Ser
        115                 120


<210> SEQ ID NO 73
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys
            20


<210> SEQ ID NO 74
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 74

Asp Ile Val Met Thr Gln Ser Pro Leu Ser Leu Pro Val Thr Pro Gly
1               5                   10                  15

Glu Pro Ala Ser Ile Ser Cys
            20


<210> SEQ ID NO 75
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 75

Glu Ile Val Met Thr Gln Ser Pro Ala Thr Leu Ser Val Ser Pro Gly
1               5                   10                  15

Glu Arg Ala Thr Leu Ser Cys
            20


<210> SEQ ID NO 76
<211> LENGTH: 23
<212> TYPE: PRT
<213> ORGANISM: Artificial Sequence
<220> FEATURE:
```

-continued

<223> OTHER INFORMATION: Description of Artificial Sequence: Synthetic
VL FR1 peptide

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence: Synthetic
VL FR1 peptide

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence: Synthetic
VL FR1 peptide

<400> SEQUENCE: 78

Asp Ile Gln Leu Thr Gln Ser Pro Ser Ser Val Ser Ala Ser Val Gly
1               5                   10                  15

Asp Arg Val Thr Ile Thr Cys
            20

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence: Synthetic
VL FR1 peptide

<400> SEQUENCE: 79

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 80
<211> LENGTH: 23
<212> TYPE: PRT
<213> ORGANISM: Artificial Sequence
<220> FEATURE:
<223> OTHER INFORMATION: Description of Artificial Sequence: Synthetic
VL FR1 peptide

<400> SEQUENCE: 80

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
VL CDR1 peptide

<400> SEQUENCE: 81

Arg Ala Ser Gln Ser Val Ser Arg Tyr Leu Ala
1 5 10

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
VL CDR1 peptide

<400> SEQUENCE: 82

Arg Ser Ser Gln Ser Leu Leu His Ser Asn Gly Tyr Asn Tyr Leu Asp
1 5 10 15

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
VL CDR1 peptide

<400> SEQUENCE: 83

Arg Ala Ser Gln Ser Val Ser Ser Asn Leu Ala
1 5 10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
VL CDR1 peptide

<400> SEQUENCE: 84

Arg Ala Ser Gln Ser Val Ser Ser Tyr Leu Ala
1 5 10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
VL CDR1 peptide

<400> SEQUENCE: 85

Arg Ala Ser Gln Ser Val Ser Arg Tyr Leu Ala
1 5 10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
VL CDR1peptide

<400> SEQUENCE: 86

Arg Ala Ser Gln Gly Ile Ser Ser Trp Leu Ala
1               5                   10

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      VL CDR1 peptide

<400> SEQUENCE: 87

Lys Ser Ser Gln Ser Val Leu Tyr Ser Ser Asn Asn Lys Asn Tyr Leu
1               5                   10                  15

Ala

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR1 peptide

<400> SEQUENCE: 88

Arg Ala Ser Gln Ser Val Ser Ser Asn Leu Ala
1               5                   10

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 89

Trp Tyr Gln Gln Lys Pro Gly Gln Ala Pro Arg Leu Leu Ile Tyr
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 90

Trp Tyr Leu Gln Lys Pro Gly Gln Ser Pro Gln Leu Leu Ile Tyr
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 91

Trp Tyr Gln Gln Lys Pro Gly Gln Ala Pro Arg Leu Leu Ile Tyr
1               5                   10                  15

<210> SEQ ID NO 92

<211> LENGTH: 15
<212> TYPE: PRT
<213> ORGANISM: Artificial Sequence
<220> FEATURE:
<223> OTHER INFORMATION: Description of Artificial Sequence: Synthetic
VL FR2 peptide

<400> SEQUENCE: 92

Trp Tyr Gln Gln Lys Pro Gly Gln Ala Pro Arg Leu Leu Ile Tyr
1 5 10 15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
VL FR2 peptide

<400> SEQUENCE: 93

Trp Tyr Gln Gln Lys Pro Gly Gln Ala Pro Arg Leu Leu Ile Tyr
1 5 10 15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
VL FR2 peptide

<400> SEQUENCE: 94

Trp Tyr Gln Gln Lys Pro Gly Lys Ala Pro Lys Leu Leu Ile Tyr
1 5 10 15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
VL FR2 peptide

<400> SEQUENCE: 95

Trp Tyr Gln Gln Lys Pro Gly Gln Pro Pro Lys Leu Leu Ile Tyr
1 5 10 15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
VL FR2 peptide

<400> SEQUENCE: 96

Trp Tyr Gln Gln Lys Pro Gly Gln Ala Pro Arg Leu Leu Ile Tyr
1 5 10 15

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
VL CDR2 peptide

<400> SEQUENCE: 97

-continued

Asp Ala Ser Asn Arg Ala Thr
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 98

Leu Gly Ser Asn Arg Ala Ser
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 99

Gly Ala Ser Thr Arg Ala Thr
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 100

Asp Ala Ser Asn Arg Ala Thr
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 101

Asp Ala Ser Asn Arg Ala Thr
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 102

Gly Ala Ser Ser Leu Gln Ser
1               5

<210> SEQ ID NO 103
<211> LENGTH: 7
<212> TYPE: PRT
<213> ORGANISM: Artificial Sequence
<220> FEATURE:

<223> OTHER INFORMATION: Description of Artificial Sequence: Synthetic
      VL CDR2 peptide

<400> SEQUENCE: 103

Trp Ala Ser Thr Arg Glu Ser
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 104

Ser Ala Ser Thr Arg Ala Thr
1               5

<210> SEQ ID NO 105
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 105

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 106
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 106

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 107
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 107

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 108
<211> LENGTH: 32
<212> TYPE: PRT
<213> ORGANISM: Artificial Sequence
<220> FEATURE:

<223> OTHER INFORMATION: Description of Artificial Sequence: Synthetic
VL FR3 polypeptide

<400> SEQUENCE: 108

Gly Ile Pro Ala Arg Phe Ser Gly Ser Gly Ser Gly Thr Asp Phe Thr
1 5 10 15

Leu Thr Ile Ser Ser Leu Glu Pro Glu Asp Phe Ala Val Tyr Tyr Cys
20 25 30

<210> SEQ ID NO 109
<211> LENGTH: 32
<212> TYPE: PRT
<213> ORGANISM: Artificial Sequence
<220> FEATURE:
<223> OTHER INFORMATION: Description of Artificial Sequence: Synthetic
VL FR3 polypeptide

<400> SEQUENCE: 109

Gly Ile Pro Ala Arg Phe Ser Gly Ser Gly Ser Gly Thr Asp Phe Thr
1 5 10 15

Leu Thr Ile Ser Ser Leu Glu Pro Glu Asp Phe Ala Val Tyr Tyr Cys
20 25 30

<210> SEQ ID NO 110
<211> LENGTH: 32
<212> TYPE: PRT
<213> ORGANISM: Artificial Sequence
<220> FEATURE:
<223> OTHER INFORMATION: Description of Artificial Sequence: Synthetic
VL FR3 polypeptide

<400> SEQUENCE: 110

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 111
<211> LENGTH: 32
<212> TYPE: PRT
<213> ORGANISM: Artificial Sequence
<220> FEATURE:
<223> OTHER INFORMATION: Description of Artificial Sequence: Synthetic
VL FR3 polypeptide

<400> SEQUENCE: 111

Gly Val Pro Asp Arg Phe Ser Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 112
<211> LENGTH: 32
<212> TYPE: PRT
<213> ORGANISM: Artificial Sequence
<220> FEATURE:
<223> OTHER INFORMATION: Description of Artificial Sequence: Synthetic
VL FR3 polypeptide

<400> SEQUENCE: 112

Gly Ile Pro Ala Arg Phe Ser Gly Ser Gly Ser Gly Thr Glu Phe Thr
1 5 10 15

Leu Thr Ile Ser Ser Leu Gln Ser Glu Asp Phe Ala Val Tyr Tyr Cys
20 25 30

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
VL CDR3 peptide

<400> SEQUENCE: 113

Gln Gln Arg Ile Ser Trp Pro Phe Thr
1 5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
VL CDR3 peptide

<400> SEQUENCE: 114

Met Gln Gly Leu Gly Leu Pro Leu Thr
1 5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
VL CDR3 peptide

<400> SEQUENCE: 115

Gln Gln Tyr Ala Ala Tyr Pro Thr
1 5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
VL CDR3 peptide

<400> SEQUENCE: 116

Gln Gln Arg His Val Trp Pro Pro Thr
1 5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
VL CDR3 peptide

<400> SEQUENCE: 117

Gln Gln Arg Phe Tyr Tyr Pro Trp Thr
1 5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
VL CDR3 peptide

<400> SEQUENCE: 118

Gln Gln Ile Tyr Thr Phe Pro Phe Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide

<400> SEQUENCE: 119

Gln Gln Phe Ala His Thr Pro Phe Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide

<400> SEQUENCE: 120

Gln Gln His His Val Trp Pro Leu Thr
1               5

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 121

Phe Gly Gly Gly Thr Lys Val Glu Ile Lys
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 122

Phe Gly Gly Gly Thr Lys Val Glu Ile Lys
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 123

Phe Gly Gly Gly Thr Lys Val Glu Ile Lys
1               5                   10

<210> SEQ ID NO 124
<211> LENGTH: 10
<212> TYPE: PRT

<213> ORGANISM: Artificial Sequence
<220> FEATURE:
<223> OTHER INFORMATION: Description of Artificial Sequence: Synthetic
VL FR4 peptide

<400> SEQUENCE: 124

Phe Gly Gly Gly Thr Lys Val Glu Ile Lys
1 5 10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
VL FR4 peptide

<400> SEQUENCE: 125

Phe Gly Gly Gly Thr Lys Val Glu Ile Lys
1 5 10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
VL FR4 peptide

<400> SEQUENCE: 126

Phe Gly Gly Gly Thr Lys Val Glu Ile Lys
1 5 10

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
VL FR4 peptide

<400> SEQUENCE: 127

Phe Gly Gly Gly Thr Lys Val Glu Ile Lys
1 5 10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
VL FR4 peptide

<400> SEQUENCE: 128

Phe Gly Gly Gly Thr Lys Val Glu Ile Lys
1 5 10

<210> SEQ ID NO 129
<211> LENGTH: 321
<212> TYPE: DNA
<213> ORGANISM: Artificial Sequence
<220> FEATURE:
<223> OTHER INFORMATION: Description of Artificial Sequence: Synthetic
VL polynucleotide

<400> SEQUENCE: 129
gaaattgtgt tgacacagtc tccagccacc ctgtctttgt ctccagggga aagagccacc 60

```
ctctcctgca gggccagtca gagtgttagc aggtacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag agaatctcct ggcctttcac ttttggcgga    300
gggaccaagg ttgagatcaa a                                              321
```

<210> SEQ ID NO 130
<211> LENGTH: 336
<212> TYPE: DNA
<213> ORGANISM: Artificial Sequence
<220> FEATURE:
<223> OTHER INFORMATION: Description of Artificial Sequence: Synthetic VL polynucleotide

<400> SEQUENCE: 130

```
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcagggact cggcctccct    300
ctcacttttg gcggagggac caaggttgag atcaaa                              336
```

<210> SEQ ID NO 131
<211> LENGTH: 318
<212> TYPE: DNA
<213> ORGANISM: Artificial Sequence
<220> FEATURE:
<223> OTHER INFORMATION: Description of Artificial Sequence: Synthetic VL polynucleotide

<400> SEQUENCE: 131

```
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tacgccgcct accctacttt tggcggaggg    300
accaaggttg agatcaaa                                                  318
```

<210> SEQ ID NO 132
<211> LENGTH: 321
<212> TYPE: DNA
<213> ORGANISM: Artificial Sequence
<220> FEATURE:
<223> OTHER INFORMATION: Description of Artificial Sequence: Synthetic VL polynucleotide

<400> SEQUENCE: 132

```
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag agacacgtct ggcctcctac ttttggcgga    300
gggaccaagg ttgagatcaa a                                              321
```

<210> SEQ ID NO 133
<211> LENGTH: 321
<212> TYPE: DNA
<213> ORGANISM: Artificial Sequence
<220> FEATURE:
<223> OTHER INFORMATION: Description of Artificial Sequence: Synthetic
VL polynucleotide

<400> SEQUENCE: 133
gaaattgtgt tgacacagtc tccagccacc ctgtctttgt ctccagggga aagagccacc 60
ctctcctgca gggccagtca gagtgttagc aggtacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag agattctact acccttggac ttttggcgga 300
gggaccaagg ttgagatcaa a 321

<210> SEQ ID NO 134
<211> LENGTH: 321
<212> TYPE: DNA
<213> ORGANISM: Artificial Sequence
<220> FEATURE:
<223> OTHER INFORMATION: Description of Artificial Sequence: Synthetic
VL polynucleotide

<400> SEQUENCE: 134
gacatccagt tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaagctcct gatctatggt gcatccagtt tgcaaagtgg ggtcccatca 180
aggttcagcg gcagtggatc tgggacagat ttcactctca ccatcagcag cctgcagcct 240
gaagattttg caacttatta ctgtcagcag atatacacct tccctttcac ttttggcgga 300
gggaccaagg ttgagatcaa a 321

<210> SEQ ID NO 135
<211> LENGTH: 339
<212> TYPE: DNA
<213> ORGANISM: Artificial Sequence
<220> FEATURE:
<223> OTHER INFORMATION: Description of Artificial Sequence: Synthetic
VL polynucleotide

<400> SEQUENCE: 135
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcagtt cgcccacact 300
cctttcactt ttggcggagg gaccaaggtt gagatcaaa 339

<210> SEQ ID NO 136
<211> LENGTH: 321
<212> TYPE: DNA
<213> ORGANISM: Artificial Sequence
<220> FEATURE:
<223> OTHER INFORMATION: Description of Artificial Sequence: Synthetic
VL polynucleotide

<400> SEQUENCE: 136

```
gaaatagtga tgacgcagtc tccagccacc ctgtctgtgt ctccagggga aagagccacc     60

ctctcctgca gggccagtca gagtgttagc agcaacttag cctggtacca gcagaaacct    120

ggccaggctc ccaggctcct catctatagc gcatccacca gggccactgg tatcccagcc    180

aggttcagtg gcagtgggtc tgggacagag ttcactctca ccatcagcag cctgcagtct    240

gaagattttg cagtttatta ctgtcagcag caccacgtct ggcctctcac ttttggcgga    300

gggaccaagg ttgagatcaa a                                              321
```

```
<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 137

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Ser Trp Pro Phe
                85                  90                  95

Thr Phe Gly Gly Gly Thr Lys Val Glu Ile Lys
            100                 105


<210> SEQ ID NO 138
<211> LENGTH: 112
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 138

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gly Leu Pro Leu Thr Phe Gly Gly Gly Thr Lys Val Glu Ile Lys
            100                 105                 110


<210> SEQ ID NO 139
```

<211> LENGTH: 106
<212> TYPE: PRT
<213> ORGANISM: Artificial Sequence
<220> FEATURE:
<223> OTHER INFORMATION: Description of Artificial Sequence: Synthetic VL polypeptide

<400> SEQUENCE: 139

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Ala Ala Tyr Pro Thr
85 90 95

Phe Gly Gly Gly Thr Lys Val Glu Ile Lys
100 105

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic VL polypeptide

<400> SEQUENCE: 140

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg His Val Trp Pro Pro
85 90 95

Thr Phe Gly Gly Gly Thr Lys Val Glu Ile Lys
100 105

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic VL polypeptide

<400> SEQUENCE: 141

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Arg Tyr
20 25 30

```
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Tyr Tyr Pro Trp
                85                  90                  95

Thr Phe Gly Gly Gly Thr Lys Val Glu Ile Lys
            100                 105


<210> SEQ ID NO 142
<211> LENGTH: 107
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 142

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Tyr Thr Phe Pro Phe
                85                  90                  95

Thr Phe Gly Gly Gly Thr Lys Val Glu Ile Lys
            100                 105


<210> SEQ ID NO 143
<211> LENGTH: 113
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 143

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Ala His Thr Pro Phe Thr Phe Gly Gly Gly Thr Lys Val Glu Ile
            100                 105                 110
```

Lys

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
VL polypeptide

<400> SEQUENCE: 144

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Ser Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln His His Val Trp Pro Leu
85 90 95

Thr Phe Gly Gly Gly Thr Lys Val Glu Ile Lys
100 105

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide
<220> FEATURE:
<221> NAME/KEY: MISC_FEATURE
<222> LOCATION: (2)..(3)
<223> OTHER INFORMATION: May or may not be present
<220> FEATURE:
<221> NAME/KEY: MOD_RES
<222> LOCATION: (4)..(4)
<223> OTHER INFORMATION: Phe, Gly, Ile or Tyr
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Phe or Ser
<220> FEATURE:
<221> NAME/KEY: MOD_RES
<222> LOCATION: (7)..(7)
<223> OTHER INFORMATION: Ser or Thr

<400> SEQUENCE: 145

Gly Gly Ser Xaa Xaa Xaa Xaa Ser Tyr
1 5

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
VH CDR2 peptide
<220> FEATURE:
<221> NAME/KEY: MOD_RES
<222> LOCATION: (1)..(1)

<223> OTHER INFORMATION: Ala, Gly, Ile, Ser, Thr or Val
<220> FEATURE:
<221> NAME/KEY: MOD_RES
<222> LOCATION: (3)..(3)
<223> OTHER INFORMATION: Ile, Asn or Ser
<220> FEATURE:
<221> NAME/KEY: MOD_RES
<222> LOCATION: (4)..(4)
<223> OTHER INFORMATION: Gly, Pro, Ser or Tyr
<220> FEATURE:
<221> NAME/KEY: MOD_RES
<222> LOCATION: (5)..(5)
<223> OTHER INFORMATION: Asp, Gly, Ile or Ser
<220> FEATURE:
<221> NAME/KEY: MOD_RES
<222> LOCATION: (6)..(6)
<223> OTHER INFORMATION: Phe, Gly or Ser
<220> FEATURE:
<221> NAME/KEY: MOD_RES
<222> LOCATION: (7)..(7)
<223> OTHER INFORMATION: Gly, Ser or absent
<220> FEATURE:
<221> NAME/KEY: MOD_RES
<222> LOCATION: (8)..(8)
<223> OTHER INFORMATION: Asn, Ser or Thr
<220> FEATURE:
<221> NAME/KEY: MOD_RES
<222> LOCATION: (9)..(9)
<223> OTHER INFORMATION: Ala, Ile, Lys or Thr
<220> FEATURE:
<221> NAME/KEY: MOD_RES
<222> LOCATION: (10)..(10)
<223> OTHER INFORMATION: Asn, Ser or Tyr
<220> FEATURE:
<221> NAME/KEY: MOD_RES
<222> LOCATION: (12)..(12)
<223> OTHER INFORMATION: Ala or Asn
<220> FEATURE:
<221> NAME/KEY: MOD_RES
<222> LOCATION: (13)..(13)
<223> OTHER INFORMATION: Asp, Pro or Gln
<220> FEATURE:
<221> NAME/KEY: MOD_RES
<222> LOCATION: (14)..(14)
<223> OTHER INFORMATION: Lys or Ser
<220> FEATURE:
<221> NAME/KEY: MOD_RES
<222> LOCATION: (15)..(15)
<223> OTHER INFORMATION: Phe, Leu or Val
<220> FEATURE:
<221> NAME/KEY: MOD_RES
<222> LOCATION: (16)..(16)
<223> OTHER INFORMATION: Lys or Gln
<220> FEATURE:
<221> NAME/KEY: MOD_RES
<222> LOCATION: (17)..(17)
<223> OTHER INFORMATION: Gln or Ser

<400> SEQUENCE: 146

```
Xaa Ile Xaa Xaa Xaa Xaa Xaa Xaa Xaa Xaa Tyr Xaa Xaa Xaa Xaa Xaa
1               5                   10                  15

Xaa
```

<210> SEQ ID NO 147
<211> LENGTH: 19
<212> TYPE: PRT
<213> ORGANISM: Artificial Sequence
<220> FEATURE:
<223> OTHER INFORMATION: Description of Artificial Sequence: Synthetic
VH CDR3 peptide
<220> FEATURE:
<221> NAME/KEY: MOD_RES
<222> LOCATION: (1)..(1)
<223> OTHER INFORMATION: Ala or Val
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(3)
<223> OTHER INFORMATION: Asp, Gly, Thr or absent
<220> FEATURE:
<221> NAME/KEY: MOD_RES
<222> LOCATION: (4)..(4)
<223> OTHER INFORMATION: Ala, Asp, Gly, Pro, Arg, Ser or absent
<220> FEATURE:
<221> NAME/KEY: MOD_RES
<222> LOCATION: (5)..(5)
<223> OTHER INFORMATION: Glu, Phe, Gly, Leu, Gln, Thr or absent
<220> FEATURE:
<221> NAME/KEY: MOD_RES
<222> LOCATION: (6)..(6)
<223> OTHER INFORMATION: Glu, Met, Gln, Trp, Tyr or absent
<220> FEATURE:
<221> NAME/KEY: MOD_RES
<222> LOCATION: (7)..(7)
<223> OTHER INFORMATION: Ala, Glu, Leu, Ser or absent
<220> FEATURE:
<221> NAME/KEY: MOD_RES
<222> LOCATION: (8)..(8)
<223> OTHER INFORMATION: Gly, Pro, Ser, Thr or absent
<220> FEATURE:
<221> NAME/KEY: MOD_RES
<222> LOCATION: (9)..(9)
<223> OTHER INFORMATION: Gly, Pro, Ser or absent
<220> FEATURE:
<221> NAME/KEY: MOD_RES
<222> LOCATION: (10)..(10)
<223> OTHER INFORMATION: Ile, Leu, Pro, Tyr or absent
<220> FEATURE:
<221> NAME/KEY: MISC_FEATURE
<222> LOCATION: (11)..(12)
<223> OTHER INFORMATION: May or may not be present
<220> FEATURE:
<221> NAME/KEY: MOD_RES
<222> LOCATION: (13)..(13)
<223> OTHER INFORMATION: Glu, Tyr or absent
<220> FEATURE:
<221> NAME/KEY: MOD_RES
<222> LOCATION: (14)..(14)
<223> OTHER INFORMATION: Asp, Gly, His, Pro, Ser, Trp, Tyr or absent
<220> FEATURE:
<221> NAME/KEY: MOD_RES
<222> LOCATION: (15)..(15)
<223> OTHER INFORMATION: Ala, Gly, Leu, Trp or Tyr
<220> FEATURE:
<221> NAME/KEY: MOD_RES
<222> LOCATION: (16)..(16)
<223> OTHER INFORMATION: Ala, Gly, Ile, Pro, Val or absent
<220> FEATURE:
<221> NAME/KEY: MOD_RES
<222> LOCATION: (17)..(17)
<223> OTHER INFORMATION: Phe, Leu or Met
<220> FEATURE:
<221> NAME/KEY: MOD_RES
<222> LOCATION: (19)..(19)
<223> OTHER INFORMATION: Ile, Leu, Val or Tyr

<400> SEQUENCE: 147

```
Xaa Xaa Xaa Xaa Xaa Xaa Xaa Xaa Xaa Xaa Trp His Xaa Xaa Xaa Xaa
1               5                   10                  15

Xaa Asp Xaa
```

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
VL CDR1 peptide
<220> FEATURE:

<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (2)..(2)
<223> OTHER INFORMATION: Ala or Ser
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Ile, Leu or Val
<220> FEATURE:
<221> NAME/KEY: MOD_RES
<222> LOCATION: (7)..(7)
<223> OTHER INFORMATION: Leu or Ser
<220> FEATURE:
<221> NAME/KEY: MOD_RES
<222> LOCATION: (8)..(8)
<223> OTHER INFORMATION: His, Tyr or absent
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Asn, Ser or absent
<220> FEATURE:
<221> NAME/KEY: MOD_RES
<222> LOCATION: (11)..(11)
<223> OTHER INFORMATION: Gly, Asn or absent
<220> FEATURE:
<221> NAME/KEY: MISC_FEATURE
<222> LOCATION: (12)..(12)
<223> OTHER INFORMATION: May or may not be present
<220> FEATURE:
<221> NAME/KEY: MOD_RES
<222> LOCATION: (13)..(13)
<223> OTHER INFORMATION: Lys, Tyr or absent
<220> FEATURE:
<221> NAME/KEY: MOD_RES
<222> LOCATION: (14)..(14)
<223> OTHER INFORMATION: Asn, Arg or Ser
<220> FEATURE:
<221> NAME/KEY: MOD_RES
<222> LOCATION: (15)..(15)
<223> OTHER INFORMATION: Asn, Trp or Tyr
<220> FEATURE:
<221> NAME/KEY: MOD_RES
<222> LOCATION: (17)..(17)
<223> OTHER INFORMATION: Ala or Asp

<400> SEQUENCE: 148

```
Xaa Xaa Ser Gln Xaa Xaa Xaa Xaa Ser Xaa Xaa Asn Xaa Xaa Xaa Leu
1               5                   10                  15

Xaa
```

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
VL CDR2 peptide
<220> FEATURE:
<221> NAME/KEY: MOD_RES
<222> LOCATION: (1)..(1)
<223> OTHER INFORMATION: Asp, Gly, Leu, Ser or Trp
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Asn, Ser or Thr
<220> FEATURE:
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (6)..(6)
<223> OTHER INFORMATION: Ala, Glu or Gln
<220> FEATURE:
<221> NAME/KEY: MOD_RES
<222> LOCATION: (7)..(7)
<223> OTHER INFORMATION: Ser or Thr

<400> SEQUENCE: 149

Xaa Xaa Ser Xaa Xaa Xaa Xaa
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide
<220> FEATURE:
<221> NAME/KEY: MOD_RES
<222> LOCATION: (1)..(1)
<223> OTHER INFORMATION: Met or Gln
<220> FEATURE:
<221> NAME/KEY: MOD_RES
<222> LOCATION: (3)..(3)
<223> OTHER INFORMATION: Phe, Gly, His, Ile, Arg or Tyr
<220> FEATURE:
<221> NAME/KEY: MOD_RES
<222> LOCATION: (4)..(4)
<223> OTHER INFORMATION: Ala, Phe, His, Ile, Leu or Tyr
<220> FEATURE:
<221> NAME/KEY: MOD_RES
<222> LOCATION: (5)..(5)
<223> OTHER INFORMATION: Ala, Gly, His, Ser, Thr, Val or Tyr
<220> FEATURE:
<221> NAME/KEY: MOD_RES
<222> LOCATION: (6)..(6)
<223> OTHER INFORMATION: Phe, Leu, Thr, Trp or Tyr
<220> FEATURE:
<221> NAME/KEY: MOD_RES
<222> LOCATION: (8)..(8)
<223> OTHER INFORMATION: Phe, Leu, Pro or Trp

<400> SEQUENCE: 150

Xaa Gln Xaa Xaa Xaa Xaa Pro Xaa Thr
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide
<220> FEATURE:
<221> NAME/KEY: MOD_RES
<222> LOCATION: (2)..(2)
<223> OTHER INFORMATION: Phe or Gly

<400> SEQUENCE: 151

Gly Xaa Thr Phe Ser Ser Tyr
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide
<220> FEATURE:
<221> NAME/KEY: MISC_FEATURE
<222> LOCATION: (2)..(3)
<223> OTHER INFORMATION: May or may not be present
<220> FEATURE:
<221> NAME/KEY: MOD_RES
<222> LOCATION: (4)..(4)
<223> OTHER INFORMATION: Phe, Gly or Ile
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Phe or Ser

<400> SEQUENCE: 152

Gly Gly Ser Xaa Xaa Xaa Ser Ser Tyr
1               5

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
VH CDR2 peptide
<220> FEATURE:
<221> NAME/KEY: MOD_RES
<222> LOCATION: (1)..(1)
<223> OTHER INFORMATION: Ala, Gly, Ile, Thr or Val
<220> FEATURE:
<221> NAME/KEY: MOD_RES
<222> LOCATION: (3)..(3)
<223> OTHER INFORMATION: Ile, Asn or Ser
<220> FEATURE:
<221> NAME/KEY: MOD_RES
<222> LOCATION: (4)..(4)
<223> OTHER INFORMATION: Gly, Pro, Ser or Tyr
<220> FEATURE:
<221> NAME/KEY: MOD_RES
<222> LOCATION: (5)..(5)
<223> OTHER INFORMATION: Asp, Gly, Ile or Ser
<220> FEATURE:
<221> NAME/KEY: MOD_RES
<222> LOCATION: (6)..(6)
<223> OTHER INFORMATION: Phe, Gly or Ser
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Asn, Ser or Thr
<220> FEATURE:
<221> NAME/KEY: MOD_RES
<222> LOCATION: (9)..(9)
<223> OTHER INFORMATION: Ala, Ile, Lys or Thr
<220> FEATURE:
<221> NAME/KEY: MOD_RES
<222> LOCATION: (10)..(10)
<223> OTHER INFORMATION: Asn, Ser or Tyr
<220> FEATURE:
<221> NAME/KEY: MOD_RES
<222> LOCATION: (13)..(13)
<223> OTHER INFORMATION: Asp or Gln
<220> FEATURE:
<221> NAME/KEY: MOD_RES
<222> LOCATION: (14)..(14)
<223> OTHER INFORMATION: Lys or Ser
<220> FEATURE:
<221> NAME/KEY: MOD_RES
<222> LOCATION: (15)..(15)
<223> OTHER INFORMATION: Phe or Val
<220> FEATURE:
<221> NAME/KEY: MOD_RES
<222> LOCATION: (16)..(16)
<223> OTHER INFORMATION: Lys or Gln

<400> SEQUENCE: 153

Xaa Ile Xaa Xaa Xaa Xaa Xaa Xaa Xaa Xaa Tyr Ala Xaa Xaa Xaa Xaa
1 5 10 15

Gly

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
VH CDR2 peptide
<220> FEATURE:
<221> NAME/KEY: MOD_RES
<222> LOCATION: (1)..(1)
<223> OTHER INFORMATION: Ala, Thr or Val
<220> FEATURE:
<221> NAME/KEY: MOD_RES
<222> LOCATION: (4)..(4)
<223> OTHER INFORMATION: Gly, Ser or Tyr
<220> FEATURE:
<221> NAME/KEY: MOD_RES
<222> LOCATION: (5)..(5)
<223> OTHER INFORMATION: Asp or Ser
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Asn, Ser or Thr
<220> FEATURE:
<221> NAME/KEY: MOD_RES
<222> LOCATION: (9)..(9)
<223> OTHER INFORMATION: Ile, Lys or Thr

<400> SEQUENCE: 154

Xaa Ile Ser Xaa Xaa Xaa Xaa Xaa Xaa Tyr Tyr Ala Asp Ser Val Lys
1 5 10 15

Gly

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Gly or Ile
<220> FEATURE:
<221> NAME/KEY: MOD_RES
<222> LOCATION: (3)..(3)
<223> OTHER INFORMATION: Ile or Asn
<220> FEATURE:

<221> NAME/KEY: MOD_RES
<222> LOCATION: (5)..(5)
<223> OTHER INFORMATION: Gly or Ile
<220> FEATURE:
<221> NAME/KEY: MOD_RES
<222> LOCATION: (6)..(6)
<223> OTHER INFORMATION: Phe or Gly
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (10)..(10)
<223> OTHER INFORMATION: Asn or Ser

<400> SEQUENCE: 155

```
Xaa Ile Xaa Pro Xaa Xaa Gly Xaa Xaa Xaa Tyr Ala Gln Lys Phe Gln
1               5                   10                  15

Gly
```

<210> SEQ ID NO 156
<211> LENGTH: 19
<212> TYPE: PRT
<213> ORGANISM: Artificial Sequence
<220> FEATURE:
<223> OTHER INFORMATION: Description of Artificial Sequence: Synthetic
VH CDR3 peptide
<220> FEATURE:
<221> NAME/KEY: MOD_RES
<222> LOCATION: (3)..(3)
<223> OTHER INFORMATION: Asp, Gly, Thr or absent
<220> FEATURE:
<221> NAME/KEY: MOD_RES
<222> LOCATION: (4)..(4)
<223> OTHER INFORMATION: Ala, Asp, Gly, Pro, Arg, Ser or absent
<220> FEATURE:
<221> NAME/KEY: MOD_RES
<222> LOCATION: (5)..(5)
<223> OTHER INFORMATION: Glu, Phe, Gly, Gln, Thr or absent
<220> FEATURE:
<221> NAME/KEY: MOD_RES
<222> LOCATION: (6)..(6)
<223> OTHER INFORMATION: Glu, Met, Trp, Tyr or absent
<220> FEATURE:
<221> NAME/KEY: MOD_RES
<222> LOCATION: (7)..(7)
<223> OTHER INFORMATION: Ala, Leu, Ser or absent
<220> FEATURE:
<221> NAME/KEY: MOD_RES
<222> LOCATION: (8)..(8)
<223> OTHER INFORMATION: Gly, Ser, Thr or absent
<220> FEATURE:
<221> NAME/KEY: MOD_RES
<222> LOCATION: (9)..(9)
<223> OTHER INFORMATION: Gly, Ser or absent
<220> FEATURE:
<221> NAME/KEY: MOD_RES
<222> LOCATION: (10)..(10)
<223> OTHER INFORMATION: Ile, Leu, Phe or absent
<220> FEATURE:
<221> NAME/KEY: MISC_FEATURE
<222> LOCATION: (11)..(12)
<223> OTHER INFORMATION: May or may not be present
<220> FEATURE:
<221> NAME/KEY: MOD_RES
<222> LOCATION: (13)..(13)
<223> OTHER INFORMATION: Glu, Tyr or absent
<220> FEATURE:
<221> NAME/KEY: MOD_RES
<222> LOCATION: (14)..(14)
<223> OTHER INFORMATION: Gly, His, Pro, Ser, Trp, Tyr or absent
<220> FEATURE:
<221> NAME/KEY: MOD_RES
<222> LOCATION: (15)..(15)
<223> OTHER INFORMATION: Ala, Gly, Leu, Trp or Tyr
<220> FEATURE:
<221> NAME/KEY: MOD_RES
<222> LOCATION: (16)..(16)
<223> OTHER INFORMATION: Ala, Gly, Ile, Pro, Val or absent
<220> FEATURE:
<221> NAME/KEY: MOD_RES
<222> LOCATION: (17)..(17)
<223> OTHER INFORMATION: Phe, Leu or Met
<220> FEATURE:
<221> NAME/KEY: MOD_RES
<222> LOCATION: (19)..(19)
<223> OTHER INFORMATION: Ile, Leu, Val or Tyr

<400> SEQUENCE: 156

Ala Arg Xaa Xaa Xaa Xaa Xaa Xaa Xaa Xaa Trp His Xaa Xaa Xaa Xaa
1 5 10 15

Xaa Asp Xaa

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
VL CDR1 peptide
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (8)..(8)
<223> OTHER INFORMATION: Arg or Ser
<220> FEATURE:
<221> NAME/KEY: MOD_RES
<222> LOCATION: (9)..(9)
<223> OTHER INFORMATION: Asn, Trp or Tyr

<400> SEQUENCE: 157

Arg Ala Ser Gln Xaa Xaa Ser Xaa Xaa Leu Ala
1 5 10

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
VL CDR1 peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (6)..(6)
<223> OTHER INFORMATION: Leu or Val
<220> FEATURE:
<221> NAME/KEY: MOD_RES
<222> LOCATION: (8)..(8)
<223> OTHER INFORMATION: His or Tyr
<220> FEATURE:
<221> NAME/KEY: MOD_RES
<222> LOCATION: (10)..(10)
<223> OTHER INFORMATION: Asn or Ser
<220> FEATURE:

<221> NAME/KEY: MOD_RES
<222> LOCATION: (11)..(11)
<223> OTHER INFORMATION: Gln or Asn
<220> FEATURE:
<221> NAME/KEY: MISC_FEATURE
<222> LOCATION: (12)..(12)
<223> OTHER INFORMATION: May or may not be present
<220> FEATURE:
<221> NAME/KEY: MOD_RES
<222> LOCATION: (13)..(13)
<223> OTHER INFORMATION: Lys or Tyr
<220> FEATURE:
<221> NAME/KEY: MOD_RES
<222> LOCATION: (17)..(17)
<223> OTHER INFORMATION: Ala or Asp

<400> SEQUENCE: 158

```
Xaa Ser Ser Gln Ser Xaa Leu Xaa Ser Xaa Xaa Asn Xaa Asn Tyr Leu
1               5                   10                  15

Xaa
```

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic VL CDR2 peptide
<220> FEATURE:
<221> NAME/KEY: MOD_RES
<222> LOCATION: (1)..(1)
<223> OTHER INFORMATION: Asp, Gly or Ser
<220> FEATURE:
<221> NAME/KEY: MOD_RES
<222> LOCATION: (4)..(4)
<223> OTHER INFORMATION: Asn or Thr

<400> SEQUENCE: 159

```
Xaa Ala Ser Xaa Arg Ala Thr
1               5
```

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic VL CDR2 peptide
<220> FEATURE:
<221> NAME/KEY: MOD_RES
<222> LOCATION: (1)..(1)
<223> OTHER INFORMATION: Asp, Gly or Ser
<220> FEATURE:
<221> NAME/KEY: MOD_RES
<222> LOCATION: (4)..(4)
<223> OTHER INFORMATION: Asn, Ser or Thr
<220> FEATURE:
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (6)..(6)
<223> OTHER INFORMATION: Ala or Gln
<220> FEATURE:
<221> NAME/KEY: MOD_RES
<222> LOCATION: (7)..(7)
<223> OTHER INFORMATION: Ser or Thr

<400> SEQUENCE: 160

```
Xaa Ala Ser Xaa Xaa Xaa Xaa
1               5
```

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
VL CDR2 peptide
<220> FEATURE:
<221> NAME/KEY: MOD_RES
<222> LOCATION: (1)..(1)
<223> OTHER INFORMATION: Leu or Trp
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Asn or Thr
<220> FEATURE:
<221> NAME/KEY: MOD_RES
<222> LOCATION: (6)..(6)
<223> OTHER INFORMATION: Ala or Glu

<400> SEQUENCE: 161

Xaa Xaa Ser Xaa Arg Xaa Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
VL CDR3 peptide
<220> FEATURE:
<221> NAME/KEY: MOD_RES
<222> LOCATION: (3)..(3)
<223> OTHER INFORMATION: His, Ile, Arg or Tyr
<220> FEATURE:
<221> NAME/KEY: MOD_RES
<222> LOCATION: (4)..(4)
<223> OTHER INFORMATION: Ala, Phe, His, Ile or Tyr
<220> FEATURE:
<221> NAME/KEY: MOD_RES
<222> LOCATION: (5)..(5)
<223> OTHER INFORMATION: Ala, Ser, Thr, Val or Tyr
<220> FEATURE:
<221> NAME/KEY: MOD_RES
<222> LOCATION: (6)..(6)
<223> OTHER INFORMATION: Phe, Trp or Tyr
<220> FEATURE:
<221> NAME/KEY: MOD_RES
<222> LOCATION: (8)..(8)
<223> OTHER INFORMATION: Phe, Leu, Pro, Trp or absent

<400> SEQUENCE: 162

Gln Gln Xaa Xaa Xaa Xaa Pro Xaa Thr
1               5

<210> SEQ ID NO 163
<211> LENGTH: 184
<212> TYPE: PRT
<213> ORGANISM: Homo sapiens

<400> SEQUENCE: 163

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser 35 40 45

Val Lys Gly Thr Asn Ala Ile Leu Trp Thr Cys Leu Gly Leu Ser Leu
50 55 60

Ile Ile Ser Leu Ala Val Phe Val Leu Met Phe Leu Leu Arg Lys Ile
65 70 75 80

Asn Ser Glu Pro Leu Lys Asp Glu Phe Lys Asn Thr Gly Ser Gly Leu
85 90 95

Leu Gly Met Ala Asn Ile Asp Leu Glu Lys Ser Arg Thr Gly Asp Glu
100 105 110

Ile Ile Leu Pro Arg Gly Leu Glu Tyr Thr Val Glu Glu Cys Thr Cys
115 120 125

Glu Asp Cys Ile Lys Ser Lys Pro Lys Val Asp Ser Asp His Cys Phe
130 135 140

Pro Leu Pro Ala Met Glu Glu Gly Ala Thr Ile Leu Val Thr Thr Lys
145 150 155 160

Thr Asn Asp Tyr Cys Lys Ser Leu Pro Ala Ala Leu Ser Ala Thr Glu
165 170 175

Ile Glu Lys Ser Ile Ser Ala Arg
180

<210> SEQ ID NO 164
<211> LENGTH: 63
<212> TYPE: DNA
<213> ORGANISM: Artificial Sequence
<220> FEATURE:
<223> OTHER INFORMATION: Description of Artificial Sequence: Synthetic Signal Peptide

<400> SEQUENCE: 164
atggcactcc ccgtaactgc tctgctgctg ccgttggcat tgctcctgca cgccgcacgc 60
ccg 63

<210> SEQ ID NO 165
<211> LENGTH: 21
<212> TYPE: PRT
<213> ORGANISM: Artificial Sequence
<220> FEATURE:
<223> OTHER INFORMATION: Description of Artificial Sequence: Synthetic Signal Peptide

<400> SEQUENCE: 165

Met Ala Leu Pro Val Thr Ala Leu Leu Leu Pro Leu Ala Leu Leu Leu
1 5 10 15

His Ala Ala Arg Pro
20

<210> SEQ ID NO 166
<211> LENGTH: 90
<212> TYPE: DNA
<213> ORGANISM: Artificial Sequence
<220> FEATURE:
<223> OTHER INFORMATION: Description of Artificial Sequence: Synthetic CD28 Hinge Domain

<400> SEQUENCE: 166
cttgataatg aaaagtcaaa cggaacaatc attcacgtga agggcaagca cctctgtccg 60
tcacccttgt tccctggtcc atccaagcca 90

<210> SEQ ID NO 167
<211> LENGTH: 30

<212> TYPE: PRT
<213> ORGANISM: Artificial Sequence
<220> FEATURE:
<223> OTHER INFORMATION: Description of Artificial Sequence: Synthetic
CD28 Hinge Domain

<400> SEQUENCE: 167

```
Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30
```

<210> SEQ ID NO 168
<211> LENGTH: 81
<212> TYPE: DNA
<213> ORGANISM: Artificial Sequence
<220> FEATURE:
<223> OTHER INFORMATION: Description of Artificial Sequence: Synthetic
CD28 TM Domain

<400> SEQUENCE: 168

```
ttctgggtgt tggtcgtagt gggtggagtc ctcgcttgtt actctctgct cgtcaccgtg     60

gcttttataa tcttctgggt t                                               81
```

<210> SEQ ID NO 169
<211> LENGTH: 27
<212> TYPE: PRT
<213> ORGANISM: Artificial Sequence
<220> FEATURE:
<223> OTHER INFORMATION: Description of Artificial Sequence: Synthetic
CD28 TM Domain

<400> SEQUENCE: 169

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 170
<211> LENGTH: 123
<212> TYPE: DNA
<213> ORGANISM: Artificial Sequence
<220> FEATURE:
<223> OTHER INFORMATION: Description of Artificial Sequence: Synthetic
CD28 Signaling Domain

<400> SEQUENCE: 170

```
agatccaaaa gaagccgcct gctccatagc gattacatga atatgactcc acgccgccct     60

ggccccacaa ggaaacacta ccagccttac gcaccaccta gagatttcgc tgcctatcgg    120

agc                                                                  123
```

<210> SEQ ID NO 171
<211> LENGTH: 41
<212> TYPE: PRT
<213> ORGANISM: Artificial Sequence
<220> FEATURE:
<223> OTHER INFORMATION: Description of Artificial Sequence: Synthetic
CD28 Signaling Domain

<400> SEQUENCE: 171

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30
```

Pro Arg Asp Phe Ala Ala Tyr Arg Ser
35 40

<210> SEQ ID NO 172
<211> LENGTH: 336
<212> TYPE: DNA
<213> ORGANISM: Artificial Sequence
<220> FEATURE:
<223> OTHER INFORMATION: Description of Artificial Sequence: Synthetic CD3z Activation Domain

<400> SEQUENCE: 172
agggtgaagt tttccagatc tgcagatgca ccagcgtatc agcagggcca gaaccaactg 60
tataacgagc tcaacctggg acgcagggaa gagtatgacg ttttggacaa gcgcagagga 120
cgggaccctg agatgggtgg caaaccaaga cgaaaaaacc cccaggaggg tctctataat 180
gagctgcaga aggataagat ggctgaagcc tattctgaaa taggcatgaa aggagagcgg 240
agaaggggaa aagggcacga cggtttgtac cagggactca gcactgctac gaaggatact 300
tatgacgctc tccacatgca agccctgcca cctagg 336

<210> SEQ ID NO 173
<211> LENGTH: 112
<212> TYPE: PRT
<213> ORGANISM: Artificial Sequence
<220> FEATURE:
<223> OTHER INFORMATION: Description of Artificial Sequence: Synthetic CD3z Activation Domain

<400> SEQUENCE: 173

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 174
<211> LENGTH: 18
<212> TYPE: PRT
<213> ORGANISM: Artificial Sequence
<220> FEATURE:
<223> OTHER INFORMATION: Description of Artificial Sequence: Synthetic Linker peptide

<400> SEQUENCE: 174

Gly Ser Thr Ser Gly Ser Gly Lys Pro Gly Ser Gly Glu Gly Ser Thr
1 5 10 15

Lys Gly

<210> SEQ ID NO 175
<211> LENGTH: 1437
<212> TYPE: DNA

<213> ORGANISM: Artificial Sequence
<220> FEATURE:
<223> OTHER INFORMATION: Description of Artificial Sequence: Synthetic
FS-21495CARDNAHxL polynucleotide

<400> SEQUENCE: 175
atggcactcc ccgtaactgc tctgctgctg ccgttggcat tgctcctgca cgccgcacgc 60
ccggaggtgc agctgttgga gtctgggggga ggcttggtac agcctggggg gtccctgaga 120
ctctcctgtg cagcctctgg attcaccttt agcagctatg ccatgagctg ggtccgccag 180
gctccaggga aggggctgga gtgggtctca gctattagtg gtagtggtgg tagcacatac 240
tacgcagact ccgtgaaggg ccggttcacc atctccagag acaattccaa gaacacgctg 300
tatctgcaaa tgaacagcct gagagccgag gacacggcgg tgtactactg cgcaagagcc 360
gagatgggag ccgtattcga catatggggt cagggtacaa tggtcaccgt ctcctcaggg 420
tctacatccg gctccgggaa gcccggaagt ggcgaaggta gtacaaaggg ggaaattgtg 480
ttgacacagt ctccagccac cctgtctttg tctccagggg aaagagccac cctctcctgc 540
agggccagtc agagtgttag caggtactta gcctggtacc aacagaaacc tggccaggct 600
cccaggctcc tcatctatga tgcatccaac agggccactg gcatcccagc caggttcagt 660
ggcagtgggt ctgggacaga cttcactctc accatcagca gcctagagcc tgaagatttt 720
gcagtttatt actgtcagca gagaatctcc tggcctttca cttttggcgg agggaccaag 780
gttgagatca aacgggccgc tgcccttgat aatgaaaagt caaacggaac aatcattcac 840
gtgaagggca agcacctctg tccgtcaccc ttgttccctg gtccatccaa gccattctgg 900
gtgttggtcg tagtgggtgg agtcctcgct tgttactctc tgctcgtcac cgtggctttt 960
ataatcttct gggttagatc caaaagaagc cgcctgctcc atagcgatta catgaatatg 1020
actccacgcc gccctggccc cacaaggaaa cactaccagc cttacgcacc acctagagat 1080
ttcgctgcct atcggagcag ggtgaagttt tccagatctg cagatgcacc agcgtatcag 1140
cagggccaga accaactgta taacgagctc aacctgggac gcagggaaga gtatgacgtt 1200
ttggacaagc gcagaggacg ggaccctgag atgggtggca aaccaagacg aaaaaacccc 1260
caggagggtc tctataatga gctgcagaag gataagatgg ctgaagccta ttctgaaata 1320
ggcatgaaag gagagcggag aaggggaaaa gggcacgacg gtttgtacca gggactcagc 1380
actgctacga aggatactta tgacgctctc cacatgcaag ccctgccacc taggtaa 1437

<210> SEQ ID NO 176
<211> LENGTH: 478
<212> TYPE: PRT
<213> ORGANISM: Artificial Sequence
<220> FEATURE:
<223> OTHER INFORMATION: Description of Artificial Sequence: Synthetic
FS-21495CARHxL polypeptide

<400> SEQUENCE: 176

Met Ala Leu Pro Val Thr Ala Leu Leu Leu Pro Leu Ala Leu Leu Leu
1 5 10 15

His Ala Ala Arg Pro Glu Val Gln Leu Leu Glu Ser Gly Gly Gly Leu
20 25 30

Val Gln Pro Gly Gly Ser Leu Arg Leu Ser Cys Ala Ala Ser Gly Phe
35 40 45

Thr Phe Ser Ser Tyr Ala Met Ser Trp Val Arg Gln Ala Pro Gly Lys
50 55 60

Gly Leu Glu Trp Val Ser Ala Ile Ser Gly Ser Gly Gly Ser Thr Tyr 65 70 75 80

Tyr Ala Asp Ser Val Lys Gly Arg Phe Thr Ile Ser Arg Asp Asn Ser
85 90 95

Lys Asn Thr Leu Tyr Leu Gln Met Asn Ser Leu Arg Ala Glu Asp Thr
100 105 110

Ala Val Tyr Tyr Cys Ala Arg Ala Glu Met Gly Ala Val Phe Asp Ile
115 120 125

Trp Gly Gln Gly Thr Met Val Thr Val Ser Ser Gly Ser Thr Ser Gly
130 135 140

Ser Gly Lys Pro Gly Ser Gly Glu Gly Ser Thr Lys Gly Glu Ile Val
145 150 155 160

Leu Thr Gln Ser Pro Ala Thr Leu Ser Leu Ser Pro Gly Glu Arg Ala
165 170 175

Thr Leu Ser Cys Arg Ala Ser Gln Ser Val Ser Arg Tyr Leu Ala Trp
180 185 190

Tyr Gln Gln Lys Pro Gly Gln Ala Pro Arg Leu Leu Ile Tyr Asp Ala
195 200 205

Ser Asn Arg Ala Thr Gly Ile Pro Ala Arg Phe Ser Gly Ser Gly Ser
210 215 220

Gly Thr Asp Phe Thr Leu Thr Ile Ser Ser Leu Glu Pro Glu Asp Phe
225 230 235 240

Ala Val Tyr Tyr Cys Gln Gln Arg Ile Ser Trp Pro Phe Thr Phe Gly
245 250 255

Gly Gly Thr Lys Val Glu Ile Lys Arg Ala Ala Ala Leu Asp Asn Glu
260 265 270

Lys Ser Asn Gly Thr Ile Ile His Val Lys Gly Lys His Leu Cys Pro
275 280 285

Ser Pro Leu Phe Pro Gly Pro Ser Lys Pro Phe Trp Val Leu Val Val
290 295 300

Val Gly Gly Val Leu Ala Cys Tyr Ser Leu Leu Val Thr Val Ala Phe
305 310 315 320

Ile Ile Phe Trp Val Arg Ser Lys Arg Ser Arg Leu Leu His Ser Asp
325 330 335

Tyr Met Asn Met Thr Pro Arg Arg Pro Gly Pro Thr Arg Lys His Tyr
340 345 350

Gln Pro Tyr Ala Pro Pro Arg Asp Phe Ala Ala Tyr Arg Ser Arg Val
355 360 365

Lys Phe Ser Arg Ser Ala Asp Ala Pro Ala Tyr Gln Gln Gly Gln Asn
370 375 380

Gln Leu Tyr Asn Glu Leu Asn Leu Gly Arg Arg Glu Glu Tyr Asp Val
385 390 395 400

Leu Asp Lys Arg Arg Gly Arg Asp Pro Glu Met Gly Gly Lys Pro Arg
405 410 415

Arg Lys Asn Pro Gln Glu Gly Leu Tyr Asn Glu Leu Gln Lys Asp Lys
420 425 430

Met Ala Glu Ala Tyr Ser Glu Ile Gly Met Lys Gly Glu Arg Arg Arg
435 440 445

Gly Lys Gly His Asp Gly Leu Tyr Gln Gly Leu Ser Thr Ala Thr Lys
450 455 460

Asp Thr Tyr Asp Ala Leu His Met Gln Ala Leu Pro Pro Arg
465 470 475

<210> SEQ ID NO 177

<211> LENGTH: 1437
<212> TYPE: DNA
<213> ORGANISM: Artificial Sequence
<220> FEATURE:
<223> OTHER INFORMATION: Description of Artificial Sequence: Synthetic
FS-21495CARDNALxH polynucleotide

<400> SEQUENCE: 177

```
atggcactcc ccgtaactgc tctgctgctg ccgttggcat tgctcctgca cgccgcacgc     60

ccggaaattg tgttgacaca gtctccagcc accctgtctt tgtctccagg ggaaagagcc    120

accctctcct gcagggccag tcagagtgtt agcaggtact tagcctggta ccaacagaaa    180

cctggccagg ctcccaggct cctcatctat gatgcatcca acagggccac tggcatccca    240

gccaggttca gtggcagtgg gtctgggaca gacttcactc tcaccatcag cagcctagag    300

cctgaagatt ttgcagttta ttactgtcag cagagaatct cctggccttt cacttttggc    360

ggagggacca aggttgagat caaacggggg tctacatccg gctccgggaa gcccggaagt    420

ggcgaaggta gtacaaaggg ggaggtgcag ctgttggagt ctgggggagg cttggtacag    480

cctggggggt ccctgagact ctcctgtgca gcctctggat tcacctttag cagctatgcc    540

atgagctggg tccgccaggc tccagggaag gggctggagt gggtctcagc tattagtggt    600

agtggtggta gcacatacta cgcagactcc gtgaagggcc ggttcaccat ctccagagac    660

aattccaaga acacgctgta tctgcaaatg aacagcctga gagccgagga cacggcggtg    720

tactactgcg caagagccga gatgggagcc gtattcgaca tatggggtca gggtacaatg    780

gtcaccgtct cctcagccgc tgcccttgat aatgaaaagt caaacggaac aatcattcac    840

gtgaagggca agcacctctg tccgtcaccc ttgttccctg gtccatccaa gccattctgg    900

gtgttggtcg tagtgggtgg agtcctcgct tgttactctc tgctcgtcac cgtggctttt    960

ataatcttct gggttagatc caaaagaagc cgcctgctcc atagcgatta catgaatatg   1020

actccacgcc gccctggccc cacaaggaaa cactaccagc cttacgcacc acctagagat   1080

ttcgctgcct atcggagcag ggtgaagttt tccagatctg cagatgcacc agcgtatcag   1140

cagggccaga accaactgta taacgagctc aacctgggac gcagggaaga gtatgacgtt   1200

ttggacaagc gcagaggacg ggaccctgag atgggtggca aaccaagacg aaaaaacccc   1260

caggagggtc tctataatga gctgcagaag gataagatgg ctgaagccta ttctgaaata   1320

ggcatgaaag gagagcggag aaggggaaaa gggcacgacg gtttgtacca gggactcagc   1380

actgctacga aggatactta tgacgctctc cacatgcaag ccctgccacc taggtaa      1437
```

<210> SEQ ID NO 178
<211> LENGTH: 478
<212> TYPE: PRT
<213> ORGANISM: Artificial Sequence
<220> FEATURE:
<223> OTHER INFORMATION: Description of Artificial Sequence: Synthetic
FS-21495CARLxH polypeptide

<400> SEQUENCE: 178

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Arg Tyr Leu Ala Trp Tyr Gln Gln Lys Pro Gly Gln Ala
    50                  55                  60
```

```
Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

Ile Ser Trp Pro Phe Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Tyr Ala Met Ser Trp Val Arg Gln Ala Pro Gly Lys Gly Leu
            180                 185                 190

Glu Trp Val Ser Ala Ile Ser Gly Ser Gly Gly Ser Thr Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Arg Ala Glu Met Gly Ala Val Phe Asp Ile Trp Gly
                245                 250                 255

Gln Gly Thr Met Val Thr Val Ser Ser Ala Ala Ala Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
        355                 360                 365

Lys Phe Ser Arg Ser Ala Asp Ala Pro Ala Tyr Gln Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
        435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg
465                 470                 475
```

<210> SEQ ID NO 179
<211> LENGTH: 1464
<212> TYPE: DNA
<213> ORGANISM: Artificial Sequence
<220> FEATURE:
<223> OTHER INFORMATION: Description of Artificial Sequence: Synthetic
PC-21497CARDNAHxL polynucleotide

<400> SEQUENCE: 179

```
atggcactcc ccgtaactgc tctgctgctg ccgttggcat tgctcctgca cgccgcacgc     60

ccgcaggtgc agctggtgga gtctggggga ggcgtggtcc agcctgggag gtccctgaga    120

ctctcctgtg cagcgtctgg attcaccttc agtagctatg gcatgcactg ggtccgccag    180

gctccaggca aggggctgga gtgggtggca gttatatcgt atgatggaag taataaatac    240

tatgcagact ccgtgaaggg ccgattcacc atctccagag acaattccaa gaacacgctg    300

tatctgcaaa tgaacagcct gagagccgag gacacggcgg tgtactactg cgccagagac    360

ggtacttatc taggtggtct ctggtacttc gacttatggg ggagaggtac cttggtcacc    420

gtctcctcag ggtctacatc cggctccggg aagcccggaa gtggcgaagg tagtacaaag    480

gggatattg tgatgactca gtctccactc tccctgcccg tcacccctgg agagccggcc    540

tccatctcct gcaggtctag tcagagcctc ctgcatagta atggatacaa ctatttggat    600

tggtacctgc agaagccagg gcagtctcca cagctcctga tctatttggg ttctaatcgg    660

gcctccgggg tccctgacag gttcagtggc agtggatcag gcacagattt tacactgaaa    720

atcagcagag tggaggctga ggatgttggg gtttattact gcatgcaggg actcggcctc    780

cctctcactt ttggcggagg gaccaaggtt gagatcaaac gggccgctgc ccttgataat    840

gaaaagtcaa acggaacaat cattcacgtg aagggcaagc acctctgtcc gtcacccttg    900

ttccctggtc catccaagcc attctgggtg ttggtcgtag tgggtggagt cctcgcttgt    960

tactctctgc tcgtcaccgt ggcttttata atcttctggg ttagatccaa aagaagccgc   1020

ctgctccata gcgattacat gaatatgact ccacgccgcc ctggccccac aaggaaacac   1080

taccagcctt acgcaccacc tagagatttc gctgcctatc ggagcagggt gaagttttcc   1140

agatctgcag atgcaccagc gtatcagcag ggccagaacc aactgtataa cgagctcaac   1200

ctgggacgca gggaagagta tgacgttttg gacaagcgca gaggacggga ccctgagatg   1260

ggtggcaaac caagacgaaa aaacccccag gagggtctct ataatgagct gcagaaggat   1320

aagatggctg aagcctattc tgaaataggc atgaaaggag agcggagaag gggaaaaggg   1380

cacgacggtt tgtaccaggg actcagcact gctacgaagg atacttatga cgctctccac   1440

atgcaagccc tgccacctag gtaa                                          1464
```

<210> SEQ ID NO 180
<211> LENGTH: 487
<212> TYPE: PRT
<213> ORGANISM: Artificial Sequence
<220> FEATURE:
<223> OTHER INFORMATION: Description of Artificial Sequence: Synthetic
PC-21497CARHxL polypeptide

<400> SEQUENCE: 180

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
```

```
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Gly Thr Tyr Leu Gly Gly Leu Trp
        115                 120                 125

Tyr Phe Asp Leu Trp Gly Arg Gly Thr Leu Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Asp Ile Val Met Thr Gln Ser Pro Leu Ser Leu Pro Val Thr Pro
                165                 170                 175

Gly Glu Pro Ala Ser Ile Ser Cys Arg Ser Ser Gln Ser Leu Leu His
            180                 185                 190

Ser Asn Gly Tyr Asn Tyr Leu Asp Trp Tyr Leu Gln Lys Pro Gly Gln
        195                 200                 205

Ser Pro Gln Leu Leu Ile Tyr Leu Gly Ser Asn Arg Ala Ser Gly Val
    210                 215                 220

Pro Asp Arg Phe Ser Gly Ser Gly Ser Gly Thr Asp Phe Thr Leu Lys
225                 230                 235                 240

Ile Ser Arg Val Glu Ala Glu Asp Val Gly Val Tyr Tyr Cys Met Gln
                245                 250                 255

Gly Leu Gly Leu Pro Leu Thr Phe Gly Gly Gly Thr Lys Val Glu Ile
            260                 265                 270

Lys Arg Ala Ala Ala Leu Asp Asn Glu Lys Ser Asn Gly Thr Ile Ile
        275                 280                 285

His Val Lys Gly Lys His Leu Cys Pro Ser Pro Leu Phe Pro Gly Pro
    290                 295                 300

Ser Lys Pro Phe Trp Val Leu Val Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460
```

Tyr Gln Gly Leu Ser Thr Ala Thr Lys Asp Thr Tyr Asp Ala Leu His
465 470 475 480

Met Gln Ala Leu Pro Pro Arg
485

<210> SEQ ID NO 181
<211> LENGTH: 1464
<212> TYPE: DNA
<213> ORGANISM: Artificial Sequence
<220> FEATURE:
<223> OTHER INFORMATION: Description of Artificial Sequence: Synthetic
PC-21497CARDNALxH polynucleotide

<400> SEQUENCE: 181
atggcactcc ccgtaactgc tctgctgctg ccgttggcat tgctcctgca cgccgcacgc 60
ccggatattg tgatgactca gtctccactc tccctgcccg tcacccctgg agagccggcc 120
tccatctcct gcaggtctag tcagagcctc ctgcatagta atggatacaa ctatttggat 180
tggtacctgc agaagccagg gcagtctcca cagctcctga tctatttggg ttctaatcgg 240
gcctccgggg tccctgacag gttcagtggc agtggatcag gcacagattt tacactgaaa 300
atcagcagag tggaggctga ggatgttggg gtttattact gcatgcaggg actcggcctc 360
cctctcactt ttggcggagg gaccaaggtt gagatcaaac gggggtctac atccggctcc 420
gggaagcccg gaagtggcga aggtagtaca aaggggcagg tgcagctggt ggagtctggg 480
ggaggcgtgg tccagcctgg gaggtccctg agactctcct gtgcagcgtc tggattcacc 540
ttcagtagct atggcatgca ctgggtccgc caggctccag gcaaggggct ggagtgggtg 600
gcagttatat cgtatgatgg aagtaataaa tactatgcag actccgtgaa gggccgattc 660
accatctcca gagacaattc caagaacacg ctgtatctgc aaatgaacag cctgagagcc 720
gaggacacgg cggtgtacta ctgcgccaga gacggtactt atctaggtgg tctctggtac 780
ttcgacttat gggggagagg taccttggtc accgtctcct cagccgctgc ccttgataat 840
gaaaagtcaa acggaacaat cattcacgtg aagggcaagc acctctgtcc gtcacccttg 900
ttccctggtc catccaagcc attctgggtg ttggtcgtag tgggtggagt cctcgcttgt 960
tactctctgc tcgtcaccgt ggcttttata atcttctggg ttagatccaa aagaagccgc 1020
ctgctccata gcgattacat gaatatgact ccacgccgcc ctggccccac aaggaaacac 1080
taccagcctt acgcaccacc tagagatttc gctgcctatc ggagcagggt gaagttttcc 1140
agatctgcag atgcaccagc gtatcagcag ggccagaacc aactgtataa cgagctcaac 1200
ctgggacgca gggaagagta tgacgttttg gacaagcgca gaggacggga ccctgagatg 1260
ggtggcaaac caagacgaaa aaacccccag gagggtctct ataatgagct gcagaaggat 1320
aagatggctg aagcctattc tgaaataggc atgaaaggag agcggagaag gggaaaaggg 1380
cacgacggtt tgtaccaggg actcagcact gctacgaagg atacttatga cgctctccac 1440
atgcaagccc tgccacctag gtaa 1464

<210> SEQ ID NO 182
<211> LENGTH: 487
<212> TYPE: PRT
<213> ORGANISM: Artificial Sequence
<220> FEATURE:
<223> OTHER INFORMATION: Description of Artificial Sequence: Synthetic
PC-21497CARHxL polypeptide

<400> SEQUENCE: 182

-continued

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Leu His Ser Asn Gly Tyr Asn Tyr Leu Asp Trp Tyr Leu Gln
    50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Gly Leu Gly Leu Pro Leu Thr Phe Gly Gly Gly Thr
        115                 120                 125

Lys Val Glu Ile Lys Arg Gly Ser Thr Ser Gly Ser Gly Lys Pro Gly
    130                 135                 140

Ser Gly Glu Gly Ser Thr Lys Gly Gln Val Gln Leu Val Glu Ser Gly
145                 150                 155                 160

Gly Gly Val Val Gln Pro Gly Arg Ser Leu Arg Leu Ser Cys Ala Ala
                165                 170                 175

Ser Gly Phe Thr Phe Ser Ser Tyr Gly Met His Trp Val Arg Gln Ala
            180                 185                 190

Pro Gly Lys Gly Leu Glu Trp Val Ala Val Ile Ser Tyr Asp Gly Ser
        195                 200                 205

Asn Lys Tyr Tyr Ala Asp Ser Val Lys Gly Arg Phe Thr Ile Ser Arg
    210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Asp Gly Thr Tyr Leu Gly
                245                 250                 255

Gly Leu Trp Tyr Phe Asp Leu Trp Gly Arg Gly Thr Leu Val Thr Val
            260                 265                 270

Ser Ser Ala Ala Ala Leu Asp Asn Glu Lys Ser Asn Gly Thr Ile Ile
        275                 280                 285

His Val Lys Gly Lys His Leu Cys Pro Ser Pro Leu Phe Pro Gly Pro
    290                 295                 300

Ser Lys Pro Phe Trp Val Leu Val Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
```

```
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485


<210> SEQ ID NO 183
<211> LENGTH: 1428
<212> TYPE: DNA
<213> ORGANISM: Artificial Sequence
<220> FEATURE:
<223> OTHER INFORMATION: Description of Artificial Sequence: Synthetic
      AJ-21508CARDNAHxL polynucleotide

<400> SEQUENCE: 183

atggcactcc ccgtaactgc tctgctgctg ccgttggcat tgctcctgca cgccgcacgc      60

ccgcaggtgc agctggtgca gtctggggct gaggtgaaga agcctggggc ctcagtgaag     120

gtttcctgca aggcatctgg atacaccttc accagctact atatgcactg ggtgcgacag     180

gcccctggac aagggcttga gtggatggga ataatcaacc ctggtggtgg tagcacaagc     240

tacgcacaga agttccaggg cagagtcacc atgaccaggg acacgtccac gagcacagtc     300

tacatggagc tgagcagcct gagatctgag gacacggcgg tgtactactg cgccagagag     360

agttggccaa tggacgtatg gggccaggga acaactgtca ccgtctcctc agggtctaca     420

tccggctccg ggaagcccgg aagtggcgaa ggtagtacaa agggggaaat agtgatgacg     480

cagtctccag ccaccctgtc tgtgtctcca ggggaaagag ccaccctctc ctgcagggcc     540

agtcagagtg ttagcagcaa cttagcctgg taccagcaga aacctggcca ggctcccagg     600

ctcctcatct atggtgcatc caccagggcc actggtatcc cagccaggtt cagtggcagt     660

gggtctggga cagagttcac tctcaccatc agcagcctgc agtctgaaga ttttgcagtt     720

tattactgtc agcagtacgc cgcctaccct acttttggcg gagggaccaa ggttgagatc     780

aaacgggccg ctgcccttga taatgaaaag tcaaacggaa caatcattca cgtgaagggc     840

aagcacctct gtccgtcacc cttgttccct ggtccatcca agccattctg ggtgttggtc     900

gtagtgggtg gagtcctcgc ttgttactct ctgctcgtca ccgtggcttt tataatcttc     960

tgggttagat ccaaaagaag ccgcctgctc catagcgatt acatgaatat gactccacgc    1020

cgccctggcc ccacaaggaa acactaccag ccttacgcac cacctagaga tttcgctgcc    1080

tatcggagca gggtgaagtt ttccagatct gcagatgcac cagcgtatca gcagggccag    1140

aaccaactgt ataacgagct caacctggga cgcagggaag agtatgacgt tttggacaag    1200

cgcagaggac gggaccctga gatgggtggc aaaccaagac gaaaaaaccc ccaggagggt    1260

ctctataatg agctgcagaa ggataagatg gctgaagcct attctgaaat aggcatgaaa    1320

ggagagcgga gaaggggaaa agggcacgac ggtttgtacc agggactcag cactgctacg    1380

aaggatactt atgacgctct ccacatgcaa gccctgccac ctaggtaa                 1428


<210> SEQ ID NO 184
<211> LENGTH: 475
<212> TYPE: PRT
<213> ORGANISM: Artificial Sequence
<220> FEATURE:
```

<223> OTHER INFORMATION: Description of Artificial Sequence: Synthetic
AJ-21508CARHxL polypeptide

<400> SEQUENCE: 184

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Gly Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Glu Ser Trp Pro Met Asp Val Trp Gly
        115                 120                 125

Gln Gly Thr Thr Val Thr Val Ser Ser Gly Ser Thr Ser Gly Ser Gly
    130                 135                 140

Lys Pro Gly Ser Gly Glu Gly Ser Thr Lys Gly Glu Ile Val Met Thr
145                 150                 155                 160

Gln Ser Pro Ala Thr Leu Ser Val Ser Pro Gly Glu Arg Ala Thr Leu
                165                 170                 175

Ser Cys Arg Ala Ser Gln Ser Val Ser Ser Asn Leu Ala Trp Tyr Gln
            180                 185                 190

Gln Lys Pro Gly Gln Ala Pro Arg Leu Leu Ile Tyr Gly Ala Ser Thr
        195                 200                 205

Arg Ala Thr Gly Ile Pro Ala Arg Phe Ser Gly Ser Gly Ser Gly Thr
    210                 215                 220

Glu Phe Thr Leu Thr Ile Ser Ser Leu Gln Ser Glu Asp Phe Ala Val
225                 230                 235                 240

Tyr Tyr Cys Gln Gln Tyr Ala Ala Tyr Pro Thr Phe Gly Gly Gly Thr
                245                 250                 255

Lys Val Glu Ile Lys Arg Ala Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400
```

```
Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475
```

```
<210> SEQ ID NO 185
<211> LENGTH: 1428
<212> TYPE: DNA
<213> ORGANISM: Artificial Sequence
<220> FEATURE:
<223> OTHER INFORMATION: Description of Artificial Sequence: Synthetic
      AJ-21508CARDNALxH polynucleotide

<400> SEQUENCE: 185

atggcactcc ccgtaactgc tctgctgctg ccgttggcat tgctcctgca cgccgcacgc      60

ccggaaatag tgatgacgca gtctccagcc accctgtctg tgtctccagg ggaaagagcc     120

accctctcct gcagggccag tcagagtgtt agcagcaact tagcctggta ccagcagaaa     180

cctggccagg ctcccaggct cctcatctat ggtgcatcca ccagggccac tggtatccca     240

gccaggttca gtggcagtgg gtctgggaca gagttcactc tcaccatcag cagcctgcag     300

tctgaagatt ttgcagttta ttactgtcag cagtacgccg cctaccctac ttttggcgga     360

gggaccaagg ttgagatcaa acgggggtct acatccggct ccgggaagcc cggaagtggc     420

gaaggtagta caaaggggca ggtgcagctg gtgcagtctg gggctgaggt gaagaagcct     480

ggggcctcag tgaaggtttc ctgcaaggca tctggataca ccttcaccag ctactatatg     540

cactgggtgc gacaggcccc tggacaaggg cttgagtgga tgggaataat caaccctggt     600

ggtggtagca caagctacgc acagaagttc cagggcagag tcaccatgac cagggacacg     660

tccacgagca cagtctacat ggagctgagc agcctgagat ctgaggacac ggcggtgtac     720

tactgcgcca gagagagttg gccaatggac gtatggggcc agggaacaac tgtcaccgtc     780

tcctcagccg ctgcccttga taatgaaaag tcaaacggaa caatcattca cgtgaagggc     840

aagcacctct gtccgtcacc cttgttccct ggtccatcca agccattctg ggtgttggtc     900

gtagtgggtg gagtcctcgc ttgttactct ctgctcgtca ccgtggcttt tataatcttc     960

tgggttagat ccaaaagaag ccgcctgctc catagcgatt acatgaatat gactccacgc    1020

cgccctggcc ccacaaggaa acactaccag ccttacgcac cacctagaga tttcgctgcc    1080

tatcggagca gggtgaagtt ttccagatct gcagatgcac cagcgtatca gcagggccag    1140

aaccaactgt ataacgagct caacctggga cgcagggaag agtatgacgt tttggacaag    1200

cgcagaggac gggaccctga gatgggtggc aaaccaagac gaaaaaaccc ccaggagggt    1260

ctctataatg agctgcagaa ggataagatg gctgaagcct attctgaaat aggcatgaaa    1320

ggagagcgga gaaggggaaa agggcacgac ggtttgtacc agggactcag cactgctacg    1380

aaggatactt atgacgctct ccacatgcaa gccctgccac ctaggtaa                 1428

<210> SEQ ID NO 186
<211> LENGTH: 475
<212> TYPE: PRT
```

<213> ORGANISM: Artificial Sequence
<220> FEATURE:
<223> OTHER INFORMATION: Description of Artificial Sequence: Synthetic
AJ-21508CARLxH polypeptide

<400> SEQUENCE: 186

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Ala Ala Tyr Pro Thr Phe Gly Gly Gly Thr Lys Val Glu Ile Lys Arg
        115                 120                 125

Gly Ser Thr Ser Gly Ser Gly Lys Pro Gly Ser Gly Glu Gly Ser Thr
    130                 135                 140

Lys Gly Gln Val Gln Leu Val Gln Ser Gly Ala Glu Val Lys Lys Pro
145                 150                 155                 160

Gly Ala Ser Val Lys Val Ser Cys Lys Ala Ser Gly Tyr Thr Phe Thr
                165                 170                 175

Ser Tyr Tyr Met His Trp Val Arg Gln Ala Pro Gly Gln Gly Leu Glu
            180                 185                 190

Trp Met Gly Ile Ile Asn Pro Gly Gly Gly Ser Thr Ser Tyr Ala Gln
        195                 200                 205

Lys Phe Gln Gly Arg Val Thr Met Thr Arg Asp Thr Ser Thr Ser Thr
    210                 215                 220

Val Tyr Met Glu Leu Ser Ser Leu Arg Ser Glu Asp Thr Ala Val Tyr
225                 230                 235                 240

Tyr Cys Ala Arg Glu Ser Trp Pro Met Asp Val Trp Gly Gln Gly Thr
                245                 250                 255

Thr Val Thr Val Ser Ser Ala Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
        355                 360                 365

Arg Ser Ala Asp Ala Pro Ala Tyr Gln Gln Gly Gln Asn Gln Leu Tyr
    370                 375                 380
```

```
Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475


<210> SEQ ID NO 187
<211> LENGTH: 1449
<212> TYPE: DNA
<213> ORGANISM: Artificial Sequence
<220> FEATURE:
<223> OTHER INFORMATION: Description of Artificial Sequence: Synthetic
      NM-21517CARDNAHxL polynucleotide

<400> SEQUENCE: 187

atggcactcc ccgtaactgc tctgctgctg ccgttggcat tgctcctgca cgccgcacgc     60

ccgcagctgc agctgcagga gtcgggccca ggactggtga agccttcgga gaccctgtcc    120

ctcacctgca ctgtctctgg tggctccatc agcagtagta gttactactg gggctggatc    180

cgccagcccc cagggaaggg gctggagtgg attgggagta tctcctatag tgggagcacc    240

tactacaacc cgtccctcaa gagtcgagtc accatatccg tagacacgtc caagaaccag    300

ttctccctga agctgagttc tgtgaccgcc gcagacacgg cggtgtacta ctgcgccaga    360

ggcaggggat atgcaaccag cttagccttc gatatctggg gtcagggtac aatggtcacc    420

gtctcctcag ggtctacatc cggctccggg aagcccggaa gtggcgaagg tagtacaaag    480

ggggaaattg tgttgacaca gtctccagcc accctgtctt tgtctccagg ggaaagagcc    540

accctctcct gcagggccag tcagagtgtt agcagctact tagcctggta ccaacagaaa    600

cctggccagg ctcccaggct cctcatctat gatgcatcca acagggccac tggcatccca    660

gccaggttca gtggcagtgg gtctgggaca gacttcactc tcaccatcag cagcctagag    720

cctgaagatt ttgcagttta ttactgtcag cagagacacg tctggcctcc tacttttggc    780

ggagggacca aggttgagat caaacgggcc gctgcccttg ataatgaaaa gtcaaacgga    840

acaatcattc acgtgaaggg caagcacctc tgtccgtcac ccttgttccc tggtccatcc    900

aagccattct gggtgttggt cgtagtgggt ggagtcctcg cttgttactc tctgctcgtc    960

accgtggctt ttataatctt ctgggttaga tccaaaagaa gccgcctgct ccatagcgat   1020

tacatgaata tgactccacg ccgccctggc cccacaagga aacactacca gccttacgca   1080

ccacctagag atttcgctgc ctatcggagc agggtgaagt tttccagatc tgcagatgca   1140

ccagcgtatc agcagggcca gaaccaactg tataacgagc tcaacctggg acgcagggaa   1200

gagtatgacg ttttggacaa gcgcagagga cgggaccctg agatgggtgg caaaccaaga   1260

cgaaaaaacc cccaggaggg tctctataat gagctgcaga aggataagat ggctgaagcc   1320

tattctgaaa taggcatgaa aggagagcgg agaaggggaa aagggcacga cggtttgtac   1380

cagggactca gcactgctac gaaggatact tatgacgctc tccacatgca agccctgcca   1440

cctaggtaa                                                           1449
```

<210> SEQ ID NO 188
<211> LENGTH: 482
<212> TYPE: PRT
<213> ORGANISM: Artificial Sequence
<220> FEATURE:
<223> OTHER INFORMATION: Description of Artificial Sequence: Synthetic
NM-21517CARHxL polypeptide

<400> SEQUENCE: 188

Met Ala Leu Pro Val Thr Ala Leu Leu Leu Pro Leu Ala Leu Leu Leu
1 5 10 15

His Ala Ala Arg Pro Gln Leu Gln Leu Gln Glu Ser Gly Pro Gly Leu
20 25 30

Val Lys Pro Ser Glu Thr Leu Ser Leu Thr Cys Thr Val Ser Gly Gly
35 40 45

Ser Ile Ser Ser Ser Ser Tyr Tyr Trp Gly Trp Ile Arg Gln Pro Pro
50 55 60

Gly Lys Gly Leu Glu Trp Ile Gly Ser Ile Ser Tyr Ser Gly Ser Thr
65 70 75 80

Tyr Tyr Asn Pro Ser Leu Lys Ser Arg Val Thr Ile Ser Val Asp Thr
85 90 95

Ser Lys Asn Gln Phe Ser Leu Lys Leu Ser Ser Val Thr Ala Ala Asp
100 105 110

Thr Ala Val Tyr Tyr Cys Ala Arg Gly Arg Gly Tyr Ala Thr Ser Leu
115 120 125

Ala Phe Asp Ile Trp Gly Gln Gly Thr Met Val Thr Val Ser Ser Gly
130 135 140

Ser Thr Ser Gly Ser Gly Lys Pro Gly Ser Gly Glu Gly Ser Thr Lys
145 150 155 160

Gly Glu Ile Val Leu Thr Gln Ser Pro Ala Thr Leu Ser Leu Ser Pro
165 170 175

Gly Glu Arg Ala Thr Leu Ser Cys Arg Ala Ser Gln Ser Val Ser Ser
180 185 190

Tyr Leu Ala Trp Tyr Gln Gln Lys Pro Gly Gln Ala Pro Arg Leu Leu
195 200 205

Ile Tyr Asp Ala Ser Asn Arg Ala Thr Gly Ile Pro Ala Arg Phe Ser
210 215 220

Gly Ser Gly Ser Gly Thr Asp Phe Thr Leu Thr Ile Ser Ser Leu Glu
225 230 235 240

Pro Glu Asp Phe Ala Val Tyr Tyr Cys Gln Gln Arg His Val Trp Pro
245 250 255

Pro Thr Phe Gly Gly Gly Thr Lys Val Glu Ile Lys Arg Ala Ala Ala
260 265 270

Leu Asp Asn Glu Lys Ser Asn Gly Thr Ile Ile His Val Lys Gly Lys
275 280 285

His Leu Cys Pro Ser Pro Leu Phe Pro Gly Pro Ser Lys Pro Phe Trp
290 295 300

Val Leu Val Val Val Gly Gly Val Leu Ala Cys Tyr Ser Leu Leu Val
305 310 315 320

Thr Val Ala Phe Ile Ile Phe Trp Val Arg Ser Lys Arg Ser Arg Leu
325 330 335

Leu His Ser Asp Tyr Met Asn Met Thr Pro Arg Arg Pro Gly Pro Thr
340 345 350

Arg Lys His Tyr Gln Pro Tyr Ala Pro Pro Arg Asp Phe Ala Ala Tyr
355 360 365

Arg Ser Arg Val Lys Phe Ser Arg Ser Ala Asp Ala Pro Ala Tyr Gln
370 375 380

Gln Gly Gln Asn Gln Leu Tyr Asn Glu Leu Asn Leu Gly Arg Arg Glu
385 390 395 400

Glu Tyr Asp Val Leu Asp Lys Arg Arg Gly Arg Asp Pro Glu Met Gly
405 410 415

Gly Lys Pro Arg Arg Lys Asn Pro Gln Glu Gly Leu Tyr Asn Glu Leu
420 425 430

Gln Lys Asp Lys Met Ala Glu Ala Tyr Ser Glu Ile Gly Met Lys Gly
435 440 445

Glu Arg Arg Arg Gly Lys Gly His Asp Gly Leu Tyr Gln Gly Leu Ser
450 455 460

Thr Ala Thr Lys Asp Thr Tyr Asp Ala Leu His Met Gln Ala Leu Pro
465 470 475 480

Pro Arg

<210> SEQ ID NO 189
<211> LENGTH: 1449
<212> TYPE: DNA
<213> ORGANISM: Artificial Sequence
<220> FEATURE:
<223> OTHER INFORMATION: Description of Artificial Sequence: Synthetic
NM-21517CARDNALxH polynucleotide

<400> SEQUENCE: 189
atggcactcc ccgtaactgc tctgctgctg ccgttggcat tgctcctgca cgccgcacgc 60
ccggaaattg tgttgacaca gtctccagcc accctgtctt tgtctccagg ggaaagagcc 120
accctctcct gcagggccag tcagagtgtt agcagctact tagcctggta ccaacagaaa 180
cctggccagg ctcccaggct cctcatctat gatgcatcca acagggccac tggcatccca 240
gccaggttca gtggcagtgg gtctgggaca gacttcactc tcaccatcag cagcctagag 300
cctgaagatt ttgcagttta ttactgtcag cagagacacg tctggcctcc tacttttggc 360
ggagggacca aggttgagat caaacggggg tctacatccg gctccgggaa gcccggaagt 420
ggcgaaggta gtacaaaggg gcagctgcag ctgcaggagt cgggcccagg actggtgaag 480
ccttcggaga ccctgtccct cacctgcact gtctctggtg gctccatcag cagtagtagt 540
tactactggg gctggatccg ccagccccca gggaaggggc tggagtggat tgggagtatc 600
tcctatagtg ggagcaccta ctacaacccg tccctcaaga gtcgagtcac catatccgta 660
gacacgtcca agaaccagtt ctccctgaag ctgagttctg tgaccgccgc agacacggcg 720
gtgtactact gcgccagagg caggggatat gcaaccagct tagccttcga tatctggggt 780
cagggtacaa tggtcaccgt ctcctcagcc gctgcccttg ataatgaaaa gtcaaacgga 840
acaatcattc acgtgaaggg caagcacctc tgtccgtcac ccttgttccc tggtccatcc 900
aagccattct gggtgttggt cgtagtgggt ggagtcctcg cttgttactc tctgctcgtc 960
accgtggctt ttataatctt ctgggttaga tccaaaagaa gccgcctgct ccatagcgat 1020
tacatgaata tgactccacg ccgccctggc cccacaagga aacactacca gccttacgca 1080
ccacctagag atttcgctgc ctatcggagc agggtgaagt tttccagatc tgcagatgca 1140
ccagcgtatc agcagggcca gaaccaactg tataacgagc tcaacctggg acgcagggaa 1200
gagtatgacg ttttggacaa gcgcagagga cgggaccctg agatgggtgg caaaccaaga 1260
cgaaaaaacc cccaggaggg tctctataat gagctgcaga aggataagat ggctgaagcc 1320

-continued

```
tattctgaaa taggcatgaa aggagagcgg agaaggggaa aagggcacga cggtttgtac   1380

cagggactca gcactgctac gaaggatact tatgacgctc tccacatgca agccctgcca   1440

cctaggtaa                                                          1449
```

```
<210> SEQ ID NO 190
<211> LENGTH: 482
<212> TYPE: PRT
<213> ORGANISM: Artificial Sequence
<220> FEATURE:
<223> OTHER INFORMATION: Description of Artificial Sequence: Synthetic
      NM-21517CARLxH polypeptide

<400> SEQUENCE: 190

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Ser Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

His Val Trp Pro Pro Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Leu Gln Leu Gln Glu Ser Gly Pro Gly Leu Val Lys
145                 150                 155                 160

Pro Ser Glu Thr Leu Ser Leu Thr Cys Thr Val Ser Gly Gly Ser Ile
                165                 170                 175

Ser Ser Ser Ser Tyr Tyr Trp Gly Trp Ile Arg Gln Pro Pro Gly Lys
            180                 185                 190

Gly Leu Glu Trp Ile Gly Ser Ile Ser Tyr Ser Gly Ser Thr Tyr Tyr
        195                 200                 205

Asn Pro Ser Leu Lys Ser Arg Val Thr Ile Ser Val Asp Thr Ser Lys
    210                 215                 220

Asn Gln Phe Ser Leu Lys Leu Ser Ser Val Thr Ala Ala Asp Thr Ala
225                 230                 235                 240

Val Tyr Tyr Cys Ala Arg Gly Arg Gly Tyr Ala Thr Ser Leu Ala Phe
                245                 250                 255

Asp Ile Trp Gly Gln Gly Thr Met Val Thr Val Ser Ser Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335
```

```
Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg


<210> SEQ ID NO 191
<211> LENGTH: 1440
<212> TYPE: DNA
<213> ORGANISM: Artificial Sequence
<220> FEATURE:
<223> OTHER INFORMATION: Description of Artificial Sequence: Synthetic
      TS-21522CARDNAHxL polynucleotide

<400> SEQUENCE: 191

atggcactcc ccgtaactgc tctgctgctg ccgttggcat tgctcctgca cgccgcacgc     60

ccggaggtgc agctggtgga gtctggggga ggcttggtac agcctggggg gtccctgaga    120

ctctcctgtg cagcctctgg attcaccttc agtagctata gcatgaactg ggtccgccag    180

gctccaggga aggggctgga gtgggtttca accattagta gtagtagtag taccatatac    240

tacgcagact ctgtgaaggg ccgattcacc atctccagag acaatgccaa gaactcactg    300

tatctgcaaa tgaacagcct gagagctgag gacacggcgg tgtactactg cgccagaggt    360

tctcaggagc acctgatttt cgattattgg ggacagggta cattggtcac cgtctcctca    420

gggtctacat ccggctccgg gaagcccgga agtggcgaag gtagtacaaa gggggaaatt    480

gtgttgacac agtctccagc caccctgtct ttgtctccag gggaaagagc caccctctcc    540

tgcagggcca gtcagagtgt tagcaggtac ttagcctggt accaacagaa acctggccag    600

gctcccaggc tcctcatcta tgatgcatcc aacagggcca ctggcatccc agccaggttc    660

agtggcagtg ggtctgggac agacttcact ctcaccatca gcagcctaga gcctgaagat    720

tttgcagttt attactgtca gcagagattc tactaccctt ggacttttgg cggagggacc    780

aaggttgaga tcaaacgggc cgctgccctt gataatgaaa agtcaaacgg aacaatcatt    840

cacgtgaagg gcaagcacct ctgtccgtca ccccttgttcc ctggtccatc caagccattc    900

tgggtgttgg tcgtagtggg tggagtcctc gcttgttact ctctgctcgt caccgtggct    960

tttataatct tctgggttag atccaaaaga agccgcctgc tccatagcga ttacatgaat   1020

atgactccac gccgccctgg ccccacaagg aaacactacc agccttacgc accacctaga   1080

gatttcgctg cctatcggag cagggtgaag ttttccagat ctgcagatgc accagcgtat   1140
```

```
cagcagggcc agaaccaact gtataacgag ctcaacctgg gacgcaggga agagtatgac   1200

gttttggaca agcgcagagg acgggaccct gagatgggtg gcaaaccaag acgaaaaaac   1260

ccccaggagg gtctctataa tgagctgcag aaggataaga tggctgaagc ctattctgaa   1320

ataggcatga aaggagagcg gagaagggga aaagggcacg acggtttgta ccagggactc   1380

agcactgcta cgaaggatac ttatgacgct ctccacatgc aagccctgcc acctaggtaa   1440
```

<210> SEQ ID NO 192
<211> LENGTH: 479
<212> TYPE: PRT
<213> ORGANISM: Artificial Sequence
<220> FEATURE:
<223> OTHER INFORMATION: Description of Artificial Sequence: Synthetic
      TS-21522CARHxL polypeptide

<400> SEQUENCE: 192

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ser Met Asn Trp Val Arg Gln Ala Pro Gly Lys
    50                  55                  60

Gly Leu Glu Trp Val Ser Thr Ile Ser Ser Ser Ser Ser Thr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Gly Ser Gln Glu His Leu Ile Phe Asp
        115                 120                 125

Tyr Trp Gly Gln Gly Thr Leu Val Thr Val Ser Ser Gly Ser Thr Ser
    130                 135                 140

Gly Ser Gly Lys Pro Gly Ser Gly Glu Gly Ser Thr Lys Gly Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Arg Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Phe Tyr Tyr Pro Trp Thr Phe
                245                 250                 255

Gly Gly Gly Thr Lys Val Glu Ile Lys Arg Ala Ala Ala Leu Asp Asn
            260                 265                 270

Glu Lys Ser Asn Gly Thr Ile Ile His Val Lys Gly Lys His Leu Cys
        275                 280                 285

Pro Ser Pro Leu Phe Pro Gly Pro Ser Lys Pro Phe Trp Val Leu Val
    290                 295                 300

Val Val Gly Gly Val Leu Ala Cys Tyr Ser Leu Leu Val Thr Val Ala
```

-continued

```
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475


<210> SEQ ID NO 193
<211> LENGTH: 1440
<212> TYPE: DNA
<213> ORGANISM: Artificial Sequence
<220> FEATURE:
<223> OTHER INFORMATION: Description of Artificial Sequence: Synthetic
      TS-21522CARDNALxH polynucleotide

<400> SEQUENCE: 193

atggcactcc ccgtaactgc tctgctgctg ccgttggcat tgctcctgca cgccgcacgc     60

ccggaaattg tgttgacaca gtctccagcc accctgtctt tgtctccagg ggaaagagcc    120

accctctcct gcagggccag tcagagtgtt agcaggtact tagcctggta ccaacagaaa    180

cctggccagg ctcccaggct cctcatctat gatgcatcca acagggccac tggcatccca    240

gccaggttca gtggcagtgg gtctgggaca gacttcactc tcaccatcag cagcctagag    300

cctgaagatt ttgcagttta ttactgtcag cagagattct actacccttg gacttttggc    360

ggagggacca aggttgagat caaacggggg tctacatccg gctccgggaa gcccggaagt    420

ggcgaaggta gtacaaaggg ggaggtgcag ctggtggagt ctgggggagg cttggtacag    480

cctggggggt ccctgagact ctcctgtgca gcctctggat tcaccttcag tagctatagc    540

atgaactggg tccgccaggc tccagggaag gggctggagt gggtttcaac cattagtagt    600

agtagtagta ccatatacta cgcagactct gtgaagggcc gattcaccat ctccagagac    660

aatgccaaga actcactgta tctgcaaatg aacagcctga gagctgagga cacggcggtg    720

tactactgcg ccagaggttc tcaggagcac ctgattttcg attattgggg acagggtaca    780

ttggtcaccg tctcctcagc cgctgccctt gataatgaaa agtcaaacgg aacaatcatt    840

cacgtgaagg gcaagcacct ctgtccgtca cccttgttcc ctggtccatc caagccattc    900

tgggtgttgg tcgtagtggg tggagtcctc gcttgttact ctctgctcgt caccgtggct    960

tttataatct tctgggttag atccaaaaga agccgcctgc tccatagcga ttacatgaat   1020

atgactccac gccgccctgg ccccacaagg aaacactacc agccttacgc accacctaga   1080
```

gatttcgctg cctatcggag cagggtgaag ttttccagat ctgcagatgc accagcgtat 1140
cagcagggcc agaaccaact gtataacgag ctcaacctgg gacgcaggga agagtatgac 1200
gttttggaca agcgcagagg acgggaccct gagatgggtg gcaaaccaag acgaaaaaac 1260
ccccaggagg gtctctataa tgagctgcag aaggataaga tggctgaagc ctattctgaa 1320
ataggcatga aaggagagcg gagaagggga aaagggcacg acggtttgta ccagggactc 1380
agcactgcta cgaaggatac ttatgacgct ctccacatgc aagccctgcc acctaggtaa 1440

<210> SEQ ID NO 194
<211> LENGTH: 479
<212> TYPE: PRT
<213> ORGANISM: Artificial Sequence
<220> FEATURE:
<223> OTHER INFORMATION: Description of Artificial Sequence: Synthetic
TS-21522CARLxH polypeptide

<400> SEQUENCE: 194

Met Ala Leu Pro Val Thr Ala Leu Leu Leu Pro Leu Ala Leu Leu Leu
1 5 10 15

His Ala Ala Arg Pro Glu Ile Val Leu Thr Gln Ser Pro Ala Thr Leu
20 25 30

Ser Leu Ser Pro Gly Glu Arg Ala Thr Leu Ser Cys Arg Ala Ser Gln
35 40 45

Ser Val Ser Arg Tyr Leu Ala Trp Tyr Gln Gln Lys Pro Gly Gln Ala
50 55 60

Pro Arg Leu Leu Ile Tyr Asp Ala Ser Asn Arg Ala Thr Gly Ile Pro
65 70 75 80

Ala Arg Phe Ser Gly Ser Gly Ser Gly Thr Asp Phe Thr Leu Thr Ile
85 90 95

Ser Ser Leu Glu Pro Glu Asp Phe Ala Val Tyr Tyr Cys Gln Gln Arg
100 105 110

Phe Tyr Tyr Pro Trp Thr Phe Gly Gly Gly Thr Lys Val Glu Ile Lys
115 120 125

Arg Gly Ser Thr Ser Gly Ser Gly Lys Pro Gly Ser Gly Glu Gly Ser
130 135 140

Thr Lys Gly Glu Val Gln Leu Val Glu Ser Gly Gly Gly Leu Val Gln
145 150 155 160

Pro Gly Gly Ser Leu Arg Leu Ser Cys Ala Ala Ser Gly Phe Thr Phe
165 170 175

Ser Ser Tyr Ser Met Asn Trp Val Arg Gln Ala Pro Gly Lys Gly Leu
180 185 190

Glu Trp Val Ser Thr Ile Ser Ser Ser Ser Ser Thr Ile Tyr Tyr Ala
195 200 205

Asp Ser Val Lys Gly Arg Phe Thr Ile Ser Arg Asp Asn Ala Lys Asn
210 215 220

Ser Leu Tyr Leu Gln Met Asn Ser Leu Arg Ala Glu Asp Thr Ala Val
225 230 235 240

Tyr Tyr Cys Ala Arg Gly Ser Gln Glu His Leu Ile Phe Asp Tyr Trp
245 250 255

Gly Gln Gly Thr Leu Val Thr Val Ser Ser Ala Ala Ala Leu Asp Asn
260 265 270

Glu Lys Ser Asn Gly Thr Ile Ile His Val Lys Gly Lys His Leu Cys
275 280 285

Pro Ser Pro Leu Phe Pro Gly Pro Ser Lys Pro Phe Trp Val Leu Val
290 295 300

```
Val Val Gly Gly Val Leu Ala Cys Tyr Ser Leu Leu Val Thr Val Ala
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475
```

<210> SEQ ID NO 195
<211> LENGTH: 1449
<212> TYPE: DNA
<213> ORGANISM: Artificial Sequence
<220> FEATURE:
<223> OTHER INFORMATION: Description of Artificial Sequence: Synthetic
RY-21527CARDNAHxL polynucleotide

<400> SEQUENCE: 195

```
atggcactcc ccgtaactgc tctgctgctg ccgttggcat tgctcctgca cgccgcacgc     60

ccgcaggtgc agctggtgga gtctgggggga ggcgtggtcc agcctgggag gtccctgaga    120

ctctcctgtg cagcgtctgg attcaccttc agtagctatg gcatgcactg ggtccgccag    180

gctccaggca aggggctgga gtgggtggca gttatatcgt atgatggaag taataaatac    240

tatgcagact ccgtgaaggg ccgattcacc atctccagag acaattccaa gaacacgctg    300

tatctgcaaa tgaacagcct gagagccgag gacacggcgg tgtactactg cgccagaact    360

gacttctgga gcggatcccc tccaggctta gattactggg gacagggtac attggtcacc    420

gtctcctcag ggtctacatc cggctccggg aagcccggaa gtggcgaagg tagtacaaag    480

ggggacatcc agttgaccca gtctccatct tccgtgtctg catctgtagg agacagagtc    540

accatcactt gtcgggcgag tcagggtatt agcagctggt tagcctggta tcagcagaaa    600

ccagggaaag cccctaagct cctgatctat ggtgcatcca gtttgcaaag tggggtccca    660

tcaaggttca gcggcagtgg atctgggaca gatttcactc tcaccatcag cagcctgcag    720

cctgaagatt ttgcaactta ttactgtcag cagatataca ccttcccttt cacttttggc    780

ggagggacca aggttgagat caaacgggcc gctgcccttg ataatgaaaa gtcaaacgga    840

acaatcattc acgtgaaggg caagcacctc tgtccgtcac ccttgttccc tggtccatcc    900

aagccattct gggtgttggt cgtagtgggt ggagtcctcg cttgttactc tctgctcgtc    960

accgtggctt ttataatctt ctgggttaga tccaaaagaa gccgcctgct ccatagcgat   1020
```

-continued

```
tacatgaata tgactccacg ccgccctggc cccacaagga aacactacca gccttacgca   1080

ccacctagag atttcgctgc ctatcggagc agggtgaagt tttccagatc tgcagatgca   1140

ccagcgtatc agcagggcca gaaccaactg tataacgagc tcaacctggg acgcagggaa   1200

gagtatgacg ttttggacaa gcgcagagga cgggaccctg agatgggtgg caaaccaaga   1260

cgaaaaaacc cccaggaggg tctctataat gagctgcaga aggataagat ggctgaagcc   1320

tattctgaaa taggcatgaa aggagagcgg agaaggggaa aagggcacga cggtttgtac   1380

cagggactca gcactgctac gaaggatact tatgacgctc tccacatgca agccctgcca   1440

cctaggtaa                                                           1449
```

```
<210> SEQ ID NO 196
<211> LENGTH: 482
<212> TYPE: PRT
<213> ORGANISM: Artificial Sequence
<220> FEATURE:
<223> OTHER INFORMATION: Description of Artificial Sequence: Synthetic
      RY-21527CARHxL polypeptide

<400> SEQUENCE: 196

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Thr Asp Phe Trp Ser Gly Ser Pro Pro
        115                 120                 125

Gly Leu Asp Tyr Trp Gly Gln Gly Thr Leu Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Asp Ile Gln Leu Thr Gln Ser Pro Ser Ser Val Ser Ala Ser Val
                165                 170                 175

Gly Asp Arg Val Thr Ile Thr Cys Arg Ala Ser Gln Gly Ile Ser Ser
            180                 185                 190

Trp Leu Ala Trp Tyr Gln Gln Lys Pro Gly Lys Ala Pro Lys Leu Leu
        195                 200                 205

Ile Tyr Gly Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ile Tyr Thr Phe Pro
                245                 250                 255

Phe Thr Phe Gly Gly Gly Thr Lys Val Glu Ile Lys Arg Ala Ala Ala
            260                 265                 270

Leu Asp Asn Glu Lys Ser Asn Gly Thr Ile Ile His Val Lys Gly Lys
```

```
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg
```

<210> SEQ ID NO 197
<211> LENGTH: 1449
<212> TYPE: DNA
<213> ORGANISM: Artificial Sequence
<220> FEATURE:
<223> OTHER INFORMATION: Description of Artificial Sequence: Synthetic RY-21527CARDNALxH polynucleotide

<400> SEQUENCE: 197

```
atggcactcc ccgtaactgc tctgctgctg ccgttggcat tgctcctgca cgccgcacgc     60

ccggacatcc agttgaccca gtctccatct tccgtgtctg catctgtagg agacagagtc    120

accatcactt gtcgggcgag tcagggtatt agcagctggt tagcctggta tcagcagaaa    180

ccagggaaag cccctaagct cctgatctat ggtgcatcca gtttgcaaag tggggtccca    240

tcaaggttca gcggcagtgg atctgggaca gatttcactc tcaccatcag cagcctgcag    300

cctgaagatt ttgcaactta ttactgtcag cagatataca ccttcccttt cacttttggc    360

ggagggacca aggttgagat caaacggggg tctacatccg gctccgggaa gcccggaagt    420

ggcgaaggta gtacaaaggg gcaggtgcag ctggtggagt ctgggggagg cgtggtccag    480

cctgggaggt ccctgagact ctcctgtgca gcgtctggat tcaccttcag tagctatggc    540

atgcactggg tccgccaggc tccaggcaag gggctggagt gggtggcagt tatatcgtat    600

gatggaagta ataaatacta tgcagactcc gtgaagggcc gattcaccat ctccagagac    660

aattccaaga acacgctgta tctgcaaatg aacagcctga gagccgagga cacggcggtg    720

tactactgcg ccagaactga cttctggagc ggatcccctc caggcttaga ttactgggga    780

cagggtacat tggtcaccgt ctcctcagcc gctgcccttg ataatgaaaa gtcaaacgga    840
```

```
acaatcattc acgtgaaggg caagcacctc tgtccgtcac ccttgttccc tggtccatcc    900

aagccattct gggtgttggt cgtagtgggt ggagtcctcg cttgttactc tctgctcgtc    960

accgtggctt ttataatctt ctgggttaga tccaaaagaa gccgcctgct ccatagcgat   1020

tacatgaata tgactccacg ccgccctggc cccacaagga aacactacca gccttacgca   1080

ccacctagag atttcgctgc ctatcggagc agggtgaagt tttccagatc tgcagatgca   1140

ccagcgtatc agcagggcca gaaccaactg tataacgagc tcaacctggg acgcagggaa   1200

gagtatgacg ttttggacaa gcgcagagga cgggaccctg agatgggtgg caaaccaaga   1260

cgaaaaaacc cccaggaggg tctctataat gagctgcaga aggataagat ggctgaagcc   1320

tattctgaaa taggcatgaa aggagagcgg agaaggggaa aagggcacga cggtttgtac   1380

cagggactca gcactgctac gaaggatact tatgacgctc tccacatgca agccctgcca   1440

cctaggtaa                                                           1449
```

<210> SEQ ID NO 198
<211> LENGTH: 482
<212> TYPE: PRT
<213> ORGANISM: Artificial Sequence
<220> FEATURE:
<223> OTHER INFORMATION: Description of Artificial Sequence: Synthetic
      RY-21527CARLxH polypeptide

<400> SEQUENCE: 198

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Val
            20                  25                  30

Ser Ala Ser Val Gly Asp Arg Val Thr Ile Thr Cys Arg Ala Ser Gln
        35                  40                  45

Gly Ile Ser Ser Trp Leu Ala Trp Tyr Gln Gln Lys Pro Gly Lys Ala
    50                  55                  60

Pro Lys Leu Leu Ile Tyr Gly Ala Ser Ser Leu Gln Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Ile
            100                 105                 110

Tyr Thr Phe Pro Phe Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Val Glu Ser Gly Gly Gly Val Val Gln
145                 150                 155                 160

Pro Gly Arg Ser Leu Arg Leu Ser Cys Ala Ala Ser Gly Phe Thr Phe
                165                 170                 175

Ser Ser Tyr Gly Met His Trp Val Arg Gln Ala Pro Gly Lys Gly Leu
            180                 185                 190

Glu Trp Val Ala Val Ile Ser Tyr Asp Gly Ser Asn Lys Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Arg Thr Asp Phe Trp Ser Gly Ser Pro Pro Gly Leu
```

```
                245                 250                 255

Asp Tyr Trp Gly Gln Gly Thr Leu Val Thr Val Ser Ser Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg


<210> SEQ ID NO 199
<211> LENGTH: 1479
<212> TYPE: DNA
<213> ORGANISM: Artificial Sequence
<220> FEATURE:
<223> OTHER INFORMATION: Description of Artificial Sequence: Synthetic
      PP-21528CARDNAHxL polynucleotide

<400> SEQUENCE: 199

atggcactcc ccgtaactgc tctgctgctg ccgttggcat tgctcctgca cgccgcacgc     60

ccgcaggtgc agctggtgca gtctggggct gaggtgaaga agcctgggtc ctcggtgaag    120

gtctcctgca aggcttctgg aggcaccttc agcagctatg ctatcagctg ggtgcgacag    180

gcccctggac aagggcttga gtggatggga gggatcatcc ctatctttgg tacagcaaac    240

tacgcacaga agttccaggg cagagtcacg attaccgcgg acgaatccac gagcacagcc    300

tacatggagc tgagcagcct gagatctgag gacacggcgg tgtactactg cgccagaact    360

cctgaatact cctccagcat atggcactat tactacggca tggacgtatg gggccaggga    420

acaactgtca ccgtctcctc agggtctaca tccggctccg ggaagcccgg aagtggcgaa    480

ggtagtacaa agggggacat cgtgatgacc cagtctccag actccctggc tgtgtctctg    540

ggcgagaggg ccaccatcaa ctgcaagtcc agccagagtg ttttatacag ctccaacaat    600

aagaactact tagcttggta ccagcagaaa ccaggacagc ctcctaagct gctcatttac    660
```

-continued

```
tgggcatcta cccgggaatc cggggtccct gaccgattca gtggcagcgg gtctgggaca    720

gatttcactc tcaccatcag cagcctgcag gctgaagatg tggcagttta ttactgtcag    780

cagttcgccc acactccttt cacttttggc ggagggacca aggttgagat caaacgggcc    840

gctgcccttg ataatgaaaa gtcaaacgga acaatcattc acgtgaaggg caagcacctc    900

tgtccgtcac ccttgttccc tggtccatcc aagccattct gggtgttggt cgtagtgggt    960

ggagtcctcg cttgttactc tctgctcgtc accgtggctt ttataatctt ctgggttaga   1020

tccaaaagaa gccgcctgct ccatagcgat tacatgaata tgactccacg ccgccctggc   1080

cccacaagga aacactacca gccttacgca ccacctagag atttcgctgc ctatcggagc   1140

agggtgaagt tttccagatc tgcagatgca ccagcgtatc agcagggcca gaaccaactg   1200

tataacgagc tcaacctggg acgcagggaa gagtatgacg ttttggacaa gcgcagagga   1260

cgggaccctg agatgggtgg caaaccaaga cgaaaaaacc cccaggaggg tctctataat   1320

gagctgcaga aggataagat ggctgaagcc tattctgaaa taggcatgaa aggagagcgg   1380

agaaggggaa aagggcacga cggtttgtac cagggactca gcactgctac gaaggatact   1440

tatgacgctc tccacatgca agccctgcca cctaggtaa                          1479
```

<210> SEQ ID NO 200
<211> LENGTH: 492
<212> TYPE: PRT
<213> ORGANISM: Artificial Sequence
<220> FEATURE:
<223> OTHER INFORMATION: Description of Artificial Sequence: Synthetic
      PP-21528CARHxL polypeptide

<400> SEQUENCE: 200

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Ser Tyr Ala Ile Ser Trp Val Arg Gln Ala Pro Gly Gln
    50                  55                  60

Gly Leu Glu Trp Met Gly Gly Ile Ile Pro Ile Phe Gly Thr Ala Asn
65                  70                  75                  80

Tyr Ala Gln Lys Phe Gln Gly Arg Val Thr Ile Thr Ala Asp Glu Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Thr Pro Glu Tyr Ser Ser Ser Ile Trp
        115                 120                 125

His Tyr Tyr Tyr Gly Met Asp Val Trp Gly Gln Gly Thr Thr Val Thr
    130                 135                 140

Val Ser Ser Gly Ser Thr Ser Gly Ser Gly Lys Pro Gly Ser Gly Glu
145                 150                 155                 160

Gly Ser Thr Lys Gly Asp Ile Val Met Thr Gln Ser Pro Asp Ser Leu
                165                 170                 175

Ala Val Ser Leu Gly Glu Arg Ala Thr Ile Asn Cys Lys Ser Ser Gln
            180                 185                 190

Ser Val Leu Tyr Ser Ser Asn Asn Lys Asn Tyr Leu Ala Trp Tyr Gln
        195                 200                 205

Gln Lys Pro Gly Gln Pro Pro Lys Leu Leu Ile Tyr Trp Ala Ser Thr
```

```
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Leu Gln Ala Glu Asp Val Ala Val
                245                 250                 255

Tyr Tyr Cys Gln Gln Phe Ala His Thr Pro Phe Thr Phe Gly Gly Gly
            260                 265                 270

Thr Lys Val Glu Ile Lys Arg Ala Ala Ala Leu Asp Asn Glu Lys Ser
        275                 280                 285

Asn Gly Thr Ile Ile His Val Lys Gly Lys His Leu Cys Pro Ser Pro
    290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 201
<211> LENGTH: 1479
<212> TYPE: DNA
<213> ORGANISM: Artificial Sequence
<220> FEATURE:
<223> OTHER INFORMATION: Description of Artificial Sequence: Synthetic
PP-21528CARDNALxH polynucleotide

<400> SEQUENCE: 201

```
atggcactcc ccgtaactgc tctgctgctg ccgttggcat tgctcctgca cgccgcacgc     60

ccggacatcg tgatgaccca gtctccagac tccctggctg tgtctctggg cgagagggcc    120

accatcaact gcaagtccag ccagagtgtt ttatacagct ccaacaataa gaactactta    180

gcttggtacc agcagaaacc aggacagcct cctaagctgc tcatttactg ggcatctacc    240

cgggaatccg gggtccctga ccgattcagt ggcagcgggt ctgggacaga tttcactctc    300

accatcagca gcctgcaggc tgaagatgtg gcagtttatt actgtcagca gttcgcccac    360

actcctttca cttttggcgg agggaccaag gttgagatca aacgggggtc tacatccggc    420

tccgggaagc ccggaagtgg cgaaggtagt acaaaggggc aggtgcagct ggtgcagtct    480
```

-continued

```
ggggctgagg tgaagaagcc tgggtcctcg gtgaaggtct cctgcaaggc ttctggaggc    540

accttcagca gctatgctat cagctgggtg cgacaggccc ctggacaagg gcttgagtgg    600

atgggaggga tcatccctat ctttggtaca gcaaactacg cacagaagtt ccagggcaga    660

gtcacgatta ccgcggacga atccacgagc acagcctaca tggagctgag cagcctgaga    720

tctgaggaca cggcggtgta ctactgcgcc agaactcctg aatactcctc cagcatatgg    780

cactattact acggcatgga cgtatggggc cagggaacaa ctgtcaccgt ctcctcagcc    840

gctgcccttg ataatgaaaa gtcaaacgga acaatcattc acgtgaaggg caagcacctc    900

tgtccgtcac ccttgttccc tggtccatcc aagccattct gggtgttggt cgtagtgggt    960

ggagtcctcg cttgttactc tctgctcgtc accgtggctt ttataatctt ctgggttaga   1020

tccaaaagaa gccgcctgct ccatagcgat tacatgaata tgactccacg ccgccctggc   1080

cccacaagga aacactacca gccttacgca ccacctagag atttcgctgc ctatcggagc   1140

agggtgaagt tttccagatc tgcagatgca ccagcgtatc agcagggcca gaaccaactg   1200

tataacgagc tcaacctggg acgcagggaa gagtatgacg ttttggacaa gcgcagagga   1260

cgggaccctg agatgggtgg caaaccaaga cgaaaaaacc cccaggaggg tctctataat   1320

gagctgcaga aggataagat ggctgaagcc tattctgaaa taggcatgaa aggagagcgg   1380

agaaggggaa aagggcacga cggtttgtac cagggactca gcactgctac gaaggatact   1440

tatgacgctc tccacatgca agccctgcca cctaggtaa                          1479
```

<210> SEQ ID NO 202
<211> LENGTH: 492
<212> TYPE: PRT
<213> ORGANISM: Artificial Sequence
<220> FEATURE:
<223> OTHER INFORMATION: Description of Artificial Sequence: Synthetic
PP-21528CARLxH polypeptide

<400> SEQUENCE: 202

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Val Leu Tyr Ser Ser Asn Asn Lys Asn Tyr Leu Ala Trp Tyr Gln
    50                  55                  60

Gln Lys Pro Gly Gln Pro Pro Lys Leu Leu Ile Tyr Trp Ala Ser Thr
65                  70                  75                  80

Arg Glu Ser Gly Val Pro Asp Arg Phe Ser Gly Ser Gly Ser Gly Thr
                85                  90                  95

Asp Phe Thr Leu Thr Ile Ser Ser Leu Gln Ala Glu Asp Val Ala Val
            100                 105                 110

Tyr Tyr Cys Gln Gln Phe Ala His Thr Pro Phe Thr Phe Gly Gly Gly
        115                 120                 125

Thr Lys Val Glu Ile Lys Arg Gly Ser Thr Ser Gly Ser Gly Lys Pro
    130                 135                 140

Gly Ser Gly Glu Gly Ser Thr Lys Gly Gln Val Gln Leu Val Gln Ser
145                 150                 155                 160

Gly Ala Glu Val Lys Lys Pro Gly Ser Ser Val Lys Val Ser Cys Lys
                165                 170                 175
```

```
Ala Ser Gly Gly Thr Phe Ser Ser Tyr Ala Ile Ser Trp Val Arg Gln
            180                 185                 190

Ala Pro Gly Gln Gly Leu Glu Trp Met Gly Gly Ile Ile Pro Ile Phe
        195                 200                 205

Gly Thr Ala Asn Tyr Ala Gln Lys Phe Gln Gly Arg Val Thr Ile Thr
    210                 215                 220

Ala Asp Glu Ser Thr Ser Thr Ala Tyr Met Glu Leu Ser Ser Leu Arg
225                 230                 235                 240

Ser Glu Asp Thr Ala Val Tyr Tyr Cys Ala Arg Thr Pro Glu Tyr Ser
                245                 250                 255

Ser Ser Ile Trp His Tyr Tyr Tyr Gly Met Asp Val Trp Gly Gln Gly
            260                 265                 270

Thr Thr Val Thr Val Ser Ser Ala Ala Ala Leu Asp Asn Glu Lys Ser
        275                 280                 285

Asn Gly Thr Ile Ile His Val Lys Gly Lys His Leu Cys Pro Ser Pro
    290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 203
<211> LENGTH: 1452
<212> TYPE: DNA
<213> ORGANISM: Artificial Sequence
<220> FEATURE:
<223> OTHER INFORMATION: Description of Artificial Sequence: Synthetic RD-21530CARDNAHxL polynucleotide

<400> SEQUENCE: 203

```
atggcactcc ccgtaactgc tctgctgctg ccgttggcat tgctcctgca cgccgcacgc      60

ccgcaggtgc agctggtgga gtctggggga ggcgtggtcc agcctgggag gtccctgaga     120

ctctcctgtg cagcgtctgg attcaccttc agtagctatg gcatgcactg ggtccgccag     180

gctccaggca aggggctgga gtgggtggca gttatatcgt atgatggaag taataaatac     240
```

```
tatgcagact ccgtgaaggg ccgattcacc atctccagag acaattccaa gaacacgctg    300

tatctgcaaa tgaacagcct gagagccgag gacacggcgg tgtactactg cgtcaagggg    360

ccgttgcagg agccgccata cgattatgga atggacgtat ggggccaggg aacaactgtc    420

accgtctcct cagggtctac atccggctcc gggaagcccg gaagtggcga aggtagtaca    480

aagggggaaa tagtgatgac gcagtctcca gccaccctgt ctgtgtctcc aggggaaaga    540

gccaccctct cctgcagggc cagtcagagt gttagcagca acttagcctg gtaccagcag    600

aaacctggcc aggctcccag gctcctcatc tatagcgcat ccaccagggc cactggtatc    660

ccagccaggt tcagtggcag tgggtctggg acagagttca ctctcaccat cagcagcctg    720

cagtctgaag attttgcagt ttattactgt cagcagcacc acgtctggcc tctcactttt    780

ggcggaggga ccaaggttga gatcaaacgg gccgctgccc ttgataatga aaagtcaaac    840

ggaacaatca ttcacgtgaa gggcaagcac ctctgtccgt caccccttgt ccctggtcca    900

tccaagccat tctgggtgtt ggtcgtagtg ggtggagtcc tcgcttgtta ctctctgctc    960

gtcaccgtgg cttttataat cttctgggtt agatccaaaa gaagccgcct gctccatagc   1020

gattacatga atatgactcc acgccgccct ggccccacaa ggaaacacta ccagccttac   1080

gcaccaccta gagatttcgc tgcctatcgg agcagggtga agttttccag atctgcagat   1140

gcaccagcgt atcagcaggg ccagaaccaa ctgtataacg agctcaacct gggacgcagg   1200

gaagagtatg acgttttgga caagcgcaga ggacgggacc ctgagatggg tggcaaacca   1260

agacgaaaaa acccccagga gggtctctat aatgagctgc agaaggataa gatggctgaa   1320

gcctattctg aaataggcat gaaaggagag cggagaaggg gaaaagggca cgacggtttg   1380

taccagggac tcagcactgc tacgaaggat acttatgacg ctctccacat gcaagccctg   1440

ccacctaggt aa                                                       1452
```

```
<210> SEQ ID NO 204
<211> LENGTH: 483
<212> TYPE: PRT
<213> ORGANISM: Artificial Sequence
<220> FEATURE:
<223> OTHER INFORMATION: Description of Artificial Sequence: Synthetic
      RD-21530CARHxL polypeptide

<400> SEQUENCE: 204

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140
```

```
Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg
```

<210> SEQ ID NO 205
<211> LENGTH: 1452
<212> TYPE: DNA
<213> ORGANISM: Artificial Sequence
<220> FEATURE:
<223> OTHER INFORMATION: Description of Artificial Sequence: Synthetic
RD-21530CARDNALxH polynucleotide

<400> SEQUENCE: 205

```
atggcactcc ccgtaactgc tctgctgctg ccgttggcat tgctcctgca cgccgcacgc     60
```

```
ccggaaatag tgatgacgca gtctccagcc accctgtctg tgtctccagg ggaaagagcc    120

accctctcct gcagggccag tcagagtgtt agcagcaact tagcctggta ccagcagaaa    180

cctggccagg ctcccaggct cctcatctat agcgcatcca ccagggccac tggtatccca    240

gccaggttca gtggcagtgg gtctgggaca gagttcactc tcaccatcag cagcctgcag    300

tctgaagatt ttgcagttta ttactgtcag cagcaccacg tctggcctct cacttttggc    360

ggagggacca aggttgagat caaacggggg tctacatccg gctccgggaa gcccggaagt    420

ggcgaaggta gtacaaaggg gcaggtgcag ctggtggagt ctgggggagg cgtggtccag    480

cctgggaggt ccctgagact ctcctgtgca gcgtctggat tcaccttcag tagctatggc    540

atgcactggg tccgccaggc tccaggcaag gggctggagt gggtggcagt tatatcgtat    600

gatggaagta ataaatacta tgcagactcc gtgaagggcc gattcaccat ctccagagac    660

aattccaaga acacgctgta tctgcaaatg aacagcctga gagccgagga cacggcggtg    720

tactactgcg tcaaggggcc gttgcaggag ccgccatacg attatggaat ggacgtatgg    780

ggccagggaa caactgtcac cgtctcctca gccgctgccc ttgataatga aaagtcaaac    840

ggaacaatca ttcacgtgaa gggcaagcac ctctgtccgt caccccttgtt ccctggtcca    900

tccaagccat tctgggtgtt ggtcgtagtg ggtggagtcc tcgcttgtta ctctctgctc    960

gtcaccgtgg cttttataat cttctgggtt agatccaaaa gaagccgcct gctccatagc   1020

gattacatga atatgactcc acgccgccct ggccccacaa ggaaacacta ccagccttac   1080

gcaccaccta gagatttcgc tgcctatcgg agcagggtga agttttccag atctgcagat   1140

gcaccagcgt atcagcaggg ccagaaccaa ctgtataacg agctcaacct gggacgcagg   1200

gaagagtatg acgttttgga caagcgcaga ggacgggacc ctgagatggg tggcaaacca   1260

agacgaaaaa acccccagga gggtctctat aatgagctgc agaaggataa gatggctgaa   1320

gcctattctg aaataggcat gaaaggagag cggagaaggg gaaaagggca cgacggtttg   1380

taccagggac tcagcactgc tacgaaggat acttatgacg ctctccacat gcaagccctg   1440

ccacctaggt aa                                                        1452
```

<210> SEQ ID NO 206
<211> LENGTH: 483
<212> TYPE: PRT
<213> ORGANISM: Artificial Sequence
<220> FEATURE:
<223> OTHER INFORMATION: Description of Artificial Sequence: Synthetic RD-21530CARLxH polypeptide

<400> SEQUENCE: 206

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Ser Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln His
            100                 105                 110
```

His Val Trp Pro Leu Thr Phe Gly Gly Gly Thr Lys Val Glu Ile Lys
115 120 125

Arg Gly Ser Thr Ser Gly Ser Gly Lys Pro Gly Ser Gly Glu Gly Ser
130 135 140

Thr Lys Gly Gln Val Gln Leu Val Glu Ser Gly Gly Gly Val Val Gln
145 150 155 160

Pro Gly Arg Ser Leu Arg Leu Ser Cys Ala Ala Ser Gly Phe Thr Phe
165 170 175

Ser Ser Tyr Gly Met His Trp Val Arg Gln Ala Pro Gly Lys Gly Leu
180 185 190

Glu Trp Val Ala Val Ile Ser Tyr Asp Gly Ser Asn Lys Tyr Tyr Ala
195 200 205

Asp Ser Val Lys Gly Arg Phe Thr Ile Ser Arg Asp Asn Ser Lys Asn
210 215 220

Thr Leu Tyr Leu Gln Met Asn Ser Leu Arg Ala Glu Asp Thr Ala Val
225 230 235 240

Tyr Tyr Cys Val Lys Gly Pro Leu Gln Glu Pro Pro Tyr Asp Tyr Gly
245 250 255

Met Asp Val Trp Gly Gln Gly Thr Thr Val Thr Val Ser Ser Ala Ala
260 265 270

Ala Leu Asp Asn Glu Lys Ser Asn Gly Thr Ile Ile His Val Lys Gly
275 280 285

Lys His Leu Cys Pro Ser Pro Leu Phe Pro Gly Pro Ser Lys Pro Phe
290 295 300

Trp Val Leu Val Val Val Gly Gly Val Leu Ala Cys Tyr Ser Leu Leu
305 310 315 320

Val Thr Val Ala Phe Ile Ile Phe Trp Val Arg Ser Lys Arg Ser Arg
325 330 335

Leu Leu His Ser Asp Tyr Met Asn Met Thr Pro Arg Arg Pro Gly Pro
340 345 350

Thr Arg Lys His Tyr Gln Pro Tyr Ala Pro Pro Arg Asp Phe Ala Ala
355 360 365

Tyr Arg Ser Arg Val Lys Phe Ser Arg Ser Ala Asp Ala Pro Ala Tyr
370 375 380

Gln Gln Gly Gln Asn Gln Leu Tyr Asn Glu Leu Asn Leu Gly Arg Arg
385 390 395 400

Glu Glu Tyr Asp Val Leu Asp Lys Arg Arg Gly Arg Asp Pro Glu Met
405 410 415

Gly Gly Lys Pro Arg Arg Lys Asn Pro Gln Glu Gly Leu Tyr Asn Glu
420 425 430

Leu Gln Lys Asp Lys Met Ala Glu Ala Tyr Ser Glu Ile Gly Met Lys
435 440 445

Gly Glu Arg Arg Arg Gly Lys Gly His Asp Gly Leu Tyr Gln Gly Leu
450 455 460

Ser Thr Ala Thr Lys Asp Thr Tyr Asp Ala Leu His Met Gln Ala Leu
465 470 475 480

Pro Pro Arg

<210> SEQ ID NO 207
<211> LENGTH: 26
<212> TYPE: PRT
<213> ORGANISM: Artificial Sequence
<220> FEATURE:
<223> OTHER INFORMATION: Description of Artificial Sequence: Synthetic VH FR1 peptide

<400> SEQUENCE: 207

Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 208
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 208

Gln Val Gln Leu Val Glu Ser Gly Gly Gly Val Val Gln Pro Gly Arg
1               5                   10                  15

Ser Leu Arg Leu Ser Cys Ala Ala Ser Gly
            20                  25

<210> SEQ ID NO 209
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 209

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 210
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 210

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 211
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

-continued

<210> SEQ ID NO 212
<211> LENGTH: 26
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 212

Gln Val Gln Leu Val Glu Ser Gly Gly Gly Val Val Gln Pro Gly Arg
1 5 10 15

Ser Leu Arg Leu Ser Cys Ala Ala Ser Gly
20 25

<210> SEQ ID NO 213
<211> LENGTH: 26
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 213

Gln Val Gln Leu Val Gln Ser Gly Ala Glu Val Lys Lys Pro Gly Ser
1 5 10 15

Ser Val Lys Val Ser Cys Lys Ala Ser Gly
20 25

<210> SEQ ID NO 214
<211> LENGTH: 26
<212> TYPE: PRT
<213> ORGANISM: Artificial Sequence
<220> FEATURE:
<223> OTHER INFORMATION: Description of Artificial Sequence: Synthetic
VH FR1 peptide

<400> SEQUENCE: 214

Gln Val Gln Leu Val Glu Ser Gly Gly Gly Val Val Gln Pro Gly Arg
1 5 10 15

Ser Leu Arg Leu Ser Cys Ala Ala Ser Gly
20 25

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 215

Phe Thr Phe Ser Ser Tyr Ala Met Ser
1 5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 216

Phe Thr Phe Ser Ser Tyr Gly Met His
1 5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 217

Tyr Thr Phe Thr Ser Tyr Tyr Met His
1 5

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 218

Gly Ser Ile Ser Ser Ser Ser Tyr Tyr Trp Gly
1 5 10

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 219

Phe Thr Phe Ser Ser Tyr Ser Met Asn
1 5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 220

Phe Thr Phe Ser Ser Tyr Gly Met His
1 5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 221

Gly Thr Phe Ser Ser Tyr Ala Ile Ser
1 5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide

<400> SEQUENCE: 222

Phe Thr Phe Ser Ser Tyr Gly Met His
1 5

<210> SEQ ID NO 223
<211> LENGTH: 14
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 223

Trp Val Arg Gln Ala Pro Gly Lys Gly Leu Glu Trp Val Ser
1 5 10

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 224

Trp Val Arg Gln Ala Pro Gly Lys Gly Leu Glu Trp Val Ala
1 5 10

<210> SEQ ID NO 225
<211> LENGTH: 14
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 225

Trp Val Arg Gln Ala Pro Gly Gln Gly Leu Glu Trp Met Gly
1 5 10

<210> SEQ ID NO 226
<211> LENGTH: 14
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 226

Trp Ile Arg Gln Pro Pro Gly Lys Gly Leu Glu Trp Ile Gly
1 5 10

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 227

Trp Val Arg Gln Ala Pro Gly Lys Gly Leu Glu Trp Val Ser
1 5 10

<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 228

Trp Val Arg Gln Ala Pro Gly Lys Gly Leu Glu Trp Val Ala
1 5 10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 229

Trp Val Arg Gln Ala Pro Gly Gln Gly Leu Glu Trp Met Gly
1 5 10

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 230

Trp Val Arg Gln Ala Pro Gly Lys Gly Leu Glu Trp Val Ala
1 5 10

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 231

Ala Ile Ser Gly Ser Gly Gly Ser Thr Tyr Tyr Ala Asp Ser Val Lys
1 5 10 15

Gly

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 232

Val Ile Ser Tyr Asp Gly Ser Asn Lys Tyr Tyr Ala Asp Ser Val Lys
1 5 10 15

Gly

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 233

Ile Ile Asn Pro Gly Gly Gly Ser Thr Ser Tyr Ala Gln Lys Phe Gln
1 5 10 15

Gly

<210> SEQ ID NO 234
<211> LENGTH: 16
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 234

Ser Ile Ser Tyr Ser Gly Ser Thr Tyr Tyr Asn Pro Ser Leu Lys Ser
1 5 10 15

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 235

Thr Ile Ser Ser Ser Ser Ser Thr Ile Tyr Tyr Ala Asp Ser Val Lys
1 5 10 15

Gly

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 236

Val Ile Ser Tyr Asp Gly Ser Asn Lys Tyr Tyr Ala Asp Ser Val Lys
1 5 10 15

Gly

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 237

Gly Ile Ile Pro Ile Phe Gly Thr Ala Asn Tyr Ala Gln Lys Phe Gln
1 5 10 15

Gly

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic
VH FR2 peptide

<400> SEQUENCE: 238

```
Val Ile Ser Tyr Asp Gly Ser Asn Lys Tyr Tyr Ala Asp Ser Val Lys
1               5                   10                  15

Gly


<210> SEQ ID NO 239
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 239

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30


<210> SEQ ID NO 240
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 240

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30


<210> SEQ ID NO 241
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 241

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30


<210> SEQ ID NO 242
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 242

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30


<210> SEQ ID NO 243
<211> LENGTH: 30
<212> TYPE: PRT
<213> ORGANISM: Artificial Sequence
<220> FEATURE:
```

<223> OTHER INFORMATION: Description of Artificial Sequence: Synthetic
VH FR3 polypeptide

<400> SEQUENCE: 243

Arg Phe Thr Ile Ser Arg Asp Asn Ala Lys Asn Ser Leu Tyr Leu Gln
1 5 10 15

Met Asn Ser Leu Arg Ala Glu Asp Thr Ala Val Tyr Tyr Cys
20 25 30

<210> SEQ ID NO 244
<211> LENGTH: 30
<212> TYPE: PRT
<213> ORGANISM: Artificial Sequence
<220> FEATURE:
<223> OTHER INFORMATION: Description of Artificial Sequence: Synthetic
VH FR3 polypeptide

<400> SEQUENCE: 244

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys
20 25 30

<210> SEQ ID NO 245
<211> LENGTH: 30
<212> TYPE: PRT
<213> ORGANISM: Artificial Sequence
<220> FEATURE:
<223> OTHER INFORMATION: Description of Artificial Sequence: Synthetic
VH FR3 polypeptide

<400> SEQUENCE: 245

Arg Val Thr Ile Thr Ala Asp Glu Ser Thr Ser Thr Ala Tyr Met Glu
1 5 10 15

Leu Ser Ser Leu Arg Ser Glu Asp Thr Ala Val Tyr Tyr Cys
20 25 30

<210> SEQ ID NO 246
<211> LENGTH: 30
<212> TYPE: PRT
<213> ORGANISM: Artificial Sequence
<220> FEATURE:
<223> OTHER INFORMATION: Description of Artificial Sequence: Synthetic
VH FR3 polypeptide

<400> SEQUENCE: 246

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys
20 25 30

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
VH CDR3 peptide

<400> SEQUENCE: 247

Ala Arg Ala Glu Met Gly Ala Val Phe Asp Ile
1 5 10

<210> SEQ ID NO 248
<211> LENGTH: 15

<212> TYPE: PRT
<213> ORGANISM: Artificial Sequence
<220> FEATURE:
<223> OTHER INFORMATION: Description of Artificial Sequence: Synthetic VH CDR3 peptide

<400> SEQUENCE: 248

Ala Arg Asp Gly Thr Tyr Leu Gly Gly Leu Trp Tyr Phe Asp Leu
1 5 10 15

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic VH CDR3 peptide

<400> SEQUENCE: 249

Ala Arg Glu Ser Trp Pro Met Asp Val
1 5

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence: Synthetic VH CDR3 peptide

<400> SEQUENCE: 250

Ala Arg Gly Arg Gly Tyr Ala Thr Ser Leu Ala Phe Asp Ile
1 5 10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic VH CDR3 peptide

<400> SEQUENCE: 251

Ala Arg Gly Ser Gln Glu His Leu Ile Phe Asp Tyr
1 5 10

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic VH CDR3 peptide

<400> SEQUENCE: 252

Ala Arg Thr Asp Phe Trp Ser Gly Ser Pro Pro Gly Leu Asp Tyr
1 5 10 15

<210> SEQ ID NO 253
<211> LENGTH: 19
<212> TYPE: PRT
<213> ORGANISM: Artificial Sequence
<220> FEATURE:
<223> OTHER INFORMATION: Description of Artificial Sequence: Synthetic VH CDR3 peptide

<400> SEQUENCE: 253

Ala Arg Thr Pro Glu Tyr Ser Ser Ser Ile Trp His Tyr Tyr Tyr Gly 1 5 10 15

Met Asp Val

<210> SEQ ID NO 254
<211> LENGTH: 16
<212> TYPE: PRT
<213> ORGANISM: Artificial Sequence
<220> FEATURE:
<223> OTHER INFORMATION: Description of Artificial Sequence: Synthetic VH CDR3 peptide

<400> SEQUENCE: 254

Val Lys Gly Pro Leu Gln Glu Pro Pro Tyr Asp Tyr Gly Met Asp Val
1 5 10 15

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic VH FR4 peptide

<400> SEQUENCE: 255

Trp Gly Gln Gly Thr Met Val Thr Val Ser Ser
1 5 10

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic VH FR4 peptide

<400> SEQUENCE: 256

Trp Gly Arg Gly Thr Leu Val Thr Val Ser Ser
1 5 10

<210> SEQ ID NO 257
<211> LENGTH: 11
<212> TYPE: PRT
<213> ORGANISM: Artificial Sequence
<220> FEATURE:
<223> OTHER INFORMATION: Description of Artificial Sequence: Synthetic VH FR4 peptide

<400> SEQUENCE: 257

Trp Gly Gln Gly Thr Thr Val Thr Val Ser Ser
1 5 10

<210> SEQ ID NO 258
<211> LENGTH: 11
<212> TYPE: PRT
<213> ORGANISM: Artificial Sequence
<220> FEATURE:
<223> OTHER INFORMATION: Description of Artificial Sequence: Synthetic VH FR4 peptide

<400> SEQUENCE: 258

Trp Gly Gln Gly Thr Met Val Thr Val Ser Ser
1 5 10

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
VH FR4 peptide

<400> SEQUENCE: 259

Trp Gly Gln Gly Thr Leu Val Thr Val Ser Ser
1 5 10

<210> SEQ ID NO 260
<211> LENGTH: 11
<212> TYPE: PRT
<213> ORGANISM: Artificial Sequence
<220> FEATURE:
<223> OTHER INFORMATION: Description of Artificial Sequence: Synthetic
VH FR4 peptide

<400> SEQUENCE: 260

Trp Gly Gln Gly Thr Leu Val Thr Val Ser Ser
1 5 10

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic
VH FR4 peptide

<400> SEQUENCE: 261

Trp Gly Gln Gly Thr Thr Val Thr Val Ser Ser
1 5 10

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
VH FR4 peptide

<400> SEQUENCE: 262

Trp Gly Gln Gly Thr Thr Val Thr Val Ser Ser
1 5 10

<210> SEQ ID NO 263
<211> LENGTH: 11
<212> TYPE: PRT
<213> ORGANISM: Artificial Sequence
<220> FEATURE:
<223> OTHER INFORMATION: Description of Artificial Sequence: Synthetic
VH CDR1 peptide
<220> FEATURE:
<221> NAME/KEY: MISC_FEATURE
<222> LOCATION: (1)..(2)
<223> OTHER INFORMATION: May or may not be present
<220> FEATURE:
<221> NAME/KEY: MOD_RES
<222> LOCATION: (3)..(3)
<223> OTHER INFORMATION: Phe, Gly, Ile or Tyr
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Phe or Ser
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (9)..(9)
<223> OTHER INFORMATION: Ala, Gly, Ser or Tyr
<220> FEATURE:
<221> NAME/KEY: MOD_RES
<222> LOCATION: (10)..(10)
<223> OTHER INFORMATION: Ile, Met or Trp
<220> FEATURE:
<221> NAME/KEY: MOD_RES
<222> LOCATION: (11)..(11)
<223> OTHER INFORMATION: Gly, His, Asn or Ser

<400> SEQUENCE: 263

```
Gly Ser Xaa Xaa Xaa Xaa Ser Tyr Xaa Xaa Xaa
1               5                   10
```

<210> SEQ ID NO 264
<211> LENGTH: 21
<212> TYPE: PRT
<213> ORGANISM: Artificial Sequence
<220> FEATURE:
<223> OTHER INFORMATION: Description of Artificial Sequence: Synthetic
VH CDR3 peptide
<220> FEATURE:
<221> NAME/KEY: MOD_RES
<222> LOCATION: (1)..(1)
<223> OTHER INFORMATION: Ala or Val
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(3)
<223> OTHER INFORMATION: Asp, Gly or Thr
<220> FEATURE:
<221> NAME/KEY: MOD_RES
<222> LOCATION: (4)..(4)
<223> OTHER INFORMATION: Asp, Gly, Pro or absent
<220> FEATURE:
<221> NAME/KEY: MOD_RES
<222> LOCATION: (5)..(5)
<223> OTHER INFORMATION: Phe, Leu, Thr or absent
<220> FEATURE:
<221> NAME/KEY: MOD_RES
<222> LOCATION: (6)..(6)
<223> OTHER INFORMATION: Pro, Gln, Arg, Trp, Tyr or absent
<220> FEATURE:
<221> NAME/KEY: MOD_RES
<222> LOCATION: (7)..(7)
<223> OTHER INFORMATION: Glu, Gly, Leu, Ser or absent
<220> FEATURE:
<221> NAME/KEY: MOD_RES
<222> LOCATION: (8)..(8)
<223> OTHER INFORMATION: Ala, Gly, Pro, Ser, Tyr or absent
<220> FEATURE:
<221> NAME/KEY: MOD_RES
<222> LOCATION: (9)..(9)
<223> OTHER INFORMATION: Ala, Glu, Gly, Pro, Gln, Ser or absent
<220> FEATURE:
<221> NAME/KEY: MOD_RES
<222> LOCATION: (10)..(10)
<223> OTHER INFORMATION: Glu, Leu, Met, Pro, Ser, Thr, Tyr or absent
<220> FEATURE:
<221> NAME/KEY: MOD_RES
<222> LOCATION: (11)..(11)
<223> OTHER INFORMATION: Asp, Gly, His, Pro, Ser, Trp or absent
<220> FEATURE:
<221> NAME/KEY: MOD_RES
<222> LOCATION: (12)..(12)
<223> OTHER INFORMATION: Ala, Gly, Ile, Leu, Tyr or absent
<220> FEATURE:
<221> NAME/KEY: MOD_RES
<222> LOCATION: (13)..(13)
<223> OTHER INFORMATION: Ala, Gly, Ile, Val, Trp or absent
<220> FEATURE:

<221> NAME/KEY: MISC_FEATURE
<222> LOCATION: (14)..(16)
<223> OTHER INFORMATION: May or may not be present
<220> FEATURE:
<221> NAME/KEY: MOD_RES
<222> LOCATION: (17)..(17)
<223> OTHER INFORMATION: Trp, Tyr or absent
<220> FEATURE:
<221> NAME/KEY: MOD_RES
<222> LOCATION: (18)..(18)
<223> OTHER INFORMATION: Pro, Gly or absent
<220> FEATURE:
<221> NAME/KEY: MOD_RES
<222> LOCATION: (19)..(19)
<223> OTHER INFORMATION: Phe, Leu or Met
<220> FEATURE:
<221> NAME/KEY: MOD_RES
<222> LOCATION: (21)..(21)
<223> OTHER INFORMATION: Ile, Leu, Val or Tyr

<400> SEQUENCE: 264

```
Xaa Xaa Xaa Xaa Xaa Xaa Xaa Xaa Xaa Xaa Xaa Xaa Xaa His Tyr Tyr
1               5                   10                  15

Xaa Xaa Xaa Asp Xaa
            20
```

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide
<220> FEATURE:
<221> NAME/KEY: MOD_RES
<222> LOCATION: (1)..(1)
<223> OTHER INFORMATION: Phe, Gly or Tyr
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (7)..(7)
<223> OTHER INFORMATION: Ala, Gly, Ser or Tyr
<220> FEATURE:
<221> NAME/KEY: MOD_RES
<222> LOCATION: (8)..(8)
<223> OTHER INFORMATION: Ile or Met
<220> FEATURE:
<221> NAME/KEY: MOD_RES
<222> LOCATION: (9)..(9)
<223> OTHER INFORMATION: His, Asn or Ser

<400> SEQUENCE: 265

```
Xaa Thr Phe Xaa Ser Tyr Xaa Xaa Xaa
1               5
```

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
VH CDR1 peptide
<220> FEATURE:
<221> NAME/KEY: MOD_RES
<222> LOCATION: (7)..(7)
<223> OTHER INFORMATION: Ala, Gly or Ser
<220> FEATURE:
<221> NAME/KEY: MOD_RES
<222> LOCATION: (9)..(9)
<223> OTHER INFORMATION: His, Asn or Ser

<400> SEQUENCE: 266

Phe Thr Phe Ser Ser Tyr Xaa Met Xaa
1 5

<210> SEQ ID NO 267
<211> LENGTH: 21
<212> TYPE: PRT
<213> ORGANISM: Artificial Sequence
<220> FEATURE:
<223> OTHER INFORMATION: Description of Artificial Sequence: Synthetic VH CDR3 peptide
<220> FEATURE:
<221> NAME/KEY: MOD_RES
<222> LOCATION: (3)..(3)
<223> OTHER INFORMATION: Asp, Thr or absent
<220> FEATURE:
<221> NAME/KEY: MOD_RES
<222> LOCATION: (4)..(4)
<223> OTHER INFORMATION: Asp, Gly or absent
<220> FEATURE:
<221> NAME/KEY: MOD_RES
<222> LOCATION: (5)..(5)
<223> OTHER INFORMATION: Phe, Thr or absent
<220> FEATURE:
<221> NAME/KEY: MOD_RES
<222> LOCATION: (6)..(6)
<223> OTHER INFORMATION: Pro, Arg, Trp, Tyr or absent
<220> FEATURE:
<221> NAME/KEY: MOD_RES
<222> LOCATION: (7)..(7)
<223> OTHER INFORMATION: Glu, Gly, Leu, Ser or absent
<220> FEATURE:
<221> NAME/KEY: MOD_RES
<222> LOCATION: (8)..(8)
<223> OTHER INFORMATION: Ala, Gly, Ser, Tyr or absent
<220> FEATURE:
<221> NAME/KEY: MOD_RES
<222> LOCATION: (9)..(9)
<223> OTHER INFORMATION: Ala, Glu, Gly, Gln or Ser
<220> FEATURE:
<221> NAME/KEY: MOD_RES
<222> LOCATION: (10)..(10)
<223> OTHER INFORMATION: Glu, Leu, Met, Pro, Ser or Thr
<220> FEATURE:
<221> NAME/KEY: MOD_RES
<222> LOCATION: (11)..(11)
<223> OTHER INFORMATION: Gly, His, Pro, Ser, Trp or absent
<220> FEATURE:
<221> NAME/KEY: MOD_RES
<222> LOCATION: (12)..(12)
<223> OTHER INFORMATION: Ala, Gly, Ile, Leu, Tyr or absent
<220> FEATURE:
<221> NAME/KEY: MOD_RES
<222> LOCATION: (13)..(13)
<223> OTHER INFORMATION: Ala, Ile, Val, Trp or absent
<220> FEATURE:
<221> NAME/KEY: MISC_FEATURE
<222> LOCATION: (14)..(16)
<223> OTHER INFORMATION: May or may not be present
<220> FEATURE:
<221> NAME/KEY: MOD_RES
<222> LOCATION: (17)..(17)
<223> OTHER INFORMATION: Trp, Tyr or absent
<220> FEATURE:
<221> NAME/KEY: MOD_RES
<222> LOCATION: (18)..(18)
<223> OTHER INFORMATION: Pro, Gly or absent
<220> FEATURE:
<221> NAME/KEY: MOD_RES
<222> LOCATION: (19)..(19)
<223> OTHER INFORMATION: Phe, Leu or Met
<220> FEATURE:
<221> NAME/KEY: MOD_RES
<222> LOCATION: (21)..(21)
<223> OTHER INFORMATION: Ile, Leu, Val or Tyr

<400> SEQUENCE: 267

Ala Arg Xaa Xaa Xaa Xaa Xaa Xaa Xaa Xaa Xaa Xaa Xaa His Tyr Tyr
1 5 10 15

Xaa Xaa Xaa Asp Xaa
20

<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic scFv G4s linker

<400> SEQUENCE: 268

Gly Gly Gly Gly Ser Gly Gly Gly Gly Ser Gly Gly Gly Gly Ser
1 5 10 15

<210> SEQ ID NO 269
<211> LENGTH: 288
<212> TYPE: DNA
<213> ORGANISM: Artificial Sequence
<220> FEATURE:
<223> OTHER INFORMATION: Description of Artificial Sequence: Synthetic CD8 DNA extracellular & transmembrane domain polynucleotide

<400> SEQUENCE: 269
gctgcagcat tgagcaactc aataatgtat tttagtcact ttgtaccagt gttcttgccg 60
gctaagccta ctaccacacc cgctccacgg ccacctaccc cagctcctac catcgcttca 120
cagcctctgt ccctgcgccc agaggcttgc cgaccggccg caggggggcgc tgttcatacc 180 agaggactgg atttcgcctg cgatatctat atctgggcac ccctggccgg aacctgcggc 240
gtactcctgc tgtccctggt catcacgctc tattgtaatc acaggaac 288

<210> SEQ ID NO 270
<211> LENGTH: 97
<212> TYPE: PRT
<213> ORGANISM: Artificial Sequence
<220> FEATURE:
<223> OTHER INFORMATION: Description of Artificial Sequence: Synthetic CD8 AA extracellular & transmembrane domain polypeptide

<400> SEQUENCE: 270

Ala Ala Ala Leu Ser Asn Ser Ile Met Tyr Phe Ser His Phe Val Pro
1 5 10 15

Arg Val Phe Leu Pro Ala Lys Pro Thr Thr Thr Pro Ala Pro Arg Pro
20 25 30

Pro Thr Pro Ala Pro Thr Ile Ala Ser Gln Pro Leu Ser Leu Arg Pro
35 40 45

Glu Ala Cys Arg Pro Ala Ala Gly Gly Ala Val His Thr Arg Gly Leu
50 55 60

Asp Phe Ala Cys Asp Ile Tyr Ile Trp Ala Pro Leu Ala Gly Thr Cys
65 70 75 80

Gly Val Leu Leu Leu Ser Leu Val Ile Thr Leu Tyr Cys Asn His Arg
85 90 95

Asn

<210> SEQ ID NO 271
<211> LENGTH: 354
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 271
gaggtgcagc tgttggagtc tgggggaggc ttggtacagc ctggggggtc cctgagactc 60
tcctgtgcag cctctggatt cacctttgac gactatgcca tggcatgggt ccgccaggct 120
ccagggaagg ggctggagtg ggtctcagct attagtgatg caggtgacag aacatactac 180
gcagactccg tgaggggccg gttcaccatc tccagagaca attccaagaa cacactgtat 240
ctgcaaatga acagcctgag agccgaggac acggcggtgt actactgcgc aagagccgag 300
atgggagccg tattcgacat atggggtcag ggtacaatgg tcaccgtctc ctca 354

<210> SEQ ID NO 272
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 272

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Asp Tyr
20 25 30

Ala Met Ala Trp Val Arg Gln Ala Pro Gly Lys Gly Leu Glu Trp Val
35 40 45

Ser Ala Ile Ser Asp Ala Gly Asp Arg Thr Tyr Tyr Ala Asp Ser Val
50 55 60

Arg Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ala Glu Met Gly Ala Val Phe Asp Ile Trp Gly Gln Gly Thr
100 105 110

Met Val Thr Val Ser Ser
115

<210> SEQ ID NO 273
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 273

Ser Cys Ala Ala Ser Gly Phe Thr Phe Asp Asp Tyr Ala Met Ala
1 5 10 15

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 274

Ala Ile Ser Asp Ala Gly Asp Arg Thr Tyr Tyr Ala Asp Ser Val Arg
1 5 10 15

Gly

<210> SEQ ID NO 275
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Ala Arg Ala Glu Met Gly Ala Val Phe Asp Ile
1 5 10

<210> SEQ ID NO 276
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 276
gaaattgtgt tgacacagtc tccagccacc ctgtctttgt ctccagggga aagagccacc 60
ctctcctgca gggccagtca gagtgttagc aggtacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag agaatctcct ggcctttcac ttttggcgga 300
gggaccaagg ttgagatcaa acgg 324

<210> SEQ ID NO 277
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 277

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Arg Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ile Ser Trp Pro Phe
85 90 95

Thr Phe Gly Gly Gly Thr Lys Val Glu Ile Lys Arg
100 105

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Arg Ala Ser Gln Ser Val Ser Arg Tyr Leu Ala
1 5 10

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

Asp Ala Ser Asn Arg Ala Thr
1 5

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Gln Gln Arg Ile Ser Trp Pro Phe Thr
1 5

<210> SEQ ID NO 281
<211> LENGTH: 1434
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281
atggcactcc ccgtaactgc tctgctgctg ccgttggcat tgctcctgca cgccgcacgc 60
ccggaggtgc agctgttgga gtctggggga ggcttggtac agcctggggg gtccctgaga 120
ctctcctgtg cagcctctgg attcaccttt gacgactatg ccatggcatg ggtccgccag 180
gctccaggga aggggctgga gtgggtctca gctattagtg atgcaggtga cagaacatac 240
tacgcagact ccgtgagggg ccggttcacc atctccagag acaattccaa gaacacactg 300
tatctgcaaa tgaacagcct gagagccgag gacacggcgg tgtactactg cgcaagagcc 360
gagatgggag ccgtattcga catatggggt cagggtacaa tggtcaccgt ctcctcaggg 420
tctacatccg gctccgggaa gcccggaagt ggcgaaggta gtacaaaggg ggaaattgtg 480
ttgacacagt ctccagccac cctgtctttg tctccagggg aaagagccac cctctcctgc 540
agggccagtc agagtgttag caggtactta gcctggtacc aacagaaacc tggccaggct 600
cccaggctcc tcatctatga tgcatccaac agggccactg gcatcccagc caggttcagt 660
ggcagtgggt ctgggacaga cttcactctc accatcagca gcctagagcc tgaagatttt 720
gcagtttatt actgtcagca gagaatctcc tggcctttca cttttggcgg agggaccaag 780
gttgagatca aacgggccgc tgcccttgat aatgaaaagt caaacggaac aatcattcac 840
gtgaagggca agcacctctg tccgtcaccc ttgttccctg gtccatccaa gccattctgg 900
gtgttggtcg tagtgggtgg agtcctcgct tgttactctc tgctcgtcac cgtggctttt 960

```
ataatcttct gggttagatc caaaagaagc cgcctgctcc atagcgatta catgaatatg   1020

actccacgcc gccctggccc cacaaggaaa cactaccagc cttacgcacc acctagagat   1080

ttcgctgcct atcggagcag ggtgaagttt tccagatctg cagatgcacc agcgtatcag   1140

cagggccaga accaactgta taacgagctc aacctgggac gcagggaaga gtatgacgtt   1200

ttggacaagc gcagaggacg ggaccctgag atgggtggca aaccaagacg aaaaaacccc   1260

caggagggtc tctataatga gctgcagaag gataagatgg ctgaagccta ttctgaaata   1320

ggcatgaaag gagagcggag aaggggaaaa gggcacgacg gtttgtacca gggactcagc   1380

actgctacga aggatactta tgacgctctc cacatgcaag ccctgccacc tagg         1434
```

```
<210> SEQ ID NO 282
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Asp Asp Tyr Ala Met Ala Trp Val Arg Gln Ala Pro Gly Lys
    50                  55                  60

Gly Leu Glu Trp Val Ser Ala Ile Ser Asp Ala Gly Asp Arg Thr Tyr
65                  70                  75                  80

Tyr Ala Asp Ser Val Arg Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ala Glu Met Gly Ala Val Phe Asp Ile
        115                 120                 125

Trp Gly Gln Gly Thr Met Val Thr Val Ser Ser Gly Ser Thr Ser Gly
    130                 135                 140

Ser Gly Lys Pro Gly Ser Gly Glu Gly Ser Thr Lys Gly Glu Ile Val
145                 150                 155                 160

Leu Thr Gln Ser Pro Ala Thr Leu Ser Leu Ser Pro Gly Glu Arg Ala
                165                 170                 175

Thr Leu Ser Cys Arg Ala Ser Gln Ser Val Ser Arg Tyr Leu Ala Trp
            180                 185                 190

Tyr Gln Gln Lys Pro Gly Gln Ala Pro Arg Leu Leu Ile Tyr Asp Ala
        195                 200                 205

Ser Asn Arg Ala Thr Gly Ile Pro Ala Arg Phe Ser Gly Ser Gly Ser
    210                 215                 220

Gly Thr Asp Phe Thr Leu Thr Ile Ser Ser Leu Glu Pro Glu Asp Phe
225                 230                 235                 240

Ala Val Tyr Tyr Cys Gln Gln Arg Ile Ser Trp Pro Phe Thr Phe Gly
                245                 250                 255

Gly Gly Thr Lys Val Glu Ile Lys Arg Ala Ala Ala Leu Asp Asn Glu
            260                 265                 270
```

Lys Ser Asn Gly Thr Ile Ile His Val Lys Gly Lys His Leu Cys Pro
275 280 285

Ser Pro Leu Phe Pro Gly Pro Ser Lys Pro Phe Trp Val Leu Val Val
290 295 300

Val Gly Gly Val Leu Ala Cys Tyr Ser Leu Leu Val Thr Val Ala Phe
305 310 315 320

Ile Ile Phe Trp Val Arg Ser Lys Arg Ser Arg Leu Leu His Ser Asp
325 330 335

Tyr Met Asn Met Thr Pro Arg Arg Pro Gly Pro Thr Arg Lys His Tyr
340 345 350

Gln Pro Tyr Ala Pro Pro Arg Asp Phe Ala Ala Tyr Arg Ser Arg Val
355 360 365

Lys Phe Ser Arg Ser Ala Asp Ala Pro Ala Tyr Gln Gln Gly Gln Asn
370 375 380

Gln Leu Tyr Asn Glu Leu Asn Leu Gly Arg Arg Glu Glu Tyr Asp Val
385 390 395 400

Leu Asp Lys Arg Arg Gly Arg Asp Pro Glu Met Gly Gly Lys Pro Arg
405 410 415

Arg Lys Asn Pro Gln Glu Gly Leu Tyr Asn Glu Leu Gln Lys Asp Lys
420 425 430

Met Ala Glu Ala Tyr Ser Glu Ile Gly Met Lys Gly Glu Arg Arg Arg
435 440 445

Gly Lys Gly His Asp Gly Leu Tyr Gln Gly Leu Ser Thr Ala Thr Lys
450 455 460

Asp Thr Tyr Asp Ala Leu His Met Gln Ala Leu Pro Pro Arg
465 470 475

<210> SEQ ID NO 283
<211> LENGTH: 1434
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 283
atggcactcc ccgtaactgc tctgctgctg ccgttggcat tgctcctgca cgccgcacgc 60
ccggaaattg tgttgacaca gtctccagcc accctgtctt tgtctccagg ggaaagagcc 120
accctctcct gcagggccag tcagagtgtt agcaggtact tagcctggta ccaacagaaa 180
cctggccagg ctcccaggct cctcatctat gatgcatcca acagggccac tggcatccca 240
gccaggttca gtggcagtgg gtctgggaca gacttcactc tcaccatcag cagcctagag 300
cctgaagatt ttgcagttta ttactgtcag cagagaatct cctggccttt cacttttggc 360
ggagggacca aggttgagat caaacggggg tctacatccg gctccgggaa gcccggaagt 420
ggcgaaggta gtacaaaggg ggaggtgcag ctgttggagt ctgggggagg cttggtacag 480
cctggggggt ccctgagact ctcctgtgca gcctctggat tcacctttga cgactatgcc 540
atggcatggg tccgccaggc tccagggaag gggctggagt gggtctcagc tattagtgat 600
gcaggtgaca gaacatacta cgcagactcc gtgaggggcc ggttcaccat ctccagagac 660
aattccaaga acacactgta tctgcaaatg aacagcctga gagccgagga cacggcggtg 720
tactactgcg caagagccga gatgggagcc gtattcgaca tatggggtca gggtacaatg 780
gtcaccgtct cctcagccgc tgcccttgat aatgaaaagt caaacggaac aatcattcac 840
gtgaagggca agcacctctg tccgtcaccc ttgttccctg gtccatccaa gccattctgg 900

```
gtgttggtcg tagtgggtgg agtcctcgct tgttactctc tgctcgtcac cgtggctttt    960

ataatcttct gggttagatc caaaagaagc cgcctgctcc atagcgatta catgaatatg   1020

actccacgcc gccctggccc cacaaggaaa cactaccagc cttacgcacc acctagagat   1080

ttcgctgcct atcggagcag ggtgaagttt tccagatctg cagatgcacc agcgtatcag   1140

cagggccaga accaactgta taacgagctc aacctgggac gcagggaaga gtatgacgtt   1200

ttggacaagc gcagaggacg ggaccctgag atgggtggca aaccaagacg aaaaaacccc   1260

caggagggtc tctataatga gctgcagaag gataagatgg ctgaagccta ttctgaaata   1320

ggcatgaaag gagagcggag aaggggaaaa gggcacgacg gtttgtacca gggactcagc   1380

actgctacga aggatactta tgacgctctc cacatgcaag ccctgccacc tagg         1434
```

```
<210> SEQ ID NO 284
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Arg Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

Ile Ser Trp Pro Phe Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Asp Asp Tyr Ala Met Ala Trp Val Arg Gln Ala Pro Gly Lys Gly Leu
            180                 185                 190

Glu Trp Val Ser Ala Ile Ser Asp Ala Gly Asp Arg Thr Tyr Tyr Ala
        195                 200                 205

Asp Ser Val Arg Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Arg Ala Glu Met Gly Ala Val Phe Asp Ile Trp Gly
                245                 250                 255

Gln Gly Thr Met Val Thr Val Ser Ser Ala Ala Ala Leu Asp Asn Glu
```

```
            260                 265                 270
Lys Ser Asn Gly Thr Ile Ile His Val Lys Gly Lys His Leu Cys Pro
            275                 280                 285

Ser Pro Leu Phe Pro Gly Pro Ser Lys Pro Phe Trp Val Leu Val Val
        290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
        355                 360                 365

Lys Phe Ser Arg Ser Ala Asp Ala Pro Ala Tyr Gln Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
        435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg
465                 470                 475

<210> SEQ ID NO 285
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 285

caggtgcagc tggtggagtc tgggggaggc gtggtccagc ctgggaggtc cctgagactc      60

tcctgtgcag cgtctggatt caccttcagt gagcatggca tgcactgggt ccgccaggct     120

ccaggcaagg ggctggagtg ggtggcagct atatcttatg atggaaggaa taaacactat     180

gcagactccg tgaagggccg attcaccatc tccagagaca attccaagaa cacgctgtat     240

ctgcaaatga acagcctgag agccgaggac acggcggtgt actactgcgc cagagacggt     300

acttatctag gtggtctctg gtacttcgac ttatggggga gaggtacctt ggtcaccgtc     360

tcctca                                                                366

<210> SEQ ID NO 286
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Glu His
            20                  25                  30

Gly Met His Trp Val Arg Gln Ala Pro Gly Lys Gly Leu Glu Trp Val
        35                  40                  45

Ala Ala Ile Ser Tyr Asp Gly Arg Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Tyr Leu Gly Gly Leu Trp Tyr Phe Asp Leu Trp
            100                 105                 110

Gly Arg Gly Thr Leu Val Thr Val Ser Ser
        115                 120
```

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

```
Phe Thr Phe Ser Glu His Gly Met His
1               5
```

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 288

```
Ala Ile Ser Tyr Asp Gly Arg Asn Lys His Tyr Ala Asp Ser Val Lys
1               5                   10                  15

Gly
```

<210> SEQ ID NO 289
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 289

```
Ala Arg Asp Gly Thr Tyr Leu Gly Gly Leu Trp Tyr Phe Asp Leu
1               5                   10                  15
```

<210> SEQ ID NO 290
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 290

```
gatattgtga tgactcagtc tccactctcc ctgcccgtca cccctggaga gccggcctcc     60
```

atctcctgca ggtctagtca gagcctcctg catagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcagggact cggcctccct 300
ctcacttttg gcggagggac caaggttgag atcaaacgg 339

<210> SEQ ID NO 291
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 291

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Leu Gly Leu Pro Leu Thr Phe Gly Gly Gly Thr Lys Val Glu Ile Lys
100 105 110

Arg

<210> SEQ ID NO 292
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 292

Arg Ser Ser Gln Ser Leu Leu His Ser Asn Gly Tyr Asn Tyr Leu Asp
1 5 10 15

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 293

Leu Gly Ser Asn Arg Ala Ser
1 5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 294

Met Gln Gly Leu Gly Leu Pro Leu Thr
1 5

<210> SEQ ID NO 295
<211> LENGTH: 1461
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 295
atggcactcc ccgtaactgc tctgctgctg ccgttggcat tgctcctgca cgccgcacgc 60
ccgcaggtgc agctggtgga gtctgggggga ggcgtggtcc agcctgggag gtccctgaga 120
ctctcctgtg cagcgtctgg attcaccttc agtgagcatg gcatgcactg ggtccgccag 180
gctccaggca aggggctgga gtgggtggca gctatatctt atgatggaag gaataaacac 240
tatgcagact ccgtgaaggg ccgattcacc atctccagag acaattccaa gaacacgctg 300
tatctgcaaa tgaacagcct gagagccgag gacacggcgg tgtactactg cgccagagac 360
ggtacttatc taggtggtct ctggtacttc gacttatggg ggagaggtac cttggtcacc 420
gtctcctcag ggtctacatc cggctccggg aagcccggaa gtggcgaagg tagtacaaag 480
ggggatattg tgatgactca gtctccactc tccctgcccg tcacccctgg agagccggcc 540
tccatctcct gcaggtctag tcagagcctc ctgcatagta atggatacaa ctatttggat 600
tggtacctgc agaagccagg gcagtctcca cagctcctga tctatttggg ttctaatcgg 660
gcctccgggg tccctgacag gttcagtggc agtggatcag gcacagattt tacactgaaa 720
atcagcagag tggaggctga ggatgttggg gtttattact gcatgcaggg actcggcctc 780
cctctcactt ttggcggagg gaccaaggtt gagatcaaac gggccgctgc ccttgataat 840
gaaaagtcaa acggaacaat cattcacgtg aagggcaagc acctctgtcc gtcacccttg 900
ttccctggtc catccaagcc attctgggtg ttggtcgtag tgggtggagt cctcgcttgt 960
tactctctgc tcgtcaccgt ggcttttata atcttctggg ttagatccaa aagaagccgc 1020
ctgctccata gcgattacat gaatatgact ccacgccgcc ctggccccac aaggaaacac 1080
taccagcctt acgcaccacc tagagatttc gctgcctatc ggagcagggt gaagttttcc 1140
agatctgcag atgcaccagc gtatcagcag ggccagaacc aactgtataa cgagctcaac 1200
ctgggacgca gggaagagta tgacgttttg gacaagcgca gaggacggga ccctgagatg 1260
ggtggcaaac caagacgaaa aaacccccag gagggtctct ataatgagct gcagaaggat 1320
aagatggctg aagcctattc tgaaataggc atgaaaggag agcggagaag gggaaaaggg 1380
cacgacggtt tgtaccaggg actcagcact gctacgaagg atacttatga cgctctccac 1440
atgcaagccc tgccacctag g 1461

<210> SEQ ID NO 296
<211> LENGTH: 487
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 296

-continued

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Glu His Gly Met His Trp Val Arg Gln Ala Pro Gly Lys
    50                  55                  60

Gly Leu Glu Trp Val Ala Ala Ile Ser Tyr Asp Gly Arg Asn Lys His
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Gly Thr Tyr Leu Gly Gly Leu Trp
        115                 120                 125

Tyr Phe Asp Leu Trp Gly Arg Gly Thr Leu Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Asp Ile Val Met Thr Gln Ser Pro Leu Ser Leu Pro Val Thr Pro
                165                 170                 175

Gly Glu Pro Ala Ser Ile Ser Cys Arg Ser Ser Gln Ser Leu Leu His
            180                 185                 190

Ser Asn Gly Tyr Asn Tyr Leu Asp Trp Tyr Leu Gln Lys Pro Gly Gln
        195                 200                 205

Ser Pro Gln Leu Leu Ile Tyr Leu Gly Ser Asn Arg Ala Ser Gly Val
    210                 215                 220

Pro Asp Arg Phe Ser Gly Ser Gly Ser Gly Thr Asp Phe Thr Leu Lys
225                 230                 235                 240

Ile Ser Arg Val Glu Ala Glu Asp Val Gly Val Tyr Tyr Cys Met Gln
                245                 250                 255

Gly Leu Gly Leu Pro Leu Thr Phe Gly Gly Gly Thr Lys Val Glu Ile
            260                 265                 270

Lys Arg Ala Ala Ala Leu Asp Asn Glu Lys Ser Asn Gly Thr Ile Ile
        275                 280                 285

His Val Lys Gly Lys His Leu Cys Pro Ser Pro Leu Phe Pro Gly Pro
    290                 295                 300

Ser Lys Pro Phe Trp Val Leu Val Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
```

```
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485


<210> SEQ ID NO 297
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297

atggcactcc ccgtaactgc tctgctgctg ccgttggcat tgctcctgca cgccgcacgc     60

ccggatattg tgatgactca gtctccactc tccctgcccg tcacccctgg agagccggcc    120

tccatctcct gcaggtctag tcagagcctc ctgcatagta atggatacaa ctatttggat    180

tggtacctgc agaagccagg gcagtctcca cagctcctga tctatttggg ttctaatcgg    240

gcctccgggg tccctgacag gttcagtggc agtggatcag gcacagattt tacactgaaa    300

atcagcagag tggaggctga ggatgttggg gtttattact gcatgcaggg actcggcctc    360

cctctcactt ttggcggagg gaccaaggtt gagatcaaac gggggtctac atccggctcc    420

gggaagcccg gaagtggcga aggtagtaca aaggggcagg tgcagctggt ggagtctggg    480

ggaggcgtgg tccagcctgg gaggtccctg agactctcct gtgcagcgtc tggattcacc    540

ttcagtgagc atggcatgca ctgggtccgc caggctccag gcaaggggct ggagtgggtg    600

gcagctatat cttatgatgg aaggaataaa cactatgcag actccgtgaa gggccgattc    660

accatctcca gagacaattc caagaacacg ctgtatctgc aaatgaacag cctgagagcc    720

gaggacacgg cggtgtacta ctgcgccaga gacggtactt atctaggtgg tctctggtac    780

ttcgacttat gggggagagg taccttggtc accgtctcct cagccgctgc ccttgataat    840

gaaaagtcaa acggaacaat cattcacgtg aagggcaagc acctctgtcc gtcacccttg    900

ttccctggtc catccaagcc attctgggtg ttggtcgtag tgggtggagt cctcgcttgt    960

tactctctgc tcgtcaccgt ggcttttata atcttctggg ttagatccaa aagaagccgc   1020

ctgctccata gcgattacat gaatatgact ccacgccgcc ctggccccac aaggaaacac   1080

taccagcctt acgcaccacc tagagatttc gctgcctatc ggagcagggt gaagttttcc   1140

agatctgcag atgcaccagc gtatcagcag ggccagaacc aactgtataa cgagctcaac   1200

ctgggacgca gggaagagta tgacgttttg gacaagcgca gaggacggga ccctgagatg   1260

ggtggcaaac caagacgaaa aaacccccag gagggtctct ataatgagct gcagaaggat   1320

aagatggctg aagcctattc tgaaataggc atgaaaggag agcggagaag gggaaaaggg   1380

cacgacggtt tgtaccaggg actcagcact gctacgaagg atacttatga cgctctccac   1440

atgcaagccc tgccacctag g                                              1461


<210> SEQ ID NO 298
<211> LENGTH: 487
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 298

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Leu His Ser Asn Gly Tyr Asn Tyr Leu Asp Trp Tyr Leu Gln
    50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Gly Leu Gly Leu Pro Leu Thr Phe Gly Gly Gly Thr
        115                 120                 125

Lys Val Glu Ile Lys Arg Gly Ser Thr Ser Gly Ser Gly Lys Pro Gly
    130                 135                 140

Ser Gly Glu Gly Ser Thr Lys Gly Gln Val Gln Leu Val Glu Ser Gly
145                 150                 155                 160

Gly Gly Val Val Gln Pro Gly Arg Ser Leu Arg Leu Ser Cys Ala Ala
                165                 170                 175

Ser Gly Phe Thr Phe Ser Glu His Gly Met His Trp Val Arg Gln Ala
            180                 185                 190

Pro Gly Lys Gly Leu Glu Trp Val Ala Ala Ile Ser Tyr Asp Gly Arg
        195                 200                 205

Asn Lys His Tyr Ala Asp Ser Val Lys Gly Arg Phe Thr Ile Ser Arg
    210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Asp Gly Thr Tyr Leu Gly
                245                 250                 255

Gly Leu Trp Tyr Phe Asp Leu Trp Gly Arg Gly Thr Leu Val Thr Val
            260                 265                 270

Ser Ser Ala Ala Ala Leu Asp Asn Glu Lys Ser Asn Gly Thr Ile Ile
        275                 280                 285

His Val Lys Gly Lys His Leu Cys Pro Ser Pro Leu Phe Pro Gly Pro
    290                 295                 300

Ser Lys Pro Phe Trp Val Leu Val Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380
```

```
Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485


<210> SEQ ID NO 299
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 299

caggtgcagc tggtgcagtc tggggctgag gtgaagaagc ctggggcctc agtgaaggtt      60

tcctgcaggg catctggata caccttcatg gagcactata tgcactgggt gcgacaggcc     120

cctggacaag ggcttgagtg gatgggagta atcgggccta gtggtggtaa gacaagctac     180

gcacagaagt tccagggcag agtcaccatg accagggaca cgtccacgag cacagtctac     240

atggagctga gcagcctgag atctgaggac acggcggtgt actactgcgc cagagagaat     300

tggccaatgg acgtatgggg ccagggaaca actgtcaccg tctcctca                  348


<210> SEQ ID NO 300
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Met Glu His
            20                  25                  30

Tyr Met His Trp Val Arg Gln Ala Pro Gly Gln Gly Leu Glu Trp Met
        35                  40                  45

Gly Val Ile Gly Pro Ser Gly Gly Lys Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
            100                 105                 110

Thr Val Ser Ser
        115
```

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 301

Tyr Thr Phe Met Glu His Tyr Met His
1 5

<210> SEQ ID NO 302
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 302

Val Ile Gly Pro Ser Gly Gly Lys Thr Ser Tyr Ala Gln Lys Phe Gln
1 5 10 15

Gly

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 303

Ala Arg Glu Ser Trp Pro Met Asp Val
1 5

<210> SEQ ID NO 304
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 304
gaaatagtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tacgccgcct accctacttt tggcggaggg 300
accaaggttg agatcaaacg g 321

<210> SEQ ID NO 305
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 305

Glu Ile Val Met Thr Gln Ser Pro Ala Thr Leu Ser Val Ser Pro Gly

-continued

```
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ala Ala Tyr Pro Thr
                85                  90                  95

Phe Gly Gly Gly Thr Lys Val Glu Ile Lys Arg
            100                 105


<210> SEQ ID NO 306
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Arg Ala Ser Gln Ser Val Ser Ser Asn Leu Ala
1               5                   10


<210> SEQ ID NO 307
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Ala Ser Thr Arg Ala Thr
1               5


<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gln Gln Tyr Ala Ala Tyr Pro Thr
1               5


<210> SEQ ID NO 309
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 309

atggcactcc ccgtaactgc tctgctgctg ccgttggcat tgctcctgca cgccgcacgc      60

ccgcaggtgc agctggtgca gtctggggct gaggtgaaga agcctggggc ctcagtgaag     120

gtttcctgca gggcatctgg atacaccttc atggagcact atatgcactg ggtgcgacag     180
```

-continued gcccctggac aagggcttga gtggatggga gtaatcgggc ctagtggtgg taagacaagc 240
tacgcacaga agttccaggg cagagtcacc atgaccaggg acacgtccac gagcacagtc 300
tacatggagc tgagcagcct gagatctgag gacacggcgg tgtactactg cgccagagag 360
aattggccaa tggacgtatg gggccaggga acaactgtca ccgtctcctc agggtctaca 420
tccggctccg ggaagcccgg aagtggcgaa ggtagtacaa agggggaaat agtgatgacg 480
cagtctccag ccaccctgtc tgtgtctcca ggggaaagag ccaccctctc ctgcagggcc 540
agtcagagtg ttagcagcaa cttagcctgg taccagcaga aacctggcca ggctcccagg 600
ctcctcatct atggtgcatc caccagggcc actggtatcc cagccaggtt cagtggcagt 660
gggtctggga cagagttcac tctcaccatc agcagcctgc agtctgaaga ttttgcagtt 720
tattactgtc agcagtacgc cgcctaccct acttttggcg gagggaccaa ggttgagatc 780
aaacgggccg ctgcccttga taatgaaaag tcaaacggaa caatcattca cgtgaagggc 840
aagcacctct gtccgtcacc cttgttccct ggtccatcca agccattctg ggtgttggtc 900
gtagtgggtg gagtcctcgc ttgttactct ctgctcgtca ccgtggcttt tataatcttc 960
tgggttagat ccaaaagaag ccgcctgctc catagcgatt acatgaatat gactccacgc 1020
cgccctggcc ccacaaggaa acactaccag ccttacgcac cacctagaga tttcgctgcc 1080
tatcggagca gggtgaagtt ttccagatct gcagatgcac cagcgtatca gcagggccag 1140
aaccaactgt ataacgagct caacctggga cgcagggaag agtatgacgt tttggacaag 1200
cgcagaggac gggaccctga gatgggtggc aaaccaagac gaaaaaaccc ccaggagggt 1260
ctctataatg agctgcagaa ggataagatg gctgaagcct attctgaaat aggcatgaaa 1320
ggagagcgga gaaggggaaa agggcacgac ggtttgtacc agggactcag cactgctacg 1380
aaggatactt atgacgctct ccacatgcaa gccctgccac ctagg 1425

<210> SEQ ID NO 310
<211> LENGTH: 475
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 310

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Lys Pro Gly Ala Ser Val Lys Val Ser Cys Arg Ala Ser Gly Tyr
35 40 45

Thr Phe Met Glu His Tyr Met His Trp Val Arg Gln Ala Pro Gly Gln
50 55 60

Gly Leu Glu Trp Met Gly Val Ile Gly Pro Ser Gly Gly Lys Thr Ser
65 70 75 80

Tyr Ala Gln Lys Phe Gln Gly Arg Val Thr Met Thr Arg Asp Thr Ser
85 90 95

Thr Ser Thr Val Tyr Met Glu Leu Ser Ser Leu Arg Ser Glu Asp Thr
100 105 110

Ala Val Tyr Tyr Cys Ala Arg Glu Ser Trp Pro Met Asp Val Trp Gly
115 120 125

Gln Gly Thr Thr Val Thr Val Ser Ser Gly Ser Thr Ser Gly Ser Gly
130 135 140

```
Lys Pro Gly Ser Gly Glu Gly Ser Thr Lys Gly Glu Ile Val Met Thr
145                 150                 155                 160

Gln Ser Pro Ala Thr Leu Ser Val Ser Pro Gly Glu Arg Ala Thr Leu
                165                 170                 175

Ser Cys Arg Ala Ser Gln Ser Val Ser Ser Asn Leu Ala Trp Tyr Gln
            180                 185                 190

Gln Lys Pro Gly Gln Ala Pro Arg Leu Leu Ile Tyr Gly Ala Ser Thr
        195                 200                 205

Arg Ala Thr Gly Ile Pro Ala Arg Phe Ser Gly Ser Gly Ser Gly Thr
    210                 215                 220

Glu Phe Thr Leu Thr Ile Ser Ser Leu Gln Ser Glu Asp Phe Ala Val
225                 230                 235                 240

Tyr Tyr Cys Gln Gln Tyr Ala Ala Tyr Pro Thr Phe Gly Gly Gly Thr
                245                 250                 255

Lys Val Glu Ile Lys Arg Ala Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475
```

<210> SEQ ID NO 311
<211> LENGTH: 1425
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 311

```
atggcactcc ccgtaactgc tctgctgctg ccgttggcat tgctcctgca cgccgcacgc      60

ccggaaatag tgatgacgca gtctccagcc accctgtctg tgtctccagg ggaaagagcc     120
```

-continued

```
accctctcct gcagggccag tcagagtgtt agcagcaact tagcctggta ccagcagaaa    180

cctggccagg ctcccaggct cctcatctat ggtgcatcca ccagggccac tggtatccca    240

gccaggttca gtggcagtgg gtctgggaca gagttcactc tcaccatcag cagcctgcag    300

tctgaagatt ttgcagttta ttactgtcag cagtacgccg cctaccctac ttttggcgga    360

gggaccaagg ttgagatcaa acgggggtct acatccggct ccgggaagcc cggaagtggc    420

gaaggtagta caaaggggca ggtgcagctg gtgcagtctg gggctgaggt gaagaagcct    480

ggggcctcag tgaaggtttc ctgcagggca tctggataca ccttcatgga gcactatatg    540

cactgggtgc gacaggcccc tggacaaggg cttgagtgga tgggagtaat cgggcctagt    600

ggtggtaaga caagctacgc acagaagttc cagggcagag tcaccatgac cagggacacg    660

tccacgagca cagtctacat ggagctgagc agcctgagat ctgaggacac ggcggtgtac    720

tactgcgcca gagagaattg gccaatggac gtatggggcc agggaacaac tgtcaccgtc    780

tcctcagccg ctgcccttga taatgaaaag tcaaacggaa caatcattca cgtgaagggc    840

aagcacctct gtccgtcacc cttgttccct ggtccatcca agccattctg ggtgttggtc    900

gtagtgggtg gagtcctcgc ttgttactct ctgctcgtca ccgtggcttt tataatcttc    960

tgggttagat ccaaaagaag ccgcctgctc catagcgatt acatgaatat gactccacgc   1020

cgccctggcc ccacaaggaa acactaccag ccttacgcac cacctagaga tttcgctgcc   1080

tatcggagca gggtgaagtt ttccagatct gcagatgcac cagcgtatca gcagggccag   1140

aaccaactgt ataacgagct caacctggga cgcagggaag agtatgacgt tttggacaag   1200

cgcagaggac gggaccctga gatgggtggc aaaccaagac gaaaaaaccc ccaggagggt   1260

ctctataatg agctgcagaa ggataagatg gctgaagcct attctgaaat aggcatgaaa   1320

ggagagcgga gaaggggaaa agggcacgac ggtttgtacc agggactcag cactgctacg   1380

aaggatactt atgacgctct ccacatgcaa gccctgccac ctagg                   1425
```

<210> SEQ ID NO 312
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Ala Ala Tyr Pro Thr Phe Gly Gly Gly Thr Lys Val Glu Ile Lys Arg
        115                 120                 125
```

```
Gly Ser Thr Ser Gly Ser Gly Lys Pro Gly Ser Gly Glu Gly Ser Thr
    130                 135                 140

Lys Gly Gln Val Gln Leu Val Gln Ser Gly Ala Glu Val Lys Lys Pro
145                 150                 155                 160

Gly Ala Ser Val Lys Val Ser Cys Arg Ala Ser Gly Tyr Thr Phe Met
                165                 170                 175

Glu His Tyr Met His Trp Val Arg Gln Ala Pro Gly Gln Gly Leu Glu
            180                 185                 190

Trp Met Gly Val Ile Gly Pro Ser Gly Gly Lys Thr Ser Tyr Ala Gln
        195                 200                 205

Lys Phe Gln Gly Arg Val Thr Met Thr Arg Asp Thr Ser Thr Ser Thr
    210                 215                 220

Val Tyr Met Glu Leu Ser Ser Leu Arg Ser Glu Asp Thr Ala Val Tyr
225                 230                 235                 240

Tyr Cys Ala Arg Glu Ser Trp Pro Met Asp Val Trp Gly Gln Gly Thr
                245                 250                 255

Thr Val Thr Val Ser Ser Ala Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475
```

<210> SEQ ID NO 313
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 313
caggtgcagc tggtgcagtc tggggctgag gtgaagaagc ctggggcctc agtgaaggtt 60

-continued

```
tcctgcaagg catctggata caccttcacg gagcactata tgcactgggt gcgacaggcc    120

cctggacaaa ggcttgagtg gatgggagta atcgggccta gtggtggtaa gacaagctac    180

gcacagaagt tccagggcag agtcaccatg accagggaca cgtccacgag cacagtctac    240

atggagctga gcagcctgag atctgaggac acggcggtgt actactgcgc cagagagagt    300

tggccaatgg acgtatgggg ccagggaaca actgtcaccg tctcctca                 348
```

```
<210> SEQ ID NO 314
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Tyr Met His Trp Val Arg Gln Ala Pro Gly Gln Arg Leu Glu Trp Met
        35                  40                  45

Gly Val Ile Gly Pro Ser Gly Gly Lys Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
            100                 105                 110

Thr Val Ser Ser
        115


<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Tyr Thr Phe Thr Glu His Tyr Met His
1               5


<210> SEQ ID NO 316
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Val Ile Gly Pro Ser Gly Gly Lys Thr Ser Tyr Ala Gln Lys Phe Gln
1               5                   10                  15

Gly


<210> SEQ ID NO 317
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 317

```
Ala Arg Glu Ser Trp Pro Met Asp Val
1               5
```

<210> SEQ ID NO 318
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 318

```
gaaatagtga tgacgcagtc tccagccacc ctgtctgtgt ctccagggga aagagccacc      60

ctctcctgca gggccagtca gagtgttagc agcaacttag cctggtacca gcagaaacct     120

ggccaggctc ccaggctcct catctatggt gcatccacca gggccactgg tatcccagcc     180

aggttcagtg gcagtgggtc tgggacagag ttcactctca ccatcagcag cctgcagtct     240

gaagattttg cagtttatta ctgtcagcag tacgccgcct accctacttt tggcggaggg     300

accaaggttg agatcaaacg g                                               321
```

<210> SEQ ID NO 319
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ala Ala Tyr Pro Thr
                85                  90                  95

Phe Gly Gly Gly Thr Lys Val Glu Ile Lys Arg
            100                 105
```

<210> SEQ ID NO 320
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

```
Arg Ala Ser Gln Ser Val Ser Ser Asn Leu Ala
1               5                   10
```

<210> SEQ ID NO 321
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 321

Gly Ala Ser Thr Arg Ala Thr
1 5

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 322

Gln Gln Tyr Ala Ala Tyr Pro Thr
1 5

<210> SEQ ID NO 323
<211> LENGTH: 1425
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 323
atggcactcc ccgtaactgc tctgctgctg ccgttggcat tgctcctgca cgccgcacgc 60
ccgcaggtgc agctggtgca gtctggggct gaggtgaaga agcctggggc ctcagtgaag 120
gtttcctgca aggcatctgg atacaccttc acggagcact atatgcactg ggtgcgacag 180
gcccctggac aaaggcttga gtggatggga gtaatcgggc ctagtggtgg taagacaagc 240
tacgcacaga agttccaggg cagagtcacc atgaccaggg acacgtccac gagcacagtc 300
tacatggagc tgagcagcct gagatctgag gacacggcgg tgtactactg cgccagagag 360
agttggccaa tggacgtatg gggccaggga acaactgtca ccgtctcctc agggtctaca 420
tccggctccg ggaagcccgg aagtggcgaa ggtagtacaa agggggaaat agtgatgacg 480
cagtctccag ccaccctgtc tgtgtctcca ggggaaagag ccaccctctc ctgcagggcc 540
agtcagagtg ttagcagcaa cttagcctgg taccagcaga aacctggcca ggctcccagg 600
ctcctcatct atggtgcatc caccagggcc actggtatcc cagccaggtt cagtggcagt 660
gggtctggga cagagttcac tctcaccatc agcagcctgc agtctgaaga ttttgcagtt 720
tattactgtc agcagtacgc cgcctaccct acttttggcg gagggaccaa ggttgagatc 780
aaacgggccg ctgcccttga taatgaaaag tcaaacggaa caatcattca cgtgaagggc 840
aagcacctct gtccgtcacc cttgttccct ggtccatcca agccattctg ggtgttggtc 900
gtagtgggtg gagtcctcgc ttgttactct ctgctcgtca ccgtggcttt tataatcttc 960
tgggttagat ccaaaagaag ccgcctgctc catagcgatt acatgaatat gactccacgc 1020
cgccctggcc ccacaaggaa acactaccag ccttacgcac cacctagaga tttcgctgcc 1080
tatcggagca gggtgaagtt ttccagatct gcagatgcac cagcgtatca gcagggccag 1140
aaccaactgt ataacgagct caacctggga cgcagggaag agtatgacgt tttggacaag 1200

```
cgcagaggac gggaccctga gatgggtggc aaaccaagac gaaaaaaccc ccaggagggt   1260

ctctataatg agctgcagaa ggataagatg gctgaagcct attctgaaat aggcatgaaa   1320

ggagagcgga gaaggggaaa agggcacgac ggtttgtacc agggactcag cactgctacg   1380

aaggatactt atgacgctct ccacatgcaa gccctgccac ctagg                   1425


<210> SEQ ID NO 324
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Glu His Tyr Met His Trp Val Arg Gln Ala Pro Gly Gln
    50                  55                  60

Arg Leu Glu Trp Met Gly Val Ile Gly Pro Ser Gly Gly Lys Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Glu Ser Trp Pro Met Asp Val Trp Gly
        115                 120                 125

Gln Gly Thr Thr Val Thr Val Ser Ser Gly Ser Thr Ser Gly Ser Gly
    130                 135                 140

Lys Pro Gly Ser Gly Glu Gly Ser Thr Lys Gly Glu Ile Val Met Thr
145                 150                 155                 160

Gln Ser Pro Ala Thr Leu Ser Val Ser Pro Gly Glu Arg Ala Thr Leu
                165                 170                 175

Ser Cys Arg Ala Ser Gln Ser Val Ser Ser Asn Leu Ala Trp Tyr Gln
            180                 185                 190

Gln Lys Pro Gly Gln Ala Pro Arg Leu Leu Ile Tyr Gly Ala Ser Thr
        195                 200                 205

Arg Ala Thr Gly Ile Pro Ala Arg Phe Ser Gly Ser Gly Ser Gly Thr
    210                 215                 220

Glu Phe Thr Leu Thr Ile Ser Ser Leu Gln Ser Glu Asp Phe Ala Val
225                 230                 235                 240

Tyr Tyr Cys Gln Gln Tyr Ala Ala Tyr Pro Thr Phe Gly Gly Gly Thr
                245                 250                 255

Lys Val Glu Ile Lys Arg Ala Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
305                 310                 315                 320
```

-continued

```
Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475
```

```
<210> SEQ ID NO 325
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 325

atggcactcc ccgtaactgc tctgctgctg ccgttggcat tgctcctgca cgccgcacgc     60

ccggaaatag tgatgacgca gtctccagcc accctgtctg tgtctccagg ggaaagagcc    120

accctctcct gcagggccag tcagagtgtt agcagcaact tagcctggta ccagcagaaa    180

cctggccagg ctcccaggct cctcatctat ggtgcatcca ccagggccac tggtatccca    240

gccaggttca gtggcagtgg gtctgggaca gagttcactc tcaccatcag cagcctgcag    300

tctgaagatt ttgcagttta ttactgtcag cagtacgccg cctaccctac ttttggcgga    360

gggaccaagg ttgagatcaa acgggggtct acatccggct ccgggaagcc cggaagtggc    420

gaaggtagta caaaggggca ggtgcagctg gtgcagtctg gggctgaggt gaagaagcct    480

ggggcctcag tgaaggtttc ctgcaaggca tctggataca ccttcacgga gcactatatg    540

cactgggtgc gacaggcccc tggacaaagg cttgagtgga tgggagtaat cgggcctagt    600

ggtggtaaga caagctacgc acagaagttc cagggcagag tcaccatgac cagggacacg    660

tccacgagca cagtctacat ggagctgagc agcctgagat ctgaggacac ggcggtgtac    720

tactgcgcca gagagagttg gccaatggac gtatggggcc agggaacaac tgtcaccgtc    780

tcctcagccg ctgcccttga taatgaaaag tcaaacggaa caatcattca cgtgaagggc    840

aagcacctct gtccgtcacc cttgttccct ggtccatcca agccattctg ggtgttggtc    900

gtagtgggtg gagtcctcgc ttgttactct ctgctcgtca ccgtggcttt tataatcttc    960

tgggttagat ccaaaagaag ccgcctgctc catagcgatt acatgaatat gactccacgc   1020

cgccctggcc ccacaaggaa acactaccag ccttacgcac cacctagaga tttcgctgcc   1080

tatcggagca gggtgaagtt ttccagatct gcagatgcac cagcgtatca gcagggccag   1140
```

-continued

```
aaccaactgt ataacgagct caacctggga cgcagggaag agtatgacgt tttggacaag   1200

cgcagaggac gggaccctga gatgggtggc aaaccaagac gaaaaaaccc ccaggagggt   1260

ctctataatg agctgcagaa ggataagatg gctgaagcct attctgaaat aggcatgaaa   1320

ggagagcgga gaaggggaaa agggcacgac ggtttgtacc agggactcag cactgctacg   1380

aaggatactt atgacgctct ccacatgcaa gccctgccac ctagg                   1425
```

<210> SEQ ID NO 326
<211> LENGTH: 475
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 326

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Ala Ala Tyr Pro Thr Phe Gly Gly Gly Thr Lys Val Glu Ile Lys Arg
        115                 120                 125

Gly Ser Thr Ser Gly Ser Gly Lys Pro Gly Ser Gly Glu Gly Ser Thr
    130                 135                 140

Lys Gly Gln Val Gln Leu Val Gln Ser Gly Ala Glu Val Lys Lys Pro
145                 150                 155                 160

Gly Ala Ser Val Lys Val Ser Cys Lys Ala Ser Gly Tyr Thr Phe Thr
                165                 170                 175

Glu His Tyr Met His Trp Val Arg Gln Ala Pro Gly Gln Arg Leu Glu
            180                 185                 190

Trp Met Gly Val Ile Gly Pro Ser Gly Gly Lys Thr Ser Tyr Ala Gln
        195                 200                 205

Lys Phe Gln Gly Arg Val Thr Met Thr Arg Asp Thr Ser Thr Ser Thr
    210                 215                 220

Val Tyr Met Glu Leu Ser Ser Leu Arg Ser Glu Asp Thr Ala Val Tyr
225                 230                 235                 240

Tyr Cys Ala Arg Glu Ser Trp Pro Met Asp Val Trp Gly Gln Gly Thr
                245                 250                 255

Thr Val Thr Val Ser Ser Ala Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
```

305 310 315 320

Trp Val Arg Ser Lys Arg Ser Arg Leu Leu His Ser Asp Tyr Met Asn
325 330 335

Met Thr Pro Arg Arg Pro Gly Pro Thr Arg Lys His Tyr Gln Pro Tyr
340 345 350

Ala Pro Pro Arg Asp Phe Ala Ala Tyr Arg Ser Arg Val Lys Phe Ser
355 360 365

Arg Ser Ala Asp Ala Pro Ala Tyr Gln Gln Gly Gln Asn Gln Leu Tyr
370 375 380

Asn Glu Leu Asn Leu Gly Arg Arg Glu Glu Tyr Asp Val Leu Asp Lys
385 390 395 400

Arg Arg Gly Arg Asp Pro Glu Met Gly Gly Lys Pro Arg Arg Lys Asn
405 410 415

Pro Gln Glu Gly Leu Tyr Asn Glu Leu Gln Lys Asp Lys Met Ala Glu
420 425 430

Ala Tyr Ser Glu Ile Gly Met Lys Gly Glu Arg Arg Arg Gly Lys Gly
435 440 445

His Asp Gly Leu Tyr Gln Gly Leu Ser Thr Ala Thr Lys Asp Thr Tyr
450 455 460

Asp Ala Leu His Met Gln Ala Leu Pro Pro Arg
465 470 475

<210> SEQ ID NO 327
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 327
caggtgcagc tgcaggagtc gggcccagga ctggtgaagc cttcacagac cctgtccctc 60
acctgtactg tctctggtgg ctccatcggg agtggtggta gttactggag ctggatccgc 120
cagcacccag ggaagggcct ggagtggatt gggttgatct attacgatgg gagcacctac 180
tacaacccgt ccctcaagag tcgagttacc atatcagtag acacgtctaa gaaccagttc 240
tccctgaagc tgagttctgt gaccgccgca gacacggcgg tgtactactg cgccagaggc 300
aggggatatg agacttcttt agccttcgat atctggggtc agggtacaat ggtcaccgtc 360
tcctca 366

<210> SEQ ID NO 328
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 328

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Gly Ser Gly
20 25 30

Gly Ser Tyr Trp Ser Trp Ile Arg Gln His Pro Gly Lys Gly Leu Glu
35 40 45

Trp Ile Gly Leu Ile Tyr Tyr Asp Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Gly Arg Gly Tyr Glu Thr Ser Leu Ala Phe Asp Ile Trp
100 105 110

Gly Gln Gly Thr Met Val Thr Val Ser Ser
115 120

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 329

Gly Ser Ile Gly Ser Gly Gly Ser Tyr Trp Ser
1 5 10

<210> SEQ ID NO 330
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 330

Leu Ile Tyr Tyr Asp Gly Ser Thr Tyr Tyr Asn Pro Ser Leu Lys Ser
1 5 10 15

<210> SEQ ID NO 331
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 331

Ala Arg Gly Arg Gly Tyr Glu Thr Ser Leu Ala Phe Asp Ile
1 5 10

<210> SEQ ID NO 332
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 332
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag agacacgtct ggcctcctac ttttggcgga 300
gggaccaagg ttgagatcaa acgg 324

<210> SEQ ID NO 333
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 333

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg His Val Trp Pro Pro
                85                  90                  95

Thr Phe Gly Gly Gly Thr Lys Val Glu Ile Lys Arg
            100                 105
```

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 334

```
Arg Ala Ser Gln Ser Val Ser Ser Tyr Leu Ala
1               5                   10
```

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 335

```
Asp Ala Ser Asn Arg Ala Thr
1               5
```

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 336

```
Gln Gln Arg His Val Trp Pro Pro Thr
1               5
```

<210> SEQ ID NO 337
<211> LENGTH: 1446
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 337
atggcactcc ccgtaactgc tctgctgctg ccgttggcat tgctcctgca cgccgcacgc 60
ccgcaggtgc agctgcagga gtcgggccca ggactggtga agccttcaca gaccctgtcc 120
ctcacctgta ctgtctctgg tggctccatc gggagtggtg gtagttactg gagctggatc 180
cgccagcacc cagggaaggg cctggagtgg attgggttga tctattacga tgggagcacc 240
tactacaacc cgtccctcaa gagtcgagtt accatatcag tagacacgtc taagaaccag 300
ttctccctga agctgagttc tgtgaccgcc gcagacacgg cggtgtacta ctgcgccaga 360
ggcaggggat atgagacttc tttagccttc gatatctggg gtcagggtac aatggtcacc 420
gtctcctcag ggtctacatc cggctccggg aagcccggaa gtggcgaagg tagtacaaag 480
ggggaaattg tgttgacaca gtctccagcc accctgtctt tgtctccagg ggaaagagcc 540
accctctcct gcagggccag tcagagtgtt agcagctact tagcctggta ccaacagaaa 600
cctggccagg ctcccaggct cctcatctat gatgcatcca acagggccac tggcatccca 660
gccaggttca gtggcagtgg gtctgggaca gacttcactc tcaccatcag cagcctagag 720
cctgaagatt ttgcagttta ttactgtcag cagagacacg tctggcctcc tacttttggc 780
ggagggacca aggttgagat caaacgggcc gctgcccttg ataatgaaaa gtcaaacgga 840
acaatcattc acgtgaaggg caagcacctc tgtccgtcac ccttgttccc tggtccatcc 900
aagccattct gggtgttggt cgtagtgggt ggagtcctcg cttgttactc tctgctcgtc 960
accgtggctt ttataatctt ctgggttaga tccaaaagaa gccgcctgct ccatagcgat 1020
tacatgaata tgactccacg ccgccctggc cccacaagga aacactacca gccttacgca 1080
ccacctagag atttcgctgc ctatcggagc agggtgaagt tttccagatc tgcagatgca 1140
ccagcgtatc agcagggcca gaaccaactg tataacgagc tcaacctggg acgcagggaa 1200
gagtatgacg ttttggacaa gcgcagagga cgggaccctg agatgggtgg caaaccaaga 1260
cgaaaaaacc cccaggaggg tctctataat gagctgcaga aggataagat ggctgaagcc 1320
tattctgaaa taggcatgaa aggagagcgg agaaggggaa aagggcacga cggtttgtac 1380
cagggactca gcactgctac gaaggatact tatgacgctc tccacatgca agccctgcca 1440
cctagg 1446

<210> SEQ ID NO 338
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Gly
        35                  40                  45

Ser Ile Gly Ser Gly Gly Ser Tyr Trp Ser Trp Ile Arg Gln His Pro
    50                  55                  60

Gly Lys Gly Leu Glu Trp Ile Gly Leu Ile Tyr Tyr Asp Gly Ser Thr

-continued 65 70 75 80

Tyr Tyr Asn Pro Ser Leu Lys Ser Arg Val Thr Ile Ser Val Asp Thr
85 90 95

Ser Lys Asn Gln Phe Ser Leu Lys Leu Ser Ser Val Thr Ala Ala Asp
100 105 110

Thr Ala Val Tyr Tyr Cys Ala Arg Gly Arg Gly Tyr Glu Thr Ser Leu
115 120 125

Ala Phe Asp Ile Trp Gly Gln Gly Thr Met Val Thr Val Ser Ser Gly
130 135 140

Ser Thr Ser Gly Ser Gly Lys Pro Gly Ser Gly Glu Gly Ser Thr Lys
145 150 155 160

Gly Glu Ile Val Leu Thr Gln Ser Pro Ala Thr Leu Ser Leu Ser Pro
165 170 175

Gly Glu Arg Ala Thr Leu Ser Cys Arg Ala Ser Gln Ser Val Ser Ser
180 185 190

Tyr Leu Ala Trp Tyr Gln Gln Lys Pro Gly Gln Ala Pro Arg Leu Leu
195 200 205

Ile Tyr Asp Ala Ser Asn Arg Ala Thr Gly Ile Pro Ala Arg Phe Ser
210 215 220

Gly Ser Gly Ser Gly Thr Asp Phe Thr Leu Thr Ile Ser Ser Leu Glu
225 230 235 240

Pro Glu Asp Phe Ala Val Tyr Tyr Cys Gln Gln Arg His Val Trp Pro
245 250 255

Pro Thr Phe Gly Gly Gly Thr Lys Val Glu Ile Lys Arg Ala Ala Ala
260 265 270

Leu Asp Asn Glu Lys Ser Asn Gly Thr Ile Ile His Val Lys Gly Lys
275 280 285

His Leu Cys Pro Ser Pro Leu Phe Pro Gly Pro Ser Lys Pro Phe Trp
290 295 300

Val Leu Val Val Val Gly Gly Val Leu Ala Cys Tyr Ser Leu Leu Val
305 310 315 320

Thr Val Ala Phe Ile Ile Phe Trp Val Arg Ser Lys Arg Ser Arg Leu
325 330 335

Leu His Ser Asp Tyr Met Asn Met Thr Pro Arg Arg Pro Gly Pro Thr
340 345 350

Arg Lys His Tyr Gln Pro Tyr Ala Pro Pro Arg Asp Phe Ala Ala Tyr
355 360 365

Arg Ser Arg Val Lys Phe Ser Arg Ser Ala Asp Ala Pro Ala Tyr Gln
370 375 380

Gln Gly Gln Asn Gln Leu Tyr Asn Glu Leu Asn Leu Gly Arg Arg Glu
385 390 395 400

Glu Tyr Asp Val Leu Asp Lys Arg Arg Gly Arg Asp Pro Glu Met Gly
405 410 415

Gly Lys Pro Arg Arg Lys Asn Pro Gln Glu Gly Leu Tyr Asn Glu Leu
420 425 430

Gln Lys Asp Lys Met Ala Glu Ala Tyr Ser Glu Ile Gly Met Lys Gly
435 440 445

Glu Arg Arg Arg Gly Lys Gly His Asp Gly Leu Tyr Gln Gly Leu Ser
450 455 460

Thr Ala Thr Lys Asp Thr Tyr Asp Ala Leu His Met Gln Ala Leu Pro
465 470 475 480

Pro Arg

<210> SEQ ID NO 339
<211> LENGTH: 1446
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 339

```
atggcactcc ccgtaactgc tctgctgctg ccgttggcat tgctcctgca cgccgcacgc     60
ccggaaattg tgttgacaca gtctccagcc accctgtctt tgtctccagg ggaaagagcc    120
accctctcct gcagggccag tcagagtgtt agcagctact tagcctggta ccaacagaaa    180
cctggccagg ctcccaggct cctcatctat gatgcatcca acagggccac tggcatccca    240
gccaggttca gtggcagtgg gtctgggaca gacttcactc tcaccatcag cagcctagag    300
cctgaagatt ttgcagttta ttactgtcag cagagacacg tctggcctcc tacttttggc    360
ggagggacca aggttgagat caaacggggg tctacatccg gctccgggaa gcccggaagt    420
ggcgaaggta gtacaaaggg gcaggtgcag ctgcaggagt cgggcccagg actggtgaag    480
ccttcacaga ccctgtccct cacctgtact gtctctggtg gctccatcgg gagtggtggt    540
agttactgga gctggatccg ccagcaccca gggaagggcc tggagtggat tgggttgatc    600
tattacgatg ggagcaccta ctacaacccg tccctcaaga gtcgagttac catatcagta    660
gacacgtcta agaaccagtt ctccctgaag ctgagttctg tgaccgccgc agacacggcg    720
gtgtactact gcgccagagg caggggatat gagacttctt tagccttcga tatctggggt    780
cagggtacaa tggtcaccgt ctcctcagcc gctgcccttg ataatgaaaa gtcaaacgga    840
acaatcattc acgtgaaggg caagcacctc tgtccgtcac ccttgttccc tggtccatcc    900
aagccattct gggtgttggt cgtagtgggt ggagtcctcg cttgttactc tctgctcgtc    960
accgtggctt ttataatctt ctgggttaga tccaaaagaa gccgcctgct ccatagcgat   1020
tacatgaata tgactccacg ccgccctggc cccacaagga aacactacca gccttacgca   1080
ccacctagag atttcgctgc ctatcggagc agggtgaagt tttccagatc tgcagatgca   1140
ccagcgtatc agcagggcca gaaccaactg tataacgagc tcaacctggg acgcagggaa   1200
gagtatgacg ttttggacaa gcgcagagga cgggaccctg agatgggtgg caaaccaaga   1260
cgaaaaaacc cccaggaggg tctctataat gagctgcaga aggataagat ggctgaagcc   1320
tattctgaaa taggcatgaa aggagagcgg agaaggggaa aagggcacga cggtttgtac   1380
cagggactca gcactgctac gaaggatact tatgacgctc tccacatgca agccctgcca   1440
cctagg                                                              1446
```

<210> SEQ ID NO 340
<211> LENGTH: 482
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 340

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
```

-continued

```
        35                  40                  45

Ser Val Ser Ser Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

His Val Trp Pro Pro Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Gln Glu Ser Gly Pro Gly Leu Val Lys
145                 150                 155                 160

Pro Ser Gln Thr Leu Ser Leu Thr Cys Thr Val Ser Gly Gly Ser Ile
                165                 170                 175

Gly Ser Gly Gly Ser Tyr Trp Ser Trp Ile Arg Gln His Pro Gly Lys
            180                 185                 190

Gly Leu Glu Trp Ile Gly Leu Ile Tyr Tyr Asp Gly Ser Thr Tyr Tyr
        195                 200                 205

Asn Pro Ser Leu Lys Ser Arg Val Thr Ile Ser Val Asp Thr Ser Lys
    210                 215                 220

Asn Gln Phe Ser Leu Lys Leu Ser Ser Val Thr Ala Ala Asp Thr Ala
225                 230                 235                 240

Val Tyr Tyr Cys Ala Arg Gly Arg Gly Tyr Glu Thr Ser Leu Ala Phe
                245                 250                 255

Asp Ile Trp Gly Gln Gly Thr Met Val Thr Val Ser Ser Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460
```

Thr Ala Thr Lys Asp Thr Tyr Asp Ala Leu His Met Gln Ala Leu Pro
465 470 475 480

Pro Arg

<210> SEQ ID NO 341
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 341
gaggtgcagc tggtggagtc tgggggaggc ttggtacagc ctgggggtc cctgagactc 60 tcctgtgcag cctctggatt caccttcagt agctatagca tgaactgggt ccgccaggct 120
ccagggaagg ggctggagtg ggtttcaacc attagtagta gtagtagtat catatactac 180
gcagactctg tgaagggccg attcaccatc tccagagaca atgccaagaa ctcactgtat 240
ctgcaaatga acagcctgag agctgaggac acggcggtgt actactgcgc cagaggttct 300
caggagcacc tgattttcga ttattgggga cagggtacat tggtcaccgt ctcctca 357

<210> SEQ ID NO 342
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 342

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Thr Ile Ser Ser Ser Ser Ser Ile Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Ser Gln Glu His Leu Ile Phe Asp Tyr Trp Gly Gln Gly
100 105 110

Thr Leu Val Thr Val Ser Ser
115

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Phe Thr Phe Ser Ser Tyr Ser Met Asn
1 5

<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

```
Thr Ile Ser Ser Ser Ser Ser Ile Ile Tyr Tyr Ala Asp Ser Val Lys
1               5                   10                  15

Gly
```

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

```
Ala Arg Gly Ser Gln Glu His Leu Ile Phe Asp Tyr
1               5                   10
```

<210> SEQ ID NO 346
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 346

```
gaaattgtgt tgacacagtc tccagccacc ctgtctttgt ctccagggga aagagccacc      60

ctctcctgca gggccagtca gagtgttagc aggtacttag cctggtacca acagaaacct     120

ggccaggctc ccaggctcct catctatgat gcatccaaca gggccactgg catcccagcc     180

aggttcagtg gcagtgggtc tgggacagac ttcactctca ccatcagcag cctagagcct     240

gaagattttg cagtttatta ctgtcagcag agattctact acccttggac ttttggcgga     300

gggaccaagg ttgagatcaa acgg                                            324
```

<210> SEQ ID NO 347
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 347

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Tyr Tyr Pro Trp
```

```
                85                  90                  95

Thr Phe Gly Gly Gly Thr Lys Val Glu Ile Lys Arg
            100                 105
```

<210> SEQ ID NO 348
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 348

```
Arg Ala Ser Gln Ser Val Ser Arg Tyr Leu Ala
1               5                   10
```

<210> SEQ ID NO 349
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

```
Asp Ala Ser Asn Arg Ala Thr
1               5
```

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

```
Gln Gln Arg Phe Tyr Tyr Pro Trp Thr
1               5
```

<210> SEQ ID NO 351
<211> LENGTH: 1437
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 351

```
atggcactcc ccgtaactgc tctgctgctg ccgttggcat tgctcctgca cgccgcacgc     60

ccggaggtgc agctggtgga gtctggggga ggcttggtac agcctggggg gtccctgaga    120

ctctcctgtg cagcctctgg attcaccttc agtagctata gcatgaactg ggtccgccag    180

gctccaggga aggggctgga gtgggtttca accattagta gtagtagtag tatcatatac    240

tacgcagact ctgtgaaggg ccgattcacc atctccagag acaatgccaa gaactcactg    300

tatctgcaaa tgaacagcct gagagctgag gacacggcgg tgtactactg cgccagaggt    360

tctcaggagc acctgatttt cgattattgg ggacagggta cattggtcac cgtctcctca    420

gggtctacat ccggctccgg gaagcccgga agtggcgaag gtagtacaaa gggggaaatt    480

gtgttgacac agtctccagc caccctgtct ttgtctccag gggaaagagc caccctctcc    540

tgcagggcca gtcagagtgt tagcaggtac ttagcctggt accaacagaa acctggccag    600

gctcccaggc tcctcatcta tgatgcatcc aacagggcca ctggcatccc agccaggttc    660
```

```
agtggcagtg ggtctgggac agacttcact ctcaccatca gcagcctaga gcctgaagat    720

tttgcagttt attactgtca gcagagattc tactaccctt ggacttttgg cggagggacc    780

aaggttgaga tcaaacgggc cgctgccctt gataatgaaa agtcaaacgg aacaatcatt    840

cacgtgaagg gcaagcacct ctgtccgtca cccttgttcc ctggtccatc caagccattc    900

tgggtgttgg tcgtagtggg tggagtcctc gcttgttact ctctgctcgt caccgtggct    960

tttataatct tctgggttag atccaaaaga agccgcctgc tccatagcga ttacatgaat   1020

atgactccac gccgccctgg ccccacaagg aaacactacc agccttacgc accacctaga   1080

gatttcgctg cctatcggag cagggtgaag ttttccagat ctgcagatgc accagcgtat   1140

cagcagggcc agaaccaact gtataacgag ctcaacctgg gacgcaggga agagtatgac   1200

gttttggaca agcgcagagg acgggaccct gagatgggtg gcaaaccaag acgaaaaaac   1260

ccccaggagg gtctctataa tgagctgcag aaggataaga tggctgaagc ctattctgaa   1320

ataggcatga aaggagagcg gagaagggga aaagggcacg acggtttgta ccagggactc   1380

agcactgcta cgaaggatac ttatgacgct ctccacatgc aagccctgcc acctagg      1437
```

```
<210> SEQ ID NO 352
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ser Met Asn Trp Val Arg Gln Ala Pro Gly Lys
    50                  55                  60

Gly Leu Glu Trp Val Ser Thr Ile Ser Ser Ser Ser Ser Ile Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Gly Ser Gln Glu His Leu Ile Phe Asp
        115                 120                 125

Tyr Trp Gly Gln Gly Thr Leu Val Thr Val Ser Ser Gly Ser Thr Ser
    130                 135                 140

Gly Ser Gly Lys Pro Gly Ser Gly Glu Gly Ser Thr Lys Gly Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Arg Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220
```

Ser Gly Thr Asp Phe Thr Leu Thr Ile Ser Ser Leu Glu Pro Glu Asp
225 230 235 240

Phe Ala Val Tyr Tyr Cys Gln Gln Arg Phe Tyr Tyr Pro Trp Thr Phe
245 250 255

Gly Gly Gly Thr Lys Val Glu Ile Lys Arg Ala Ala Ala Leu Asp Asn
260 265 270

Glu Lys Ser Asn Gly Thr Ile Ile His Val Lys Gly Lys His Leu Cys
275 280 285

Pro Ser Pro Leu Phe Pro Gly Pro Ser Lys Pro Phe Trp Val Leu Val
290 295 300

Val Val Gly Gly Val Leu Ala Cys Tyr Ser Leu Leu Val Thr Val Ala
305 310 315 320

Phe Ile Ile Phe Trp Val Arg Ser Lys Arg Ser Arg Leu Leu His Ser
325 330 335

Asp Tyr Met Asn Met Thr Pro Arg Arg Pro Gly Pro Thr Arg Lys His
340 345 350

Tyr Gln Pro Tyr Ala Pro Pro Arg Asp Phe Ala Ala Tyr Arg Ser Arg
355 360 365

Val Lys Phe Ser Arg Ser Ala Asp Ala Pro Ala Tyr Gln Gln Gly Gln
370 375 380

Asn Gln Leu Tyr Asn Glu Leu Asn Leu Gly Arg Arg Glu Glu Tyr Asp
385 390 395 400

Val Leu Asp Lys Arg Arg Gly Arg Asp Pro Glu Met Gly Gly Lys Pro
405 410 415

Arg Arg Lys Asn Pro Gln Glu Gly Leu Tyr Asn Glu Leu Gln Lys Asp
420 425 430

Lys Met Ala Glu Ala Tyr Ser Glu Ile Gly Met Lys Gly Glu Arg Arg
435 440 445

Arg Gly Lys Gly His Asp Gly Leu Tyr Gln Gly Leu Ser Thr Ala Thr
450 455 460

Lys Asp Thr Tyr Asp Ala Leu His Met Gln Ala Leu Pro Pro Arg
465 470 475

<210> SEQ ID NO 353
<211> LENGTH: 1437
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 353
atggcactcc ccgtaactgc tctgctgctg ccgttggcat tgctcctgca cgccgcacgc 60
ccggaaattg tgttgacaca gtctccagcc accctgtctt tgtctccagg ggaaagagcc 120
accctctcct gcagggccag tcagagtgtt agcaggtact tagcctggta ccaacagaaa 180
cctggccagg ctcccaggct cctcatctat gatgcatcca acagggccac tggcatccca 240
gccaggttca gtggcagtgg gtctgggaca gacttcactc tcaccatcag cagcctagag 300
cctgaagatt ttgcagttta ttactgtcag cagagattct actacccttg gacttttggc 360
ggagggacca aggttgagat caaacggggg tctacatccg gctccgggaa gcccggaagt 420
ggcgaaggta gtacaaaggg ggaggtgcag ctggtggagt ctgggggagg cttggtacag 480
cctggggggt ccctgagact ctcctgtgca gcctctggat tcaccttcag tagctatagc 540
atgaactggg tccgccaggc tccagggaag gggctggagt gggtttcaac cattagtagt 600

```
agtagtagta tcatatacta cgcagactct gtgaagggcc gattcaccat ctccagagac    660

aatgccaaga actcactgta tctgcaaatg aacagcctga gagctgagga cacggcggtg    720

tactactgcg ccagaggttc tcaggagcac ctgattttcg attattgggg acagggtaca    780

ttggtcaccg tctcctcagc cgctgccctt gataatgaaa agtcaaacgg aacaatcatt    840

cacgtgaagg gcaagcacct ctgtccgtca cccttgttcc ctggtccatc caagccattc    900

tgggtgttgg tcgtagtggg tggagtcctc gcttgttact ctctgctcgt caccgtggct    960

tttataatct tctgggttag atccaaaaga agccgcctgc tccatagcga ttacatgaat   1020

atgactccac gccgccctgg ccccacaagg aaacactacc agccttacgc accacctaga   1080

gatttcgctg cctatcggag cagggtgaag ttttccagat ctgcagatgc accagcgtat   1140

cagcagggcc agaaccaact gtataacgag ctcaacctgg gacgcaggga agagtatgac   1200

gttttggaca agcgcagagg acgggaccct gagatgggtg gcaaaccaag acgaaaaaac   1260

ccccaggagg gtctctataa tgagctgcag aaggataaga tggctgaagc ctattctgaa   1320

ataggcatga aaggagagcg gagaagggga aaagggcacg acggtttgta ccagggactc   1380

agcactgcta cgaaggatac ttatgacgct ctccacatgc aagccctgcc acctagg      1437
```

<210> SEQ ID NO 354
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Arg Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

Phe Tyr Tyr Pro Trp Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Tyr Ser Met Asn Trp Val Arg Gln Ala Pro Gly Lys Gly Leu
            180                 185                 190

Glu Trp Val Ser Thr Ile Ser Ser Ser Ser Ser Ile Ile Tyr Tyr Ala
        195                 200                 205
```

-continued

```
Asp Ser Val Lys Gly Arg Phe Thr Ile Ser Arg Asp Asn Ala Lys Asn
    210                 215                 220

Ser Leu Tyr Leu Gln Met Asn Ser Leu Arg Ala Glu Asp Thr Ala Val
225                 230                 235                 240

Tyr Tyr Cys Ala Arg Gly Ser Gln Glu His Leu Ile Phe Asp Tyr Trp
                245                 250                 255

Gly Gln Gly Thr Leu Val Thr Val Ser Ser Ala Ala Ala Leu Asp Asn
            260                 265                 270

Glu Lys Ser Asn Gly Thr Ile Ile His Val Lys Gly Lys His Leu Cys
        275                 280                 285

Pro Ser Pro Leu Phe Pro Gly Pro Ser Lys Pro Phe Trp Val Leu Val
    290                 295                 300

Val Val Gly Gly Val Leu Ala Cys Tyr Ser Leu Leu Val Thr Val Ala
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475
```

```
<210> SEQ ID NO 355
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 355

caggtgcagc tggtggagtc tgggggaggc gtggtccagc ctgggaggtc cctgagactc     60

tcctgtgcag cgtctggatt caccttcggg agctatggca tgcactgggt ccgccaggct    120

ccaggcaagg ggctggagtg ggtggcagtt atacattatg atggaagtgt tgaatactat    180

gcagactccg tgaagggccg attcaccatc tccagagaca attccaagga cacgctgtat    240

ctgcaaatga acagcctgag agccgaggac acggcggtgt actactgcgc cagaactgac    300

ttctggagcg gatcccctcc aagcttagat tactggggac agggtacatt ggtcaccgtc    360

tcctca                                                               366


<210> SEQ ID NO 356
<211> LENGTH: 122
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 356

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Gly Ser Tyr
20 25 30

Gly Met His Trp Val Arg Gln Ala Pro Gly Lys Gly Leu Glu Trp Val
35 40 45

Ala Val Ile His Tyr Asp Gly Ser Val Glu Tyr Tyr Ala Asp Ser Val
50 55 60

Lys Gly Arg Phe Thr Ile Ser Arg Asp Asn Ser Lys Asp Thr Leu Tyr
65 70 75 80

Leu Gln Met Asn Ser Leu Arg Ala Glu Asp Thr Ala Val Tyr Tyr Cys
85 90 95

Ala Arg Thr Asp Phe Trp Ser Gly Ser Pro Pro Ser Leu Asp Tyr Trp
100 105 110

Gly Gln Gly Thr Leu Val Thr Val Ser Ser
115 120

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 357

Phe Thr Phe Gly Ser Tyr Gly Met His
1 5

<210> SEQ ID NO 358
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 358

Val Ile His Tyr Asp Gly Ser Val Glu Tyr Tyr Ala Asp Ser Val Lys
1 5 10 15

Gly

<210> SEQ ID NO 359
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 359

Ala Arg Thr Asp Phe Trp Ser Gly Ser Pro Pro Ser Leu Asp Tyr
1 5 10 15

<210> SEQ ID NO 360
<211> LENGTH: 324

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 360

gacatccagt tgacccagtc tccatcttcc gtgtctgcat ctgtaggaga cagagtcacc     60

atcacttgtc gggcgagtcg gggtattagc agctggttag cctggtatca gcagaaacca    120

gggaaagccc ctaagctcct gatctatggt gcatccagtt tgcaaagtgg ggtcccatca    180

aggttcagcg gcagtggatc tgggacagat ttcactctca ccatcagcag cctgcagcct    240

gaagattttg caacttatta ctgtcagcag atatacacct tccctttcac ttttggcgga    300

gggaccaagg ttgagatcaa acgg                                           324


<210> SEQ ID NO 361
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Asp Ile Gln Leu Thr Gln Ser Pro Ser Ser Val Ser Ala Ser Val Gly
1               5                   10                  15

Asp Arg Val Thr Ile Thr Cys Arg Ala Ser Arg Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Tyr Thr Phe Pro Phe
                85                  90                  95

Thr Phe Gly Gly Gly Thr Lys Val Glu Ile Lys Arg
            100                 105


<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Arg Ala Ser Arg Gly Ile Ser Ser Trp Leu Ala
1               5                   10


<210> SEQ ID NO 363
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gly Ala Ser Ser Leu Gln Ser
1               5
```

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Gln Gln Ile Tyr Thr Phe Pro Phe Thr
1               5

<210> SEQ ID NO 365
<211> LENGTH: 1446
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 365
atggcactcc ccgtaactgc tctgctgctg ccgttggcat tgctcctgca cgccgcacgc 60
ccgcaggtgc agctggtgga gtctggggga ggcgtggtcc agcctgggag gtccctgaga 120
ctctcctgtg cagcgtctgg attcaccttc gggagctatg gcatgcactg ggtccgccag 180
gctccaggca aggggctgga gtgggtggca gttatacatt atgatggaag tgttgaatac 240
tatgcagact ccgtgaaggg ccgattcacc atctccagag acaattccaa ggacacgctg 300
tatctgcaaa tgaacagcct gagagccgag gacacggcgg tgtactactg cgccagaact 360
gacttctgga gcggatcccc tccaagctta gattactggg gacagggtac attggtcacc 420
gtctcctcag ggtctacatc cggctccggg aagcccggaa gtggcgaagg tagtacaaag 480
ggggacatcc agttgaccca gtctccatct tccgtgtctg catctgtagg agacagagtc 540
accatcactt gtcgggcgag tcggggtatt agcagctggt tagcctggta tcagcagaaa 600
ccagggaaag cccctaagct cctgatctat ggtgcatcca gtttgcaaag tggggtccca 660
tcaaggttca gcggcagtgg atctgggaca gatttcactc tcaccatcag cagcctgcag 720
cctgaagatt ttgcaactta ttactgtcag cagatataca ccttcccttt cacttttggc 780
ggagggacca aggttgagat caaacgggcc gctgcccttg ataatgaaaa gtcaaacgga 840
acaatcattc acgtgaaggg caagcacctc tgtccgtcac ccttgttccc tggtccatcc 900
aagccattct gggtgttggt cgtagtgggt ggagtcctcg cttgttactc tctgctcgtc 960
accgtggctt ttataatctt ctgggttaga tccaaaagaa gccgcctgct ccatagcgat 1020
tacatgaata tgactccacg ccgccctggc cccacaagga aacactacca gccttacgca 1080
ccacctagag atttcgctgc ctatcggagc agggtgaagt tttccagatc tgcagatgca 1140
ccagcgtatc agcagggcca gaaccaactg tataacgagc tcaacctggg acgcagggaa 1200
gagtatgacg ttttggacaa gcgcagagga cgggaccctg agatgggtgg caaaccaaga 1260
cgaaaaaacc cccaggaggg tctctataat gagctgcaga aggataagat ggctgaagcc 1320
tattctgaaa taggcatgaa aggagagcgg agaaggggaa aagggcacga cggtttgtac 1380
cagggactca gcactgctac gaaggatact tatgacgctc tccacatgca agccctgcca 1440
cctagg 1446

<210> SEQ ID NO 366
<211> LENGTH: 482

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Gly Ser Tyr Gly Met His Trp Val Arg Gln Ala Pro Gly Lys
    50                  55                  60

Gly Leu Glu Trp Val Ala Val Ile His Tyr Asp Gly Ser Val Glu Tyr
65                  70                  75                  80

Tyr Ala Asp Ser Val Lys Gly Arg Phe Thr Ile Ser Arg Asp Asn Ser
                85                  90                  95

Lys Asp Thr Leu Tyr Leu Gln Met Asn Ser Leu Arg Ala Glu Asp Thr
            100                 105                 110

Ala Val Tyr Tyr Cys Ala Arg Thr Asp Phe Trp Ser Gly Ser Pro Pro
        115                 120                 125

Ser Leu Asp Tyr Trp Gly Gln Gly Thr Leu Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Asp Ile Gln Leu Thr Gln Ser Pro Ser Ser Val Ser Ala Ser Val
                165                 170                 175

Gly Asp Arg Val Thr Ile Thr Cys Arg Ala Ser Arg Gly Ile Ser Ser
            180                 185                 190

Trp Leu Ala Trp Tyr Gln Gln Lys Pro Gly Lys Ala Pro Lys Leu Leu
        195                 200                 205

Ile Tyr Gly Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ile Tyr Thr Phe Pro
                245                 250                 255

Phe Thr Phe Gly Gly Gly Thr Lys Val Glu Ile Lys Arg Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380
```

Gln Gly Gln Asn Gln Leu Tyr Asn Glu Leu Asn Leu Gly Arg Arg Glu
385 390 395 400

Glu Tyr Asp Val Leu Asp Lys Arg Arg Gly Arg Asp Pro Glu Met Gly
405 410 415

Gly Lys Pro Arg Arg Lys Asn Pro Gln Glu Gly Leu Tyr Asn Glu Leu
420 425 430

Gln Lys Asp Lys Met Ala Glu Ala Tyr Ser Glu Ile Gly Met Lys Gly
435 440 445

Glu Arg Arg Arg Gly Lys Gly His Asp Gly Leu Tyr Gln Gly Leu Ser
450 455 460

Thr Ala Thr Lys Asp Thr Tyr Asp Ala Leu His Met Gln Ala Leu Pro
465 470 475 480

Pro Arg

<210> SEQ ID NO 367
<211> LENGTH: 1446
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 367
atggcactcc ccgtaactgc tctgctgctg ccgttggcat tgctcctgca cgccgcacgc 60
ccggacatcc agttgaccca gtctccatct tccgtgtctg catctgtagg agacagagtc 120
accatcactt gtcgggcgag tcggggtatt agcagctggt tagcctggta tcagcagaaa 180
ccagggaaag cccctaagct cctgatctat ggtgcatcca gtttgcaaag tggggtccca 240
tcaaggttca gcggcagtgg atctgggaca gatttcactc tcaccatcag cagcctgcag 300
cctgaagatt ttgcaactta ttactgtcag cagatataca ccttcccttt cacttttggc 360
ggagggacca aggttgagat caaacggggg tctacatccg gctccgggaa gcccggaagt 420
ggcgaaggta gtacaaaggg gcaggtgcag ctggtggagt ctgggggagg cgtggtccag 480
cctgggaggt ccctgagact ctcctgtgca gcgtctggat tcaccttcgg gagctatggc 540
atgcactggg tccgccaggc tccaggcaag gggctggagt gggtggcagt tatacattat 600
gatggaagtg ttgaatacta tgcagactcc gtgaagggcc gattcaccat ctccagagac 660
aattccaagg acacgctgta tctgcaaatg aacagcctga gagccgagga cacggcggtg 720
tactactgcg ccagaactga cttctggagc ggatcccctc caagcttaga ttactgggga 780
cagggtacat tggtcaccgt ctcctcagcc gctgcccttg ataatgaaaa gtcaaacgga 840
acaatcattc acgtgaaggg caagcacctc tgtccgtcac ccttgttccc tggtccatcc 900
aagccattct gggtgttggt cgtagtgggt ggagtcctcg cttgttactc tctgctcgtc 960
accgtggctt ttataatctt ctgggttaga tccaaaagaa gccgcctgct ccatagcgat 1020
tacatgaata tgactccacg ccgccctggc cccacaagga aacactacca gccttacgca 1080
ccacctagag atttcgctgc ctatcggagc agggtgaagt tttccagatc tgcagatgca 1140
ccagcgtatc agcagggcca gaaccaactg tataacgagc tcaacctggg acgcagggaa 1200
gagtatgacg ttttggacaa gcgcagagga cgggaccctg agatgggtgg caaaccaaga 1260
cgaaaaaacc cccaggaggg tctctataat gagctgcaga aggataagat ggctgaagcc 1320
tattctgaaa taggcatgaa aggagagcgg agaaggggaa aagggcacga cggtttgtac 1380
cagggactca gcactgctac gaaggatact tatgacgctc tccacatgca agccctgcca 1440
cctagg 1446

<210> SEQ ID NO 368
<211> LENGTH: 482
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 368

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Val
            20                  25                  30

Ser Ala Ser Val Gly Asp Arg Val Thr Ile Thr Cys Arg Ala Ser Arg
        35                  40                  45

Gly Ile Ser Ser Trp Leu Ala Trp Tyr Gln Gln Lys Pro Gly Lys Ala
    50                  55                  60

Pro Lys Leu Leu Ile Tyr Gly Ala Ser Ser Leu Gln Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Ile
            100                 105                 110

Tyr Thr Phe Pro Phe Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Val Glu Ser Gly Gly Gly Val Val Gln
145                 150                 155                 160

Pro Gly Arg Ser Leu Arg Leu Ser Cys Ala Ala Ser Gly Phe Thr Phe
                165                 170                 175

Gly Ser Tyr Gly Met His Trp Val Arg Gln Ala Pro Gly Lys Gly Leu
            180                 185                 190

Glu Trp Val Ala Val Ile His Tyr Asp Gly Ser Val Glu Tyr Tyr Ala
        195                 200                 205

Asp Ser Val Lys Gly Arg Phe Thr Ile Ser Arg Asp Asn Ser Lys Asp
    210                 215                 220

Thr Leu Tyr Leu Gln Met Asn Ser Leu Arg Ala Glu Asp Thr Ala Val
225                 230                 235                 240

Tyr Tyr Cys Ala Arg Thr Asp Phe Trp Ser Gly Ser Pro Pro Ser Leu
                245                 250                 255

Asp Tyr Trp Gly Gln Gly Thr Leu Val Thr Val Ser Ser Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350
```

```
Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg
```

<210> SEQ ID NO 369
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 369

```
caggtgcagc tggtgcagtc tggggctgag gtgaagaagc ctgggtcctc ggtgaaggtc     60

tcctgcaagg cttctggagg caccctcagc agcctggcta tcagctgggt gcgacaggcc    120

cctggacaag ggcttgagtg gatgggaggg gtcatcccta tcttgggtcg ggcaaactac    180

gcacagaagt tccagggcag agtcacgatt accgcggacg agtccacgag cacagcctac    240

atggagctga gcagcctgag atctgaggac acggcggtgt actactgcgc cagaactcct    300

gaatactcct ccagcatatg gcactattac tacggcatgg acgtatgggg ccagggaaca    360

actgtcaccg tctcctca                                                   378
```

<210> SEQ ID NO 370
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 370

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Ser Leu
            20                  25                  30

Ala Ile Ser Trp Val Arg Gln Ala Pro Gly Gln Gly Leu Glu Trp Met
        35                  40                  45

Gly Gly Val Ile Pro Ile Leu Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                85                  90                  95

Ala Arg Thr Pro Glu Tyr Ser Ser Ser Ile Trp His Tyr Tyr Tyr Gly
            100                 105                 110

Met Asp Val Trp Gly Gln Gly Thr Thr Val Thr Val Ser Ser
        115                 120                 125


<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Gly Thr Leu Ser Ser Leu Ala Ile Ser
1               5


<210> SEQ ID NO 372
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Gly Val Ile Pro Ile Leu Gly Arg Ala Asn Tyr Ala Gln Lys Phe Gln
1               5                   10                  15

Gly


<210> SEQ ID NO 373
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Ala Arg Thr Pro Glu Tyr Ser Ser Ser Ile Trp His Tyr Tyr Tyr Gly
1               5                   10                  15

Met Asp Val


<210> SEQ ID NO 374
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 374

gacatcgtga tgacccagtc tccagactcc ctggctgtgt ctctgggcga gagggccacc      60

atcaactgca agtccagcca gagtgtttta tacagctcca acaataagaa ctacttagct     120

tggtaccagc agaaaccagg acagcctcct aagctgctca tttactgggc atctacccgg     180

gaatccgggg tccctgaccg attcagtggc agcgggtctg ggacagattt cactctcacc     240

atcagcagcc tgcaggctga agatgtggca gtttattact gtcagcagtt cgcccacact     300

cctttcactt ttggcggagg gaccaaggtt gagatcaaac gg                        342


<210> SEQ ID NO 375
```

-continued

<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 375

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Phe Ala His Thr Pro Phe Thr Phe Gly Gly Gly Thr Lys Val Glu Ile
100 105 110

Lys Arg

<210> SEQ ID NO 376
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 376

Lys Ser Ser Gln Ser Val Leu Tyr Ser Ser Asn Asn Lys Asn Tyr Leu
1 5 10 15

Ala

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 377

Trp Ala Ser Thr Arg Glu Ser
1 5

<210> SEQ ID NO 378
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 378

Gln Gln Phe Ala His Thr Pro Phe Thr
1 5

<210> SEQ ID NO 379
<211> LENGTH: 1476

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 379
atggcactcc ccgtaactgc tctgctgctg ccgttggcat tgctcctgca cgccgcacgc 60
ccgcaggtgc agctggtgca gtctggggct gaggtgaaga agcctgggtc ctcggtgaag 120
gtctcctgca aggcttctgg aggcaccctc agcagcctgg ctatcagctg ggtgcgacag 180
gcccctggac aagggcttga gtggatggga ggggtcatcc ctatcttggg tcgggcaaac 240
tacgcacaga agttccaggg cagagtcacg attaccgcgg acgagtccac gagcacagcc 300
tacatggagc tgagcagcct gagatctgag gacacggcgg tgtactactg cgccagaact 360
cctgaatact cctccagcat atggcactat tactacggca tggacgtatg gggccaggga 420
acaactgtca ccgtctcctc agggtctaca tccggctccg ggaagcccgg aagtggcgaa 480
ggtagtacaa agggggacat cgtgatgacc cagtctccag actccctggc tgtgtctctg 540
ggcgagaggg ccaccatcaa ctgcaagtcc agccagagtg ttttatacag ctccaacaat 600
aagaactact tagcttggta ccagcagaaa ccaggacagc ctcctaagct gctcatttac 660
tgggcatcta cccgggaatc cggggtccct gaccgattca gtggcagcgg gtctgggaca 720
gatttcactc tcaccatcag cagcctgcag gctgaagatg tggcagttta ttactgtcag 780
cagttcgccc acactccttt cacttttggc ggagggacca aggttgagat caaacgggcc 840
gctgcccttg ataatgaaaa gtcaaacgga acaatcattc acgtgaaggg caagcacctc 900
tgtccgtcac ccttgttccc tggtccatcc aagccattct gggtgttggt cgtagtgggt 960
ggagtcctcg cttgttactc tctgctcgtc accgtggctt ttataatctt ctgggttaga 1020
tccaaaagaa gccgcctgct ccatagcgat tacatgaata tgactccacg ccgccctggc 1080
cccacaagga aacactacca gccttacgca ccacctagag atttcgctgc ctatcggagc 1140
agggtgaagt tttccagatc tgcagatgca ccagcgtatc agcagggcca gaaccaactg 1200
tataacgagc tcaacctggg acgcagggaa gagtatgacg ttttggacaa gcgcagagga 1260
cgggaccctg agatgggtgg caaaccaaga cgaaaaaacc cccaggaggg tctctataat 1320
gagctgcaga aggataagat ggctgaagcc tattctgaaa taggcatgaa aggagagcgg 1380
agaaggggaa aagggcacga cggtttgtac cagggactca gcactgctac gaaggatact 1440
tatgacgctc tccacatgca agccctgcca cctagg 1476

<210> SEQ ID NO 380
<211> LENGTH: 492
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 380

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Lys Pro Gly Ser Ser Val Lys Val Ser Cys Lys Ala Ser Gly Gly
35 40 45

Thr Leu Ser Ser Leu Ala Ile Ser Trp Val Arg Gln Ala Pro Gly Gln

```
    50                  55                  60

Gly Leu Glu Trp Met Gly Gly Val Ile Pro Ile Leu Gly Arg Ala Asn
65                  70                  75                  80

Tyr Ala Gln Lys Phe Gln Gly Arg Val Thr Ile Thr Ala Asp Glu Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Thr Pro Glu Tyr Ser Ser Ser Ile Trp
        115                 120                 125

His Tyr Tyr Tyr Gly Met Asp Val Trp Gly Gln Gly Thr Thr Val Thr
    130                 135                 140

Val Ser Ser Gly Ser Thr Ser Gly Ser Gly Lys Pro Gly Ser Gly Glu
145                 150                 155                 160

Gly Ser Thr Lys Gly Asp Ile Val Met Thr Gln Ser Pro Asp Ser Leu
                165                 170                 175

Ala Val Ser Leu Gly Glu Arg Ala Thr Ile Asn Cys Lys Ser Ser Gln
            180                 185                 190

Ser Val Leu Tyr Ser Ser Asn Asn Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Leu Gln Ala Glu Asp Val Ala Val
                245                 250                 255

Tyr Tyr Cys Gln Gln Phe Ala His Thr Pro Phe Thr Phe Gly Gly Gly
            260                 265                 270

Thr Lys Val Glu Ile Lys Arg Ala Ala Ala Leu Asp Asn Glu Lys Ser
        275                 280                 285

Asn Gly Thr Ile Ile His Val Lys Gly Lys His Leu Cys Pro Ser Pro
    290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480
```

-continued

Tyr Asp Ala Leu His Met Gln Ala Leu Pro Pro Arg
485 490

<210> SEQ ID NO 381
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 381
atggcactcc ccgtaactgc tctgctgctg ccgttggcat tgctcctgca cgccgcacgc 60
ccggacatcg tgatgaccca gtctccagac tccctggctg tgtctctggg cgagagggcc 120
accatcaact gcaagtccag ccagagtgtt ttatacagct ccaacaataa gaactactta 180
gcttggtacc agcagaaacc aggacagcct cctaagctgc tcatttactg ggcatctacc 240
cgggaatccg gggtccctga ccgattcagt ggcagcgggt ctgggacaga tttcactctc 300
accatcagca gcctgcaggc tgaagatgtg gcagtttatt actgtcagca gttcgcccac 360
actcctttca cttttggcgg agggaccaag gttgagatca aacgggggtc tacatccggc 420
tccgggaagc ccggaagtgg cgaaggtagt acaaaggggc aggtgcagct ggtgcagtct 480
ggggctgagg tgaagaagcc tgggtcctcg gtgaaggtct cctgcaaggc ttctggaggc 540
accctcagca gcctggctat cagctgggtg cgacaggccc ctggacaagg gcttgagtgg 600
atgggagggg tcatccctat cttgggtcgg gcaaactacg cacagaagtt ccagggcaga 660
gtcacgatta ccgcggacga gtccacgagc acagcctaca tggagctgag cagcctgaga 720
tctgaggaca cggcggtgta ctactgcgcc agaactcctg aatactcctc cagcatatgg 780
cactattact acggcatgga cgtatggggc cagggaacaa ctgtcaccgt ctcctcagcc 840
gctgcccttg ataatgaaaa gtcaaacgga acaatcattc acgtgaaggg caagcacctc 900
tgtccgtcac ccttgttccc tggtccatcc aagccattct gggtgttggt cgtagtgggt 960
ggagtcctcg cttgttactc tctgctcgtc accgtggctt ttataatctt ctgggttaga 1020
tccaaaagaa gccgcctgct ccatagcgat tacatgaata tgactccacg ccgccctggc 1080
cccacaagga aacactacca gccttacgca ccacctagag atttcgctgc ctatcggagc 1140
agggtgaagt tttccagatc tgcagatgca ccagcgtatc agcagggcca gaaccaactg 1200
tataacgagc tcaacctggg acgcagggaa gagtatgacg ttttggacaa gcgcagagga 1260
cgggaccctg agatgggtgg caaaccaaga cgaaaaaacc cccaggaggg tctctataat 1320
gagctgcaga aggataagat ggctgaagcc tattctgaaa taggcatgaa aggagagcgg 1380
agaaggggaa aagggcacga cggtttgtac cagggactca gcactgctac gaaggatact 1440
tatgacgctc tccacatgca agccctgcca cctagg 1476

<210> SEQ ID NO 382
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 382

Met Ala Leu Pro Val Thr Ala Leu Leu Leu Pro Leu Ala Leu Leu Leu
1 5 10 15

-continued

```
His Ala Ala Arg Pro Asp Ile Val Met Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Val Leu Tyr Ser Ser Asn Asn Lys Asn Tyr Leu Ala Trp Tyr Gln
    50                  55                  60

Gln Lys Pro Gly Gln Pro Pro Lys Leu Leu Ile Tyr Trp Ala Ser Thr
65                  70                  75                  80

Arg Glu Ser Gly Val Pro Asp Arg Phe Ser Gly Ser Gly Ser Gly Thr
                85                  90                  95

Asp Phe Thr Leu Thr Ile Ser Ser Leu Gln Ala Glu Asp Val Ala Val
            100                 105                 110

Tyr Tyr Cys Gln Gln Phe Ala His Thr Pro Phe Thr Phe Gly Gly Gly
        115                 120                 125

Thr Lys Val Glu Ile Lys Arg Gly Ser Thr Ser Gly Ser Gly Lys Pro
    130                 135                 140

Gly Ser Gly Glu Gly Ser Thr Lys Gly Gln Val Gln Leu Val Gln Ser
145                 150                 155                 160

Gly Ala Glu Val Lys Lys Pro Gly Ser Ser Val Lys Val Ser Cys Lys
                165                 170                 175

Ala Ser Gly Gly Thr Leu Ser Ser Leu Ala Ile Ser Trp Val Arg Gln
            180                 185                 190

Ala Pro Gly Gln Gly Leu Glu Trp Met Gly Gly Val Ile Pro Ile Leu
        195                 200                 205

Gly Arg Ala Asn Tyr Ala Gln Lys Phe Gln Gly Arg Val Thr Ile Thr
    210                 215                 220

Ala Asp Glu Ser Thr Ser Thr Ala Tyr Met Glu Leu Ser Ser Leu Arg
225                 230                 235                 240

Ser Glu Asp Thr Ala Val Tyr Tyr Cys Ala Arg Thr Pro Glu Tyr Ser
                245                 250                 255

Ser Ser Ile Trp His Tyr Tyr Tyr Gly Met Asp Val Trp Gly Gln Gly
            260                 265                 270

Thr Thr Val Thr Val Ser Ser Ala Ala Ala Leu Asp Asn Glu Lys Ser
        275                 280                 285

Asn Gly Thr Ile Ile His Val Lys Gly Lys His Leu Cys Pro Ser Pro
    290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
```

```
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 383
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 383

caggtgcggc tggtggagtc tgggggggc gtggtccagc ctgggaggtc cctgagactc     60

tcctgtgcag cgtctggatt caccttcagt agctatggca tacactgggt ccgccaggct    120

ccaggcaagg ggctggagtg ggtggcagtt atagggtatg atggacagga gaaatactat    180

gcagactccg tgaagggccg attcaccatc tccagagaca attccaagaa cacgctgtat    240

ctgcaaatga acagcctgag agccgaggac acggcggtgt actactgcgt caaggggccg    300

ttgcaggagc cgccatacgc ttttgggatg gacgtatggg gccagggaac aactgtcacc    360

gtctcctca                                                            369


<210> SEQ ID NO 384
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

Gln Val Arg Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Gly Tyr Asp Gly Gln Glu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Ala Phe Gly Met Asp Val
            100                 105                 110

Trp Gly Gln Gly Thr Thr Val Thr Val Ser Ser
        115                 120


<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 385

Phe Thr Phe Ser Ser Tyr Gly Ile His
1 5

<210> SEQ ID NO 386
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 386

Val Ile Gly Tyr Asp Gly Gln Glu Lys Tyr Tyr Ala Asp Ser Val Lys
1 5 10 15

Gly

<210> SEQ ID NO 387
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 387

Val Lys Gly Pro Leu Gln Glu Pro Pro Tyr Ala Phe Gly Met Asp Val
1 5 10 15

<210> SEQ ID NO 388
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 388
gaaatagtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatagc gcatccacca gggccactgg tatcccagcc 180
aggttcagtg gcagtgggtc tgggacagag ttcactctca ccatcagcag cctgcagtct 240
gaagattttg cagtttatta ctgtcagcag caccacgtct ggcctctcac ttttggcgga 300
gggaccaagg ttgagatcaa acgg 324

<210> SEQ ID NO 389
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 389

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

-continued

```
Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His His Val Trp Pro Leu
                85                  90                  95

Thr Phe Gly Gly Gly Thr Lys Val Glu Ile Lys Arg
            100                 105
```

```
<210> SEQ ID NO 390
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Arg Ala Ser Gln Ser Val Ser Ser Asn Leu Ala
1               5                   10


<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Ser Ala Ser Thr Arg Ala Thr
1               5


<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gln Gln His His Val Trp Pro Leu Thr
1               5


<210> SEQ ID NO 393
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 393

atggcactcc ccgtaactgc tctgctgctg ccgttggcat tgctcctgca cgccgcacgc      60

ccgcaggtgc ggctggtgga gtctgggggg ggcgtggtcc agcctgggag gtccctgaga     120

ctctcctgtg cagcgtctgg attcaccttc agtagctatg gcatacactg ggtccgccag     180

gctccaggca aggggctgga gtgggtggca gttatagggt atgatggaca ggagaaatac     240

tatgcagact ccgtgaaggg ccgattcacc atctccagag acaattccaa gaacacgctg     300

tatctgcaaa tgaacagcct gagagccgag gacacggcgg tgtactactg cgtcaagggg     360

ccgttgcagg agccgccata cgcttttggg atggacgtat ggggccaggg aacaactgtc     420
```

```
accgtctcct cagggtctac atccggctcc gggaagcccg gaagtggcga aggtagtaca    480

aagggggaaa tagtgatgac gcagtctcca gccaccctgt ctgtgtctcc aggggaaaga    540

gccaccctct cctgcagggc cagtcagagt gttagcagca acttagcctg gtaccagcag    600

aaacctggcc aggctcccag gctcctcatc tatagcgcat ccaccagggc cactggtatc    660

ccagccaggt tcagtggcag tgggtctggg acagagttca ctctcaccat cagcagcctg    720

cagtctgaag attttgcagt ttattactgt cagcagcacc acgtctggcc tctcactttt    780

ggcggaggga ccaaggttga gatcaaacgg gccgctgccc ttgataatga aaagtcaaac    840

ggaacaatca ttcacgtgaa gggcaagcac ctctgtccgt caccccttgt ccctggtcca    900

tccaagccat tctgggtgtt ggtcgtagtg ggtggagtcc tcgcttgtta ctctctgctc    960

gtcaccgtgg cttttataat cttctgggtt agatccaaaa gaagccgcct gctccatagc   1020

gattacatga atatgactcc acgccgccct ggccccacaa ggaaacacta ccagccttac   1080

gcaccaccta gagatttcgc tgcctatcgg agcagggtga agttttccag atctgcagat   1140

gcaccagcgt atcagcaggg ccagaaccaa ctgtataacg agctcaacct gggacgcagg   1200

gaagagtatg acgttttgga caagcgcaga ggacgggacc ctgagatggg tggcaaacca   1260

agacgaaaaa acccccagga gggtctctat aatgagctgc agaaggataa gatggctgaa   1320

gcctattctg aaataggcat gaaaggagag cggagaaggg gaaaagggca cgacggtttg   1380

taccagggac tcagcactgc tacgaaggat acttatgacg ctctccacat gcaagccctg   1440

ccacctagg                                                           1449
```

<210> SEQ ID NO 394
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

```
Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Ile His Trp Val Arg Gln Ala Pro Gly Lys
    50                  55                  60

Gly Leu Glu Trp Val Ala Val Ile Gly Tyr Asp Gly Gln Glu Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Ala
        115                 120                 125

Phe Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175
```

```
Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg
```

<210> SEQ ID NO 395
<211> LENGTH: 1449
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 395

```
atggcactcc ccgtaactgc tctgctgctg ccgttggcat tgctcctgca cgccgcacgc     60

ccggaaatag tgatgacgca gtctccagcc accctgtctg tgtctccagg ggaaagagcc    120

accctctcct gcagggccag tcagagtgtt agcagcaact tagcctggta ccagcagaaa    180

cctggccagg ctcccaggct cctcatctat agcgcatcca ccagggccac tggtatccca    240
```

```
gccaggttca gtggcagtgg gtctgggaca gagttcactc tcaccatcag cagcctgcag    300

tctgaagatt ttgcagttta ttactgtcag cagcaccacg tctggcctct cacttttggc    360

ggagggacca aggttgagat caaacggggg tctacatccg gctccgggaa gcccggaagt    420

ggcgaaggta gtacaaaggg gcaggtgcgg ctggtggagt ctgggggggg cgtggtccag    480

cctgggaggt ccctgagact ctcctgtgca gcgtctggat tcaccttcag tagctatggc    540

atacactggg tccgccaggc tccaggcaag gggctggagt gggtggcagt tatagggtat    600

gatggacagg agaaatacta tgcagactcc gtgaagggcc gattcaccat ctccagagac    660

aattccaaga acacgctgta tctgcaaatg aacagcctga gagccgagga cacggcggtg    720

tactactgcg tcaaggggcc gttgcaggag ccgccatacg cttttgggat ggacgtatgg    780

ggccagggaa caactgtcac cgtctcctca gccgctgccc ttgataatga aaagtcaaac    840

ggaacaatca ttcacgtgaa gggcaagcac ctctgtccgt caccccttgtt ccctggtcca    900

tccaagccat tctgggtgtt ggtcgtagtg ggtggagtcc tcgcttgtta ctctctgctc    960

gtcaccgtgg cttttataat cttctgggtt agatccaaaa gaagccgcct gctccatagc   1020

gattacatga atatgactcc acgccgccct ggccccacaa ggaaacacta ccagccttac   1080

gcaccaccta gagatttcgc tgcctatcgg agcagggtga agttttccag atctgcagat   1140

gcaccagcgt atcagcaggg ccagaaccaa ctgtataacg agctcaacct gggacgcagg   1200

gaagagtatg acgttttgga caagcgcaga ggacgggacc ctgagatggg tggcaaacca   1260

agacgaaaaa acccccagga gggtctctat aatgagctgc agaaggataa gatggctgaa   1320

gcctattctg aaataggcat gaaaggagag cggagaaggg gaaaagggca cgacggtttg   1380

taccagggac tcagcactgc tacgaaggat acttatgacg ctctccacat gcaagccctg   1440

ccacctagg                                                          1449
```

```
<210> SEQ ID NO 396
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Ser Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln His
            100                 105                 110

His Val Trp Pro Leu Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140
```

Thr Lys Gly Gln Val Arg Leu Val Glu Ser Gly Gly Gly Val Val Gln
145 150 155 160

Pro Gly Arg Ser Leu Arg Leu Ser Cys Ala Ala Ser Gly Phe Thr Phe
165 170 175

Ser Ser Tyr Gly Ile His Trp Val Arg Gln Ala Pro Gly Lys Gly Leu
180 185 190

Glu Trp Val Ala Val Ile Gly Tyr Asp Gly Gln Glu Lys Tyr Tyr Ala
195 200 205

Asp Ser Val Lys Gly Arg Phe Thr Ile Ser Arg Asp Asn Ser Lys Asn
210 215 220

Thr Leu Tyr Leu Gln Met Asn Ser Leu Arg Ala Glu Asp Thr Ala Val
225 230 235 240

Tyr Tyr Cys Val Lys Gly Pro Leu Gln Glu Pro Pro Tyr Ala Phe Gly
245 250 255

Met Asp Val Trp Gly Gln Gly Thr Thr Val Thr Val Ser Ser Ala Ala
260 265 270

Ala Leu Asp Asn Glu Lys Ser Asn Gly Thr Ile Ile His Val Lys Gly
275 280 285

Lys His Leu Cys Pro Ser Pro Leu Phe Pro Gly Pro Ser Lys Pro Phe
290 295 300

Trp Val Leu Val Val Val Gly Gly Val Leu Ala Cys Tyr Ser Leu Leu
305 310 315 320

Val Thr Val Ala Phe Ile Ile Phe Trp Val Arg Ser Lys Arg Ser Arg
325 330 335

Leu Leu His Ser Asp Tyr Met Asn Met Thr Pro Arg Arg Pro Gly Pro
340 345 350

Thr Arg Lys His Tyr Gln Pro Tyr Ala Pro Pro Arg Asp Phe Ala Ala
355 360 365

Tyr Arg Ser Arg Val Lys Phe Ser Arg Ser Ala Asp Ala Pro Ala Tyr
370 375 380

Gln Gln Gly Gln Asn Gln Leu Tyr Asn Glu Leu Asn Leu Gly Arg Arg
385 390 395 400

Glu Glu Tyr Asp Val Leu Asp Lys Arg Arg Gly Arg Asp Pro Glu Met
405 410 415

Gly Gly Lys Pro Arg Arg Lys Asn Pro Gln Glu Gly Leu Tyr Asn Glu
420 425 430

Leu Gln Lys Asp Lys Met Ala Glu Ala Tyr Ser Glu Ile Gly Met Lys
435 440 445

Gly Glu Arg Arg Arg Gly Lys Gly His Asp Gly Leu Tyr Gln Gly Leu
450 455 460

Ser Thr Ala Thr Lys Asp Thr Tyr Asp Ala Leu His Met Gln Ala Leu
465 470 475 480

Pro Pro Arg

<210> SEQ ID NO 397
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 397
caggtgcagc tggtggagtc tgggggaggc gtggtccagc ctgggaggtc cctgagactc 60

```
tcctgtgcag cgtctggatt caccttcagt agccgtggca tgcactgggt ccgccaggct    120

ccaggcaagg ggctggagtg ggtggcagtt atagggtatg atggacagga gaaatactat    180

gcagactccg tgaagggccg attcaccatc tccagagaca attccaagaa cacgctgtat    240

ctgcaaatga acagcctgag agccgaggac acggcggtgt actactgcgt caaggggccg    300

ttgcaggagc cgccatacga ttatggaatg gacgtatggg gccagggaac aactgtcacc    360

gtctcctca                                                            369


<210> SEQ ID NO 398
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Arg
            20                  25                  30

Gly Met His Trp Val Arg Gln Ala Pro Gly Lys Gly Leu Glu Trp Val
        35                  40                  45

Ala Val Ile Gly Tyr Asp Gly Gln Glu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Asp Tyr Gly Met Asp Val
            100                 105                 110

Trp Gly Gln Gly Thr Thr Val Thr Val Ser Ser
        115                 120


<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Phe Thr Phe Ser Ser Arg Gly Met His
1               5


<210> SEQ ID NO 400
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Val Ile Gly Tyr Asp Gly Gln Glu Lys Tyr Tyr Ala Asp Ser Val Lys
1               5                   10                  15

Gly


<210> SEQ ID NO 401
```

<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 401

Val Lys Gly Pro Leu Gln Glu Pro Pro Tyr Asp Tyr Gly Met Asp Val
1 5 10 15

<210> SEQ ID NO 402
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 402
gaaatagtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatagc gcatccacca gggccactgg tatcccagcc 180
aggttcagtg gcagtgggtc tgggacagag ttcactctca ccatcagcag cctgcagtct 240
gaagattttg cagtttatta ctgtcagcag caccacgtct ggcctctcac ttttggcgga 300
gggaccaagg ttgagatcaa acgg 324

<210> SEQ ID NO 403
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 403

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Ser Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln His His Val Trp Pro Leu
85 90 95

Thr Phe Gly Gly Gly Thr Lys Val Glu Ile Lys Arg
100 105

<210> SEQ ID NO 404
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 404

Arg Ala Ser Gln Ser Val Ser Ser Asn Leu Ala 1 5 10

<210> SEQ ID NO 405
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 405

Ser Ala Ser Thr Arg Ala Thr
1 5

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 406

Gln Gln His His Val Trp Pro Leu Thr
1 5

<210> SEQ ID NO 407
<211> LENGTH: 1449
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 407
atggcactcc ccgtaactgc tctgctgctg ccgttggcat tgctcctgca cgccgcacgc 60
ccgcaggtgc agctggtgga gtctggggga ggcgtggtcc agcctgggag gtccctgaga 120
ctctcctgtg cagcgtctgg attcaccttc agtagccgtg gcatgcactg ggtccgccag 180
gctccaggca aggggctgga gtgggtggca gttatagggt atgatggaca ggagaaatac 240
tatgcagact ccgtgaaggg ccgattcacc atctccagag acaattccaa gaacacgctg 300
tatctgcaaa tgaacagcct gagagccgag gacacggcgg tgtactactg cgtcaagggg 360
ccgttgcagg agccgccata cgattatgga atggacgtat ggggccaggg aacaactgtc 420
accgtctcct cagggtctac atccggctcc gggaagcccg gaagtggcga aggtagtaca 480
aagggggaaa tagtgatgac gcagtctcca gccaccctgt ctgtgtctcc aggggaaaga 540
gccaccctct cctgcagggc cagtcagagt gttagcagca acttagcctg gtaccagcag 600
aaacctggcc aggctcccag gctcctcatc tatagcgcat ccaccagggc cactggtatc 660
ccagccaggt tcagtggcag tgggtctggg acagagttca ctctcaccat cagcagcctg 720
cagtctgaag attttgcagt ttattactgt cagcagcacc acgtctggcc tctcactttt 780
ggcggaggga ccaaggttga gatcaaacgg gccgctgccc ttgataatga aaagtcaaac 840
ggaacaatca ttcacgtgaa gggcaagcac ctctgtccgt cacccttgtt ccctggtcca 900
tccaagccat tctgggtgtt ggtcgtagtg ggtggagtcc tcgcttgtta ctctctgctc 960
gtcaccgtgg cttttataat cttctgggtt agatccaaaa gaagccgcct gctccatagc 1020
gattacatga atatgactcc acgccgccct ggccccacaa ggaaacacta ccagccttac 1080
gcaccaccta gagatttcgc tgcctatcgg agcagggtga agttttccag atctgcagat 1140

```
gcaccagcgt atcagcaggg ccagaaccaa ctgtataacg agctcaacct gggacgcagg   1200

gaagagtatg acgttttgga caagcgcaga ggacgggacc ctgagatggg tggcaaacca   1260

agacgaaaaa acccccagga gggtctctat aatgagctgc agaaggataa gatggctgaa   1320

gcctattctg aaataggcat gaaaggagag cggagaaggg gaaaagggca cgacggtttg   1380

taccagggac tcagcactgc tacgaaggat acttatgacg ctctccacat gcaagccctg   1440

ccacctagg                                                           1449
```

```
<210> SEQ ID NO 408
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Arg Gly Met His Trp Val Arg Gln Ala Pro Gly Lys
    50                  55                  60

Gly Leu Glu Trp Val Ala Val Ile Gly Tyr Asp Gly Gln Glu Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300
```

```
Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg


<210> SEQ ID NO 409
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 409

atggcactcc ccgtaactgc tctgctgctg ccgttggcat tgctcctgca cgccgcacgc     60

ccggaaatag tgatgacgca gtctccagcc accctgtctg tgtctccagg ggaaagagcc    120

accctctcct gcagggccag tcagagtgtt agcagcaact tagcctggta ccagcagaaa    180

cctggccagg ctcccaggct cctcatctat agcgcatcca ccagggccac tggtatccca    240

gccaggttca gtggcagtgg gtctgggaca gagttcactc tcaccatcag cagcctgcag    300

tctgaagatt ttgcagttta ttactgtcag cagcaccacg tctggcctct cacttttggc    360

ggagggacca aggttgagat caaacggggg tctacatccg gctccgggaa gcccggaagt    420

ggcgaaggta gtacaaaggg gcaggtgcag ctggtggagt ctgggggagg cgtggtccag    480

cctgggaggt ccctgagact ctcctgtgca gcgtctggat tcaccttcag tagccgtggc    540

atgcactggg tccgccaggc tccaggcaag gggctggagt gggtggcagt tatagggtat    600

gatggacagg agaaatacta tgcagactcc gtgaagggcc gattcaccat ctccagagac    660

aattccaaga acacgctgta tctgcaaatg aacagcctga gagccgagga cacggcggtg    720

tactactgcg tcaaggggcc gttgcaggag ccgccatacg attatggaat ggacgtatgg    780

ggccagggaa caactgtcac cgtctcctca gccgctgccc ttgataatga aaagtcaaac    840

ggaacaatca ttcacgtgaa gggcaagcac ctctgtccgt caccccttgt ccctggtcca    900

tccaagccat tctgggtgtt ggtcgtagtg ggtggagtcc tcgcttgtta ctctctgctc    960
```

-continued

```
gtcaccgtgg cttttataat cttctgggtt agatccaaaa gaagccgcct gctccatagc   1020

gattacatga atatgactcc acgccgccct ggccccacaa ggaaacacta ccagccttac   1080

gcaccaccta gagatttcgc tgcctatcgg agcagggtga agttttccag atctgcagat   1140

gcaccagcgt atcagcaggg ccagaaccaa ctgtataacg agctcaacct gggacgcagg   1200

gaagagtatg acgttttgga caagcgcaga ggacgggacc ctgagatggg tggcaaacca   1260

agacgaaaaa acccccagga gggtctctat aatgagctgc agaaggataa gatggctgaa   1320

gcctattctg aaataggcat gaaaggagag cggagaaggg gaaaagggca cgacggtttg   1380

taccagggac tcagcactgc tacgaaggat acttatgacg ctctccacat gcaagccctg   1440

ccacctagg                                                          1449
```

<210> SEQ ID NO 410
<211> LENGTH: 483
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 410

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Ser Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln His
            100                 105                 110

His Val Trp Pro Leu Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Val Glu Ser Gly Gly Gly Val Val Gln
145                 150                 155                 160

Pro Gly Arg Ser Leu Arg Leu Ser Cys Ala Ala Ser Gly Phe Thr Phe
                165                 170                 175

Ser Ser Arg Gly Met His Trp Val Arg Gln Ala Pro Gly Lys Gly Leu
            180                 185                 190

Glu Trp Val Ala Val Ile Gly Tyr Asp Gly Gln Glu Lys Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Val Lys Gly Pro Leu Gln Glu Pro Pro Tyr Asp Tyr Gly
                245                 250                 255

Met Asp Val Trp Gly Gln Gly Thr Thr Val Thr Val Ser Ser Ala Ala
            260                 265                 270
```

Ala Leu Asp Asn Glu Lys Ser Asn Gly Thr Ile Ile His Val Lys Gly
275 280 285

Lys His Leu Cys Pro Ser Pro Leu Phe Pro Gly Pro Ser Lys Pro Phe
290 295 300

Trp Val Leu Val Val Val Gly Gly Val Leu Ala Cys Tyr Ser Leu Leu
305 310 315 320

Val Thr Val Ala Phe Ile Ile Phe Trp Val Arg Ser Lys Arg Ser Arg
325 330 335

Leu Leu His Ser Asp Tyr Met Asn Met Thr Pro Arg Arg Pro Gly Pro
340 345 350

Thr Arg Lys His Tyr Gln Pro Tyr Ala Pro Pro Arg Asp Phe Ala Ala
355 360 365

Tyr Arg Ser Arg Val Lys Phe Ser Arg Ser Ala Asp Ala Pro Ala Tyr
370 375 380

Gln Gln Gly Gln Asn Gln Leu Tyr Asn Glu Leu Asn Leu Gly Arg Arg
385 390 395 400

Glu Glu Tyr Asp Val Leu Asp Lys Arg Arg Gly Arg Asp Pro Glu Met
405 410 415

Gly Gly Lys Pro Arg Arg Lys Asn Pro Gln Glu Gly Leu Tyr Asn Glu
420 425 430

Leu Gln Lys Asp Lys Met Ala Glu Ala Tyr Ser Glu Ile Gly Met Lys
435 440 445

Gly Glu Arg Arg Arg Gly Lys Gly His Asp Gly Leu Tyr Gln Gly Leu
450 455 460

Ser Thr Ala Thr Lys Asp Thr Tyr Asp Ala Leu His Met Gln Ala Leu
465 470 475 480

Pro Pro Arg

<210> SEQ ID NO 411
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 411

Gly Gly Gly Gly Ser Gly Gly Gly Gly Ser Gly Gly Gly Gly Ser Gly
1 5 10 15

Gly Gly Gly Ser
20

<210> SEQ ID NO 412
<211> LENGTH: 112
<212> TYPE: PRT
<213> ORGANISM: Homo sapiens

<400> SEQUENCE: 412

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

```
Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 413
<211> LENGTH: 6762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 413

ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggctttccc cgtcaagctc taaatcgggg gctcccttta gggttccgat    180

ttagtgcttt acggcacctc gaccccaaaa aacttgatta gggtgatggt tcacgtagtg    240

ggccatcgcc ctgatagacg gtttttcgcc ctttgacgtt ggagtccacg ttctttaata    300

gtggactctt gttccaaact ggaacaacac tcaaccctat ctcggtctat tcttttgatt    360

tataagggat tttgccgatt tcggcctatt ggttaaaaaa tgagctgatt taacaaaaat    420

ttaacgcgaa ttttaacaaa atattaacgc ttacaatttg ccattcgcca ttcaggctgc    480

gcaactgttg ggaagggcga tcggtgcggg cctcttcgct attacgccag ctggcgaaag    540

ggggatgtgc tgcaaggcga ttaagttggg taacgccagg gttttcccag tcacgacgtt    600

gtaaaacgac ggccagtgaa ttgtaatacg actcactata gggcgacccg ggatggcgc     660

gccagtaatc aattacgggg tcattagttc atagcccata tatggagttc cgcgttacat    720

aacttacggt aaatggcccg cctggctgac cgcccaacga cccccgccca ttgacgtcaa    780

taatgacgta tgttcccata gtaacgccaa tagggacttt ccattgacgt caatgggtgg    840

agtatttacg gtaaactgcc cacttggcag tacatcaagt gtatcatatg ccaagtacgc    900

cccctattga cgtcaatgac ggtaaatggc ccgcctggca ttatgcccag tacatgacct    960

tatgggactt tcctacttgg cagtacatct acgtattagt catcgctatt accatgctga   1020

tgcggttttg gcagtacatc aatgggcgtg gatagcggtt tgactcacgg ggatttccaa   1080

gtctccaccc cattgacgtc aatgggagtt tgttttggca ccaaaatcaa cgggactttc   1140

caaaatgtcg taacaactcc gccccattga cgcaaatggg cggtaggcgt gtacggtggg   1200

aggtctatat aagcagagct ggtttagtga accggggtct ctctggttag accagatctg   1260

agcctgggag ctctctggct aactagggaa cccactgctt aagcctcaat aaagcttgcc   1320

ttgagtgctt caagtagtgt gtgcccgtct gttgtgtgac tctggtaact agagatccct   1380

cagacccttt tagtcagtgt ggaaaatctc tagcagtggc gcccgaacag ggacttgaaa   1440

gcgaaaggga aaccagagga gctctctcga cgcaggactc ggcttgctga agcgcgcacg   1500

gcaagaggcg aggggcggcg actggtgagt acgccaaaaa ttttgactag cggaggctag   1560

aaggagagag atgggtgcga gagcgtcagt attaagcggg ggagaattag atcgcgatgg   1620

gaaaaaattc ggttaaggcc agggggaaag aaaaaatata aattaaaaca tatagtatgg   1680

gcaagcaggg agctagaacg attcgcagtt aatcctggcc tgttagaaac atcagaaggc   1740

tgtagacaaa tactgggaca gctacaacca tcccttcaga caggatcaga agaacttaga   1800
```

-continued

```
tcattatata atacagtagc aaccctctat tgtgtgcatc aaaggataga gataaaagac   1860
accaaggaag ctttagacaa gatagaggaa gagcaaaaca aaagtaagac caccgcacag   1920
caagccgccg ctgatcttca gacctggagg aggagatatg agggacaatt ggagaagtga   1980
attatataaa tataaagtag taaaaattga accattagga gtagcaccca ccaaggcaaa   2040
gagaagagtg gtgcagagag aaaaaagagc agtgggaata ggagctttgt tccttgggtt   2100
cttgggagca gcaggaagca ctatgggcgc agcgtcaatg acgctgacgg tacaggccag   2160
acaattattg tctggtatag tgcagcagca gaacaatttg ctgagggcta ttgaggcgca   2220
acagcatctg ttgcaactca cagtctgggg catcaagcag ctccaggcaa gaatcctggc   2280
tgtggaaaga tacctaaagg atcaacagct cctggggatt tggggttgct ctggaaaact   2340
catttgcacc actgctgtgc cttggaatgc tagttggagt aataaatctc tggaacagat   2400
ttggaatcac acgacctgga tggagtggga cagagaaatt aacaattaca caagcttaat   2460
acactcctta attgaagaat cgcaaaacca gcaagaaaag aatgaacaag aattattgga   2520
attagataaa tgggcaagtt tgtggaattg gtttaacata acaaattggc tgtggtatat   2580
aaaattattc ataatgatag taggaggctt ggtaggttta agaatagttt ttgctgtact   2640
ttctatagtg aatagagtta ggcagggata ttcaccatta tcgtttcaga cccacctccc   2700
aaccccgagg ggacccgaca ggcccgaagg aatagaagaa gaaggtggag agagagacag   2760
agacagatcc attcgattag tgaacggatc tcgacggtat cggttaactt ttaaaagaaa   2820
aggggggatt ggggggtaca gtgcagggga aagaatagta gacataatag caacagacat   2880
acaaactaaa gaattacaaa aacaaattac aaaattcaaa attttatcgc gatcgcggaa   2940
tgaaagaccc cacctgtagg tttggcaagc tagcttaagt aacgccattt tgcaaggcat   3000
ggaaaataca taactgagaa tagagaagtt cagatcaagg ttaggaacag agagacagca   3060
gaatatgggc caaacaggat atctgtggta agcagttcct gccccggctc agggccaaga   3120
acagatggtc cccagatgcg gtcccgccct cagcagtttc tagagaacca tcagatgttt   3180
ccagggtgcc ccaaggacct gaaaatgacc ctgtgcctta tttgaactaa ccaatcagtt   3240
cgcttctcgc ttctgttcgc gcgcttctgc tccccgagct caataaaaga gcccacaacc   3300
cctcactcgg cgcgccagtc cttcgaagta gatctttgtc gatcctacca tccactcgac   3360
acacccgcca gcggccgctg ccaagcttcc gagctctcga attaattcac ggtacccacc   3420
atggcctagg gagactagtc gaatcgatat caacctctgg attacaaaat ttgtgaaaga   3480
ttgactggta ttcttaacta tgttgctcct tttacgctat gtggatacgc tgctttaatg   3540
cctttgtatc atgctattgc ttcccgtatg gctttcattt tctcctcctt gtataaatcc   3600
tggttgctgt ctctttatga ggagttgtgg cccgttgtca ggcaacgtgg cgtggtgtgc   3660
actgtgtttg ctgacgcaac ccccactggt tggggcattg ccaccacctg tcagctcctt   3720
tccgggactt tcgctttccc cctccctatt gccacggcgg aactcatcgc cgcctgcctt   3780
gcccgctgct ggacaggggc tcggctgttg ggcactgaca attccgtggt gttgtcgggg   3840
aagctgacgt cctttcatgg gctgctcgcc tgtgttgcca cctggattct gcgcgggacg   3900
tccttctgct acgtcccttc ggccctcaat ccagcggacc ttccttcccg cggcctgctg   3960
ccggctctgc ggcctcttcc gcgtcttcgc cttcgccctc agacgagtcg gatctccctt   4020
tgggccgcct ccccgcctgg ttaattaaag tacctttaag accaatgact tacaaggcag   4080
ctgtagatct tagccacttt ttaaaagaaa aggggggact ggaagggcga attcactccc   4140
```

-continued

```
aacgaagaca agatctgctt tttgcttgta ctgggtctct ctggttagac cagatctgag   4200
cctgggagct ctctggctaa ctagggaacc cactgcttaa gcctcaataa agcttgcctt   4260
gagtgcttca agtagtgtgt gcccgtctgt tgtgtgactc tggtaactag agatccctca   4320
gaccctttta gtcagtgtgg aaaatctcta gcaggcatgc cagacatgat aagatacatt   4380
gatgagtttg gacaaaccac aactagaatg cagtgaaaaa aatgctttat ttgtgaaatt   4440
tgtgatgcta ttgctttatt tgtaaccatt ataagctgca ataaacaagt taacaacaac   4500
aattgcattc attttatgtt tcaggttcag ggggaggtgt gggaggtttt ttggcgcgcc   4560
atcgtcgagg ttccctttag tgagggttaa ttgcgagctt ggcgtaatca tggtcatagc   4620
tgtttcctgt gtgaaattgt tatccgctca caattccaca caacatacga gccggaagca   4680
taaagtgtaa agcctggggt gcctaatgag tgagctaact cacattaatt gcgttgcgct   4740
cactgcccgc tttccagtcg ggaaacctgt cgtgccagct gcattaatga atcggccaac   4800
gcgcggggag aggcggtttg cgtattgggc gctcttccgc ttcctcgctc actgactcgc   4860
tgcgctcggt cgttcggctg cggcgagcgg tatcagctca ctcaaaggcg gtaatacggt   4920
tatccacaga atcaggggat aacgcaggaa agaacatgtg agcaaaaggc cagcaaaagg   4980
ccaggaaccg taaaaaggcc gcgttgctgg cgtttttcca taggctccgc ccccctgacg   5040
agcatcacaa aaatcgacgc tcaagtcaga ggtggcgaaa cccgacagga ctataaagat   5100
accaggcgtt tccccctgga agctccctcg tgcgctctcc tgttccgacc ctgccgctta   5160
ccggatacct gtccgccttt ctcccttcgg gaagcgtggc gctttctcat agctcacgct   5220
gtaggtatct cagttcggtg taggtcgttc gctccaagct gggctgtgtg cacgaacccc   5280
ccgttcagcc cgaccgctgc gccttatccg gtaactatcg tcttgagtcc aacccggtaa   5340
gacacgactt atcgccactg gcagcagcca ctggtaacag gattagcaga gcgaggtatg   5400
taggcggtgc tacagagttc ttgaagtggt ggcctaacta cggctacact agaagaacag   5460
tatttggtat ctgcgctctg ctgaagccag ttaccttcgg aaaaagagtt ggtagctctt   5520
gatccggcaa acaaaccacc gctggtagcg gtggtttttt tgtttgcaag cagcagatta   5580
cgcgcagaaa aaaaggatct caagaagatc ctttgatctt ttctacgggg tctgacgctc   5640
agtggaacga aaactcacgt taagggattt tggtcatgag attatcaaaa aggatcttca   5700
cctagatcct tttaaattaa aaatgaagtt ttaaatcaat ctaaagtata tatgagtaaa   5760
cttggtctga cagttaccaa tgcttaatca gtgaggcacc tatctcagcg atctgtctat   5820
ttcgttcatc catagttgcc tgactccccg tcgtgtagat aactacgata cgggagggct   5880
taccatctgg ccccagtgct gcaatgatac cgcgagaccc acgctcaccg gctccagatt   5940
tatcagcaat aaaccagcca gccggaaggg ccgagcgcag aagtggtcct gcaactttat   6000
ccgcctccat ccagtctatt aattgttgcc gggaagctag agtaagtagt tcgccagtta   6060
atagtttgcg caacgttgtt gccattgcta caggcatcgt ggtgtcacgc tcgtcgtttg   6120
gtatggcttc attcagctcc ggttcccaac gatcaaggcg agttacatga tcccccatgt   6180
tgtgcaaaaa agcggttagc tccttcggtc ctccgatcgt tgtcagaagt aagttggccg   6240
cagtgttatc actcatggtt atggcagcac tgcataattc tcttactgtc atgccatccg   6300
taagatgctt ttctgtgact ggtgagtact caaccaagtc attctgagaa tagtgtatgc   6360
ggcgaccgag ttgctcttgc ccggcgtcaa tacgggataa taccgcgcca catagcagaa   6420
ctttaaaagt gctcatcatt ggaaaacgtt cttcggggcg aaaactctca aggatcttac   6480
cgctgttgag atccagttcg atgtaaccca ctcgtgcacc caactgatct tcagcatctt   6540
```

-continued

```
ttactttcac cagcgtttct gggtgagcaa aaacaggaag gcaaaatgcc gcaaaaaagg   6600

gaataagggc gacacggaaa tgttgaatac tcatactctt cctttttcaa tattattgaa   6660

gcatttatca gggttattgt ctcatgagcg gatacatatt tgaatgtatt tagaaaaata   6720

aacaaatagg ggttccgcgc acatttcccc gaaaagtgcc ac                      6762
```

UNITED STATES PATENT AND TRADEMARK OFFICE
CERTIFICATE OF CORRECTION

PATENT NO. : 10,689,450 B2
APPLICATION NO. : 15/476309
DATED : June 23, 2020
INVENTOR(S) : Jed Wiltzius et al.

Page 1 of 1

It is certified that error appears in the above-identified patent and that said Letters Patent is hereby corrected as shown below:

In the Claims

In Column 476, Line 48, Claim 26, delete "(CD11C)," and insert -- (CD11c), --.

In Column 476, Line 53, Claim 26, delete "LyI08)," and insert -- Ly108), --.

In Column 477, Line 21, Claim 35, delete "any one of claim" and insert -- claim --.

In Column 477, Line 65, Claim 47, delete "method treating" and insert -- method of treating --.

In Column 478, Line 8, Claim 48, delete "(PMBC)," and insert -- (PMBCL), --.

In Column 478, Line 26, Claim 48, delete "gammapathy" and insert -- gammopathy --.

In Column 482, Line 2, Claim 71, delete "(PMBC)," and insert -- (PMBCL), --.

In Column 482, Line 21, Claim 71, delete "gammapathy" and insert -- gammopathy --.

Signed and Sealed this
First Day of September, 2020

Andrei Iancu
*Director of the United States Patent and Trademark Office*